US009206434B2

(12) United States Patent
Hau et al.

(10) Patent No.: US 9,206,434 B2
(45) Date of Patent: Dec. 8, 2015

(54) HETEROLOGOUS BIOMASS DEGRADING ENZYME EXPRESSION IN THERMOANAEROBACTERIUM SACCHAROLYTICUM

(75) Inventors: Heidi Hau, Lebanon, NH (US); Charles Rice, Hopkinton, NH (US); Chris Herring, Lebanon, NH (US); John McBride, Lyme, NH (US); Arthur J. Shaw, IV, Grantham, NH (US); Erin Wiswall, Danbury, NH (US)

(73) Assignee: Enchi Corporation, Waltham, MA (US)

( * ) Notice: Subject to any disclaimer, the term of this patent is extended or adjusted under 35 U.S.C. 154(b) by 586 days.

(21) Appl. No.: 13/141,952

(22) PCT Filed: Dec. 23, 2009

(86) PCT No.: PCT/US2009/069443
§ 371 (c)(1),
(2), (4) Date: Oct. 19, 2011

(87) PCT Pub. No.: WO2010/075529
PCT Pub. Date: Jul. 1, 2010

(65) Prior Publication Data
US 2012/0040409 A1   Feb. 16, 2012

Related U.S. Application Data

(60) Provisional application No. 61/140,607, filed on Dec. 23, 2008, provisional application No. 61/259,791, filed on Nov. 10, 2009.

(51) Int. Cl.
| | | |
|---|---|---|
| *C12P 7/10* | (2006.01) | |
| *C12P 19/14* | (2006.01) | |
| *C12N 9/42* | (2006.01) | |
| *C12N 15/74* | (2006.01) | |
| *C12P 7/06* | (2006.01) | |

(52) U.S. Cl.
CPC .............. *C12N 15/74* (2013.01); *C12N 9/2437* (2013.01); *C12P 7/065* (2013.01); *C12P 7/10* (2013.01); *Y02E 50/16* (2013.01); *Y02E 50/17* (2013.01)

(58) Field of Classification Search
None
See application file for complete search history.

(56) References Cited

U.S. PATENT DOCUMENTS

| | | | |
|---|---|---|---|
| 5,925,515 | A | 7/1999 | Van Hartingsveldt et al. |
| 2006/0105442 | A1 | 5/2006 | Wu et al. |
| 2007/0031953 | A1 | 2/2007 | Dunson, Jr. et al. |
| 2008/0050774 | A1 | 2/2008 | Berka et al. |

FOREIGN PATENT DOCUMENTS

| | | |
|---|---|---|
| WO | WO 2007/053600 A2 | 5/2007 |
| WO | WO 2007/130984 A2 | 11/2007 |
| WO | WO 2009/035595 A1 | 3/2008 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Accession Q08166. Nov. 1, 1996.*
Cantarel, B.L., et al., "The Carbohydrate-Active EnZymes database (CAZy): an expert resource for Glycogenomics," *Nucleic Acids Res.* 37(*Database issue*):D233-D238, Cantarel, B.L., et al. (Open Access Article), England (Published Online 2008).
Desai, S.G., et al., "Cloning of L-lactate dehydrogenase and elimination of lactic acid production via gene knockout in *Thermoanaerobacterium saccharolyticum* JW/SL-YS485," *Appl. Microbiol. Biotechnol.* 65:600-605, Springer-Verlag, Germany (2004).
Jung, E.D., et al., "DNA sequences and expression in *Streptomyces lividans* of an exoglucanase gene and an endoglucanase gene from *Thermomonospora fusca*," *Appl. Environ. Microbiol.*59(9):3032-3043, American Society for Microbiology, United States (1993).
Kotula, L. and Curtis, P.J., "Evaluation of foreign gene codon optimization in yeast: expression of a mouse IG kappa chain," *Biotechnology (NY)* 9(12):1386-1389, Nature Publishing Company, United States (1991).
Mai, V. and Wiegel, M.V., "Advances in Development of a Genetic System for *Thermoanaerobacterium* spp.: Expression of Genes Encoding Hydrolytic Enzymes, Development of a Second Shuttle Vector, and Integration of Genes into the Chromosome," *Appl. Environ. Microbiol.* 66(11):4817-21, American Society for Microbiology, United States (2000).
Nakamura, Y., et al., "Codon usage tabulated from the international DNA sequence databases: status for the year 2000," *Nuleic Acids Res.* 28(1):292 , Oxford University Press, England (2000).

(Continued)

*Primary Examiner* — Christian Fronda
(74) *Attorney, Agent, or Firm* — Sterne, Kessler, Goldstein & Fox P.L.L.C.

(57) ABSTRACT

Thermophilic gram-positive anaerobic host cells, for example *Thermoanaerobacterium saccharolyticum* ("*T sacch*"), express heterologous biomass degrading enzymes, such as cellulases, and are able to produce useful fermentation products from cellulose. Useful fermentation products include, for example, ethanol, acetic acid, lactic acid or CO2. In order to provide maximum expression and activity levels, biomass degrading enzymes can be expressed from codon-optimized nucleotide sequences, can be expressed under the control of a high-efficiency promoter, and/or can be fused to a signal peptide. In addition, the host cell, for example, a *T sacch* host cell, can be genetically altered to further improve ethanol production, for example by disrupting the production of organic products other than ethanol.

13 Claims, 13 Drawing Sheets

(56) References Cited

OTHER PUBLICATIONS

Figure 1:
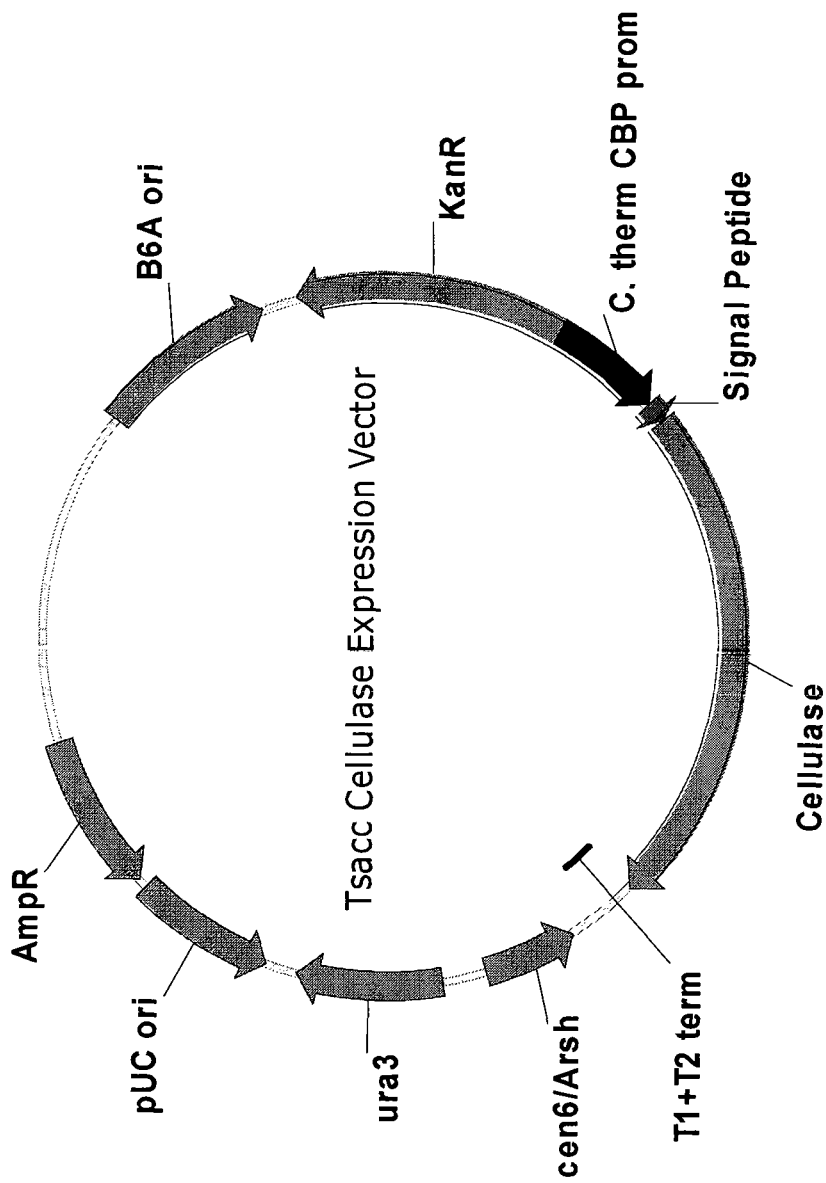

Reyrat, J.-M., et al., "Counterselectable markers: Untapped Tools for Bacterial Genetics and Pathogenesis," *Infec. Immun.* 66(9):4011-4017, American Society for Microbiology, United States (1998).

Sasaguri, S., et al., "Codon optimization prevents premature polyadenylation of heterologously-expressed cellulases from termite-gut symbionts in *Aspergillus oryzae*," *J. Gen. Appl. Microbiol.* 54(6):343-351, Institute of Applied Microbiology University of Tokyo, Japan (2008).

Sharp, P.M. and Li, W.-H., "The codon Adaptation Index—a measure of directional synonymous codon usage bias, and its potential applications," *Nuleic Acids Res.* 15(3):1281-1295, IRL Press Limited, England (1987).

Shaw, A.J. et al., "Metabolic engineering of a thermophilic bacterium to produce ethanol at high yield," *Proc Natl Acad Sci USA* 105(37):13769-13774, The National Academy of Sciences of the USA, United States (2008).

International Search Report for International Application No. PCT/US2009/69443, International Searching Authority, United States, mailed on Nov. 17, 2010.

Written Opinion for International Application No. PCT/US2009/69443, International Searching Authority, United States, completed Jun. 2, 2010.

International Preliminary Report on Patentability for International Application No. PCT/US2009/69443, International Searching Authority, United States, issued Jun. 29, 2011.

Oak Ridge National Laboratory Computational Biology genome annotation, accessed at http://genome.ornl.gov/cgi-bin/Blast/blastform.cgi?blastorgs=tsac:08apr08:, accessed Apr. 2008.

\* cited by examiner

HETEROLOGOUS BIOMASS DEGRADING ENZYME EXPRESSION IN THERMOANAEROBACTERIUM SACCHAROLYTICUM

This is the U.S. National Phase of International Application No. PCT/US2009/069443, filed Dec. 23, 2009, which claims the benefit of U.S. Provisional Application No. 61/140,607, filed Dec. 23, 2008, and U.S. Provisional Application No. 61/259,791, filed Nov. 10, 2009, each of which is hereby incorporated by reference in its entirety.

REFERENCE TO A SEQUENCE LISTING SUBMITTED ELECTRONICALLY VIA EFS-WEB

The content of the electronically submitted sequence listing (Name: sequencelisting.ascii.txt, Size: 441,593 bytes; and Date of Creation: Jun. 23, 2011) is herein incorporated by reference in its entirety.

BACKGROUND OF THE INVENTION

1. Field of the Invention

The present invention relates to the field of molecular biology, and in particular, to the expression of heterologous biomass degrading enzymes in gram-positive thermophilic anaerobic bacteria.

2. Background Art

Thermophilic microorganisms are useful for a variety of industrial processes. For example, thermophilic microorganisms can be used as biocatalysts in reactions at higher operating temperatures than can be achieved with mesophilic microorganisms. Thermophilic organisms are particularly useful in biologically mediated processes for energy conversion, such as the production of ethanol from plant biomass, because higher operating temperatures allow more convenient and efficient removal of ethanol in vaporized form from the fermentation medium.

The ability to metabolically engineer thermophilic microorganisms to improve various properties (e.g., ethanol production, breakdown of lignocellulosic materials), would allow the benefit of higher operating temperatures to be combined with the benefits of using industrially important enzymes from a variety of sources in order to improve efficiency and lower the cost of production of various industrial processes, such as energy conversion and alternative fuel production.

Thermophilic anaerobic gram-positive bacteria such as *Thermoanaerobacterium saccharolyticum* ("*T. sacch*") can be particularly useful in methods of energy conversion since they can grow at temperatures above 40° C. and are readily able to utilize cellobiose (a disaccharide) and xylose (a monosaccharide) as energy sources. However, *T. sacch* are not able to hydrolyze cellulose efficiently. Previous experiments have demonstrated that it is possible to expresses heterologous cellulases in *T. sacch* (Mai and Wiegel, *Applied and Environmental Microbiology*, 66: 4817-4821 (2000)). However, major shortcomings of the previous strains were that ethanol was not the sole metabolic product and that they were unable to achieve sufficient levels of secreted enzyme to be industrially useful. In contrast, the present invention provides *T. sacch* and other transformed thermophilic anaerobic bacteria that express high levels of heterologous cellulases that can efficiently produce ethanol or other useful fermentation products such as lactic acid, acetic acid, or $CO_2$ from cellulose.

BRIEF SUMMARY OF THE INVENTION

The present invention is directed to cellulytic thermophilic gram-positive anaerobic host cells, such as *Thermoanaerobacterium saccharolyticum*. The host cells of the invention express heterologous biomass degrading enzymes. In some embodiments, the host cells can produce ethanol from cellulose.

In particular, isolated nucleic acids comprising polynucleotides which encode polypeptides comprising an amino acid sequence selected from the group consisting of SEQ ID NOs: 1-38 and an amino acid sequence selected from the group consisting of SEQ ID NOs: 108-148 are described. In some embodiments, the polynucleotide is codon-optimized for expression in *Thermoanaerobacterium saccharolyticum*. In addition, vectors and host cells comprising such nucleic acids are provided. The host cell can be a member of the genus *Thermoanaerobacterium*, such as *T. thermosulfurgenes*, *T. polysaccharolyticum*, *T. thermosaccharolyticum* or *T. saccharolyticum*. Furthermore, proteins encoded by such nucleic acids are also described.

Transformed *Thermoanaerobacterium saccharolyticum* host cells comprising at least one heterologous polynucleotide comprising a nucleic acid encoding a biomass degrading enzyme, wherein the host cell lacks a gene that is necessary for producing lactic acid as a fermentation product or lacks a gene that is necessary for producing acetic acid as a fermentation product or lacks both are also described. In some embodiments, such host cells do not contain heterologous markers. In some embodiments, the gene that is necessary for lactic acid production encodes lactate dehydrogenase. In some embodiments, the gene that is necessary for acetic acid production is phosphotransacetylase or acetate kinase.

Transformed thermophilic anaerobic bacterial host cells comprising heterologous polynucleotides comprising a nucleic acid encoding a biomass degrading enzyme operably linked to a cellobiose phosphotransferase promoter are also described.

Transformed thermophilic anaerobic bacterial host cells comprising at least one heterologous polynucleotide comprising a nucleic acid encoding a fusion protein, wherein the fusion protein comprises a signal peptide and a heterologous biomass degrading enzyme, and wherein the signal peptide comprises a sequence selected from the group consisting of SEQ ID NOs: 1-38 are also described.

In some embodiments, the host cells can be selected from a group consisting of *Acetogenium kivui*, *Caldanaerobacter proteolyticus*, *Caldanaerobium fijiensis*, *Clostridium thermoamylolyticum*, *Clostridium thermocopriae*, *Clostridium thermosaccharolyticum*, *Clostridium uzonii*, *Desulfotomaculum thermobenzoicum*, *Garciaella petrolearia*, *Soehngenia saccharolytica*, *Thermoanaerobacter acetoethylicus*, *Thermoanaerobacter brockii*, *Thermoanaerobacter ethanolicus*, *Thermoanaerobacter finii*, *Thermoanaerobacter inferii*, *Thermoanaerobacter lacticus*, *Thermoanaerobacter pseudethanolicus*, *Thermoanaerobacter pseudethanolicus*, *Thermoanaerobacter siderophilus*, *Thermoanaerobacter subterraneus*, *Thermoanaerobacter sulfurigignens*, *Thermoanaerobacter sulfurophilus*, *Thermoanaerobacter tengcongensis*, *Thermoanaerobacter thermohydrosulfuricus*, *Thermoanaerobacter uzonensis* strain, *Thermoanaerobacter wiegelii*, *Thermoanaerobium lactoethylicum*, and *Thermobacteroides acetoethylicus*. In some particular embodiments, the host cell is a member of the genus *Thermoanaerobacterium*. In yet another embodiment, the host cell is a *T. thermosulfurgenes*, *T. polysaccharolyticum*, *T. thermosaccharolyti*- cum or *T. saccharolyticum* host cell. In still another embodiment, the host cell is a *T. saccharolyticum* host cell.

Transformed *Thermoanaerobacterium saccharolyticum* host cells comprising at least one heterologous polynucleotide comprising a nucleic acid encoding a biomass degrading enzyme, wherein the nucleic acid encoding the biomass degrading enzyme is codon-optimized for expression in *Thermoanaerobacterium saccharolyticum* are also described.

In addition, transformed *Thermoanaerobacterium saccharolyticum* host cells comprising at least one heterologous polynucleotide comprising a nucleic acid encoding a biomass degrading enzyme, wherein the biomass degrading enzyme is not a biomass degrading enzyme from an anaerobic bacteria are described herein.

In some embodiments, the biomass degrading enzyme is a fungal biomass degrading enzyme or a biomass degrading enzyme from a microorganism residing in the termite gut. In other embodiments, the biomass degrading enzyme is derived from *Thermobifida fusca, Caldocellum saccharolyticum, Clostridium stercorarium, Eubacterium cellulosolvens, Cellulomonas fimi, Acidothermus cellulolyticus, Butyrivibrio fibrisolvens, Anaerocellum thermophilum, Trichoderma reesei, Coptotermes formosanus, Nasutitermes takasagoensis, Talaromyces emersonii, Neosartorya fischeri* or *Caldicellulosiruptor kristjanssonii*.

In some embodiments, the host cell comprises a nucleic acid encoding a heterologous biomass degrading enzyme and has decreased protease activity compared to a wild-type cell. The decreased protease activity can be the result of decreased activity of a protease. For example, the decreased protease activity can be the result of decreased activity of a polypeptide comprising an amino acid sequence selected from the group consisting of SEQ ID NOs: 164-168. In some embodiments, the host cell comprises a nucleic acid encoding a heterologous biomass degrading enzyme and has increased chaperone activity compared to a wild-type cell. The increased chaperone activity can be, for example, the result of the overexpression of a chaperone selected from the group consisting of *E. coli* HSP60/GroEL, *E. coli* HSP60/GroES, *E. coli* HSP70/DnaK, *E. coli* DnaJ, *E. coli* GrpE, *E. coli* HSP90/HtpG, *E. coli* HSP100/Clp family, *E. coli* peptidyl prolyl isomerase Trigger Factor, *Bacillus subtilis* Ffh, *Bacillus subtilis* HBsu, *Bacillus subtilis* FtsY, *Bacillus subtilis* CsaA and *Bacillus subtilis* FlhF.

In some embodiments, the thermophilic anaerobic bacterial host cell lacks a gene that is necessary for producing lactic acid as a fermentation product. The gene that is necessary for producing lactic acid as a fermentation product can be lactate dehydrogenase. In some embodiments, the host cell lacks a gene that is necessary for producing acetic acid as a fermentation product. The gene that is necessary for producing acetic acid as a fermentation product can be phosphotransacetylase or acetate kinase.

In some embodiments, the thermophilic anaerobic bacterial host cells can hydrolyze cellulose. In other embodiments, the host cell can grow on crystalline cellulose. In still other embodiments, the host cell can grow on Avicel. In some embodiments, the host cell has at least 10 U/mg activity.

In some embodiments, the thermophilic anaerobic bacterial host cell expresses a biomass degrading enzyme wherein the sequence encoding the biomass degrading enzyme is operably associated with a cellobiose phosphotransferase (CBP) promoter. The CBP promoter can be the *Clostridium thermocellum* CBP promoter. The CBP promoter can comprise the sequence of SEQ ID NO:153.

In some embodiments, the biomass degrading enzyme is fused to a signal peptide. The signal peptide can comprise an amino acid sequence selected from the group consisting of SEQ ID NOs: 1-38. The signal peptide can be fused to the N-terminus of the biomass degrading enzyme. The signal peptide can be encoded by a nucleic acid codon-optimized for expression in *Thermoanaerobacterium saccharolyticum*.

In some embodiments, the biomass degrading enzyme comprises an amino acid sequence selected from the group consisting of SEQ ID NOs: 108-148. In some embodiments, the nucleic acid encoding the biomass degrading enzyme is codon-optimized for expression in *Thermoanaerobacterium saccharolyticum*. In some embodiments, the biomass degrading enzyme is fused to a cellulose binding module (CBM).

In some embodiments, the host cell further comprises a second heterologous polynucleotide comprising a nucleic acid encoding a biomass degrading enzyme.

In some embodiments, the biomass degrading enzyme is a cellulase.

Methods for hydrolyzing a cellulosic substrate, comprising contacting the cellulosic substrate with a thermophilic anaerobic bacterial host cell expressing a biomass degrading enzyme are also described herein. In addition, methods for producing ethanol from a cellulosic substrate comprising contacting the cellulosic substrate with a thermophilic anaerobic bacterial host cell expressing a biomass degrading enzyme are also described herein. The methods can further comprise contacting the substrate with exogenous enzymes. The contacting can occur in anaerobic conditions.

The cellulosic substrate can be a lignocellulosic biomass selected from the group consisting of grass, switch grass, cord grass, rye grass, reed canary grass, miscanthus, sugar-processing residues, sugarcane bagasse, agricultural wastes, rice straw, rice hulls, barley straw, corn cobs, cereal straw, wheat straw, canola straw, oat straw, oat hulls, corn fiber, stover, soybean stover, corn stover, forestry wastes, recycled wood pulp fiber, paper sludge, sawdust, hardwood, softwood, and combinations thereof.

Methods of producing products such as acetic acid from a cellulosic substrate comprising contacting said cellulosic substrate with a thermophilic anaerobic bacterial host cell expressing a biomass degrading enzyme are also described herein. Similarly, methods of producing lactic acid from a cellulosic substrate comprising contacting said cellulosic substrate with a thermophilic anaerobic bacterial host cell expressing a biomass degrading enzyme are also described herein.

Methods of producing a biomass degrading enzyme comprising culturing a thermophilic anaerobic bacterial host cell expressing a biomass degrading enzyme under conditions suitable for protein expression and purifying the biomass degrading enzyme are also described herein.

Methods of producing ethanol from a cellulosic substrate comprising contacting the cellulosic substrate with a *Thermoanaerobacterium saccharolyticum*, wherein the *Thermoanaerobacterium saccharolyticum* expresses a heterologous cellulase and (i) has increased chaperone activity compared to wild-type *Thermoanaerobacterium saccharolyticum* and/or (ii) has decreased protease activity compared to wild-type *Thermoanaerobacterium saccharolyticum* are also described.

BRIEF DESCRIPTION OF THE DRAWINGS/FIGURES

FIG. 1. Vector map showing basic genetic elements that can be used for cloning cellulases in *T. sacch*. The plasmid contains the *Clostridium thermocellum* CBP cellobiose phosphotransferase (CBP) promoter; *E. coli* T1 and T2 terminator; an exogenous cellulase gene (the native sequence from host organism or codon-optimized sequence of the cellulase); signal peptide (native signal sequence from host organism, a codon optimized native signal sequence from host organism, endogenous *T. sacch* signal sequence, signal sequence from another gram positive organism, or codon-optimized signal sequence from another gram positive organism); *S. cerevisiae* URA3 auxotrophic marker; cen6/Arsh yeast origin of replication; the B6A *T. sacch* origin of replication; and the kanamycin (KanR) and ampicillin (AmpR) resistance markers.

Figure 2:
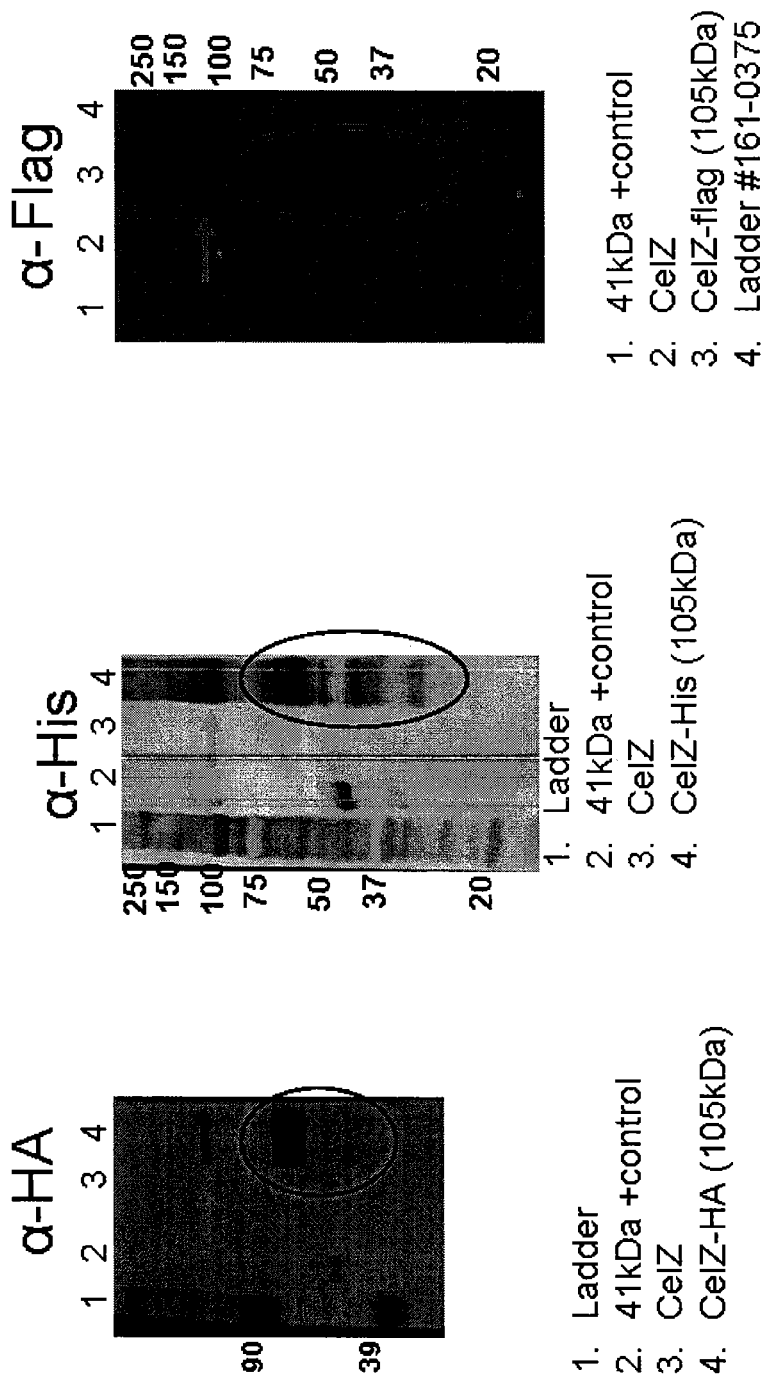

FIG. 2. Western blot of *T. sacch* supernatants showing CelZ (native *C. stercorarium* sequence) expression. Anti-6×His, anti-Flag, and anti-HA antibodies were used to detect CelZ with His, Flag and HA tags expressed in a *T. sacch* strain. In each blot, "ladder" indicates the lane loaded with a molecular weight protein ladder; "41 kDA+control" indicates the lane loaded with *E. coli* whole cell lysates expressing His, Flag and HA tagged protein (positive control); "CelZ" indicates the lane loaded with supernatant from *T. sacch* expressing CelZ with no tag; and "CelZ-HA," "CelZ-His," and "CelZ-flag" indicate lanes loaded with supernatant from *T. sacch* expressing CelZ fusion proteins. CelZ fusions are designated by the arrows, and possible proteolysis products are circled.

Figure 3:
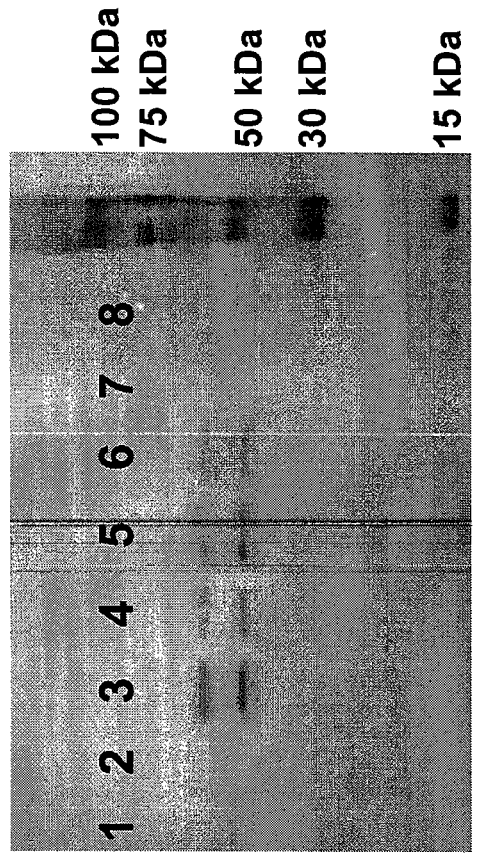

FIG. 3. Western blot of *T. sacch* supernatants showing E5 and CBH1 expression. Anti-His antibodies were used to detect His tagged proteins expressed in the *T. sacch* strain M0355. Supernatants from M0355 transformed with vectors encoding *Cellulomonas fimi* cex (lanes 1 and 2), *Talaromyces emersonii* CBH1 (lanes 3 and 4), *T. fusca* CelE (E5) (lanes 5 and 6) and *Nasutitermes takasagoensis* NtEG (lanes 7 and 8) were assayed for protein expression. Lanes 1, 3, 5 and 7 were obtained from overnight cultures, and lanes 2, 4, 6 and 8 were obtained from stationary cultures.

Figure 4:
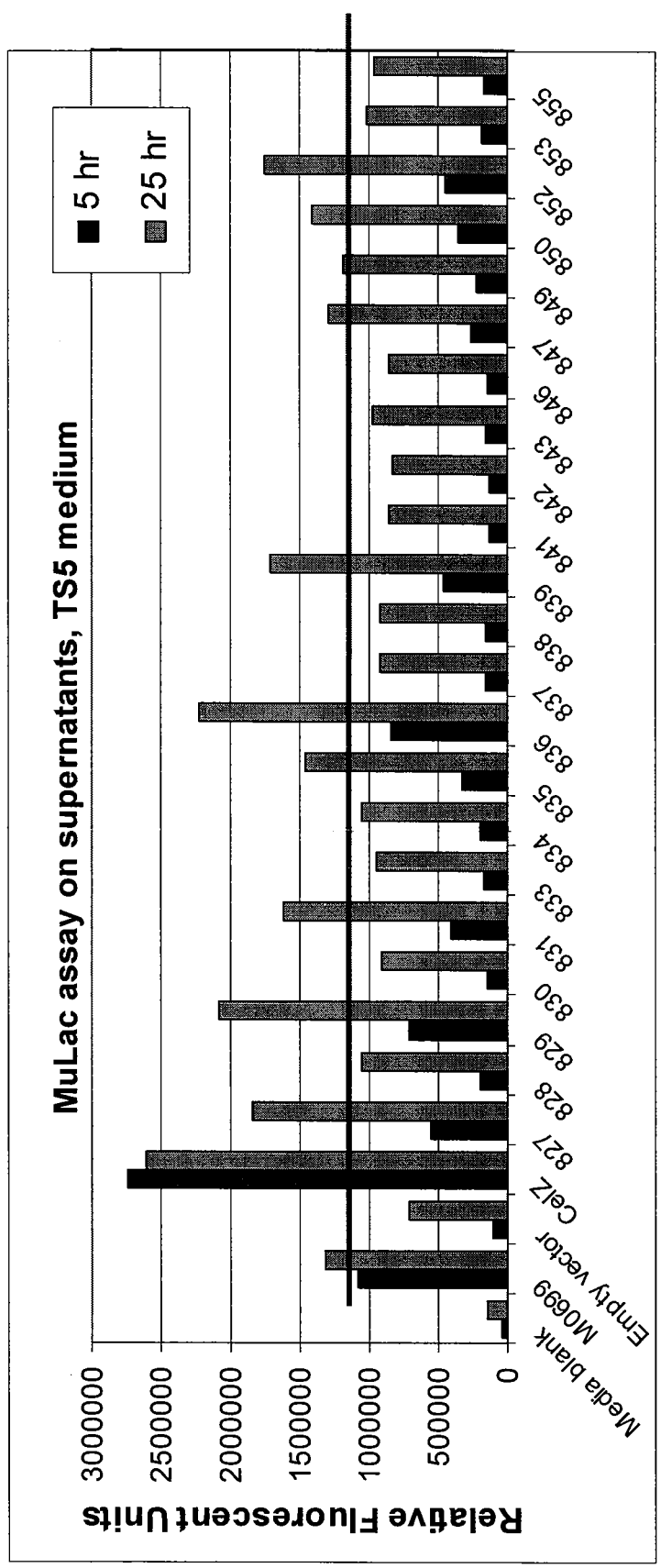

FIG. 4. Bar graph showing activity of *T. sacch* transformants in MuLac assay. *T. sacch* were transformed with genes as described in Example 5. The ability of the resulting strains to cleave MuLac was compared to that of the parent strain, M0699, which is an MO355-derived strain adapted for fast growth in a chemostat.

Figure 5:
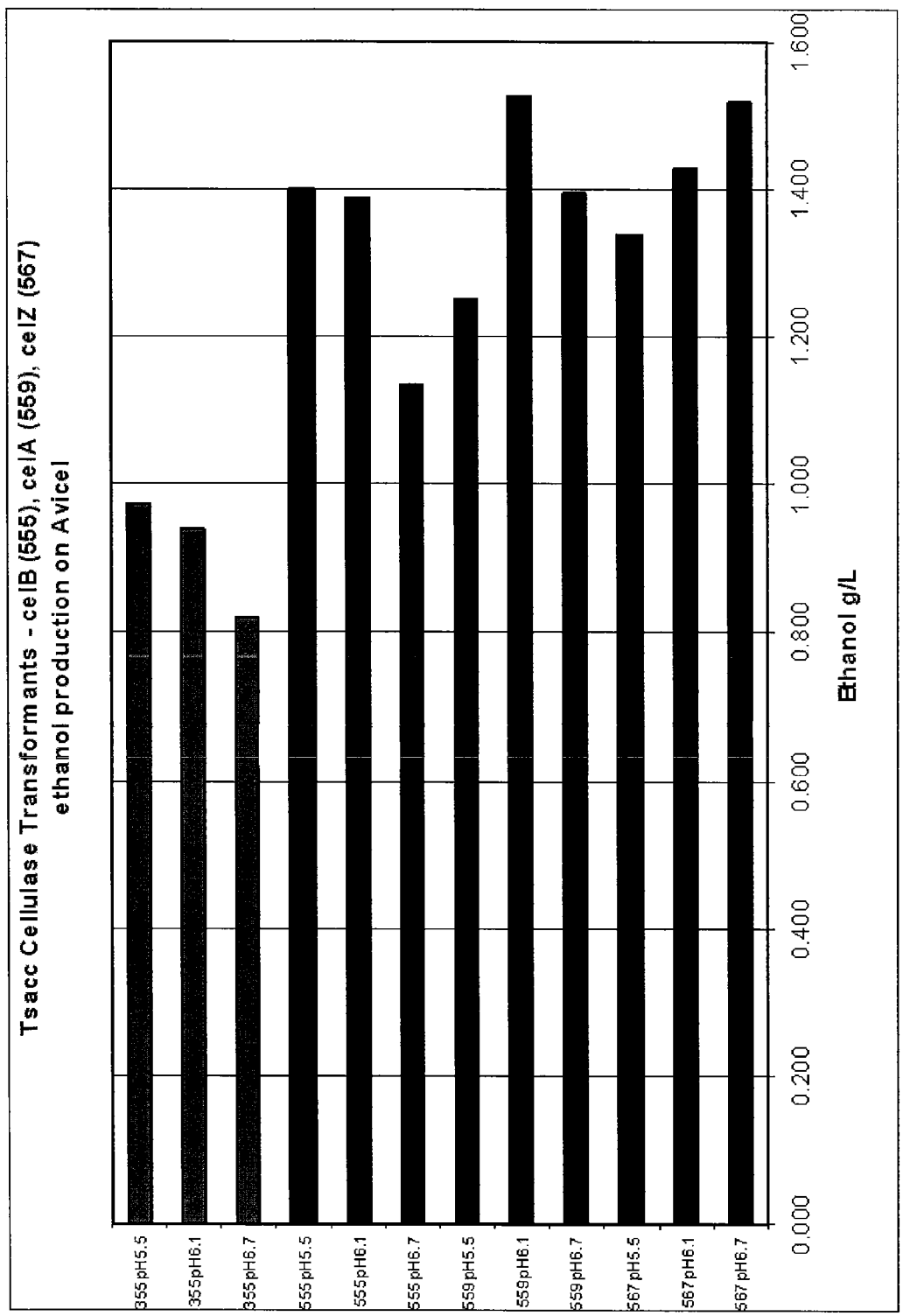

FIG. 5. Bar graph of ethanol production from M0355 transformants. *T. sacch* were transformed with PCR-cloned CelB from *Caldicellulosiruptor kristjanssonii* ("*T. sacch* 555"), CelA from *Anaerocellum thermophilum* ("*T. sacch* 559"), and CelZ from *Clostridium stercorarium* ("*T. sacch* 567"). The ability of the resulting strains to produce ethanol from Avicel was compared to that of the parent *T. sacch* strain, M0355. Ethanol production assays were performed at pH 5.5, 6.1 and 6.7.

Figure 6:
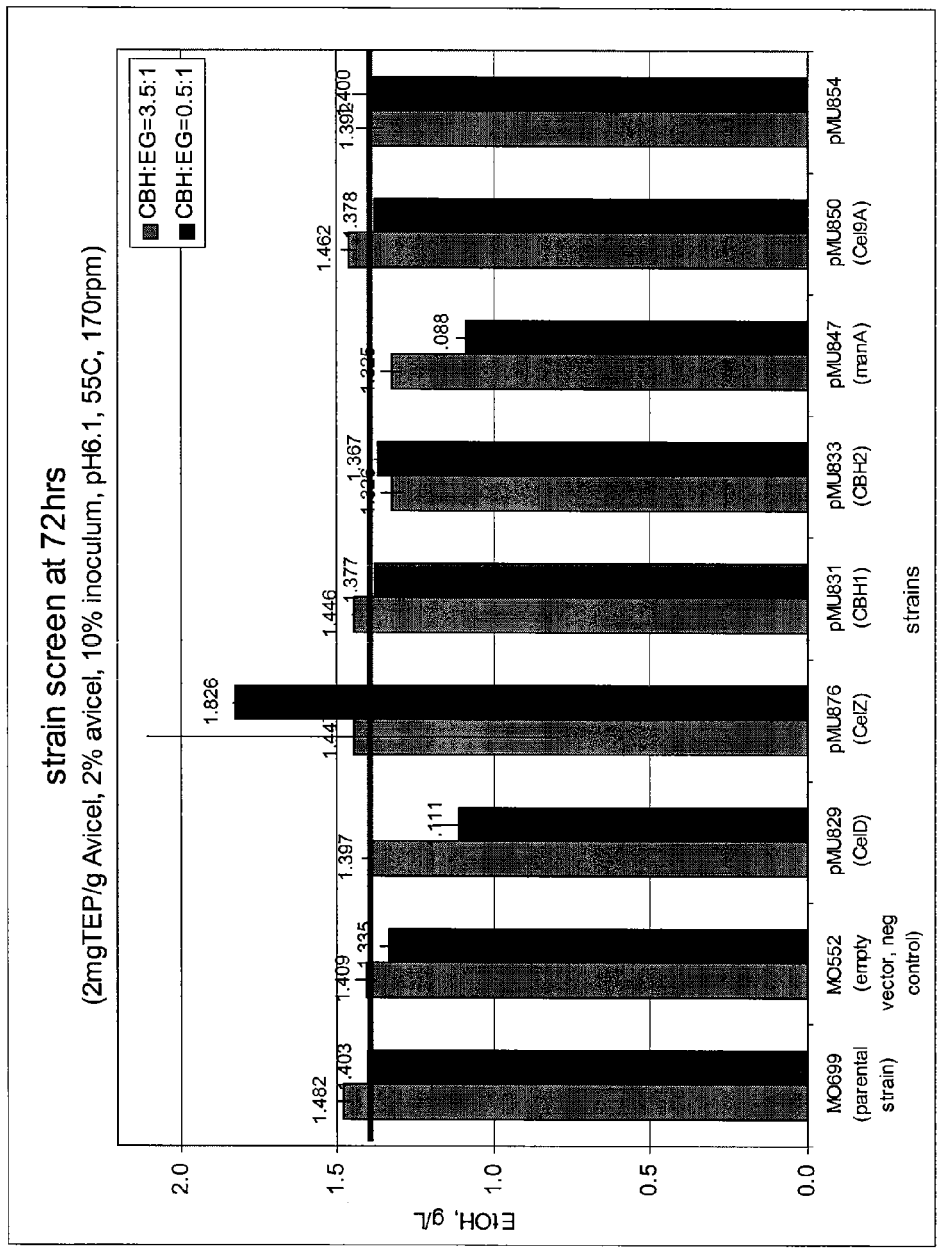

FIG. 6. Bar graph of ethanol production from M0699 transformants. *T. sacch* were transformed with PCR-cloned genes from the labeled biomass degrading enzymes. The ability of the resulting strains to produce ethanol from Avicel was compared to that of the parent *T. sacch* strain, M0699.

Figure 7A:
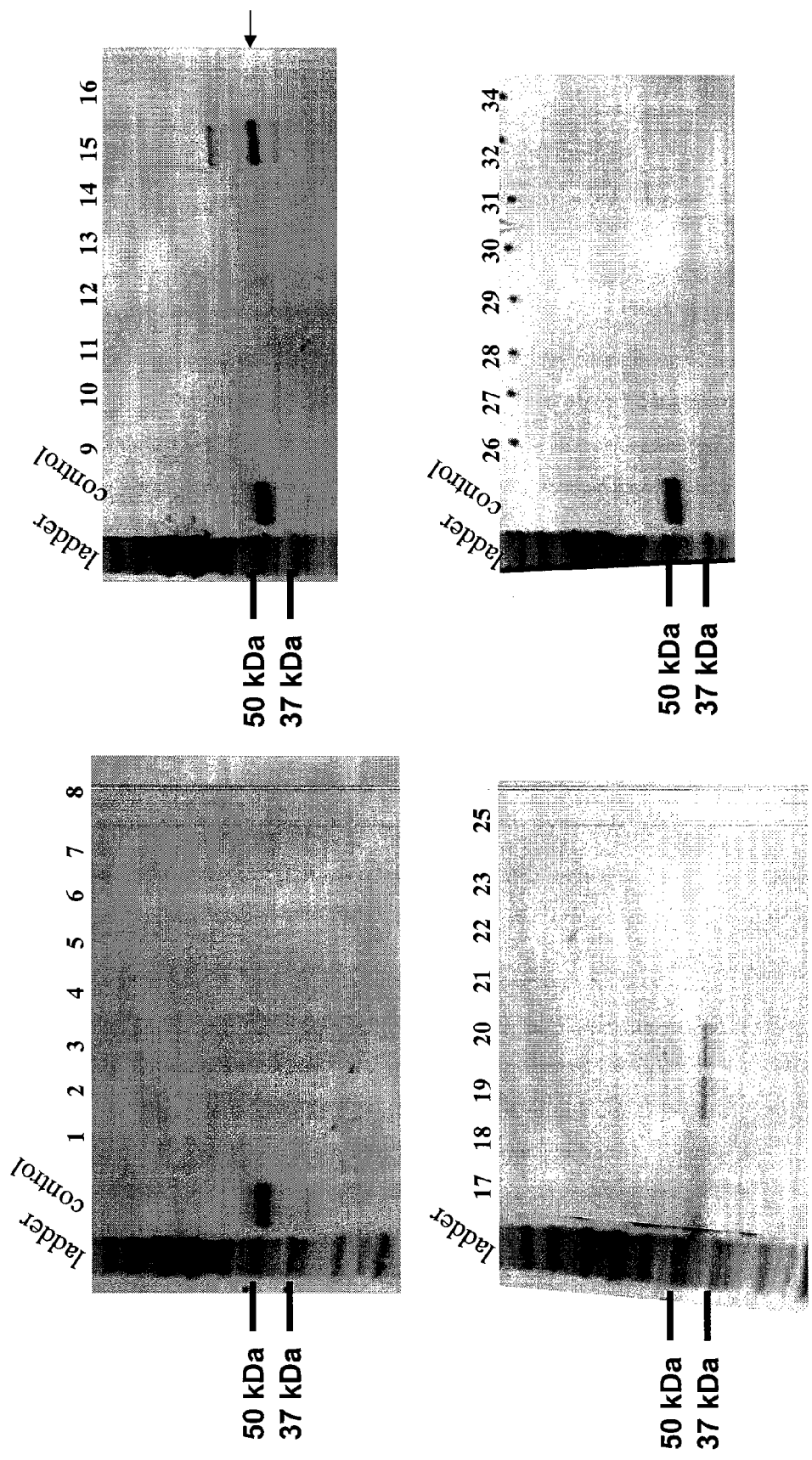
Figure 7B:
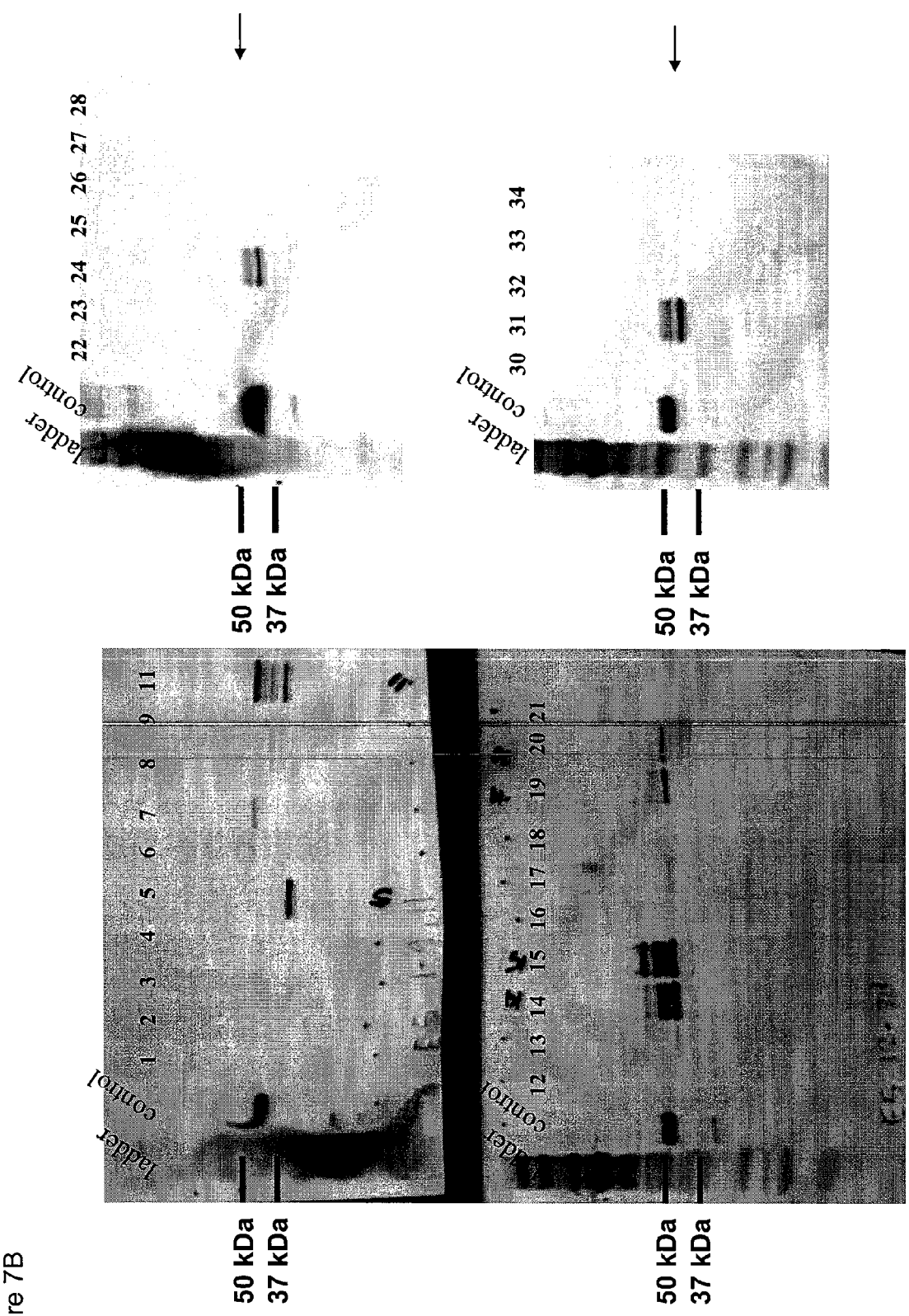
Figure 7C:
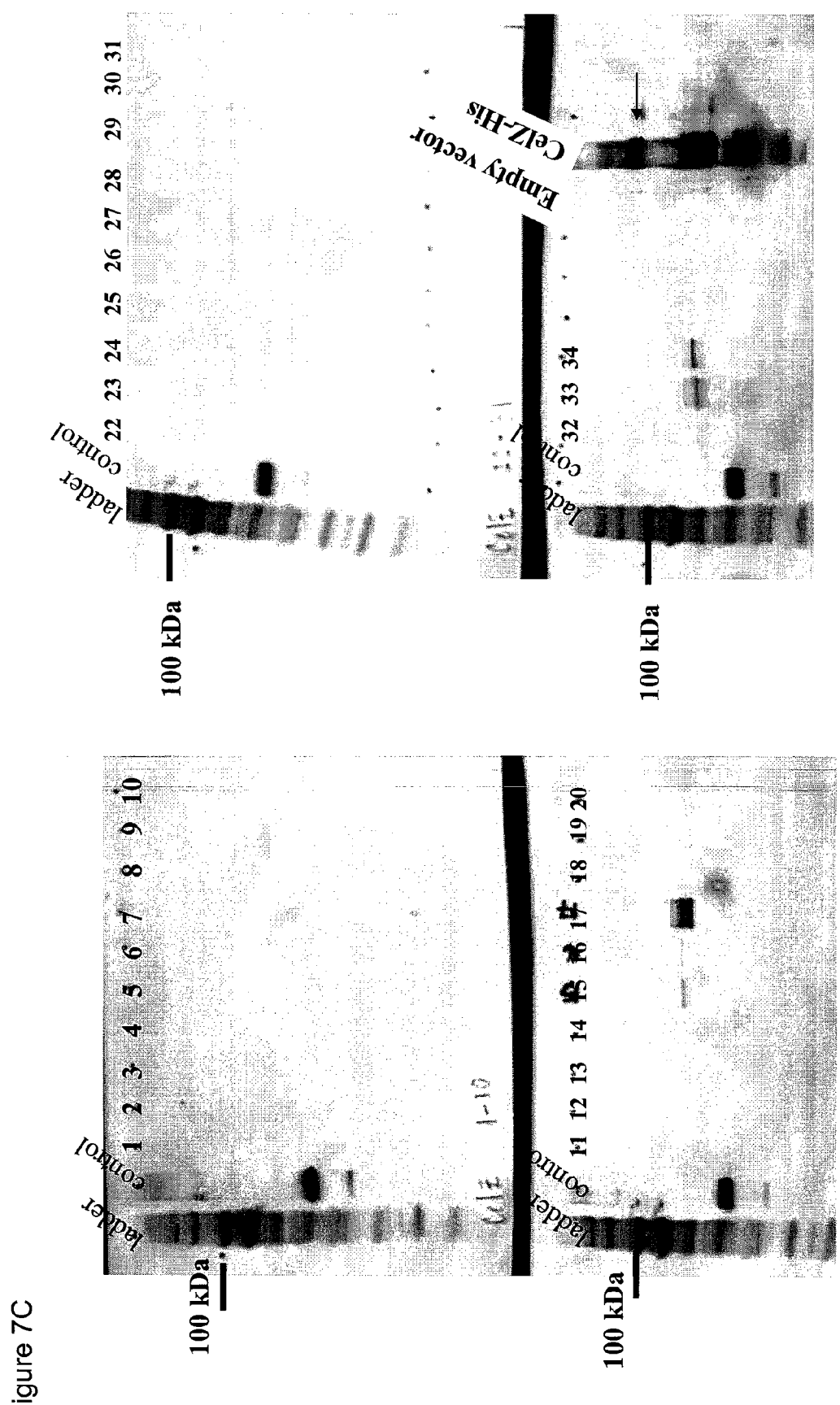

FIG. 7. Western blots of CBH1:6×His (*Talaromyces emersonii*) (FIG. 7A), E5:6×His (*Thermobifida fusca*) (FIG. 7B), and CelZ:6×His (*Clostridium stercorarium*) (FIG. 7C) fused to various signal peptides. Anti-6×His antibodies were used to detect the fusion proteins. In each blot, "ladder" indicates the lane loaded with a molecular weight protein ladder; "control" indicates the lane loaded with *E. coli* whole cell lysates expressing His-tagged protein (positive control); lane assignments correspond to the signal peptide number cloned upstream of each cellulase as outlined in Table 3. In FIG. 7C, "empty vector" refers to overexpression of the same plasmid vector backbone that contains CelZ, but that lacks the CelZ coding sequence, and "CelZ-His" refers to expression of CelZ with the native, non-codon optimized *Clostridium stercorarium* signal peptide.

Figure 8:
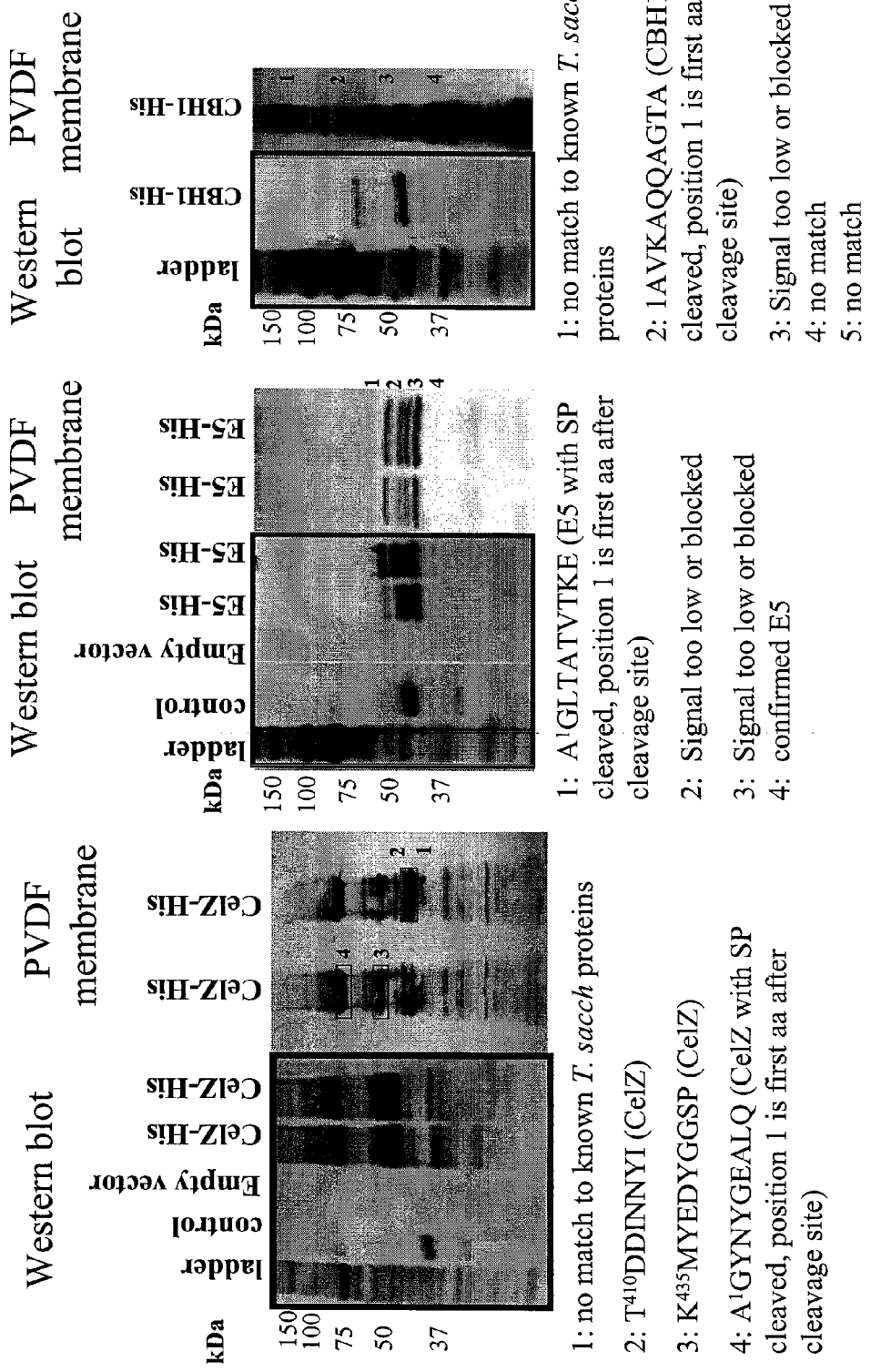

FIG. 8. Western blots and PVDF membranes showing proteolytic bands resulting from heterologous expression of cellulases in *T. sacch*. The numbered bands in the PVDF membranes were cut out and sequenced. The resulting sequences are shown below the corresponding Western and PVDF images.

FIG. 9. *T. emersonii* CBH1 expressed in *T. sacch* is enzymatically active. Heterologous CBH1 activity was measured using an in-gel MuLac assay (FIG. 9A), an Avicel conversion assay (FIG. 9B), and fermentation bottle experiments (FIG. 9C). In FIG. 9A, the Simply Blue staining (right panel) shows the total protein content measured in the MuLac assay, and the fluorescence (left panel) shows Cbh1 enzyme activity measured in the MuLac assay. In FIG. 9B, the height of the bars indicates the percent of Avicel converted by *T. sacch* over 24 and 48 hour time periods. In FIG. 9C, the height of the bars indicates the amounts of ethanol, cellobiose, glucose, and xylose produced in *T. sacch* fermentation experiments.

DETAILED DESCRIPTION OF THE INVENTION

Definitions

A "vector," e.g., a "plasmid" or "YAC" (yeast artificial chromosome) refers to an extrachromosomal element often carrying one or more genes that are not part of the central metabolism of the cell, and is usually in the form of a circular double-stranded DNA molecule. Such elements can be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. The plasmids or vectors of the present invention can be stable and self-replicating. The plasmids or vectors of the present invention can also be suicide vectors, or vectors that cannot replicate in the host cell. Such vectors are useful for forcing insertion of the nucleotide sequence into the host chromosome.

An "expression vector" is a vector that is capable of directing the expression of genes to which it is operably associated.

The term "heterologous" as used herein refers to an element of a vector, plasmid or host cell that is derived from a source other than the endogenous source. Thus, for example, a heterologous sequence could be a sequence that is derived from a different gene or plasmid from the same host, from a different strain of host cell, or from an organism of a different taxonomic group (e.g., different kingdom, phylum, class, order, family genus, or species, or any subgroup within one of these classifications). The term "heterologous" is also used synonymously herein with the term "exogenous."

The term "domain" as used herein refers to a part of a molecule or structure that shares common physical or chemical features, for example hydrophobic, polar, globular, helical domains or properties, e.g., a DNA binding domain or an ATP binding domain. Domains can be identified by their homology to conserved structural or functional motifs. Examples of cellobiohydrolase (CBH) domains include the catalytic domain (CD) and the cellulose binding domain (CBD).

A "nucleic acid," "polynucleotide," or "nucleic acid molecule" is a polymeric compound comprised of covalently linked subunits called nucleotides. Nucleic acid includes polyribonucleic acid (RNA) and polydeoxyribonucleic acid (DNA), both of which can be single-stranded or double-stranded. DNA includes cDNA, genomic DNA, synthetic DNA, and semi-synthetic DNA.

An "isolated nucleic acid molecule" or "isolated nucleic acid fragment" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences are described herein according to the normal convention of giving only the sequence in the 5' to 3' direction along the non-transcribed strand of DNA (i.e., the strand having a sequence homologous to the mRNA).

A "gene" refers to an assembly of nucleotides that encode a polypeptide, and includes cDNA and genomic DNA nucleic acids. "Gene" also refers to a nucleic acid fragment that expresses a specific protein, including intervening sequences (introns) between individual coding segments (exons), as well as regulatory sequences preceding (5' non-coding sequences) and following (3' non-coding sequences) the coding sequence. "Native gene" refers to a gene as found in nature with its own regulatory sequences.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified, e.g., in Sambrook, J., Fritsch, E. F. and Maniatis, T. MOLECULAR CLONING: A LABORATORY MANUAL, Second Edition, Cold Spring Harbor Laboratory Press, Cold Spring Harbor (1989), particularly Chapter 11 and Table 11.1 therein (hereinafter "Maniatis", entirely incorporated herein by reference). The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. For more stringent conditions, washes are performed at higher temperatures in which the washes are identical to those above except for the temperature of the final two 30 min washes in 0.2×SSC, 0.5% SDS are increased to 60° C. Another set of highly stringent conditions uses two final washes in 0.1×SSC, 0.1% SDS at 65° C. An additional set of highly stringent conditions are defined by hybridization at 0.1×SSC, 0.1% SDS, 65° C. and washed with 2×SSC, 0.1% SDS followed by 0.1×SSC, 0.1% SDS.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see, e.g., Maniatis at 9.50-9.51). For hybridizations with shorter nucleic acids, i.e., oligonucleotides, the position of mismatches becomes more important, and the length of the oligonucleotide determines its specificity (see, e.g., Maniatis, at 11.7-11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration can be adjusted as necessary according to factors such as length of the probe.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as determined by the match between strings of such sequences.

As known in the art, "similarity" between two polypeptides is determined by comparing the amino acid sequence and conserved amino acid substitutes thereto of the polypeptide to the sequence of a second polypeptide.

"Identity" and "similarity" can be readily calculated by known methods, including but not limited to those described in: *Computational Molecular Biology* (Lesk, A. M., ed.) Oxford University Press, NY (1988); *Biocomputing: Informatics and Genome Projects* (Smith, D. W., ed.) Academic Press, NY (1993); *Computer Analysis of Sequence Data, Part I* (Griffin, A. M., and Griffin, H. G., eds.) Humana Press, NJ (1994); *Sequence Analysis in Molecular Biology* (von Heinje, G., ed.) Academic Press (1987); and *Sequence Analysis Primer* (Gribskov, M. and Devereux, J., eds.) Stockton Press, NY (1991). Preferred methods to determine identity are designed to give the best match between the sequences tested. Methods to determine identity and similarity are codified in publicly available computer programs. Sequence alignments and percent identity calculations can be performed using the Megalign program of the LASERGENE bioinformatics computing suite (DNASTAR Inc., Madison, Wis.). Multiple alignments of the sequences disclosed herein were performed using the Clustal method of alignment (Higgins and Sharp (1989) CABIOS. 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

Suitable nucleic acid sequences or fragments thereof (isolated polynucleotides of the present invention) encode polypeptides that are at least about 70% to 75% identical to the amino acid sequences reported herein, at least about 80%, 85%, or 90% identical to the amino acid sequences reported herein, or at least about 95%, 96%, 97%, 98%, 99%, or 100% identical to the amino acid sequences reported herein. Suitable nucleic acid fragments are at least about 70%, 75%, or 80% identical to the nucleic acid sequences reported herein, at least about 80%, 85%, or 90% identical to the nucleic acid sequences reported herein, or at least about 95%, 96%, 97%, 98%, 99%, or 100% identical to the nucleic acid sequences reported herein. Suitable nucleic acid fragments not only have the above identities/similarities but typically encode a polypeptide having at least 50 amino acids, at least 100 amino acids, at least 150 amino acids, at least 200 amino acids, or at least 250 amino acids.

A DNA or RNA "coding region" is a DNA or RNA molecule which is transcribed and/or translated into a polypeptide in a cell in vitro or in vivo when placed under the control of appropriate regulatory sequences. "Suitable regulatory regions" refer to nucleic acid regions located upstream (5' non-coding sequences), within, or downstream (3' non-coding sequences) of a coding region, and which influence the transcription, RNA processing or stability, or translation of the associated coding region. Regulatory regions can include enhancers, operators, promoters, translation leader sequences, RNA processing sites, effector binding sites and stem-loop structures. The boundaries of the coding region are determined by a start codon at the 5' (amino) terminus and a translation stop codon at the 3' (carboxyl) terminus. A coding region can include, but is not limited to, prokaryotic regions, cDNA from mRNA, genomic DNA molecules, synthetic DNA molecules, or RNA molecules. If the coding region is intended for expression in a eukaryotic cell, a polyadenylation signal and transcription termination sequence will usually be located 3' to the coding region.

An "isoform" is a protein that has the same function as another protein but which is encoded by a different gene and can have small differences in its sequence.

A "paralogue" is a protein encoded by a gene related by duplication within a genome.

An "orthologue" is gene from a different species that has evolved from a common ancestral gene by speciation. Normally, orthologues retain the same function in the course of evolution as the ancestral gene.

"Open reading frame" is abbreviated ORF and means a length of nucleic acid, either DNA, cDNA or RNA, that comprises a translation start signal or initiation codon, such as an ATG or AUG, and a termination codon and can be potentially translated into a polypeptide sequence.

"Promoter" refers to a DNA fragment capable of controlling the expression of a coding sequence or functional RNA. In general, a coding region is located 3' to a promoter. Promoters can be derived in their entirety from a native gene, or be composed of different elements derived from different promoters found in nature, or even comprise synthetic DNA segments. It is understood by those skilled in the art that different promoters can direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths can have identical promoter activity. A promoter is generally bounded at its 3' terminus by the transcription initiation site and extends upstream (5' direction) to include the minimum number of bases or elements necessary to initiate transcription at levels detectable above background. Within the promoter will be found a transcription initiation site (conveniently defined for example, by mapping with nuclease S1), as well as protein binding domains (consensus sequences) responsible for the binding of RNA polymerase.

A coding region is "under the control" of transcriptional and translational control elements in a cell when RNA polymerase transcribes the coding region into mRNA, which is then translated into the protein encoded by the coding region.

"Transcriptional and translational control regions" are DNA regulatory regions, such as promoters, enhancers, terminators, and the like, that provide for the expression of a coding region in a host cell. In eukaryotic cells, polyadenylation signals are control regions.

The term "operably associated" refers to the association of nucleic acid sequences on a single nucleic acid fragment so that the function of one is affected by the other. For example, a promoter is operably associated with a coding region when it is capable of affecting the expression of that coding region (i.e., that the coding region is under the transcriptional control of the promoter). Coding regions can be operably associated to regulatory regions in sense or antisense orientation.

The term "expression," as used herein, refers to the transcription and stable accumulation of sense (mRNA) or antisense RNA derived from the nucleic acid fragment of the invention. Expression can also refer to translation of mRNA into a polypeptide.

Host Cells Expressing Heterologous Biomass Degrading Enzymes

In order to address the limitations of the previous systems, the present invention provides host cells expressing biomass degrading enzymes that can be effectively and efficiently utilized to produce fermentation products from cellulose. For example, the host cells can be used to produce ethanol, lactic acid, acetic acid or $CO_2$. In some embodiments, this host cells are used to produce ethanol. Host cells are genetically engineered (transduced or transformed or transfected) with the polynucleotides encoding heterologous biomass degrading enzymes which are described in more detail below. The polynucleotides encoding the biomass degrading enzymes can be introduced to the host cell on a vector of the invention, which can be, for example, a cloning vector or an expression vector comprising a sequence encoding a heterologous cellulase. The host cells can comprise polynucleotides of the invention as integrated copies or plasmid copies.

In particular, the host cells can be thermophilic gram-positive anaerobic bacteria. For example, in one embodiment, the host cell is a member of the genus *Thermoanaerobacterium*. The *Thermoanaerobacterium* can be, for example, *T. thermosulfurgenes*, *T. polysaccharolyticum* or *T. saccharolyticum*. In another particular embodiment, the host cell is a *Thermoanaerobacterium saccharolyticum* ("*T. sacch*") cell. In yet another embodiment, the host cell is a thermophilic anaerobe with 16s rRNA sequences that are similar to that of *T. sacch*. For example, the host cell can be an *Acetogenium kivui*, *Caldanaerobacter proteolyticus*, *Caldanaerobium fijiensis*, *Clostridium thermoamylolyticum*, *Clostridium thermocopriae*, *Clostridium thermosaccharolyticum*, *Clostridium uzonii*, *Desulfotomaculum thermobenzoicum*, *Garciaella petrolearia*, *Soehngenia saccharolytica*, *Thermoanaerobacter acetoethylicus*, *Thermoanaerobacter brockii*, *Thermoanaerobacter ethanolicus*, *Thermoanaerobacter finii*, *Thermoanaerobacter inferii*, *Thermoanaerobacter lacticus*, *Thermoanaerobacter pseudethanolicus*, *Thermoanaerobacter pseudethanolicus*, *Thermoanaerobacter siderophilus*, *Thermoanaerobacter subterraneus*, *Thermoanaerobacter sulfurigignens*, *Thermoanaerobacter sulfurophilus*, *Thermoanaerobacter tengcongensis*, *Thermoanaerobacter thermohydrosulfuricus*, *Thermoanaero-* bacter uzonensis strain, *Thermoanaerobacter wiegelii*, *Thermoanaerobium lactoethylicum*, or *Thermobacteroides acetoethylicus* cell.

In some embodiments of the present invention, the host cell is a modified thermophilic gram-positive anaerobic bacteria. Thermophilic gram-positive anaerobic bacteria can convert sugars into either lactic acid, acetic acid or ethanol, for example. Therefore, by decreasing the amount of lactic acid and/or acetic acid produced, the amount of ethanol produced under given conditions can be increased.

Therefore, the host cell can be altered to decrease the production of lactic acid. For example, the host cell can comprise a mutation or deletion in a gene that is necessary for producing lactic acid as a fermentation product. Thus, the host cell can be, for example, a host cell wherein lactate dehydrogenase activity is decreased or eliminated. The host cell can, for example, comprise a mutation or deletion in a lactate dehydrogenase coding or regulatory sequence. The host cell can also be altered to decrease the production of acetic acid. For example, the host cell can comprise a mutation or deletion in a gene that is necessary for producing acetic acid as a fermentation product. Thus, the host cell can be, for example, a host cell wherein phosphotransacetylase activity is decreased or eliminated. The host cell can, for example, comprise a mutation or deletion in a phosphotransacetylase coding or regulatory sequence. The host cell can also be, for example, a host cell wherein acetate kinase activity is decreased or eliminated. The host cell can, for example, comprise a mutation or deletion in a acetate kinase coding or regulatory sequence.

Examples of such host cells are described in International Patent Application Number PCT/US2006/042442 (filed Oct. 31, 2006) and PCT/US2007/016947 (filed May 1, 2007), which are herein incorporated by reference in their entireties. The host cell can be, for example, M0355 (described herein) or ALK1 or ALK2 (described in PCT/US2006/042442 and PCT/US2007/016947).

Lactic acid and/or acetic acid production can also be reduced or eliminated using methods other than genetic modification. For example, the host cells can be cultured under conditions that decrease lactic acid and/or acetic acid production. The host cells can, for example, be contacted with substances that inhibit lactic acid and/or acetic acid production pathways. The molecules can be, for example, small molecules, peptide inhibitors or interfering RNAs.

The host cell can also be a cell in which foreign DNA has been removed. For example, the host cell can be a cell that does not comprise heterologous markers, such as antibiotic markers. The removal of foreign DNA can be accomplished using techniques known in the art. For example, methods of counterselection, such as those described in Reyrat et al., *Infection and Immunity* 66:4011-4017 (1998), can be used to remove transgenic or heterologous sequences or plasmids. The host cell can be a cell that does not comprise any heterologous DNA other than the DNA comprising a sequence encoding the heterologous biomass degrading enzyme. Therefore, the host cell be a cell comprising a nucleic acid comprising a polynucleotide which encodes a heterologous biomass degrading enzyme, wherein the nucleic acid comprising a polynucleotide which encodes a biomass degrading enzyme is the only heterologous DNA in the cell.

By improving biomass degrading enzyme expression and secretion, cellulose hydrolysis can be enhanced. Thus, the host cells can also be modified to improve protein expression and/or protein secretion. For example, protease sequences may be removed. Proteases are enzymes that catalyze the breakdown of proteins into smaller peptides or amino acids. Proteases include endopeptidases and exopeptidases. A protease gene can, for example, be removed using chromosomal integration techniques in which an unrelated sequence (e.g. an antibiotic marker) replaces all or a portion of the wild-type protease-encoding sequence in its normal chromosomal location. In particular, the protease genes encoding the proteins shown in Table 1 below could be removed either individually or in combination.

TABLE 1

Exemplary Proteases/Peptidases That Can Be Removed According to the Present Invention.

| Description | Sequence |
|---|---|
| Trypsin-like serine protease typically periplasmic contain C-terminal PDZ domain peptidase S1 and S6 chymotrypsin | MQNGDNRNVKRPSYLTTVIVIAVITSLIFTYIAPKFLWGKVIPLPYTNTAP LKKEVIIPKAEPSTIAEAVAKKDTQAVVGISSIEYERQYYILEKQVEGVGS GFIVDKNGYIITNNHVASPESKKLTIYLSDGSTLPGKVLWSDSTLDLSVVK INAKNLPTIPLGDSDKVQVGQTVIAIGNPLGLRFERTVTSGIISALNRSLPL EENNKQKIMEDLIQTDASINPGNSGGPLVDAQGNAIGINTAKVTTAEGLG FAIPINIVKPIIKKVIATGTFKAPYLGIVGYDREIASYINADVVIAEGIYVAD IDPAGPAKKAGIKKGYILLEVDGKPVDTMVQLKTVIYSRNIGDKVSVKY RTLTGNIGMTTITLGK (SEQ ID NO: 164) |
| Trypsin-like serine protease typically periplasmic contain C-terminal PDZ domain 2-alkenal reductase | MDIENEQTKRLNENDMENLNENADDVVTENFTNNDLNKIHKVSMTNDY QDKNDEENAKNDLENSKKSVGKIIKRFRRRMLASFIVVALIAALIGGGIV GGIMVYTNSGQKTQVINRYLPLSSNNSNSNLIVNIAKIVSPSVVGIDTSAT YSNGFRSAFVSEGSGSGIIIDSQGYIVTNYHVIEGASTITVSLSDGRKFSAQ LIGKDSNTDLAVLKINATNLTAAKLGDSSKLEVGDLAVAIGNPLGESFAG TVTAGIISGLNRNLQSDYGPVNLIQTDAAINPGNSGGPLVNSNGEVVGITS VKLTSTDDNSTQSSFGMFQSQSTPVEGMGFAIPINEAKPIINELIKHGYVE RPMMGVSVQEVTQQDAAQYNIPVGLYIAQVQQGSGADEAGLQAGDVIT AVDGTKVQTFDALQSIISKHKVGDTITVTFWRNGRTMSTKVKLMSSSNA Q (SEQ ID NO: 165) |
| Trypsin-like serine protease typically | MDFENEQNKNIGENEIDNFRTDDALGSDDIKGENIDDTQEIKATYGAEES GTYTNPRVEFRSNKKSLGKMVKRFRRRMLVSFVAVALIAALIGGGTVAG IMKYTNLGQQTQVINRYLPLSSSDNNNYSLIANIAKIVSPSVVGIDTSVSY SNGFGSALVPEGSGSGIIIDSQGYIVTNNHVVDGASKITVNLSDGRKFPAQ |

TABLE 1-continued

Exemplary Proteases/Peptidases That Can Be Removed According to the Present Invention.

| Description | Sequence |
|---|---|
| periplasmic contain C-terminal PDZ domain 2-alkenal reductase | LIGKDSKTDLAVLKINATNLIPAKLGDSSKLEVGDLAVAIGNPLGESFAGT VTAGIISGLNRNLQSDYGPVNLIQTDAAINPGNSGGPLVNSNGEVVGITSV KLTSTGGSDTQDPFGMFQSQSTPVEGMGFAIPINEAKPIIDDLIKHGYVER PMMGVSVQEVTQQDAAQYNIPVGLYIAQVQQGSGADEAGLQAGDVITA VDGTKVQTFDALQSIISKHKVGDTITVTFWRNGRTMSTKVKLMSSSNAQ (SEQ ID NO: 166) |
| Trypsin-like serine protease typically periplasmic contain C-terminal PDZ domain 2-alkenal reductase | MEFNNGFENYRLPDVNPKNDKKSLGKMVKRYRRKMFMSFVAVALVAA LAGGALGAGIVKYADTGNTQVVNRYLPLSSDNNNFNLITNIVKAVSPSV VGIDTYISGYGAYGYGGNSYVEEGSGSGIIIDSEGHIVTNDHVVEGASKIT VNLSDGRKFPAQLVGKDSRTDLAVLKINATNLTPAKLGDSSKLEVGELA VAIGNPLGDSFAGTATAGIISGLNRNLQSDYGPVNLIQTDAAINPGNSGP LVNSVGEVIGITSIKLTSTGGSSSGDPFGLFQSQSVPLEGMGFAIPINEAKPI IEELIRKGYVERPVIGVSVQQITQQQANQYNIPVGLYIAQVQQGSGADAA GLQAGDIITAVDGTNVTTFNQLENILNNHKIGDVISVTVWRNGQTLTVNV KLSGSNGQ (SEQ ID NO: 167) |
| Subtilisin-like serine protease peptidase S8 and S53 subtilisin kexin sedolisin | MDIISALILSSVIQSLYPKSKIDSRLLRKASIYRSECVSAIVYSNLPYDALKK KIESIGGTIKYELPIINGWAVNIPCNKLNIIAKNKGIKFIAEDSTVKTQLNIA TQEIKSREANDHGYTGKGVTIAFLDTGIYPHPDFTKPKNRIIAFHDIVNGK KSPYDDNGHGTHVAGDAASSGYLSDGKYKGVAPEANIVSVKVLDSRGS GSTSDILSGMQWILDNKDKYNIRIVSLSIGETPSLPPFLDPLVKGVDRLWR SGLVVVVAAGNSGPSMNSITSPGNSMNVITVGAVDDKRTVDTSDDEIAN FSGRGSAFLPKPDVVAPGVKIVSAASGNVPIGTDDNILLNKSYRTASGTS MATPIVAGAAALLLEKNPSLTNYQIKNILKSTTTNVDHYRYYSQGYGMI NVEMALKKV (SEQ ID NO: 168) |

Host cells can also be cultured with exogenously added protease inhibitors in order to decrease protease activity.

Alternatively, or in addition to removing protease genes from host cells, chaperone proteins or components of the secretion system can be over-expressed in the host cells to improve protein expression and/or protein secretion. Chaperone proteins are proteins that assist in three-dimensional folding and unfolding or assembly and disassembly of macromolecular structures, including proteins, without being part of the final macromolecular structures. Chaperones can prevent unfavorable interactions of a substrate (e.g. a protein) and can guide the substrate (e.g. a protein) into a productive export and folding pathway. The chaperone proteins or components of the secretion system can be overexpressed, for example, by transforming host cells with a plasmid comprising a nucleotide sequence encoding the chaperone protein or the component of the secretion system. The overexpressed chaperones can be endogenous chaperones or heterologous chaperones. For example, *E. coli* HSP60/GroEL, HSP60/GroES, HSP70/DnaK, DnaJ, GrpE, HSP90/HtpG, HSP100/Clp family, and/or peptidyl prolyl isomerase Trigger Factor can be overexpressed. In addition, a secretion-specific chaperone from *Bacillus subtilis* such as Ffh, HBsu, FtsY, CsaA and/or FlhF can be overexpressed. Chaperone proteins can be overexpressed either individually or in combination. Proteins that are important for disulfide bond formation can be overexpressed. For example, *Bacillus subtilis* BdbA, BdbB, BdbC, and/or BdbD can be overexpressed. *E. coli* DsbA, B, C, D, and/or G can also be overexpressed. Proteins that are important in Gram positive SEC-mediated protein secretion such as SecA, SecY, SecE, SecG, SecDF can be overexpressed, and proteins important in extracytoplasmic folding such as *Bacillus subtilis* PrsA can be overexpressed.

Other mechanisms of improving expression and secretion of heterologous cellulases include expression through non-sec mediated mechanisms such as TAT-mediated transport, ATP-binding cassette (ABC) transporters and/or pseudopilin/pilin export.

In some embodiments, the heterologous biomass degrading enzyme is expressed without a tag (e.g. a purification or reporter tag such as HA, His, FLAG) that can interfere with successful folding and/or translocation of the heterologous biomass degrading enzyme.

Additionally strains that have been altered to create a chemostat strain that can be selected in rich medium with inhibitor cocktails can be used. Auxostat strains that are selected on minimal medium can also be used. In some embodiments, the strains are derived from, for example *T. sacch* or MO355, and altered to improve characteristics for large-scale production of fuels or chemicals from lignocellulosic biomass. These characteristics include faster growth rates, the ability to grow on inexpensive media, the ability to use a wider array of nutrients, and tolerance to ethanol, solvents, oxygen, temperature changes, pH changes, high or low nutrient levels, or inhibitory substances produced from pretreatment of lignocellulosic biomass. Methods to introduce these characteristics include classical mutagenesis and screening or selection, directed genetic engineering, extended propagation by serial transfer or continuous culture, or a combination of those approaches.

In some embodiments of the present invention the thermophilic gram-positive anaerobic bacteria can grow at temperatures above about 40° C., about 55° C., about 50° C., about 55° C., about 60° C., about 65° C., about 70° C., about 75° C., or about 80° C. In some embodiments of the present invention the thermophilic gram-positive anaerobic bacteria can produce ethanol, or another fermentation product, from cellulose at temperatures above about 40° C., about 45° C., about 50° C., about 55° C., about 60° C., about 65° C., about 70° C., about 75° C., or about 80° C.

In some embodiments of the present invention, the thermophilic gram-positive anaerobic bacteria can grow at temperatures from about 40° C. to 90° C., about 40° C. to 80° C., about 40° C. to 75° C., about 40° C. to 70° C., about 40° C. to 65° C., about 40° C. to 60° C., or about 40° C. to 55° C. In some embodiments of the present invention, the thermophilic gram-positive anaerobic bacteria can grow at temperatures from about 45° C. to 90° C., about 45° C. to 45° C., about 45° C. to 75° C., about 45° C. to 70° C., about 45° C. to 65° C., about 45° C. to 60° C., or about 45° C. to 55° C. In some embodiments of the present invention, the thermophilic gram-positive anaerobic bacteria can grow at temperatures from about 50° C. to 50° C., about 50° C. to 80° C., about 50° C. to 75° C., about 50° C. to 70° C., about 50° C. to 65° C., about 50° C. to 60° C., or about 50° C. to 55° C. In some embodiments of the present invention, the thermophilic gram-positive anaerobic bacteria can grow at temperatures from about 55° C. to 90° C., about 55° C. to 80° C., about 55° C. to 75° C., about 55° C. to 70° C., about 55° C. to 65° C., or about 55° C. to 60° C.

In certain aspects, the present invention relates to host cells containing the polynucleotide constructs described below. The host cells can express one or more heterologous biomass degrading enzyme polypeptides. In some embodiments, the host cell comprises a combination of polynucleotides that encode heterologous biomass degrading enzymes or fragments, variants or derivatives thereof. The host cell can, for example, comprise multiple copies of the same nucleic acid sequence, for example, to increase expression levels, or the host cell can comprise a combination of unique polynucleotides. In other embodiments, the host cell comprises a single polynucleotide that encodes a heterologous biomass degrading enzyme or a fragment, variant or derivative thereof.

Introduction of a polynucleotide encoding biomass degrading enzymes into a host cell can be done by methods known in the art. Introduction of polynucleotides encoding heterologous biomass degrading enzymes into host cells, can be effected, for example, by lithium acetate transformation, spheroplast transformation, or transformation by electroporation, as described in *Current Protocols in Molecular Biology*, 13.7.1-13.7.10. Introduction of the construct in other host cells can be effected, for example, by calcium phosphate transfection, DEAE-Dextran mediated transfection, or electroporation. (Davis, L., et al., *Basic Methods in Molecular Biology*, (1986)).

The transformed host cells or cell cultures, as described above, can be examined for biomass degrading enzyme protein content. For the use of secreted heterologous biomass degrading enzymes, protein content can be determined by analyzing the host (e.g., bacteria) cell supernatants. In certain embodiments, high molecular weight material can be recovered from the cell supernatant either by acetone precipitation or by buffering the samples with disposable de-salting cartridges. Proteins, including tethered heterologous biomass degrading enzymes, can also be recovered and purified from recombinant cell cultures by methods including spheroplast preparation and lysis, cell disruption using glass beads, and cell disruption using liquid nitrogen for example. Additional protein purification methods include trichloroacetic acid, ammonium sulfate or ethanol precipitation, acid extraction, anion or cation exchange chromatography, phosphocellulose chromatography, hydrophobic interaction chromatography, affinity chromatography, hydroxylapatite chromatography, gel filtration, and lectin chromatography. Protein refolding steps can be used, as necessary, in completing configuration of the mature protein. Finally, high performance liquid chromatography (HPLC) can be employed for final purification steps.

Protein analysis methods include methods such as the traditional Lowry method, the bicinchoninic acid protein assay reagent (Pierce) or the protein assay method according to BioRad's manufacturer's protocol. Using such methods, the protein content of saccharolytic enzymes can be estimated. Additionally, to accurately measure protein concentration a heterologous biomass degrading enzyme can be expressed with a tag, for example a His-tag or HA-tag and purified by standard methods using, for example, antibodies against the tag, a standard nickel resin purification technique or similar approach.

The transformed host cells or cell cultures, as described above, can be further analyzed for hydrolysis of cellulose (e.g., by a sugar detection assay), for a particular type of biomass degrading enzyme activity, for example for cellulase activity (e.g., by measuring the individual endoglucanase, cellobiohydrolase or β-glucosidase activity) or for total cellulase activity. Endoglucanase activity can be determined, for example, by measuring an increase of reducing ends in an endoglucanase specific CMC substrate. Cellobiohydrolase activity can be measured, for example, by using insoluble cellulosic substrates such as the amorphous substrate phosphoric acid swollen cellulose (PASC) or microcrystalline cellulose (Avicel) and determining the extent of the substrate's hydrolysis. β-glucosidase activity can be measured by a variety of assays, e.g., using cellobiose.

A total cellulase activity, which includes the activity of endoglucanase, cellobiohydrolase and β-glucosidase, can hydrolyze crystalline cellulose synergistically. Total cellulase activity can thus be measured using insoluble substrates including pure cellulosic substrates such as Whatman No. 1 filter paper, cotton linter, microcrystalline cellulose, bacterial cellulose, algal cellulose, and cellulose-containing substrates such as dyed cellulose, alpha-cellulose or pretreated lignocellulose. Specific activity of cellulases can also be detected by methods known to one of ordinary skill in the art, such as by the Avicel assay (described supra) that would be normalized by protein (cellulase) concentration measured for the sample.

In some embodiments, the host cell can grow on crystalline cellulose. For example, in some embodiments, the host cell can grow on Avicel. In some particular embodiments, the host cell can grow on crystalline cellulose or Avicel more efficiently than an untransformed cell. In another particular embodiment, the host cell can grow on crystalline cellulose or Avicel more efficiently than wild-type *T. sacch*.

In some embodiments, the host cell a particular activity on a substrate. The substrate can be, for example, Avicel, carboxymethylcellulose (CMC), or acid-swollen cellulose. The particular activity of the host cell on the substrate can be, for example, at least about 1 U/mg, at least about 2 U/mg, at least about 3 U/mg, at least about 4 U/mg, at least about 5 U/mg, at least about 6 U/mg, at least about 7 U/mg, at least about 8 U/mg, at least about 9 U/mg, at least about 10 U/mg, at least about 15 U/mg, at least about 20 U/mg, at least about 25 U/mg, at least about 30 U/mg, at least about 35 U/mg, at least about 40 U/mg, at least about 50 U/mg, at least about 75 U/mg, or at least about 100 U/mg cellulase activity.

In some embodiments, the host cell has at least about 1 U/mg, at least about 2 U/mg, at least about 3 U/mg, at least about 4 U/mg, at least about 5 U/mg, at least about 6 U/mg, at least about 7 U/mg, at least about 8 U/mg, at least about 9 U/mg, at least about 10 U/mg, at least about 15 U/mg, at least about 20 U/mg, at least about 25 U/mg, at least about 30 U/mg, at least about 35 U/mg, at least about 40 U/mg, at least about 50 U/mg, at least about 75 U/mg, or at least about 100 U/mg endoglucanase activity.

In some embodiments, the host cell has at least about 1 U/mg, at least about 2 U/mg, at least about 3 U/mg, at least about 4 U/mg, at least about 5 U/mg, at least about 6 U/mg, at least about 7 U/mg, at least about 8 U/mg, at least about 9

U/mg, at least about 10 U/mg, at least about 15 U/mg, at least about 20 U/mg, at least about 25 U/mg, at least about 30 U/mg, at least about 35 U/mg, at least about 40 U/mg, at least about 50 U/mg, at least about 75 U/mg, or at least about 100 U/mg exoglucanase activity.

In some embodiments, the host cell has at least about 1 U/mg, at least about 2 U/mg, at least about 3 U/mg, at least about 4 U/mg, at least about 5 U/mg, at least about 6 U/mg, at least about 7 U/mg, at least about 8 U/mg, at least about 9 U/mg, at least about 10 U/mg, at least about 15 U/mg, at least about 20 U/mg, at least about 25 U/mg, at least about 30 U/mg, at least about 35 U/mg, at least about 40 U/mg, at least about 50 U/mg, at least about 75 U/mg, or at least about 100 U/mg cellobiohydrolase activity.

One aspect of the invention is thus related to the efficient production of biomass degrading enzymes to aid in the digestion of cellulose and generation of ethanol or another useful fermentation product. A biomass degrading enzyme can be, for example, any enzyme involved in cellulase digestion, metabolism and/or hydrolysis, including an endoglucanase, exoglucanase, or β-glucosidase.

In additional embodiments, the transformed host cells or cell cultures are assayed for production of a useful fermentation product such as ethanol. Ethanol production can be measured by techniques known to one or ordinary skill in the art e.g. by a standard HPLC refractive index method.

*T. sacch* host cells can also be used to produce enzymes that can be purified and used in subsequent applications. The methods comprise transforming a *T. sacch* host cell with a sequence encoding a heterologous enzyme, culturing the transformed host cell under conditions suitable for protein expression and purifying the enzyme.

Biomass Degrading Enzymes

Biomass degrading enzymes can be heterologously expressed in *T. sacch* and other thermophilic anaerobic bacterial host cell. According to the present invention, biomass degrading enzymes are proteins that catalyze or enhance the breakdown of biological matter into simpler compounds. The largest component of plant biomass is cellulose, followed by hemicellulose and lignin. Cellulose is broken down by hydrolysis, catalyzed by cellulase enzymes. Cellulases can occur as individual enzymes or large multi-enzyme complexes. Cellulose can form tightly packed crystalline structures that are recalcitrant to enzymatic hydrolysis, and a wide variety of proteins exist in nature that act in different ways to break it down. For example, some enzymes show a high degree of endoglucanase activity, hydrolyzing bonds in the middle of cellulose chains. Others show a high degree of exoglucanase activity, releasing mono- or disaccharides from the ends of cellulose chains. Some are highly active on crystalline cellulose while others are most active on oligomeric chains of glucose. These proteins often consist of different functional modules or domains, often with glycoside hydrolase or carbohydrate binding activity. Based on amino acid sequence and protein structure, known glycoside hydrolases have been organized into 113 different families, and carbohydrate binding domains have been organized into 52 families (http://www.cazy.org; Cantarel et al. *Nucleic Acids Res.* Volume 37: D233-D238 (2008), which is herein incorporated by reference in its entirety). Changing just a few amino acids can alter the substrate specificity of a protein, so these families sometimes contain proteins with different specificities and functions.

The breakdown of cellulose can be catalyzed or enhanced by the action of enzymes other than glycoside hydrolases. These include swollenin and expansins, which may disrupt intermolecular hydrogen bonding without hydrolysis.

Enzymes that act on hemicellulose or lignin can also enhance the degradation of cellulose by increasing the accessibility of the cellulose fibers. Hemicellulose is more complex than cellulose, but is not crystalline. It contains predominantly xylose, but also the sugars arabinose, galactose, and mannose. Since these component sugars are polymerized in a variety of combinations and linkages, hemicellulose is very diverse. Enzymes that break down hemicellulose include xylanases, xylosidases, xyloglucanases, mannanases, mannosidases, galactanases, galactosidases, arabinases or arabinofuranosidases. Enzymes that degrade lignin and may enhance the activity of other biomass degrading enzymes include lignin peroxidase, some cellobiose dehydrogenases, and aryl alcohol oxidase.

Thus, according to the present invention, biomass degrading enzymes include, for example, cellulases, endoglucanases, exogluconases, glucoside hydrolases, xylanases, xylosidases, xyloglucanases, mannanases, mannosidases, galactanases, galactosidases, arabinases, arabinofuranosidases, lignin peroxidase, some cellobiose dehydrogenases, aryl alcohol oxidase proteinases, nucleases and carbohydrate active enzymes such as amylases, chitosanases, fructosidases or glycosyltransfereases. In some embodiments of the present invention, the biomass degarding enzyme is a cellulase.

According to the present invention the expression of heterologous biomass degrading enzymes in a host cell can be used advantageously to produce ethanol from cellulosic sources. The expression of heterologous biomass degrading enzymes in a host cell can be used advantageously to produce acetic acid, lactic acid or $CO_2$ from cellulosic sources. Biomass degrading enzymes from a variety of sources can be heterologously expressed to successfully increase efficiency of fermentation product (e.g. ethanol) production. For example, the biomass degrading enzymes can be from fungi (including yeast), bacteria, plant, protozoan or termite sources. Biomass degrading enzymes from termite sources include biomass degrading enzymes encoded by the termite genome as well as biomass degrading enzymes encoded by the microorganisms that reside in the termite gut. In some embodiments, the biomass degrading enzyme is not a biomass degrading enzyme from an anaerobic bacteria. In other embodiments, the biomass degrading enzyme is a biomass degrading enzyme derived from an organism selected from the group consisting of *Thermobifida fusca, Caldocellum saccharolyticum, Clostridium stercorarium, Eubacterium cellulosolvens, Cellulomonas fimi, Acidothermus cellulolyticus, Butyrivibrio fibrisolvens, Anaerocellum thermophilum, Trichoderma reesei, Coptotermes formosanus, Nasutitermes takasagoensis, Talaromyces emersonii, Neosartorya fischeri* and *Caldicellulosiruptor kristjanssonii*.

In some embodiments of the invention, multiple biomass degrading enzymes from a single organism are co-expressed in the same host cell. In some embodiments of the invention, multiple biomass degrading enzymes from different organisms are co-expressed in the same host cell. In particular, biomass degrading enzymes from two, three, four, five, six, seven, eight, nine or more organisms can be co-expressed in the same host cell.

In some embodiments of the present invention, the biomass degrading enzyme is a cellulase. Cellulases of the present invention include both endoglucanases or exoglucanases. The cellulases can be, for example, endoglucanases, β-glucosidases or cellobiohydrolases. In certain embodiments of the invention, the endoglucanase(s) can be an endoglucanase I or an endoglucanase II isoform, paralogue or orthologue. In certain embodiments, the β-glucosidase is a β-glucosidase I or a β-glucosidase II isoform, paralogue or orthologue. In certain embodiments of the invention, the cellobiohydrolase (s) can be a cellobiohydrolase I and/or a cellobiohydrolase II isoform, paralogue or orthologue.

In certain embodiments, the cellulase comprises an amino acid sequence that is at least about 70, about 80, about 90, about 95, about 96, about 97, about 98, about 99, or 100% identical to an amino acid sequence selected from SEQ ID NOs:108-148, (as shown below in Table 2). As a practical matter, whether any polypeptide is at least 70%, 80%, 85%, 90%, 95%, 96%, 97%, 98%, 99% or 100% identical to a polypeptide of the present invention can be determined conventionally using known computer programs. Methods for determining percent identity, as discussed in more detail below in relation to polynucleotide identity, are also relevant for evaluating polypeptide sequence identity.

Some embodiments of the invention encompass a polypeptide comprising at least 10, 20, 30, 40, 50, 60, 70, 80, 90, 100, 200, 300, 400, or 500 or more consecutive amino acids of any of SEQ ID NOs:108-148, or domains, fragments, variants, or derivatives thereof.

TABLE 2

Exemplary Biomass Degrading Enzymes That Can Be Used According to the Present Invention

| Organism and Protein (Gene) | Codon-Optimized DNA Sequence | Accession Number and Amino Acid Sequence |
|---|---|---|
| *Thermobifida fusca* E1 (gene: celA) | ATGCTTAGAAGACCTAGATCAAGATCACCTCTTGTAGCACTTACAGCAGC AACATGCAGAGTAGCACTTGGAGGAACAGCAGTACCTGCACAAGCAGATG AAGTAAATCAAATAAGAAATGGAGATTTTTCATCAGGAACAGCACCTTGG TGGGGAACAGAAAATATACAACTTAATGTAACAGATGGAATGCTTTGCGT AGATGTACCTGGAGGAACAGTAAATCCTTGGGATGTAATAATAGGACAAG ATGATATACCTCTTATAGAAGGAGAATCATATGCATTTTCATTTACAGCAT CATCAACAGTACCTGTATCAATAAGAGCACTTGTACAAGAACCTGTAGAA CCTTGGACAACACAAATGGATGAAAGAGCACTTCTTGGACCTGAAGCAGA AACATATGAATTTGTATTTACATCAAATGTAGATTGGGATGATGCACAAGT AGCATTTCAAATAGGAGGATCAGATGAACCTTGGACATTTTGCCTTGATGA TGTAGCACTTCTTGGAAGAGCAGAACCTCCTGTATATGAACCTGATACAG GACCTAGAGTAAGAGTAAATCAAGTAGGATATCTTCCTCATGGACCTAAA AAAGCAACAGTAGTAACAGATGCAACATCAGCACTTACATGGGAACTTGC AGATGCAGATGGAAATGTAGTAGCATCAGGACAAACAAAACCTCATGGA GCAGATTCATCATCAGGACTTAATGTACATACAGTAGATTTTTCATCATAT ACAACAAAAGGATCAGATTATACACTTACAGTAGATGGAGAAACATCATA TCCTTTTGATATAGATGAATCAGTATATGAAGAACTTAGAGTAGATGCACT TTCATTTTATTATCCTCAAAGATCAGGAATAGAAATACTTGATTCAATAGC ACCTGGATATGGAAGACCTGCAGGACATATAGGAGTACCTCCTAATCAAG GAGATACAGATGTACCTTGCGCACCTGGAACATGCGATTATTCACTTGATG TATCAGGAGGATGGTATGATGCAGGAGATCATGGAAAATATGTAGTAAAT GGAGGAATATCAGTACATCAAATAATGTCAATATATGAAAGATCACAACT TGCAGATACAGCACAACCTGATAAACTTGCAGATTCAACACTTAGACTTCC TGAAACAGGAAATGGAGTACCTGATGTACTTGATGAAGCAAGATGGGAAA TGGAATTTCTTCTTAAAATGCAAGTACCTGAAGGAGAACCTCTTGCAGGA ATGGCACATCATAAAATACATGATGAACAATGGACAGGACTTCCTCTTCTT CCTTCAGCAGATCCTCAACCTAGATATCTTCAACCTCCTTCAACAGCAGCA ACACTTAATCTTGCAGCAACAGCAGCACAATGCGCAAGAGTATTTGAACC TTTTGATGAAGATTTTGCAGCAGAATGCCTTGCAGCAGCAGAAACAGCAT GGGATGCAGCAAAAGCAAATCCTAATATATATGCACCTGCATTTGGAGAA GGAGGAGGACCTTTATAATGATAATAATGTAACAGATGAATTTTATTGGGC AGCAGCAGAACTTTTTCTTACAACAGGAAAAGAAGAATATAGAGATGCAG TAACATCATCACCTCTTCATACAGATGATGAAGAAGTATTTAGAGATGGA GCATTTGATTGGGGATGGACAGCAGCACTTGCAAGACTTCAACTTGCAAC AATACCTAATGATCTTGCAGATAGAGATAGAGTAAGACAATCAGTAGTAG ATGCAGCAGATATGTATCTTGCAAATGTAGAAACATCACCTTGGGGACTT GCATATAAACCTAATAATGGAGTATTTGTATGGGGATCAAATTCAGCAGT ACTTAATAATATGGTAATACTTGCAGTAGCATTTGATCTTACAGGAGATAC AAAATATAGAGATGGAGTACTTGAAGGAATGGATTATATATTTGGAAGAA ATGCACTTAATCAATCATATGTAACAGGATATGGAGATAAAGATTCAAGA AATCAACATTCAAGATGGTATGCACATCAACTTGATCCTAGACTTCCTAAT CCTCCTAAAGGAACACTTGCAGGAGGACCTAATTCAGATTCAACAACATG GGATCCTGTAGCACAATCAAAACTTACAGGATGCGCACCTCAAATGTGCT ATATAGATCATATAGAATCATGGTCAACAAATGAACTTACAATAAATTGG AATGCACCTCTTTCATGGATAGCATCATTTATAGCAGATCAAGATGATGCA GGAGAACCTGGAGGAGAAGAACCTGGACCTGGAGATGATGAAACACCTC CTTCAAAACCTGGAAATCTTAAAGCATCAGATATAACAGCAACATCAGCA ACACTTACATGGGATGCATCAACAGATAATGTAGGAGTAGTAGGATATAA AGTATCACTTGTAAGAGATGGAGATGCAGAAGAAGTAGGAACAACAGCA CAAACATCATATACACTTACAGGACTTTCAGCAGATCAAGAATATACAGT ACAAGTAGTAGCATATGATGCAGCAGGAAATCTTTCAACACCTGCAACAG TAACATTTACAACAGAAAAAGAAGATGAAACACCTACACCTTCAGCATCA TGCGCAGTAACATATCAAACAAATGATTGGCCTGGAGGATTTACAGCATC AGTAACACTTACAAATACAGGATCAACACCTTGGGATTCATGGGAACTTA GATTTACATTTCCTTCAGGACAAACAGTATCACATGGATGGTCAGCAAATT GGCAACAATCAGGATCAGATGTAACAGCAACATCACTTCCTTGGAATGGA TCAGTACCTCCTGGAGGAGGATCAGTAAATATAGGATTTAATGGAACATG GGGAGGATCAAATACAAAACCTGAAAAATTTACAGTAAATGGAGCAGTAT GCTCAATAGGA (SEQ ID NO: 77) | AAC06387<br>MLRRPRSRSPLVALTAATCRVA<br>LGGTAVPAQADEVNQIRNGDFS<br>SGTAPWWGTENIQLNVTDGML<br>CVDVPGGTVNPWDVIIGQDDIPL<br>IEGESYAFSFTASSTVPVSIRALV<br>QEPVEPWTTQMDERALLGPEAE<br>TYEFVFTSNVDWDDAQVAFQIG<br>GSDEPWTFCLDDVALLGRAEPP<br>VYEPDTGPRVRVNQVGYLPHGP<br>KKATVVTDATSALTWELADAD<br>GNVVASGQTKPHGADSSSGLNV<br>HTVDFSSYTTKGSDYTLTVDGE<br>TSYPFDIDESVYEELRVDALSFY<br>YPQRSGIEILDSIAPGYGRPAGHI<br>GVPPNQGDTDVPCAPGTCDYSL<br>DVSGGWYDAGDHGKYVVNGGI<br>SVHQIMSIYERSQLADTAQPDKL<br>ADSTLRLPETGNGVPDVLDEAR<br>WEMEFLLKMQVPEGEPLAGMA<br>HHKIHDEQWTGLPLLPSADPQP<br>RYLQPPSTAATLNLAATAAQCA<br>RVFEPFDEDFAAECLAAAETAW<br>DAAKANPNIYAPAFGEGGGPYN<br>DNNVTDEFYWAAAELFLTTGKE<br>EYRDAVTSSPLHTDDEEVFRDG<br>AFDWGWTAAALARLQLATIPNDL<br>ADRDRVRQSVVDAADMYLANV<br>ETSPWGLAYKPNNGVFVWGSN<br>SAVLNNMVILAVAFDLTGDTKY<br>RDGVLEGMDYIFGRNALNQSYV<br>TGYGDKDSRNQHSRWYAHQLD<br>PRLPNPPKGTLAGGPNSDSTTW<br>DPVAQSKLTGCAPQMCYIDHIES<br>WSTNELTINWNAPLSWIASFIAD<br>QDDAGEPGGEEPGPGDDETPPS<br>KPGNLKASDITATSATLTWDAS<br>TDNVGVVGYKVSLVRDGDAEE<br>VGTTAQTSYTLTGLSADQEYTV<br>QVVAYDAAGNLSTPATVTFTTE<br>KEDETPTPSASCAVTYQTNDWP<br>GGFTASVTLTNTGSTPWDSWEL<br>RFTFPSGQTVSHGWSANWQQSG<br>SDVTATSLPWNGSVPPGGGSVNI<br>GFNGTWGGSNTKPEKFTVNGA<br>VCSIG (SEQ ID NO: 108) |

TABLE 2-continued

Exemplary Biomass Degrading Enzymes That Can Be Used According to the Present Invention

| Organism and Protein (Gene) | Codon-Optimized DNA Sequence | Accession Number and Amino Acid Sequence |
|---|---|---|
| *Thermobifida fusca* E2 (gene: celB) | ATGTCACCTAGACCTCTTAGAGCACTTCTTGGAGCAGCAGCAGCAGCACTT GTATCAGCAGCAGCACTTGCATTTCCTTCACAAGCAGCAGCAAATGATTCA CCTTTTTATGTAAATCCTAATATGTCATCAGCAGAATGGGTAAGAAATAAT CCTAATGATCCTAGAACACCTGTAATAAGAGATAGAATAGCATCAGTACC TCAAGGACATGGTTTGCACATCATAATCCTGGACAAATAACAGGACAAG TAGATGCACTTATGTCAGCAGCACAAGCAGCAGGAAAAATACCTATACTT GTAGTATATAATGCACCTGGAAGAGATTGCGGAAATCATTCATCAGGAG AGCACCTTCACATTCAGCATATAGATCATGGATAGATGAATTTGCAGCAG GACTTAAAAATAGACCTGCATATATAATAGTAGAACCTGATCTTATATCAC TTATGTCATCATGCATGCAACATGTACAACAAGAAGTACTTGAAACAATG GCATATGCAGGAAAAGCACTTAAAGCAGGATCATCACAAGCAGAAATATA TTTTGATGCAGGACATTCAGCATGGCATTCACCTGCACAAATGGCATCATG GCTTCAACAAGCAGATATATCAAATTCAGCACATGGAATAGCAACAAATA CATCAAATTATAGATGGACAGCAGATGAAGTAGCATATGCAAAAGCAGTA CTTTCAGCAATAGGAAATCCTTCACTTAGAGCAGTAATAGATACATCAAGA AATGGAAATGGACCTGCAGGAAATGAATGGTGCGATCCTTCAGGAAGAG CAATAGGAACACCTTCAACAACAAATACAGGAGATCCTATGATAGATGCA TTTCTTTGGATAAAACTTCCTGGAGAAGCAGATGGATGCATAGCAGGAGC AGGACAATTTGTACCTCAAGCAGCATATGAAATGGCAATAGCAGGAG GAACAAATCCTAATCCTAATCCTACACCTACACCTACACCTACAC CTACACCTCCTCCTGGATCATCAGGAGCATGCACAGCAACATATACAATA GCAAATGAATGGAATGATGGATTTCAAGCAACAGTAACAGTAACAGCAAA TCAAAATATAACAGGATGGACAGTAACATGGACATTTACAGATGGACAAA CAATAACAAATGCATGGAATGCAGATGTATCAACATCAGGATCATCAGTA ACAGCAAGAAATGTAGGACATAATGGAACTTTCACAAGGAGCATCAAC AGAATTTGGATTTGTAGGATCAAAAGGAAATTCAAATTCAGTACCTACAC TTACATGCGCAGCATCAGTAACAGGATATGGAGATAAAGATTCAAGAAAT CAACATTCAAGATGGTATGCACATCAACTTGATCCTAGACTTCCTAATCCT CCTAAGGAACACTTGCAGGAGGACCTAATTCAGATTCAACAACATGGGA TCCTGTAGCACAATCAAAACTTACAGGATGCGCACCTCAAATGTGCTATAT AGATCATATAGAATCATGGTCAACAAATGAACTTACAATAAATTGGAATG CACCTCTTTCATGGATAGCATCATTTATAGCAGATCAAGATGATGCAGGAG AACCTGGAGGAGAAGAACCTGGACCTGGAGATGATGAAACACCTCCTTCA AAACCTGGAAATCTTAAAGCATCAGATATAACAGCAACATCAGCAACACT TACATGGGATGCATCAACAGATAATGTAGGA GTAGTAGGATATATAAAGTATCACTTGTAAGAGATGGAGATGCAGAAGAAGT AGGAACAACAGCACAAACATCATATACACTTACAGGACTTTTCAGCAGATC AAGAATATACAGTACAAGTAGTAGCATATGATGCAGCAGGAAATCTTTCA ACACCTGCAACAGTAACATTTACAACAGAAAAGAAGATGAAACACCTAC ACCTTCAGCATCATGCGCAGTAACATATCAAACAAATGATTGGCCTGGAG GATTTACAGCATCAGTAACACTTACAAATACAGGATCAACACCTTGGGAT TCATGGGAACTTAGATTTACATTTCCTTCAGGACAAACAGTATCCACATGGA TGGTCAGCAAATTGGCAACAATCAGGATCAGATGTAACAGCAACATCACT TCCTTGGAATGGATCAGTACCTCCTGGAGGAGGATCAGTAAATATAGGAT TTAATGGAACATGGGGAGGATCAAATCAAAACCTGAAAAATTTACAGTA AATGGAGCAGTATGCTCAATAGGA (SEQ ID NO: 78) | P26222<br>MSPRPLRALLGAAAAALVSAAA<br>LAFPSQAAANDSPFYVNPNMSS<br>AEWVRNNPNDPRTPVIRDRIASV<br>PQGTWFAHHNPGQITGQVDAL<br>MSAAQAAGKIPILVVYNAPGRD<br>CGNHSSGGAPSHSAYRSWIDEF<br>AAGLKNRPAYIIVEPDLISLMSSC<br>MQHVQQEVLETMAYGKALKA<br>GSSQARIYFDAGHSAWHSPAQM<br>ASWLQQADISNSAHGIATNTSN<br>YRWTADEVAYAKAVLSAIGNPS<br>LRAVIDTSRNGNGPAGNEWCDP<br>SGRAIGTPSTTNTGDPMIDAFLW<br>IKLPGEADGCIAGAGQFVPQAA<br>YEMAIAAGGTNPNPNPNPTPTPT<br>PTPTPPPGSSGDACTATYTIANEW<br>NDGFQATVTVTANQNITGWTVT<br>WTFTDGQTITNAWNADVSTSGS<br>SVTARNVGHNGTLSQGASTEFG<br>FVGSKGNSNSVPTLTCAAS (SEQ ID NO: 109) |
| *Thermobifida fusca* E3 (gene: celC) | ATGTCAAAAGTAAGAGCTACTAATAGAAGGTCTTGGATGAGGAGAGGATT AGCTGCAGCTAGCGGCTTAGCACTTGGCGCTTCTATGGTAGCATTTGCTGC TCCTGCTAATGCTGCTGGTTGTTCAGTGGATTACACTGTAAATTCTTGGG TACAGGCTTTACTGCTAATGTCACAATAACTAACTTAGGAAGCGCTATTAA CGGTTGACAGTTGGAGTGGGACTTTCCGGGCAACCAACAGGTGACAAACT TGTGGAATGGAACTTACACACAAAGTGGTCAGCATGTATCAGTTTCTAAC GCACCATATAATGCATCTATACCGGCTAATGGAACGGTAGAGTTTGGTTTT AATGGTAGTTACTCAGGCTCTAACGATATTCCTAGCTCATTTAAGTTAAAC GGAGTTACATGCGATGGTAGTGACGATCCGGATCCAGAGCCTAGTCCGTC ACCATCACCTAGCCCGAGTCCAACTGACCCTGATGAACCGGGCGGACCAA CAAATCCGCCTACGAATCCTGGTGAAAAAGTTGACAACCCATTTGAAGGC GCTAAGTTGTATGTCAACCCTGTTTGGAGCGCAAAAGCAGCTGCAGAGCC AGGCGGTTCAGCTGTGGCAAACGAAAGTACTGCAGTCTGGTTGGATAGAA TAGGAGCAATAGAGGGAAACGACTCTCCGACGACTGGTAGCATGGGATTA AGAGATCACCTTGAGGAAGCTGTAAGGCAAAGCGGTGGCGACCCTTTGAC AATACAGGTAGTCATATACAATTTACCTGGTAGAGACTGCGCAGCTCTTGC TTCAAATGGCGAATTGGGACCGGACGAGTTAGACAGATACAAGTCAGAGT ATATTGACCCTATAGCTGATATTATGTGGGACTTTGCAGATTACGAAAACC TTAGGATAGTTGCTATTATAGAGATTGATAGTTTACCTAATCTTGTTACAA ACGTGGGAGGTAACGTGGAACTGAACTTTGCGCATATATGAAGCAGAAT GGAGGTTATGTTAATGGCGTAGGCTATGCTTTAAGAAAATTGGGAGAAAT ACCTAACGTTTATAACTACATAGACGCACTTCATCATGGCTGGATTGATG GGACTCAAATTTTGGCCCATCTGTAGATATATTTTATGAGGCAGCTAACGC TTCAGGTAGTACAGTGGACTACGTTCACGGCTTTATAAGTAACACGGCAA ATTATTCTGCTACAGTAGAACCTTACCTTGATGTGAACGGCACTGTAAATG GACAGTTAATTAGGCAGTCAAAATGGGTCGATTGGAATCAATATGTGGAC GAATTGAGTTTTGTTCAGGATTTAAGGCAAGCATTGATTGCAAAGGGGTTTT | AAA62211<br>MSKVRATNRRSWMRRGLAAAS<br>GLALGASMVAFAAPANAAGCS<br>VDYTVNSWGTGFTANVTITNLG<br>SAINGWTLEWDFPGNQQVTNL<br>WNGTYTQSGQHVSVSNAPYNA<br>SIPANGTVEFGFNGSYSGSNDIPS<br>SFKLNGVTCDGSDDPDPEPSPSP<br>SPSPSPTDPDEPGGPTNPPTNPGE<br>KVDNPFEGAKLYVNPVWSAKA<br>AAEPGGSAVANESTAVWLDRIG<br>AIEGNDSPTTGSMGLRDHLEEA<br>VRQSGGDPLTIQVVIYNLPGRDC<br>AALASNGELGPDELDRYKSEYI<br>DPIADIMWDFADYENLRIVAIIEI<br>DSLPNLVTNVGGNGGTELCAY<br>MKQNGGYVNGVGYALRKLGEI<br>PNVYNYIDAAHHGWIGWDSNF<br>GPSVDIFYEAANASGSTVDYVH<br>GFISNTANYSATVEPYLDVNGT<br>VNGQLIRQSKWVDWNQYVDEL<br>SFVQDLRQALIAKGFRSDIGMLI<br>DTSRNGWGGPNRPTGPSSSTDL<br>NTYVDESRIDRRIHPGNWCNQA<br>GAGLGERPTVNPAPGVDAYVW<br>VKPPGESDGASEEIPNDEGKGFD<br>RMCDPTYQGNARNGNNPSGAL |

TABLE 2-continued

Exemplary Biomass Degrading Enzymes That Can Be Used According to the Present Invention

| Organism and Protein (Gene) | Codon-Optimized DNA Sequence | Accession Number and Amino Acid Sequence |
|---|---|---|
| | AGATCAGATATTGGAATGCTTATTGATACATCTAGGAACGGTTGGGGAGG<br>CCCAAATAGACCTACAGGTCCATCAAGTAGCACTGATCTTAATACATATGT<br>AGACGAGTCTAGAATAGATAGAAGGATACATCCCGGGTAACTGGTGCAATC<br>AAGCAGGCGCTGGTCTTGGCGAAAGGCCAACGGTAAACCCTGCACCAGGT<br>GTTGATGCTTATGTGTGGGTTAAACCTCCAGGTGAATCAGATGGAGCAAG<br>TGAGGAAATTCCTAATGACGAGGGCAAGGGTTTTGATAGAATGTGCGATC<br>CAACATATCAAGGAAATGCTAGGAACGGCAATAACCCTAGCGGCGCTTTG<br>CCAAATGCTCCTATTAGTGGCCACTGGTTTTCAGCACAGTTTAGGGAACTT<br>TTAGCAAATGCATATCCACCTTTA (SEQ ID NO: 79) | PNAPISGHWFSAQFRELLANAYP<br>PL (SEQ ID NO: 110) |
| *Thermobifida fusca* E4 (gene: celD) | ATGTCAGTTACAGAACCTCCACCTAGAAGAAGGGGCAGGCATAGTAGAGC<br>AAGGAGATTTTTAACTAGCCTTGGAGCTACTGCTGCATTAACTGCTGGTAT<br>GCTTGGAGTTCCACTTGCTACGGGAACAGCTCACGCAGAGCCGGCTTTTAA<br>TTATGCTGAAGCTCTTCAAAAAGTATGTTTTTTTACGAAGCACAAAGATC<br>AGGCAAGTTACCAGAAAATAACAGAGTGTCTTGGAGAGGTGATAGCGGTC<br>TTAATGACGGCGCAGACGTTGGATTGGACCTTACGGGCGGATGGTATGAC<br>GCTGGTGACCACGTAAAATTTGGTTTTCCTATGGCATTTACAGCTACTATG<br>CTTGCTTGGGGTGCAATTGAAAGTCCAGAGGGTTACATTAGAAGTGGTCA<br>GATGCCGTATCTTAAGGATAATCTTAGATGGGTAAACGATTACTTTATAAA<br>AGCACACCCTAGCCCAAACGTTTTATACGTCCAGGTAGGCGACGGCGACG<br>CAGATCATAAATGGTGGGGACCGGCTGAGGTTATGCCAATGGAAAGACCG<br>AGCTTTAAGGTTGATCCTAGTTGTCCTGGCAGTGACGTTGCAGCTGAAACG<br>GCTGCAGCTATGGCAGCTTCAAGTATTGTCTTTGCTGACGATGACCCTGCT<br>TACGCTGCAACTTTGGTGCAACATGCTAAACAGCTTTATACATTTGCAGAC<br>ACTTATAGGGAGTATACTCAGATTGCGTGCCAGCAGGAGCTTTTTATAAT<br>TCTTGGAGTGGATACCAAGATGAACTTGTCTGGGGAGCTTATTGGTTATAC<br>AAAGCAACAGGTGATGATAGCTACTTGGCAAAGGCTGAATATGAGTACGA<br>TTTTCTTTCAACTGAGCAGCAAACTGACTTAAGGAGTTATAGGTGGACAAT<br>AGCTTGGGACGATAAATCTTACGGAACTTACGTACTTCTTGCAAAGGAGA<br>CAGGCAAGCAAAAATACATAGACGACGCTAATAGATGGTTAGACTATTGG<br>ACGGTGGGAGTGAACGGTCAAAGGGTACCTTACTCACCTGGCGGTATGGC<br>TGTGTTGGACACTTGGGGAGCACTTAGGTACGCTGCAAACACAGCTTTTGT<br>AGCATTAGTTTACGCTAAAGTTATTGACGATCCAGTTAGAAAGCAAAGGT<br>ATCACGACTTTGCAGTGAGGCAGATTAATTACGCTTTAGGTGATAATCCAA<br>GAAACTCAAGTTACGTAGTGGGCTTTGGAAACAATCCTCCAAGGAATCCA<br>CATCACAGGACGGCACATGGCTCTTGGACTGCAGTATAGCATCTCCGGC<br>TGAGAATAGGCATGTGCTTTATGGCGCATTAGTTGGAGGCCCTGGCAGTCC<br>AAATGACGCATATACTGATGATAGACAAGACTACGTGGCAAACGAAGTTG<br>CTACGGACTACAACGCTGGATTTTCAAGTGCTCTTGCTATGTTAGTAGAAG<br>AGTACGGCGGTACGCCACTTGCTGATTTTCCACCTACAGAGGAACCAGAT<br>GGACCGGAGATATTTGTTGAAGCTCAGATTAATACACCGGGAACGACATT<br>TACTGAAATAAAAGCAATGATAAGAAATCAAAGCGGCTGGCCTGCAAGA<br>ATGTTAGACAAGGGCACTTTTAGGTACTGGTTTACGTTGGACGAGGGAGT<br>AGATCCAGCAGATATTACAGTATCTAGTGCATACAATCAGTGCGACTC<br>CAGAAGATGTTCACCACGTTAGCGGTGACCTTTATTACGTTGAGATTGATT<br>GCACAGGTGAGAAGATTTTTCCAGGCGGTCAGTCTGAACATAGGAGAGAG<br>GTTCAATTTAGAATAGCTGGTGGACCTGGCTGGGATCCATCTAACGATTGG<br>TCATTTCAGGGTATAGGAAACGAATTGCTCCTGCACCATACATTGTCCTT<br>TATGACGATGGCGTCCCGGTGTGGGGTACAGCACCGGAAGAGGGCGAAG<br>AGCCGGAGGTGGAGAGGGCCCAGGCGGTGGCGAGGAACCTGGTGAGGA<br>CGTAACACCACCTTCTGCACCTGGTAGCCCTGCTGTGAGGGACGTAACATC<br>TACATCAGCAGTACTTACTTGGAGTGCAAGCTCTGATACGGGAGGCTCAG<br>GAGTTGCTGGCTATGACGTATTTTTAAGAGCAGGCACAGGACAAGAACAG<br>AAAGTGGGCAGTACAACAAGGACTTCTTTTACTCTTACGGGTTTAGAACCG<br>GATACGACTTATATAGCAGCTGTTGTGGCTAGAGATAATGCTGGTAACGT<br>ATCTCAAAGATCAACAGTTAGTTTTACAACGTTGGCAGAGAACGGCGAG<br>GCCCAGATGCATCTTGCACTGTCGGTTATTCTACTAACGATTGGGATTCAG<br>GATTTACGGCAAGTATAAGGATTACATACCACGGTACGGCTCCTCTTAGCA<br>GTTGGGAGCTTAGTTTTACTTTTCCAGCTGGCCAGCAAGTGACTCATGGCT<br>GGAATGCAACATGGAGACAGGACGGTGCTGCTGTCACGGCTACTCCTATG<br>AGTTGGAATAGCTCTTTAGCACCGGGCGCAACGGTTGAGGTGGGATTTAA<br>TGGTTCATGGAGTGGAAGCAATACTCCACCAACTGACTTTACTTTGAATGG<br>CGAGCCATGCGCACTTGCA (SEQ ID NO: 80) | P26221<br>MSVTEPPPRRRGRHSRARRFLTS<br>LGATAALTAGMLGVPLATGTA<br>HAEPAFNYAEALQKSMFFYEAQ<br>RSGKLPENNRVSWRGDSGLNDG<br>ADVGLDLTGGWYDAGDHVKFG<br>FPMAFTATMLAWGAIESPEGYIR<br>SGQMPYLKDNLRWVNDYFIKA<br>HPSPNVLYVQVGDGDADHKW<br>WGPAEVMPMERPSFKVDPSCPG<br>SDVAAETAAAMAASSIVFADDD<br>PAYAATLVQHAKQLYTFADTYR<br>GVYSDCVPAGAFYNSWSGYQD<br>ELVWGAYWLYKATGDDSYLAK<br>AEYEYDFLSTEQQTDLRSYRWTI<br>AWDDKSYGTYVLLAKETGKQK<br>YIDDANRWLDYWTVGVNGQRV<br>PYSPGGMAVLDTWGALRYAAN<br>TAFVALVYAKVIDDPVRKQRYH<br>DFAVRQINYALGDNPRNSSYVV<br>GFGNNPPRNPHHRTAHGSWTDS<br>IASPAENRHVLYGALVGGPGSP<br>NDAYTDDRQDYVANEVATDYN<br>AGFSSALAMLVEEYGGTPLADF<br>PPTEEPDGPEIFVEAQINTPGTTF<br>TEIKAMIRNQSGWPARMLDKGT<br>FRYWFTLDEGVDPADITVSSAY<br>NQCATPEDVHHVSGDLYYVEID<br>CTGEKIFPGGQSEHRREVQFRIA<br>GGPGWDPSNDWSFQGIGNELAP<br>APYIVLYDDGVPVWGTAPEEGE<br>EPGGGEGPGGGEEPGEDVTPPSA<br>PGSPAVRDVTSTSAVLTWSASS<br>DTGGSGVAGYDVFLRAGTGQE<br>QKVGSTTRTSFTLTGLEPDTTYI<br>AAVVARDNAGNVSQRSTVSFTT<br>LAENGGGPDASCTVGYSTNDW<br>DSGFTASIRITYHGTAPLSSWELS<br>FTFPAGQQVTHGWNATWRQDG<br>AAVTATPMSWNSSLAPGATVEV<br>GFNGSWSGSNTPPTDFTLNGEPC<br>ALA (SEQ ID NO: 111) |
| *Thermobifida fusca* E5 (gene: celE) | ATGGCAAAGAGCCCAGCTGCAAGAAAGGGAAGGCCACCTGTAGCAGTTG<br>CTGTAACAGCAGCTCTTGCATTATTGATAGCATTACTTTCTCCAGGCGTTG<br>CTCAAGCAGCTGGCCTTACGGCTACAGTAACTAAGGAGAGCTCTTGGGAT<br>AATGGATATTCAGCAAGCGTGACAGTTAGAAACGACACTAGCTCAACTGT<br>CTCTCAGTGGGAGGTAGTGTTAACATTGCCTGGAGGTACAGTTGCAC<br>AAGTATGGAATGCTCAGCATACTTCTAGCGGAAATAGTCACACATTTACTG<br>GTGTTTCATGGAACAGCACGATTCCGCCTGGCGGACACAGCAAGTTCAGGT<br>TTTATAGCAAGTGGATCAGGTGAACCAACTCATTGTACAATAAACGGTGC<br>ACCTTGCGATGAGGGCAGCGAACCGGGCGGACCCAGGTGGCCCAGGAACG<br>CCAAGCCCAGATCCGGGTACACAACCAGGAACGGGTACTCCGGTTGAGAG | Q01786 AND AAC09379<br>MAKSPAARKGRPPVAVAVTAA<br>LALLIALLSPGVAQAAGLTATVT<br>KESSWDNGYSASVTVRNDTSST<br>VSQWEVVLTLPGGTTVAQVWN<br>AQHTSSGNSHTFTGVSWNSTIPP<br>GGTASSGFIASGSGEPTHCTING<br>APCDEGSEPGGPGGPGTPSPDPG<br>TQPGTGTPVERYGKVQVCGTQL<br>CDEHGNPVQLRGMSTHGIQWFD |

TABLE 2-continued

Exemplary Biomass Degrading Enzymes That Can Be Used According to the Present Invention

| Organism and Protein (Gene) | Codon-Optimized DNA Sequence | Accession Number and Amino Acid Sequence |
|---|---|---|
| | ATATGGTAAGGTCCAAGTTTGCGGAACGCAGTTGTGCGACGAGCACGGCA ACCCGGTGCAATTGAGAGGAATGAGTACTCACGGTATACAATGGTTTGAT CACTGTTTAACGGACAGTTCTTTGGATGCATTGGCTTACGATTGGAAGGCA GATATTATAAGACTTAGTATGTACATTCAAGAGGACGGTTATGAAACTAA CCCTAGAGGATTTACTGACAGGATGCACCAGTTGATTGACATGGCTACTGC AAGGGGCTTATACGTGATAGTTGACTGGCATATATTGACGCCAGGCGACC CTCACTACAACCTTGATAGGGCTAAAACATTTTTTGCAGAAATAGCTCAGA GACACGCAAGTAAGACTAATGTCTTGTACGAGATTGCTAACGAACCAAAT GGAGTGTCTTGGGCAAGCATTAAGTCTTACGCTGAGGAAGTTATACCTGTA ATAAGACAGAGGGACCCAGACTCTGTCATTATAGTCGGAACAAGGGGTTG GTCAAGTCTTGGAGTGAGCGAAGGCAGCGGACCACGGTCAGATTGCTGCAA ATCCTGTTAACGCTTCAAATATTATGTATGCATTTCACTTTTACGCTGCTTC TCACAGAGATAATTATTTAAACGCATTGAGGGAAGCTAGCGAACTTTTTCC GGTTTTTGTGACTGAGTTTGGAACAGAAACATACACTGGCGACGGAGCAA ACGATTTTCAGATGGCTGACAGATATATTGACTTAATGGCAGAAAGAAAA ATTGGTTGGACAAAGTGGAATTATTCTGATGATTTTAGGTCAGGAGCTGTT TTTCAGCCAGGCACTTGCGCAAGTGGTGGACCTTGGAGCGGCTCTAGCTTG AAGGCTTCAGGCCAATGGGTAAGGAGCAAGTTGCAGTCT (SEQ ID NO: 81) | HCLTDSSLDALAYDWKADIIRLS MYIQEDGYETNPRGFTDRMHQL IDMATARGLYVIVDWHILTPGD PHYNLDRAKTFFAEIAQRHASK TNVLYEIANEPNGVSWASLKSYA EEVIPVIRQRDPDSVIIVGTRGWS SLGVSEGSGPAEIAANPVNASNI MYAFHFYAASHRDNYLNALRE ASELFPVFVTEFGTETYTGDGAN DFQMADRYIDLMAERKIGWTK WNYSDDFRSGAVFQPGTCASGG PWSGSSLKASGQWVRSKLQS (SEQID NO: 112) |
| *Thermobifida fusca* Endoglucanase (gene: cel5B) | ATGACACCTTTAACTAGAAGGCTTAGGGCAGGAGCTGCAGCTATAGCAAT TGGTGCTTCAGCATTGATACCACTTACATCTAGCCCGGCTGCTGCTTCAGG CACTGCAGATTGGCTTCATACAGACGGAAATAGAATTGTAGATTCAGCTG GTAACGAAGTTTGGTTGACTGGCGCAAATTGGTTTGGATTTAATACATCTG AGAGAATGTTTCACGGTTTATGGGCAGCTAATATAGAGGACATAACAAGT GCTATGGCAGAGAGGGGCATAAATATGGTGAGAGTACCGATTAGTACGCA ACTTTTGTTAGAATGGAAGAATGGTCAGGCTGGTCCTTCAGGCGTTAACGA ATATGTCAACCCTGAGCTTGCAGGAATGAACACTTGAGGTTTTTGATTA CTGGTTACAATTATGCGAAGAGTATGGTTGAAGGTTATGTTAGATGTACA TTCTGCAGAAGCTGATAACTCTGGCCACTACTATCCTGTGTGGTATAAAGG TGATATAACTACAGAAGATTTTTATACTGCATGGGAGTGGGTTACAGAAA GATATAGAATAATGATACAATAGTAGCAGCTGATATTAAAAACGAACCG CATGGAAAGGCTAATGAGACTCCTAGGGCAAAGTGGGATGGCAGTACAG ATATAGACAATTTTAAACACGTTTGTGAGACTGCTGGTAAAAGGATTCTTG CAATAAACCCAAACATGTTGATTTTGTGTGAAGGTATAGAGATATACCCTA AGGACGGCCAGGATTGGTCATCTACAGACGGAAGGGATTACTACTCAACT TGGTGGGGTGGAAATCTTAGAGGCGTTGCTGATCACCCAGTAGACTTAGG AGCACACCAAGATCAGTTGGTATACTCACCTCATGATTATGGCCCATCTGT TTTTGAACAACCGTGGTTTGAAGGCGAGTGGAACAGACAGACTCTTACAG AGGACGTGTGGAGGCCAAATTGGTTATATATTCACGAAGATGATATAGCT CCACTTCTTATTGGTGAGTGGGGAGGCTTTTTTAGACGGCGGTGACAATGA GAAGTGGATGACTGCATTGAGATCTCTTATAATTGATGAGAAGATGCATC ACACATTTTGGGCTTTAAATCCGAACTCAGGAGATACTGGTGGATTGCTTA ATTATGATTGGACAACATGGGATGAAGCAAAATACGCTTTTTTAAAGCCT GCATTGTGGCAAGATGCTAACGAAAATTTGTGGGATTGGATCACGACGT CCCTTTGGGAGGCGTGGGATCAACTACAGGTGTTAGTCTTAATCAGTATTA CGGTGGAGGTGGACCTTCACAGCCTCCAACTGAACCGACTGAACCGCCTA CTGAACCAACGGAACCTCCGACAGAACCGACGGAGCCTCCAGCAAATCCT ACAGGCGCTTTAGAAGTATACTATAGGAATAACTCTTTAGCAGCTGATGA CTCACAAATTGCACCGGGCTTAAGATTGGTTAATACTGGATCATCTACGGT AGACCTTGCTGATGTGGAAATTCATTATTTTACAAATGAACCTGGCGG TACTTTACAGTTTACATGCGATTGGGCTCAAGTTGGCTGCGCTAATGTAAA TGCATCTTTTACATTCACTTAGCGCACCAGGCGCTGATACATCACTTGTGCT TACATTGTCTGGCAGTCTTGCTCCTGGTGCAAGCACAGAGCTTCAAGGCAG AATACACACAGCAAATTGGGCAAATTTTGACGAGTCAGATGACTATAGTA GGGGAACGAATACTGACTGGGAATTGAGCGAAGTTATAACTGCATATCTT GGAGGCACATTAGTATGGGGTACACCGCCTGCT (SEQ ID NO: 82) | AAP56348 AND AY298814.1 MTPLTRRLRAGAAAIAIGASALI PLTSSPAAASGTADWLHTDGNR IVDSAGNEVWLTGANWFGFNTS ERMFHGLWAANIEDITSAMAER GINMVRVPISTQLLLEWKNGQA GPSGVNEYVNPELAGMNTLEVF DYWLQLCEEYGLKVMLDVHSA EADNSGHYYPVWYKGDITTEDF YTAWEVTERYKNNDTIVAADI KNEPHGKANETPRAKWDGSTDI DNFKHVCETAGKRILAINPNMLI LCEGIEIYPKDGQDWSSTDGRD YYSTWWGGNLRGVADHPVDLG AHQDQLVYSPHDYGPSVFEQPW FEGEWNRQTLTEDVWRPNWLYI HEDDIAPLLIGEWGGFLDGGDN EKWMTALRSLIIDEKMHHTFWA LNPNSGDTGGLLNYDWTTWDE AKYAFLKPALWQDANGKFVGL DHDVPLGGVGSTTGVSLNQYYG GGGPSQPPTEPTEPPTEPTEPPTE PTEPPANPTGALEVYYRNNSLA ADDSQIAPGLRLVNTGSSTVDA DVEIHYYFTNEPGGTLQFTCDW AQVGCANVNASFTSLSAPGADT SLVLTLSGSLAPGASTELQGRIH TANWANFDESDDYSRGTNTDW ELSEVITAYLGGTLVWGTPPA (SEQ ID NO: 113) |
| *Thermobifida fusca* Beta-1,4-exocellulase E6 (gene: celF) | ATGAGATCACTTCTTTCACCTAGAAGATGGAGAACACTTGCATCAGGAGC ACTTGCAGCAGCACTTGCAGCAGCAGTACTTTCACCTGGAGTAGCACATG CAGCAGTAGCATGCTCAGTAGATTATGATGATTCAAATGATTGGGGATCA GGATTTGTAGCAGAAGTAAAAGTAACAAATGAAGGATCAGATCCTATACA AAATTGGCAAGTAGGATGGACATTTCCTGGAAATCAACAAATAACAAATG GATGGAATGGAGTATTTTCACAATCAGGAGCAAATGTAACAGTAAGATAT CCTGATTGGAATCCTAATATAGCACCTGGAGCAACAATATCATTTGGATTT CAAGGAACATATTCAGGATCAAATGATGCACCTACATCATTTACAGTAAA TGGAGTAACATGCTCAGGATCACAACCTGCAAATCTTCCTCCTGATGTAAC ACTTACATCACCTGCAAATAATTCAACATTTCTTGTAAATGATCCTATAGA ACTTACAGCAGTAGCATCAGATCCTGATGGATCAATAGATAGAGTAGAAT TTGCAGCAGATAATACAGTAATAGGAATAGATACAACATCACCTTATTCA TTTACATGGACAGATGCAGCAGGATCATATTCAGTAACAGCAATAGC ATATGATGATCAAGGACAAGCAGTATCAGCACCTATAGCAATAAGAG TACTTGATAGAGCAGCAGTAATAGCATCACCTCCTACAGTAAGAGTACCT CAAGGAGGAACAGCAGATTTTGAAGTAAGACTTTCAAATCAACCTTCAGG AAATGTAACAGTAACAGTAGCAAGAACATCAGGATCATCAGATCTTACAG | AAD39947 MRSLLSPRRWRTLASGALAAAL AAAVLSPGVAHAAVACSVDYD DSNDWGSGFVAEVKVTNEGSDP IQNWQVGWTFPGNQQITNGWN GVFSQSGANVTVRYPDWNPNIA PGATISFGFQGTYSGSNDAPTSF TVNGVTCSGSQPANLPPDVTLTS PANNSTFLVNDPIELTAVASDPD GSIDRVEFAADNTVIGIDTTSPYS FTWTDAAAGSYSVTAIAYDDQG ARTVSAPIAIRVLDRAAVIASPPT VRVPQGGTADFEVRLSNQPSGN VTVTVARTSGSSDLTVSSGSQLQ FTSSNWNQPQKVTIASADNGGN LAEAVFTVSAPGHDSAEVTVREI DPNTSSYDQAFLEQYEKIKDPAS |

TABLE 2-continued

Exemplary Biomass Degrading Enzymes That Can Be Used According to the Present Invention

| Organism and Protein (Gene) | Codon-Optimized DNA Sequence | Accession Number and Amino Acid Sequence |
|---|---|---|
| | TATCATCAGGATCACAACTTCAATTTACATCATCAAATTGGAATCAACCTC<br>AAAAAGTAACAATAGCATCAGCAGATAATGGAGGAAATCTTGCAGAAGC<br>AGTATTTACAGTATCAGCACCTGGACATGATTCAGCAGAAGTAACAGTAA<br>GAGAAATAGATCCTAATACATCATCATATGATCAAGCATTTCTTGAACAAT<br>ATGAAAAAATAAAAGATCCTGCATCAGGATATTTTAGAGAATTTAATGGA<br>CTTCTTGTACCTTATCATTCAGTAGAAACAATGATAGTAGAAGCACCTGAT<br>CATGGACATCAAACAACATCAGAAGCATTTTCATATTATCTTTGGCTTGAA<br>GCATATTATGGAAGAGTAACAGGAGATTGGAAACCTCTTCATGATGCATG<br>GGAATCAATGGAAACATTTATAATACCTGGAACAAAAGATCAACCTACAA<br>ATTCAGCATATAAT<br>CCTAATTCACCTGCAACATATATACCTGAACAACCTAATGCAGATGGATAT<br>CCTTCACCTCTTATGAATAATGTACCTGTAGGACAAGATCCTCTTGCACAA<br>GAACTTTCATCAACATATGGAACAAATGAAATATATGGAATGCATTGGCT<br>TCTTGATGTAGATAATGTATATGGATTTGGATTTTGCGGAGATGGAACAGA<br>TGATGCACCTGCATATATAAATACATCATCAAAGAGGAGCAATCAG<br>TATGGGAAACAATACCTCATCCTTCATGCGATGATTTTACACATGGAGGAC<br>CTAATGGATATCTTGATCTTTTTACAGATGATCAAAATTATGCAAAACAAT<br>GGAGATATACAAATGCACCTGATGCAGATGCAAGAGCAGTACAAGTAATG<br>TTTTGGGCACATGAATGGGCAAAAGAACAAGGAAAAGAAAATGAAATAG<br>CAGGACTTATGGATAAAGCATCAAAAATGGGAGATTATCTTAGATATGCA<br>ATGTTTGATAAATATTTTAAAAAATAGGAAATTGCGTAGGAGCAACATC<br>ATGCCCTGGAGGACAAGGAAAAGATTCAGCACATTATCTTCTTTCATGGTA<br>TTATTCATGGGGAGGATCACTTGATACATCATCAGCATGGGCATGGAGAA<br>TAGGATCATCATCATCACATCAAGGATATCAAAATGTACTTGCAGCATATG<br>CACTTTCACAAGTACCTGAACTTCAACCTGATTCACCTACAGGAGTACAAG<br>ATTGGGCAACATCATTTGATAGACAACTTGAATTTCTTCAATGGCTTCAAT<br>CAGCAGAAGGAGGAATAGCAGGAGCAACAAATTCATGGAAAGGATC<br>ATATGACACCTCCTACAGGACTTTCACAATTTTATGGAATG<br>TATTATGATTGGCAACCTGTATGGAATGATCCTCCTTCAAATAATTGGTTT<br>GGATTTCAAGTATGGAATATGGAAAGAGTAGCACAACTTTATTATGTAAC<br>AGGAGATGCAAGAGCAGAAGCAATACTTGATAAATGGGTACCTTGGGCAA<br>TACAACATACAGATGTAGATGCAGATAATGGAGGACAAAATTTTCAAGTA<br>CCTTCAGATCTTGAATGGTCAGGACAACCTGATACATGGACAGGAACATA<br>TACAGGAAATCCTAATCTTCATGTACAAGTAGTATCATATTCACAAGATGT<br>AGGAGTAACAGCAGCACTTGCAAAAACACTTATGTATTATGCAAAAAGAT<br>CAGGAGATACAACAGCACTTGCAACAGCAGAAGGACTTCTTGATGCACTT<br>CTTGCACATAGAGATTCAATAGGAATAGCAACACCTGAACAACCTTCATG<br>GGATAGACTTGATGATCCTTGGGATGGATCAGAAGGACTTTATGTACCTCC<br>TGGATGGTCAGGAACAATGCCTAATGGAGATAGAATAGAACCTGGAGCAA<br>CATTTCTTTCAATAAGATCATTTTATAAAAATGACCTGCACCTATAGTAGAAA<br>GAAGCACATCTTAATGATCCTCAAAATGTACCTGCACCTATAGTAGAAA<br>GACATAGATTTTGGGCACAAGTAGAAATAGCAACAGCATTTGCAGCACAT<br>GATGAACTTTTTGGA<br>GCAGGAGCACCT (SEQ ID NO: 83) | GYFREFNGLLVPYHSVETMIVE<br>APDHGHQTTSEAFSYYLWLEAY<br>YGRVTGDWKPLHDAWESMETF<br>IIPGTKDQPTNSAYNPNSPATYIP<br>EQPNADGYPSPLMNNVPVGQDP<br>LAQELSSTYGTNEIYGMHWLLD<br>VDNVYGFGFCGDGTDDAPAYIN<br>TYQRGARESVWETIPHPSCDDFT<br>HGGPNGYLDLFTDDQNYAKQW<br>RYTNAPDADARAVQVMFWAHE<br>WAKEQGKENEIAGLMDKASKM<br>GDYLRYAMFDKYFKKIGNCVG<br>ATSCPGGQGKDSAHYLLSWYYS<br>WGGSLDTSSAWAWRIGSSSSHQ<br>GYQNVLAAYALSQVPELQPDSP<br>TGVQDWATSFDRQLEFLQWLQS<br>AEGGIAGGATNSWKGSYDTPPT<br>GLSQFYGMYYDWQPVWNDPPS<br>NNWFGFQVWNMERVAQLYYV<br>TGDARAEAILDKWVPWAIQHTD<br>VDADNGGQNFQVPSDLEWSGQ<br>PDTWTGTYTGNPNLHVQVVSYS<br>QDVGVTAALAKTLMYYAKRSG<br>DTTALATAEGLLDALLAHRDSI<br>GIATPEQPSWDRLDDPWDGSEG<br>LYVPPGWSGTMPNGDRIEPGAT<br>FLSIRSFYKNDPLWPQVEAHLND<br>PQNVPAPIVERHRFWAQVEIATA<br>FAAHDELFGAGAP (SEQ ID NO: 114) |
| *Thermobifida fusca* Cellulose 1,4-beta-cellobiosidase/ endoglucanase. Glycosyl Hydrolase family 9 (locus_tag = Tfu_1627) | ATGGGAGCACTTCCTTGGTGGGCATCAGCAGTAAGATCATCATCACAATTT<br>GAATCACCTTATGGAAGAACATCAGTACTTAGAAGACCTAGATCAAGATC<br>ACCTCTTGTAGCACTTACAGCACAACATGCGCACTTGCACTTGGAAGGAA<br>CAGCAGTACCTGCACAAGCAGATGAAGTAAATCAAATAAGAAATGGAGA<br>TTTTTCATCAGGAACAGCACCTTGGTGGGGAACAGAAAATATACAACTTA<br>ATGTAACAGATGGAATGCTTTGCGTAGATGTACCTGGAGGAACAGTAAAT<br>CCTTGGGATGTAATAATAGGACAAGATGATATACCTCTTATAGAAGGAGA<br>ATCATATGCATTTTCATTTACAGCATCATCAACATGTACCTGTATCAATAAG<br>AGCACTTGTACAAGAACCTGTAGAACCTTGGACAACAAATGGATGAAA<br>GAGCACTTCTTGGACCTGAAGCAGAAACATATGAATTTGTATTTACATCAA<br>ATGTAGATTGGGATGATGCACAAGTAGCATTTCAAATAGGAGGATCAGAT<br>GAACCTTGGACATTTTGCCTTGATGATGTAGCACTTCTTGGAGGAGCAGAA<br>CCTCCTGTATATGAACCTGATACAGGACCTAGAGTAAGAGTAAATCAAGT<br>AGGATATCTTCCTCATGGACCTAAAAAGCAACAGTAGTAACAGATGCAA<br>CATCAGCACTTACATGGGAACTTGCAGATGCAGATGGAAATGTAGTAGCA<br>TCAGGACAAACAAAACCTCATGGAGCAGATTCATCATCTGGACTTAATGT<br>ACATACAGTAGATTTTTCATCATATACAACAAAAGGATCAGATTATACACT<br>TACAGTAGATGGAGAAACATCATATCCTTTTGATATAGATGAATCAGTATA<br>TGAAGAACTTAGAGTAGATGCACTTTCATTTTATTATCCTCAAAGATCAGG<br>AATAGAAATACTTGATTCAATAGCACCTGGATATGGAAGACCTGCAGGAC<br>ATATAGGAGTACCTCCTAATCAAGGAGATACAGATGTACCTTGCGCACCT<br>GGAACATGCGATTATTCACTTGATGTATCAGGAGGATGGTATGATGCAGG<br>AGATCATGGAAAATATGTAGTAAATGGAGGAATATCAGTACATCAAATAA<br>TGTCAATATATGAAAGATCAACACTTGCAGATACAGCACAACCTGATAAA<br>CTTGCAGATTCAACACTTAGACTTCCTGAAACAGGAAATGGAGTACCTGA<br>TGTACTTGATGAAGCAAGATGGGAAATGGAATTTCTTCTTAAAATGCAAG<br>TACCTGAAGGAGAACCTCTTGCAGGAATGGCACATCATAAAATACATGAT<br>GAACAATGGACAGGACTTCCTCTTCCTTCAGCAGATCCTCAACCTAGA<br>TATCTTCAACCTCCTTCAACAGCAGCAACACTTAATCTTGCAGCAACAGCA | AAZ55662 AND CP000088<br>MGALPWWASAVRSSSQFESPYG<br>RTSVLRRPRSRSPLVALTAATCA<br>VALGGTAVPAQADEVNQIRNGD<br>FSSGTAPWWGTENIQLNVTDGM<br>LCVDVPGGTVNPWDVIIGQDDIP<br>LIEGESYAFSFTASSTVPVSIRAL<br>VQEPVEPWTTQMDERALLGPEA<br>ETYEFVFTSNVDWDDAQVAFQI<br>GGSDEPWTFCLDDVALLGGAEP<br>PVYEPDTGPRVRVNQVGYLPHG<br>PKKATVVTDATSALTWELADA<br>DGNVVASGQTKPHGADSSSGLN<br>VHTVDFSSYTTKGSDYTLTVDG<br>ETSYPFDIDESVYEELRVDALSF<br>YYPQRSGIEILDSIAPGYGRPAG<br>HIGVPPNQGDTDVPCAPGTCDY<br>SLDVSGGWYDAGDHGKYVVNG<br>GISVHQIMSIYERSQLADTAQPD<br>KLADSTLRLPETGNGVPDVLDE<br>ARWEMEFLLKMQVPEGEPLAG<br>MAHHKIHDEQWTGLPLLPSADP<br>QPRYLQPPSTAATLNLAATAAQ<br>CARVFEPFDEDPAAECLAAAET<br>AWDAAKANPNIYAPAFGEGGGP<br>YNDNNVTDEFYWAAAELFLTT<br>GKEEYRDAVTSSPLHTDDEEVF<br>RDGAFDWGWTAALARLQLATIP<br>NDLADRDRVRQSVVDAADMYL |

TABLE 2-continued

Exemplary Biomass Degrading Enzymes That Can Be Used According to the Present Invention

| Organism and Protein (Gene) | Codon-Optimized DNA Sequence | Accession Number and Amino Acid Sequence |
|---|---|---|
| | GCACAATGCGCAAGAGTATTTGAACCTTTTGATGAAGATTTTGCAGCAGA ATGCCTTGCAGCAGCAGAAACAGCATGGGATGCAGCAAAAGCAAATCCTA ATATATATGCACCTGCATTTGGAGAAGGAGGAGGACCTTATAATGATAAT AATGTAACAGATGAATTTTATTGGGCAGCAGCAGAACTTTTTCTTACAACA GGAAAAGAAGAATATAGAGATGCAGTAACATCATCACCTCTTCATACAGA TGATGAAGAAGTATTTAGAGATGGAGCATTTGATTGGGGATGGACAGCAG CACTTGCAAGACTTCAACTTGCAACAATACCTAATGATCTTGCAGATAGAG ATAGAGTAAGACAATCAGTAGTAGATGCAGCAGATATGTATCTTGCAAAT GTAGAAACATCACCTTGGGGACTTGCATATAAACCTAATAATGGAGTATTT GTATGGGGATCAAATTCAGCAGTACTTAATAATATGGTAATACTTGCAGTA GCATTTGATCTTACAGGAGATACAAAATATAGAGATGGAGTACTTGAAGG AATGGATTATATATTTGGAAGAAATGCACTTAATCAATCATATGTAACAG GATATGGAGATAAAGATTCAAGAAATCAACATTCAAGATGGTATGCACAT CAACTTGATCCTAGACTTCCTAATCCTCCTAAAGGAACACTTGCAGGAGGA CCTAATTCAGATTCAACAACATGGGATCCTGTAGCACAATCAAAACTTAC AGGATGCGCACCTCAAATGTGCTATATAGATCATAGAATCATGGTCAA CAAATGAACTTACAATA AATTGGAATGCACCTCTTTCATGGATAGCATCATTTATAGCAGATCAAGAT GATGCAGGAGAACCTGGAGGAGAAGAACCTGGACCTGGAGATGATGAAA CACCTCCTTCAAAACCTGGAAATCTTAAAGCATCAGATATAACAGCAACA TCAGCAACACTTACATGGGATGCATCAACAGATAATGTAGGAGTAGTAGG ATATAAAGTATCACTTGTAAGAGATGGAGATGCAGAAGAAGTAGGAACA ACAGCACAAACATCATATACACTTACAGGACTTTCAGCAGATCAAGAATA TACAGTACAAGTAGTAGCATATGATGCAGCAGGAAATCTTTCAACACCTG CAACAGTAACATTTACAACAGAAAAAGAAGATGAAACACCTACACCTTCA GCATCATGCGCAGTAACATATCAAACAAATGATTGGCCTGGAGGATTTAC AGCATCAGTAACACTTACAAATACAGGATCAACACCTTGGGATTCATGGG AACTTAGATTTACATTTCCTTCAGGACAACAGTATCACATGGATGGTCAGC AAATTGGCAACAATCAGGATCAGATGTAACAGCAACATCACTTCCTTGGA ATGGATCAGTACCTCCTGGAGGATCAGTAAATATAGGATTTAATGGAACA TGGGGAGGATCAAATACAAAACCTGAAAATTTACAGTAAATGGAGCAGT ATGCTCAATAGGA (SEQ ID NO: 84) | ANVETSPWGLAYKPNNGVFVW GSNSAVLNNMVILAVAFDLTGD TKYRDGVLEGMDYIFGRNALNQ SYVTGYGDKDSRNQHSRWYAH QLDPRLPNPPKGTLAGGPNSDST TWDPVAQSKLTGCAPQMCYIDH IESWSTNELTINWNAPLSWIASFI ADQDDAGEPGGEEPGPGDDETP PSKPGNLKASDITATSATLTWDA STDNVGVVGYKVSLVRDGDAE EVGTTAQTSYTLTGLSADQEYT VQVVAYDAAGNLSTPATVTFTT EKEDETPTPSASCAVTYQTNDW PGGFTASVTLTNTGSTPWDSWE LRFTFPSGQTVSHGWSANWQQS GSDVTATSLPWNGSVPPGGSVNI GFNGTWGGSNTKPEKFTVNGA VCSIG (SEQ ID NO: 115) |
| Caldicellulos iruptor kristjanssonii Predicted based on amino acid sequence - Contig 00135 or2202 | AAAACAGCAAGGCTTTTGGTGTGTTTTGTTTTGGTGTGCTTTATACTTACTA CAACGATTTTGCTTGATAATAACAAGGGAGAGGCAGCAATGTACAACTAT GGTGAGGCTTTGCAAAAGGCTATTATGTTTTACGAGTTTCAGATGTCAGGC AAGTTGCCGAAATGGATAAGGAATAACTGGAGGGGAGACTCAGGCCTTAA CGACGGCAAAGACAATAAGATAGACCTTACTGGAGGTTGGTATGACGCTG GCGATCATGTCAAGTTTAACTTGCCAATGAGCTATACTGCAACAATGTTAG CATGGGCTGTCTACGAATATAAGGACGCTTTTGTGAAAAGCGGACAATTA CAGCACATTCTTAACCAAATAGAGTGGGTAAACGACTATTTTGTGAAGTG CCACCCTGAAAAATACGTGTACTATTACCAAGTGGGTGATGGCGGTAAGG ATCACGCATGGTGGGGACCGGCTGAGGTTATGCCTATGGAAAGGCCTTCA TATAAAGTGACGAAAACTAATCCTGGCTCAACTGTAGTTGCAGAAACGGC TGCAGCTTTAGCTGCTGGAGTATAGTTATTAAGCAAAGAAATAGTAAGA AAGCTAGGATTTATCTTAAGCACGCAAAGGAGTTGTATGACTTTGCAGCA GAGACAAAGTCTGACGCTGGTTATACTGCAGCTAATGGCTATTACAATAG CTGGTCAGGATTTTGGGACGAATTAAGTTGGGCAGCAGTATGGTTGTACTT GGCAACGGGTGATAAATACTATTTAAGCGAGGCTAAGAAATATGTGAGCA ATTGGCCAAAAATTGCTGGTTCAAATACGATTGACTATAGGTGGGCTCATT GCTGGGATGACGTACACTATGGAGCAGCATTGCTTTTAGCAAAAATAACA GATGAGAACACGTATAAACAGATTGTCGAAAAGCACCTTGATTATTGGAC TATTGGTTACCAGGGACAAAGGATAAAATACACACCAAAGGGCCTTGCTT GGTTAGATCAGTGGGGTAGTTTGAGATACGAACTACGACAGCTTTTTTAG CTTTTGTGTATTCAGACTGGAAAGGATGTCCTAGTTCAAAGAAGAAAGTGT ACAGAAAATTTGGAGAAGGTCAAGTGAACTACGCTTTGGGCAGCTCAGGT AGGAGTTTTGTTGTGGGATTTGGAAAAAACCCTCCAAAAAGACCTCATCA TAGAACTGCTCATGGCAGTTGGGCAAATTCTCAATCAGAACCACCTTATCA CAGGCATATTTTGTATGGTGCTTTGGTGGCGGTCCAGGTTTAGATGATAG CTATTCAGACGATGTTGGAAACTACGTAAATAACGAAGTTGCTTGCAGATTA CAATGCTGGCTTTGTCGGAGCTTTAGCTAAAATGTACTTGTTATACGGTGG AAAACCTATACCAAACTTTAAGGCAATAGAAAAGCCATCAAATGACGAGT TTTTTGTTGAAGCAGGCATTAATGCAAGCGGTTCAAATTTTGTTGAGATTA AGGCTATTGTATATAACCAAGTGGATGGCCAGCAAGAGTTACGAACAAT CTTAAGTTTGGTACTACATAAACCTTTCTGAGATTGTATCACAAGGTTAT AAACCTTCACAAATAAGCCTTAACACAAATTACACCAGGGAGCTAAAGT ATCAGGACCATATGTTGTAGATTCTAAGAAACATCTTTATTACATTCTTAT AGATTTTAGTGGTACGCCGATTTACCCTGGTGGACAGGACAAGTACAAAA AAGAGGTACATTTAGAATTGCAGCTCCTCAAACGCAAGATGGGATAAC TCAAACGACTATAGCTTTAAGGACTTGATAAAACAGGTGGCGGCCAAGT CATAAAGACAAGTACATTCCATTGTACGACGGTAAAAATTAGTTTGGG GAATAGAGCCGAATACTAAGAATTTAACGCTTAGGACAAGCCAGATACCG GCAAATGGTGATGCAGACAAAAAGAGCAAAACGATTCTTTCTAAGAATAC GAGCTCAGCTAAGACAAGTTCTAAACAGAACAAGGAAGTAAAGAACGTG | KTARLLVCFVLVCFILTTTILLDN NKGEAAMYNYGEALQKAIMFY EFQMSGKLPKWIRNNWRGDSG LNDGKDNKIDLTGGWYDAGDH VKFNLPMSYTATMLAWAVYEY KDAFVKSGQLQHILNQIEWVND YFVKCHPEKYVYYYQVGDGGK DHAWWGPAEVMPMERPSYKVT KTNPGSTVVAETAAALAAGSIVI KQRNSKKARIYLKHAKELYDFA AETKSDAGYTAANGYYNSWSG FWDELSWAAVWLYLATGDKYY LSEAKKYVSNWPKIAGSNTIDY RWAHCWDDVHYGAALLLAKIT DENTYKQIVEKHLDYWTIGYQG QRIKYTPKGLAWLDQWGSLRY ATTTAFLAFVYSDWKGCPSSKK KVYRKFGEGQVNYALGSSGRSF VVGFGKNPPKRPHHRTAHGSW ANSQSEPPYHRHILYGALVGGP GLDDSYSDDVGNYVNNEVACD YNAGFVGALAKMYLLYGGKPIP NFKAIEKPSNDEFFVEAGINASG SNFVEIKAIVYNQSGWPARVTN NLKFRYYINLSEIVSQGYKPSQIS LNTNYNQGAKVSGPYVVDSKK HLYYILIDFSGTPIYPGGQDKYK KEVQFRIAAPQNARWDNSNDYS FKGLDKTGGGQVIKTKYIPLYD GKKLVWGIEPNTKNLTLRTSQIP ANGDADKKSKTILSKNTSSAKTS SKQNKEVKNVVKVLYKNMEIN KTSNSIRLYLKIINNSQETIDLSK VKIRYWYTADDGVMKQSAVCD WAQIGAVNVTFRFVRLRKAVA KADHYLEIGFTNNAGKIQPGKD SGDIQLRFNKSNWGNYDQSND WSWVQSMTSYGENKKITLYIDG KLVWGQEPTKDT (SEQ ID NO: 116) |

TABLE 2-continued

Exemplary Biomass Degrading Enzymes That Can Be Used According to the Present Invention

| Organism and Protein (Gene) | Codon-Optimized DNA Sequence | Accession Number and Amino Acid Sequence |
|---|---|---|
| | GTGAAGGTACTTTACAAAAATATGGAAATTAACAAGACGAGTAACAGCAT<br>TAGGTTATACTTGAAGATAATTAATAACAGCCAGGAAACGATAGATTTGA<br>GCAAGGTGAAAATTAGATATTGGTACACTGCTGACGATGGAGTCATGAAA<br>CAGAGCGCAGTATGTGACTGGGCACAAATAGGTGCTGTCAATGTAACATT<br>TAGATTTGTGAGGTTAAGGAAAGCAGTGGCAAAAGCTGATCATTACTTAG<br>AGATTGGTTTTACAAACAACGCTGGTAAAATTCAGCCTGGAAAAGACTCA<br>GGCGATATTCAGCTTAGGTTTAATAAGTCAAACTGGGGCAACTACGACCA<br>ATCAAACGACTGGTCTTGGGTACAGTCTATGACAAGTTACGGAGAAAATA<br>AAAAGATAACTTTGTATATTGACGGCAAGTTGGTGTGGGGACAGGAGCCG<br>ACAAAAGACACA (SEQ ID NO: 85) | |
| Caldicellulos iruptor kristjanssonii Predicted based on amino acid sequence - Contig 00163 or2461 | ATGAAAAAAATAATATTAAAGTCAGGAATACTTTTGTTAGTGGTAATTTTG<br>ATAGTGTCTATACTTCAATTTTTACCGGTGTTTGCACAGAGCACACCTAT<br>GAAAAGGAGAAGTACCCTCATCTTTTAGGTAACCAGGCAGTCAAAAAGCC<br>ATCTGTGGCAGGACTTCAGATAATTGAAAAAAACGGCAAGAAATACC<br>TTGCTGACCAGAAGGGTGAGATTATTCAACTTAGGGGCATGAGTACTCAC<br>GGATTACAATGGTATGGCGATATAATTAACAAAAACGCTTTTGAGGCTTTA<br>AGCAAGGACTGGGAATGTAACGTAGTGAGGTTAGCAATGTACGTGGGCGA<br>GGGAGGTTATGCTAGTAATCCGTCTATAAAACAGAAAGTGATTGAGGGCA<br>TAAAATTGGCTATAGAAAACGACATGTATGTGATTGTGGACTGGCATGTTT<br>TAAACCCAGGAGATCCAAACGCTGAGATATATAAGGCGCTAAGGATTTT<br>TTTAAGGAGATTGCAACGAGTTTTCCAAACGATTATCACATAATTTATGAG<br>CTTTGCAACGAGCCTAACCCAAATGAGCCAGGTGTAGAAAATTCATTAGA<br>CGGATGGAAGAAGGTAAAAGCATATGCTGAGCCGATTATAAAAATGTTGA<br>GAAGCTTTGGCAATCAAAATATAATTATAGTTGGCAGTCCAAATTGGAGT<br>CAAAGACCTGATTTTGCTATACAGGATCCTATTAACGACAAAAACGTGAT<br>GTACAGCGTTCACTTTTATTCTGGCACTCATAAGGTGGATTGGTTATGTGTT<br>TGAGAATATGAAGAATGCTTTTGAGAATGGCGTACCAATATTTGTCAGCG<br>AATGGGAACGTCTTTAGCTTCAGGTGATGGAGGCCCTTATTTAGATGAA<br>GCTGATAAATGGTTAGAGTACCTTAACAGCAATTATATTTCTTGGGTGAAT<br>TGGAGTCTTTCAAACAAGAACGACTAGCGCTGCATTTGTGCCATATGTT<br>TCTGGTATGCACGATGCTACGAGCTTGGATCCTGGAGATGCAAAGTTTG<br>GGATATAAAAGAACTTTCAATAAGCGGCGAGTACGTGAGAGCAAGAATA<br>AAGGGCATTGCTTACAAGCCAATTGAGAGGAATAGTCAGATTAAAGAGGG<br>AGAAACAGCACCTCTTGGCAAAAAGTCCTTCCGTCAACTTTTGAGGATG<br>ATACAAGACAAGGTTGGGATTGGGACGGCCCGAGCGGCGTCAAGGGCCCT<br>ATAACTATAGAATCAATTAATGGAAGTAAAGTGCTTAGTTTTGAGGTTGA<br>ATATCCTGAGAAGAAACCGCAGGATGGCTGGGCTACAGCAGCTAGACTTA<br>TATTAAAAGAAATAAACGCAAAAGGGAGGACAACAAATATTTGGCATTT<br>GACTTTTACATTAAGCCTGAGAGGGTGTCTAAAGGAATTGATTCAGATATTT<br>CTTGCTTTTAGCCCACCGAGTTTAGGATACTGGGCTCAAGTTCAGGACTCA<br>TTTAACATAGACTTGCTTAAGTTGAGTTCTGCAAGAAAAACTGAAGAGGG<br>ATTGTACAAGTTTAACGTGTTTTTTGACCTTGACAAGATTCAGGATGGTAA<br>AGTCCTTTCACCAGATACATTACTTAGGGATATATTAAGGGATATAGCTGA<br>CGGTAACAGCGACTTTAAGGGAAAAATGTTTATTGACAACGTGAGGTTTA<br>CAAATATATTGTTTGAGGATATTAGCTTTGAGAGCAGCCTTTACGACACTG<br>TGAGCAAGTTGTATAGCAAGAGAGTCATTAAGGGCACAAGCGCATTTAAG<br>TACCTTCCTGACAGATCTATTACGAGGGCAGAGTTTGCAGCTTTATGCGTA<br>AGAACATTGAACCTTAAGATAGAGAAGTACGACGGTAGATTTAGCGACGT<br>AAAGTCAAGCGCTTGGTACTCAGATGTGGTCTATACAGCATACAAGAACG<br>GTCTTTTTGGACAAGAAAAAACAAGTTTTTCCTGAGAGGATAATGAAG<br>AGGGAAGAGGTGCTGCATTAGCAATTGAAGTTTATAAGAGGTTGACGGG<br>CAAGATAGAGGTGAGCTTAGACGATATACAAATTGCAGATGAGGGATTAA<br>TTAACCCTCAGTATAGGGAATCTGTGAAACTTGCAGTGAAGTTGGGAATA<br>TTTGAATTATATTCAGACGGTACATTTGCACCGGGCAAGAGTATAAGCAG<br>AGGCGAGGTCGCAACAATTTTTTACAATTTACTTAACTTGGCTGGTAAAAT<br>T (SEQ ID NO: 86) | MKKIILKSGILLLVVILIVSILQILP<br>VFAQSTPYEKEKYPHLLGNQAV<br>KKPSVAGRLQIIEKNGKKYLAD<br>QKGEIIQLRGMSTHGLQWYGDII<br>NKNAFEALSKDWECNVVRLAM<br>YVGEGGYASNPSIKQKVIEGIKL<br>AIENDMYIVDWHVLNPGDPNA<br>EIYKGAKDFFKEIATSFPNDYHII<br>YELCNEPNPNEPGVENSLDGWK<br>KVKAYAEPIIKMLRSLGNQNIIIV<br>GSPNWSQRPDFAIQDPINDKNV<br>MYSVHFYSGTHKVDGYVFENM<br>KNAFENGVPIFVSEWGTSLASG<br>DGGPYLDEADKWLEYLNSNYIS<br>WVNWSLSNKNETSAAFVPYVS<br>GMHDATSLDPGDDKVWDIKELS<br>ISGEYVRARIKGIAYKPIERNSQI<br>KEGETAPLGEKVLPSTFEDDTRQ<br>GWDWDGPSGVKGPITIESINGSK<br>VLSFEVEYPEKKPQDGWATAAR<br>LILKEINAKREDNKYLAFDFYIK<br>PERVSKGMIQIFLAFSPPSLGYW<br>AQVQDSFNIDLLKLSSARKTEEG<br>LYKFNVFFDLDKIQDGKVLSPDT<br>LLRDIIIVIADGNSDFKGKMFIDN<br>VRFTNILFEDISFESSLYDTVSKL<br>YSKRVIKGTSAFKYLPDRSITRA<br>EFAALCVRTLNLKIEKYDGRFSD<br>VKSSAWYSDVVYTAYKNGLFG<br>QEKNKFFPERIMKREEVAALAIE<br>VYKRLTGKIEVSLDDIQIADEGLI<br>NPQYRESVKLAVKLGIFELYSDG<br>TFAPGKSISRGEVATIFYNLLNL<br>AGKI (SEQ ID NO: 117) |
| Caldicellulos iruptor kristjanssonii Predicted based on amino acid sequence - Contig00032 geneor1015 | ATGAAAGGATGCGTATATGGAAAACTTAAAAGATTTTCAGCACTTATACTT<br>GCAATACTTTTCTTGTAGCAATACTTATAGGAATAGGATCAGCAAAAGTA<br>TCAAAAGTATCAGGAGCAACAAAAAAGTCATTTATGGAATTTAATTTTGA<br>AAATAAACTTCAACACCTTTTAAAGCATCAGGAAATCAATGGTACTTA<br>AAATAGATTCAACAACAGCAGCAGAAGGATCATTTTCACTTCTTGCATCA<br>GGAAGAAAACAAATAGATGATGGAGTACTTCTTGATGTAACAAATCTTAT<br>AGATTATTCAAATGAATATACAATAGCACTTTATGTATATCAATAATCATC<br>AAAACTTCAAAGATTTGTAGTATCATCAGAAATAGAAACAAAATCAGGAA<br>AAGAAAATAAACTTCTTTGCGAAAAAGTAATAATACCTAATAATTGGAAA<br>AAACTTGATACATCACTTAATCTTACAGAACTTAAAGGAATAAAAAAGT<br>ATGGCTTAAAATATATGTACCTACATCAACAAATTTTATAGATCTTTT<br>TTTACACTTAAAGTATCAGATAATTCACATCTTATAAAATTTGAATCATTT<br>GAAGATAAATCAATAGCAGGATTTATACCTCAAGATAAAAATGCAAACT<br>TTCAGTATCAAAAGAAAAAGCATATCAAGGAACATATTCAATAAAACTTC<br>AACAAACAGCAAAAAACAAAATACAACAGTAACACTTCCTGTAAAAGG<br>AACATTTGAAAAGGAAAATCATATTCAATATCATTTTATGTATATCAACC | MKGCVYGKLKRFSALILAILFLV<br>AILIGIGSAKSVKVSGATKKSFM<br>EFNFENKLATPFKASGKSMVLKI<br>DSTTAAEGSFSLLASGRKQIDDG<br>VLLDVTNLIDYSNEYTIALYVYH<br>KSSKLQRFVVSSEIETKSGKENK<br>LLCEKVIIPNNWKKLDTSLNLTE<br>LKGIKKVWLKIYVPTSTTNFYID<br>LFTLKVSDNSHLIKFESFEDKSIA<br>GFIPQDKKCKLSVSKEKAYQGT<br>YSIKLQQTAKKQNTTVTLPVKG<br>TFEKGKSYSISFYVYQPILKSLNL<br>AIGVRFLENGKNTKEIVLGKVTV<br>PRNKWTETFASYTPSLDSKVKD<br>FVIFIKPLSDVSYYYLDNFTISDD<br>GWYSAVPDLDLPSLSEKYKDYF |

TABLE 2-continued

Exemplary Biomass Degrading Enzymes That Can Be Used According to the Present Invention

| Organism and Protein (Gene) | Codon-Optimized DNA Sequence | Accession Number and Amino Acid Sequence |
|---|---|---|
| | TATACTTAAATCACTTAATCTTGCAATAGGAGTAAGATTTCTTGAAAATGG AAAAATACAAAAGAAATAGTACTTGGAAAAGTAACAGTACCT AGAAATAAATGGACAGAAACATTTGCATCATATACACCTTCACTTGATTCA AAAGTAAAAGATTTTGTAATATTTATAAAACCTCTTTCAGATGTATCATAT TATTATCTTGATAATTTTACAATATCAGATGATGGATGGTATTCAGCAGTA CCTGATCTTGATCTTCCTTCACTTTTCAGAAAAATATAAAGATTATTTTAAA GTAGGAGTAGCAGTACCTTATAAAGCACTTACAAATCCTGTAGATGTAGC ATTTATAAAAAGACATTTTAATTCAATAACAGCAGAAAATGAAATGAAAC CTGAAGCACTTGAACCTTATGAAGGAACATTTAATTTTTCAATAGCAGATG AATATCTTGATTTTTGCAAAAAAATAATATAGCAATAAGAGGACATACA CTTGTATGGCATCAACAAACACCTTCATGGTTTTTTGAAAATCCTCAAACA GGAGAAAAACTTACAAATTCAGAA AAAGATAAAAAATACTTCTTGAAAGACTTAAAAAATATATACAAACAGT AGTATCAAGATATAAAGGAAGAATATATGCATGGGATGTAGTAAATGAAG CAATAGATGAAAATCAACCTGATGGATTTAGAAGATCAGATTGGTTTAAT ATACTTGGACCTGAATATATAGAAAAGCATTTATATATGCACATCAAGC AGATCCTAATGCACTTCTTTTTTATAATGATTATTCAACAGAAAATCCTGT AAAAAGAGAATATATATATAAACTTATAAAAGATCTTAAAGAAAAAGGA GTACCTATACATGGAGTAGGACTTCAATGCCATATAACAGTATCATGGCCT TCAGTAGAAGAAGTAGAAAGAACAATAAAACTTTTTTCATCAATACCTGG AATAAAAATACATGTAACAGAAATAGATATATCAGTAGCAAAAGAATTTG GAGAAGATATAGATGAAGAAACAAAAAGATATCTTCTTATACAACAAGCA AGAAAACTTAAAGATCTTTTTGAAGTATTTAAAAAATATAAAAATGTAGT AACATCAGTATCATTTTGGGGACTTAAAGATGATTATTCATGGCTTAAAGG AGATTTTCCTCTTCTTTTTGATAAAGATTATCAACCTAAATTTGCATTTTGG TCACTTATAGATCCTTCAGTAGTACCTGAAGAA (SEQ ID NO: 87) | KVGVAVPYKALTNPVDVAFIKR HFNSITAENEMKPEALEPYEGTF NFSIADEYLDFCKKNNIAIRGHT LVWHQQTPSWFFENPQTGEKLT NSEKDKKILLERLKKYIQTVVSR YKGRIYAWDVVNEAIDENQPDG FRRSDWFNILGPEYIEKAFIYAH QADPNALLFYNDYSTENPVKRE YIYKLIKDLKEKGVPIHGVGLQC HITVSWPSVEEVERTIKLFSSIPGI KIHVTEIDISVAKEFGEDIDEETK RYLLIQQARKLKDLFEVFKKYK NVVTSVSFWGLKDDYSWLKGD FPLLFDKDYQPKFAFWSLIDPSV VPEE (SEQ ID NO: 118) |
| *Caldicellulosiruptor kristjanssonii* Predicted based on amino acid sequence - Contig00132 geneor2152 | ATGAAAGAAAACTTATATCACTTATACTTGTATTTATATTTACATTGCA CTTCTTCTTCCTGCATATGCAGATCAAAATCTTCCTGGAACATCATCATCA CAAACAGTAACATCATCAACATATGATACAACACAAACACAAACATATCA AACAACACAAAATCAACATATTCACAAACATATAATACACAAAATTCAA CACCTACACCTACACCTACACCTACACCTACACCTTAACACACCTAC CTACACCTACACCTACACCTACAACAGTAACATCAACATATTCATCAACAT ATTCATCAAATTCAACAATAAATGTAATACCTCCTATATCAAATGATAATA TAAAACTTAAAGAACCTCAAAAACTTACAAAAGAACAAAAAAAACAAT AATATCACTTATATGGCAAATAAATCAACTTAGAGTAAAATTCAATAAAA TAAATGCAGAATAAATTATCTTAGAGCAAAATAAATGCATATGTACAA GCAGCAAAAGATATGATAAAATATTTTAATCAAGAATGAATAAAAT AATAAATGAAGTAAATAAACAATATCACAACTTCAAAAGAACTTAATA AAAAAATTATTCATCATCAAAAGTAGCAGAACTTAATAAACAACTTAAT CAAAAACTTAATGAACTTAAAGTATATGAAGAAGTATATAAAAATCAACA ACAACAAGCAGTAGATCAAGCAGTATATCAAATAAAACAATTTGTAGATC AAATACAACCTACAGTATCACAAAAAGTATATCAAATAAATACAATAGAT AAACAAATAAAAGTAAAACTTTATGAATATCATCAAATAGCAAAAACATC AGATTATAATAAAATGGTATCAATACTTAATGAAGTAGTATCACTTTATCA AACAAAGTAAATACAATATCAGAAATAAAAAATCTTTATACAGATATAC TTTCAAAAATAGAAAATATAGTAAAAAATTCACTTAATATGCCTAAAAAA TATATACAACCTATGCAAGAAAAAAAATAACATACCTGGAAAAGGAA ATTCAAAAATAGAAATAGAAATAAAAAAAAAATCCTCAACAACCTCAAAA AGGAAAAAAAAAA (SEQ ID NO: 88) | MKRKLISLILVFIFTLALLLPAYA DQNLPGTSSSQTVTSSTYDTTQT QTYQTTQNTTYSQTYNTQNSTP TPTPTPTPTPITTPTPTPTPTTV TSTYSSTYSSNSTINVIPPISNDNI KLKEPQKLTKEQKKTIISLIWQIN QLRVKFNKINAEVNYLRAKINA YVQAAKRYDKIFFNQEMNKIIN EVNKTISQLQKELNKKNYSSSK VAELNKQLNQKLNELKVYEEV YKNQQQQAVDQAVYQIKQFVD QIQPTVSQKVYQINTIDKQIKVK LYEYHQIAKTSDYNKMVSILNE VVSLYQTKVNTISEIKNLYTDILS KIENIVKNSLNMPKKYIQPMQEK KITIPGKGNSKIEIEIKKNPQQPQ KGKKK (SEQ ID NO: 119) |
| *Caldicellulosiruptor kristjanssonii* Predicted based on amino acid sequence - Contig00041 geneor1107 | CTTTCACCTACACCTACAAAACACCTACACCTACATCAACACCTGCACCT ACACAAACACCTACAGTAACACCTACACCTACACCTAATGCAGGAGGAAT ACTTATAATAACAGATACAATAGTAGTAAAAGCAGGACAAACATATGATG GAAAAGGAGTAAAAATAATAGCACAAGGAATGGGAGATGGATCACAATC AGAAAATCAAAAACCTATATTTAAACTTGAAAAAGGAGCAAAACTTAAA ATGTAATAATAGGAGCACCTGGATGCGATGGAATACATTGCTATGGAGAT AATGTAATAGAAAATGTAATGTGGGAAGATGTAGGAGAAGATGCACTTAC AGTAAAAGGAGAAGGAGTAGTAGAAGTAATAGGAGGATCAGCAAAAGAA GCAGCAGATAAAGTATTTCAACTTAATGCACCTTGCACATTTAAAGTAAA AAATTTTACAGCAACAAATATAGGAAAACTTGTAAGACAAAATGGAGGAA CAACATTTAAAGTAGTAATATATCTTGAAAATGTAACACTTAATAATGTAA AATCATGCGTAGCAAATCAGATTCACCTGTATCAGAACTTTGGTATCATA ATCTTGTAGTAAATAATTGCAAAACACTTTTTGAATTTCCTTCACAATCAC AAATACATCAATAT (SEQ ID NO: 89) | LSPTPTKTPTPTSTPAPTQTPTVT PTPTPNAGGILIITDTIVVKAGQT YDGKGVKIIAQGMGDGSQSENQ KPIFKLEKGAKLKNVIIGAPGCD GIHCYGDNVIENVMWEDVGED ALTVKGEGVVEVIGGSAKEAAD KVFQLNAPCTFKVKNFTATNIG KLVRQNGGTTFKVVIYLENVTL NNVKSCVAKSDSPVSELWYHNL VVNNCKTLFEFPSQSQIHQY (SEQ ID NO: 120) |
| *Caldicellulosiruptor kristjanssonii* Predicted based on amino acid sequence - Contig 00091 | GTGAGCATAGAGAAAGAGTTAATGATCTTTTGCAGAAAATGACTATTGA GGAGAAGGTGTATCAGTTGACTTCTATATTAGTCCAAGATATTCTTGAAAA TGACAAGTTTAGCCCGCAGAAAGCTAAGGAAAAAATACCTAACGGAATTG GTCAGATAACAAGGCTTGCTGGCGCAAGTAATTTGAGCCCAGAAGAGGCA GCAAAAACTGCTAATGAAATTCAAAGTTTCTTATAGAGAACACAAGGTT GGGAATACCAGCTATGATTCATGAGGAGTCTTGTTCAGGTTTTATGGCTAA GGGCGCAACTGTATTTCCTCAGTCTATTGGAGTTGCTTGCACATTTGACAA CGAAATTGTGGAAGAACTTGCAAAAGTGATAAGGACACAGATGAAAGCT | VSIEKRVNDLLQKMTIEEKVYQ LTSILVQDILENDKFSPQKAKEKI PNGIGQITRLAGASNLSPEEAAK TANEIQKFLIENTRLGIPAMIHEE SCSGFMAKGATVFPQSIGVACTF DNEIVEELAKVIRTQMKAVGAH QALAPLIDVARDARWGRVEETF GEDPYLVANMAVSYVKGLQGD |

TABLE 2-continued

Exemplary Biomass Degrading Enzymes That Can Be Used According to the Present Invention

| Organism and Protein (Gene) | Codon-Optimized DNA Sequence | Accession Number and Amino Acid Sequence |
|---|---|---|
| or1761 | GTGGGTGCACACCAGGCTTTGGCACCATTAATTGACGTCGCTAGGGATGC AAGATGGGGCAGAGTTGAAGAGACTTTTGGTGAGGACCCTTACTTAGTAG CTAATATGGCAGTTTCTTATGTAAAGGGATTACAGGGCGACGATATAAAG GACGGAATAGTGGCAACAGGTAAGCATTTTGTTGGCTACGCAATGAGTGA GGGCGGAATGAATTGGGCACCAGTACACATTCCTGAAAGAGAATTGAGGG AAGTTTACTTGTATCCTTTTGAGGTCGCAGTTAAGGTGGCAGGCCTTAAA GTATAATGCCTGCTTATCACGAGATTGATGGCATTCCGTGCCACGCTAATA GAAAATTGTTAACAGATATAGCTAGGGGAGAGTGGGGTTTTGATGGAATA TATGTTTCTGATTACAGCGGTGTGAAGAATTTACTTGACTATCACAAGAGC GTCAAGACGTATGAAGAAGCAGCTGCTCTTAGCTTGTGGGCTGGATTAGA TATTGAGTTGCCTAAAATAGAGTGTTTATTGAAAGCAACGCACT TAAAGAAGGTAAATTTGATATGGCTTTAGTGGACGCTGCAGTGAAAAGAG TATTGGAAATGAAGTTTAGACTTGGCCTTTTTGACAATCCATACATTAAGA CAGAAGGTGTTGTAGAACTTTTTGACAACAAAGAGCAAAGGCAACTTAGC AGAAAAGTGGCACAAGAAAGTATAGTGCAATCAATTTTTGAGGCTATTAAG TCCGTTAAGCAAGGACCTTAAGAAAATTGCAGTGATTGGCCCGAACGCAA ACAGTGTTAGAAACTTATTGGGTGACTATTCTTACCCGGCTCATATTGCTA CTTTGGAAATGTTTTTTATTAAAGAGGACAGGGAGTGGGCAATGAGGAA GAGTTTGTGAAGAATGTCATTAACATGAAGTCAATTTTTGAGGCTATTAAG GATAAGGTGAGCTCTAACACTGAAGTCGTGTACGCAAAAGGTTGCGATGT AAATAGCCAAGATAAATCAGGTTTTGAAGAGGCAAAGAAAGCTGCTGAA GGCGCAGATGCAGTTATATTAGTAGTAGGAGACAAGGCAGGATTAAGATT AGATTGCACGAGCGGCAGTCTAGAGATAGAGCATTGTTTGAGGCTTCCAG GCGTACAAGAAGATCTTGTCAAGGAAATTGTTTCTGTGAATCCAAACACG GTGGTTGTATTGGTTAATGGCAGACCAGTTGCACTTGATTGGATAATGGAA AATGTGAAAGCTGTACTTGAGGCATGGTTTCCAGGTGAAGAGGGCGCAGA TGCTGTCGCAGATATTTTGTTGGAGACTATAATCCAGGCGGCAAGTTGGC TATTAGCTTTCCAAGAGATGTAGGTCAAGTTCCAGTATATTACGGACACAA ACCGTCAGGCGGCAAATCTTGCTGGCACGGAGATTATGTTGAAATGTCAA CGAAGCCGTTGTTGCCTTTTGGCTACGTTTGTCTTATACAACGTTTGAGT ACAAGAACTTTGCTATAGAAAAAGAAGATTGGTATGGACGAAAGTATT AAAGTTTCAGTAGAAGTTGAAAACACAGGAAAATACGAGGGCGACGAGA TAGTCCAACTTTATACGAGAAAGGAAGAGTATCTTGTGACAAGGCCAGTA AAAGAATTGAAGGGATATAAAGAGTGCACTTAAAACCGGGCGAAAAGA AGAAAGTTGTGTTTGAATTATATCCGGACTTATTTGCTTTTTATGACTACG ACATGAATAGGGTGGTTACTCCTGGTGTAGTTGAAGTGATGATTGGCGCTT CAAGTGAAGATATTAAGTTTACTGGCACGTTTGAGATAGTGGGTGAGAAA AAGGACGCAAAAGAGATTAAGAATTACTTGAGCAGAGCTTGGTGTGAA (SEQ ID NO: 90) | DIKDGIVATGKHFVGYAMSEGG MNWAPVHIPERELREVYLYPFE VAVKVAGLKSIMPAYHEIDGIPC HANRKLLTDIARGEWGFDGIYV SDYSGVKNLLDYHKSVKTYEEA AALSLWAGLDIELPKIECFTEEFI KALKEGKFDMALVDAAVKRVL EMKFRLGLFDNPYIKTEGVVELF DNKEQRQLSRKVAQESMVLLK NDSFLPLSKDLKKIAVIGPNANS VRNLLGDYSYPAHIATLEMFFIK EDRGVGNEEEFVKNVINMKSIFE AIKDKVSSNTEVVYAKGCDVNS QDKSGFEEAKKAAEGADAVILV VGDKAGLRLDCTSGESRDRASL RLPGVQEDLVKEIVSVNPNTVV VLVNGRPVALDWIMENVKAVL EAWFPGEEGADAVADILFGDYN PGGKLAISFPRDVGQVPVYYGH KPSGGKSCWHGDYVEMSTKPLL PFGYGLSYTTFEYKNFAIEKEKI GMDESIKVSVEVENTGKYEGDE IVQLYTRKEEYLVTRPVKELKG YKRVHLKPGEKKKVVFELYPDL FAFYDYDMNRVVTPGVVEVMI GASSEDIKFTGTFEIVGEKKDAK EIKNYLSRAWCE (SEQ ID NO: 121) |
| Caldicellulos iruptor kristjanssonii Predicted based on amino acid sequence - Contig 00017 or0462 | TTAAATAAACTTCCTAGATATAAGGGCTTTAATTTGTTAGGCTTGTTTGTA CCAGGCAGGATACTTGGATTTTTTGAGGACGATTTTAAGTGGATGGGCGA ATGGGGTTTTAACTTTGCAAGGATTCCTATGAACTACAGGAACTGGTTTGT TGAGGGATCATCTGACATAAAAGAGGAAATTTTGCAAATGATAGACAGA TTATAGAGTGGGGCGAAAAGTACGAGATACATATTTGTCTTAACATACAC GGCGCTCCAGGATATTGCGTAAATGAAAAGACAAAACAGGGCTACAATTT GTGGAAAGACGAAGAACCTTTAGAGCTTTTTGTAAGCTACTGGCAAACTTT TGCTAAAAGGTATAAGGGCATAAGCAGTAAAATGCTTTCATTTAACCTTAT AAACGAGCCAAGGCAATTTTCTGAGGAAGAAATGACTAAGGAGGACTTTA TTAGGGTTATGACTTACACAACTCAGAAAATAAGGGAGATAGGAAAGGAG AGGTTAATTATAGTGGACGGTGTGGATTATGGCAATGAGCCTGTTGTAGA ATTAGCAAACTTGGCGTGGCACAATCATGTAGAGCATATACCGTTTGA GGTCAGTCATTGGGGTGCAGAATGGGTTGAAGGCTCAAGAAATTTTCAA AACCTAGTTGGCCATTAGTAAGAGAAATGGAGAAATTGTGGATAAAGAG TACTTGAAGAAGCACTACGAGAAATGGGCTAAGTTGATTTCATTAGGTGT GGGAGTGATATGCGGAGAAGGTGAGCATATAAATACACGCCGCACGAT GTGGTCATAAGATGGTTTAGCGATGTATTAGATATTCTTAAGGAATTTGGT ATAGGTATTGCTTTATGGAACCTTAGGGGTCCATTTGGTATTATAGATAGC GGTAGAGAAGATGTTGAATACGAAGATTTTATGGACACAAATTGGACAG AAAGTTGTTAGAATTGCTTCAAAGATTT (SEQ ID NO: 91) | LNKLPRYKGFNLLGLFVPGRILG FFEDDDFKWMGEWGFNFARIPM NYRNWFVEGSSDIKEEILQMIDR VIEWGEKYEIHICLNIHGAPGYC VNEKTKQGYNLWKDEEPLELFV SYWQTFAKRYKGISSKMLSFNLI NEPRQFSEEEMTKEDFIRVMTYT TQKIREIGKERLIIVDGVDYGNEP VVELANLGVAQSCRAYIPFEVS HWGAEWVEGSRNFTKPSWPLV RENGEIVDKEYLKKHYEKWAK LISLGVGVICGEGGAYKYTPHD VVIRWFSDVLDILKEFGIGIALW NLRGPFGIIDSGREDVEYEDFYG HKLDRKLLELLQRF (SEQ ID NO: 122) |
| Caldocellum saccharolyticum Biomass degrading enzyme (celA) | ATGGTTGTGACATTTCTTTTTATATTAGGCGTCGTTTACGGAGTAAAGCCG TGGCAAGAAGCAAGAGCTGGGAGTTTTAACTATGGAGAGGCATTACAGAA AGCAATTATGTTTTATGAATTTCAAATGTCGGGTAAATTGCCAAATTGGGT AAGAAATAATTGGAGAGGATGTTCTGCTCTTAAAGACGGGCAAGACATG GTCTTGATTTGACAGGTGGATGGTTTGATGCAGGCGATCATGTTAAATTTA ATTTACCAATGAGCTATACAGGTACGATGTTATCATGGGCAGCTTACGAAT ATAAGGATGCTTTTGTTAAGAGTGGTCAACTTGAACATATACTAAATCAAA TCGAATGGGTAAATGACTATTTCGTTAAGTGCCATCCTTCAAAATATGTTT ATTACTACCAGGTAGGCGATGGCGGCAAAGACCATGCCTGGTGGGCCCG GCAGAAGTAATGCAGATGGAGAGACCTTCATTTAAGGTGACACAATCATC ACCTGGCTCAGCAGTGGTTGCTGAAACAGCTGCTTCTTTGGCGGCCGCTTC AATAGTCCTTAAAGATAGGAATCCTACTAAAGCAGCTACTTACTTGCAAC ATGCAAAGGATTTATACGAATTTGCCGAAGTAACAAAATCTGATAGTGGT | L32742 AND AAA91086 MVVTFLFILGVVYGVKPWQEAR AGSFNYGEALQKAIMFYEFQMS GKLPNWVRNNWRGDSALKDGQ DNGLDLTGGWFDAGDHVKFNL PMSYTGTMLSWAAYEYKDAFV KSGQLEHILNQIEWVNDYFVKC HPSKYVYYQVGDGGKDHAW WGPAEVMQMERPSFKVTQSSPG SAVVAETAASLAAASIVLKDRN PTKAATYLQHAKDLYEFAEVTK SDSGYTAANGYYNSWSGFYDEL SWAAVWLYLATNDSTYLTKAE |

TABLE 2-continued

Exemplary Biomass Degrading Enzymes That Can Be Used According to the Present Invention

| Organism and Protein (Gene) | Codon-Optimized DNA Sequence | Accession Number and Amino Acid Sequence |
|---|---|---|
| | TATACTGCAGCAAATGGTTACTATAATTCATGGTCCGGTTTTTATGACGAA<br>CTTTCATGGGCCGCAGTATGGTTGGCAACTAATGATTCTACATAT<br>TTAACAAAAGCCGAATCTTACGTTCAAAATTGGCCAAAAATAAGCGGTTC<br>TAATATTATAGATTACAAGTGGGCTCATTGCTGGGATGATGTGCATAATGG<br>TGCTGCTCTTTTACTCGCTAAGATCACTGATAAAGATACATACAAACAAT<br>TATTGAATCACATCTTGATTATTGGACCACTGGTTATAATGGAGAAAGGAT<br>AAAATACACACCAAAAGGACTGGCATGGTTAGATCAGTGGGGGTCTCTTA<br>GGTATGCAACGACAACAGCGTTTCTTGCATTTGTTTATTCAGATTGGAGTG<br>GTTGCCCTACAGGCAAAAAGAAACTTATAGAAAGTTTGGTGAATCTCAG<br>ATAGATTACGCACTTGGATCTACTGGTAGATCATTTGTCGTAGGTTTTGGC<br>ACAAACCCCCCTAAAAGACCTCATCATAGACAGCACACTCTTCTTGGGC<br>AGATTCTCAATCAATCCCGAGTTACCATAGACATACATTATATGGGGCCTT<br>AGTAGGGGGGCCAGGATCAGATGATTCATATACTGATGATATATCAAATT<br>ATGTGAATAACGAGGTAGCTTGCGATTATAATGCAGGGTTTGTTGGAGCA<br>TTAGCAAAGATGTATTTATTATATGGTGGGAATCCATTCCCAGATTTTAAA<br>GCCATAGAAACACCAACCAACGACGAATTCTTTGTAGAAGCGGGTATAAA<br>TGCTTCTGGTACAAATTTCATTGAAATAAAAGCAATCGTTAATAATCAGTC<br>AGGATGGCCTGCAAGGGCAACTAATAAGTTAAAATTTAGATACTTTGTAG<br>ATTTGTCAGAACTTATTAAAGCAGGATATAGCCCAAACCAGTTAACTTTGT<br>CGACAAATTATAATCAAGGCGCTAAAGTAAGTGGACCTTACGTGTGGGAT<br>AGCTCAAGAAATATATACTACATATTAGTTGACTTTACAGGCACGTTGATA<br>TACCCTGGCGGACAAGATAAGTACAAGAAAGAAGTGCAGTTTAGAATAGC<br>TGCTCCGCAAAATGTACAATGGGACAATAGCAATGACTACTCGTTTCAAG<br>ATATAAAAGGCGTATCTTCTGGTTCGGTGGTTAAGACAAAATATATTCCTC<br>TTTATGATGAAGATATAAAGGTATGGGAGAAGAGCCAGGAACATCTGGT<br>GTAAGCCCTACTCCTACGGCAAGTGTAACACCTACTCCTACGCCTACGCCG<br>ACTGCAACTCCAACTCCAACACCAACGCCAACAGTTACTCCAACACCAAC<br>TGTTACAGCAACACCTACCCCGACCCCTACTCCAACAAGTACACCTACGGT<br>AACACCTACACCTACTCCTGTTAGCACACCTGCTACATCTGGGCAAATTAA<br>AGTGTTATACGCCAACAAAGAAACTAATTCCACAACTAATACAATTAGAC<br>CATGGTTGAAAGTTGTAAATTCAGGCTCTAGCAGCATCGACTTGAGCAGA<br>GTAACAATTAGATATTGGTATACAGTTGATGGCGAAAGGTCAATCTGC<br>AATTAGCGACTGGGCACAAATAGGTGCTAGCAATGTCACATTTAAATTTGT<br>GAAATTGTCATCAAGTGTATCAGGTGCTGATTACTACCTTGAGATTGGATT<br>TAAATCTGGAGCAGGACAATTACAGCCAGGCAAGGATACTGGAGAGATAC<br>AAATCAGATTTAATAAGGATGATTGGAGCAACTATAACCAAGGAAATGAT<br>TGGAGCTGGATTCAAAGCATGACGTCTTACGGCGAAAATGAAAAGTCAC<br>AGCTTATATAGACGGCGTTTTGGTATGGGACAGGAACCGAGCGGTACTA<br>CACCAGCTCCTACATCAACACCTACTGTCACAGTIACCCCTACACCAACTC<br>CGACACCAACCTGTGACACCAACTCCAACAGTCACTGCAACACCTACACCA<br>ACACCTGACCCCAACATCAACTCCAGTTTTCAACACCAGCTACAGGCGGTCA<br>AATAAAAGTTCTTTATGCAAACAAAGAAACCAATTCAACAACAAATACTA<br>TACGGCCCTGGCTGAAAGTAGTTAACTCAGGCTCATCATCTATTGACCTTT<br>CTAGAGTTACAATAAGATACTGGTATACAGTAGACGGTGAAAGAGCCACAA<br>TCTGCTATTTCTGATTGGGCCAAATAGGAGCATCAAACGTTACGTTTAAA<br>TTCGTCAAATTGTCATCGAGCGTGTCAGGAGCTGATTATTATCTTGAAATT<br>GGCTTTAAATCTGGCGCTGGACAGTTACAACGGGTAAAGATACAGGAGA<br>AATTCAAATTAGGTTTAACAAGGATGATTGGTCAAACTACAATCAGGGCA<br>ATGATTGGAGTTGGATTCAATCTATGCAAGTTACGGAGAGAATGAAAAA<br>GTTACGGCTTATATAGATGGCGTCCTTGTATGGGGCAAGAGCCAAGCGG<br>CGCTACTCCTGCACCAACAGTTACTCCGACTCCAACGGTAACGCCAACTCC<br>TACACCTGCACCTACACCTACAGCTACCCCAACTCCTACACCATCGAGTACAC<br>GGTCACACCTACGCCCACGGTAGCCCCAACTCCTACACCATCGAGTACAC<br>CAAGTGGCCTGGGCAAATATGGACAAAGTTTATGTGGCTATGGAACAAA<br>ATACATGACCCAGCTAGCGGCTATTTCAATCAAGATGGAATACCGTATCAT<br>AGTGTGGAAACTTTGATTTGTGAAGCACCTGATTATGGCCATCTTACTACT<br>TCTGAGGCATTTTCATACTACGTATGGTTGAGGCGGTTTATGGAAAATTA<br>ACAGGAGATTGGTCAAAATTTAAAACTGCCTGGGATACACTTGAAAAATA<br>TATGACCTAGTGCTGAGGATCAGCCTATGCGATCATATGACCCGAATA<br>AACCAGCAACATATGCTGGAGAATGGGAAACACCGGATAAGTACCCTAGC<br>CCCTTAGAATTTAATGTACCTGTTGGCAAAGATCCGTTACATAATGAATTA<br>GTTAGCACATATGGATCTACGCTTATGTATGGTATGCACTGGTTAATGGAT<br>GTTGATAACTGGTATGGCTACGAAAACGTGGAGATGGCGTTAGCAGAGC<br>ATCTTTTATAAATACATTTCAGAGGGGACCAGAAGAATCTGTTTGGGAAA<br>CAGTGCCACATCCATCATGGGAAGAGTTTAAATGGGGTGGACCAAACGGC<br>TTTTTGGATTTGTTTATTAAAGATCAAAATTATTCAAAACAATGGAGATAC<br>ACTAATGCGCCTGACGCAGATGCAAGAGCAATTCAAGCCACTTACTGGGC<br>TAAGGTTTGGGCAAAGAACAAGGCAAGTTTAATGAAATAAGCAGTTATG<br>TTGGTAAGGCAGCTAAAATGGGCGATTACTTAAGATATGCTATGTTCGATA<br>AGTACTTTAAACCTCTGGGATGCCAAGATAAGAATGCAGCAGGGGGTACG<br>GGATATGATTCAGCTCACTATTTACTTAGTTGGTATTATGCTTGGGGAGGA<br>GCTTTGGACGGAGCATGGTCGTGGAAAATAGGATGCTCACATGCTCATTTT<br>GGATATCAAAATCCAATGGCAGCTTGGGCATTAGCAAATGACTCGGATAT<br>GAAACCAAAATCGCCAAATGGAGCTTCAGATTGGGCAAAATCATTAAAGA | SYVQNWPKISGSNIIDYKWAHC<br>WDDVHNGAALLLAKITDKDTY<br>KQIIESHLDYWTTGYNGERIKYT<br>PKGLAWLDQWGSLRYATTTAF<br>LAFVYSDWSGCPTGKKETYRKF<br>GESQIDYALGSTGRSFVVGFGTN<br>PPKRPHHRTAHSSWADSQSIPSY<br>HRHTLYGALVGGPGSDDSYTDD<br>ISNYVNNEVACDYNAGFVGALA<br>KMYLLYGGNPIPDFKAIETPTND<br>EFFVEAGINASGTNFIEIKAIVNN<br>QSGWPARATNKLKFRYFVDLSE<br>LIKAGYSPNQLTLSTNYNQGAK<br>VSGPYVWDSSRNIYYILVDFTGT<br>LIYPGGQDKYKKEVQFRIAAPQ<br>NVQWDNSNDYSFQDIKGVSSGS<br>VVKTKYIPLYDEDIKVWGEEPG<br>TSGVSPTPTASVTPTPTPTATP<br>TPTPTPTVTPTPTVTATPTPTPTP<br>TSTPTVTPTPTPVSTPATSGQIKV<br>LYANKETNSTTNTIRPWLKVVN<br>SGSSSIDLSRVTIRYWYTVDGER<br>AQSAISDWAQIGASNVTFKFVK<br>LSSSVSGADYYLEIGFKSGAGQL<br>QPGKDTGEIQIRFNKDDWSNYN<br>QGNDWSWIQSMTSYGENEKVT<br>AYIDGVLVWGQEPSGTTPAPTST<br>PTVTVTPTPTPTVTPTPTVTAT<br>PTPTPTPTSTPVSTPATGGQIKVL<br>YANKETNSTTNTIRPWLKVVNS<br>GSSSIDLSRVTIRYWYTVDGERA<br>QSAISDWAQIGASNVTFKFVKLS<br>SSVSGADYYLEIGFKSGAGQLQP<br>GKDTGEIQIRFNKDDWSNYNQG<br>NDWSWIQSMTSYGENEKVTAYI<br>DGVLVWGQEPSGATPAPTVTPT<br>PTVTPTPTPAPTPTATPTPTPT<br>VTPTPTVAPTPTPSSTPSGLGKY<br>GQRFMWLWNKIHDPASGYFNQ<br>DGIPYHSVETLICEAPDYGHLTT<br>SEAFSYYVWLEAVYGKLTGDW<br>SKFKTAWDTLEKYMIPSAEDQP<br>MRSYDPNKPATYAGEWETPDK<br>YPSPLEFNVPVGKDPLHNELVST<br>YGSTLMYGMHWLMDVDNWYG<br>YGKRGDGVSRASFINTFQRGPEE<br>SVWETVPHPSWEEFKWGGPNGF<br>LDLFIKDQNYSKQWRYTNAPDA<br>DARAIQATYWAKVWAKEQGKF<br>NEISSYVGKAAKMGDYLRYAM<br>FDKYFKPLGCQDKNAAGGTGY<br>DSAHYLLSWYYAWGGALDGA<br>WSWKIGCSHAHFGYQNPMAAW<br>ALANDSDMKPKSPNGASDWAK<br>SLKRQIEFYRWLQSAEGAIAGG<br>ATNSWNGRYEKYPAGTATFYG<br>MAYEPNPVYRDPGSNTWFGFQ<br>AWSMQRVAEYYYVTGDKDAG<br>TLLEKWVSWIKSVVKLNSDGTF<br>AIPSTLDWSGQPDTWNGTYTGN<br>PNLHVKVVDYGTDLGITASLAN<br>ALLYYSAGTKKYGVFDEEAKNL<br>AKELLDRMWKLYRDEKGLSAP<br>EKRADYKRFFEQEVYIPAGWTG<br>KMPNGDVIKSGVKFIDIRSKYKQ<br>DPDWPKLEAAYKSGQVPEFRYH<br>RFWAQCDIAIVNATYEILFGNQ<br>(SEQ ID NO: 123) |

TABLE 2-continued

Exemplary Biomass Degrading Enzymes That Can Be Used According to the Present Invention

| Organism and Protein (Gene) | Codon-Optimized DNA Sequence | Accession Number and Amino Acid Sequence |
|---|---|---|
| | GACAGATAGAATTTTATAGATGGTTGCAATCAGCCGAAGGCGCCATAGCA<br>GGCGGTGCAACGAATTCATGGAATGGTAGATATGAAAAATACCCTGCAGG<br>AACAGCAACATTTTATGGTATGGCCTATGAACCGAATCCCGTATATAGGG<br>ATCCCGGAAGTAATACGTGGTTTGGATTTCAGGCTTGGTCCATGCAGAGA<br>GTAGCTGAATATTATTATGTAACAGGCGATAAAGATGCAGGCACTCTTTTA<br>GAAAAATGGGTATCATGGATCAAATCTGTCGTAAAATTAAATAGCGATGG<br>GACATTTCGATACCCTCTACATTGGATTGGTCAGGACAACCAGATACGTG<br>GAATGGCACGTATACAGGAAATCCAAACCTTCATGTTAAAGTCGTGGACT<br>ATGGAACAGATTTAGGCATAACAGCAAGCTTGGCAAATGCTTTGTTGTACT<br>ATTCCGCAGGGACTAAAAAATATGGTGTATTTGACGAAGAAGCTAAAAAT<br>CTTGCAAAAGAGTTGCTTGACAGGATGGTGGAAACTCTACAGAGATGAAAA<br>AGGACTTTCTGCACCAGAAAAGAGAGCCGATTATAAAAGATTTTTCGAAC<br>AAGAAGTGTACATACCTGCAGGATGGACTGGAAAAATGCCAAATGGCGAT<br>GTTATTAAAAGTGGCGTTAAGTTTATAGATATAAGATCAAAATACAAGCA<br>GGATCCAGATTGCCAAAACTAGAAGCAGCTTACAAATCAGGGCAAGTTC<br>CTGAATTTAGATATCATAGATTTTGGGCACAATGCGATATCGCAATTGTTA<br>ACGCAACTTACGAAATTCTTTTTTGGCAATCAG (SEQ ID NO: 92) | |
| *Caldocellum saccharolyticum* CelB (coded_by = "X13602.1: 679 . . . 3798") | ATGAAAAGAAACCTTTTTAGAATAGTATCAAGGGTTGTGCTTATTGCTTTT<br>ATTGCATCAATTAGCTTGGTCGGAGCAATGAGCTATTTTCCTGTGGAAACA<br>CAAGCTGCACCAGATTGGAGCATACCGAGCTTATGTGAGAGCTATAAGGA<br>CGATTTTATGATAGGAGTTGCTATTCCGGCAAGATGCCTTTCAAATGATAC<br>AGACAAAAGAATGGTACTTAAACACTTTAACAGTATTACTGCAGAGAATG<br>AGATGAAGCCAGAGAGCTTATTGGCTGGCCAGACAAGTACTGGATTAAGT<br>TATAGATTTAGCACGGCTGACGCATTTGTTGATTTTGCTAGTACGAATAAG<br>ATTGGCATTAGGGGACACACTTTAGTATGGCATAATCAGACACCGGACTG<br>GTTTTTAAGGACAGCAATGGACAAAGACTTAGCAAAGACGCATTGTTAG<br>CTAGACTTAAACAATATATATACGACGTGGTTGGTAGGTACAAAGGTAAA<br>GTCTATGCATGGGATGTAGTTAACGAGGCAATTGATGAAAATCAGCCTGA<br>TTCTTATAGGAGAAGCACATGGTACGAAATTTGCGGACCAGAATACATTG<br>AAAAGGCATTTATTTGGGCTCACGAAGCAGATCCTAATGCAAATTTATCC<br>ACAATGATTATAACACGGAGATAAGCAAAAAGAGGGACTTATAGCAAC<br>ATGGTGAAGAACCTTAAGGACAAGGGCATTCCAATACACGGCATAGGCAT<br>GCAGTGCCACATAAATGTCAACTGGCCGAGTGTAAGTGAAATTGAAAATA<br>GCATTAAGTTATTTTCAAGCATTCCTGGTATAGAGATACACATAACTGAGT<br>TGGACATGTCTTTGTATAACTACGGTTCTTCAGAGAACTACAGCACTCCAC<br>CTCAAGATCTTTTACAGAAGCAATCTCAAAAGTATAAAGAGATATTTACTA<br>TGTTGAAGAAATATAAAAACGTTGTCAAGAGCGTGACATTTTGGGGACTT<br>AAAGATGACTATAGTTGGTTAAGATCATTTTACGGCAAGAACGACTGGCC<br>ATTACTTTTTTTGAGGACTACAGCGCTAAACCAGCATACTGGGCTGTTAT<br>TGAAGCAAGTGGCGTAACTACATCAAGTCCTACGCCAACACCGACTCCTA<br>CAGTTACGGTGACACCGACACCAACTCCAACACCTACGCCGACAGTCACT<br>GCAACGCCGACTCCTACGCCAACGCCTGTTTCTACTCCAGCAACAGGCGG<br>ACAGATTAAAGTGCTTTATGCTAACAAGGAAACAAATAGTACTACAAATA<br>CAATTAGACCTTGGTTAAAAGTAGTTAATTCAGGAAGCTCTAGTATAGATC<br>TTTCTAGGGTAACGATTAGGTACTGGTATACTGTCGATGGAGAAAGAGCA<br>CAGTCTGCAGTTAGTGATTGGGCTCAGATTGGTGCAAGCAATGTAACATTT<br>AAGTTTGTAAAATTATCAAGTTCTGTCTCAGGAGCAGATTATTACTTGGAG<br>ATAGGCTTTAAGTCTGGTGCTGGACAACTTCAACCTGGTAAGGATACGGG<br>TGAAATTCAGATAAGATTTAATAAAAGCGATTGGTCTAATTACAACCAGG<br>GCAATGACTGGTCATGGCTTCAGAGCATGACATCATATGGCGAAAATGAG<br>AAAGTGACGGCTTATATTGACGGTGTTTTAGTCTGGGGTCAAGAGCCTAGT<br>GGCGCTACGCCTGCTCCGACGATGACAGTGGCACCGACTGCTACACCGAC<br>GCCAACTTTATCTCCGACGGTTACTCCGACGCCAGCACCGACTCAGACGG<br>CTATACCAACTCCTACGCTTACTCCTAACCCGACACCAACAAGTTCTATTC<br>CGGATGATACGAATGATGACTGGTTGTACGTAAGTGGCAACAAAATTGTC<br>GATAAGGATGGCAGACAGTTTGGCTTACTGGCATAAATTGGTTTGGCTAC<br>AACACAGGTACGAACGTGTTTGACGGCGTCTGGTCATGTAATTTGAAAGA<br>CACTTTAGCTGAGATAGCAAATAGGGGATTTAATTTGCTTAGAGTCCCAAT<br>AAGCGCAGAATTAATTTTGAACTGGAGTCAAGGTATATATCCGAAACCAA<br>ATATTAACTACTATGTAAATCCAGAGTTGAAGGGAAAAATAGCTTAGAG<br>GTTTTTGATATAGTCGTCGACACATGCAAAGAAGTTGGCTTGAAAATAAT<br>GCTTGATATTCATTCTATAAAAACGGACGCTATGGGTCATATTTATCCAGT<br>ATGGTATGACGAAAAATTTACGCCTGAGGATTTTTACAAGGCATGCGAAT<br>GGATAACGAACAGATACAAAATGACGATACTATTATTGCTTTTGACCTT<br>AAAAACGAACCACATGGAAAGCCGTGGCAGGATACAACATTTGCAAAAT<br>GGGACAATAGCACTGATATTAACAACTGGAAGTACGCTGCTGAGACTTGC<br>GCAAAGAGAATTTTGAATATAAACCCTAATCTTTTAATTGTAATAGAGGGC<br>ATTGAGGCATACCCGAAAGACGATGTGACTTGGACATCTAAGTCATCAG<br>CGATTATTACAGTACGTGGTGGGGTGGAAATTTAAGAGGCGTTAGGAAAT<br>ATCCAATAAATTTGGGTAAATATCAGAACAAGGTCGTGTATAGCCCTCAT<br>GATTACGGTCCTTCTGTATATCAGCAACCTTGGTTTTATCCGGGCTTTACTA<br>AAGAATCATTACTTCAGGACTGTTGGAGGCCTAACTGGGCATATATAATG<br>GAAGAAAAATATTGCACCTTTGCTTATAGGAGAGTGGGGAGGCCATTTAGA | X13602 and CAA31936<br>MKRNLFRIVSRVVLIAFIASISLV<br>GAMSYFPVETQAAPDWSIPSLCE<br>SYKDDFMIGVAIPARCLSNDTD<br>KRMVLKHFNSITAENEMKPESL<br>LAGQTSTGLSYRFSTADAFVDF<br>ASTNKIGIRGHTLVWHNQTPDW<br>FFKDSNGQRLSKDALLARLKQY<br>IYDVVGRYKGKVYAWDVVNEA<br>IDENQPDSYRRSTWYEICGPEYI<br>EKAFIWAHEADPNAKLFYNDYN<br>TEISKKRDFIYNMVKNLKSKGIPI<br>HGIGMQCHINVNWPSVSEIENSI<br>KLFSSIPGIEIHITELDMSLYNYG<br>SSENYSTPPQDLLQKQSQKYKEI<br>FTMLKKYKNVVKSTFWGLKDD<br>YWLRSFYGKNDWPLLFFEDYSA<br>KPAYWAVIEASGVTTSSPTPTPT<br>PTVTVTPTPTPTPTVTATPTPT<br>PTPVSTPATGGQIKVLYANKETN<br>STTNTIRPWLKVVNSGSSSIDLSR<br>VTIRYWYTVDGERAQSAVSDW<br>AQIGASNVTFKFVKLSSSVSGAD<br>YYLEIGFKSGAGQLQPGKDTGEI<br>QIRFNKSDWSNYNQGNDWSWL<br>QSMTSYGENEKVTAYIDGVLV<br>WGQEPSGATPAPTMTVAPTATP<br>TPTLSPTVTPTPAPTQTAIPTPTL<br>TPNPTPTSSIPDDTNDDWLYVSG<br>NKIVDKDGRPVWLTGINWFGYN<br>TGTNVFDGVWSCNLKDTLAEIA<br>NRGFNLLRVPISAELILNWSQGI<br>YPKPNINYYVNPELEGKNSLEVF<br>DIVVQTCKEVGLKIMLDIHSIKT<br>DAMGHIYPVWYDEKFTPEDFYK<br>ACEWITNRYKNDDTIIAFDLKNE<br>PHGKPWQDTTFAKWDNSTDINN<br>WKYAAETCAKRILNINPNLLIVI<br>EGIEAYPKDDVTWTSKSSSDYY<br>STWWGGNLRGVRKYPINLGKY<br>QNKVVYSPHDYGPSVYQQPWF<br>YPGFTKESLLQDCWRPNWAYIM<br>EENIAPLLIGEWGGHLDGADNE<br>KWMKYLRDYIIENHIHHTFWCF<br>NANSGDTGGLVGYDFTTWDEK<br>KYSFLKPALWQDSQGRFVGLDH<br>KRPLGTNGKNINITTYYNNNEPE<br>PVPASK (SEQ ID NO: 124) |

TABLE 2-continued

Exemplary Biomass Degrading Enzymes That Can Be Used According to the Present Invention

| Organism and Protein (Gene) | Codon-Optimized DNA Sequence | Accession Number and Amino Acid Sequence |
|---|---|---|
| | TGGTGCTGATAACGAGAAATGGATGAAGTACTTAAGGGATTATATTATAG AGAACCATATTCATCACACGTTTTGGTGCTTTAATGCTAACAGTGGAGATA CAGGCGGTTTAGTGGGTTACGACTTTACTACATGGGACGAGAAGAAATAC AGCTTTTTGAAGCCAGCTTTATGGCAAGACAGCCAGGGCAGATTTGTAGG TTTAGATCATAAAAGGCCTTTGGGCACTAATGGAAAGAACATAAATATTA CGACGTACTACAACAACAATGAACCTGAGCCAGTTCCTGCTTCAAAG (SEQ ID NO: 93) | |
| Caldocellum saccharolyticum beta-mannanase (manA) | ATGAGACTAAAAACAAAAATAAGAAAGAAATGGTTAAGTGTTTTATGCAC AGTAGTGTTTTTGTTGAATATTCTTTTTATAGCTAATGTCACAATTTTACCT AAAGTTGGAGCAGCTACAAGTAATGATGAGTTGTAAAAGTCATGACAAG CACTCTTATAGGCACTAATCATGCCCATTGTTGGTACCGTGACAGATTGGA CACACAGCTTTAAGAGGGATCAGAAGTTGGGGCATGAATTCGGTTAGAGTAG TGTTGTCAAATGGTTACAGATGGACAAAATCCCCGCATCCGAAGTTGCA AATATAATAAGCTTGTCAAGAAGTCTTGGATTCAAAGCAATAATCCTTGA AGTGCACGATACGACAGGTTATGGAGAAGATGGAGCAGCTTGCTCTTTAG CACAGGCTGTGGAATACTGGAAAGAATAAAGAGCGTATTAGATGGCAAT GAAGATTTTGTTATTATAAACATTGGAAATGAGCCGTATGGTAATAATAAT TATCAAAATTGGGTAAATGATACTAAAAATGCAATAAAAGCTACTAAGAGA TGCAGGATTTAAGCATACTATTATGGTAGATGCACCTAATTGGGGTCAAG ATTGGTCAAATACGATGAGAGATAATGCTCAATCTATAATGGAAGCTGAT CCTTTTAAGGAATCTTGTATTTTCTATACATATGTACGGGGTTTATAATACA GCCAGCAAGTAGAAGAATATATAAAATCTTTTGTGAGTAAAGGTTTACC TTTAGTTATAGGTGAGTTTGGCCACCAACACAGATGGAGATCCAGATG AAGAGGCAATAGTTAGATATGCAAAGCAATATAAAATTGGATTGTTTAGT TGGAGCTGGTGTGGCAATTCTTCATACGTAGGGTATTTAGATATGGTCAAT AATTGGGACCCAAATAACCCTACTCCTTGGGGGCAATGGTACAAAACGAA TGCAATAGGCACTTCTTCTACACCTACACCAACAAGCACAGTGACTCCTAC ACCAACACCAACACCTACTCCTACGCCAACAGTAACAGCAACACCAACAC CTACACCTACACCTGTTTCAACACCAGCGACATCTGGTCAAATAAAAGTGT TGTACGCTAATAAGGAAACGAACAGTACAACGAATACTATCGACCCTTGG CTTAAAGTAGTTAATTCAGGCTCTAGTTCTATAGACCTTAGTAGGGTGACT ATCAGGTATTGGTATACAGTAGATGGGAAAGGGCCCAGTCAGCAATAAG CGACTGGGCTCAGATAGGAGCATCCAATGTAACATTTAAATTCGTGAAGC TTAGCTCATCAGTATCTGGCGCTGATTACTATCTTGAAATTGGATTTAAAA GCGGGGCCGGACAACTACAGCCTGGGAAAGATACAGGTGAAATACAAT GAGATTTAATAAAGACGATTGGTCAAATTATAACCAAGGTAATGACTGGA GTTGGATACAGTCCATGACAAGTTATGCGAAATGAAAAGGTAACAGCT TACATAGATGGTGTATTGGTTGGGGACAGGAACCATCAGGCGCAACACC TGCACCTGCACCGACAGCAACTCCAACACCTACTCCGACAGTAACACCAA CACCTACAGTAACGCCAACGCCAACGGTTACAGCAACTCCAACGCCAACA CCAACCCCTACACCTACACCAGTTTCAACGCCTGCGACTGGAGGACAAAT AAAGGTTCTTTATGCAAATAAAGAAACAAATTCGACAACGAATACTATCA GGCCTTGGTTAAAGGTAGTTAATAGCGGGAGTTCTAGTATAGATCTTAGTA GAGTCACAATAAGATATTGGTATACTGTAGATGGTGAAAGAGCACAAAGT GCAATATCAGATTGGGCACAAATTGCGCATCTAATGTCACATTTAAATTT GTTAAGCTTTCGTCGTCAGTCAGTGGGCAGATTACTATTTGGAGATCGGT TTCAAATCTGGGCAGGCCAATTGCAGCCAGGTAAGGATACAGGCGAGAT ACAAATCAGATTCAATAAATCTGATTGGTCCAACTATAATCAAGGCAACG ATTGGTCATGGATACAGTCTATGACTAGTTATGGAGAGAACGAAAAGGTG ACTGCTTACATTGATGGAGTTTTAGTCTGGGGACAAGAGCCCAGCGGAAC TACACCGAGCCCGACATCAACACCAACTGTTACGGTAACACCTACACCAA CGCCGACTCCAACTCCGACTCCTACACCAACGGTAACGCCAACACCGACT GTAACTCCAACTCCTACAGTCACAGCCACACCGACTCCTACCCCAACACCC ATCCCTACAGTAACACCATTACCTACAATATCTCCAAGCCCTTCTGTAGTG GAAATTACGATAAATACAAATGCAGGCAGAACAAGATAAGTCCATACAT CTATGGTGCTAATCAAGATATTGAAGGCGTAGTACACAGTGCCAGAAGAT TGGGAGGCAATAGACTAACAGGTTATAATTGGGAAAATAATTTTAGCAAC GCGGGCAACGATTGGTATCATTCCAGTGACGATTACTTATGTTGGTCAATG GGAATCTCAGGAGAAGATGCTAAAGTACCCGCAGCAGTAGTTTCAAAATT TCACGAGTACTCTCTAAAGAATAATGCATACAGCCGTGACTTTACAAT GGCTGGTTATGTATCTAAGGACAATTATGGTACTGTCAGTGAAAATGAAA CAGCACCATCGAATAGATGGGCTGAAGTAAATTTAAAAAGGATGCGCCT TTGTCCCTTAATCCAGACCTGAACGATAACTTTGTTTATATGGATGAGTTT ATTAATTATTTAATAAACAAATATGGAATGGCCTCGTCTCCTACTGGTATA AAAGGATATATTCTGGACAACGAACCAGATCTTTGGGCGAGCACCCACCC GAGAATACATCCAAATAAAGTAACATGTAAAGAATTGATTGAGAAAGTG TAGAACTTGCAAAAGTAATTAAGACACTTGATCCTTCTGCGGAAGTATTTG GCTATGCATCATATGGTTTTATGGGATATTACTCGCTACAGGACGCGCCGG ATTGGAATCAGGTTAAGGGGGAACATCGATGGTTATAAGTTGGTATTTA GAACAAATGAAAAAGCATCCGATTCATTTGGAAAAGGTTATTAGATGT ATTAGATTTACACTGGTATCCTGAGGCAAGGGGAGGGAATATCAGAGTTT GCTTTGACGGTGAAAATGATACCTCAAAAGAAGTAGTAATCGCTAGGATG CAAGCCCCAAGAACTCTATGGGACCCTACATATAAACAAGTGTTAAGGG | L01257 AND AAA71887 MRLKTKIRKKWLSVLCTVVFLL NILFIANVTILPKVGAATSNDGV VKIDTSTLIGTNHACWYRDRL DTALRGIRSWGMNSVRVVLSNG YRWTKIPASEVANIISLSRSLGFK AIILEVHDTTGYGEDGAACSLAQ AVEYWKEIKSVLDGNEDFVIINI GNEPYGNNNYQNWVNDTKNAI KALRDAGFKHTIMVDAPNWGQ DWSNTMRDNAQSIMEADPLRN LVFSIHMYGVYNTASKVEEYIKS FVDKGLPLVIGEFGHQHTDGDP DEEAIVRYAKQYKIGLFSWSWC GNSSYVGYLDMVNNWDPNNPT PWGQWYKTNAIGTSSTPTPTST VTPTPTPTPTPTPTVTATPTPTPT PVSTPATSGQIKVLYANKETNST TNTIRPWLKVVNSGSSSIDLSRV TIRYWYTVDGERAQSAISDWAQ IGASNVTFKFVKLSSSVSGADYY LEIGFKSGAGQLPGKDTGEIQM RFNKDDWSNYNQGNDWSWIQS MTSYGENEKVTAYIDGVLVWG QEPSGATPAPAPTATPTPTPTVTP TPTVTPTPTVTATPTPTPTPTPT VSTPATGGQIKVLYANKETNSTT NTIRPWLKVVNSGSSSIDLSRVTI RYWYTVDGERAQSAISDWAQIG ASNVTFKFVKLSSSVSGADYL EIGFKSGAGQLPGKDTGEIQIR FNKSDWSNYNQGNDWSWIQSM TSYGENEKVTAYIDGVLVWGQE PSGTTPSPTSPTVTVTPTPTPTP TPTPTPTVTPTPTVTPTPTVTATP TPTPTPIPTVTPLPTISPSPSVVEIT INTNAGRTQISPYIYGANQDIEG VVHSARRLGGNRLTGYNWENN FSNAGNDWYHSSDDYLCWSMG ISGEDAKVPAAVVSKFPHEYSLK NNAYSAVTLQMAGYVSKDNYG TVSENETAPSNRWAEVFKFKKDA PLSLNPDLNDNFVYMDEFINYLI NKYGMASSPTGIKGYILDNEPDL WASTHPRIHPNKVTCKELIEKSV ELAKVIKTLDPSAEVFGYASYGF MGYYSLQDAPDWNQVKGEHR WFISWYLEQMKKASDSFGKRLL DVLDLHWYPEARGGNIRVCFDG ENDTSKEVVIARMQAPRTLWDP TYKTSVKGQITAGENSWINQWF SDYLPIIPNVKADIEKYYPGTKL AISEFDYGGRNHISGGIALADVL GIFGKYGVNFAARWGDSGSYA AAAYNIYLNYDGKGSKYGNTN VSANTSDVENMPVYASINGQDD SELHIILINRNYDQKLQVKINITS TPKYTKAEIYGFDSNSPEYKKM GNIDNIESNVFTLEVPKFNGVSH SITLDFNVSIKIIQNEVIKFIRNLV FMRALV (SEQ ID NO: 125) |

TABLE 2-continued

Exemplary Biomass Degrading Enzymes That Can Be Used According to the Present Invention

| Organism and Protein (Gene) | Codon-Optimized DNA Sequence | Accession Number and Amino Acid Sequence |
|---|---|---|
| | ACAAATAACGGCTGGAGAAAATTCGTGGATAAATCAGTGGTTTTCAGATT ATCTCCCAATTATCCCAAATGTTAAGGCCGATATTGAGAAGTACTATCCAG GTACAAAGCTAGCTATAAGCGAATTTGACTATGGGGGTCGTAACCACATA TCTGGAGGAATTGCTTTAGCTGACGTACTAGGCATTTTTGGCAAATATGGC GTTAATTTTGCGGCTAGATGGGGCGATTCAGGTTCATATGCCGCAGCTGCA TATAACATATATCTTAATTATGATGGAAAGGGTTCGAAATATGGTAATACG AATGTTTCTGCAAATACAAGTGACGTAGAGAATATGCCGGTATATGCTTCA ATAAACGGTCAAGACGATTCAGAATTGCATATAATACTTATCAACAGGAA CTACGATCAAAAATTACAGGTTAAAATTAATATTACATCAACTCCAAAAT ACACAAAAGCAGAAATATACGGATTCGATTCTAATAGCCCTGAATATAAA AAGATGGGAAATATAGACAATATTGAGTCTAACGTTTTTACCCTTGAAGTG CCAAAATTTAATGGCGTGAGCCATAGCATCACATTAGATTTTAACGTGTCC ATCAAAATTATTCAAATGAAGTAATCAAGTTTATCAGAAATTTAGTGTTC ATGAGGGCACTTGTT (SEQ ID NO: 94) | |
| Clostridium stercorarium Avicellase I (celZ) | ATGAGAAAATTTTGGTCTTTTGCAATAATTATATCTTTACTTGTAACAGGA TTGTTTATTCATACTCCTAAAGCTGAGGCAGCTGGTTACAATTACGGCGAA GCTCTTCAAAAGGCAATAATGTTTTACGAGTTTCAGAGGAGCGGAAAGTT GCCAGAGAACAAGAGGGACAATTGGAGGGTGACAGCGGCTTAAATGAT GGAGCAGATGTTGGTTTAGACCTTACAGGCGGATGGTATGATGCTGGTGA TCACGTGAAGTTTAATTTGCCTATGGCATATAGTCAAACTATGTTAGCTTG GGCAGCTTACGAAGCAGAAGAAGCTCTTGAAAGATCAGGCCAGATGGGAT ATTTGTTAGACGCAATAAAAATGGGTTTCTGATTATCTTATAAAATGCCACC CAAGTCCTAATGTTTTTTACTACCAGGTGGGTGATGGCCACTTGGACCATT CATGGTGGGGCCCGGCAGAAGTAATGCAAATGGATAGACCAGCTTATAAA GTAGACCTTGCTAATCCAGGTTCTACAGTAGTGGCAGAGGCTGCAGCTGCT TTGGCTGACGCTGCAGTAGTTTTTGCAGATAGAGATCCTGCATACGCTGCA ACTTGTATACAACATGCAAAGGAGTTGTATAATTTTGCAGAGATTACAAA GTCAGATTCTGGCTACACAGCAGCTAGTGGCTTTTACGATAGCCACTCAGG ATTTTATGACGAGCTTAGCTGGGCTGGCGTTTGGCTTTATTTAGCTACAGG CGATGAAACATACCTTAACAAAGCTGAACAATATGTGGCACTACTGGGGTA CTGAGCCACAAACAAATATAATTTCTTATAAGTGGGCACATTGTTGGGAC GACGTTCATTACGGAGCTTGCTTGCTTTTAGCAAAAATTACTGGCAAACAA ATATACAAAGAGGCAATAGAAAGACACCTTGATTATTGGAGCGTTGGTTA CAACGGAGAGAGGGTTCATTATACACCTAAGGGATTGGCTTGGTTGGATA GCTGGGGAAGTCTTAGATATGCTACGACAACTGCCATTTTTGCCAAGTGTTT ACGCAGATTGGGAGGGCTGCAGCAGGGAAAAAGCTGCAATTTATAATGAC TTTGCTAAACAACAGATAGATTACGCATTGGGCTCAAGTGGTAGATCTTAT GTAGTTGGTTTTGGCGTGAATCCGCCAAAAAGACCGCACCACAGGACTGC TCACAGTTCTTGGGCTGATTCTATGAGTGTTCCTGACTACCACAGACACGT ACTTATAGGTGCTTTAGTTGGAGGCCCAGGTAAGGACGATTCATACACGG ATGACATAAACAATTATATAAATAACGAGGTTGCTTGCGATTACAATGCT GGTTTTGTGGGCGCATTGGCTAAGATGTATGAAGATTACGGCGGATCTCCG ATACCTGACTTGAATGCTTTTGAGGAAATAACTAACGATGAATTTTTTGTT ATGGCAGGAATTAATGCATCTGGCCAGAATTTTATAGAGATTAAGGCATT ACTTCATAATCAATCAGGTTGGCCTGCTAGGGTAGCAGATAAGTTAAGTTT TAGGTATTTTGTCGATTTAACGGAGTTAATAGAGGCTGGATACAGCGCTTC TGACGTCAACAATAACTACAAATTATAACGCAGGCGCAAAAGTAACTGGTT TACACCCATGGAATGAAGCTGAGAACATTTATTACGTGAACGTTGATTTTA CGGGAACAAAGATATATCCTGGCGGTCAGTCAGCATACAGAAAAGAGGTG CAGTTTAGGATTGCTGCTCCACAGAATACGAATTTTTGGAATAATGACAAC GATTATTCATTTAGGGATATAAAAGGCGTTACAAGCGGCAATACAGTCAA AACAGTGTATATTCCTGTTTATGACGATGGTGTGTTAGTTTTTGGAGTGGA AAATGGAATAAAGTACGGTAACACTTACTTAAGAGAAGGAACGGATTACA CGGTCAGCGGCGACACTGTGACAATATTGAAATCATTTCTTAATAGCTTTG ATACTTCAACAGTTCAGTTAATATTTGACTTTAGCGCTGGTAGGGATCCAG TATTGACGTGAACATAATTGACACGACAACGAGCGCAAAGTAGTCCCA ACAACGGCAGATTTTGACAAAAATCCGGATGCATCTAGAGATGTTAAAGT GAAATTAGTACCTAATGAAATACGCTTCTTGCAGTGAAAAAGACGGTG AGGCTTTGGTGTTAGGCAGGGACTACAGTATAGATGGCGACGAGGTAACA ATATTTAGGGAGTATTTAGCTGATCAGCCGGTAGGCAGAGTGACTCTTACA TTTGACTTTGATAGGGGTACTGATCCGGTTTTAACAATTAATATAACGGAT AGCAGGCAAGTAGAGACAGGAGTTATACAAATTCAGATGTTTAACGGCAA CACGAGTGATAAAACTAACGGTATAATGCCGAGGTACAGGTTGACAAACA CTGGAACAACACCTATAAGATTGAGTGATGTAAAAATAAGGTACTACTAC ACAATAGACGGAGAGAAGGATCAAAATTTTTGGTGCGACTGGTCAAGTGT AGGTTCTAATAATATTACGGGTACATTTGTAAAGATGGCTGAGCCAAAAG AGGGCGCAGATTATTACCTTGAAACGGGTTTTACTGATGGCGCTGGCTATT TGCAGCCAAATCAAAGCATTGAGGTTCAGAACAGATTTAGTAAGGCAGAC TGGACTGATTATATACAAACGAATGATTATAGCTTTAGCACTAACACGTCA TACGGTTCAAACGACAGGATTACTGTGTACATTAGCGGTGTGTTGGTTAGC GGAATAGAACCA (SEQ ID NO: 95) | CAA39010 AND X55299 MRKFWSFAIIISLLVTGLFIHTPK AEAAGYNYGEALQKAIMFYEFQ RSGKLPENKRDNWRGDSGLND GADVGLDLTGGWYDAGDHVKF NLPMAYSQTMLAWAAYEAEEA LERSGQMGYLLDAIKWVSDYLI KCHPSPNVFYYQVGDGHLDHS WWGPAEVMQMDRPAYKVDLA NPGSTVVAEAAAALASAAVVFA DRDPAYAATCIQHAKELYNFAEI TKSDSGYTAASGFYDSHSGFYD ELSWAGVWLYLATGDETYLNK AEQYVAYWGTEPQTNIISYKWA HCWDDVHYGACLLLAKITGKQI YKEAIERHLDYWSVGYNGERV HYTPKGLAWLDSWGSLRYATT TAFLASVYADWEGCSREKAAIY NDFAKQQIDYALGSSGRSYVVG FGVNPPKRPHHRTAHSSWADSM SVPDYHRHVLIGALVGGPGKDD SYTDDINNYINNEVACDYNAGF VGALAKMYEDYGGSPIPDLNAF EEITNDEFFVMAGINASGQNFIEI KALLHNQSGWPARVADKLSFR YFVDLTELIEAGYSASDVTITTN YNAGAKVTGLHPWNEAENIYY VNVDFTGTKIYPGGQSAYRKEV QFRIAAPQNTNFWNNDNDYSFR DIKGVTSGNTVKTVYIPVYDDG VLVFGVENGIKYGNTYLREGTD YTVSGDTVTILKSFLNSFDTSTV QLIFDFSAGRDPVLTVNIIDTTTS ASIVPTTADFDKNPDASRDVKV KLVPNGNTLLAVKKDGEALVLG RDYSIDGDEVTIFREYLADQPVG RVTLTFDFDRGTDPVLTINITDSR QVETGVIQIQMFNGNTSDKTNGI MPRYRLTNTGTTPIRLSDVKIRY YYTIDGEKDQNFWCDWSSVGS NNITGTFVKMAEPKEGADYYLE TGFTDGAGYLQPNQSIEVQNRFS KADWTDYIQTNDYSFSTNTSYG SNDRITVYISGVLVSGIEP (SEQ ID NO: 126) |

TABLE 2-continued

Exemplary Biomass Degrading Enzymes That Can Be Used According to the Present Invention

| Organism and Protein (Gene) | Codon-Optimized DNA Sequence | Accession Number and Amino Acid Sequence |
|---|---|---|
| *Clostridium stercorarium* Avicellase II (celY) | ATGAAAAGAAGGTTAATGAAGGGAATATCATTGTTAACGCTTGTATTTTTG ATTGGTATAATGTTGCAACTTAGCTTAAAGAGCGAATTAACAGCTTACGCT AGTAGCGATGACCCTTACAAGCAGAGGTTTTTGGAATTATGGGAGGAATT GCATGACCCTTCTAATGGTTATTTTAGTTCACACGGCATTCCTTACCATGC AGTTGAAACATTAATAGTGGAAGCTCCTGACTACGGCCACTTGACTACATC AGAAGCAATGTCTTACTATTTATGGTTGGAGGCTTTATACGGCAAATTTAC AGGTGACTTTAGCTATTTTATGAAGGCATGGAGACAATTGAAAATACA TGATACCTACAGAGCAAGACCAGCCTAACAGGAGCATGGCAGGCTATAAC CCTGCAAAACCGGCTACGTACGCACCTGAATGGGAAGAACCGAGTATGTA CCCATCACAGTTAGACTTTAGCGCACCAGTGGGCATAGACCCAATATACA ACGAGTTGGTTAGCACATACGGAACACAATATCATCGGTATGCACTGG TTGCTTGACGTTGATAATTGGTACGGCTTTGGAAGAAGGCAGATAGAAT TAGTTCTCCAGCTTATATAAACACTTTTCAGAGGGGAAGTCAGGAGAGCG TATGGGAAACAATACCTCAACCGTGTTGGGATGACTTAACAATTGGAGGA AGAAATGGCTTTCTTGACTTGTTTGTGGACGCTCAGTACTTCACCACAA TTTAAGTATACAAACGCACCGGACGCTGATGCTAGAGCTATACAGGCAAC ATACTGGGCAAACCAGTGGGCAAAAGAACATGGAGTTAATTTGAGTCAAT ACGTGAAAAAGGCATCAAGAATGGGTGATTACCTTAGATATGCAATGTTT GATAATATTTTAGAAAAATTGGCGACTCTAAGCAGGCTGGAACGGGATA CGATGCAGCACACTACTTACTTAGCTGGTACTACGCTTGGGGAGGCGGTAT AACAGCTGATTGGGCTTGGATTATAGGCTGCTCACACGTTCACGCTGGCTA CCAAAATCCAATGACAGCATGGATTCTTGCTAACGACCCGGAATTTAAAC CAGAATCTCCTAACGGAGCAAACGACTGGGCTAAGAGCTTGGAAAGGCAA TTAGAGTTTTTACCAATGGCTTCAAAGTGCTGAAGGCGCAATAGCTGGAGG TGCTACAAATTCTTACAAGGAAGATACGAAACATTGCCGGCTGGTATTA GCACATTTTACGGTATGGCATACGAAGAACACCCTGTGTACCTTGATCCAG GTAGTAACACATGGTTTGGCTTTCAGGCTTGGACGATGCAGAGGGTTGCA GAGTACTATTACTTAACTGGTGACACAAGAGCTGAGCAGCTTTTGGATAA ATGGGTGGATTGGATTAAAAGCGTGGTTAGGTTAAACTCAGATGCACAT TTGAAATTCCTGCAACTTGGAGTGGTCTGGACAGCCTGATACGTGGACTG GTACATATACTGGAAACCCTAATTTACATGTAAGTGTCGTTTCTTATAGGA CTGACTTGGGCGCAGCTGGATCTTTGGCTAATGCTTTGCTTTATTATGCAA AGAACAAGCGGCGACGATGAGGCTAGAAATTTAGCTAAAGAATTGCTTGAC AGAATGTGGAACCTTTACAGAGATGACAAGGGATTGAGCGCACCGGAAAC TAGAGAGGATTATGTGAGGTTTTTTGAACAAGAAGTCTACGTGCCACAGG GTTGGAGCGGAACAATGCCTAATGCCGAATCGGAATTCCGGTTGTTACT TTTCTTGATATAAGGAGTAAATACTTGAATGATCCGGACTATCCTAAGTTG CAACAGGCTTACAACGAAGGAAAGCACCGGTCTTTAATTATCACAGATT TTGGGCTCAATGCGACATAGCTATAGCAAACGGATTGTACAGCATTTTATT TGGCTCTGACAAGCAAACGATTCATTTATAACACCTACAAGTGCAACATT TGACAAAAACAATCAGGAAGATATATCTGTAACAGTGACTTATAATGGCA ACACTTTGCTTGGCATAAAGAGCGGTTCTTCATATTTGATAGAAGGCGTTG ACTATATAGTCAATGGCGACGTGATTATTATAAAGAAAGAGTTTCTTGCTG GTCAGGCTACAGGAAGTATTAGCTTGCTTTTTGACTTTAGCGCAGGCTTAG ACAGAACATTAACAATTGACATAATAGACACTGGTGGAGGCGAAGAGCCG GTTGAGCCAGTAGAACCTGTTGAGGGTGTTTTAATTATACAGTCATTTAAC GCAAACACACAGGAGATTTCAAATAGCATTATGCCTAGGTTTAGAATTTAT AATTCAGGTAATACAAGCATTCCATTGAGCGAAGTGAAACTTAGGTATTA CTACACAGTAGACGGCGATAAACCTCAAATTTTTGGTCGCGATTGGGCAT CTATTGGTTCATCTAATGTGACTGGAACATTTGTGAAAATGGATGCAGCTA CAACGGGTGCTGATTACTATTTAGAGATAGGATTTACTCCGCAGGCTGGCA CTTTAGAGCCTGGAGCTAGTATAGAAGTACAGGGTAGGTTTAGTAAAATA GACTGGACGGACTATACTCAGACTAATGACTATAGCTTTAACCCGACAGC TTCTTCATATGTGGACTTTAACAAGATTACTGCATACATAAGCGGCAACCT TGTTTATGGTATTGAGCCT (SEQ ID NO: 96) | CAA93280 MKRRLMKGISLLTLVFLIGIMLQ LSLKSELTAYASSDDPYKQRFLE LWEELHDPSNGYFSSHGIPYHA VETLIVEAPDYGHLTTSEAMSY YLWLEALYGKFTGDFSYFMKA WETIEKYMIPTEQDQPNRSMAG YNPAKPATYAPEWEEPSMYPSQ LDFSAPVGIDPIYNELVSTYGTN TIYGMHWLLDVDNWYGFGRRA DRISSPAYINTFQRGSQESVWETI PQPCWDDLTIGGRNGFLDLFVG DSQYSAQFKYTNAPDADARAIQ ATYWANQWAKEHGVNLSQYV KKASRMGDYLRYAMFDKYFRK IGDSKQAGTGYDAAHYLLSWY YAWGGGITADWAWIIGCSHVH AGYQNPMTAWILANDPEFKPES PNGANDWAKSLERQLEFYQWL QSAEGAIAGGATNSYKGRYETL PAGISTFYGMAYEEHPVYLDPGS NTWFGFQAWTMQRVAEYYYLT GDTRAEQLLDKWVDWIKSVVR LNSDGTFEIPGNLEWSGQPDTW TGTYTGNPNLHVSVVSYRTDLG AAGSLANALLYYAKTSGDDEAR NLAKELLDRMWNLYRDDKGLS APETREDYVRFFEQEVYVPQGW SGTMPNGDRIEPGVTFLDIRSKY LNDPDYPKLQQAYNEGKAPVFN YHRFWAQCDIAIANGLYSILFGS EQANDSFITPTSATFDKNNQEDI SVTVTYNGNTLLGIKSGSSYLIE GVDYIVNGDVIIIKKEFLAGQAT GSISLLFDFSAGLDRTLTIDIIDTG GGEEPVEPVEPVEGVLIIQSFNA NTQEISNSIMPRFRIYNSGNTSIPL SEVKLRYYYTVDGDKPQNFWC DWASIGSSNVTGTFVKMDGATT GADYYLEIGFTPQAGTLEPGASI EVQGRFSKIDWTDYTQTNDYSF NPTASSYVDFNKITAYISGNLVY GIEP (SEQ ID NO: 127) |
| *Eubacterium cellulo- solvens* Cel5A (cel5A) | ATGAAGGAAATTGGTTAAAGGACGTACTTAGAAAGGTTTGCAGTTATAGC TATGATGTTGGTGATGGTCTTTACACTTTTGCCTGCAACTGCTCAAGGTAC GGAAGCAGCTTCAGGCGACATTGTATTGTTTAGCGGCTCAAAACACGTTG AGTTTACGGATTGGGGTGGCACAGACTGGCCAAGTGCATACGAATTACAG CCGCCTTACCAAACTATGCCATTTGATTTGAACAAGAATTTTGAGATTAAA GTTGATTATTCAGGTGCTGATATAGTGTTGATTTTTGCAAGATGGGAACAC GGTTCTAAACCGCAGATATGGGCACAAATTTCACCGTATTACGTTGTTGAT GGCACAGCTGTTTTTACGAAGGAACAGATAGCTAAAGCATATGGAAGTGA CGATTTTTCAGACTTAGATTATATAGGTGTGAAACCGTTGCCTGCTGATGG TATGACAGTTACAAAGATAGTCGCAAGCTATACGAGTGGATCATCTG ACGACGTGGATATTAATCTTAAGGGAATTGCTGGAGAGTGGGCTAACGGC GTAAATATAGGATGGAATTTGGGTAACACTCTTGATGCATATGACACGAA CAGGTTTAAGAGCTCAAAAACAATCCTGCTGATATAGAAACCTGCTGGGGT GCTGGGAAACCCAGTCACTACGAAGGCAATGATAGATGACATAAAGGCT CAAGGCTTTAACGCTGTGAGGGTTCCGTGACATGGATTTTGAAATAGA CGATAACGACGGTTATAAGGTGAATGAGGCTTGGATGGCAAGGGTTAAAG AGGTTGTAGACTATGTCATGGATAATGATTTGTATTGCATTTTAAACGTAC ATCACGATACAGGAGAGCAGGGCTGGTTAAAGGCTTCTACAGCAAATTAC | BAE46390 MKGNWLKDVLRRFAVIAMMLV MVFTLLPATAQGTEAASGDIVLF SGSKHVEFTDWGGTDWPSAYEL QPPYQTMPFDLNKNFEIKVDYS GADIVLIFARWEHGSKPQIWAQI SPYYVVDGTAVFTKEQIAKAYG SDDFSDLDYIGVKPLPSADGMT VTKIVASYTSGSSDDVDINLKGI AGEWANGVNIGWNLGNTLDAY DTNRFKSSKGHNNPADIETCWG NPVTTKAMIDDIKAQGFNAVRV PVTWDFEIDDNDGYKVNEAWM ARVKEVVDYVMDNDLYCILNV HHDTGEQGWLKASTANYNKNV KKFKALWKQIAAEFKNYDNKL AFEGFNEMLDEKNSWNYPGTD AGDAINLYNQAFVDVVRASGG |

TABLE 2-continued

Exemplary Biomass Degrading Enzymes That Can Be Used According to the Present Invention

| Organism and Protein (Gene) | Codon-Optimized DNA Sequence | Accession Number and Amino Acid Sequence |
|---|---|---|
| | AATAAAAACGTTAAGAAATTTAAAGCACTTTGGAAACAAATAGCTGCAGA GTTTAAAAACTACGACAACAAACTTGCTTTTGAGGGCTTTAATGAGATGTT AGACGAAAAAAATAGTTGGAATTATCCTGGTACAGATGCTGGAGATGCTA TAAATTTGTATAACCAGGCATTTGTCGACGTGGTCAGAGCATCTGGTGGCA AGAATGGAAAAAGGCCGCTTATATGTAATACATATGCAGGCTGTACTGAG GCTGGTGCTTTGAACAGCTTTAAGATTCCGAACGATACTGTTGATAACGCA ATAATTGCTCAGGTACATTTTTATCAACCAACGGGATACTGTTTTGACATG AATCCTAACCAGGGTCAAACATGGATGTCGACTACAAACATGTGGCGG AGAGTCAGCTGCAGACACATTGGCTATGATGCTTTATAAAAGATTTACGG AAAAGGGCATTCCATGCATAGTTGGAGAGTTTGCAGCTTCTCACAAAAAG AACGACGACAACAGAGCAGAATGGGTGGATTACTACGTTAGAAAGACGG GAACATATGGTGTGAAATGTTTTGGTGGGATAATGGAGGTACATTTACGC CGAATTACAGCACTGGTCTTGATTATTACAACTCAATGGGCATTTACAACA GGAATACAATGCAGTTTGAGTACCCAAAGGTAGCAGACGCTCTTGTGAAT GCTGCAAACGGAGGTGCTAAACCGACTACAGCTCCGACTAAAAAGCCAAC ATCTACTCCAAAGCCGACGGCTACATTGAAACCGACTACAAAGCCTACGA CTAAGCCTACAACGAAACCTAATCCGACGAGTGGCGCAGACTCTGGTGAA ATAATTCTTTTTTCTGGTAGTAATCACGCTGATTTTAAAGCATGGGGCGGT GATGATTGGCCTTCAGCTTTTGAAATAAGTCCTAAATATGAGCCAATGAAG TTAGACCTTAATAAAAACTTTGAAATAAAGGTGGATTACAACGGAGCAGA CATTGTTCTTATATTTGCTAGGTGGGATAAGGATATTTGGGCTCAGATAAG CCCATACTATGTCGTAGACGGTACTGCAGTATTACTAAAGAGCAAATTGC AAAGGCTTACGGTTCAGATGACTTTTCAGAATTAGACTATATGACTGTTAA GCCTCTTCCGAGTGAAGAAGGCGTAACTGTTACAAAAGTGAGCGGTATTT ACACAAATGGAGGCTCTGAGGATGTTGACATAAACTTGAAAGGCATAGCT GGTGAATGGGCAAACGGTGTTAACATTGGCTGGAACCTTGGAAATACATT GGACGCTTACGATACTAATAGATTTACGAGAACAAAGGGACACAATAACC CGGCAGATATTGAAACGTGTTGGGGTAATCCGGTTACAACTAAAGCTATG ATTGACGATATTAAAGCACAGGGATTTAACGCAGTCAGAGTCCCAGTTAC TTGGGATTACGAGATTGACGACAACGACGGATACAAAGTTAACGAGGCTT GGATGGCTAGAGTGAAGGAAGTAGTGGATTACGTTATGGATAATGATATG TATTGCATAGTCAATGTGCACCACGACACGGGTGAACAAGGATGGCTTAA GGCAAGCACAGCAAATTATGCTAAAAATGAAAAAAAGTTTAAGGCTTTGT GGAAGCAGATTGCAGCTGAATTTAAGAACTACGACCACAAGTTAGCATTT GAAGGCTTTAATGAGATGCTTGATGAGAAGAACTCATGGAACTACCCAGG TGCTGATGCAGGAGAAGCAATTAACCTTTACAATCAGGCTTTTGTGGATGT AGTGAGGGCTAGCGGCGAAAAAACTCTGATAGACCATTAATTTGCAACA CTTACGCTGGTTGCACGGAAGCAGGCGCACTTAATTCATTTGAAATACCAA ACGACACAGTTGAGAACGCTATTATAGCACAAGTCCACTTTTACCAGCCG ACTGGTTATTGTTTTGATATGAATCCAATCAAGGCCAGAATATGGACGTT GATTATAAGACTTGCGGAGGCGAAAGTGCAGCTGATACGCTTGCAATGAT GTTGTACAAGAGGTTTACAGAGAAAGGTATACCGTGTATTGTGGGTGAAT TTGCTGCAAGCCATAAACAAAACGACGATAATAGGGCAGCATGGGTCGAC TATGTTGTGTCTAAAACAGGCAAATACGGCGTTAAGTGCTTTTGGTGGGAT AACGGTGGCACGTTTACACCAAACTATTCAACGGGATTAGACTACTATAA TAGTATGGGTATATATAATAGAAACACTATGAAGTTTGAATATCCTAAGT GGCTGATGCATTGGTAAAAGCAGCTAATGGTGGAACTATGCCGACAGTAG CACCAACGAAGAAACCTACAGCAACACCGACTCCAACAAAAAAACCTACT AGCACACCGAAGCCTACAGTTAAACCGACGCAAACGCCGAAACCAACAA GAAAGCCGGGAAAAGAGTAAAATATTCAGCTTTAGATTTGGACGGCAAT GTGAGTAGTGGTAATCTTATTCCA (SEQ ID NO: 97) | KNGKRPLICNTYAGCTEAGALN SFKIPNDTVDNAIIAQVHFYQPT GYCFDMNPNQGQNMDVDYKTC GGESAADTLAMMLYKRFTEKGI PCIVGEFAASHKKNDDNRAEWV DYVVRKTGTYGVKCFWWDNG GTFTPNYSTGLDYYNSMGIYNR NTMQFEYPKVADALVNAANGG AKPTTAPTKKPTSTPKPTATLKP TTKPTTKPTTKPNPTSGADSGEII LFSGSNHADFKAWGGDDWPSA FEISPKYEPMKLDLNKNFEIKVD YNGADIVLIFARWDKDIWAQISP YYVVDGTAVFTKEQIAKAYGSD DFSGLDYIAVKPLPSEEGVTVTK VSGIYTNGGSEDVDINLKGIAGE WANGVNIGWNLGNTLDAYDTN RFTRTKGHNNPADIETCWGNPV TTKAMIDDIKAQGFNAVRVPVT WDYEIDDNDGYKVNEAWMAR VKEVVDYVMDNDMYCIVNVHH DTGEQGWLKASTANYAKNEKK FKALWKQIAAEFKNYDHKLAFE GFNEMLDEKNSWNYPGADAGE AINLYNQAFVDVVRASGGKNSD RPLICNTYAGCTEAGALNSFEIP NDTVENAIIAQVHFYQPTGYCFD MNPNQGQNMDVDYKTCGGESA ADTLAMMLYKRFTEKGIPCIVG EFAASHKQNDDNRAAWVDYVV SKTGKYGVKCFWWDNGGTFTP NYSTGLDYYNSMGIYNRNTMKF EYPKVADALVKAANGGTMPTV APTKKPTATPTPKKPTSTPKPT VKPTQTPKPTRKPGKRVKYSAL DLDGNVSSGNLIP (SEQ ID NO: 128) |
| Celulomonas fimi CenC (cenC) | ATGGTTAGCAGAAGGTCTAGCCAAGCAAGAGGAGCTTTGACGGCAGTGGT TGCTACTCTTGCATTGGCTTTAGCTGGTAGTGGCACGGCATTAGCTGCATC GCCTATAGGGGAAGGAACATTCGATGACGGCCCTGAAGGTTGGGTAGCTT ATGGAACTGATGGTCCGTTGGATACATCAACAGGCGCTCTTTGTGTTGCAG TCCCAGCTGGCTCTGCACAGTACGGAGTGGGTGTCGTACTTAATGGCGTTG CTATTGAAGAGGGAACACATATACATTAAGGTATACAGCAACGGCTTCT ACAGACGTAACGGTGAGAGCATTAGTTGGGCAAAACGGTGCACCATATGG CACAGTTCTTGACACGAGTCCGGCTTTGACGTCAGAACCTAGACAGGTAA CTGAAACATTCACTGCATCAGCTACACCCAGCACCTCTGCTGCAGACG ATCCGGAGGGCCAAATAGCTTTTCAGTTAGGTGGCTTCAGCGCAGATGCTT GGACATTTTGCCTTGACGATGTGGCATTAGATAGCGAAGTAGAGCTTTTAC CTCATACGAGTTTCGCAGAATCTTTGGGCCCGTGGAGCTTGTATGGAACTT CGGAGCCAGTCTTTGCTGATGGGAGAATGTGTGTGGATCTTCCGGGTGGTC AGGGTAATCCTTGGGATGCTGGATTAGTCTATAATGGGGTACCGGTGGGC GAAGGTGAGAGTTACGTTTTGTCGTTTACAGCAAGTGCTACGCCGGATATG CCAGTAAGAGTCCTTGTGGGAGAAGGGGGTGGAGCTTATAGGACTGCTTT TGAACAGGGATCTGCACCGTTACTTGGGGAGCCAGCAACGAGGGAGTACG CTTTCACTAGCAACCTTACGTTTCCGCCTGACGGCGATGCACCAGGTCAGG TGGCATTTCACCTTGGAAAGGCTGGAGCATACGAATTTTGCATTTCACAAG TAAGTTTAACGACTTCTGCAACACCTCCGCCAGGTTACGAACCTGACACTG GACCGAGAGTTAGAGTAAATCAGGTCGGTTATTTACCATTCGGTCCGAAG AGAGCAACACTTGTGACTGACGCAGCAGAACCGGTTGCTTGGGAATTAAG | CAA40993 MVSRRSSQARGALTAVVATLAL ALAGSGTALAASPIGEGTFDDGP EGWVAYGTDGPLDTSTGALCV AVPAGSAQYGVGVVLNGVAIEE GTTYTLRYTATASTDVTVRALV GQNGAPYGTVLDTSPALTSEPR QVTETFTASATYPATPAADDPE GQIAFQLGGFSADAWTFCLDDV ALDSEVELLPHTSFAESLGPWSL YGTSEPVFADGRMCVDLPGGQG NPWDAGLVYNGVPVGEGESYV LSFTASATPDMPVRVLVGEGGG AYRTAFEQGSAPLTGEPATREY AFTSNLTFPPDGDAPGQVAFHL GKAGAYEFCISQVSLTTSATPPP GYEPDTGPRVRVNQVGYLPFGP KRATLVTDAAEPVAWELRDAD GVVVADGTSEPRGVEPSAAQAV HVLDFSDVTTQGAGYTLVADGE TSRPFDIDGDLYQQLRYDALNY FYLARSGTEIEADVVGEEYARE |

TABLE 2-continued

Exemplary Biomass Degrading Enzymes That Can Be Used According to the Present Invention

| Organism and Protein (Gene) | Codon-Optimized DNA Sequence | Accession Number and Amino Acid Sequence |
|---|---|---|
| | GGATGCTGATGGTGTAGTTGTCGCAGATGGAACGAGTGAACCTAGAGGCG TTGAACCATCAGCTGCACAAGCTGTACATGTTTTAGACTTTTCGGATGTAA CTACGCAGGGAGCTGGCTATACACTTGTTGCTGACGGAGAAACGAGTAGA CCGTTTGATATAGACGGTGATTTATACCAACAGTTAAGATACGACGCTTTG AATTATTTCTATCTTGCAAGAAGCGGAACTGAAATTGAAGCAGACGTCGTT GGTGAAGAATACGCAAGGGAGGCAGGACACGTAGGCGTGGCACCAAACC AAGGCGACACAGACGTGCCTTGTATTGGTCCTAGAGATTATTACGACGGA TGGACTTGCGATTACAGGTTAGACGTTTCGGGAGGTTGGTACGACGCTGGT GATCACGGAAAATACGTAGTCAACGGGGGCATTGCAGTGGGTCAATTACT TCAGACTTATGAAAGGGCTTTGCATGCAGGGACAGCAGATGCTTTAGCAG ACGGCACGCTTGATGTTCCGGAACACGGTAATGATGTACCAGACGTCTTA GACGAGGCTAGGTGGGAGCTTGAATGGATGCTTTCGATGATTGTCCCTGA AGGAGAGTATGCTGGGATGGTTCATCATAAAGTTCACGACGAGGGATGGA CTGGTTTACCTTTGCTTCCTGCAGACGATCCGCAAGCTAGGAGTTTGCATA GGCCAAGCACAGCTGCTACACTTAATTTAAGCGCAGTTGCTCAGACTCTTT TAGAGGCTAGGCTTCTTGAACCTTACGATCCACAACTTGCTCAGACTCTTTTAGAG GCAGCTAGAACTACATGGGCAGCTGCACAAGAACACCTGCTCTTTACGC ACCTGGTGAGGCAGGGGCTGACGGCGGAGGCGCTTATAACGATAGTCAGG TAGCTGACGGTTTTATTGGGCTGCTGCAGAGCTTTACTTGACGACTGGCG AGGACGCATTCGCAACGGCAGTCACTACGTCACCGCTTCATACTGCTGAC GTCTTTACGGCTGACGGCTTTGGGTGGGCAGCGTTGCAGCTTTGGGTAGG CTTGACTTAGCTACAGTCCCTAATGAACTTCCGGGATTAGATGCTGTACAA AGTTCAGTGGTTGAAGGCGCACAGGAATATTTGGCTGCACAGGCTGGACA AGGTTTTGGAAGTCTTTATAGCCCACCGGGTGGCGAGTACGTGTGGGGTTC TAGTAGCCAAGTCGCAAACAATTTAGTGGTTGTTGCTACAGCTTATGATCT TACAGGCGACGAGAGGTTCAGAGCAGCTACTCTTGAAGGACTTGATTACC TTTTTGGTAGGAATGCTTTAAACCAAAGTTATGTCACTGGTTGGGGAGGG TTGCTTCACACCAGCAACATTCTAGGTGGTTTGCACATCAATTCGATCCAT CTTTGCCTTCGCCGCCTCCAGGCTCGCTTGCTGGCGGGCCGAATAGCCAGG CTGCAACTTGGGACCCAACTACAAAGGCAGCTTTCCCTGACGGGTGCGCT CCTAGCGCTTGCTACGTTGATGAAATACAGGCTTGGTCAACGAACGAGTT AACGGTAAACTGGAACTCGGCTCTTAGTTGGGTGCTTCATGGGTAGCTGA TCAGGGGTCTGCAGAGCCAGTCCCGACGGCACCAGTTGTGACAAGACAAC CTGTTGACGCAACAGTAGCTTTAGGAGCAGACGCAACTTTCACAGCAGAG GCTTCAGGTGTGCCAGCTCCTACAGTTAGGTGGCAAGTTAGAGCAGGAAG GGGGTGGAAGGACGTCGCTGGTGCAACAGGCACTACATTGCTAACAGTGAGGG CAACTGCTAGAACTGATGGGACGAGGTATAGAGCAGTATTTACTAACGCA GCTGGGAGTGTGGAGAGCGCAGTTGTAAGGCTTACAGTCGAAAGAGCAGC TCCAGTGGTTACACAACATCCAGCTGATGTTAGAGCAAGGGTAGGTACGA GGGCAGTGTTTAGGGCAGCAGCTGACGGATATCCAACACCGTGTGTTGTT GGCAAGTCAGATGGGGGGCGGTTCTTGGAGGCCAATTCCTTGGGCAACG AGCACTACATTATCGGTACCAGTGACAGTACTTGCTGCAGGAACTGAATA CAGGGCTGTTTTTACAAATGCAGTAGGTACTGCTGCAACAGAGCCTGCTG AACTTGCAGTCCAAAGACCGAGGAGT (SEQ ID NO: 98) | AGHVGVAPNQGDTDVPCIGPRD YYDGWTCDYRLDVSGGWYDA GDHGKYVVNGGIAVGQLLQTY ERALHAGTADALADGTLDVPEH GNDVPDVLDEARWELEWMLSM IVPEGEYAGMVHHKVHDEGWT GLPLLPADDPQARSLHRPSTAAT LNLSAVAAQGARLLEPYDPQLA QTLLEAARTTWAAAQEHPALY APGEAGADGGGAYNDSQVADE FYWAAAELYLTTGEDAFATAVT TSPLHTADVFTADGFGWGSVAA LGRLDLATVPNELPGLDAVQSS VVEGAQEYLAAQAGQGFGSLYS PPGGEYVWGSSSQVANNLVVV ATAYDLTGDERFRAATLEGLDY LFGRNALNQSYVTGWGEVASH QQHSRWFAHQLDPSLPSPPPGSL AGGPNSQAATWDPTTKAAFPDG CAPSACYVDEIQAWSTNELTVN WNSALSWVASWVADQGSAEPV PTAPVVTRQPVDATVALGADAT FTAEASGVPAPTVRWQVRAGRG WKDVAGATGTTLTVRATARTD GTRYRAVFTNAAGSVESAVVRL TVERAAPVVTQHPADVRARVGT RAVFRAAADGYPTPCVVWQVR WGGGSWRPIPWATSTTLSVPVT VLAAGTEYRAVFTNAVGTAATE PAELAVQRPRS (SEQ ID NO: 129) |
| Celulomonas fimi Exo- glucanase (cex) | ATGCCTAGAACAACTCCAGCACCTGGACATCCAGCTAGGGGTGCAAGGAC AGCACTTAGGACGACAAGAAGGAGAGCAGCTACGTTGGTAGTTGGGGCTA CGGTAGTCTTGCCTGCTCAAGCAGCAACAACTTTAAAAGAGGCAGCTGAT GGAGCTGGTAGAGACTTTGGCTTTGCTCTTGATCCAAATAGGTTATCGGAA GCACAGTACAAAGCAATTGCAGATTCTGAATTTAACTTAGTTGTGGCTGAG AATGCAATGAAATGGGATGCTACTGAACCTAGCCAAAATTCATTCTCGTTC GGAGCTGGCGACAGGGTTGCTTCATATGCAGCTGACACGGGCAAGGAACT TTATGGACACACATTGGTTTGGCATAGCCAGTTACCAGACTGGGCAAAGA ACTTGAACGGTTCGGCATTTGAGTCAGCTATGGTAAATCACGTGACTAAA GTTGCAGATCATTTTGAAGGCAAGGTAGCTTCATGGGATGTAGTGAACGA GGCTTTCGCAGATGGAGATGGTCCTCCACAAGATAGCGCTTTCCAACAGA AGTTGGGCAATGGATACATTGAAACGGCTTTCAGGGCAGCAAGGGCTGCA GATCCTACAGCTAAGTTGTGTATAAACGATTACAATGTAGAAGGTATTAAT GCAAAGAGTAATTCACTTTACGATTTGGTTAAAGACTTCAAAGCTAGGGG CGTCCCATTAGATTGCGTGGGATTTCAGTCTCATCTTATAGTTGGTCAAGT ACCTGGCGATTTTAGGCAAAACTTAACAGATTTGCAGGTTGGGAGTTGG ATGTTAGGATTACTGAACTTGATATAAGAATGAGAACACCAAGCGACGCT ACTAAATTAGCAACACAGGCAGCTGATTATAAAAAGGTAGTCCAGGCATG TATGCAAGTGACAAGGTGCCAGGGTGTGACTGTGTGGGGTATTACAGATA AATATTCATGGGTACCTGACGTGTTTCCAGGCGAGGGGGCAGCTCTTGTGT GGGACGCTTCTTACGCTAAAAAGCCTGCATATGCTGTGATGGAAGCA TTCGGCGCTTCGCCAACACCAACTCCTACGACACCTACACCGACTCCAACA ACGCCGACGCCTACGCCAACTAGCGGCCCTGCTGGATGCCAAGTATTATG GGGGTAATCAGTGGAATACGGGCTTCAACAACTAATGGACAGGTAAAAA ATACTTCGAGCGCTCCAGTAGATGGTTGGACATTAACATTTTCTTTTCCTA GCGGACAACAAGTGACTCAGGCTTGGTCAAGTACAGTTACTCAATCTGGC AGCGCAGTAACAGTGAGAAATGCTCCATGGAACGGTTCAATTCCTGCTGG AGGCACTGCTCAGTTTGGTTTTAATGGATCTCACACAGGCACAAATGCTGC ACCAACTGCTTTTTCTTTAAATGGAACACCTTGTACTGTAGGTCTCGAGTG | AAA56791 MPRTTPAPGHPARGARTALRTT RRRAATLVVGATVVLPAQAATT LKEAADGAGRDFGFALDPNRLS EAQYKAIADSEFNLVVAENAMK WDATEPSQNSFSFGAGDRVASY AADTGKELYGHTLVWHSQLPD WAKNLNGSAFESAMVNHVTKV ADHFEGKVASWDVVNEAFADG DGPPQDSAFQQKLGNGYIETAF RAARAADPTAKLCINDYNVEGI NAKSNSLYDLVKDFKARGVPLD CVGFQSHLIVGQVPGDFRQNLQ RFADLGVDVRITELDIRMRTPSD ATKLATQAADYKKVVQACMQV TRCQGVTVWGITDKYSWVPDV FPGEGAALVWDASYAKKPAYA AVMEAFGASPTPTPTPTPTPTT PTPTPTSGPAGCQVLWGVNQW NTGFTANVTVKNTSSAPVDGWT LTFSFPSGQQVTQAWSSTVTQSG SAVTVRNAPWNGSIPAGGTAQF GFNGSHTGTNAAPTAFSLNGTP CTVG (SEQ ID NO: 130) |

TABLE 2-continued

Exemplary Biomass Degrading Enzymes That Can Be Used According to the Present Invention

| Organism and Protein (Gene) | Codon-Optimized DNA Sequence | Accession Number and Amino Acid Sequence |
|---|---|---|
| | ATAAAACGAAAGGCTCAGTCGAAAGACTGGGCCTTTCGTTTTATCTGTTGT TTGTCGGTGAACGCTCTCCTGAGTAGGACAAATCCGCCGGGAGCGGATTT GAACGTTGCGAAGCAACGGCCCGGAGGGTGGCGGGCAGGACGCCCGCCA TAAACTGCCAGGCATCAAATTAAGCAGAAGGCCATCCTGACGGATGGCCT TTT (SEQ ID NO: 99) | |
| *Acidothermus cellulolyticus* glycoside hydrolase, family 5 (locus_tag = "Acel_0614") Cel5A | ATGCCGAGGGCATTAAGGAGAGTCCCGGGGTCAAGGGTTATGCTTAGAGT GGGTGTAGTTGTGGCTGTATTGGCATTAGTTGCAGCTTTGGCTAATTTAGC AGTTCCTAGGCCAGCAAGAGCTGCTGGCGGAGGTTATTGGCACACAAGCG GCAGAGAGATATTAGATGCTAATAACGTGCCTGTTAGGATTGCAGGCATT AACTGGTTCGGATTTGAAACGTGTAATTACGTAGTTCACGGCCTTTGGAGC AGAGACTATAGGAGTATGTTGGATCAAATTAAGTCATTAGGATACAATAC AATAAGACTTCCATACAGCGATGACATTCTTAAGCCGGGGACGATGCCGA ACTCGATAAACTTTTACCAGATGAATCAAGATTTACAGGGCTTGACGAGTT TACAAGTGATGGATAAAATTGTAGCATACGCTGGACAGATAGGTTTAAGA ATAATTCTTGACAGGCATAGACCTGATTGCTCAGGTCAAAGTGCATTATGG TATACGAGTAGTGTCTCAGAAGCTACATGGGATATCTGATTTGCAAGCACTT GCACAGAGGTACAAGGGGAACCCAACAGTGGTGGGGTTTGATTACACAA CGAGCCACATGATCCGGCTTGCTGGGGTTGTGGAGATCCTAGCATTGATTG GAGATTGGCTGCAGAGAGGGCTGGTAATGCTGTGCTTAGTGTAAATCCGA ACTTATTGATATTGTGGAAGGCGTTCAAAGTTATAACGGTGACTCATACT GGTGGGGTGGAAATCTTCAGGGCGCTGGTCAATATCCTGTAGTTTTAAACG TACCGAACAGACTTGTATATAGCGCTCACGACTATGCAACTTCAGTTTATC CTCAGACATGGTTTAGTGACCCAACTTTTCCTAATAACATGCCAGGAATTT GGAATAAGACTGGGGCTACCTTTTTAACCAAAACATAGCACCAGTGTGG TTAGGTGAGTTCGGTACTACTTTGCAGTCTACAACAGACCAGACTTGGCTT AAAACATTAGTGCAGTATTTAAGACCAACTGCACAATACGGCGCTGATAG CTTTCAGTGGACTTTTTGGAGTTGGAATCCTGACAGTGGCGATACTGGGG AATATTGAAGGATGATTGGCAAACTGTTGATACGGTGAAAGATGGTTATC TTGCACCTATAAAAAGTAGCATATTCGACCCTGTGGGAGCTAGTGCTAGCC CTTCATCTCAACCTAGCCCATCTGTTTCACCTAGTCCAAGCCCGTCACCAA GCGCAAGTAGAACTCCGACTCCTACGCCAACACCGACTGCTTCTCCAACTC CTACGTTGACTCCGACGGCTACGCCGACTCCTACGCAAGCCCGACGCCA AGTCCAACGGCTGCTTCTGGAGCAAGATGTACGGCTTCTTATCAGGTAAAT TCTGACTGGGGTAACGGGTTTACGGTGACAGTCGCTGTGACTAATTCAGGT TCGGTAGCTACAAAGACTTGGACAGTAAGCTGGACTTTTGGAGGCAACCA AACAATTACAAACTCTTGGAACGCTGCAGTTACTCAAAACGGTCAGTCTGT GACAGCAAGAAACATGTCGTATAATAACGTAATACAGCCTGGCCAAAACA CTACATTTGGATTCCAGGCTTCTTATACTGGATCAAACGCAGCTCCGACAG TGGCATGCGCTGCATCACTCGAGTGATAAAACGAAAGGCTCAGTCGAAAG ACTGGGCCTTTCGTTTTATCTGTTGTTTGTCGGTGAACGCTCTCCTGAGTAG GACAAATCCGCCGGGAGCGGATTTGAACGTTGCGAAGCAACGGCCCGGAG GGTGGCGGGCAGGACGCCCGCCATAAACTGCCAGGCATCAAATTAAGCAG AAGGCCATCCTGACGGATGGCCTTTT (SEQ ID NO: 100) | ABK52387 MPRALRRVPGSRVMLRVGVVV AVLALVAALANLAVPRPARAA GGGYWHTSGREILDANNVPVRI AGINWFGFETCNYVVHGLWSR DYRSMLDQIKSLGYNTIRLPYSD DILKPGTMPNSINFYQMNQDLQ GLTSLQVMDKIVAYAGQIGLRII LDRHRPDCSGQSALWYTSSVSE ATWISDLQALAQRYKGNPTVVG FDLHNEPHDPACWGCGDPSIDW RLAAERAGNAVLSVNPNLLIFVE GVQSYNGDSYWWGGNLQGAG QYPVVLNVPNRLVYSAHDYATS VYPQTWFSDPTFPNNMPGIWNK NWGYLFNQNIAPVWLGEFGTTL QSTTDQTWLKTLVQYLRPTAQY GADSFQWTFWSWNPDSGDTGGI LKDDWQTVDTVKDGYLAPIKSS IFDPVGASASPSSQPSPSVSPSPSP SPSASRTPTPTPTPTASPTPTLTPT ATPTPTASPTPSPTAASGARCTA SYQVNSDWGNGFTVTAVTNS GSVATKTWTVSWTFGGNQTITN SWNAAVTQNGQSVTARNMSYN NVIQPGQNTTFGFQASYTGSNA APTVACAAS (SEQ ID NO: 131) |
| *Acidothermus cellulolyticus* glycoside hydrolase family protein (locus_tag = "Acel_0617") | ATGCCTGGGCTTAGAAGGAGACTTAGGGCTGGTATAGTTTCTGCAGCTGC ATTGGGCTCTTTAGTTAGCGGGCTTGTGGCAGTCGCTCCAGTAGCACATGC TGCAGTAACTTTAAAAGCTCAGTACAAAAACAACGATAGTGCACCTTCGG ATAATCAGATTAAACCAGGGTTGCAACTTGTGAATACGGGCAGCTCTAGC GTCGATTTGAGTACTGTAACGGTTAGGTATTGGTTTACTAGGGATGGAGGT TCAAGTACATTAGTATATAACTGTGACTGGGCTGCAATGGGTTGCGGTAAC ATTAGGGCATCCTTTGGCAGCGTGAATCCAGCAACACCTACAGCAGATAC GTACCTTCAGTTGAGTTTTACTGGAGGTACGTTAGCTGCTGGTGGGTCGAC GGGGGAAATTCAAACAGAGTTAATAAATCGGACTGGTCAAACTTTGACG AGACAAACGATTATTCATACGGTACTAACACGACATTTCAAGACTGGACG AAAGTCACTGTCTACGTAAATGGCGTGCTTGTATGGGGAACTGAGCCATC AGGTGCAACAGCATCACCGTCTGCTAGCGCAACTCCAGCCCTTCATCTAG CCCGACGACAAGTCCTTGAGTTCTCCAAGCCCTTCAAGTTCTCCGACTCC GACACCTTGAGTAGCTCTCCACCTCCATCATCGAACGACCCGTACATACA GAGGTTTTTAACAATGTACAATAAAATTCACGATCCTGCTAATGGCTATTT TAGCCCTCAGGGAGATACCTTACCATAGCGTTGAAACGTTAATTGTCGAAGC ACCAGACTACGGGCACGAAACGACTTCAGAGGCTTATTCGTTCTGGCTTTG GTTAGAAGCTACTACGGGGCTGTGACAGGTAACTGGACCATTTAATA ACGCATGGACGACTATGGAAACGTACATGATTCCTCAGCACGCAGACCAA CCTAACAACGCATCGTACAATCCTAATAGTCCGTCTAGCTATGCACCAGA AGAGCCGCTTCCATCTATGTATCCAGTAGCTATAGATTCATCGGTTCCGGT AGGACATGATCCTTTAGCAGCTGAGTTGCAGTCTACATACGGTACGCCTGA CATTTACGGAATGCACTGGTTGGCAGATGTCGATAACATTTACGGATATGG CGACGGCCCGGGTGGTGCACTGCAAATCTGCCCCTTCAGCTAAAGGAGTTT CGTACATTAATACTTTTCAAGAGGTAGTCAGGAAAGTGTTTGGGAAACA GTAACGCAGCCAACATGTGATAACGGAAAGTACGGGGAGCACACGGTT ACGTTGACTTATTTATACAGGGCAGCACACCACCTCAATGGAAATACACA GACGCTCCTGACGCAGACGCAAGGGCTGTACAGGCAGCTTATTGGGCTTA CACTTGGGCTTCAGCACAAGGTAAGGCTTCAGCTATTGCACCTACTATAGC | YP_872376 MPGLRRRLRAGIVSAAALGSLV SGLVAVAPVAHAAVTLKAQYK NNDSAPSDNQIKPGLQLVNTGSS SVDLSTVTVRYWFTRDGGSSTL VYNCDWAAMGCGNIRASFGSV NPATPTADTYLQLSFTGGTLAA GGSTGEIQNRVNKSDWSNFDET NDYSYGTNTTFQDWTKVTVYV NGVLVWGTEPSGATASPSASAT PSPSSSPTTSPSSSPSPSSSPTPTPS SSSPPPSSNDPYIQRFLTMYNKIH DPANGYFSPQGIPYHSVETLIVE APDYGHETTSEAYSFWLWLEAT YGAVTGNWTPFNNAWTTMETY MIPQHADQPNNASYNPNSPASY APEEPLPSMYPVAIDSSVPVGHD PLAAELQSTYGTPDIYGMHWLA DVDNIYGYGDSPGGGCELGPSA KGVSYINTFQRGSQESVWETVT QPTCDNGKYGGAHGYVDLFIQG STPPQWKYTDAPDADARAVQA AYWAYTWASAQGKASAIAPTIA KAAKLGDYLRYSLFDKYFKQV GNCYPASSCPGATGRQSETYLIG WYYAWGGSSQGWAWRIGDGA AHFGYQNPLAAWAMSNVTPLIP LSPTAKSDWAASLQRQLEFYQW LQSAEGAIAGGATNSWNGNYGT |

TABLE 2-continued

Exemplary Biomass Degrading Enzymes That Can Be Used According to the Present Invention

| Organism and Protein (Gene) | Codon-Optimized DNA Sequence | Accession Number and Amino Acid Sequence |
|---|---|---|
| | TAAGGCTGCAAAATTGGGAGACTATTTGAGATACAGCTTATTCGACAAAT<br>ATTTTAAACAAGTCGGAAATTGCTACCCAGCTAGTTCTTGCCCAGGTGCAA<br>CGGGGAGACAGTCAGAGACTTACTTGATAGGGTGGTATTACGCTTGGGA<br>GGGAGTTCTCAGGGATGGGCATGGAGAATAGGTGATGGGGCTGCTCACTT<br>CGGATATCAGAACCCTCTTGCTGCATGGGCAATGAGCAATGTGACACCGC<br>TTATTCCTTTAAGCCCAACGGCTAAGTCAGACTGGGCAGCTTCGCTTCAAA<br>GACAGTTGGAGTTCTACCAATGGTTACAGAGCGCTGAGGGTGCAATTGCT<br>GGAGGGGCTACTAACAGCTGGAATGGCAATTATGGCACACCTCCAGCTGG<br>CGATAGTACATTCTACGGGATGGCTTATGATTGGGAGCCTGTTTATCACGA<br>CCCACCTAGCAACAATTGGTTTGGATTCCAGGCATGGTCGATGGAGAGGG<br>TAGCTGAGTACTATTACGTCACGGGTGATCCGAAAGCAAAGGCTTTGCTTG<br>ACAAATGGGTGGCTTGGGTTAAACCAAATGTAACTACAGGAGCATCTTGG<br>AGCATTCCTAGTAACTTATCTTGGTCAGGGCAACCGGACACGTGGAACCC<br>AAGTAATCCTGGCACTAACGCTAATTTGCATGTCACAATTACGAGTAGCG<br>GTCAGGATGTGGGAGTGGCAGCAGCTTTAGCTAAAACTTTAGAGTATTAC<br>GCTGCAAAGTCAGGCGATACAGCTAGTAGAGACTTGGCTAAAGGTCTTTT<br>AGATAGCATATGGAATAACGATCAAGATAGCCTTGGTGTATCAACACCAG<br>AGACAAGAACGGATTACAGTAGATTCACACAGGTTTATGATCCTACTACA<br>GGCGATGCCTTTACATTCCGAGCGGTTGGACGGGAACTAGTGCCGAACGG<br>GGATCAAATAAAGCCTGGAGCTACATTCTTATCTATAAGAAGCTGGTATA<br>CAAAAGATCCACAGTGGTCGAAAGTACAGGCTTACTTGAACGGTGGCCCT<br>GCACCGACGTTTAATTATCATAGGTTTTGGGCTGAAAGTGACTTCGCAATG<br>GCTAACGCAGATTTTGGTATGCTTTCCAAGCGGATCGCCATCACCGACG<br>CCAAGTCCAACGCCGACTTCTAGTCCTTCACCGACACCTAGCAGTTCTCCT<br>ACGCCGAGTCCTAGCCCATCGCCGACGGGTGACACTACTCCTCCGTCGGT<br>GCCGACTGGTTTACAGGTCACTGGCACTACGACTTCGAGTGTTTCTTTGTC<br>ATGGACAGCTTCGACAGACAACGTTGGAGTAGCACATTATAATGTGTATA<br>GGAATGGAACACTTGTAGGACAACCTACTGCAACGAGTTTTACGGATACT<br>GGTTTAGCTGCAGGGACATCGTATACGTACACTGTAGCTGCAGTCGATGC<br>AGCTGGGAATACGAGCGCTCAGTCAAGTCCAGTGACAGCAACAACGGCAA<br>GTCGAGTCCTAGCCCATCACCTAGTCCGACTCCGACGAGTAGCCCCTTCGC<br>CGACACCGTCACCTACACCGTCACCGACAAGCACGAGTGGGGCAAGCTGT<br>ACTGCTACATATGTTGTAAATTCAGATTGGGGCTCGGGTTTCACGACTACA<br>GTCACGGTGACTAATACTGGCACAAGAGCAACTTCGGGCTGGACGGTGAC<br>TTGGAGTTTCGCTGGGAACCAAACAGTCACTAACTACTGGAACACGGCTTT<br>GACACAAAGCGGAAAGAGTGTAACGGCAAAAAATCTTAGTTATAATAACG<br>TAATTCAGCCGGGACAATCGACAACGTTTGGGTTTAATGGCAGTTATAGC<br>GGTACTAACACGGCACCAACATTGTCTTGCACTGCAAGT (SEQ ID NO: 101) | PPAGDSTFYGMAYDWEPVYHD<br>PPSNNWFGFQAWSMERVAEYY<br>YVTGDPKAKALLDKWVAWVKP<br>NVTTGASWSIPSNLSWSGQPDT<br>WNPSNPGTNANLHVTITSSGQD<br>VGVAAALAKTLEYYAAKSGDT<br>ASRDLAKGLLDSIWNNDQDSLG<br>VSTPETRTDYSRFTQVYDPTTGD<br>GLYIPSGWTGTMPNGDQIKPGA<br>TFLSIRSWYTKDPQWSKVQAYL<br>NGGPAPTFNYHRFWAESDFAM<br>ANADFGMLFPSGSPSPTPSPTPTS<br>SPSPTPSSSPTPSPSPSPTGDTTPP<br>SVPTGLQVTGTTTSSVSLSWTAS<br>TDNVGVAHYNVYRNGTLVGQP<br>TATSFTDTGLAAGTSYTYTVAA<br>VDAAGNTSAQSSPVTATTASPSP<br>SPSPSPTPTSSPSPTPSPTPSPTSTS<br>GASCTATYVVNSDWGSGFTTTV<br>TVTNTGTRATSGWTVTWSFAG<br>NQTVTNYWNTALTQSGKSVTA<br>KNLSYNNVIQPGQSTTFGFNGSY<br>SGTNTAPTLSCTAS (SEQ ID NO: 132) |
| *Acido-<br>thermus<br>cellulolyticus*<br>Biomass<br>degrading<br>enzyme<br>(locus_tag =<br>"Acel_0135") | ATGGGAACATATCCTATAAGATCGGTCAGCGGTGGCGTTGCACTTGCTGC<br>ATGCGCTGTTCTTACTATGACAACGGCTGCAGCAGCTACGCCTATTCACGA<br>TGCTAGTTCGCCTCACACTATTCCACCTCATGCTAGGTTGTACACACCGCC<br>ACCGGACAAAGGAGCAATTAAGCAAATAACAGATTTACTTAAAGCTAGGG<br>ACGTCAGGGACGCAAGATTGATTGCTGAGATGATAAGCACTCCTCAGGCA<br>GTTTGGTTTACGGGGGGTACACCGGATCAGGTGAGAAGGGACGTCCACAG<br>AGTTGTTACTAAAGCAGCTGCACACCACGCAATTCCTGTGTTAGTTGCTTA<br>CAATATACCGTTTAGAGATTGCTCACAGTACAGCGCTGGAGGCGCTGTTG<br>ATACAGCAGCATATGAGGCTTGGATAGATGGCTTTGCAGCAGGCATAGGA<br>GATAAGAGAGCTATAGTTCTTTTGGAACCTGATAGTTTAGGCATAATACCA<br>TACAACACAGATATTAATGGAAATGCTGAGTGGTGCAAGCCAGACCTTTC<br>AGGTACAGGCCTTACACCTGACGAGGCTAACCAAGCTAGATATGATCAAT<br>TAAATTATGCAGTGGACGCTCTTGAAGCACACAGAAATGTATCTGTTTACC<br>TTGATGGTACGCATAGCGGTTGGTTAGGCGTAGGAGATATAGCTCAAAGA<br>CTTGTGAGGGCTGGTGTTCAGAGAGCTCAAGGCTTTTTTGTAAACGTGAGT<br>AATTATCAAACTACAGAGAGGCAGATAAAGTACGGAACATGGATTTCAGA<br>ATGCATAGCATTTGCAAATGACCCAGAAGAGGGTGGGTGGAGATTAGGCC<br>ATTATTCTTGGTGTGCTAGCCAATACTATCCTGCAAATCCTAACGACTTTTC<br>AACTTGGGTTCAGACAGATCAGTGGTACGCTAGTAATTTGGGTACTGCAGT<br>ACCAACAACTCACTTCGTCATTGACACTTCTAGAAACGGAAGGGGTCCGA<br>ACGATATGACAGCTTATGCTGCAGCTCCTTATAACCAGCCTGCTAGCGTAA<br>TATCGGCTCTTCAGGGAGGAAGTTGGTGCAACCCACCTGGCAGAGGTTTA<br>GGATTGAGGCCTACAGTGAATACAGGCGTTCCTCTTTTAGACGCTTACCTT<br>TGGGTAAAGATTCCAGGTGAATCTGATGGACAGTGCGATGCAGCTGGCGG<br>TGCTAGGGCTTGGGATTATAGCGCTTACACTGAACCTGGATGGCCAACAG<br>ACCCTTCACACAGGCTTTATTCGATCCTTTATGGGGCCTTTACGACCCGC<br>CAGCAGGGCAATGGTTTCCTCAACAGGCTTTACAACTTGCTCAACTTGCAG<br>TGCCTCCGTTGCAACCACAGTGGCCTGTTCCACCAGTCCATCAC (SEQ ID NO: 102) | ABK51910 AND YP_871896<br>MGTYPIRSVSGGVALAACAVLT<br>MTTAAAATPIHDASSPHTIPPHA<br>RLYTPPPDKGAIKQITDLLKARD<br>VRDARLIAEMISTPQAVWFTGG<br>TPDQVRRDVHRVVTKAAAHHAI<br>PVLVAYNIPFRDCSQYSAGGAV<br>DTAAYEAWIDGFAAGIGDKRAI<br>VLLEPDSLGIIPYNTDINGNAEW<br>CKPDLSGTGLTPDEANQARYDQ<br>LNYAVDALEAHRNVSVYLDGT<br>HSGWLGVGDIAQRLVRAGVQR<br>AQGFFVNVSNYQTTERQIKYGT<br>WISECIAFANDPEEGGWRLGHY<br>SWCASQYYPANPNDFSTWVQT<br>DQWYASNLGTAVPTTHFVIDTS<br>RNGRGPNDMTAYAAAPYNQPA<br>SVISALQGGSWCNPPGRGLGLRP<br>TVNTGVPLLDAYLWVKIPGESD<br>GQCDAAGGARAWDYSAYTEPG<br>WPTDPSQQALFDPLWGLYDPPA<br>GQWFPQQALQLAQLAVPPLQPQ<br>WPVPPVHH (SEQ ID NO: 133) |
| *Butyrivibrio<br>fibrisolvens*<br>Cellulase<br>1(end1) | ATGCATAAGAGCAAGTGTATTAAAAGGGTCTTTACATTTTTGTTAGCACTT<br>TTTGTTTTTGTCATGGCAATTCCTGCAACTAAGGTCAGTGCTGCTGGAGGT<br>ACGGATAGGAGCGCTACTCAAGTAGTTTCTGACATGAGAGTTGGCTGGAA<br>TATTGGTAACTCACTTGACAGTTTTGGTCAGAGCTATAATTTTCCATACAC<br>GAGCCTTAATGAAACGTATTGGGGCAACCCCGGCAACAACTAAGGCTTTAA | P20847<br>MHKSKCIKRVFTFLLALFVFVM<br>AIPATKVSAAGGTDRSATQVVS<br>DMRVGWNIGNSLDSFGQSYNFP<br>YTSLNETYWGNPATTKALIDEV |

TABLE 2-continued

Exemplary Biomass Degrading Enzymes That Can Be Used According to the Present Invention

| Organism and Protein (Gene) | Codon-Optimized DNA Sequence | Accession Number and Amino Acid Sequence |
|---|---|---|
| | TTGACGAGGTCGCAAAGGCTGGATTTAATACAATAAGGATTCCTGTAAGT TGGGGACAATACACGACAGGCAGTGACTACCAGATTCCAGATTTGTCAT GAATAGGGTAAAAGAGGTGGTTGACTATTGTATTGTTAACGATATGTACG TTATTCTTAACAGCCACCATGATATAAACAGCGACTATTGCTTTTACGTCC CGAATAACGCAAACAAGGACAGGTCTGAAAAATACTTTAAGAGCATTTGG ACGCAGATAGCTAAGGAGTTTAAGAACTACGATTACCACCTTGTATTTGA AACGATGAATGAGCCTAGATTAGTCGGACATGGTGAAGAATGGTGGTTTC CGAGGAATAACCCATCAAATGACATTAGGGAAGCAGTAGCTTGCATTAAT GACTATAACCAAGTTGCATTAGACGCTATTAGGGCAACAGGCGGCAATAA CGCAACTAGATGTGTAATGGTTCCAGGTTACGACGCATCTATTGAAGGCTG CATGACAGACGGATTTAAAATGCCGAACGATACGGCTTCAGGTAGGTTGA TTCTTTCAGTACACGCATACATACCGTATTACTTTGCTTTGGCATCAGACA CATACGTGACTAGGTTTGACGATAACCTTAAATATGACATAGACAGTTTTT TTAATGACCTTAATTCTAAATTTTTGAGCAGGAACATTCCAGTCGTGGTCG GCGAAACATCTGCAACAAACAGGACAATACGGCTGAAGGATTTAAATG GGCAGATTATTACTGGGGAAGAGCTGCAAGATACAGTAACGTTGCTATGG TTTTATGGGATAACAACATTTACCAGAATAACAGCGCTGGTTCAGACGGA GAGTGTCACATGTACATAGATAGGAACTCACTTCAGTGGAAAGATCCTGA AATTATAAGTACTATTATGAAGCACGTGGACGGAACTCCAGCAACGATTA ACGGAAAAGAAATACCGTCTACTGAACAACCTGATCCAACACCGGTAGAT CCTGACCCAACACCAGTAGACCCTGATCCGACGCCGGTTGATCCAGACCC TACACCAGTTGATCCTGATCCGCAACCAGTCGATCCGACGCCTGTTTCAGG AGCATTGAAGGCTGAATACACGATTAACAACTGGGGCAGCGGTTATCAGG TTCTTATTAAAGTCAAAAATGATAGCGCTTCTAGAGTGGATGGATGGACG CTTAAGATTTCTAAATCAGAGGTTAAGATAGATTCTAGTTGGTGCGTAAAT ATAGCTGAAGAAGGCGGTTATTACGTTATAACTCCTATGTCATGGAACAGT AGTTTGGAGCCATCTGCAAGTGTTGACTTTGGTATTCAGGGAAGCGGCAGT ATAGGAACAAGTGTCAACATATCTGTGCAA (SEQ ID NO: 103) | AKAGFNTIRIPVSWGQYTTGSD YQIPDFVMNRVKEVVDYCIVND MYVILNSHHDINSDYCFYVPNN ANKDRSEKYFKSIWTQIAKEFK NYDYHLVFETMNEPRLVGHGEE WWFPRNNPSNDIREAVACINDY NQVALDAIRATGGNNATRCVM VPGYDASIEGCMTDGFKMPNDT ASGRLILSVHAYIPYYFALASDT YVTRFDDNLKYDIDSFFNDLNS KFLSRNIPVVVGETSATNRNNTA ERVKWADYYWGRAARYSNVA MVLWDNNIYQNNSAGSDGECH MYIDRNSLQWKDPEIISTIMKHV DGTPATINGKEIPSTEQPDPTPVD PDPTPVDPDPTPVDPDPTPVDPD PQPVDPTPVSGALKAEYTINNW GSGYQVLIKVKNDSASRVDGWT LKISKSEVKIDSSWCVNIAEEGG YYVITPMSWNSSLEPSASVDFGI QGSGSIGTSVNISVQ (SEQ ID NO: 134) |
| Anaerocellum thermophilum 1,4-beta-glucanase (celA) | GGATCATTTAATTATGGTGAAGCATTACAAAAAGCTATAATGTTTTACGAG TTTCAGATGTCTGGCAAGTTGCCTAACTGGGTAAGAAACAACTGGAGGGG AGATAGCATTGAAAGACGGTCAAGATAATGGCTTAGACCTTACTGGAG GTTGGTTTGATGCTGGCGATCATGTTAAGTTTAATTTGCCAATGAGTTATA CTGGAACGATGTTATCATGGGCAGTGTACGAATATAAGGACGCTTTTGTCA AAAGCGGTCAGCTTGAGCACATTTTGAATCAAATAGAGTGGGTAAATGAT TACTTTGTGAAGTGTCACCCGTCTAAATATGTTCTACTACTACCAGGTTGGC GATGGAAGTAAAGATCATGCATGGTGGGGTCCTGCTGAAGTAATGCAAAT GGAAAGACCATCATTTAAGGTTACACAGTCTAGCCCGGGCAGTACTGTAG TGACAGAAACGGCAGCTTCATTAGCAGCTGCATCTATTGTTCTTAAAGACA GGAATCCTACTAAGGCTGCAACATATTTGCAACATGCCAAAGAATTATAT GAGTTTGCAGAAGTCACAAAAAGCGATGCTGGATATACGAGCAGCAAATGG TTATTATAACTCATGGAGTGGCTTTTACGATGAACTTTCTTGGGCTGCAGT ATGGTTGTATTTAGCTACTAATGACAGCACATACCTTACGAAGGCAGAGTC ATATGTTCAAAATTGGCCAAAAATAAGTGGATCTAACACTATTGATTACA AATGGGCTCATTGCTGGGATGACGTGCACAATGGTGCAGCTTTATTGCTTG CAAAGATAACAGGCAAAGATATTTATAAACAGATAATAGAAAGCCATTTA GATTATTGGATTACGGGATACAATGGTGAAAGAATAAAGTATACTCCTAA AGGATTGGCTTGGCTTGACCAATGGGGCTCATTAAGGTACGCAACAACAA CGGCTTTTTTGGCATTTGTATATAGTGATTGGGTTGGTTGTCCATCTACTAA GAAAGAGATTTATAGAAAATTTGGAGAGAGCCAGATAGATTACGCTCTTG GCTCAGCTGGTAGATCTTTTGTCGTAGGATTTGGCACAAACCCGCCTAAGA GGCCACATCACAGAACTGCTCATTCAAGTTGGGCAGACAGCCAATCTATT CCTTCATATCACAGGCACACTTTATACGGTGCTTTGGTGGGAGGCCCAGGT AGTGATGATAGCTATACAGACGATATATCTAATTACGTTAATAACGAAGT AGCATGCGATTATAATGCAGGATTTGTCGGCGCTCTTGCAAAAATGTATCA GTTATACGGTGGAAATCCGATACCTGACTTTAAAGCTATTGAAACGCCAA CTAATGATGAATTTTTTGTGGAAGCAGGCATAAACGCTTCAGGAACAAT TTTATTGAGATAAAGGCAATTGTTAATAACCAAGTGGTTGGCCTGCTAAA GCAACGGATAAATTGAAGTTTAGATATTTTGTAGACCTTAGCGAATTAATA AAAGCTGGATACTCTCCAAATCAGTTAACTTTGTCAACAAATTATAACCAA GGCGCAAAGGTTAGTGGTCCGTACGTTGGTGGATGACTCGAAAAATATTTA TTATATACTTGTCGATTTTACGGGAACTTTAATATACCCTGGCGGTCAAGA CAAATATAAGAAAGAGGTGCAGTTTAGAATTGCAGCTCCACAAAATGTTC AGTGGGATAACTCTAATGACTACTCATTTCAGGATATAAAGGGAGTCAGT AGCGGCTCTGTAGTGAAAACAAAATATATTCCTTTGTACGACGGTGACGTT AAGGTTTGGGGAGATGGCCCGGGTACATCTGGAGCTACGCCGACTCCAAC AGCAACGGCAACGCCTACTCCGACACCTACTGTTACTCCTACGCCGACAC CTACGCCGACTTCTACTGCAACTCCGACGCCTACGCCTACTCCAACGGTGA CACCGACTCCTACGCCAACGCCTACTGCAACACCGACAGCGACCTACACCA CCAACTTCTACGCCCATCAAGCACCGTTGCTGGCGGACAGATTAAAGT CTTGTACGCAAATAAGGAGACTAATTCTACAACGAACACGATTAGGCCAT GGTTAAAAGTGGTCAATACAGGATCATCTTCAATAGACTTATCTAGGGTA ACGATTAGATACTGGTATACGGTTGACGGCGATAAAGCACAAAGCGCTAT ATCTGACTGGGCACAGATTGGTGCAAGTAACGTTACGTTTAAATTTGTAAA | CAB06786 GSFNYGEALQKAIMFYEFQMSG KLPNWVRNNWRGDSALKDGQD NGLDLTGGWFDAGDHVKFNLP MSYTGTMLSWAVYEYKDAFVK SGQLEHILNQIEWVNDYFVKCH PSKYVYYYQVGDGSKDHAWW GPAEVMQMERPSFKVTQSSPGS TVVTETAASLAAASIVLKDRNPT KAATYLQHAKELYEFAEVTKSD AGYTAANGYYNSWSGFYDELS WAAVWLYLATNDSTYLTKAES YVQNWPKISGSNTIDYKWAHC WDDVHNGAALLLAKITGKDIYK QIIESHLDYWITGYNGERIKYTP KGLAWLDQWGSLRYATTTAFL AFVYSDWVGCPSTKKEIYRKFG ESQIDYALGSAGRSFVVGFGTNP PKRPHHRTAHSSWADSQSIPSYH RHTLYGALVGGPGSDDSYTDDI SNYVNNEVACDYNAGFVGALA KMYQLYGGNPIPDFKAIETPTND EFFVEAGINASGTNFIEIKAIVNN QSGWPAKATDKLKFRYFVDLSE LIKAGYSPNQLTLSTNYNQGAK VSGPYVWDASKNIYYILVDFTG TLIYPGGQDKYKKEVQFRIAAPQ NVQWDNSNDYSFQDIKGVSSGS VVKTKYIPLYDGDVKVWGDGP GTSGATPTPTATATPTPTPVTPT PTPTPTSTATPTPTPTPVTPTPTP TPTATPTSTPTPTSTPSSTPVAGG QIKVLYANKETNSTTNTIRPWLK VVNTGSSSIDLSRVTIRYWYTVD GDKAQSAISDWAQIGASNVTFK FVKLSSSVSGADYYLEIGFKSGA GQLQAGKDTGEIQIRFNKSDWS NYNQGNDWSWMQSMTNYGEN VKVTAYIDGVLVWGQEPSGATP TPTAPTVTPTPTPTPTSTPTA TPTATPTPTPTPSSTPVAGGQIKV LYANKETNSTTNTIRPWLKVVN TGSSSDDLSRVTIRYWYTVDGDK AQSAISDWAQIGASNVTFKFVK LSSSVSGADYYLEIGFKSGAGQL |

TABLE 2-continued

Exemplary Biomass Degrading Enzymes That Can Be Used According to the Present Invention

| Organism and Protein (Gene) | Codon-Optimized DNA Sequence | Accession Number and Amino Acid Sequence |
|---|---|---|
| | GTTATCATCTAGTGTTTCTGGAGCAGATTATTACCTTGAAATAGGCTTTAA AAGCGGAGCAGGACAGTTACAAGCTGGAAAGGATACGGGCGAGATTCAA ATAAGGTTTAATAAAAGCGATTGGTCTAATTATAACCAAGGAAACGACTG GTCATGGATGCAGAGCATGACAAACTATGGCGAAAATGTGAAAGTAACTG CTTATATTGATGGAGTATTAGTGTGGGGACAAGAACCAAGCGGTGCTACA CCTACGCCAACTGCTACGCCTGCACCGACAGTAACTCCTACGCCGACACC AACACCGACGAGTACACCTACGGCAACTCCGACTGCTACGCCGACACCAA CTCCAACGCCGAGCTCTACTCCTGTGGCAGGCGGTCAAATAAAGGTACTTT ATGCTAACAAAGAAACGAACAGCACTACAAATACAATAAGACCGTGGCTT AAGGTCGTAAACACTGGCAGTTCAAGTATTGATTTGAGCAGAGTTACAAT AAGGTATTGGTACACAGTGGATGGAGACAAGGCTCAGTCAGCAATAAGCG ATTGGGCTCAAATAGGCGCTTCAAATGTGACGTTTAAATTTGTAAAATTGA GTAGTTCAGTCAGCGGCGCTGACTACTATTTAGAGATTGGATTTAAGTCTG GTGCTGGTCAACTTCAGGCTGGTAAAGACACTGGTGAAATACAGATTAGA TTTAACAAGTCAGATTGGAGTAACTATAATCAAGGAAATGATTGGAGTTG GATGCAGTCTATGACGAATTACGGAGAGAACGTAAAGGTTACAGCATACA TAGACGGCGTGCTTGTATGGGTCAGGAACCTTCAGGTGCAACTCCGACT CCAACAGCAACGCCGGCTCCTACGGTTACACCGACTCCTACGCCGACTCCT ACGTCAACGCCGACTGCTACACCTACAGCAACACCAACGCCTACTCCTAC ACCTTCTTCAACGCCTAGCGTTGTAGGTGAATACGGACAGAGATTATATGTG GTTGTGGAATAAAATTCACGATCCGGCTAACGGCTATTTTAATCAAGATGG TATACCATATCACTCTGTCGAGACTCTTATTTGTGAAAGACCTGACTACGG ACACTTAACAACATCGATCATTTAGTTATTACGTGGTTGGAGGCTGT TTACGGCAAGTTGACGGGTGATTGGAGCAAATTTAAAACTGCATGGGATA CATTAGAAAAGTACATGATACCGTCTGCTGAGGACCAACCAATGAGGTCA TACGATCCTAATAAACCAGCAACTTACGCTGGAGAGTGGGAAACACCTGA TAAATACCCGAGTCCATTGGAATTTAACGTACCTGTAGGTAAGGACCCACT TCATAATGAGTTAGTTAGCACGTATGGATCTACTTTGATGTACGGCATGCA CTGGCTTATGGATGTAGATAATTGGTATGGTTACGGAAAAAGAGGCGACG GTGTCTCAAGGGCAAGTTTTATTAACACATTTCAGAGAGGACCTGAAGAA AGCGTGTGGGAGACAGTTCCGCATCCATCTTGGGAAGAATTTAAGTGGGG CGGTCCTAATGGATTTTTAGATTTATTTATAAAAGATCAAAATTATTCAA ACAGTGGAGATATACGGACGCACCTGATGCTGATGCAAGGCTATTCAAG CAACTTACTGGGCTAAGGTATGGGCAAAAGAGCAGGGCAAATTTAATGAA ATAAGTAGCTACGTGGCTAAGGCAGCTAGAATGGGTGACTACTTGAGGTA CGCAATGTTTGATAAATATTTTAAACCACTTGATGCCAAGATAAGAACG CTGCAGGCGGTACAGGATACGACTCTGCTCACTATTTACTTTCATGGTACT ACGCATGGGCGGTGCTTTAGCGGAGCATGGAGTTGGAAATAGGAAGC TCTCACGTTCATTTTGGCTACCAGAATCCTATGGCTGCATGGGCATTGGCT AACGATTCAGATATGAAGCCGAAAAGTCCAAACGGTGCAAGCGATTGGGC TAAATCTCTTAAGAGACAAATTGAGTTTTATAGATGGTTACAATCAGCAGA AGGAGCTATAGCAGGCGGTGCTACGAATAGTTGGAATGGAAGGTATGAAA AATACCCTGCAGGCACTGCTACATTTTATGGTATGGCATACGAGCCAAACC CTGTATATCACGATCCGGGAAGCAATACGTGGTTTGGCTTTCAGGCTTGGT CTATGCAAAGAGTTGTAGAATACTATTATGTCACTGGTGACAAAGATGCA GGAGCTTTGCTTGAAAGTGGGTGTCATGGTTAAATCAGTAGTCAAATT AAATAGTGATGGCACATTTGCAATTCCAAGCACATTGGACTGGAAGAGGC AGCCTGATACGTGGAACGGTGCTTACACTGGAAATTCTAATCTTCATGTGA AAGTTGTAGATTATGGCACAGACTTAGGTATAACGGCATCATTGGCAAAC GCTCTTTTATACTATAGTGCAGGAACTAAGAAATACGGCGTCTTTGATGAG GGTGCTAAAAATTTGGCAAAGGAACTTTTAGATAGAATGTGGAAATTGTA TAGGGACGAAAAAGGACTTAGCGCTCCGGAGAAGAGGGCAGATTATAAA AGATTTTTTGAACAAGAAGTGTACATTCCAGCTGGCTGGATAGGTAAGAT GCCTAATGGAGATGTTATAAAATCTGGCGTAAAATTTATTGACATAAGGTC AAAGTATAAACAGGATCCAGATTGGCCTAAATTAGAGGCAGCTTACAAGA GTGGTCAAGCACCGGAATTTAGATATCATAGATTTTGGGCTCAGTGTGACA TTGCAATAGCTAACGCAACATATGAAATTTTGTTTGGAAATCAA (SEQ ID NO: 104) | QAGKDTGEIQIRFNKSDWSNYN QGNDWSWMQSMTNYGENVKV TAYIDGVLVWGQEPSGATPTPT ATPAPTVTPTPTPTPSTPATPT ATPTPTPTPSSTPSVVGEYGQRF MWLWNKIHDPANGYFNQDGIP YHSVETLICERPDYGHLTTSEAF SYYVWLEAVYGKLTGDWSKFK TAWDTLEKYMIPSAEDQPMRSY DPNKPATYAGEWETPDKYPSPL EFNVPVGKDPLHNELVSTYGST LMYGMHWLMDVDNWYGYGK RGDGVSRASFINTFQRGPEESVW ETVPHPSWEEFKWGGPNGFLDL FIKDQNYSKQWRYTDAPDADA RAIQATYWAKVWAKEQGKFNE ISSYVAKAARMGDYLRYAMFD KYFKPLGCQDKNAAGGTGYDS AHYLLSWYYAWGGALDGAWS WKIGSSHVHFGYQNPMAAWAL ANDSDMKPKSPNGASDWAKSL KRQIEFYRWLQSAEGAIAGGAT NSWNGRYEKYPAGTATFYGMA YEPNPVYHDPGSNTWFGFQAWS MQRVVEYYYVTGDKDAGALLE KWVSWVKSVVKLNSDGTFAIPS TLDWKRQPDTWNGAYTGNSNL HVKVVDYGTDLGITASLANALL YYSAGTKKYGVFDEGAKNLAK ELLDRMWKLYRDEKGLSAPEK RADYKRFFEQEVYIPAGWIGKM PNGDVIKSGVKFIDIRSKYKQDP DWPKLEAAYKSGQAPEFRYHRF WAQCDIAIANATYEILFGNQ (SEQ ID NO: 135) |
| Anaerocellum thermophilum Endoglucanase (celD) | ATGAGGAAAATTATTTTAAAGTTTTGTGCACTTATGATGGTAGTGATATTG ATTGTGTCAATACTTCAAATTTTGCCTGTGTTTGCTCAGTCAATATTATATG AAAAGGAAAAGTACCCGCATTTACTTGGTAATCAGGTTGTCAAAAAGCCA AGCGTGGCTGGTAGGTTGCAGATTATAGAGAAGGATGGCAAGAAATATTT AGCTGATCAAAAAGGTGAAATAATTCAGTTGAGGGGTATGAGCACACACG GCTTACAATGGTATGGAGATATAATAAACAAGAATGCTTTTAAGGCTCTTA GCAAGGACTGGGAATGCAACGTCATAAGGTTAGCTATGTATGTGGGAGAG GGTGGATATGCTTCAAATCCTTCAATTAAAGAGAAAGTGATAGAGGGTAT AAAGTTGGCAATTGAAAATGATATGTATGTGATTGTCGACTGGCATGTTTT AAACCCGGGCGATCCTAACGCAGAGATTTATAAGGGAGCAAAAGATTTTT TTAAAGAAATAGCTACTAGCTTTCCTAACGACTATCATATTATATACGAGC TTTGCAATGAGCCAAACCCTAATGAGCCAGGTGTTGAAAATTCTTTAGACG GATGGAAAAAGGTGAAGCATATGCTCAACCTATTATAAAGATGTTGAGG TCATTGGGAAATCAAAACATAATTATAGTGGGAAGCCCTAATTGGAGTCA GAGGCCGGATTTTGCAATACAAGATCCGATAAACGACAAAAACGTGATGT | CAB01405 MRKIILKFCALMMVVILIVSILQI LPVFAQSILYEKEKYPHLLGNQV VKKPSVAGRLQIIEKDGKKYLA DQKGEIIQLRGMSTHGLQWYGD IINKNAFKALSKDWECNVIRLA MYVGEGGYASNPSIKEKVIEGIK LAIENDMYVIVDWHVLNPGDPN AEIYKGAKDFFKEIATSFPNDYH IIYELCNEPNPNEPGVENSLDGW KKVKAYAQPIIKMLRSLGNQNII VGSPNWSQRPDFAIQDPINDKN VMYSVHFYSGTHKVDGYVFEN MKNAFENGVPIFVSEWGTSLAS GDGGPYLDEADKWLEYLNSNYI |

TABLE 2-continued

Exemplary Biomass Degrading Enzymes That Can Be Used According to the Present Invention

| Organism and Protein (Gene) | Codon-Optimized DNA Sequence | Accession Number and Amino Acid Sequence |
|---|---|---|
| | ACTCTGTACACTTTTACAGCGGCACGCATAAAGTCGACGGATATGTATTTG<br>AGAATATGAAAAACGCTTTTGAGAATGGTGTGCCTAATTTTGTGACGAAT<br>GGGGAACGAGTCTTGCATCTGGAGATGGTGGACCATATTTAGATGAAGCT<br>GATAAATGGTTAGAATATTTAAACAGCAACTACATATCATGGGTAAACTG<br>GTCATTGAGCAATAAAAACGAGACAAGCGCAGCTTTTGTACCTTACATAA<br>ATGGCATGCACGATGCTACTCCACTTGATCCTGGTGATGATAAGGTCTGGG<br>ATATTGAAGAGTTGTCTATAAGCGGTGAGTATGTGAGAGCAAGGATAAAA<br>GGAATTGCTTACCAACCAATTAAAAGGGACAATAAGATAAAAGAGGGTG<br>AGAATGCACCTTTGGGCGAAAAGGTACTTCCAAGCACATTTGAGGATGAC<br>ACAAGGCAGGGCTGGGATTGGGATGGACCATCTGGCGTAAAAGGCCCAAT<br>TACTATAGAATCAGCTAATGGCTCAAAAGCATTATCTTTTAACGTGGAATA<br>CCCGGAGAAGAAACCTCAAGATGGCTGGGCAACAGCAGCTAGATTGATAT<br>TGAAGGACATAAATGTCGAGAGGGGCAATAATAAGTACCTTGCATTTGAC<br>TTTTATCTTAAGCCGGACAGAGCTTCAAAAGGTATGATACAGATGTTTTTG<br>GCTTTTAGCCCACCTAGTTTAGGATACTGGGCTCAAGTTCAAGATTCTTTT<br>AACATAGATTTGGGTAAGACGGTCAAGTGTAAAAAGGACAGGAGAACGG<br>AGGTTTACAAGTTTAACGTGTTTTTTGATTTGGACAAGATACAGGACAACA<br>AGGTGCTTTCACCGGACACATTGTTAAGGGATATTATAGTCGTTATTGCAG<br>ATGGAAACAGTGACTTTAAGGGAAAGATGTACATTGATAACGTGAGGTTT<br>ACAAACATTGTTGAAGATATTAATTTTGAAAACTCTTTATATGACGTT<br>ATAGATAAACTTTATAGCAAGGGAATAATTAAAGGTATATCTGTCTTTAAG<br>TATTTACCAGATAAGAATATAACGAGAGCTGAGTTTGCAGCTTTATGCGTA<br>AGAGCTCTTAATTTAAAAATTGAGAAGTACGATGGTAGGTTTAGCGACGT<br>CAAAAGCGGTAATTGGTACTCAGATGTGGTTTACACGGCATACAAGAACA<br>AATTATTTGAGATAAAGGAAATAAGTTTTTTCCTGAGAATATATTGAAGA<br>GGGAAGAGGCTGTGGCATTGCTATAGAAGTTTACAAGAGACTTACAGGC<br>AAAATAGAGGTGAATACAGACGACGTTCCAATAGCTGACGAGAAGTTAAT<br>TAACCCACAGTACAGGGAAAGCGTTAAGTTGGCTATAAAGTTGGGTATAG<br>TGGATTTGTACTCAGACGGAACTTTTGAGCCAAATAAATCTGTATCAAGAG<br>GCGAAGTAGCAACTATTTTATACAACCTTCTCGAGTGATAAAACGAAAGG<br>CTCAGTCGAAAGACTGGGCCTTTCGTTTTATCTGTTGTTTGTCGGTGAACG<br>CTCTCCTGAGTAGGACAAATCCGCCGGGAGCGGATTTGAACGTTGCGAAG<br>CAACGGCCCGGAGGGTGGCGGGCAGGACGCCCGCCATAAACTGCCAGGC<br>ATCAAATTAAGCAGAAGGCCATCCTGACGGATGGCCTTTT (SEQ ID NO: 105) | SWVNWSLSNKNETSAAFVPYIN<br>GMHDATPLDPGDDKVWDIEELS<br>ISGEYVRARIKGIAYQPIKRDNKI<br>KEGENAPLGEKVLPSTFEDDTR<br>QGWDWDGPSGVKGPITIESANG<br>SKALSFNVEYPEKKPQDGWATA<br>ARLILKDINVERGNNKYLAFDFY<br>LKPDRASKGMIQMFLAFSPPSLG<br>YWAQVQDSFNIDLGKTVKCKK<br>DRRTEVYKFNVFFDLDKIQDNK<br>VLSPDTLLRDIIVVIADGNSDFK<br>GKMYIDNVRFTNTLFEDINFENS<br>LYDVIDKLYSKGIIKGISVFKYLP<br>DKNITRAEFAALCVRALNLKIEK<br>YDGRFSDVKSGNWYSDVVYTA<br>YKNKLFEIKENKFFPENILKREE<br>AVALAIEVYKRLTGKIEVNTDD<br>VPIADEKLINPQYRESVKLAIKL<br>GIVDLYSDGTFEPNKSVSRGEVA<br>TILYNL (SEQ ID NO: 136) |
| *Anaerocellum thermophilum* Predicted based on amino acid sequence - Contig 00009 or0219 | ATGAAAAAGAGAAATTTAAGATATTATATTTGTTTCTTATAATTGTACTT<br>TCAGTTTCTTTTATAATTAGTATTGTGTTTCCTAGCTTTTTTAAGGCAGCTC<br>AAACAACTAGCACAAACATTAATTTTGAAGGAAGGGATAAGTTGACGTTT<br>TTTGCATACGGTAAGGCTAAGATTACTATAGATCAGAACATTGCTCAAGAA<br>GGGAAAAAAGAGCATAAAAGTCACAGACAGGAAGAGTGTCTGGGATTCT<br>TTTGGCATAGATGTCAAGGACGTGTTGCAAAGGGGCAAGACATGGGTGGT<br>GAGCGCTTACGTGAAACATAAAGGTAAGAAACCAATAGAGTTTAGCATTA<br>CGGCTATATACAATGACGGAAGGGGTTTGAAGTACCTTCAGTTGGGCGAA<br>AAAATAGTGATACCTAACAAATGGGACAAATTGTGGCTAAGTGGAAACC<br>AACTCTTAAGAACCCTATGGACCTTATAATTGCAATTCACCCTACAGTCGA<br>TAAGACTACGGCTTACAATGTTGACAACATTCAGATAATGACTGAAGAGG<br>TGTACCAGTCACAAGCAGTAGTTTTTAAGGACACATTTGAAAGCAACTTG<br>ACAAACTGGCAGCCTAGAGGAGATACTGTAAAACTTAAAATTGATAATAC<br>TAAGTCACACAACGGTAACAAGTCTTTGTACGTGTCAGGTAGGTCTGCTTT<br>TTGGCACGGAGTTCAAATTCCAGTAACTAAGTACTTAGTTGCAGGAAAGG<br>TGTACAAGTTTTCAGTTTGGTTATACCATCAAAGTATTGACAAGCAGGCT<br>TTGGATTGACAATTCAAAGGAAGATGGCTAACGACGAACAATATAAGTAC<br>GACTGGATTACGGGTAGCCAGATTGAAGGAGATGGATGGGTAGAAATATC<br>AGGCAACTATTACGTGCCTAAAGATGGCAAGATTGAAGAGTTAGTGTTTT<br>GTGTCTCAAGCTGGAATCCGACTCTTGCATTTTGGGTGGATGATGTGACAA<br>TTTCAGACCCTTTTAAGTTGCAGGGCCGAATTACAACTTGCCTAGCTTAA<br>AAGAGAAGTACAAAGAGGACTTTAAGGTAGGTGTAGCAATAGGATATGG<br>CGAATTAATTTCTGATATTGACACACAATTTATAAAGAAACATTTTAACAG<br>TATTACTCCTGGTAACGAGATGAAGCCTGAGAGCGTTTTAAAGGGTCCAA<br>ACAATTACGACTTTACTATTGCAGACGCTTTTGTGGACTTTGCAACAAGA<br>ACAAGATGGGCATAAGGGGTCATACATTGGTATGGCATAACCAAACGCCT<br>GATTGGTTTTTTAAGGATGAGAACGGTAACTTTTTGAAGAAAGACGAATT<br>GCTTAAGAGGTTGAAGAACCACATTTACACAGTGGTGTCAAGATATAAGG<br>GTAAAATACACGATGGATGTAGTTAACGAGCTATAGATGAAACTCAA<br>CCGGACGGCTACAGGAGATCTAATTGGTATAACATTTGCGGACCAGAATA<br>TATTGAGAAGGCATTTATATGGGCACACGAAGCTGACCCTCAAGCTAAAT<br>TATTTTACAACGACTATAACACGGAAATACCACAGAAAGAATGTTTATA<br>TATACATGATAAAAACCTTAAGGCAAAGGGCTGTCCGATTCATGGTAT<br>TGGATTGCAGTGCCACATAAACATAGATAATCCTAGCGTAGAGGACATTG<br>AAGAGACTATTAAACTTTTTCTACTATACCGGGTTTGGAGATACAAATTA<br>CGGAACTTGACATGAGCTTTTATCAGTGGGGTTCATCAGTGTACTATGCTG<br>AACCTTCTAGAGAAATGTTATTGAAGCAGGCAAAAAAGTACTACGAATTA<br>TTTAACCTTTTTAAGAAGTACAAGAACGTAATAAAGTCTGTGACATTTTGG | MKKRKFKILYLFLIIVLSVSFIISI<br>VFPSFFKAAQTTSTNINFEGRDK<br>LTFFAYGKAKITIDQNIAQEGKK<br>SIKVTDRKSVWDSFGIDVKDVL<br>QRGKTWVVSAYVKHKGKKPIEF<br>SITAIYNDGRGLKYLQLGEKIVIP<br>NKWDKIVAKWKPTLKNPMDLII<br>AIHPTVDKTTAYNVDNIQIMTEE<br>VYQSQAVVFKDTFESNLTNWQP<br>RGDTVKLKIDNTKSHNGNKSLY<br>VSGRSAFWHGVQIPVTKYLVAG<br>KVYKFSVWLYHQSIDKQGFGLT<br>IQRKMANDEQYKYDWITGSQIE<br>GDGWVEISGNYYVPKDGKIEEL<br>VFCVSSWNPTLAFWVDDVTISD<br>PFKLQGPNYNLPSLKEKYKEDF<br>KVGVAIGYGELISDIDTQFIKKHF<br>NSITPGNEMKPESVLKGPNNYDF<br>TIADAFVDFATKNKMGIRGHTL<br>VWHNQTPDWFFKDENGNFLKK<br>DELLKRLKNHIYTVVSRYKGKI<br>YAWDVVNEAIDETQPDGYRRSN<br>WYNICGPEYIEKAFIWAHEADP<br>QAKLFYNDYNTEIPQKRMFIYN<br>MIKNLKAKGVPIHGIGLQCHINI<br>DNPSVEDIEETIKLFSTIPGLEIQI<br>TELDMSFYQWGSSVYYAEPSRE<br>MLLKQAKKYYELFNLFKKYKN<br>VIKSVTFWGLKDDNSWLRGVFN<br>KPDFPLLFDEHYDGKPAFWALI<br>DYSILPQNANLPTPPAIPKVKAK<br>K (SEQ ID NO: 137) |

TABLE 2-continued

Exemplary Biomass Degrading Enzymes That Can Be Used According to the Present Invention

| Organism and Protein (Gene) | Codon-Optimized DNA Sequence | Accession Number and Amino Acid Sequence |
|---|---|---|
| | GGCTTAAAGGATGACAATTCTTGGTTAAGGGGCGTATTTAATAAGCCAGA CTTTCCTCTTTTGTTTGACGAGCATTACGACGGAAAGCCTGCATTTTGGGC TTTAATTGACTATAGCATATTGCCTCAAAACGCTAACTTGCCAACACCTCC AGCAATTCCGAAGGTTAAAGCAAAGAAGTGATAAAACGAAAGGCTCAGT CGAAAGACTGGGCCTTTCGTTTTATCTGTTGTTTGTCGGTGAACGCTCTCCT GAGTAGGACAAATCCGCCGGGAGCGGATTTGAACGTTGCGAAGCAACGGC CCGGAGGGTGGCGGGCAGGACGCCCGCCATAAACTGCCAAGGCATCAAATT AAGCAGAAGGCCATCCTGACGGATGGCCTTTT (SEQ ID NO: 106) | |
| Anaerocellum thermophilum Predicted based on amino acid sequence - Contig 00029 or0692 | ATGCCTACAGTAACACCAAATCCTACATCAACGCCTAGCATATTAGATGA CACAAACGACGATTGGTTGTATGTCAGCGGAAATAAAATTGTGGACAAGG ACGGTAAACCTGTATGGTTGACTGGCATAAATTGGTTTGGATATAATACTG GTACTAATGTATTTGACGGCGTCTGGTCTTGCAATTTAAAGGACACTCTTG CAGAGATTGCTAACAGAGGCTTTAATTTGCTTAGGATTCCTATATCAGCAG AGATAATTTTGAACTGGAGTCAGGGAATTTATCCAAAACCTAATATAAAC TACTACGTGAACCCTGAGCTTGAGGGTAAAAATAGCTTGGAGGTGTTTGA CATTGTCGTTCAAATATGCAAAGAGGTTGGATTAAAGATTATGTTGGATAT TCATAGCATTAAGACAGACGCTATGGGTCATATTTATCCGGTGTGGTATGA CGATAAATTTACTCCTGAGGATTTTTATAAAGCATGCGAATGGATAACAA ACAGGTACAAGAATGATGACACTATTATAGCTTTTGATTTGAAGAATGAA CCACACGGCAAACCTTGGCAGGACACGACATTTGCAAAATGGGATAATAG CACTGATATTAACAACTGGAAGTACGCAGCTGAAACGTGCGCAAAGAGGA TATTGAACATAAACCCGAACTTGTTTATAGTGGAAGGTATTGAGGCAT ACCCGAAAGACGACGTAACATGGACGTCAAATCTTACAGCGATTATTAC AGTACGTGGTGGGGTGGCAATTTAAGAGGAGTTAAAAAATACCCAATTAA CTTGGGAAAGTACCAGAACAAGGTGGTATACAGCCCTCATGATTATGGCC CATCTGTTTATCAACAGCCTTGGTTTTACATCTTGGATTTACGAAGGAAGTT TGTTGCAGGATTGCTGGAGGCCTAACTGGGCTTATATATGGAAGAGAAT ATTGCTCCATTGCTTATTGGTGAGTGGGGCGGATATTTAGACGGTGCTGAC AATGAAAAATGGATGAGATATCTTAGGGATTATATAATTGAGAACCACAT ACACCACACGTTTTGGTGCTTTAACGCAAACAGCGGAGATACTGGCGGTA TGGTAGGATATGATTTTACGACATGGGACGAGAAGAAATACAGTTTTTA AAACCAGCTTTGTGGCAAGATTCTCAGGGTAGGTTTGTTGGTTTAGACCAT AAAAGGCCATTAGGAACAAATGGAAAAAACATTAATATTACAATATACTA CAACAACAATGAGCCTGCTCCAGTTCCTGCTGCAAAA (SEQ ID NO: 107) | MPTVTPNPTSPSILDDTNDDWL YVSGNKIVDKDGKPVWLTGIN WFGYNTGTNVFDGVWSCNLKD TLAEIANRGFNLLRIPISAEIILNW SQGIYPKPNINYVVNPELEGKNS LEVFDIVVQICKEVGLKIMLDIH SIKTDAMGHIYPVWYDDKFTPE DFYKACEWITNRYKNDDTIIAPD LKNEPHGKPWQDTTFAKWDNS TDINNWKYAAETCAKRILNINPN LLIVIEGIEAYPKDDVTWTSKSY SDYYSTWWGGNLRGVKKYPIN LGKYQNKVVYSPHDYGPSVYQ QPWFYPGFTKESLLQDCWRPN WAYIMEENIAPLLIGEWGGYLD GADNEKWMRYLRDYIIENHIHH TFWCFNANSGDTGGMVGYDFT TWDEKKYSFLKPALWQDSQGR FVGLDHKRPLGTNGKNINITIYY NNNEPAPVPAAK (SEQ ID NO: 138) |
| Trichoderma reesei Exoglucanase 1 (gene: cbh1) | ATGTACAGAAAGTTAGCAGTCATAAGCGCTTTTCTTGCAACAGCTAGGGC ACAATCTGCTTGTACTTTGCAGAGCGAAACACATCCTCCATTAACTTGGCA AAATGCAGTTCAGGCGGTACATGTACTCAGCAAACAGGCAGCGTAGTTA TAGATGCAAATTGGAGGTGGACGCACACGCTACTAATAGCAGTACAAATTGC TACGACGGAAATACTTGGTCAAGCACTCTTTGTCCTGATAACGAAACATGT GCAAAGAATTGTGCTTAGATGGTGCTGCATATGCTAGTACGTATGGCGTA ACTACGAGCGGCAATTCATTATCTATAGGTTTTGTTACACAGAGCGCACAA AAGAACGTGGGCGCTAGGTTATATCTTATGGCATCAGACACTACATACCA GGAGTTTACATTACTTGGAAACGAATTTAGCTTTGATGTAGACGTCAGTCA ATTGCCATGTGGCCTTAACGGCGCTTTGTATTTTGTATCAATGGACGCAGA TGGAGGCGTTTCTAAATACCCGACAAACACTGCTGGTGCAAAATACGGAA CTGGTTATTGCGATAGTCAATGTCCAAGGGATTTAAAGTTTATTAATGGCC AGGCAAATGTTGAAGGATGGAACCTAGTTCTAACAATGCAAATACTGGC ATTGGAGGACATGGTTCATGCTGTAGTGAAATGGATATATGGGAAGCAAA CTCTATAAGCGAGGCTTTGACTCCTCATCCTTGCACGACAGTGGGCCAAG AGATTTGTGAAGGCGATGGTTGCGGAGGCACTTACTCAGACAATAGGTAC GGCGGTACGTGTGATCCAGATGCTGCGACTGGAATCCTTACAGACTTGG TAACACTTCTTTTTATGGACCGGGTTCTTCTTTTACGCTTGACACTACAAAA AAATTGACAGTTGTGACTCAGTTTGAAACGTCTGGCGCAATAAATAGATA CTATGTTCAAAACGGTGAACGTTTCAGCAACCGAATCTGCGCAGCTTGGCTC TTATTCAGGTAACGAATTAAATGACGATTATTGTACAGCAGAAGAGGCTG AATTTGGAGGCTCTAGTTTTTCAGATAAGGGAGGTTTAACACAGTTTAAGA AAGCTACGAGTGGTGGCATGGTACTTGTAATGAGCTTATGGGATGATTACT ACGCTAATATGTTGTGGCTTGATTCAACTTACCCAACTAACGAAACAAGCA GTACTCCTGGCGCAGTAAGGGGTTCATGCAGCACGTCATCTGGTGTACCG GCTCAGGTCGAGAGTCAAAGTCCTAACGCTAAGGTTACTTTTTCAAACATA AATTTTGGACCTATAGGATCTACAGGGAACCCTAGCGGAGGCAACCCACC TGGAGGTAACAGAGGCACGACGACAACAAGAAGGCCAGCTACAACAACT GGCTCTAGCCCAGGCCCGACTCAGTCACATTACGGTCAGTGCGGAGGTAT AGGTTACGGACCTACTGTCTGCGCAAGCGGAACTACATGTCAGGTCTT GAACCCTTATTACTCTCAATGCTTGCTCGAGTGATAAAACGAAAGGCTCAG TCGAAAGACTGGGCCTTTCGTTTTATCTGTTGTTTGTCGGTGAACGCTCTCC TGAGTAGGACAAATCCGCCGGGAGCGGATTTGAACGTTGCGAAGCAACGG CCCGGAGGGTGGCGGGCAGGACGCCCGCCATAAACTGCCAGGCATCAAAT TAAGCAGAAGGCCATCCTGACGGATGGCCTTTT (SEQ ID NO: 169) | P62694 MYRKLAVISAFLATARAQSACT LQSETHPPLTWQKCSSGGTCTQ QTGSVVIDANWRWTHATNSSTN CYDGNTWSSTLCPDNETCAKNC CLDGAAYASTYGVTTSGNSLSIG FVTQSAQKNVGARLYLMASDTT YQEFTLLGNEFSFDVDVSQLPCG LNGALYFVSMDADGGVSKYPT NTAGAKYGTGYCDSQCPRDLKF INGQANVEGWEPSSNNANTGIG GHGSCCSEMDIWEANSISEALTP HPCTTVGQEICEGDGCGGTYSD NRYGGTCDPDGCDWNPYRLGN TSFYGPGSSFTLDTTKKLTVVTQ FETSGAINRYYVQNGVTFQQPN AELGSYSGNELNDDYCTAEEAE FGGSSFSDKGGLTQFKKATSGG MVLVMSLWDDYYANMLWLDS TYPTNETSSTPGAVRGSCSTSSG VPAQVESQSPNAKVTFSNIKFGP IGSTGNPSGGNPPGGNRGTTTTR RPATTTGSSPGPTQSHYGQCGGI GYSGPTVCASGTTCQVLNPYYS QCL (SEQ ID NO: 139) |

TABLE 2-continued

Exemplary Biomass Degrading Enzymes That Can Be Used According to the Present Invention

| Organism and Protein (Gene) | Codon-Optimized DNA Sequence | Accession Number and Amino Acid Sequence |
|---|---|---|
| Trichoderma reesei CBH2 (gene: cbh2) | ATGATAGTAGGAATTTTAACTACGTTAGCAACATTGGCAACTTTGGCTGCA AGCGTACCTTTAGAAGAGAGACAAGCATGTTCTAGCGTGTGGGGCCAGTG CGGTGGACAAAATTGGAGTGGACCTACATGTTGCGCTAGCGGTAGTACTT GCGTATACAGCAACGATTACTATTCTCAATGCCTTCCTGGCGCAGCTAGCT CTTCTTCAAGTACAAGGGCTGCTAGCACGACTTCAAGAGTTTCACCGACTA CGTCTAGGTCTAGCTCAGCTACTCCTCCACCTGGTAGTACAACAACTAGAG TGCCTCCGGTGGGTTCTGGCACAGCTACTTACACGGGTAATCCATTTGTTG GCGTAACTCCTTGGGCAAACGCTTATTACGCATCAGAAGTGAGTTCTTTAG CAATTCCATCTTTGACAGGCGCTATGGCTACAGCAGCAGCTGCTGTTGCTA AAGTACCTTCATTTATGTGGTTGGACACTTTAGATAAAACTCCTCTTATGG AGCAGACGTTAGCAGATATTAGGACAGCTAACAAAAATGGTGGCAATTAT GCTGGACAGTTTGTAGTCTACGACCTTCCTGACAGGGATTGTGCTGCACTT GCTTCTAACGGTGAATACTCAATAGCAGACGGCGGCGTCGCTAAGTATAA AAATTACATTGATACGATTAGACAGATAGTTGTAGAGTACTCAGATATAA GGACATTGTTGGTGATTGAGCCGGACAGCGTTGGAACGTGGACTACGCTG TGGGTACACCTAAATGCGCTAACGCACAGTCAGCATATTTAGAATGCATA AACTACGCAGTCACACAATTAAACTTGCCAAATGTGGCTATGTACCTTGAC GCTGGACATGCTGGCTGGTTAGGTTGGCCTGCAAATCAAGATCCGGCTGC ACAATTGTTTGCAAACGTTTACAAGAATGCTTCAAGTCCTAGAGCACTTAG GGGACTTGCAACTAATGTGGCTAACTATAATGGCTGGAACATAACAAGCC CACCTTCTTACACTCAGGGAAATGCTGTTTATAACGAAAGTTGTATATTC ACGCAATAGGTCCTTTGTTGGCAAACCACGGTTGGTCTAATGCATTTTTTA TTACAGACCAGGGTAGAAGTGGAAAACAACCTACAGGACAGCAGTG GGGTGATTGGTGTAACGTAATTGGCACTGGATTTGGCATAAGGCCATCAG CAAATACGGGTGACTCTTTGTTGGACAGTTTTGTGTGGGTCAAGCCAGGCG GTGAGTGTGATGGAACGTCTGACTCAAGCGCTCCAAGATTTGACTCACACT GCGCATTACCGGATGCTTTACAACCAGCTCCTCAAGCAGGCGCATGGTTTC AGGCTTATTTTGTCCAGTTGCTTACAAACGCTAACCCTAGCTTTTTA (SEQ ID NO: 170) | AAA34210 MIVGILTTLATLATLAASVPLEE RQACSSVWGQCGGQNWSGPTC CASGSGSTCVYSNDYYSQCLPGAA SSSSSSTRAASTTSRVSPTTSRSSS ATPPPGSTTTRVPPVGSGTATYS GNPFVGVTPWANAYYASEVSSL AIPSLTGAMATAAAAVAKVPSF MWLDTLDKTPLMEQTLADIRTA NKNGGNYAGQFVVYDLPDRDC AALASNGEYSIADGGVAKYKNY IDTIRQIVVEYSDIRTLLVIEPDSL ANLVTNLGTPKCANAQSAYLEC INYAVTQLNLPNVAMYLDAGH AGWLGWPANQDPAAQLFANVY KNASSPRALRGLATNVANYNG WNITSPPSYTQGNAVYNEKLYIH AIGPLLANHGWSNAFFITDQGRS GKQPTGQQQWGDWCNVIGTGF GIRPSANTGDSLLDSFVWVKPG GECDGTSDSSAPRFDSHCALPDA LQPAPQAGAWFQAYFVQLLTN ANPSFL (SEQ ID NO: 140) |
| Trichoderma reesei Endoglucanase 1 (EG1) | ATGGCACCTTCAGTAACGCTTCCGCTTACGACAGCTATATTAGCAATAGCT AGGCTTGTTGCAGCTCAACAGCCTGGAACGTCTACACCAGAGGTTCCACCC GAAATTAACTACATATAAGTGTACAAAAAGCGGTGGCTGCGTAGCACAAG ATACGAGTGTTGTGTTGGACTGAATTACAGGTGGATGCATGATGCTAACT ATAATAGTTGTACAGTAAACGGCGGTGTCAATACAACGTTGTGCCCAGAT GAAGCAACGTGCGGCAAGAATTGCTTTATAGAAGGCGTTGACTACGCTGC TAGCGGAGTGACAACAAGCGGCAGTTCATTGACAATGAACCAGTATATGC CATCTAGCAGTGGAGGTTACAGTTCAGTCAGCCCAAGATTGTATTTACTTG ATTCAGATGGCGAGTATGTGATGTTAAAATTAAACGGACAAGAACTTAGT TTTGACGTTGATTTGTCTGCTTTACCTTGTGGTGAGAACGGCAGCCTTTACT TATCACAGATGGATGAGAATGGTGGCGCAAATCAATACAACACAGCTGGC GCAAATTACGGAAGTGGCTATTGCGACGCTCAGTGTCCAGTGCAAACTTG GAGGAACGGCACATTGAATACATCTCATCAAGGATTTTGTTGCAACGAGA TGGATATCTTGAAGGTAACAGCAGAGCAAATCTGCCTCATTCCTCACTCAT GCACAGCAACTGCATGTGATAGTGCTGGATGCGGCTTTAATCCATATGGAT CAGGATATAAAAGCTATTACGGGCCTGGTGACACAGTAGACTTCAAAG ACATTTACAATAATTACTCAGTTTAACACTGACAATGGCTCTCCATCAGGC AATTTGGTCAGCATAACTAGGAAATATCAACAGAATGGAGTGGATATTCC TAGTGCACAACCGGGAGGCGATACAATATCAAGTTGTCCAAGTGCTTCTG CTTACGGCGGTTTGGCAACTATGGGTAAAGCACTTAGTAGCGGTATGGTGT TGGTTTTTTCAATTTGGAACGATAATTCTCAGTACATGAATTGGCTTGACT CTGGAAACGCTGGCCCCATGCTCAAGTACAGAGGGAAATCCAAATCAACATT TTAGCAAACAATCCAAATACACACGTCGTGTTTTCTAACATAAGGATGGGGT GATATTGGTAGTACAACGAATAGTACTGCTCCTCCACCTCCGCCTGCAAGC TCTACAACATTTAGTACTACTAGGAGAAGCTCAACGACTAGCAGTAGCCC ATCATGTACTCAAACACATTGGGGCCAGTGCGGTGGAATAGGCTACTCTG GCTGCAAGACGTGCACAAGTGGACGACTTGTCAATACTCTAATGATTAC TATTCTCAATGCTTG (SEQ ID NO: 171) | AAA34212 MAPSVTLPLTTAILAIARLVAAQ QPGTSTPEVHPKLTTYKCTKSGG CVAQDTSVVLDWNYRWMHDA NYNSCTVNGGVNTTLCPDEATC GKNCFIEGVDYAASGVTTSGSSL TMNQYMPSSSGGYSSVSPRLYL LDSDGEYVMLKLNGQELSFDVD LSALPCGENGSLYLSQMDENGG ANQYNTAGANYGSGYCDAQCP VQTWRNGTLNTSHQGFCCNEM DILEGNSRANALTPHSCTATACD SAGCGFNPYGSGYKSYYGPGDT VDTSKTFTIITQFNTDNGSPSGNL VSITRKYQQNGVDIPSAQPGGDT ISSCPSASAYGGLATMGKALSSG MVLVFSIWNDNSQYMNWLDSG NAGPCSSTEGNPSNILANNPNTH VVFSNIRWGDIGSSTTNSTAPPPPP ASSTTFSTTRRSSTTSSSPSCTQT HWGQCGGIGYSGCKTCTSGTTC QYSNDYYSQCL (SEQ ID NO: 141) |
| Coptotermes formosanus endo-b-1,4-glucanase (gene: CfEG4) | ATGAGGGTCTTTGTGTGCTTGCTTAGTGCATTGGCTCTTTGCCAAGCAGCT TACGACTATAAACGGTATTAAAGAACTCTCTTTTGTTTTACAGACACAG AGGAGCGGAAAGTTACCAGCTGATCAAAAGGTCACTTGGAGAAAGATTC AGCATTAAACGACAAAGGTCAGAAGGGCGAGGATTTAACTGGAGGTTATT ACGACGCTGGTGATTTTGTGAAGTTTGGCTTTCCGATGGCATATACTGTGA CGGTTCTTGCTTGGGGTTTGGTAGATTATGAAAGCGCATATTCTACAGCAG GAGCTCTTGACGATGGAAGAAAGGCACTTAAGTGGGGTACAGACTATTTT TTGAAAGCACATACAGCTGCAAACGAGTTTTATGGCCAAGTTGGACAGGG TGATGTAGATCACGCTTACTGGGGCAGACCTGAGGACATGACTATGTCTA GGCCAGCATATAAGATAGACTCAAAGCCAGGGAGCGACTTGGCTGCT GAAACAGCTGCAGCTCTTGCAGCTACTGCTATTGCATATAAGAGTGCAGA TTCTACTTATAGTAATAACTTAATAACACATGCAAGCAATTGTTGATTT TGCTAATAATTATAGAGGCAAGTATAGCGATTCTATTACAGACGCAAAAA ACTTTTATGCTAGCGGTGATTACAAGGATGAGCTTGTTTGGGCAGCTGCAT GGTTATATAGAGCTACTAATGACAATACATACTTGACTAAAGCAGAATCA TTAGCAAACGAATTCGGCTTGGGCAGCTGGAATGGGGCATTCAATTGGGACAACAAAATTAGCGGCGTACAGGTACTG CTGCTCACATCTAAACAAGCTTATAAAGACAAAGTGCAAGGCTATGTCGATTATCTTGTA | BAB40697 MRVFVCLLSALALCQAAYDYK TVLKNSLLFYEAQRSGKLPADQ KVTWRKDSALNDKGQKGEDLT GGYYDAGDFVKFGFPMAYTVT VLAWGLVDYESAYSTAGALDD GRKALKWGTDYFLKAHTAANE FYGQVGQGDVDHAYWGRPED MTMSRPAYKIDTSKPGSDLAAE TAAALAATAIAYKSADSTYSNN LITHAKQLFDFANNYRGKYSDSI TDAKNFYASGDYKDELVWAAA WLYRATNDNTYLTKAESLYNEF GLGSWNGAFNWDNKISGVQVL LALTSKQAYKDKVQGYVDYLV |

TABLE 2-continued

Exemplary Biomass Degrading Enzymes That Can Be Used According to the Present Invention

| Organism and Protein (Gene) | Codon-Optimized DNA Sequence | Accession Number and Amino Acid Sequence |
|---|---|---|
| | CTTTATAACGAGTTTGGACTTGGTAGTTGGAATGGCGCTTTTAATTGGGAT AACAAAATAAGCGGAGTGCAAGTGTTATTGGCTAAGTTAACAAGCAAGCA GGCTTACAAAGACAAGGTGCAAGGTTACGTTGATTATTTAGTATCTTCACA AAAAAAGACGCCAAAAGGCCTTGTGTACATTGACCAGTGGGGCACTTTAA GGCATGCTGCTAATAGTGCATTGATAGCATTGCAAGCTGCAGATTTAGGC ATAAATGCTGCATCTTATAGACAATATGCTAAAAAACAGATAGACTACGC TTTAGGTGATGGCGGTAGGTCTTATGTTGTAGGATTTGGCACAAACCCTCC AGTTAGACCTCATCATAGATCAAGTTCTTGTCCAGATGCACCAGCTGCATG CGATTGGAATACTTATAACAGTGCTGGTCCAAACGCTCACGTATTGACAG GCGCTCTTGTTGGCGGTCCTGATTCTAATGATTCATATACTGACAGTAGGT CAGATTATATATCTAATGAGGTAGCAACAGATTACAACGCTGGCTTTCAA AGCGCTGTTGCAGGCTTACTTAAGGCTGGAGTACTCGAGTGATAAAACGA AAGGCTCAGTCGAAAGACTGGGCCTTTCGTTTTATCTGTTGTTTGTCGGTG AACGCTCTCCTGAGTAGGACAAATCCGCCGGGAGCGGATTTGAACGTTGC GAAGCAACGGCCCGGAGGGTGGCGGGCAGGACGCCCGCCATAAACTGCC AGGCATCAAATTAAGCAGAAGGCCATCCTGACGGATGGCCTTTT (SEQ ID NO: 172) | SSQKKTPKGLVYIDQWGTLRHA ANSALIALQAADLGINAASYRQ YAKKQIDYALGDGGRSYVVGF GTNPPVRPHHRSSSCPDAPAACD WNTYNSAGPNAHVLTGALVGG PDSNDSYTDSRSDYISNEVATDY NAGFQSAVAGLLKAGV (SEQ ID NO: 142) |
| Nasutitermes takasagoensis endo-b-1,4-glucanase (gene: NtEG) | ATGAGAGTATTTTTGTGCTTGCTTAGTGCATTGGCTCTTTGCCAAGCAGCTT ATGATTACAAACAGGTGTTGAGAGACTCTTTGCTTTTTTACGAAGCACAAA GGTCTGGAAGATTACCAGCTGACCAGAAGGTCACTTGGAGAAAAGATAGT GCATTAAATGACCAAGGTGATCAAGGACAGGATTTAACTGGCGGTTATTT TGACGCTGGCGATTTTGTGAAATTTGGATTTCCAATGGCTTATACAGCTAC TGTTTTGGCATGGGGCTTGATAGATTTTGAGGCTGGCTACTCATCTGCAGG AGCTCTTGACGATGGTAGGAAAGCAGTGAAGTGGGCTACGGATTATTTTA TAAAGGCACACACGAGCCAGAATGAATTTTACGGTCAGGTGGGCCAGGGT GATGCTGACCATGCCATTTTGGGGCAGACCTGAGGATATGACGATGGCTAG ACCAGCATATAAGATAGACACGAGTAGGCCTGGTTCAGACTTGGCTGGTG AAACTGCTGCAGCTTTAGCAGCTGCATCTATTGTTTTTAGAAATGTAGATG GTACGTACAGTAATAACTTGCTTACTCATGCTAGGCAGTTGTTTGACTTTG CAAATAATTATAGGGGTAAATATAGTGATTCAATAACAGATGCTAGAAAC TTTTACGCAAGTGCTGATTACAGAGATGAATTGGTGTGGGCAGCTGCATG GCTTTACAGGGCAACTAACGATAATACGTACTTGAACACAGCAGAGAGCC TTTATGACGAATTTGGCCTTCAAACTGGGGCGGAGGTTTGAATTGGGATT CAAAGGTCAGTGGAGTCCAGGTACTTTTGGCAAAGTTGACAAACAAGCAG GCATACAAAGACACAGTGCAGTCTTTATGTAAATTACCTTATTAATAACCAA CAGAAAACTCCAAAGGGCTTATTATACATAGACATGTGGGGTACACTTAG GCACGCAGCTAATGCTGCATTTATTATGTTAGAAGCAGCTGAGTTAGGATT GAGCGCAAGTTCATATAGGCAATTTGCTCAAACACAGATAGATTACGCAC TTGGCGATGGTGGAAGGTCATTTGTTTGTGGCTTTGGTTCTAATCCTCCAA CTAGGCCTCATCATAGGTCAAGCTCTTGCCCGCCTGCTCCAGCAACATGTG ACTGGAACACTTTTAACAGTCCGGACCCTAACTATCACGTGTTGAGTGGCG CTCTTGTGGGCGGACCTGACCAGAATGACAACTACGTTGATGATAGGAGT GATTATGTGCATAATGAAGTGGCAACTGACTACAACGCAGGCTTTCAGAG CGCATTAGCTGCACTTGTAGCATTAGGCTATTGATAAAACGAAAGGCTCA GTCGAAAGACTGGGCCTTTCGTTTTATCTGTTGTTTGTCGGTAACGCTCTC CTGAGTAGGACAAATCCGCCGGGAGCGGATTTGAACGTTGCGAAGCAACG GCCCGGAGGGTGGCGGGCAGGACGCCCGCCATAAACTGCCAGGCATCAA ATTAAGCAGAAGGCCATCCTGACGGATGGCCTTTT (SEQ ID NO: 173) | BAA33708 MRVFLCLLSALALCQAAYDYK QVLRDSLLFYEAQRSGRLPADQ KVTWRKDSALNDQGDQGQDLT GGYFDAGDFVKFGFPMAYTAT VLAWGLIDFEAGYSSAGALDDG RKAVKWATDYFIKAHTSQNEFY GQVGQGDADHAFWGRPEDMT MARPAYKIDTSRPGSDLAGETA AALAAASIVFRNVDGTYSNNLL THARQLFDFANNYRGKYSDSIT DARNFYASADYRDELVWAAAW LYRATNDNTYLNTAESLYDEFG LQNWGGGLNWDSKVSGVQVLL AKLTNKQAYKDTVQSYVNYLIN NQQKTPKGLLYIDMWGTLRHA ANAAFIMLEAAELGLSASSYRQF AQTQIDYALGDGGRSFVCGFGS NPPTRPHHRSSSCPPAPATCDWN TFNSPDDPNYHVLSGALVGGPDQ NDNYVDDRSDYVHNEVATDYN AGFQSALAALVALGY (SEQ ID NO: 143) |
| Talaromyces emersonii CBH1 | AGAAGGGCACTTTTGCTTTCATCTAGCGCTATACTTGCTGTGAAGGCACAG CAGGCTGGAACAGCTACTGCAGAAAATCATCCTCCGTTAACTTGGCAAGA GTGTACGGCTCCTGGTAGTTGCACAACTCAGAACGGCGCAGTGGTCCTTG ATGCTAACTGGAGGTGGGTACACGACGTGAACGGATACACAAATTGTTAC ACGGGTAATACTTGGGATCCGACATATTGTCCGGACGATGAAACTTGTGCT CAGAACTGCGCTCTTGATGGCGCAGATTACGAGGGAACATATGGTGTGAC TTCATCTGGCAGCTCTCTTAAGTTAAATTTTGTCACTGGTTCAAACGTAGG CTCTAGGCTTTACTTGTTACAGGACGATAGCACTTACCAGATATTTAAACT TTTAAATAGAGAATTTAGTTTTGATGTAGACGTGTCAAACTTACCATGTGG CTTAAACGGAGCTTTGTACTTTGTTGCAATGGATGCAGATGGAGGCGTTTC TAAATACCCAAACAATAAGGCAGGAGCTAAATACGGCACTGGATATTGTG ACAGTCAGTGTCCAAGGGATTTAAAATTTATAGATGGTGAGGCAAACGTG GAAGGCTGGCAACCTTCAAGTAATAACGCAAATACTGGAATTGGTGACCA TGGTTCTTGCTGTGCTGAAATGGATGTGTGGGAGGCTAATTCTATTAGCAA CGCTGTAACTCCACACCCTTGCGACACACCTGGACAAACAATGTGTAGTG GCGACGATTGCGGTGGACTTTATTCTAATGACAGGTATGCTGGCACATGT GATCCTGACGGATGTGATTTTAATCCATATAGAATGGGAAATACATCTTTT TATGGCCCTGGTAAAATTATAGACACAACTAAACCATTTACAGTGGTAAC GCAGTTTCTTACTGACGACGGACTGACACGGGACATTAGCAGAAGATTA AGAGGTTTTACATACAAAACAGTAACGTGATACCTCAGCCGAACTCAGAT ATTAGCGGTGTTACTGGAAACTCAATTACAACTGAGTTTTGCACTGCACAG AAACAAGCATTTGGAGATACTGACGATTTTTCTCAGCACGGCGGATTGGCT AAGATGGGCGCAGCAATGCAACAGGGTATGGTTTTAGTGATGTCATTATG GGATGATTACGCTGCACAAATGTTGTGGCTTGATAGTGATTACCCTACTGA | AAL89553 MLRRALLLSSSAILAVKAQQAG TATAENHPPLTWQECTAPGSCT TQNGAVVLDANWRWVHDVNG YTNCYTGNTWDPTYCPDDETCA QNCALDGADYEGTYGVTSSGSS LKLNFVTGSNVGSRLYLLQDDS TYQIFKLLNREFSFDVDVSNLPC GLNGALYFVAMDADGGVSKYP NNKAGAKYGTGYCDSQCPRDL KFIDGEANVEGWQPSSNNANTG IGDHGSCCAEMDVWEANSISNA VTPHPCDTPGQTMCSGDDCGGT YSNDRYAGTCDPDGCDFNPYR MGNTSFYGPGKIIDTTKPFTVVT QFLTDDGTDTGTLSEIKRFYIQN SNVIPQPNSDISGVTGNSITTEFC TAQKQAFGDTDDFSQHGGLAK MGAAMQQGMVLVMSLWDDYA AQMLWLDSDYPTDADPTTPGIA RGTCPTDSGVPSDVESQSPNSYV TYSNIKFGPINSTFTAS (SEQ ID NO: 144) |

TABLE 2-continued

Exemplary Biomass Degrading Enzymes That Can Be Used According to the Present Invention

| Organism and Protein (Gene) | Codon-Optimized DNA Sequence | Accession Number and Amino Acid Sequence |
|---|---|---|
| | CGCTGACCCTACGACACCTGGTATTGCTAGAGGAACTTGCCCAACAGATA GCGGCGTTCCTTCTGACGTAGAATCACAGAGTCCAAACTCATACGTTACTT ACAGCAACATAAAATTTGGTCCTATTAACTCAACATTTACGGCTAGTTGAT AAAACGAAAGGCTCAGTCGAAAGACTGGGCCTTTCGTTTTATCTGTTGTTT GTCGGTGAACGCTCTCCTGAGTAGGACAAATCCGCCGGGAGCGGATTTGA ACGTTGCGAAGCAACGGCCCGGAGGGTGGCGGGCAGGACGCCCGCCATA AACTGCCAGGCATCAAATTAAGCAGAAGGCCATCCTGACGGATGGCCTTT T (SEQ ID NO: 174) | |
| Neosartorya fischeri putative endo-glucanase | ATGCTTGCAAGTACATTTTCATATAGAATGTACAAAACTGCTCTTATATTG GCAGCTCTTTTGGGAAGCGGTCAGGCTCAGCAAGTTGGCACATCACAAGC TGAAGTTCATCCTTCAATGACTTGGCAATCTTGTACTGCTGGTGGCAGTTG CACAACAAATAACGGCAAGGTGGTAATTGATGCTAACTGGAGGTGGGTTC ACAAAGTGGGAGACTATACAAATTGTTACACTGGTAACACATGGGATAAG ACTTTGTGTCCGGACGATGCAACATGTGCTAGTAATTGCCTTAGAGGGC GCTAATTATCAGTCAACTTACGGAGCAACAACATCTGGTGATAGCCTTAG ATTGAATTTTGTCACGACGAGTCAACAGAAAAATATTGGAAGTAGGTTGT ATATGATGAAAGATGACACTACATACGAAATGTTTAAGTTGTTAAACCAA GAATTTACATTTGACGTGGATGTTTCTAACCTTCCGTGTGGACTTAATGGT GCTTTGTACTTTGTGGCAATGGATGCTGATGGCGGAATGAGCAAATATCCA ACTAATAAAGCTGGTGCTAAGTACGGCACAGGATATTGTGATTCACAATG TCCTAGAGACTTAAAATTTATTAACGGTCAGGCTAACGTAGAGGGCTGGC AACCAAGTTCTAATGATGCAAACGCTGGAACTGGTAATCATGGATCATGT TGCGCTGAAATGGATATTTGGGAAGCAAATTCAATTTCAACAGCTTTTACT CCTCACCCATGCGACACACCTGGCCAGGTAATGTGTACAGGTGATGCATG CGGTGGAACTTACTCTAGCGATAGGTATGGCGAACATGTGACCCAGATG GCTGCGATTTTAACTCATTTAGACAGGGAAACAAAACATTTTATGGACCTG GCATGACAGTAGATACTAAGAGTAAATTTACAGTGGTAACACAGTTTATA ACTGATGATGGAACGGCTTCAGGAACTCTTAAGGAAATTAAAAGATTTTA CGTGCAAAACGGAAAAGTAATACCAAATAGCGAATCTACGTGGAGTGGA GTGGGAGGCAATTCTATAACAAATGACTATTGTACTGCTCAGAAGAGCTT ATTTAAAGATCAGAATGTTTTTGCAAAACATGGTGGAATGGAGGGAATGG GCGCTGCTTTGGCACAAGGTATGGTTCTTGTGATGAGCTTATGGGATGACC ATGCTGCTAATATGTTGTGGCTTGACTCTAATTATCCGACTACGGCAAGTA GCTCTACTCCTGGCGTTGCTAGGGGCACTTGCGATATTTCTAGCGGAGTCC CTGCAGACGTTGAAGCTAATCACCCAGATGCAAGTGTTGTGTACAGCAAC ATAAAGGTTGGACCTATAGGTAGCACATTTAACAGTGGAGGTTCTAATCC AGGCGGTGGCACGACAACTACGGCAAAACCGACGACAACTACAACGACT GCAGGCAGCCCTGGCGGTACGGGCGTCGCTCAGCACTATGGTCAATGTGG AGGTAATGGCTGGCAGGGACCGACTACGTGCGCTTCTCCATATACTTGTCA AAAGTTAAATGATTTTTATTCACAGTGCTTG (SEQ ID NO: 175) | XP_00125827<br>MLASTFSYRMYKTALILAALLG<br>SGQAQQVGTSQAEVHPSMTWQ<br>SCTAGGSCTTNNGKVVIDANWR<br>WVHKVGDYTNCYTGNTWDKT<br>LCPDDATCASNCALEGANYQST<br>YGATTSGDSLRLNFVTTSQQKNI<br>GSRLYMMKDDTTYEMFKLLNQ<br>EFTFDVDVSNLPCGLNGALYFV<br>AMDADGGMSKYPTNKAGAKY<br>GTGYCDSQCPRDLKFINGQANV<br>EGWQPSSNDANAGTGNHGSCC<br>AEMDIWEANSISTAFTPHPCDTP<br>GQVMCTGDACGGTYSSDRYGG<br>TCDPDGCDFNSFRQGNKTFYGP<br>GMTVDTKSKFTVVTQFITDDGT<br>ASGTLKEIKRFYVQNGKVIPNSE<br>STWSGVGGNSITNDYCTAQKSL<br>FKDQNVFAKHGGMEGMGAALA<br>QGMVLVMSLWDDHAANMLWL<br>DSNYPTTASSSTPGVARGTCDIS<br>SGVPADVEANHPDASVVYSNIK<br>VGPIGSTFNSGGSNPGGGTTTTA<br>KPTTTTTAGSPGGTGVAQHYG<br>QCGGNGWQGPTTCASPYTCQK<br>LNDFYSQCL (SEQ ID NO: 145) |
| Coptotermes formosanus EG | ATGAGATTTCCTTCAATATTTACAGCAGTACTTTTTGCAGCATCATCAGCA CTTGCAGCATATGATTATAAAACAGTACTTAAAAATTCACTTCTTTTTTAT GAAGCACAAAGATCAGGAAAACTTCCTGCAGATCAAAAAGTAACATGGA GAAAAGATTCAGCACTTAATGATAAAGGACAAAAAGGAGAAGATCTTAC AGGAGGATATTATGATGCAGGAGATTTTGTAAAATTTGGATTTCCTATGGC ATATACAGTAACAGTACTTGCATGGGGACTTGTAGATTATGAATCAGCAT ATTCAACAGCAGGAGCACTTGATGATGGAAGAAAAGCACTTAAATGGGA ACAGATTATTTTCTTAAAGCACATACAGCAGCAAATGAATTTTATGGACAA GTAGGACAAGGAGATGTAGATCATGCATATTGGGGAAGACCTGAAGATAT GACAATGTCAAGACCTGCATATAAAATAGACATCAAAACCTGGATCAG ATCTTGCAGCAGAAACAGCAGCAGCACTTGCAGCAACAGCAATAGCATAT AAATCAGCAGATTCAACATATTCAAATAATCTTATAACACATGCAAAACA ACTTTTTGATTTTGCAAATAATTATAGAGGAAAATATTCAGATTCAATAAC AGATGCAAAAAATTTTTATGCATCAGGAGATTATAAAGATGAACTTGTAT GGGCAGCAGCATGGCTTTATAGAGCAACAAATGATAATACATATCTTACA AAAGCAGAATCACTTTATAATGAATTTGGACTTGGATCATGGAATGGAGC ATTTAATTGGGATAATAAAATATCAGGAGTACAAGTACTTCTTGCAAAACT TACATCAAAACAAGCATATAAAGATAAAGTACAAGGATATGATTATC TTGTATCATCACAAAAAAAAAACACCTAAAGGACTTGTATATATAGATCAA TGGGGAACACTTAGACATGCAGCAAATTCAGCACTTATAGCACTTCAAGC AGCAGATCTTGGAATAAATGCAGCATCATATAGACAATATGCAAAAAAAC AAATAGATTATGCACTTGGAGATGGAGGAAGATCATATGTAGTAGGATTT GGAACAAATCCTGTACGTAAGACCTCATCATAGATCATCATCATGCCCTGAT GCACCTGCAGCATGCGATTGGAATACATATAATTCAGCAGGACCTAATGC ACATGTACTTACAGGAGCACTTGTAGGAGGACCTGATTCAAATGATTCAT ATACAGATTCAAGATCAGATTATATATCAAATGAAGTAGCAACAGATTAT AATGCAGGATTTCAATCAGCAGTAGCAGGACTTCTTAAAGCAGGAGTA (SEQ ID NO: 176) | MRFPSIFTAVLFAASSALAAYDY<br>KTVLKNSLLFYEAQRSGKLPAD<br>QKVTWRKDSALNDKGQKGEDL<br>TGGYYDAGDFVKFGFPMAYTV<br>TVLAWGLVDYESAYSTAGALD<br>DGRKALKWGTDYFLKAHTAAN<br>EFYGQVGQGDVDHAYWGRPED<br>MTMSRPAYKIDTSKPGSDLAAE<br>TAAALAATAIAYKSADSTYSNN<br>LITHAKQLFDFANNYRGKYSDSI<br>TDAKNFYASGDYKDELVWAAA<br>WLYRATNDNTYLTKAESLYNEF<br>GLGSWNGAFNWDNKISGVQVL<br>LAKLTSKQAYKDKVQGYVDYL<br>VSSQKKTPKGLVYIDQWGTLRH<br>AANSALIALQAADLGINAASYR<br>QYAKKQIDYALGDGGRSYVVG<br>FGTNPPVRPHHRSSSCPDAPAAC<br>DWNTYNSAGPNAHVLTGALVG<br>GPDSNDSYTDSRSDYISNEVATD<br>YNAGFQSAVAGLLKAGV (SEQ ID NO: 146) |

TABLE 2-continued

Exemplary Biomass Degrading Enzymes That Can Be Used According to the Present Invention

| Organism and Protein (Gene) | Codon-Optimized DNA Sequence | Accession Number and Amino Acid Sequence |
|---|---|---|
| Chrysosporium lucknowense CBH2b | ATGGCAAAAAAACTTTTTATAACAGCAGCACTTGCAGCAGCAGTACTTGC AGCACCTGTAATAGAAGAAAGACAAAATTGCGGAGCAGTATGGACACAA TGCGGAGGAAATGGATGGCAAGGACCTACATGCTGCGCATCAGGATCAAC ATGCGTAGCACAAAATGAATGGTATTCACAATGCCTTCCTAATTCACAAGT AACATCATCATCAACAACACCTTCATCAACATCAACATCACAAAGATCAACAT CAACATCATCATCAACAAGATCAGGATCATCATCATCATCATCAACA ACACCTCCTCCTGTATCATCACCTGTAACATCAATACCTGGAGGAGCAACA TCAACAGCATCATATTCAGGAAATCCTTTTTCAGGAGTAAGACTTTTTGCA AATGATTATTATAGATCAGAAGTACATAATCTTGCAATACCTTCAATGACA GGAACACTTGCAGCAAAAGCATCAGCAGTAGCAGAAGTACCTTCATTTCA ATGGCTTGATAGAAATGTAACAATAGATCTTATGGTACAACACTTTC ACAAGTAAGAGCACTTAATAAAGCAGGAGCAAATCCTCCTTATGCAGCAC AACTTGTAGTATATGATCTTCCTGATAGAGATTGCGCAGCAGCAGCATCAA ATGGAGAATTTTCAATAGCAAATGGAGGAGCAGCAAATTATAGATCATAT ATAGATGCAATAAGAAAGCAATATATAATAGAATATTCAGATATAGAATAAT ACTTGTAATAGAACCTGATTCAATGGCAAATATGGTAACAAATATGAATG TAGCAAAATGCTCAAATGCAGCATCAACATATCATGAACTTACAGTATAT GCACTTAAACAACTTAATCTTCCTAATGTAGCAATGTATCTTGATGCAGGA CATGCAGGATGGCTTGGATGGCCTGCAAATATACAACCTGCAGCAGAACT TTTTGCAGGAATATATAATGATGCAGGAAAACCTGCAGCAGTAAGAGGAC TTGCAACAAATGTAGCAAATTATAATGCATGGTCAATAGCATCAGCACCTT CATATACATCACCTAATCCTAATTATGATGAAAAACATTATATAGAAGCAT TTTCACCTCTTCTTAATTCAGCAGGATTTCCTGCAAGATTTATAGTAGATAC AGGAAGAAATGGAAAACAACCTACAGGACAACAACAATGGGGAGATTGG TGCAATGTAAAAGGAACAGGATTTGGAGTAAGACCTACAGCAAATACAGG ACATGAACTTGTAGATGCATTTGTATGGGTAAAACCTGGAGGAGAATCAG ATGGAACATCAGATACATCAGCAGCAAGATATGATTATCATTGCGGACTT TCAGATGCACTTCAACCTGCACCTGAAGCAGGACAATGGTTTCAAGCATA TTTTGAACAACTTCTTACAAATGCAAATCCTCCTTTT (SEQ ID NO: 177) | MAKKLFITAALAAAVLAAPVIE ERQNCGAVWTQCGGNGWQGPT CCASGSTCVAQNEWYSQCLPNS QVTSSTTPSSTSTSQRSTSTSSST TRSGSSSSSSTTPPPVSSPVTSIPG GATSTASYSGNPFSGVRLFAND YYRSEVHNLAIPSMTGTLAAKA SAVAEVPSFQWLDRNVTIDTLM VQTLSQVRALNKAGANPPYAA QLVVYDLPDRDCAAAASNGEFS IANGGAANYRSYIDAIRKHIIEYS DIRIILVIEPDSMANMVTNMNVA KCSNAASTYHELTVYALKQLNL PNVAMYLDAGHAGWLGWPANI QPAAELFAGIYNDAGKPAAVRG LATNVANYNAWSIASAPSYTSP NPNYDEKHYIEAFSPLLNSAGFP ARFIVDTGRNGKQPTGQQQWG DWCNVKGTGFGVRPTANTGHE LVDAFVWVKPGGESDGTSDTSA ARYDYHCGLSDALQPAPEAGQ WFQAYFEQLLTNANPPF (SEQ ID NO: 147) |
| S. f. BGLI | ATGGTATCATTTACATCACTTCTTGCAGGAGTAGCAGCAATATCAGGAGTA CTTGCAGCACCTGCAGCAGAAGTAGAATCAGTAGCAGTAGAAAAAAGATC AGATTCAAGAGTACCTATACAAAATTATACACAATCACCTTCACAAAGAG ATGAATCATCACAATGGGTATCACCTCATTATTATCCTACACCTCAAGGAG GAAGACTTCAAGATGTATGGCAAGAAGCATATGCAAGAGCAAAAGCAAT AGTAGGACAAATGACAATAGTAGAAAAAGTAAATCTTACAACAGGAACA GGATGGCAACTTGATCCTTGCGTAGGAAATACAGGATCAGTACCTAGATT TGGAATACCTAATCTTTGCCTTCAAGATGGACCTCTTGGAGTAAGATTGC AGATTTTGTAACAGGATATCCTTCAGGACTTGCAACAGGAGCAACATTTA ATAAAGATCTTTTTCTTCAAAGAGGACAAGCACTTGGACATGAATTTAATT CAAAAGGAGTACATATAGCACTTGGACCTGCAGTAGGACCTCTTGGAGTA AAAGCAAGAGGAGGAAGAAATTTTGAAGCATTTGGATCAGATCCTTATCT TCAAGGAACAGCAGCAGCAGCAACAATAAAAGGACTTCAAGAAAATAAT GTAATGGCATGCGTAAAACATTTTATAGGAAATGAACAGGAAAAATATAG ACAACCTGATGATATAAATCCTGCAACAAATCAAACAACAAAAGAAGCAA TATCAGCAAATATACCTGATAGAGCAATGCATGAACTTTATCTTTGGCCTT TTGCAGATTCAGTAAGAGCAGGAGTAGGATCAGTAATGTGCTCATATAAT AGAGTAAATACATATGCATGCGAAAATTCATATATGATGAATCATCTT CTTAAAGAAGAACTTGGATTTCAAGGATTTGTAGTATCAGATTGGGGAGC ACAACTTTCAGGAGTATATTCAGCAATATCAGGACTTGATATGTCAATGCC TGGAGAAGTATATGGAGGATGGAATACAGGAACATCATTTTGGGGACAAA ATCTTACAAAAGCAATATATAATGAACAGTACCTATAGAAAAGACTTGAT GATATGGCAACAAGAATACTTGCAGCACTTTATGCAACAAATTCATTTCCT ACAGAAGATCATCTTCCTAATTTTTCATCATGGACAACAAAAGAATATGG AAATAAATATTATGCAGATAATACAACAGAAATAGTAAAAGTAAATTATC ATGTAGATCCTTCAAATGATTTTACAGAAGATACAGCACTTAAAGTAGCA GAAGAATCAATAGTACTTCTTAAAAATGAAAATAATACACTTCCTATATCA CCTGAAAAAGCAAAAAGACTTCTTCTTTCAGGAATAGCAGCAGGACCTGA TCCTATAGGATATCAATGCGAAGATCAATCATGCACAAATGGAGCACTTTT TCAAGGATGGGGATCAGGATCAGTAGGATCACCTAAATATCAAGTAACAC CTTTTGAAGAAATATCATATCTTGCAAGAAAAAATAAAATGCAATTTGATT ATATAAGAGAATCATATGATCTTGCACAAGTAACAAAAGTAGCATCAGAT GCACATCTTTCAATAGTAGTAGTATCAGCAGCATCAGGAGAAGGATATAT AACAGTAGATGGAAATCAAGGAGATAGAAGAAATCTTACACTTTGGAATA ATGGAGATAAACTTATAGAAACAGTAGCAGAAAATTGCGCAAATACAGTA GTAGTAGTAACATCAACAGGACAAATAAATTTTGAAGGATTTGCAGATCA TCCTAATGTAACAGCAATAGTATGGCAGGACCTCTTGGAGATAGATCAG GAACAGCAATAGCAAATATACTTTTTGGAAAAGCAAATCCTTCAGGACAT CTTCCTTTTACAATAGCAAAAACAGATGATTATATACCTATAGAAACA TATTCACCTTCATCAGGAGAACCTGAAGATAATCATCTTGTAGAAAATGAT CTTCTTGTAGATTATAGATTTTGAAGAAAAAATATAGAACCTAGATAT GCATTTGGATATGGACTTTCATATAATGAATATGAAGTATCAAATGCAAA AGTATCAGCAGCAAAAAAAGTAGATGAAGAACTTCCTGAACCTGCAACAT ATCTTTCAGAATTTTCATATCAAAATGCAAAAGATTCAAAAAATCCTTCAG | MVSFTSLLAGVAAISGVLAAPA AEVESVAVEKRSDSRVPIQNYT QSPSQRDESSQWVSPHYYPTPQ GGRLQDVWQEAYARAKAIVGQ MTIVEKVNLTTGTGWQLDPCVG NTGSVPRFGIPNLCLQDGPLGVR FADFVTGYPSGLATGATFNKDL FLQRGQALGHEFNSKGVHIALG PAVGPLGVKARGGRNFEAFGSD PYLQGTAAAATIKGLQENNVMA CVKHFIGNEQEKYRQPDDINPAT NQTTKEAISANIPDRAMHELYL WPFADSVRAGVGSVMCSYNRV NNTYACENSYMMNHLLKEELG FQGFVVSDWGAQLSGVYSAISG LDMSMPGEVYGGWNTGTSFWG QNLTKAIYNETVPIERLDDMATR ILAALYATNSFPTEDHLPNFSSW TTKEYGNKYYADNTTEIVKVNY HVDPSNDFTEDTALKVAEESIVL LKNENNTLPISPEKAKRLLLSGIA AGPDPIGYQCEDQSCTNGALFQ GWGSGSVGSPKYQVTPFEEISYL ARKNKMQFDYIRESYDLAQVTK VASDAHLSIVVVSAASGEGYITV DGNQGDRRNLTLWNNGDKLIET VAENCANTVVVVTSTGQINFEG FADHPNVTAIVWAGPLGDRSGT AIANILFGKANPSGHLPFTIAKTD DDYIPIETYSPSSGEPEDNHLVEN DLLVDYRYFEEKNIEPRYAFGY GLSYNEYEVSNAKVSAAKKVDE ELPEPATYLSEFSYQNAKDSKNP SDAFAPTDLNRVNEYLYPYLDS NVTLKDGNYEYPDGYSTEQRTT PIQPGGGLGGNDALWEVAYKVE VDVQNLGNSTDKFVPQLYLKHP EDGKFETPIQLRGFEKVELSPGE KKTVEFELLRRDLSVWDTTRQS WIVESGTYEALIGVAVNDIKTSV LFTI (SEQ ID NO: 148) |

TABLE 2-continued

Exemplary Biomass Degrading Enzymes That Can Be Used According to the Present Invention

| Organism and Protein (Gene) | Codon-Optimized DNA Sequence | Accession Number and Amino Acid Sequence |
|---|---|---|
| | ATGCATTTGCACCTACAGATCTTAATAGAGTAAATGAATATCTTTATCCTT<br>ATCTTGATTCAAATGTAACACTTAAAGATGGAAATTATGAATATCCTGATG<br>GATATTCAACAGAACAAAGAACAACACCTATACAACCTGGAGGAGGACTT<br>GGAGGAAATGATGCACTTTGGGAAGTAGCATATAAAGTAGAAGTAGATGT<br>ACAAAATCTTGGAAATTCAACAGATAAATTTGTACCTCAACTTTATCTTAA<br>ACATCCTGAAGATGGAAAATTTGAAACACCTATACAACTTAGAGGATTTG<br>AAAAAGTAGAACTTTCACCTGGAGAAAAAAAAACAGTAGAATTTGAACTT<br>CTTAGAAGAGATCTTTCAGTATGGGATACAACAAGACAATCATGGATAGT<br>AGAATCAGGAACATATGAAGCACTTATAGGAGTAGCAGTAAATGATATAA<br>AAACATCAGTACTTTTTACAATA (SEQ ID NO: 178) | |

In certain aspects of the invention, the polypeptides and polynucleotides of the present invention are provided in an isolated form, e.g., purified to homogeneity.

The present invention also encompasses polypeptides which comprise, or alternatively consist of, an amino acid sequence which is at least about 80%, 85%, 90%, 95%, 96%, 97%, 98%, 99% similar to the polypeptide of any of SEQ ID NOs:108-148, and to portions of such polypeptide with such portion of the polypeptide generally containing at least 30 amino acids and more preferably at least 50 amino acids.

As known in the art "similarity" between two polypeptides is determined by comparing the amino acid sequence and conserved amino acid substitutes thereto of the polypeptide to the sequence of a second polypeptide.

The present invention further relates to a domain, fragment, variant, derivative, or analog of the polypeptide of any of SEQ ID NOs:108-148.

Fragments or portions of the polypeptides of the present invention can be employed for producing the corresponding full-length polypeptide by peptide synthesis; therefore, the fragments can be employed as intermediates for producing the full-length polypeptides.

Fragments of biomass degrading enzymes, for example cellulases including cellobiohydrolase, endoglucanase or beta-glucosidase polypeptides, or mannanases of the present invention encompass domains, proteolytic fragments, deletion fragments and in particular, fragments of *Thermobifida fusca, Caldocellum saccharolyticum, Clostridium stercorarium, Eubacterium cellulosolvens, Cellulomonas fimi, Acidothermus cellulolyticus, Butyrivibrio fibrisolvens, Anaerocellum thermophilum, Trichoderma reesei, Coptotermes formosanus, Nasutitermes takasagoensis, Talaromyces emersonii, Neosartorya fischeri* or *Caldicellulosiruptor kristjanssonii* cellobiohydrolase, endoglucanase or beta-glucosidase polypeptides which retain any specific biological activity of biomass degrading enzyme such as the cellobiohydrolase, endoglucanase, mannanase or beta-glucosidase proteins. Polypeptide fragments further include any portion of the polypeptide which comprises a catalytic activity of biomass degrading enzyme such as the cellobiohydrolase, endoglucanase, mannanase or beta-glucosidase proteins.

The variant, derivative or analog of the polypeptide of any of SEQ ID NOs:108-148, can be (i) one in which one or more of the amino acid residues are substituted with a conserved or non-conserved amino acid residue (preferably a conserved amino acid residue) and such substituted amino acid residue can or can not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide for purification of the polypeptide or (v) one in which a fragment of the polypeptide is soluble, i.e., not membrane bound, yet still binds ligands to the membrane bound receptor. Such variants, derivatives and analogs are deemed to be within the scope of those skilled in the art from the teachings herein.

The polypeptides of the present invention further include variants of the polypeptides. A "variant" of the polypeptide can be a conservative variant, or an allelic variant. As used herein, a conservative variant refers to alterations in the amino acid sequence that do not adversely affect the biological functions of the protein. A substitution, insertion or deletion is said to adversely affect the protein when the altered sequence prevents or disrupts a biological function associated with the protein. For example, the overall charge, structure or hydrophobic-hydrophilic properties of the protein can be altered without adversely affecting a biological activity. Accordingly, the amino acid sequence can be altered, for example to render the peptide more hydrophobic or hydrophilic, without adversely affecting the biological activities of the protein.

By an "allelic variant" is intended alternate forms of a gene occupying a given locus on a chromosome of an organism. Genes II, Lewin, B., ed., John Wiley & Sons, New York (1985). Non-naturally occurring variants can be produced using art-known mutagenesis techniques. Allelic variants, though possessing a slightly different amino acid sequence than those recited above, will still have the same or similar biological functions associated with the *Thermobifida fusca, Caldocellum saccharolyticum, Clostridium stercorarium, Eubacterium cellulosolvens, Cellulomonas fimi, Acidothermus cellulolyticus, Butyrivibrio fibrisolvens, Anaerocellum thermophilum, Trichoderma reesei, Coptotermes formosanus, Nasutitermes takasagoensis, Talaromyces emersonii, Neosartorya fischeri* or *Caldicellulosiruptor kristjanssonii* biomass degrading enzyme.

The allelic variants, the conservative substitution variants, and members of the biomass degrading enzyme families, will have an amino acid sequence having at least 75%, at least 80%, at least 90%, at least 95% amino acid sequence identity with a *Thermobifida fusca, Caldocellum saccharolyticum, Clostridium stercorarium, Eubacterium cellulosolvens, Cellulomonas fimi, Acidothermus cellulolyticus, Butyrivibrio fibrisolvens, Anaerocellum thermophilum, Trichoderma reesei, Coptotermes formosanus, Nasutitermes takasagoensis, Talaromyces emersonii, Neosartorya fischeri* or *Caldicellulosiruptor kristjanssonii* biomass degrading enzyme sequence set forth in any one of SEQ ID NOs:108-148. Identity or homology with respect to such sequences is defined herein as the percentage of amino acid residues in the candidate sequence that are identical with the known peptides, after aligning the sequences and introducing gaps, if necessary, to achieve the maximum percent homology, and not considering any conservative substitutions as part of the sequence identity. N-terminal, C-terminal or internal extensions, deletions, or insertions into the peptide sequence shall not be construed as affecting homology.

Thus, the proteins and peptides of the present invention include molecules comprising the amino acid sequence of SEQ ID NOs:108-148 or fragments thereof having a consecutive sequence of at least about 3, 4, 5, 6, 10, 15, 20, 25, 30, 35 or more amino acid residues of the *Thermobifida fusca, Caldocellum saccharolyticum, Clostridium stercorarium, Eubacterium cellulosolvens, Cellulomonas fimi, Acidothermus cellulolyticus, Butyrivibrio fibrisolvens, Anaerocellum thermophilum, Trichoderma reesei, Coptotermes formosanus, Nasutitermes takasagoensis, Talaromyces emersonii, Neosartorya fischeri* or *Caldicellulosiruptor kristjanssonii* biomass degrading enzyme sequences; amino acid sequence variants of such sequences wherein at least one amino acid residue has been inserted N- or C-terminal to, or within, the disclosed sequence; amino acid sequence variants of the disclosed sequences, or their fragments as defined above, that have been substituted by another residue. Contemplated variants further include those containing predetermined mutations by, e.g., homologous recombination, site-directed or PCR mutagenesis, and the corresponding proteins of other animal species, including but not limited to bacterial, fungal, insect, rabbit, rat, porcine, bovine, ovine, equine and non-human primate species, the alleles or other naturally occurring variants of the family of proteins; and derivatives wherein the protein has been covalently modified by substitution, chemical, enzymatic, or other appropriate means with a moiety other than a naturally occurring amino acid (for example, a detectable moiety such as an enzyme or radioisotope).

Using known methods of protein engineering and recombinant DNA technology, variants can be generated to improve or alter the characteristics of the cellulase polypeptides. For instance, one or more amino acids can be deleted from the N-terminus or C-terminus of the secreted protein without substantial loss of biological function.

Thus, the invention further includes *Thermobifida fusca, Caldocellum saccharolyticum, Clostridium stercorarium, Eubacterium cellulosolvens, Cellulomonas fimi, Acidothermus cellulolyticus, Butyrivibrio fibrisolvens, Anaerocellum thermophilum, Trichoderma reesei, Coptotermes formosanus, Nasutitermes takasagoensis, Talaromyces emersonii, Neosartorya fischeri* or *Caldicellulosiruptor kristjanssonii* biomass degrading enzyme polypeptide variants which show substantial biological activity. Such variants include deletions, insertions, inversions, repeats, and substitutions selected according to general rules known in the art so as have little effect on activity.

The skilled artisan is fully aware of amino acid substitutions that are either less likely or not likely to significantly effect protein function (e.g., replacing one aliphatic amino acid with a second aliphatic amino acid), as further described below.

For example, guidance concerning how to make phenotypically silent amino acid substitutions is provided in Bowie et al., "Deciphering the Message in Protein Sequences: Tolerance to Amino Acid Substitutions," *Science* 247:1306-1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. (Cunningham and Wells, *Science* 244:1081-1085 (1989).) The resulting mutant molecules can then be tested for biological activity.

As the authors state, these two strategies have revealed that proteins are often surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved. Moreover, tolerated conservative amino acid substitutions involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

The terms "derivative" and "analog" refer to a polypeptide differing from the *Thermobifida fusca, Caldocellum saccharolyticum, Clostridium stercorarium, Eubacterium cellulosolvens, Cellulomonas fimi, Acidothermus cellulolyticus, Butyrivibrio fibrisolvens, Anaerocellum thermophilum, Trichoderma reesei, Coptotermes formosanus, Nasutitermes takasagoensis, Talaromyces emersonii, Neosartorya fischeri* or *Caldicellulosiruptor kristjanssonii* biomass degrading enzyme polypeptide, but retaining essential properties thereof. Generally, derivatives and analogs are overall closely similar, and, in many regions, identical to the *Thermobifida fusca, Caldocellum saccharolyticum, Clostridium stercorarium, Eubacterium cellulosolvens, Cellulomonas fimi, Acidothermus cellulolyticus, Butyrivibrio fibrisolvens, Anaerocellum thermophilum, Trichoderma reesei, Coptotermes formosanus, Nasutitermes takasagoensis, Talaromyces emersonii, Neosartorya fischeri* or *Caldicellulosiruptor kristjanssonii* biomass degrading enzyme polypeptides. The term "derivative" and "analog" when referring to *Thermobifida fusca, Caldocellum saccharolyticum, Clostridium stercorarium, Eubacterium cellulosolvens, Cellulomonas fimi, Acidothermus cellulolyticus, Butyrivibrio fibrisolvens, Anaerocellum thermophilum, Trichoderma reesei, Coptotermes formosanus, Nasutitermes takasagoensis, Talaromyces emersonii, Neosartorya fischeri* or *Caldicellulosiruptor kristjanssonii* biomass degrading enzyme polypeptides of the present invention include any polypeptides which retain at least some of the activity of the corresponding native polypeptide, e.g., the exoglucanase activity, or the activity of the its catalytic domain.

Derivatives of *Thermobifida fusca, Caldocellum saccharolyticum, Clostridium stercorarium, Eubacterium cellulosolvens, Cellulomonas fimi, Acidothermus cellulolyticus, Butyr-* ivibrio fibrisolvens, Anaerocellum thermophilum, Trichoderma reesei, Coptotermes formosanus, Nasutitermes takasagoensis, Talaromyces emersonii, Neosartorya fischeri or Caldicellulosiruptor kristjanssonii biomass degrading enzyme polypeptides of the present invention, are polypeptides which have been altered so as to exhibit additional features not found on the native polypeptide. Derivatives can be covalently modified by substitution, chemical, enzymatic, or other appropriate means with a moiety other than a naturally occurring amino acid (for example, a detectable moiety such as an enzyme or radioisotope). Examples of derivatives include fusion proteins.

An analog is another form of a Thermobifida fusca, Caldocellum saccharolyticum, Clostridium stercorarium, Eubacterium cellulosolvens, Cellulomonas fimi, Acidothermus cellulolyticus, Butyrivibrio fibrisolvens, Anaerocellum thermophilum, Trichoderma reesei, Coptotermes formosanus, Nasutitermes takasagoensis, Talaromyces emersonii, Neosartorya fischeri or Caldicellulosiruptor kristjanssonii biomass degrading enzyme polypeptide of the present invention. An "analog" also retains substantially the same biological function or activity as the polypeptide of interest, e.g., functions as a cellobiohydrolase. An analog includes a proprotein which can be activated by cleavage of the proprotein portion to produce an active mature polypeptide.

The polypeptide of the present invention can be a recombinant polypeptide, a natural polypeptide or a synthetic polypeptide, preferably a recombinant polypeptide.

Also provided in the present invention are allelic variants, orthologs, and/or species homologs. Procedures known in the art can be used to obtain full-length genes, allelic variants, splice variants, full-length coding portions, orthologs, and/or species homologs of genes encoding any of SEQ ID NOs: 108-148, using information from the sequences disclosed herein or the clones deposited with the ATCC. For example, allelic variants and/or species homologs can be isolated and identified by making suitable probes or primers from the sequences provided herein and screening a suitable nucleic acid source for allelic variants and/or the desired homologue.

Tethered and Secreted Biomass Degrading Enzymes

According to the present invention, the biomass degrading enzymes, for example cellulases, can be either tethered or secreted. As used herein, a protein is "tethered" to an organism's cell surface if at least one terminus of the protein is bound, covalently and/or electrostatically for example, to the cell membrane or cell wall. It will be appreciated that a tethered protein can include one or more enzymatic regions that can be joined to one or more other types of regions at the nucleic acid and/or protein levels (e.g., a promoter, a terminator, an anchoring domain, a linker, a signaling region, etc.). While the one or more enzymatic regions may not be directly bound to the cell membrane or cell wall (e.g., such as when binding occurs via an anchoring domain), the protein is nonetheless considered a "tethered enzyme" according to the present specification.

Tethering can, for example, be accomplished by incorporation of an anchoring domain into a recombinant protein that is heterologously expressed by a cell, or by prenylation, fatty acyl linkage, glycosyl phosphatidyl inositol anchors or other suitable molecular anchors which can anchor the tethered protein to the cell membrane or cell wall of the host cell. A tethered protein can be tethered at its amino terminal end or optionally at its carboxy terminal end.

As used herein, "secreted" means released into the extracellular milieu, for example into the media. Although tethered proteins can have secretion signals as part of their immature amino acid sequence, they are maintained as attached to the cell surface, and do not fall within the scope of secreted proteins as used herein.

As used herein, "flexible linker sequence" refers to an amino acid sequence which links two amino acid sequences, for example, a cell wall anchoring amino acid sequence with an amino acid sequence that contains the desired enzymatic activity. The flexible linker sequence allows for necessary freedom for the amino acid sequence that contains the desired enzymatic activity to have reduced steric hindrance with respect to proximity to the cell and can also facilitate proper folding of the amino acid sequence that contains the desired enzymatic activity.

In some embodiments of the present invention, the tethered biomass degrading enzymes are tethered by a flexible linker sequence linked to an anchoring domain. In some embodiments, the anchoring domain is of CWP2 (for carboxy terminal anchoring) or FLO1 (for amino terminal anchoring) from S. cerevisiae.

In some embodiments, heterologous secretion signals can be added to the expression vectors of the present invention to facilitate the extra-cellular expression of biomass degrading enzyme proteins. In some embodiments, the heterologous secretion signal is the secretion signal from T. reesei Xyn2.

Fusion Proteins Comprising Biomass Degrading Enzymes

The present invention also encompasses fusion proteins. For example, the fusion proteins can be a fusion of a heterologous biomass degrading enzyme and a second peptide. The heterologous biomass degrading enzyme and the second peptide can be fused directly or indirectly, for example, through a linker sequence. The fusion protein can comprise for example, a second peptide that is N-terminal to the heterologous biomass degrading enzyme and/or a second peptide that is C-terminal to the heterologous biomass degrading enzyme. Thus, in certain embodiments, the polypeptide of the present invention comprises a first polypeptide and a second polypeptide, wherein the first polypeptide comprises a heterologous biomass degrading enzyme. In some specific embodiments, the polypeptide of the present invention comprises a first polypeptide and a second polypeptide, wherein the first polypeptide comprises a heterologous cellulase.

According to one embodiment of the present invention, the fusion protein can comprise a first and second polypeptide wherein the first polypeptide comprises a heterologous biomass degrading enzyme and the second polypeptide comprises a signal peptide. The signal peptide can be the signal sequence that is natively associated with the heterologous biomass degrading enzyme, a T. sacch signal sequence, or a signal sequence from another gram positive organism. Exemplary signal sequences from T. sacch and other gram-positive organisms are listed below in Tables 2 and 3. The signal sequences can be encoded by their native genes or can be codon-optimized for expression, e.g. for expression in T. sacch. (Codon-optimization is described in more detail below.) In some embodiments, the signal peptide is N-terminal to the biomass degrading enzyme. In some embodiments, the fusion protein comprises a signal peptide, a linker sequence and a biomass degrading enzyme.

TABLE 3

Signal Sequences from *T. sacch* and other Gram Positive Organisms.

| SEQ ID NO | Organism Derived | Gene Derived | Signal Peptide Amino Acid Sequence |
|---|---|---|---|
| 1 | *T. saccharolyticum* | extracellular solute-binding protein family 1 | MKLFKKIMLIMLSIMLIVSASACG TGSSGSSNSNASKS |
| 2 | *T. saccharolyticum* | Ig domain protein | MNKILKIFSVFLGAFLIFVNMSIN EAKADP |
| 3 | *T. saccharolyticum* | Arabinogalactan endo-1,4-beta-galactosidase | MNNKKGIVAFIIILTMIFSNLTFVD ANI |
| 4 | *T. saccharolyticum* | Mannan endo-1,4-beta-mannosidase | VKKFCILLMCIIILSGCKFNSVTS SGK |
| 5 | *T. saccharolyticum* | alpha amylase catalytic region | MKKTFKLILVLMLSLTLVFGLTA PIQAAS |
| 6 | *Lactococcus lactis* | secreted, uncharacterized protein | MKKKIISAILMSTVILSAAAPLSG VYA |
| 7 | *Lactococcus lactis* | secreted, uncharacterized protein | MKFNKKRVAIATFIALIFVSFFTIS SIQDNQTNAA |
| 8 | Typical Gram positive | identity to Tsacch cellulose 1,4-beta-cellobiosidase | MKSIVNRVVSIVTALIMIFGTSLFS QHIRAFA |
| 9 | *Staphylococcus aureus* | thermonuclease | MKSNKSLAMIVVAIIIVGVLAFQF MNH |
| 10 | *Staphylococcus aureus* | thermonuclease | MTEYLLSAGICMAIVSILLIGMAIS |
| 11 | *Bacillus licheniformis* | Alpha-amylase | MKQQKRLYARLLTLLFALIFLLP HSAAAAAN |
| 12 | *Bacillus licheniformis* | Alpha-amylase | MKQHKRLYARLLPLLFALIFLLS HSAAAAAS |
| 13 | *T. saccharolyticum* | glucan 1,4-alpha-glucosidase | LNRKLIKYLPVLFLASSVLSGCGN NNISSMK |
| 14 | *T. saccharolyticum* | extracellular solute-binding protein family 1 | MGKKFISIFVVTILLIAALLSGCST KQNTAS |
| 15 | *T. saccharolyticum* | glycoside hydrolase family 18 | MRIKKAFFMLIAAFIVLSLFLFNF AKTSASA |
| 16 | *T. saccharolyticum* | Predicted Cellulase | MSKIARQIITVFVTLVLAVYSIPII GATS |
| 17 | *T. saccharolyticum* | extracellular solute-binding protein family 1 | MFKKIIVTVLAVILTIGALTGCSSS TNSSGS |
| 18 | *T. saccharolyticum* | extracellular solute-binding protein family 1 | MKSKKLLSVLIVSVMIFSVFLSGC GSAKNSKSA |
| 19 | *T. saccharolyticum* | glycoside hydrolase family 18 | MKKYKRYIAMMLIFVMVLATVS LAGCKSSVKKPVTSKR |
| 20 | *T. saccharolyticum* | Predicted Cellulase | LNKLHINKWYFFVGMLAMFAVI MSLILKDTSLTF |
| 21 | *T. saccharolyticum* | Secretion protein HlyD | MNKKVIIITSIILVVAAGATYYFT KSKATP |
| 22 | *T. saccharolyticum* | Endo-1,4-beta-xylanase | MLNFKRIFTLICTFLVSLSLLTVT AFADT |
| 23 | *T. saccharolyticum* | hypothetical protein | MKKLMLILLSLILVVSVTACGKI |
| 24 | *T. saccharolyticum* | conserved hypothetical protein | MLSKNLPIKILSVVIAFILWLYVM GEK |
| 25 | *T. saccharolyticum* | extracellular solute-binding protein family 1 | MKRLKKLMLVLLSMILIISASAC GTNSNNSSSSNASN |

TABLE 3-continued

Signal Sequences from T. sacch and other Gram Positive Organisms.

| SEQ ID NO | Organism Derived | Gene Derived | Signal Peptide Amino Acid Sequence |
|---|---|---|---|
| 26 | T. saccharolyticum | Amylase | MKKTFKLILVLMLSLTLVFGLTA PIQAAS |
| 27 | T. saccharolyticum | XynA precursor | MKSIVNRVVSIVTALIMIFGTSLFS QHIRAFADD |
| 28 | T. saccharolyticum | conserved hypothetical protein (Spot #4, Experiment HH23) | VKKFVSIFLAVMLIAAIPVFGLAAQ |
| 29 | T. saccharolyticum | N-acetylmuramoyl-L-alanine amidase (Spot #11, Experiment HH9) | MLKKIIATMLILSLVVIPFMAFADD |
| 30 | T. saccharolyticum | hypothetical protein (Spot #18, Experiment HH32) | VKKIYGLILVFVVMLAVIGIVYA DS |
| 31 | T. saccharolyticum | extracellular solute-binding protein family 1 (Spot #19, Experiment HH32) | MIRSKMLKTVSMLLVLVMIITAF TAC |
| 32 | Caldocellum saccharolyticum | Cellulase - ManA | MRLKTKIRKKWLSVLCTVVFLLN ILFIANVTILPKVGAAT |
| 33 | Caldocellum saccharolyticum | Cellulase - celA | MKTARLLVCFVLVCFILTTTILLD NNKGEAAM |
| 34 | Clostridium Stercorarium | Cellulase - celZ | MRKFWSFAIIISLLVTGLFIHTPKA EAAG |
| 35 | Thermobifida fusca | Cel9A (beta-1,4-endoglucanase precursor) | MSVTEPPPRRRGRHSRARRFLTS LGA TAALTAGMLGVPLATGTAHAEP |
| 36 | Caldocellum saccharolyticum | celA; | MVVTFLFILGVVYGVKPWQEAR AGS |
| 37 | Caldocellum saccharolyticum | celB (Cleavage 28/29) | MKRNLFRIVSRVVLIAFIASISLVG AMSY |
| 38 | Caldocellum saccharolyticum | celB (Cleavage 36-37) | MKRNLFRIVSRVVLIAFIASISLVG AM SYFPVETQAA |

The signal sequence can be encoded by a native nucleotide sequence or can be encoded by a codon-optimized sequence. (Codon-optimized sequences are described in more detail below.) Sequences encoding the signal peptides in Table 3 that have been codon-optimized for expression in T. sacch are shown below in Table 4.

TABLE 4

Codon-Optimized Signal Sequences from T. sacch and other Gram Positive Organisms.

| SEQ ID NO | Organism Derived | Gene Derived | Codon-Optimized Nucleotide Sequence |
|---|---|---|---|
| 39 | T. saccharolyticum | extracellular solute-binding protein family 1 | ATGAAACTGTTTAAAAAAATTATGCT GATTATGCTGAGCATTATGCTGATTGT GAGCGCGAGCGCGTGCGGCACCGGC AGCAGCGGCAGCAGCAACAGCAACG CGAGCAAAAGC |
| 40 | T. saccharolyticum | Ig domain protein | ATGAACAAAATTCTGAAAATTTTTAG GCTGTTTCTGGGCGCGTTTCTGATTTT TGTGAACATGAGCATTAACGAAGCGA AAGCGGATCCG |

TABLE 4-continued

Codon-Optimized Signal Sequences from *T. sacch* and other Gram Positive Organisms.

| SEQ ID NO | Organism Derived | Gene Derived | Codon-Optimized Nucleotide Sequence |
|---|---|---|---|
| 41 | *T. saccharolyticum* | Arabinogalactan endo-1,4-beta-galactosidase | ATGAACAACAAAAAAGGCATTGTGGC GTTTATTATTATTCTGACCATGATTTT TAGCAACCTGACCTTTGTGGATGCGA ACATT |
| 42 | *T. saccharolyticum* | Mannan endo-1,4-beta-mannosidase | GTGAAAAAATTTTGCATTCTGCTGAT GTGCATTATTATTCTGATTAGCGGCTG CAAATTTAACAGCGTGACCAGCAGCG GCAAA |
| 43 | *T. saccharolyticum* | alpha amylase catalytic region | ATGAAAAAAACCTTTAAACTGATTCT GGTGCTGATGCTGAGCCTGACCCTGG TGTTTGGCCTGACCGCGCCGATTCAG GCGGCGAGC |
| 44 | *Lactococcus lactis* | secreted, uncharacterized protein | ATGAAGAAAAGATAATAAGCGCTAT TCTTATGAGCACAGTGATACTTTCTGC GGCCGCACCTTTAAGTGGTGTTTATG CT |
| 45 | *Lactococcus lactis* | secreted, uncharacterized protein | ATGAAATTTAATAAAAAGAGAGTTGC CATAGCAACATTTATTGCCTTAATATT TGTGTCATTTTTCACAATTTCTTCTAT ACAGGATAATCAAACCAATGCGGCA |
| 46 | Typical Gram positive | identity to Tsacch cellulose 1,4-beta-cellobiosidase | ATGAAATCAATTGTCAATAGAGTGGT AAGCATTGTTACTGCTCTTATAATGAT TTTTGGTACTTCATTATTTTCTCAGCA CATTAGAGCGTTTGCA |
| 47 | *Staphylococcus aureus* | thermonuclease | ATGAAAAGTAATAAATCGTTAGCTAT GATAGTCGTTGCAATAATAGTCG GGGTATTAGCTTTTCAGTTTATGAACC AC |
| 48 | *Staphylococcus aureus* | thermonuclease | ATGACAGAATATATTGTTATCAGCAGG TATTTGCATGGCAATAGTATCAATATT ATTAATAGGAATGGCAATTTCA |
| 49 | *Bacillus licheniformis* | Alpha-amylase | ATGAAACAACAAAAAAGGCTTTATGC AAGACTTTTAACATTATTGTTTGCATT GATATTCTTGCTTCCACATTCTGCAGC AGCAGCAGCTAAC |
| 50 | *Bacillus licheniformis* | Alpha-amylase | ATGAAACAGCACAAAAGACTGTATGC AAGATTGCTACCTTTGTTGTTTGCTCT GATATTTTATTGAGCCACTCGGCGG CTGCTGCAGCCTCA |
| 51 | *T. saccharolyticum* | glucan 1,4-alpha-glucosidase | TTGAATAGAAAACTTATAAAATACCT ACCTGTATTATTTCTTGCATCCAGTGT GCTAAGCGGATGTGGAAACAATAATA TATCAAGTATGAAA |
| 52 | *T. saccharolyticum* | extracellular solute-binding protein family 1 | ATGGGTAAAAAATTTATAAGCATTTT TGTTTGTCACAATACTTTGATAGCTGC TTTGCTTTCTGGATGTTCAACAAAACA AAACACTGCTTCC |
| 53 | *T. saccharolyticum* | glycoside hydrolase family 18 | ATGCGTATAAAAAAAGCTTTTTTTAT GCTGATAGCAGCTTTTATAGTTCTATC TTTGTTTTTGTTTAATTTCGCTAAAAC CAGTGCATCGGCG |
| 54 | *T. saccharolyticum* | Predicted Cellulase | ATGAGCAAGATAGCGAGACAGATAA TAACTGTTTTCGTGACCCTTGTACTGG CAGTATATTCTATCCCTATTATTGGGG CAACCAGT |

TABLE 4-continued

Codon-Optimized Signal Sequences from *T. sacch* and other Gram Positive Organisms.

| SEQ ID NO | Organism Derived | Gene Derived | Codon-Optimized Nucleotide Sequence |
|---|---|---|---|
| 55 | T. saccharolyticum | extracellular solute-binding protein family 1 | ATGTTTAAAAAAATTATTGTCACAGT GCTTGCAGTAATTTTGACAATTGGAG CATTAACAGGATGTTCATCTTCTACTA ATAGTAGTGGTAGT |
| 56 | T. saccharolyticum | extracellular solute-binding protein family 1 | ATGAAAAGTAAAAAGTTGTTGTCAGT TTTAATTGTATCAGTAATGATATTTTC TGTATTTTTATCTGGGTGTGGCAGTGC TAAAAACTCTAAATCAGCA |
| 57 | T. saccharolyticum | glycoside hydrolase family 18 | ATGAAAAAATATAAAAGATATATTGC GATGATGTTGATTTTTGTCATGGTACT TGCAACTGTATCATTAGCCGGATGCA AAAGCTCAGTTAAAAAGCCAGTTACT TCTAAAAGA |
| 58 | T. saccharolyticum | Predicted Cellulase | TTGAATAAATTGCATATTAATAAATG GTACTTTTTTGTAGGTATGCTTGCTAT GTTTGCTGTAATTATGAGTCTAATCTT AAAAGATACATCTTTAACCTTT |
| 59 | T. saccharolyticum | Secretion protein HlyD | ATGAATAAAAAGGTAATAATTATAAC CAGCATTATTTTGGTAGTTGCAGCAG GCGCTACTTACTACTTTACAAAAAGC AAAGCCACGCCT |
| 60 | T. saccharolyticum | Endo-1,4-beta-xylanase | ATGTTAAACTTTAAGAGAATTTTTAC GTTAATTTGCACTTTTTTGGTTAGTTT AAGTTTGCTTACGGTTACTGCATTTGC AGATACA |
| 61 | T. saccharolyticum | hypothetical protein | ATGAAAAAATTAATGTTGATTTTACTT TCTTTAATATTGGTAGTTAGTGTAACT GCCTGCGGGAAAATA |
| 62 | T. saccharolyticum | conserved hypothetical protein | ATGCTGAGTAAAAATCTACCTATAAA GATACTTTCGGTTGTAATAGCATTTAT ATTATGGCTTTATGTGATGGGTGAGA AG |
| 63 | T. saccharolyticum | extracellular solute-binding protein family 1 | ATGAAAAGATTAAAAAAACTCATGTT AGTTTTGCTATCGATGATTCTGATTAT TTCGGCATCAGCTTGTGGAACTAACT CAAACAATTCAAGTAGTTCCAATGCC TCTAAT |
| 64 | T. saccharolyticum | Amylase | ATGAAAAAAACGTTTAAATTGATATT GGTGCTGATGCTTTCACTTACACTTGT TTTTGGATTGACAGCACCAATACAGG CAGCTTCT |
| 65 | T. saccharolyticum | XynA precursor | ATGAAGAGTATTGTAAACAGAGTTGT ATCTATCGTTACAGCTTTAATAATGAT TTTTGGGACATCACTGTTTTCACAACA CATAAGGGCATTTGCTGATGAC |
| 66 | T. saccharolyticum | conserved hypothetical protein (Spot #4, Experiment HH23) | GTGAAAAAGTTTGTTTCTATCTTTTTG GCAGTTATGCTGATTGCAGCTATTCC AGTGTTTGGTTTAGCGGCTCAG |
| 67 | T. saccharolyticum | N-acetylmuramoyl-L-alanine amidase (Spot #11, Experiment HH9) | ATGTTAAAAAAAATAATTGCAACAAT GTTAATTTTATCATTAGTTGTCATTCC ATTCATGGCTTTTGCAGATGAT |
| 68 | T. saccharolyticum | hypothetical protein (Spot #18, Experiment HH32) | GTGAAGAAGATTTATGGATTGATATT GGTATTTGTTGTGATGTTAGCTGTAAT TGGAATTGTGTACGCTGATTCG |

TABLE 4-continued

Codon-Optimized Signal Sequences from *T. sacch* and other Gram Positive Organisms.

| SEQ ID NO | Organism Derived | Gene Derived | Codon-Optimized Nucleotide Sequence |
|---|---|---|---|
| 69 | *T. saccharolyticum* | extracellular solute-binding protein family 1 (Spot #19, Experiment HH32) | ATGATTAGAAGTAAGATGTTGAAAAC AGTAAGTATGTTGCTGGTGCTAGTGA TGATTATAACAGCATTTACTGCATGT |
| 70 | *Caldocellum saccharolyticum* | Cellulase - ManA | ATGAGACTAAAAACAAAAATAAGAA AGAAATGGTTAAGTGTTTTATGCACA GTAGTGTTTTTGTTGAATATTCTTTTT ATAGCTAATGTCACAATTTTACCTAA AGTTGGAGCAGCTACA |
| 71 | *Caldocellum saccharolyticum* | Cellulase - celA | ATGAAAACAGCAAGGCTTTTGGTGTG TTTTGTTTTGGTGTGCTTTATACTTAC TACAACGATTTTGCTTGATAATAACA AGGGAGAGGCAGCAATG |
| 72 | *Clostridium Stercorarium* | Cellulase - celZ | ATGAGAAAATTTTGGTCTTTTGCAAT AATTATATCTTTACTTGTAACAGGATT GTTTATTCATACTCCTAAAGCTGAGG CAGCTGGT |
| 73 | *Thermobifida fusca* | Cel9A (beta-1,4-endoglucanase precursor) | ATGTCAGTAACAGAACCTCCTCCTAG AAGAAGAGGAAGACATTCAAGAGCA AGAAGATTT CTTACATCACTTGGAGCAACAGCAGC ACTTACAGCAGGAATGCTTGGAGTAC CTCTTGCA ACAGGAACAGCACATGCAGAACCT |
| 74 | *Caldocellum saccharolyticum* | celA; | ATGGTAGTAACATTTCTTTTTATACTT GGAGTAGTATATGGAGTAAAACCTTG GCAAGAA GCAAGAGCAGGATCA |
| 75 | *Caldocellum saccharolyticum* | celB (Cleavage 28/29) | ATGAAAAGAAATCTTTTTAGAATAGT ATCAAGAGTAGTACTTATAGCATTTA TAGCATCA ATATCACTTGTAGGAGCAATGTCATAT |
| 76 | *Caldocellum saccharolyticum* | celB (Cleavage 36-37) | ATGAAAAGAAATCTTTTTAGAATAGT ATCAAGAGTAGTACTTATAGCATTTA TAGCATCA ATATCACTTGTAGGAGCAATGTCATA TTTTCCTGTAGAAACACAAGCAGCA |

According to another embodiment, the fusion protein can comprise a first and second polypeptide, wherein the first polypeptide comprises a heterologous biomass degrading enzyme and the second polypeptide comprises a polypeptide used to facilitate purification or identification or a reporter peptide. The reporter polypeptide or the polypeptide used to facilitate purification or identification can be, for example, a HIS-tag, a GST-tag, a FLAG-tag, an HA-tag, a MYC-tag or a fluorescent protein (e.g. GFP). In some embodiments, a tag (e.g. a polypeptide used to facilitate purification or identification or a reporter peptide) is fused to the N-terminus of the heterologous biomass degrading enzyme. In some embodiments, the tag is fused to the C-terminus of the heterologous biomass degrading enzyme. In some embodiments, the tag is not at either the N- or C-terminus of the heterologous biomass degrading enzyme, but is instead inserted into the heterologous biomass degrading enzyme sequence.

According to yet another embodiment, the fusion protein can comprise a first and second polypeptide, wherein the first polypeptide comprises a heterologous biomass degrading enzyme and the second polypeptide comprises an anchoring peptide. In some embodiments, the anchoring domain is of CWP2 (for carboxy terminal anchoring) or FLO1 (for amino terminal anchoring) from *S. cerevisiae*.

According to yet another embodiment, the fusion protein can comprise a first and second polypeptide, wherein the first polypeptide comprises a heterologous biomass degrading enzyme, such as a cellulase and the second polypeptide comprises a cellulose binding module (CBM). In some embodiments, the CBM is from for example, *T. reesei* Cbh1 or Cbh2 or from *C. lucknowense* Cbh2b. In some particular embodiments, the CBM is fused to a cellobiohydrolase.

In certain other embodiments, the first polypeptide and the second polypeptide are fused via a linker sequence. The linker sequence can, in some embodiments, be encoded by a codon-optimized polynucleotide. (Codon-optimized polynucleotides are described in more detail below.) An amino acid sequence corresponding to a codon-optimized linker 1 according to the invention is a flexible linker-strep tag-TEV site-FLAG-flexible linker fusion and corresponds to GGGGSGGGGS AWHPQFGG ENLYFQG DYKDDDK GGGGSGGGGS (SEQ ID NO: 149).

The DNA sequence is as follows:

(SEQ ID NO: 150)
GGAGGAGGTGGTTCAGGAGGTGGTGGGTCTGCTTGGCATCCACAATTTGG

AGGAGGCGGTGGTGAAAATCTGTATTTCCAGGGAGGCGGAGGTGATTACA

AGGATGACGACAAAGGAGGTGGTGGATCAGGAGGTGGTGGCTCC

An amino acid sequence corresponding to another optimized linker is a flexible linker-strep tag-linker-TEV site-flexible linker and corresponds to GGGGSGGGGS WSHPQFEK GG ENLYFQG GGGGSGGGGS (SEQ ID NO:151). The DNA sequence is as follows:

(SEQ ID NO: 152)
ggtggcggtggatctggaggaggcggttcttggtctcacccacaatttga aaagggtggagaaaacttgtactttcaaggcggtggtggaggttctggcg gaggtggctccggctca.

Polynucleotides Encoding Heterologous Biomass Degrading Enzymes

The present invention also includes isolated polynucleotides encoding biomass degrading enzymes of the present invention. Thus, the polynucleotides of the invention can encode for example, mannanases or cellulases, such as endoglucanases, β-glucosidases or cellobiohydrolases.

In some particular embodiments of the invention, the polynucleotide encodes an endoglucanase which is a endo-1,4-β-glucanase or isoform, paralogue, or orthologue thereof. In certain embodiments, the polynucleotide encodes a β-glucosidase I or a β-glucosidase II or an isoform, paralogue, or orthologue thereof. In certain embodiments of the invention, the polynucleotide encodes a cellobiohydrolase I and/or an cellobiohydrolase II or an isoform, paralogue, or orthologue thereof.

In particular embodiments of the present invention, the polynucleotide encodes a biomass degrading enzyme described in Table 2. In some embodiments, the polynucleotide encodes a polypeptide comprising a sequence at least about 70, about 80, about 90, about 95, about 96, about 97, about 98, about 99, or 100% identical to the sequence of a biomass degrading enzyme described in Table 2.

In certain aspects the polynucleotide can encode an endoglucanase, cellobiohydrolase or β-glucosidase derived from, for example, a fungal, bacterial, protozoan or termite source.

The present invention also encompasses variants of the biomass degrading enzyme genes, as described above. Variants can contain alterations in the coding regions, non-coding regions, or both. Examples are polynucleotide variants containing alterations which produce silent substitutions, additions, or deletions, but do not alter the properties or activities of the encoded polypeptide. In certain embodiments, nucleotide variants are produced by silent substitutions due to the degeneracy of the genetic code. In further embodiments, *Thermobifida fusca, Caldocellum saccharolyticum, Clostridium stercorarium, Eubacterium cellulosolvens, Cellulomonas fimi, Acidothermus cellulolyticus, Butyrivibrio fibrisolvens, Anaerocellum thermophilum, Trichoderma reesei, Coptotermes formosanus, Nasutitermes takasagoensis, Talaromyces emersonii, Neosartorya fischeri* or *Caldicellulosiruptor kristjanssonii* biomass degrading enzyme polynucleotide variants can be produced for a variety of reasons, e.g., to optimize codon expression for a particular host. Codon optimized polynucleotides of the present invention are discussed further below.

The present invention also encompasses an isolated polynucleotide encoding a fusion protein. In certain embodiments, the nucleic acid encoding a fusion protein comprises a first polynucleotide encoding a biomass degrading enzyme, e.g. a cellobiohydrolase, and a second polynucleotide encoding for a CBM. The CBM can be, for example, a CBM from *T. reesei* Cbh1 or Cbh2.

The present invention also encompasses an isolated polynucleotide encoding a fusion protein that comprises a first polynucleotide encoding a biomass degrading enzyme and a second polynucleotide encoding a signal sequence.

In further embodiments of the fusion polynucleotide, the first and second polynucleotides are in the same orientation, or the second polynucleotide is in the reverse orientation of the first polynucleotide. In additional embodiments, the first polynucleotide is either 5' or 3' to the second polynucleotide. In certain other embodiments, the first polynucleotide and/or the second polynucleotide are codon-optimized polynucleotides, for example, polynucleotides codon-optimized for expression in *T. sacch*. In particular embodiments of the nucleic acid encoding a fusion protein, the first polynucleotide is a codon-optimized signal peptide and the second polynucleotide encodes for a codon-optimized biomass degrading enzyme, for example a cellulase.

Also provided in the present invention are allelic variants, orthologs, and/or species homologs. Procedures known in the art can be used to obtain full-length genes, allelic variants, splice variants, full-length coding portions, orthologs, and/or species homologs of genes corresponding to any of SEQ ID NOs: 77-107, using information from the sequences disclosed herein or the clones deposited with the ATCC. For example, allelic variants and/or species homologs can be isolated and identified by making suitable probes or primers from the sequences provided herein and screening a suitable nucleic acid source for allelic variants and/or the desired homologue.

By a nucleic acid having a nucleotide sequence at least, for example, 95% "identical" to a reference nucleotide sequence of the present invention, it is intended that the nucleotide sequence of the nucleic acid is identical to the reference sequence except that the nucleotide sequence can include up to five point mutations per each 100 nucleotides of the reference nucleotide sequence encoding the particular polypeptide. In other words, to obtain a nucleic acid having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. The query sequence can be an entire sequence shown of any of SEQ ID NOs:77-107, or any fragment or domain specified as described herein.

As a practical matter, whether any particular nucleic acid molecule or polypeptide is at least 80%, 85%, 90%, 95%, 96%, 97%, 98% or 99% identical to a nucleotide sequence or polypeptide of the present invention can be determined conventionally using known computer programs. A method for determining the best overall match between a query sequence (a sequence of the present invention) and a subject sequence, also referred to as a global sequence alignment, can be determined using the FASTDB computer program based on the algorithm of Brutlag et al. (*Comp. App. Biosci.* (1990) 6:237-245.) In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to be made for the purposes of the present invention.

Some embodiments of the invention encompass a nucleic acid molecule comprising at least 10, 20, 30, 35, 40, 50, 60, 70, 80, 90, 100, 200, 300, 400, 500, 600, 700, or 800 consecutive nucleotides or more of any of SEQ ID NOs: 77-107, or domains, fragments, variants, or derivatives thereof.

The polynucleotide of the present invention can be in the form of RNA or in the form of DNA, which DNA includes cDNA, genomic DNA, and synthetic DNA. The DNA can be double stranded or single-stranded, and if single stranded can be the coding strand or non-coding (anti-sense) strand. The coding sequence which encodes the mature polypeptide can be identical to the coding sequence encoding SEQ ID NO: 108-148, or can be a different coding sequence which coding sequence, as a result of the redundancy or degeneracy of the genetic code, encodes the same mature polypeptide as the DNA of any one of SEQ ID NOs: 77-107.

In certain embodiments, the present invention provides an isolated polynucleotide comprising a nucleic acid fragment which encodes at least 10, at least 20, at least 30, at least 40, at least 50, at least 60, at least 70, at least 80, at least 90, at least 95, or at least 100 or more contiguous amino acids of SEQ ID NOs: 108-148.

The polynucleotide encoding for the mature polypeptide of SEQ ID NOs: 108-148 or can include: only the coding sequence for the mature polypeptide; the coding sequence of any domain of the mature polypeptide; and the coding sequence for the mature polypeptide (or domain-encoding sequence) together with non coding sequence, such as introns or non-coding sequence 5' and/or 3' of the coding sequence for the mature polypeptide.

Thus, the term "polynucleotide encoding a polypeptide" encompasses a polynucleotide which includes only sequences encoding for the polypeptide as well as a polynucleotide which includes additional coding and/or non-coding sequences.

In further aspects of the invention, nucleic acid molecules having sequences at least about 90%, 95%, 96%, 97%, 98% or 99% identical to the nucleic acid sequences disclosed herein, encode a polypeptide having mannanase, cellobiohydrolase (Cbh), endoglucanase (Eg) or β-glucosidase (Bgl) functional activity. By "a polypeptide having mannanase, Cbh, Eg or Bgl functional activity" is intended polypeptides exhibiting activity similar, but not necessarily identical, to a functional activity of the mannanase, Cbh, Eg or Bgl polypeptides of the present invention, as measured, for example, in a particular biological assay. For example, a Cbh, Eg or Bgl functional activity can routinely be measured by determining the ability of Cbh, Eg or Bgl polypeptide to hydrolyze cellulose, or by measuring the level of Cbh, Eg or Bgl activity.

Of course, due to the degeneracy of the genetic code, one of ordinary skill in the art will immediately recognize that a large portion of the nucleic acid molecules having a sequence at least 90%, 95%, 96%, 97%, 98%, or 99% identical to the nucleic acid sequence of any of SEQ ID NOs: 77-107, or fragments thereof, will encode polypeptides having mannanase, Cbh, Eg or Bgl functional activity. In fact, since degenerate variants of any of these nucleotide sequences all encode the same polypeptide, in many instances, this will be clear to the skilled artisan even without performing the above described comparison assay. It will be further recognized in the art that, for such nucleic acid molecules that are not degenerate variants, a reasonable number will also encode a polypeptide having mannanase, Cbh, Eg or Bgl functional activity.

The polynucleotides of the present invention also comprise nucleic acids encoding a *Thermobifida fusca, Caldocellum saccharolyticum, Clostridium stercorarium, Eubacterium cellulosolvens, Cellulomonas fimi, Acidothermus cellulolyticus, Butyrivibrio fibrisolvens, Anaerocellum thermophilum, Trichoderma reesei, Coptotermes formosanus, Nasutitermes takasagoensis, Talaromyces emersonii, Neosartorya fischeri* or *Caldicellulosiruptor kristjanssonii* biomass degrading enzyme, or domain, fragment, variant, or derivative thereof, fused to a polynucleotide encoding a marker sequence which allows for detection of the polynucleotide of the present invention. In one embodiment of the invention, expression of the marker is independent from expression of the biomass degrading enzyme. The marker sequence can be, for example, the kanamycin (KanR) or ampicillin (ampR) resistance marker.

Codon Optimized Polynucleotides

According to one embodiment of the invention, the polynucleotides encoding heterologous biomass degrading enzymes can be codon optimized. As used herein the term "codon optimized coding region" means a nucleic acid coding region that has been adapted for expression in the cells of a given organism by replacing at least one, or more than one, or a significant number, of codons with one or more codons that are more frequently used in the genes of that organism.

In general, highly expressed genes in an organism are biased towards codons that are recognized by the most abundant tRNA species in that organism. One measure of this bias is the "codon adaptation index" or "CAI," which measures the extent to which the codons used to encode each amino acid in a particular gene are those which occur most frequently in a reference set of highly expressed genes from an organism.

The CAI of codon optimized sequences of the present invention corresponds to between about 0.8 and 1.0, between about 0.8 and 0.9, or about 1.0. A codon optimized sequence can be further modified for expression in a particular organism, depending on that organism's biological constraints. For example, large runs of "As" or "Ts" (e.g., runs greater than 4, 4, 5, 6, 7, 8, 9, or 10 consecutive bases) can be removed from the sequences if these are known to effect transcription negatively. Furthermore, specific restriction enzyme sites can be removed for molecular cloning purposes. Examples of such restriction enzyme sites include PacI, AscI, BamHI, BglII, EcoRI and XhoI. Additionally, the DNA sequence can be checked for direct repeats, inverted repeats and mirror repeats with lengths of ten bases or longer, which can be modified manually by replacing codons with "second best" codons, i.e., codons that occur at the second highest frequency within the particular organism for which the sequence is being optimized.

Deviations in the nucleotide sequence that comprise the codons encoding the amino acids of any polypeptide chain allow for variations in the sequence coding for the gene. Since each codon consists of three nucleotides, and the nucleotides comprising DNA are restricted to four specific bases, there are 64 possible combinations of nucleotides, 61 of which encode amino acids (the remaining three codons encode signals ending translation). The "genetic code" which shows which codons encode which amino acids is reproduced herein as Table 5. As a result, many amino acids are designated by more than one codon. For example, the amino acids alanine and proline are coded for by four triplets, serine and arginine by six, whereas tryptophan and methionine are coded by just one triplet. This degeneracy allows for DNA base composition to vary over a wide range without altering the amino acid sequence of the proteins encoded by the DNA.

TABLE 5

The Standard Genetic Code

|   | T | C | A | G |
|---|---|---|---|---|
| T | TTT Phe (F) | TCT Ser (S) | TAT Tyr (Y) | TGT Cys (C) |
|   | TTC Phe (F) | TCC Ser (S) | TAC Tyr (Y) | TGC |
|   | TTA Leu (L) | TCA Ser (S) | TAA Ter | TGA Ter |
|   | TTG Leu (L) | TCG Ser (S) | TAG Ter | TGG Trp (W) |
| C | CTT Leu (L) | CCT Pro (P) | CAT His (H) | CGT Arg (R) |
|   | CTC Leu (L) | CCC Pro (P) | CAC His (H) | CGC Arg (R) |
|   | CTA Leu (L) | CCA Pro (P) | CAA Gln (Q) | CGA Arg (R) |
|   | CTG Leu (L) | CCG Pro (P) | CAG Gln (Q) | CGG Arg (R) |
| A | ATT Ile (I) | ACT Thr (T) | AAT Asn (N) | AGT Ser (S) |
|   | ATC Ile (I) | ACC Thr (T) | AAC Asn (N) | AGC Ser (S) |
|   | ATA Ile (I) | ACA Thr (T) | AAA Lys (K) | AGA Arg (R) |
|   | ATG Met (M) | ACG Thr (T) | AAG Lys (K) | AGG Arg (R) |

TABLE 5-continued

The Standard Genetic Code

|   | T | C | A | G |
|---|---|---|---|---|
| G | GTT Val (V) | GCT Ala (A) | GAT Asp (D) | GGT Gly (G) |
|   | GTC Val (V) | GCC Ala (A) | GAC Asp (D) | GGC Gly (G) |
|   | GTA Val (V) | GCA Ala (A) | GAA Glu (E) | GGA Gly (G) |
|   | GTG Val (V) | GCG Ala (A) | GAG Glu (E) | GGG Gly (G) |

Many organisms display a bias for use of particular codons to code for insertion of a particular amino acid in a growing peptide chain. Codon preference or codon bias, differences in codon usage between organisms, is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

Given the large number of gene sequences available for a wide variety of animal, plant and microbial species, it is possible to calculate the relative frequencies of codon usage. Codon usage tables are readily available, for example, at http://phenotype.biosci.umbc.edu/codon/sgd/index.php (visited May 7, 2008) or at http://www.kazusa.or.jp/codon/ (visited Mar. 20, 2008), and these tables can be adapted in a number of ways. See Nakamura, Y., et al. "Codon usage tabulated from the international DNA sequence databases: status for the year 2000" *Nucl. Acids Res.* 28:292 (2000). Codon usage tables for *T. sacch* are reproduced below as Table 6. This table uses mRNA nomenclature, and so instead of thymine (T) which is found in DNA, the tables use uracil (U) which is found in RNA. The Table has been adapted so that frequencies are calculated for each amino acid, rather than for all 64 codons.

TABLE 6

Codon Usage Table for *T. sacch* Genes

| Codon amino acid | number | percent of total for that amino acid |
|---|---|---|
| gca Ala(A) | 22296 | 42.7% |
| gcc Ala(A) | 6263 | 12.0% |
| gcg Ala(A) | 6264 | 12.0% |
| gcu Ala(A) | 17444 | 33.4% |
| --- Ala(A) | 52267 |  |
| aga Arg(R) | 16756 | 54.4% |
| agg Arg(R) | 8884 | 28.8% |
| cga Arg(R) | 1434 | 4.7% |
| cgc Arg(R) | 1359 | 4.4% |
| cgg Arg(R) | 766 | 2.5% |
| cgu Arg(R) | 1606 | 5.2% |
| --- Arg(R) | 30805 |  |

TABLE 6-continued

Codon Usage Table for *T. sacch* Genes

| Codon amino acid | number | percent of total for that amino acid |
|---|---|---|
| aac Asn(N) | 12538 | 25.4% |
| aau Asn(N) | 36747 | 74.6% |
| --- Asn(N) | 49285 | |
| gac Asp(D) | 14268 | 26.8% |
| gau Asp(D) | 38893 | 73.2% |
| --- Asp(D) | 53161 | |
| ugc Cys(C) | 3793 | 49.0% |
| ugu Cys(C) | 3951 | 51.0% |
| --- Cys(C) | 7744 | |
| caa Gln(Q) | 12380 | 60.8% |
| cag Gln(Q) | 7995 | 39.2% |
| --- Gln(Q) | 20375 | |
| gaa Glu(E) | 40410 | 71.6% |
| gag Glu(E) | 16008 | 28.4% |
| --- Glu(E) | 56418 | |
| gga Gly(G) | 19768 | 34.9% |
| ggc Gly(G) | 14373 | 25.3% |
| ggg Gly(G) | 6265 | 11.0% |
| ggu Gly(G) | 16293 | 28.7% |
| --- Gly(G) | 56699 | |
| cac His(H) | 3690 | 30.8% |
| cau His(H) | 8280 | 69.2% |
| --- His(H) | 11970 | |
| aua Ile(I) | 44748 | 53.8% |
| auc Ile(I) | 10130 | 12.2% |
| auu Ile(I) | 28235 | 34.0% |
| --- Ile(I) | 83113 | |
| cua Leu(L) | 5252 | 6.7% |
| cuc Leu(L) | 2663 | 3.4% |
| cug Leu(L) | 5688 | 7.3% |
| cuu Leu(L) | 20734 | 26.6% |
| uua Leu(L) | 25840 | 33.2% |
| uug Leu(L) | 17680 | 22.7% |
| --- Leu(L) | 77857 | |
| aaa Lys(K) | 51040 | 69.6% |
| aag Lys(K) | 22335 | 30.4% |
| --- Lys(K) | 73375 | |
| aug Met(M) | 22651 | 100.0% |
| --- Met(M) | 22651 | |
| uuc Phe(F) | 6336 | 17.2% |
| uuu Phe(F) | 30486 | 82.8% |
| --- Phe(F) | 36822 | |
| cca Pro(P) | 10445 | 37.8% |
| ccc Pro(P) | 1400 | 5.1% |
| ccg Pro(P) | 4309 | 15.6% |
| ccu Pro(P) | 11477 | 41.5% |
| --- Pro(P) | 27631 | |
| agc Ser(S) | 10467 | 19.8% |
| agu Ser(S) | 8520 | 16.1% |
| uca Ser(S) | 14241 | 26.9% |
| ucc Ser(S) | 3064 | 5.8% |
| ucg Ser(S) | 4567 | 8.6% |
| ucu Ser(S) | 12124 | 22.9% |
| --- Ser(S) | 52983 | |
| uaa Ter(.) | 1633 | 56.0% |
| uag Ter(.) | 515 | 17.7% |
| uga Ter(.) | 767 | 26.3% |
| --- Ter(.) | 2915 | |
| aca Thr(T) | 19780 | 47.7% |
| acc Thr(T) | 3191 | 7.7% |
| acg Thr(T) | 7026 | 16.9% |
| acu Thr(T) | 11458 | 27.6% |
| --- Thr(T) | 41455 | |
| ugg Trp(W) | 6653 | 100.0% |
| --- Trp(W) | 6653 | |
| uac Tyr(Y) | 13547 | 36.8% |
| uau Tyr(Y) | 23304 | 63.2% |
| --- Tyr(Y) | 36851 | |
| gua Val(V) | 21945 | 36.6% |
| guc Val(V) | 8166 | 13.6% |
| gug Val(V) | 10754 | 17.9% |
| guu Val(V) | 19077 | 31.8% |
| --- Val(V) | 59942 | |
| TOTAL | 860972 | |

By utilizing this or similar tables, one of ordinary skill in the art can apply the frequencies to any given polypeptide sequence, and produce a nucleic acid fragment of a codon-optimized coding region which encodes the polypeptide, but which uses codons optimal for a given species. Codon-optimized coding regions can be designed by various different methods.

In one method, a codon usage table is used to find the single most frequent codon used for any given amino acid, and that codon is used each time that particular amino acid appears in the polypeptide sequence. For example, referring to Table 6 above, for leucine, the most frequent codon is UUA, which is used 33.2% of the time. Thus all the leucine residues in a given amino acid sequence would be assigned the codon UUA.

In another method, the actual frequencies of the codons are distributed randomly throughout the coding sequence. Thus, using this method for optimization, if a hypothetical polypeptide sequence had 100 leucine residues, referring to Table 6 for frequency of usage in the *T. sacch*, about 7, or 7% of the leucine codons would be CUA, about 3, or 3% of the leucine codons would be CUC, about 7, or 7% of the leucine codons would be CUG, about 27, or 27% of the leucine codons would be CUU, about 33, or 33% of the leucine codons would be UUA, and about 23, or 23% of the leucine codons would be UUG.

These frequencies would be distributed randomly throughout the leucine codons in the coding region encoding the hypothetical polypeptide. As will be understood by those of ordinary skill in the art, the distribution of codons in the sequence can vary significantly using this method; however, the sequence always encodes the same polypeptide.

When using the methods above, the term "about" is used precisely to account for fractional percentages of codon frequencies for a given amino acid. As used herein, "about" is defined as one amino acid more or one amino acid less than the value given. The whole number value of amino acids is rounded up if the fractional frequency of usage is 0.50 or greater, and is rounded down if the fractional frequency of use is 0.49 or less. Using again the example of the frequency of usage of leucine in human genes for a hypothetical polypeptide having 62 leucine residues, the fractional frequency of codon usage would be calculated by multiplying 62 by the frequencies for the various codons. Thus, 6.7 percent of 62 equals 4.15 CUA codons, or "about 4," i.e., 3, 4, or 5 CUA codons, 3.4 percent of 62 equals 2.10. CUC codons or "about 2," i.e., 1, 2, or 3 CUC codons, 7.3 percent of 62 equals 4.52 CUG codons, or "about 5," i.e., 4, 5, or 6 CUG codons, 26.6 percent of 62 equals 16.49 CUU codons or "about 16," i.e., 15, 16, or 17 CUU codons, 33.2 percent of 62 equals 20.59 UUA codons or "about 21," i.e., 20, 21, or 22 CUA codons, and 22.7 percent of 62 equals 14.07 UUG codons, or "about 14," i.e., 13, 14, or 15 UUG codons.

Randomly assigning codons at an optimized frequency to encode a given polypeptide sequence, can be done manually by calculating codon frequencies for each amino acid, and then assigning the codons to the polypeptide sequence randomly. Additionally, various algorithms and computer software programs are readily available to those of ordinary skill in the art. For example, the "EditSeq" function in the Lasergene Package, available from DNAstar, Inc., Madison, Wis., the backtranslation function in the Vector NTI Suite, available from InforMax, Inc., Bethesda, Md., and the "backtranslate" function in the GCG—Wisconsin Package, available from Accelrys, Inc., San Diego, Calif. In addition, various resources are publicly available to codon-optimize coding region sequences, e.g., the "backtranslation" function at http://www.entelechon.com/bioinformatics/backtranslation.php?lang=eng (visited Apr. 15, 2008). Constructing a rudimentary algorithm to assign codons based on a given frequency can also easily be accomplished with basic mathematical functions by one of ordinary skill in the art.

A number of options are available for synthesizing codon optimized coding regions designed by any of the methods described above, using standard and routine molecular biological manipulations well known to those of ordinary skill in the art. In one approach, a series of complementary oligonucleotide pairs of 80-90 nucleotides each in length and spanning the length of the desired sequence are synthesized by standard methods. These oligonucleotide pairs are synthesized such that upon annealing, they form double stranded fragments of 80-90 base pairs, containing cohesive ends, e.g., each oligonucleotide in the pair is synthesized to extend 3, 4, 5, 6, 7, 8, 9, 10, or more bases beyond the region that is complementary to the other oligonucleotide in the pair. The single-stranded ends of each pair of oligonucleotides is designed to anneal with the single-stranded end of another pair of oligonucleotides. The oligonucleotide pairs are allowed to anneal, and approximately five to six of these double-stranded fragments are then allowed to anneal together via the cohesive single stranded ends, and then they ligated together and cloned into a standard bacterial cloning vector, for example, a TOPO® vector available from Invitrogen Corporation, Carlsbad, Calif. The construct is then sequenced by standard methods. Several of these constructs consisting of 5 to 6 fragments of 80 to 90 base pair fragments ligated together, i.e., fragments of about 500 base pairs, are prepared, such that the entire desired sequence is represented in a series of plasmid constructs. The inserts of these plasmids are then cut with appropriate restriction enzymes and ligated together to form the final construct. The final construct is then cloned into a standard bacterial cloning vector, and sequenced. Additional methods would be immediately apparent to the skilled artisan. In addition, gene synthesis is readily available commercially.

In certain embodiments, an entire polypeptide sequence, or fragment, variant, or derivative thereof is codon-optimized by any of the methods described herein. Various desired fragments, variants or derivatives are designed, and each is then codon-optimized individually. In addition, partially codon-optimized coding regions of the present invention can be designed and constructed. For example, the invention includes a nucleic acid fragment of a codon-optimized coding region encoding a polypeptide in which at least about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 100% of the codon positions have been codon-optimized for a given species. That is, they contain a codon that is preferentially used in the genes of a desired species, e.g., *T. sacch*, in place of a codon that is normally used in the native nucleic acid sequence.

In certain embodiments a codon-optimized sequence is fused to non-codon-optimized sequence. For example, in the case of a fusion protein, for example, a signal peptide fused to a cellulase, the sequence encoding the signal peptide and the sequence encoding the cellulase can both be codon-optimized. Alternatively, only the sequence encoding the signal peptide can be codon-optimized or only the sequence encoding the cellulase can be codon-optimized.

In additional embodiments, a full-length polypeptide sequence is codon-optimized for a given species resulting in a codon-optimized coding region encoding the entire polypeptide, and then nucleic acid fragments of the codon-optimized coding region, which encode fragments, variants, and derivatives of the polypeptide are made from the original codon-optimized coding region. As would be well understood by those of ordinary skill in the art, if codons have been randomly assigned to the full-length coding region based on their frequency of use in a given species, nucleic acid fragments encoding fragments, variants, and derivatives would not necessarily be fully codon optimized for the given species. However, such sequences are still much closer to the codon usage of the desired species than the native codon usage. The advantage of this approach is that synthesizing codon-optimized nucleic acid fragments encoding each fragment, variant, and derivative of a given polypeptide, although routine, would be time consuming and would result in significant expense.

The codon-optimized coding regions can be, for example, versions encoding a biomass degrading enzyme from *Thermobifida fusca, Caldocellum saccharolyticum, Clostridium stercorarium, Eubacterium cellulosolvens, Cellulomonas fimi, Acidothermus cellulolyticus, Butyrivibrio fibrisolvens, Anaerocellum thermophilum, Trichoderma reesei, Coptotermes formosanus, Nasutitermes takasagoensis, Talaromyces emersonii, Neosartorya fischeri* or *Caldicellulosiruptor kristjanssonii* or domains, fragments, variants, or derivatives thereof.

Codon optimization is carried out for a particular species by methods described herein, for example, in certain embodiments codon-optimized coding regions encoding polypeptides of *Thermobifida fusca, Caldocellum saccharolyticum, Clostridium stercorarium, Eubacterium cellulosolvens, Cellulomonas fimi, Acidothermus cellulolyticus, Butyrivibrio fibrisolvens, Anaerocellum thermophilum, Trichoderma reesei, Coptotermes formosanus, Nasutitermes takasagoensis, Talaromyces emersonii, Neosartorya fischeri* or *Caldicellulosiruptor kristjanssonii*, or domains, fragments, variants, or derivatives thereof are optimized according to *T. sacch* usage. Also provided are polynucleotides, vectors, and other expression constructs comprising codon optimized coding regions encoding polypeptides of *Thermobifida fusca, Caldocellum saccharolyticum, Clostridium stercorarium, Eubacterium cellulosolvens, Cellulomonas fimi, Acidothermus cellulolyticus, Butyrivibrio fibrisolvens, Anaerocellum thermophilum, Trichoderma reesei, Coptotermes formosanus, Nasutitermes takasagoensis, Talaromyces emersonii, Neosartorya fischeri* or *Caldicellulosiruptor kristjanssonii* biomass degrading enzymes or domains, fragments, variants, or derivatives thereof, and various methods of using such polynucleotides, vectors and other expression constructs.

In certain embodiments described herein, a codon-optimized coding region encoding any of SEQ ID NOs: 108-148 or domain, fragment, variant, or derivative thereof, is optimized according to codon usage in a gram positive anaerobic bacteria. In some embodiments, the sequences are codon-optimized specifically for expression in *T. sacch*. In some embodiments, a sequence is simultaneously codon-optimized for optimal expression in both *T. sacch* and another organism such as another gram positive anaerobic bacteria. Alternatively, a codon-optimized coding region encoding any of SEQ ID NOs: 108-148 can be optimized according to codon usage in any plant, animal, or microbial species.

Vectors and Methods of Using Vectors in Host Cells

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which can be, for example, a cloning vector or an expression vector. The vector can be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides and vectors can be employed for producing polypeptides by recombinant techniques. Thus, for example, the polynucleotide can be included in any one of a variety of expression vectors for expressing a polypeptide. Such vectors include chromosomal, nonchromosomal and synthetic DNA sequences, e.g., derivatives of SV40; bacterial plasmids; and yeast plasmids. Such vectors also include "suicide vectors" which cannot are not self-replicating but can be replicated after insertion into the host chromosome. Other vectors can also be used.

The appropriate DNA sequence can be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively associated with an appropriate expression control sequence(s) (promoter) to direct mRNA synthesis. Any suitable promoter to drive gene expression in the host cells of the invention can be used. The promoter can be, for example, a high expression promoter. Additionally the *E. coli*, lac or trp, and other promoters known to control expression of genes in prokaryotic or lower eukaryotic cells can be used. In some embodiments, the promoter is a native *T. sacch* promoter. In other embodiments, a *Clostridium thermocellum* promoter can be used. In other embodiments, a cellobiose phosphotransferase (CBP) promoter is used. In one specific embodiment, a *Clostridium thermocellum* CBP promoter is used. For example, the *Clostridium thermocellum* CBP promoter can have the following sequence (SEQ ID NO:153):

```
gagtcgtgactaagaacgtcaaagtaattaacaatacagctatttttctc atgcttttaccccctttcataaaatttaattttatcgttatcataaaaaat tatagacgttatattgcttgccgggatatagtgctgggcattcgttggtg caaaatgttcggagtaaggtggatattgatttgcatgttgatctattgca ttgaaatgattagttatccgtaaatattaattaatcatatcataaattaa ttatatcataattgttttgacgaatgaaggttttggataaattatcaag taaaggaacgctaaaaattttggcgtaaaatatcaaaatgaccacttgaa ttaatatggtaaagtagatataatattttggtaaacatgccttcagcaag gttagattagctgtttccgtataaattaaccgtatggtaaaacggcagtc agaaaaataagtcataagattccgttatgaaaatatacttcggtagttaa taataagagatatgaggtaagagatacaagataagagatataaggtacga atgtataagatggtgcttttaggcacactaaataaaaaacaaataaacga aaatttaaggaggacgaaag
```

In addition, the expression vectors can contain one or more selectable marker genes to provide a phenotypic trait for selection of transformed host cells such as chloramphenicol, thiamphenicol, streptomycin, tetracycline, ampicillin or kanamycin resistance genes. The expression vectors can also contain other selectable markers such as URA3, HIS3, LEU2, TRP1, LYS2, ADE2, dihydrofolate reductase, neomycin (G418) resistance or zeocin resistance.

The expression vector can also contain a ribosome binding site for translation initiation. The expression vector can also contain a transcription terminator. The transcription terminator can be, for example, E. coli T1 and T2 terminator. Thus, the sequence of the terminator can be: aacgaaaggctcagtcgaaagactgggc-ctttcgtttatctgagtttgtcggt-gaacgctacctgagtaggacaaatccgccgggagcgg atttgaacgttgcgaag-caacggcccggagggtggcgggcaggacgcccgccataaactgccaggcat-caaattaagcagaaggccatc ctgacggatggcctttt (SEQ ID NO: 163). The vector can also include appropriate sequences for amplifying expression, or can include additional regulatory regions. The vector can also include an origin of replication, for example a yeast origin of replication, such as a cen6/Arsh origin of replication, and/or a pUC origin of replication. The vector can also include an origin of replication for replication in T. sacch., for example, the B6A T. sacch origin of replication.

The expression vector can be a vector that is thermostable and can autonomously replicate in thermophilic hosts. The vector can comprise a sequence or sequences derived from the pB6A plasmid. Examples of vectors that can be used are described in more detail in International Patent Application PCT/US2008/010545, filed on Sep. 10, 2008, which is herein incorporated by reference in its entirety.

Expression in a host cell can also be accomplished by integrating the heterologous nucleotide sequence into the host chromosome. For example, a gene encoding a biomass degrading enzyme could be inserted into a host chromosome by building a construct comprising DNA sequences upstream and downstream from the desired point of insertion. For strain M0355, a useful insertion point is the site of the ldh deletion. The following ldh upstream DNA sequence can be used:

```
                                             (SEQ ID NO: 154)
Ctcatcgaggtatccaagcgattcaatagtaacagtccttgtatgccctc tttctttatcacgatatccatctgcaatagataggtatattcttccggaa ctgcgtctacttttctttaaatacacattaaactccccaataaaattca atataactatattataccacaatccataataatccgcaaccaaaatga caaaaatttaaaaaaattttacccaaaatcgttagtaaaattgctggttc cgggttacgctacataaaattttgctgcaaaactagggtaaaaaaaatac aaaccatgcgtcaatagaaattgacggcagtatattaaagcagtataatg aatatatggaaaaacaaagggcaatataatattaaaagggaaatataaa cctgaatataaggaaaagttgcttaatttagccaaattttttactgataa tggctttgttcctactgaacatgcattgaatgaaatacttgggaaaacag cttctggaagattgccagatgacaaacagatgttattggatgtattacaa aatggtgaaaattatattgaacctaatggcaatatagtcaggtataaaaa tggcatatcaatacatatcgataaagaacatggctggataattactataa ctccaaggaaacgaatagtaaaggaatggaggcgaattaatgagtaatgt cgcaatgcaattaatagaaatttgtcggaaatatgtaaataataatttaa acataaatgaatttatcgaagactttcaagtgctttatgaacaaaagcaa gatttattgacagatgaagaaatgagcttgtttgatgatatttatatggc
``` ttgtgaatactatgaacaggatgaaaatataagaaatgaatatcacttgt atattggagaaaatgaattaagacaaaaagtgcaaaaacttgtaaaaaag ttagcagcataataaaccgctaaggcatgatagctaaag The following ldh downstream DNA sequence can be used:

```
                                            (SEQ ID NO: 155)
Ccgcaagagattatatcgagtgcctttaagaaggctaaaaattacgaaga tgtgatacacaaaaggcaaaagattacggcaaaaacataccggatagtc aagttaaaggagtattgaaacagatagagattactgccttaaaccatgta gacaagattgtcgctgctgaaaagacgatgcagatagattccctcgtgaa gaaaaatatgtcttatgatatgatggatgcattgcaggatatagagaagg atttgataaatcagcagatgttctacaacgaaaatctaataaacataacc aatccgtatgtgaggcagatattcactcagatgagggatgatgagatgcg atttatcactatcatacagcagaacatagaatcgttaaagtcaaagccga ctgagcccaacagcatagtatatacgacgccgagggaaaataaatgaaag tagctattataggagcaggctcggcaggcttaactgcagctataaggctt gaatctatgggataaagcctgatatatttgagagaaaatcgaaagtcgg cgatgcttttaaccatgtaggaggacttttaaatgtcataaataggccaa taaatgatcctttagagtatctaaaaaataactttgatgtagctattgca ccgcttaacaacatagacaagattgtgatgcatgggccaacagtcactcg cacaattaaaggcagaaggcttggatactttatgctgaaagggcaaggag aattgtcagtagaaagccaactatacaagaaattaaagacaaatgtcaat tttgatgtccacgcagactacaagaacctaaaggaaatttatgattatgt cattgtagcaactggaaatcatcagataccaaatgagttaggatgttggc agacgcttgttgatacgaggcttaaaattgctgaggtaatcggtaaattc gacccg
```

Using methods commonly known to those in the art, the following DNA fragments can be added to the construct in between the ldh upstream and downstream regions in this order: a strong promoter active in T. sacch, a ribosome binding site, a gene encoding a biomass degrading enzyme, an intrinsic terminator, a counter-selectable marker and an antibiotic resistance gene. The construct can then be cloned into a plasmid replicon that replicates in E. coli but not in T. sacch. After verification of the sequence, the plasmid DNA can be transformed into T. sacch. Cells in which the DNA has undergone recombination to integrate into the chromosome can be isolated using selection for the encoded antibiotic resistance gene. These cells are then subjected to counterselection to remove the antibiotic resistance gene.

Thus, vectors containing the appropriate DNA sequence as described herein, as well as an appropriate promoter or control sequence, can be employed to transform an appropriate host to permit the host to express the protein. Such vectors can include, for example, self-replicating vectors or vectors for use in chromosomal integration.

Thus, in certain aspects, the present invention relates to host cells containing the above-described constructs. The host cell can be a host cell as described elsewhere in the application. The host cell can be, for example, a bacterial cell, such as a gram-positive anaerobic bacteria e.g., T. sacch. The selection of an appropriate host is deemed to be within the scope of those skilled in the art from the teachings herein.

Methods of Using Host Cells

The present invention is also directed to use of host cells to produce ethanol or other fermentation products from cellulosic substrates. Such methods can be accomplished, for example, by contacting a cellulosic substrate with a host cell of the present invention.

Numerous cellulosic substrates can be used in accordance with the present invention. Substrates for cellulose activity assays can be divided into two categories, soluble and insoluble, based on their solubility in water. Soluble substrates include xylans, cellodextrins or derivatives, carboxymethyl cellulose (CMC), or hydroxyethyl cellulose (HEC). Insoluble substrates include crystalline cellulose, microcrystalline cellulose (Avicel), amorphous cellulose, such as phosphoric acid swollen cellulose (PASC), dyed or fluorescent cellulose, and pretreated lignocellulosic biomass. These substrates are generally highly ordered cellulosic material and thus only sparingly soluble.

It will be appreciated that suitable lignocellulosic material can be any feedstock that contains soluble and/or insoluble cellulose, where the insoluble cellulose can be in a crystalline or non-crystalline form. In various embodiments, the lignocellulosic biomass comprises, for example, wood, corn, corn stover, sawdust, bark, leaves, agricultural and forestry residues, grasses such as switchgrass, ruminant digestion products, municipal wastes, paper mill effluent, newspaper, cardboard or combinations thereof.

In some embodiments, the invention is directed to a method for hydrolyzing a cellulosic substrate, for example a cellulosic substrate as described above, by contacting the cellulosic substrate with a host cell of the invention. In some embodiments, the invention is directed to a method for fermenting cellulose. Such methods can be accomplished, for example, by culturing a host cell in a medium that contains insoluble cellulose to allow saccharification and fermentation of the cellulose.

In some embodiments, the host cells expressing heterologous biomass degrading enzymes show increased efficiency of ethanol production. For example, in some embodiments, the host cell expressing the heterologous biomass degrading enzyme produces at least about 1.5 times, about 2 times, about 3 times, about 5 times, about 10 times, about 20 times, about 50 times, about 100 times or about 1000 times as much ethanol as an untransformed host cell grown in the same conditions. In some embodiments, the host cell expressing the heterologous biomass degrading enzyme produces at least about 1.5 times, about 2 times, about 3 times, about 5 times, about 10 times, about 20 times, about 50 times, about 100 times or about 1000 times as much ethanol as wild-type $T.$ $sacch$ grown in the same conditions.

In some embodiments, the host cells expressing heterologous biomass degrading enzymes show increased efficiency of acetic acid, lactic acid or $CO_2$ production. For example, in some embodiments, the host cell expressing the heterologous biomass degrading enzyme produces at least about 1.5 times, about 2 times, about 3 times, about 5 times, about 10 times, about 20 times, about 50 times, about 100 times or about 1000 times as much acetic acid, lactic acid or $CO_2$ as an untransformed host cell grown in the same conditions. In some embodiments, the host cell expressing the heterologous biomass degrading enzyme produces at least about 1.5 times, about 2 times, about 3 times, about 5 times, about 10 times, about 20 times, about 50 times, about 100 times or about 1000 times as much acetic acid, lactic acid or $CO_2$ as wild-type $T.$ $sacch$ grown in the same conditions.

In some embodiments, the host cells comprising heterologous biomass degrading enzymes show increased ability to hydrolyze a cellulosic substrate. For example, in some embodiments, the host cell expressing the biomass degrading enzyme hydrolyzes a cellulosic substrate at a rate that is at least about 1.5 times, about 2 times, about 3 times, about 5 times, about 10 times, about 20 times, about 50 times, about 100 times or about 1000 times the rate of hydrolysis by an untransformed host cell grown in the same conditions. In some embodiments, the host cell expressing the biomass degrading enzyme hydrolyzes a cellulosic substrate at a rate that is at least about 1.5 times, about 2 times, about 3 times, about 5 times, about 10 times, about 20 times, about 50 times, about 100 times or about 1000 times the rate of hydrolysis by wildtype $T.$ $sacch$ grown in the same conditions.

In some embodiments, the host cells comprising heterologous biomass degrading enzymes show increased ability to ferment cellulose. For example, in some embodiments, the host cell expressing the biomass degrading enzyme ferment cellulose at a rate that is at least about 1.5 times, about 2 times, about 3 times, about 5 times, about 10 times, about 20 times, about 50 times, about 100 times or about 1000 times the rate of fermentation by an untransformed host cell grown in the same conditions. In some embodiments, the host cell expressing the biomass degrading enzyme ferment cellulose at a rate that is at least about 1.5 times, about 2 times, about 3 times, about 5 times, about 10 times, about 20 times, about 50 times, about 100 times or about 1000 times the rate of fermentation by wildtype $T.$ $sacch$ grown in the same conditions.

The production of ethanol, or other fermentation product can, according to the present invention, be performed at temperatures of at least about above about 40° C., about 55° C., about 50° C., about 55° C., about 60° C., about 65° C., about 70° C., about 75° C., or about 80° C. In some embodiments of the present invention, the host cell can produce the fermentation product, such as ethanol, from cellulose at temperatures from about 40° C. to 90° C., about 40° C. to 80° C., about 40° C. to 75° C., about 40° C. to 70° C., about 40° C. to 65° C., about 40° C. to 60° C., or about 40° C. to 55° C. In some embodiments of the present invention, the host cell can produce the fermentation product such as ethanol from cellulose at temperatures from about 45° C. to 90° C., about 45° C. to 45° C., about 45° C. to 75° C., about 45° C. to 70° C., about 45° C. to 65° C., about 45° C. to 60° C., or about 45° C. to 55° C. In some embodiments of the present invention, the host cell can produce the fermentation product such as ethanol from cellulose at temperatures from about 50° C. to 50° C., about 50° C. to 80° C., about 50° C. to 75° C., about 50° C. to 70° C., about 50° C. to 65° C., about 50° C. to 60° C., or about 50° C. to 55° C. In some embodiments of the present invention, the host cell can produce the fermentation product such as ethanol from cellulose at temperatures from about 55° C. to 90° C., about 55° C. to 80° C., about 55° C. to 75° C., about 55° C. to 70° C., about 55° C. to 65° C., or about 55° C. to 60° C.

Culture conditions can also be changed by varying the pH. For example, the pH can be from about 4.0 to 7.5, from about 4.5 to 7.0, from about 5.0 to 6.5 or from about 5.5 to 6.5. The pH can also be from about 4.0 to 5.0, from about 5.0 to 6.0, from about 6.0 to 7.0, or from about 6.0 to 7.5. The pH can also be from about 4.0 to 4.5, from about 4.5 to 5.0, from about 5.0 to 5.5, from about 5.5 to 6.0, from about 6.0 to about 6.5, or from about 6.5 to 7.0.

In some embodiments, the host cells comprising heterologous biomass degrading enzymes, such as cellulases, are grown in anaerobic conditions. In some embodiments, the host cells comprising heterologous biomass degrading enzymes, such as cellulases, grown in anaerobic conditions can produce ethanol, or another product of fermentation, from cellulose in the absence of externally added enzymes. In some embodiments, the host cells comprising heterologous cellulases grown in anaerobic conditions can decrease the amount of externally added enzymes required to produce a given amount of ethanol, or another fermentation product, from a given amount of cellulose in a given time period.

In some embodiments, methods of producing ethanol, acetic acid, lactic acid, $CO_2$, or another useful fermentation product can comprise contacting a cellulosic substrate with a host cell of the invention and additionally contacting the cellulosic substrate with externally produced biomass degrading enzymes. Exemplary externally produced biomass degrading enzymes, such as cellulases, are commercially available and are known to those of skill in the art.

Therefore, the invention is also directed to methods of reducing the amount of externally produced biomass degrading enzymes required to produce a given amount of ethanol from cellulose comprising contacting the cellulose with externally produced biomass degrading enzymes and with a host cell. In some embodiments, the same amount of ethanol production can be achieved using at least about 5%, 10%, 15%, 20%, 25%, 30%, or 50% less externally produced biomass degrading enzymes.

In some embodiments, the methods comprise producing ethanol, or another fermentation product at a particular rate. For example, in some embodiments, ethanol, or another fermentation product, is produced at a rate of at least about 0.1 mg per hour per liter, at least about 0.25 mg per hour per liter, at least about 0.5 mg per hour per liter, at least about 0.75 mg per hour per liter, at least about 1.0 mg per hour per liter, at least about 2.0 mg per hour per liter, at least about 5.0 mg per hour per liter, at least about 10 mg per hour per liter, at least about 15 mg per hour per liter, at least about 20.0 mg per hour per liter, at least about 25 mg per hour per liter, at least about 30 mg per hour per liter, at least about 50 mg per hour per liter, at least about 100 mg per hour per liter, at least about 200 mg per hour per liter, or at least about 500 mg per hour per liter.

In some embodiments, the host cells of the present invention can produce ethanol, or another fermentation product, at a rate of at least about 0.1 mg per hour per liter, at least about 0.25 mg per hour per liter, at least about 0.5 mg per hour per liter, at least about 0.75 mg per hour per liter, at least about 1.0 mg per hour per liter, at least about 2.0 mg per hour per liter, at least about 5.0 mg per hour per liter, at least about 10 mg per hour per liter, at least about 15 mg per hour per liter, at least about 20.0 mg per hour per liter, at least about 25 mg per hour per liter, at least about 30 mg per hour per liter, at least about 50 mg per hour per liter, at least about 100 mg per hour per liter, at least about 200 mg per hour per liter, or at least about 500 mg per hour per liter more than a control strain (lacking heterologous biomass degrading enzymes) and grown under the same conditions. In some embodiments, the ethanol or other fermentation product can be produced in the absence of any externally added biomass degrading enzymes.

Ethanol production can be measured using any method known in the art. For example, the quantity of ethanol in fermentation samples can be assessed using HPLC analysis. Many ethanol assay kits are commercially available that use, for example, alcohol oxidase enzyme based assays. Methods of determining ethanol production are within the scope of those skilled in the art from the teachings herein.

In some embodiments, the host cells expressing biomass degrading enzymes can be used to produce and purify the biomass degrading enzymes. Methods of purifying the expressed proteins have been described elsewhere in the application and are known to those of skill in the art. For example, antibody purification, protein A, trichloroacetic acid, ammonium sulfate or ethanol precipitation, acid extraction, anion or cation exchange chromatography, phosphocellulose chromatography, hydrophobic interaction chromatography, affinity chromatography, hydroxylapatite chromatography, gel filtration, and lectin chromatography methods can be used to purify the heterologous biomass degrading enzymes. The proteins can be purified and stored in any convenient form including frozen or lyophilized forms and liquid, solid or powder forms.

In some embodiments, transformed *T. sacch* host cells can be used to produce an enzyme useful in separate applications. This can be accomplished by transforming a *T. sacch* host cell with a sequence encoding a heterologous enzyme, culturing the transformed host cell under conditions suitable for protein expression and purifying the enzyme.

The following embodiments of the invention will now be described in more detail by way of these non-limiting examples.

EXAMPLES

Example 1

Creation of M0355 Strain

A strain of *T. sacch* that was engineered to remove genes necessary for acetate and lactate production has previously been described. Shaw A J et al. *Proc Natl Acad Sci.* 105: 13769-74 (2008). However, selection for plasmids based on kanamycin resistance cannot be performed using this strain because the kanamycin resistance gene is already present in it. Thus, the strain M0355 was engineered to remove genes necessary for acetate and lactate production, but does not contain any antibiotic resistance genes. Strain M0355 was made using the widely-implemented strategy of counterselection to remove unwanted DNA sequences from the bacterial genome of a *Thermoanaerobacterium saccharolyticum* strain. (See Reyrat et al. *Infection and Immunity* 66:4011-4017 (1998)).

The following DNA sequence was removed from the thermophilic anaerobic bacterium *Thermoanaerobacterium saccharolyticum* JW/SL-YS485 (DSM #8691). This is a non-hazardous, non-pathogenic bacterium that is unlikely to grow if released into the environment since will not grow in the presence of atmospheric levels of oxygen. This deleted sequence encodes the proteins acetate kinase and phosphotransacetylase.

(SEQ ID NO: 156)
TTATTCAAAACATCATTGAAAAAGCTAAAAGCGATAAAAAGAAAATTGTT

CTGCCAGAAGGTGCAGAACCCAGGACATTAAAAGCTGCTGAAATAGTTTT

AAAAGAAGGGATTGCAGATTTAGTGCTTCTTGGAAATGAAGATGAGATAA

GAAATGCTGCAAAAGACTTGGACATATCCAAAGCTGAAATCATTGACCCT

GTAAAGTCTGAAATGTTTGATAGGTATGCTAATGATTTCTATGAGTTAAG

GAAGAACAAAGGAATCACGTTGGAAAAAGCCAGAGAAACAATCAAGGATA

ATATCTATTTTGGATGTATGATGGTTAAAGAAGGTTATGCTGATGGATTG

GTATCTGGCGCTATTCATGCTACTGCAGATTTATTAAGACCTGCATTTCA

GATAATTAAAACGGCTCCAGGAGCAAAGATAGTATCAAGCTTTTTTATAA

-continued

TGGAAGTGCCTAATTGTGAATATGGTGAAAATGGTGTATTCTTGTTTGCT

GATTGTGCGGTCAACCCATCGCCTAATGCAGAAGAACTTGCTTCTATTGC

CGTACAATCTGCTAATACTGCAAAGAATTTGTTGGGCTTTGAACCAAAAG

TTGCCATGCTATCATTTTCTACAAAAGGTAGTGCATCACATGAATTAGTA

GATAAAGTAAGAAAAGCGACAGAGATAGCAAAAGAATTGATGCCAGATGT

TGCTATCGACGGTGAATTGCAATTGGATGCTGCTCTTGTTAAAGAAGTTG

CAGAGCTAAAAGCGCCGGGAAGCAAAGTTGCGGGATGTGCAAATGTGCTT

ATATTCCCTGATTTACAAGCTGGTAATATAGGATATAAGCTTGTACAGAG

GTTAGCTAAGGCAAATGCAATTGGACCTATAACACAAGGAATGGGTGCAC

CGGTTAATGATTTATCAAGAGGATGCAGCTATAGAGATATTGTTGACGTA

ATAGCAACAACAGCTGTGCAGGCTCAATAAAATGTAAAGTATGGAGGATG

AAAATTATGAAAATACTGGTTATTAATTGCGGAAGTTCTTCGCTAAAATA

TCAACTGATTGAATCAACTGATGGAAATGTGTTGGCAAAAGGCCTTGCTG

AAAGAATCGGCATAAATGATTCCATGTTGACACATAATGCTAACGGAGAA

AAAATCAAGATAAAAAAGACATGAAAGATCACAAAGACGCAATAAAATT

GGTTTTAGATGCTTTGGTAAACAGTGACTACGGCGTTATAAAAGATATGT

CTGAGATAGATGCTGTAGGACATAGAGTTGTTCACGGAGGAGAATCTTTT

ACATCATCAGTTCTCATAAATGATGAAGTGTTAAAAGCGATAACAGATTG

CATAGAATTAGCTCCACTGCACAATCCTGCTAATATAGAAGGAATTAAAG

CTTGCCAGCAAATCATGCCAAACGTTCCAATGGTGGCGGTATTTGATACA

GCCTTTCATCAGACAATGCCTGATTATGCATATCTTTATCCAATACCTTA

TGAATACTACACAAAGTACAGGATTAGAAGATATGGATTTCATGGCACAT

CGCATAAATATGTTTCAAATAGGGCTGCAGAGATTTTGAATAAACCTATT

GAAGATTTGAAAATCATAACTTGTCATCTTGGAAATGGCTCCAGCATTGC

TGCTGTCAAATATGGTAAATCAATTGACACAAGCATGGGATTTACACCAT

TAGAAGGTTTGGCTATGGGTACACGATCTGGAAGCATAGACCCATCCATC

ATTTCGTATCTTATGGAAAAAGAAAATATAAGCGCTGAAGAAGTAGTAAA

TATATTAAATAAAAAATCTGGTGTTTACGGTATTTCAGGAATAAGCAGCG

ATTTTAGAGACTTAGAAGATGCCGCCTTTAAAAATGGAGATGAAAGAGCT

CAGTTGGCTTTAAATGTGTTTGCATATCGAGTAAAGAAGACGATTGGCGC

TTATGCAGCAGCTATGGGAGGCGTCGATGTCATTGTATTTACAGCAGGTG

TTGGTGAAAATGGTCCTGAGATACGAGAATTTATACTTGATGGATTAGAG

TTTTTAGGGTTCAGCTTGGATAAAGAAAAAAATAAAGTCAGAGGAAAAGA

AACTATTATATCTACGCCGAATTCAAAA

The DNA sequence of the region from which the above sequence was removed is as follows (the underlined nucleotides are the site of the deletion):

(SEQ ID NO: 157)
CGTGCCCATTGTGAAGTGGATTGTATTCTACAATTAAACCTAATACGCTC

ATAATATGCGCCTTTCTAAAAAATTATTAATTGTACTTATTATTTTATAA

AAAATATGTTAAAATGTAAAATGTGTATACAATATATTTCTTCTTAGTAA

GAGGAATGTATAAAAATAAATATTTTAAAGGAAGGGACGATCTTATGAGC

AGTTAGCGTGATGGTTGTGCCTACTAATGAAGAATACATGATTGCTAAAG

ATACTGAAAAGATTGTAAAGAGTATAAAATAGCATTCTTGACAAATGTTT

ACCCCATTAGTATAATTAATTTTGGCAATTATATTGGGGTGAGAAAATGA

AAATTGATTTATCAAAAATTAAAGGACATAGGGGCCGCAGCATCGAAGTC

AACTACGTA

The following sequence was also removed. This sequence encodes the protein lactate dehydrogenase:

(SEQ ID NO: 158)
CGGTATTTTTATGCAATTAAAAGGATGAAATGATATCTGATAAACTGCGA

AAAAGTATTTTAGAAAATAACTATAAAGATAATATTTCAAATCAATAAGG

ACAAAATAAGATTAAAATTTAGACAATTTCATCAAAACTATGTTATAATA

TTATTAAAGGAAAATACATATTATTTAGGAGGCGATGTAATGAGCAAGGT

AGCAATAATAGGATCTGGTTTTGTAGGTGCAACATCGGCATTTACGCTGG

CATTAAGTGGGACTGTGACAGATATCGTGCTGGTGGATTTAAACAAGGAC

AAGGCTATAGGCGATGCACTGGACATAAGCCATGGCATACCGCTAATACA

GCCTGTAAATGTGTATGCAGGTGACTACAAAGATGTGAAAGGCGCAGATG

TAATAGTTGTGACAGCAGGTGCTGCTCAAAAGCCGGGAGAGACACGGCTT

GACCTTGTAAAGAAAAATACAGCCATATTTAAGTCCATGATACCTGAGCT

TTTAAAGTACAATGACAAGGCCATATATTTGATTGTGACAAATCCCGTAG

ATATACTGACGTACGTTACATACAAGATTTCTGGACTTCCATGGGCAGA

GTTTTTGGTTCTGGCACCGTTCTTGACAGCTCAAGGTTTAGATACCTTTT

AAGCAAGCACTGCAATATAGATCCGAGAAATGTCCACGGAAGGATAATCG

GCGAGCATGGTGACACAGAGTTTGCAGCATGGAGCATAACAAACATATCG

GGTATATCATTTAATGAGTACTGCAGCATATGCGGACGCGTCTGCAACAC

AAATTTCAGAAAGGAAGTAGAAGAAGAAGTCGTAAATGCTGCTTACAAGA

TAATAGACAAAAAAGGTGCTACATACTATGCTGTGGCAGTTGCAGTAAGA

AGGATTGTGGAGTGCATCTTAAGAGATGAAAATTCCATCCTCACAGTATC

ATCTCCATTAAATGGACAGTACGGCGTGAAAGATGTTTCATTAAGCTTGC

CATCTATCGTAGGCAGGAATGGCGTTGCCAGGATTTTGGACTTGCCTTTA

TCTGACGAAGAAGTGGAGAAGTTTAGGCATTCAGCAAGTGTCATGGCAGA

TGTCATAAAACAATTAGATATATAATCAAATTATGTTGGGAGGCTTCACA

TATGTGTGGTGAGGCCTCTTTTTATGTATATAAGGGATGCAATGTGGAAA

ATCTAATAACGGTGATGCAAAATGCAGAATATGAGC

The DNA sequence of the region from which the above sequence was removed is as follows (the underlined nucleotides are the site of the deletion):

(SEQ ID NO: 159)
GTAAATAATAATTTAAACATAAATGAATTTATCGAAGACTTTCAAGTGCT

TTATGAACAAAAGCAAGATTTATTGACAGATGAAGAAATGAGCTTGTTTG

ATGATATTTATATGGCTTGTGAATACTATGAACAGGATGAAAATATAAGA

-continued

```
AATGAATATCACTTGTATATTGGAGAAAATGAATTAAGACAAAAAGTGCA

AAAACTTGTAAAAAAGTTAGCAGCATAATAAACCGCTNAGGCATGATAGC

TAAAGCCCGCAAGAGATTATATCGAGTGCCTTTAAGAAGGCTAAAAATTA

CGAAGATGTGATACACAAAAAGGCAAAAGATTACGGCAAAAACATACCGG

ATAGTCAAGTTAAAGGAGTATTGAAACAG
```

The counterselection strategy that was used resulted in a strain that was completely free of transgenic or heterologous sequences or plasmid. No "scars" were introduced into the genome other than a single unexpected "C" cytosine base at the site of one of the deletions. No antibiotic markers or other foreign DNA is present in the M0355 strain. The major change made was to remove DNA from the original strain (JW/SL-YS485 (DSM #8691)).

Example 2

Expression of CelZ in *T. sacch*

The gene CelZ was PCR-amplified from genomic DNA from *C. stercorarium* and then cloned into a plasmid vector as shown in FIG. 1. After verification of plasmid construction, the plasmid DNA was transformed into *T. sacch* strain M0355 and selected by plating on agar plates containing kanamycin. *T. sacch* M0355 strains expressing CelZ (native *C. stercorarium* sequence) alone or CelZ fused to C-terminal tags 6×His (HHHHHH) (SEQ ID NO:160), Flag (DYKDDDDK) (SEQ ID NO:161), or Hemagglutinin (HA) (YPYDVPDYA) (SEQ ID NO:162) were grown overnight to an $OD_{600}$>2.0 in M122 media, pH 6.1 supplemented with 5 g/L cellobiose. Cells were separated from supernatants by centrifugation, and supernatant proteins were precipitated using a DOC/TCA method. Proteins were separated by SDS-PAGE gel electrophoresis on Novex® 4-20% Tris-Glycine Gels and transferred to polyvinylidene fluoride (PVDF) membranes. Proteins were detected using either anti-6×His (Qiagen 34660), anti-Flag (Abram 18230) or anti-HA (Abram 18181) primary antibodies and Alkaline phosphatases-conjugated secondary goat anti-mouse IgG (Santa Cruz sc-2008). As shown in FIG. 2, western blots revealed that CelZ fusion proteins were expressed by *T. sacch*.

Example 3

Expression of E5 and CBH1 in *T. sacch*

Vectors encoding *T. fusca* E5, *Talaromyces emersonii* CBH1, *Cellulomonas fimi* cex and *Nasutitermes takasagoensiswere* NtEG were also transformed in the M0355 strain. In these experiments, the transformed cells were grown in M122C, pH 6.1 with 5 ug/mL thiamphenicol at 47° C. Overnight cultures and cultures in stationary phase ($OD_{600}$=1.9-2.1) for 2 hours were assayed for protein expression. Cells were separated from supernatant by centrifugation, and 5 mL culture supernatant was precipitated overnight using DOC/TCA. Protein pellets were resuspended in SDS-PAGE gel loading buffer and analyzed by gel electrophoresis prior to Western blotting with anti His antibodies. Both E5 and CBH1 were detected from culture supernatants from both overnight and stationary cultures as shown in FIG. 3.

Example 4

Growth of Transformed *T. Sacch* on Avicel

Plasmids containing PCR-cloned cellulase genes celB (*Caldicellulosiruptor kristjanssonii*), celA (*Anaerocellum thermophilum*), and celZ (*Clostridium stercorarium*) were used to transform *T. sacch* M0355. Plasmids containing codon-optimized cellulase genes cel5A (*Acidothermus cellulolyticus* 11B), celD (*Anaerocellum thermophilum*), cbh1 (*T. reesei*), cbh2 (*T. reesei*), celZ (*Clostridium stercorarium*), manA (*Caldocellum saccharolyticum*), celD (*Thermobifida fusca*) and end1 (*Butyrivibrio fibrisolvens*) were used to transform *T. sacch* M0699, a derivative of M0355 adapted for fast growth in a chemostat. The resulting strains were grown on rich medium containing 2% Avicel. Plates were incubated for 96 hours at 55° C. followed by a washing with 1M Tris and staining with a 0.5% solution of Pontamine Orange 6RN and Direct Blue I dyes (Pylam Products). The stained plate revealed clearing zones for celZ and celA transformants as compared to the M0355 parent (negative control) and cel5A, celD (*A. thermophilum*), cbh1, cbh2, celZ, manA, celD (*T. fusca*) and end1 as compared to the M0699 parent (negative control). *C. thermocellum* was used as a positive control. *T. sacch* containing a plasmid encoding for *T. fusca* cel9A with its native promoter also showed a clearing zone in this type of assay.

Example 5

Biomass Degrading Enzyme Activity in the MuLac Assay

In order to perform MuLac assays, supernatants from transformed cultures are mixed with MuLac, a fluorescent substrate for beta-lactosidase or galactosidase and glucosidase activities, and Relative Fluorescent Light Units are detected over time. Cleavage of MuLac releases 4-methylumbelliferone that is detected by fluorescence (ex. 355 nm and em. 460 nm).

MO699 was transformed with vectors containing sequences encoding the following proteins as described in Table 2 above: *C. fimi* Cex (827), *A. celluloyticus* 11B Cel5A (828), *A. thermophilum* celD (829), *C. formosanus* CfEG4 (830), *T. reesei* CBH1 (831), *T. reesei* CBH2 (833), *T. fusca* Cel5A, CelE (834), *C. saccharolyticum* CelB (contig 00091 geneor1761) (835), *C. saccharolyticum* ManA (836), *T. reesei* EG1 (837), *T. fusca* CelC (838), *A. cellulolyticus* 11B Biomass degrading enzyme (839), *C. saccharolyticum* CelB (contig 00009 geneor0219) (841), *C. saccharolyticum* CelB (contig 00029; geneor 0692) (842), *N. fischeri* putative biomass degrading enzyme (843), *C. stercorarium* Avicellase I (846), *C. saccharolyticum* CelB (contig 00135 geneor2202) (847), *C. stercorarium* Avicellase II (849), *T. fusca* CelD (850), *A. celluloyticus* 11B secreted biomass degrading enzyme (852), *A. thermophilum* Cel A (853) and *T. fusca* Cel5A, CelE (855). The resulting transformed strains were cultured in TS5-rich media with 100 ug/mL kanamycin, 55° C. to an $OD_{600}$ greater than 2.0. Supernatants were separated from cells after spinning at 19K, 4° C. Supernatants were poured into a new, clean tube, and cells were discarded. 50 μl of 4 mM 4-Methylumbelliferyl β-D-lactoside (MuCell), MGT #M0554 was made in 50 mM Citrate Buffer pH 6.1 and pipetted into analytical 96-well plate. 50 ul culture supernatants was added. Plates were incubated at 55° C. for timecourse. Fluorescence was read in microtiter plate reader (ex. 355 nm and em. 460 nm). The results are shown in FIG. 4 and demonstrate that *T. sacch* expressing *C. stercorarium* CelZ, *C. fimi* Cex, *A. thermophilum* celD, *T. reesei* CBH1, *C. saccharolyticum* CelB (contig 00091 geneor1761), *C. saccharolyticum* ManA, *A. cellulolyticus* 11B Biomass degrading enzyme, *C. saccharolyticum* CelB (contig 00135 geneor2202), *C. stercorarium* Avicellase II, *T. fusca* CelD, and *A. celluloyticus* 11B secreted biomass degrading enzyme show activity in the MuLac assay that is greater than the MO699 strain from which they were derived. In addition, *T. sacch* containing plasmids encoding for *T. fusca* cel9A or *B. fibrisolvens* end1 with their native promoters showed activity in a MuLac assay.

Example 6

Ethanol Production by *T. Sacch* Expressing Heterologous Biomass Degrading Enzymes Plasmids containing PCR-cloned cellulase genes celB from *Caldicellulosiruptor kristjanssonii* ("*T. sacch* 555"), celA from *Anaerocellum thermophilum* ("*T. sacch* 559"), and celZ from *Clostridium stercorarium* ("*T. sacch* 567") were used to transform *T. sacch*. Cultures of the transformed strain, and the control parent strain, M0355, were grown in bottles at 25 ml volumes containing M122 media supplemented with 2% Avicel with 1 g/L yeast extract and 1 g/L xylose as a starting sugar. Cultures were grown at 47° C. with 2.5 μg/ml thiamphenicol at either pH 5.5, 6.1, or 6.7, with samples collected at 0 and 96 hours for HPLC analysis. As shown in FIG. 5, there was an increase in ethanol production (0.3-0.6 g/L) at all three pH levels for the cellulase transformants when compared to the parent *T. sacch* M0355 strain indicating some cellulolytic activity.

Example 7

Ethanol Production by *T. Sacch* Expressing Heterologous Biomass Degrading Enzymes Plasmids containing PCR-cloned or codon-optimized cellulase genes celD (*Anaerocellum thermophilum*, pMU829), cbh1 (*T. reesei*, pMU831), cbh2 (*T. reesei*, pMU833), celZ (*Clostridium stercorarium*, pMU876), Contig00135 geneor2202 (*Caldicellulosiruptor kristjanssonii* pMU847), celD (*Thermobifida fusca* pMU850), and end1 (*Butyrivibrio fibrisolvens* pMU854) were used to transform *T. sacch* M0699. Cultures of the transformed strain, and the control parent strain, M0699, were grown in bottles at 25 ml volumes containing TS5 media supplemented with 2% Avicel and exogenous enzymes. Cultures were grown at 55° C. at pH 6.1 with samples collected at 24 and 72 hours for HPLC analysis. As shown in FIG. 6, there was an increase in ethanol production (0.5 g/L) for the cellulase transformants pMU876 (celZ) when compared to the parent *T. sacch* M0699 strain indicating some cellulolytic activity.

Example 8

Expression of Identified Heterologous Cellulases in *T. sacch*

In order to identify cellulases that increase cellulose digestion and ethanol production in *T. sacch*, codon-optimized sequences encoding the biomass degrading enzymes of Table 2 (SEQ ID NO:108-148) are cloned into a *T. sacch* expression vector. The *T. sacch* expression vector comprises a *C. therm* promoter, a signal peptide, the codon-optimized cellulase-encoding sequence and the *E. coli* T1 and T2 terminator. The signal peptide is a signal peptide selected from the signal peptides of Tables 2 and 3. The vectors are transformed into MO355. The presence of the heterologous cellulase in the transformed host cells is confirmed by genetic assay (e.g. PCR assay) enzyme assay (e.g. assay for cellulase activity) or by analytical methodology. Transformed host cells are grown on cellulosic substrates (e.g. Avicel) and ethanol production is monitored. Transformed host cells that produce large quantities of ethanol are used in a consolidated bioprocessing system, optionally in combination with externally added enzymes to produce ethanol Example 9

Identification and Expression of Cellulases from *T. sacch*-Related Organisms

In order to identify cellulases from organisms related to *T. sacch* that increase cellulose digestion and ethanol production when expressed in *T. sacch*, DNA is prepared from an organism or group of organisms likely to contain biomass degrading enzymes. This can be done by obtaining organisms that contain similar 16S rRNA sequences, evaluated using BLAST search. These organisms may be obtained from repositories of microorganisms or by isolating them from natural environments. DNA can also be prepared directly from mixed cultures of microorganisms or from microorganisms residing in the natural environment. A library of different DNA fragments is then generated. This library can consist of *T. sacch* replication-ready plasmids into which fragments of the DNA have been inserted. The library can also consist of plasmids or linear DNA constructs designed to integrate into the *T. sacch* chromosome. A strong promoter active in *T. sacch* may be positioned up and downstream of cloning sites to drive gene expression in both directions. This may be useful if no promoter was included in the DNA fragment that was cloned, or if the promoter present in that DNA is not active in *T. sacch* under the conditions used. The DNA constructs are transformed into *T. sacch* and transformed host cells are either selected or assayed for protein expression and/or increased biomass degradation. Organisms that are mildly cellulolytic are passaged serially and selected for increased cellulase activity. Transformed host cells that produce large quantities of ethanol are used in a consolidated bioprocessing system, optionally in combination with externally added enzymes to produce ethanol.

In another variation, the DNA is not cloned but instead directly transformed into *T. sacch*. By mechanisms either native to or introduced into *T. sacch*, some portion of the DNA is then integrated into the chromosome. Cells that integrated DNA sequences encoding biomass degrading enzymes can then be isolated by selection or screening.

Example 10

Screening of Signal Peptides

A comprehensive signal peptide library was tested in combination with three different cellulases in order to identify signal peptides that commonly promote secretion in *T. sacch*. Signal peptides were cloned upstream of histidine-tagged CBH1 (*Talaromyces emersonii*), E5 (*Thermobifida fusca*), and CelZ (*Clostridium stercorarium*) and over-expressed in T. sacch strain M0699. The predicted protein sizes for CBH1, E5, and CelZ are 48 kDa, 48 kDa, and 105 kDa, respectively. T. sacch culture supernatants were harvested during logarithmic growth phase, and protease inhibitors were added. Proteins were precipitated with sodium deoxycholate (DOC) and trichloroacetic acid (TCA) overnight. Protein pellets were resuspended in SDS-PAGE gel loading buffer that contained DTT and analyzed by gel electrophoresis on Novex® 4-20% Tris-glycine gels prior to Western blotting. Anti-6×His antibodies were used to detect CBH1:6×His (*Talaromyces emersonii*) (FIG. 7A), E5:6×His (*Thermobifida fusca*) (FIG. 7B), and CelZ:6×His (*Clostridium stercorarium*) (FIG. 7C) fusion proteins. CBH1 and E5 could be detected by Western analysis when expressed as fusion with a T. sacch signal peptide of SEQ ID NO:15. Additionally, CBH1 could be detected when fused to T. sacch signal peptides SEQ ID NO:19 and 20, and E5 was detected when fused to T. sacch signal peptides of SEQ ID NO: 5, 7, 11, 13, 14, 17, 19, 20, 24 and 31. However, fusion to these signal peptides resulted in detection of bands smaller or larger that the predicted protein size. These bands may be the result of truncated proteins due to proteolysis, conformational changes or incomplete translation from a premature stop codon, for example. Larger bands may have resulted from protein aggregation or post-translational modifications. A CelZ band of predicted size was detected by Western blot only when fused to the native *Clostridium stercorarium* CelZ signal peptide sequence. Fusions with a T. sacch signal peptide SEQ ID NO: 15, 16, 17, 33, and 34 resulted in bands that were smaller than the predicted size.

Example 11

Evidence of Proteolysis of Heterologous Cellulases in T. sacch

Multiple bands, in addition to a band at the expected size of CelZ were visible by Western blot when CelZ was heterologously expressed in T. sacch. See FIG. 2. The multiplicity of bands was observed in samples collected from T. sacch heterologously expressing CelZ:HA, CelZ:His and CelZ:Flag fusions. Therefore, the multiplicity of bands was not the result of a particular protein tag. In order to determine if the extraneous bands were due to culture growing conditions, T. sacch cultures expressing CelZ were grown at multiple pHs (5.5, 6.1, and 6.7). In order to determine if the extraneous bands were due to methods of sample preparation, T. sacch cultures expressing CelZ were processed in three different ways: 1) no treatment; 2) sodium deoxycholate (DOC) and trichloroacetic acid (TCA) precipitation; and 3) filtration through 10 kDa MWCO filter. A similar banding pattern was observed in anti-His Western blots regardless of culture growing conditions or sample preparation techniques. These results indicated that the extra bands were not due to growth pH or sample processing.

In order to determine if the banding pattern was the result of proteolysis, N-terminal sequencing of the bands was performed. Histidine-tagged CBH1 (*Talaromyces emersonii*) and E5 (*Thermobifida fusca*) were cloned downstream of a T. sacch signal peptide of SEQ ID NO:15, and CelZ (*Clostridium stercorarium*) was cloned with the native C. stercorarium CelZ signal peptide (SEQ ID NO:34). The heterologous cellulases were over-expressed in T. sacch strain M0699. The T. sacch culture supernatants were harvested during logarithmic growth phase, and protease inhibitors were added. Proteins were precipitated with DOC/TCA overnight. Protein pellets were resuspended in SDS-PAGE gel loading buffer that contained DTT and analyzed by gel electrophoresis on Novex® 4-20% Tris-glycine gels prior to Western blotting. Anti-6×His antibodies were used to detect CBH1:6×His, E5:6×His, and CelZ:6×His fusion proteins. FIG. 8. In addition, the fusion proteins were purified from T saccharolyticum supernatants by fast performance liquid chromatography (FPLC) using a cobalt resin. Eluant was separated by electrophoresis on Novex® 4-20% Tris-glycine gels. Samples were transferred to a PVDF membrane and stained with Coomassie. After destaining, bands were cut out and identified by N-terminal sequencing. The resulting sequences, shown in FIG. 8, correspond to sequences of the heterologous cellulase being expressed. This data indicates that there is T. sacch-mediated proteolysis of secreted cellulases. Cleavage sites that were consistent with serine-protease cleavage were identified. Cleavage sites consistent with trypsin-like cleavage were also identified.

Example 12

T. emersonii CBH1:His shows Hydrolytic Activity in T. Saccharolyticum

In order to determine if T. emersonii CBH1 was enzymatically active when expressed in T. sacch, an in-gel MuLac assay was performed. In this experiment, approximately 30 L of T. saccharolyticum was grown in TSC1 medium with 30 g/L maltodextrin. The TSC1 media recipe is shown below:

| TSC1 Media recipe (made up for 1 liter inoculum for the 40 liters) | | | |
|---|---|---|---|
| | 1 liter fermentation | 40 liter medium | Comments |
| $NH_4SO_4$ | 1.85 | 74 | |
| $KH_2PO_4$ | 1 | 40 | |
| $MgSO_4$ | 1 | 40 | |
| $CaCl_2*2H_2O$ | 0.1 | 4 | |
| $FeSO_4*7H_2O$ | 0.05 | 2 | |
| NaCitrate | 2 | 80 | |
| yeast extract | 8.5 | 340 | |
| maltodextrin | 30 | 1200 | separately sterilized |
| resazurin | 1 | 40 | |
| water | Bring up to 1 L autoclave 40 min | Bring up to 40 L autoclave 2 hours | Use distilled water |

Figure 9A:
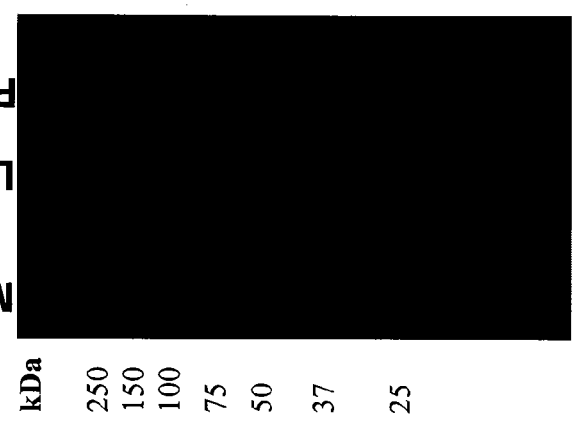
Figure 9A:
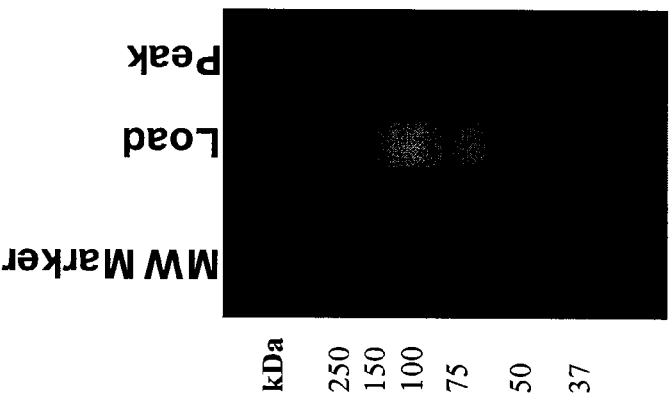

Supernatant was separated from cells by spinning and clarified of residual cells using a 500 kDa MWCO filter. The permeate was retained and concentrated in a 10 kDa MWCO filter. Retentate was diafiltered into 50 mM Na phosphate, 300 mM NaCl, pH 7.4 and purified by FPLC using a Pierce cobalt column. Samples of the material loaded onto the column (FIG. 9A "load") and a sample of the fraction that was retained on the column and eluted with an imidazole gradient (FIG. 9A "peak") were obtained and applied to a 4-20% SDS-PAGE gel and separated electrophoretically. The gel was then incubated in 100 mM succinate, pH 5.8 to remove the SDS and equilibrate the gel to the optimal pH. The gel was then incubated in 100 mM succinate, pH 5.8 with 0.5 mM 4-methylumbelliferyl cellobioside (MuCell), a fluorescent substrate for CBH1. After incubating for an additional 2 hours at 45° C., the gel was visualized on a Syngene G:Box with a CCD camera after exciting the MuCell with UV light. Bands containing enzymes that can digest the MuCell fluoresce. FIG. 9A, left panel. The gel was also stained with Simply Blue safe stain to visualize all of the proteins present in each sample and to estimate the amount of protein in each sample. FIG. 9A, right panel. Based on this staining, there is significantly less protein present in the peak sample compared to the load sample (approximately 10%). FIG. 9A, right panel. Both the load and the peak appeared to be positive for MuCel. FIG. 9A, left panel.

Figure 9B:
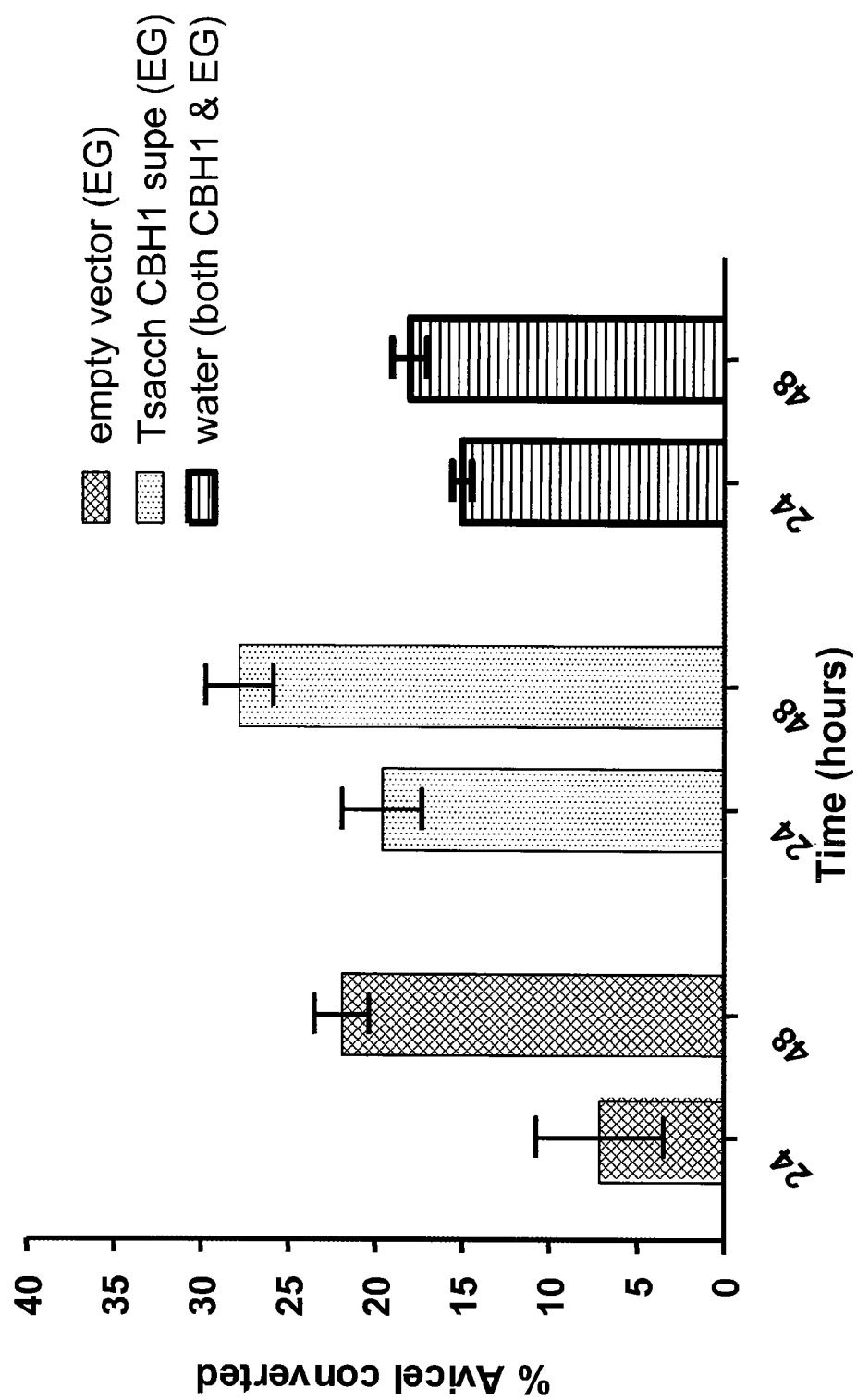

The activity of *T. emersonii* CBH1 in *T. sacch* was also assessed by measuring the percent of Avicel conversion using the reducing sugar (DNS) method. Commercially available exogenous endoglucanase (EG) (2 mg/g) from AB Enzymes batch number EL2007025L and *T. saccharolyticum* supernatants from empty vector controls or CBH1-expressing strains were added to 2% Avicel. A water control was performed in which 2 mg/g total of EG and commercially available exogenous CBH1 (AB Enzymes thermostable, mono-component) was added. Measurements were taken at 24 hours and 48 hours, and at both time points a greater percentage of Avicel was converted by the CBH1-expressing *T. sacch* strain than either of the controls. FIG. 9B.

Figure 9C:
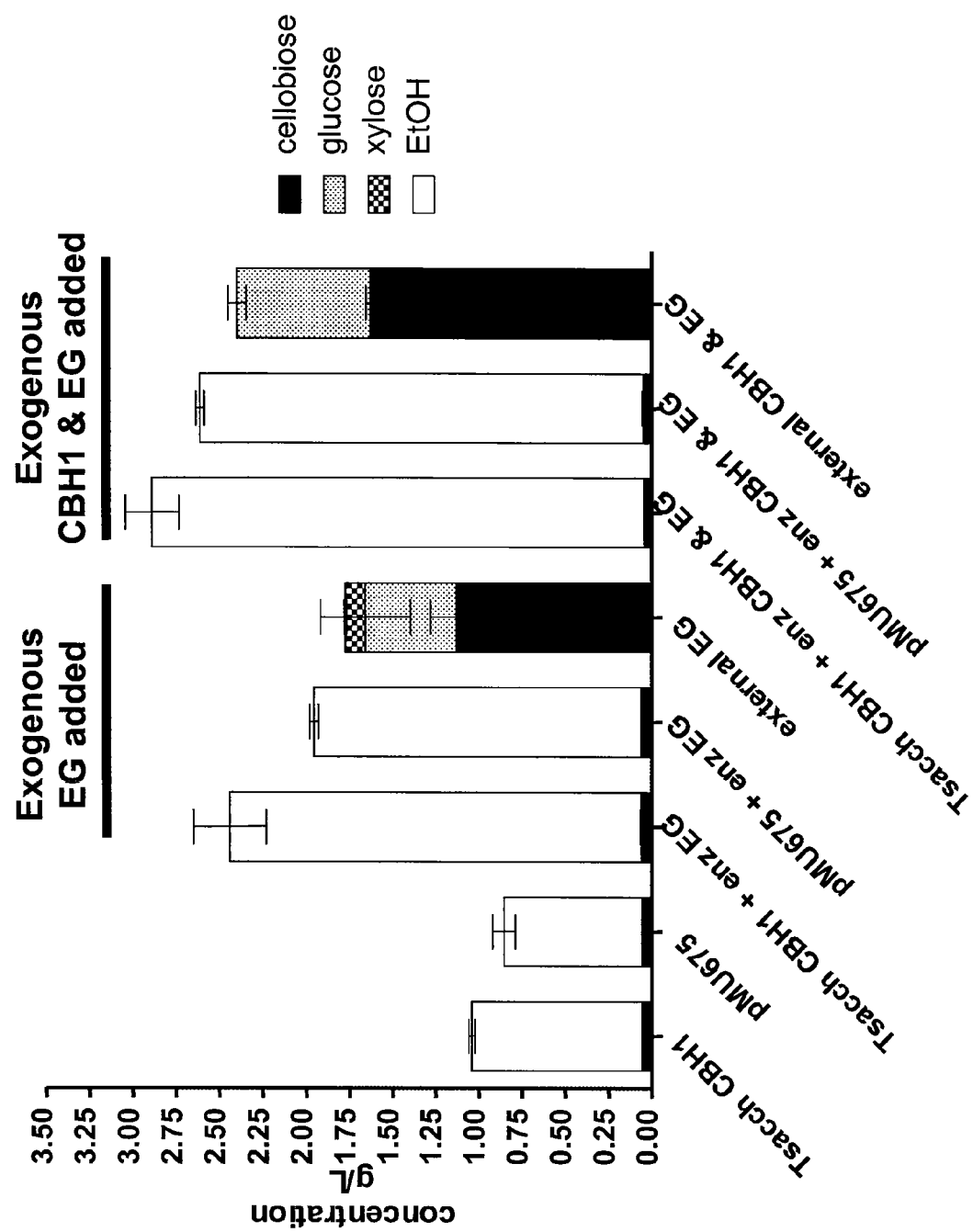

The activity of *T. emersonii* CBH1 in *T. sacch* was also assessed using fermentation bottle experiments. These experiments were performed with 2% Avicel in TSC1 medium and *T. saccharolyticum* transformed with an empty vector control or a CBH1-containing plasmid. Commercially available exogenous EG (2 mg/g) or EG and CBH1 in a ratio of 1:3.5 (2 mg/g) was added to each bottle. Cellobiose, glucose, xylose, and ethanol concentrations were measured by HPLC using a 300×7.8 mm BioRad Aminex HPX 87H column, an ion-moderated partition chromatography technique, at 72 hours. CBH1-expressing *T. sacch* increased the concentration of ethanol produced under all of the conditions tested. FIG. 9C.

Example 13

Increased Heterologous Cellulase Activity in *T. sacch* in Protease Knock-Outs

In order to decrease the proteolysis of heterologous cellulases in *T. sacch*, *T. sacch* strains lacking a gene encoding a protease are created. For example, knock-outs are created using phosphotransacetylase (pta) and acetate kinase (ack) genes for genetic marker removal via selection with halogenacetate compounds (e.g. fluoroacetate) as described in U.S. Provisional Application No. 61/113,978, which is herein incorporated by reference in its entirety. A recombinant *T. sacch* strain expressing the heterologous cellulase in a wild-type background and a recombinant *T. sacch* strain expressing the heterologous cellulase in the protease knock-out background are cultured under the same conditions, and the concentration of cellulases is measured by Western Blot. An increase in the intensity of the band corresponding to the size of the heterologous cellulase and a decrease in the intensity of the multiplicity of smaller bands indicates a decrease in the proteolysis of the heterologous cellulase. In addition, ethanol production by both strains is measured as described in the Examples above. An increase in ethanol production in the protease knock-out indicates an increase in the enzymatic activity of heterologously expressed cellulase in *T. sacch*.

These examples illustrate possible embodiments of the present invention. While the invention has been particularly shown and described with reference to some embodiments thereof, it will be understood by those skilled in the art that they have been presented by way of example only, and not limitation, and various changes in form and details can be made therein without departing from the spirit and scope of the invention. Thus, the breadth and scope of the present invention should not be limited by any of the above-described exemplary embodiments, but should be defined only in accordance with the following claims and their equivalents.

All documents cited herein, including journal articles or abstracts, published or corresponding U.S. or foreign patent applications, issued or foreign patents, or any other documents, are each entirely incorporated by reference herein, including all data, tables, figures, and text presented in the cited documents.

What is claimed is:

1. An isolated nucleic acid comprising a polynucleotide which encodes a polypeptide comprising the amino acid sequence of SEQ ID NO: 15 and the amino acid sequence of SEQ ID NO: 126.

2. The nucleic acid of claim 1, wherein the polynucleotide is codon-optimized for expression in *Thermoanaerobacterium saccharolyticum*.

3. A vector comprising the nucleic acid of claim 1.

4. A host cell comprising the nucleic acid of claim 1.

5. The host cell of claim 4, wherein the host cell is a member of the genus *Thennoanaerobacteium*.

6. A transformed *Thermounaerobacterium saccharolyticum* host cell comprising at least one heterologous polynucleotide comprising a nucleic acid encoding a biomass degrading enzyme, wherein the polynucleotide encodes the amino acid sequence of SEQ ID NO: 126, and wherein the host cell lacks genes encoding lactate dehydrogenase, phosphotransacetylase, and acetate kinase.

7. The transformed host cell of claim 6, wherein the heterologous polynucleotide comprising a nucleic acid encoding a biomass degrading enzyme is operably linked to a cellobiose phosphotransferase (CBP) promoter or *E. coil* T1 and T2 terminator sequences or a combination thereof.

8. The transformed host cell of claim 6, wherein the transformed host cell has decreased protease activity compared to wild-type *Thermoctnaerobacierium saccharolyticum* or increased chaperone activity, compared to wild-type *Thermoanaerobacterium saccharolyticum*.

9. The transformed host cell of claim 8, wherein said transformed host cell comprises a heterologous nucleic acid encoding a protein selected from the group consisting of: *E. coli* DsbA, *E. coli* B, *E. coli* C, *E. coli* D, *E. coli* G, *Bacillus subtilis* BdbA, *Bacillus subtilis* BdbB, *Bacillus subtilis* BdbC, *Bacillus subtilis* BdbD, *Bacillus subtilis* PrsA, SecA, SecY, SecE, SecG, SecDF, and combinations thereof.

10. The transformed host cell of claim 6, wherein the transformed host cell can grow on Avicel.

11. The transformed host cell of claim 6, wherein the transformed host cell has at least 10 U/mg cellulase activity.

12. The transformed host cell of claim 7, wherein the CBP promoter is the *Clostridium thermocellum* CBP promoter.

13. The transformed host cell of claim 8, wherein said transformed host cell comprises a heterologous nucleic acid encoding a chaperone selected from the group consisting of *E. coli* HSP60/GroEL, *E. coli* HSP60/GroES, *E. coli* HSP70/DnaK, *E. coli* DnaJ, *E. coli* GrpE, *E. coli* HSP90/HtpG, *E. coli* HSP100/Clp family, *E. coli* peptidyl prolyl isomerase Trigger Factor, *Bacillus subtilis* Ffh, *Bacillus subtilis* HBsu, *Bacillus subtilis* FtsY, *Bacillus subtilis* CsaA *Bacillus subtilis* FlhF. and combinations thereof.

* * * * *

SEQUENCE LISTING

<160> NUMBER OF SEQ ID NOS: 178

<210> SEQ ID NO 1
<211> LENGTH: 38
<212> TYPE: PRT
<213> ORGANISM: Thermoanearobacterium saccharolyticum

<400> SEQUENCE: 1

Met Lys Leu Phe Lys Lys Ile Met Leu Ile Met Leu Ser Ile Met Leu
1               5                   10                  15

Ile Val Ser Ala Ser Ala Cys Gly Thr Gly Ser Ser Gly Ser Ser Asn
            20                  25                  30

Ser Asn Ala Ser Lys Ser
        35

<210> SEQ ID NO 2
<211> LENGTH: 30
<212> TYPE: PRT
<213> ORGANISM: Thermoanearobacterium saccharolyticum

<400> SEQUENCE: 2

Met Asn Lys Ile Leu Lys Ile Phe Ser Val Phe Leu Gly Ala Phe Leu
1               5                   10                  15

Ile Phe Val Asn Met Ser Ile Asn Glu Ala Lys Ala Asp Pro
            20                  25                  30

```
<210> SEQ ID NO 3
<211> LENGTH: 28
<212> TYPE: PRT
<213> ORGANISM: Thermoanearobacterium saccharolyticum

<400> SEQUENCE: 3

Met Asn Asn Lys Lys Gly Ile Val Ala Phe Ile Ile Ile Leu Thr Met
1               5                   10                  15

Ile Phe Ser Asn Leu Thr Phe Val Asp Ala Asn Ile
            20                  25

<210> SEQ ID NO 4
<211> LENGTH: 28
<212> TYPE: PRT
<213> ORGANISM: Thermoanearobacterium saccharolyticum

<400> SEQUENCE: 4

Val Lys Lys Phe Cys Ile Leu Leu Met Cys Ile Ile Ile Leu Ile Ser
1               5                   10                  15

Gly Cys Lys Phe Asn Ser Val Thr Ser Ser Gly Lys
            20                  25

<210> SEQ ID NO 5
<211> LENGTH: 29
<212> TYPE: PRT
<213> ORGANISM: Thermoanearobacterium saccharolyticum

<400> SEQUENCE: 5

Met Lys Lys Thr Phe Lys Leu Ile Leu Val Leu Met Leu Ser Leu Thr
1               5                   10                  15

Leu Val Phe Gly Leu Thr Ala Pro Ile Gln Ala Ala Ser
            20                  25

<210> SEQ ID NO 6
<211> LENGTH: 27
<212> TYPE: PRT
<213> ORGANISM: Lactococcus lactis

<400> SEQUENCE: 6

Met Lys Lys Lys Ile Ile Ser Ala Ile Leu Met Ser Thr Val Ile Leu
1               5                   10                  15

Ser Ala Ala Ala Pro Leu Ser Gly Val Tyr Ala
            20                  25

<210> SEQ ID NO 7
<211> LENGTH: 35
<212> TYPE: PRT
<213> ORGANISM: Lactococcus lactis

<400> SEQUENCE: 7

Met Lys Phe Asn Lys Lys Arg Val Ala Ile Ala Thr Phe Ile Ala Leu
1               5                   10                  15

Ile Phe Val Ser Phe Phe Thr Ile Ser Ser Ile Gln Asp Asn Gln Thr
            20                  25                  30

Asn Ala Ala
        35

<210> SEQ ID NO 8
<211> LENGTH: 32
<212> TYPE: PRT
<213> ORGANISM: Unknown
```

```
<220> FEATURE:
<223> OTHER INFORMATION: Typical Gram positive

<400> SEQUENCE: 8

Met Lys Ser Ile Val Asn Arg Val Val Ser Ile Val Thr Ala Leu Ile
1               5                   10                  15

Met Ile Phe Gly Thr Ser Leu Phe Ser Gln His Ile Arg Ala Phe Ala
            20                  25                  30

<210> SEQ ID NO 9
<211> LENGTH: 27
<212> TYPE: PRT
<213> ORGANISM: Staphylococcus aureus

<400> SEQUENCE: 9

Met Lys Ser Asn Lys Ser Leu Ala Met Ile Val Val Ala Ile Ile Ile
1               5                   10                  15

Val Gly Val Leu Ala Phe Gln Phe Met Asn His
            20                  25

<210> SEQ ID NO 10
<211> LENGTH: 25
<212> TYPE: PRT
<213> ORGANISM: Staphylococcus aureus

<400> SEQUENCE: 10

Met Thr Glu Tyr Leu Leu Ser Ala Gly Ile Cys Met Ala Ile Val Ser
1               5                   10                  15

Ile Leu Leu Ile Gly Met Ala Ile Ser
            20                  25

<210> SEQ ID NO 11
<211> LENGTH: 31
<212> TYPE: PRT
<213> ORGANISM: Bacillus licheniformis

<400> SEQUENCE: 11

Met Lys Gln Gln Lys Arg Leu Tyr Ala Arg Leu Leu Thr Leu Leu Phe
1               5                   10                  15

Ala Leu Ile Phe Leu Leu Pro His Ser Ala Ala Ala Ala Ala Asn
            20                  25                  30

<210> SEQ ID NO 12
<211> LENGTH: 31
<212> TYPE: PRT
<213> ORGANISM: Bacillus licheniformis

<400> SEQUENCE: 12

Met Lys Gln His Lys Arg Leu Tyr Ala Arg Leu Leu Pro Leu Leu Phe
1               5                   10                  15

Ala Leu Ile Phe Leu Leu Ser His Ser Ala Ala Ala Ala Ala Ser
            20                  25                  30

<210> SEQ ID NO 13
<211> LENGTH: 31
<212> TYPE: PRT
<213> ORGANISM: Thermoanearobacterium saccharolyticum

<400> SEQUENCE: 13

Leu Asn Arg Lys Leu Ile Lys Tyr Leu Pro Val Leu Phe Leu Ala Ser
1               5                   10                  15

Ser Val Leu Ser Gly Cys Gly Asn Asn Asn Ile Ser Ser Met Lys
```

<210> SEQ ID NO 14
<211> LENGTH: 31
<212> TYPE: PRT
<213> ORGANISM: Thermoanearobacterium saccharolyticum

<400> SEQUENCE: 14

Met Gly Lys Lys Phe Ile Ser Ile Phe Val Val Thr Ile Leu Leu Ile
1               5                   10                  15

Ala Ala Leu Leu Ser Gly Cys Ser Thr Lys Gln Asn Thr Ala Ser
            20                  25                  30

<210> SEQ ID NO 15
<211> LENGTH: 31
<212> TYPE: PRT
<213> ORGANISM: Thermoanearobacterium saccharolyticum

<400> SEQUENCE: 15

Met Arg Ile Lys Lys Ala Phe Phe Met Leu Ile Ala Ala Phe Ile Val
1               5                   10                  15

Leu Ser Leu Phe Leu Phe Asn Phe Ala Lys Thr Ser Ala Ser Ala
            20                  25                  30

<210> SEQ ID NO 16
<211> LENGTH: 29
<212> TYPE: PRT
<213> ORGANISM: Thermoanearobacterium saccharolyticum

<400> SEQUENCE: 16

Met Ser Lys Ile Ala Arg Gln Ile Ile Thr Val Phe Val Thr Leu Val
1               5                   10                  15

Leu Ala Val Tyr Ser Ile Pro Ile Ile Gly Ala Thr Ser
            20                  25

<210> SEQ ID NO 17
<211> LENGTH: 31
<212> TYPE: PRT
<213> ORGANISM: Thermoanearobacterium saccharolyticum

<400> SEQUENCE: 17

Met Phe Lys Lys Ile Ile Val Thr Val Leu Ala Val Ile Leu Thr Ile
1               5                   10                  15

Gly Ala Leu Thr Gly Cys Ser Ser Ser Thr Asn Ser Ser Gly Ser
            20                  25                  30

<210> SEQ ID NO 18
<211> LENGTH: 33
<212> TYPE: PRT
<213> ORGANISM: Thermoanearobacterium saccharolyticum

<400> SEQUENCE: 18

Met Lys Ser Lys Lys Leu Leu Ser Val Leu Ile Val Ser Val Met Ile
1               5                   10                  15

Phe Ser Val Phe Leu Ser Gly Cys Gly Ser Ala Lys Asn Ser Lys Ser
            20                  25                  30

Ala

<210> SEQ ID NO 19
<211> LENGTH: 38
<212> TYPE: PRT
<213> ORGANISM: Thermoanearobacterium saccharolyticum

```
<400> SEQUENCE: 19

Met Lys Lys Tyr Lys Arg Tyr Ile Ala Met Met Leu Ile Phe Val Met
1               5                   10                  15

Val Leu Ala Thr Val Ser Leu Ala Gly Cys Lys Ser Ser Val Lys Lys
            20                  25                  30

Pro Val Thr Ser Lys Arg
        35

<210> SEQ ID NO 20
<211> LENGTH: 34
<212> TYPE: PRT
<213> ORGANISM: Thermoanearobacterium saccharolyticum

<400> SEQUENCE: 20

Leu Asn Lys Leu His Ile Asn Lys Trp Tyr Phe Phe Val Gly Met Leu
1               5                   10                  15

Ala Met Phe Ala Val Ile Met Ser Leu Ile Leu Lys Asp Thr Ser Leu
            20                  25                  30

Thr Phe

<210> SEQ ID NO 21
<211> LENGTH: 30
<212> TYPE: PRT
<213> ORGANISM: Thermoanearobacterium saccharolyticum

<400> SEQUENCE: 21

Met Asn Lys Lys Val Ile Ile Ile Thr Ser Ile Ile Leu Val Val Ala
1               5                   10                  15

Ala Gly Ala Thr Tyr Tyr Phe Thr Lys Ser Lys Ala Thr Pro
            20                  25                  30

<210> SEQ ID NO 22
<211> LENGTH: 29
<212> TYPE: PRT
<213> ORGANISM: Thermoanearobacterium saccharolyticum

<400> SEQUENCE: 22

Met Leu Asn Phe Lys Arg Ile Phe Thr Leu Ile Cys Thr Phe Leu Val
1               5                   10                  15

Ser Leu Ser Leu Leu Thr Val Thr Ala Phe Ala Asp Thr
            20                  25

<210> SEQ ID NO 23
<211> LENGTH: 23
<212> TYPE: PRT
<213> ORGANISM: Thermoanearobacterium saccharolyticum

<400> SEQUENCE: 23

Met Lys Lys Leu Met Leu Ile Leu Leu Ser Leu Ile Leu Val Val Ser
1               5                   10                  15

Val Thr Ala Cys Gly Lys Ile
            20

<210> SEQ ID NO 24
<211> LENGTH: 27
<212> TYPE: PRT
<213> ORGANISM: Thermoanearobacterium saccharolyticum

<400> SEQUENCE: 24

Met Leu Ser Lys Asn Leu Pro Ile Lys Ile Leu Ser Val Val Ile Ala
```

```
1               5                   10                  15
Phe Ile Leu Trp Leu Tyr Val Met Gly Glu Lys
            20                  25
```

<210> SEQ ID NO 25
<211> LENGTH: 37
<212> TYPE: PRT
<213> ORGANISM: Thermoanearobacterium saccharolyticum

<400> SEQUENCE: 25

```
Met Lys Arg Leu Lys Lys Leu Met Val Leu Leu Ser Met Ile Leu
1               5                   10                  15

Ile Ile Ser Ala Ser Ala Cys Gly Thr Asn Ser Asn Asn Ser Ser
            20                  25                  30

Ser Asn Ala Ser Asn
        35
```

<210> SEQ ID NO 26
<211> LENGTH: 29
<212> TYPE: PRT
<213> ORGANISM: Thermoanearobacterium saccharolyticum

<400> SEQUENCE: 26

```
Met Lys Lys Thr Phe Lys Leu Ile Leu Val Leu Met Leu Ser Leu Thr
1               5                   10                  15

Leu Val Phe Gly Leu Thr Ala Pro Ile Gln Ala Ala Ser
            20                  25
```

<210> SEQ ID NO 27
<211> LENGTH: 34
<212> TYPE: PRT
<213> ORGANISM: Thermoanearobacterium saccharolyticum

<400> SEQUENCE: 27

```
Met Lys Ser Ile Val Asn Arg Val Val Ser Ile Val Thr Ala Leu Ile
1               5                   10                  15

Met Ile Phe Gly Thr Ser Leu Phe Ser Gln His Ile Arg Ala Phe Ala
            20                  25                  30

Asp Asp
```

<210> SEQ ID NO 28
<211> LENGTH: 25
<212> TYPE: PRT
<213> ORGANISM: Thermoanearobacterium saccharolyticum

<400> SEQUENCE: 28

```
Val Lys Lys Phe Val Ser Ile Phe Leu Ala Val Met Leu Ile Ala Ala
1               5                   10                  15

Ile Pro Val Phe Gly Leu Ala Ala Gln
            20                  25
```

<210> SEQ ID NO 29
<211> LENGTH: 25
<212> TYPE: PRT
<213> ORGANISM: Thermoanearobacterium saccharolyticum

<400> SEQUENCE: 29

```
Met Leu Lys Lys Ile Ile Ala Thr Met Leu Ile Leu Ser Leu Val Val
1               5                   10                  15

Ile Pro Phe Met Ala Phe Ala Asp Asp
            20                  25
```

```
<210> SEQ ID NO 30
<211> LENGTH: 25
<212> TYPE: PRT
<213> ORGANISM: Thermoanearobacterium saccharolyticum

<400> SEQUENCE: 30

Val Lys Lys Ile Tyr Gly Leu Ile Leu Val Phe Val Val Met Leu Ala
1               5                   10                  15

Val Ile Gly Ile Val Tyr Ala Asp Ser
            20                  25

<210> SEQ ID NO 31
<211> LENGTH: 26
<212> TYPE: PRT
<213> ORGANISM: Thermoanearobacterium saccharolyticum

<400> SEQUENCE: 31

Met Ile Arg Ser Lys Met Leu Lys Thr Val Ser Met Leu Leu Val Leu
1               5                   10                  15

Val Met Ile Ile Thr Ala Phe Thr Ala Cys
            20                  25

<210> SEQ ID NO 32
<211> LENGTH: 40
<212> TYPE: PRT
<213> ORGANISM: Caldocellum saccharolyticum

<400> SEQUENCE: 32

Met Arg Leu Lys Thr Lys Ile Arg Lys Lys Trp Leu Ser Val Leu Cys
1               5                   10                  15

Thr Val Val Phe Leu Leu Asn Ile Leu Phe Ile Ala Asn Val Thr Ile
            20                  25                  30

Leu Pro Lys Val Gly Ala Ala Thr
        35                  40

<210> SEQ ID NO 33
<211> LENGTH: 32
<212> TYPE: PRT
<213> ORGANISM: Caldocellum saccharolyticum

<400> SEQUENCE: 33

Met Lys Thr Ala Arg Leu Leu Val Cys Phe Val Leu Val Cys Phe Ile
1               5                   10                  15

Leu Thr Thr Thr Ile Leu Leu Asp Asn Asn Lys Gly Glu Ala Ala Met
            20                  25                  30

<210> SEQ ID NO 34
<211> LENGTH: 29
<212> TYPE: PRT
<213> ORGANISM: Clostridium Stercorarium

<400> SEQUENCE: 34

Met Arg Lys Phe Trp Ser Phe Ala Ile Ile Ile Ser Leu Leu Val Thr
1               5                   10                  15

Gly Leu Phe Ile His Thr Pro Lys Ala Glu Ala Ala Gly
            20                  25

<210> SEQ ID NO 35
<211> LENGTH: 48
<212> TYPE: PRT
<213> ORGANISM: Thermobifida fusca
```

<400> SEQUENCE: 35

Met Ser Val Thr Glu Pro Pro Arg Arg Gly Arg His Ser Arg
1               5                   10                  15

Ala Arg Arg Phe Leu Thr Ser Leu Gly Ala Thr Ala Ala Leu Thr Ala
            20                  25                  30

Gly Met Leu Gly Val Pro Leu Ala Thr Gly Thr Ala His Ala Glu Pro
        35                  40                  45

<210> SEQ ID NO 36
<211> LENGTH: 25
<212> TYPE: PRT
<213> ORGANISM: Caldocellum saccharolyticum

<400> SEQUENCE: 36

Met Val Val Thr Phe Leu Phe Ile Leu Gly Val Val Tyr Gly Val Lys
1               5                   10                  15

Pro Trp Gln Glu Ala Arg Ala Gly Ser
            20                  25

<210> SEQ ID NO 37
<211> LENGTH: 29
<212> TYPE: PRT
<213> ORGANISM: Caldocellum saccharolyticum

<400> SEQUENCE: 37

Met Lys Arg Asn Leu Phe Arg Ile Val Ser Arg Val Val Leu Ile Ala
1               5                   10                  15

Phe Ile Ala Ser Ile Ser Leu Val Gly Ala Met Ser Tyr
            20                  25

<210> SEQ ID NO 38
<211> LENGTH: 37
<212> TYPE: PRT
<213> ORGANISM: Caldocellum saccharolyticum

<400> SEQUENCE: 38

Met Lys Arg Asn Leu Phe Arg Ile Val Ser Arg Val Val Leu Ile Ala
1               5                   10                  15

Phe Ile Ala Ser Ile Ser Leu Val Gly Ala Met Ser Tyr Phe Pro Val
            20                  25                  30

Glu Thr Gln Ala Ala
        35

<210> SEQ ID NO 39
<211> LENGTH: 114
<212> TYPE: DNA
<213> ORGANISM: Artificial Sequence
<220> FEATURE:
<223> OTHER INFORMATION: Codon-Optimized Thermoanearobacterium
      saccharolyticum signal sequence

<400> SEQUENCE: 39
atgaaactgt ttaaaaaaat tatgctgatt atgctgagca ttatgctgat tgtgagcgcg    60
agcgcgtgcg gcaccggcag cagcggcagc agcaacagca cgcgagcaa aagc           114

<210> SEQ ID NO 40
<211> LENGTH: 90
<212> TYPE: DNA
<213> ORGANISM: Artificial Sequence
<220> FEATURE:
<223> OTHER INFORMATION: Codon-Optimized Thermoanearobacterium saccharolyticum signal sequence

<400> SEQUENCE: 40

```
atgaacaaaa ttctgaaaat ttttagcgtg tttctgggcg cgtttctgat ttttgtgaac    60
atgagcatta acgaagcgaa agcggatccg                                      90
```

<210> SEQ ID NO 41
<211> LENGTH: 84
<212> TYPE: DNA
<213> ORGANISM: Artificial Sequence
<220> FEATURE:
<223> OTHER INFORMATION: Codon-Optimized Thermoanearobacterium
      saccharolyticum signal sequence

<400> SEQUENCE: 41

```
atgaacaaca aaaaaggcat tgtggcgttt attattattc tgaccatgat ttttagcaac    60
ctgacctttg tggatgcgaa catt                                            84
```

<210> SEQ ID NO 42
<211> LENGTH: 84
<212> TYPE: DNA
<213> ORGANISM: Artificial Sequence
<220> FEATURE:
<223> OTHER INFORMATION: Codon-Optimized Thermoanearobacterium
      saccharolyticum signal sequence

<400> SEQUENCE: 42

```
gtgaaaaaat tttgcattct gctgatgtgc attattattc tgattagcgg ctgcaaattt    60
aacagcgtga ccagcagcgg caaa                                            84
```

<210> SEQ ID NO 43
<211> LENGTH: 87
<212> TYPE: DNA
<213> ORGANISM: Artificial Sequence
<220> FEATURE:
<223> OTHER INFORMATION: Codon-Optimized Thermoanearobacterium
      saccharolyticum signal sequence

<400> SEQUENCE: 43

```
atgaaaaaaa cctttaaact gattctggtg ctgatgctga gcctgaccct ggtgtttggc    60
ctgaccgcgc cgattcaggc ggcgagc                                         87
```

<210> SEQ ID NO 44
<211> LENGTH: 81
<212> TYPE: DNA
<213> ORGANISM: Artificial Sequence
<220> FEATURE:
<223> OTHER INFORMATION: Codon-Optimized Lactococcus lactis signal
      sequence

<400> SEQUENCE: 44

```
atgaagaaaa agataataag cgctattctt atgagcacag tgatactttc tgcggccgca    60
cctttaagtg gtgtttatgc t                                               81
```

<210> SEQ ID NO 45
<211> LENGTH: 105
<212> TYPE: DNA
<213> ORGANISM: Artificial Sequence
<220> FEATURE:
<223> OTHER INFORMATION: Codon-Optimized Lactococcus lactis signal
      sequence

<400> SEQUENCE: 45

```
atgaaattta ataaaaagag agttgccata gcaacattta ttgccttaat atttgtgtca    60 ttttcacaa tttcttctat acaggataat caaaccaatg cggca                    105
```

<210> SEQ ID NO 46
<211> LENGTH: 96
<212> TYPE: DNA
<213> ORGANISM: Artificial Sequence
<220> FEATURE:
<223> OTHER INFORMATION: Codon-Optimized Typical Gram positive signal
      sequence

<400> SEQUENCE: 46

```
atgaaatcaa ttgtcaatag agtggtaagc attgttactg ctcttataat gattttggt    60 acttcattat tttctcagca cattagagcg tttgca                              96
```

<210> SEQ ID NO 47
<211> LENGTH: 81
<212> TYPE: DNA
<213> ORGANISM: Artificial Sequence
<220> FEATURE:
<223> OTHER INFORMATION: Codon-Optimized Staphylococcus aureus signal
      sequence

<400> SEQUENCE: 47

```
atgaaaagta ataaatcgtt agctatgata gtcgttgcaa taataatagt cggggtatta    60
gcttttcagt ttatgaacca c                                              81
```

<210> SEQ ID NO 48
<211> LENGTH: 75
<212> TYPE: DNA
<213> ORGANISM: Artificial Sequence
<220> FEATURE:
<223> OTHER INFORMATION: Codon-Optimized Staphylococcus aureus signal
      sequence

<400> SEQUENCE: 48

```
atgacagaat atttgttatc agcaggtatt tgcatggcaa tagtatcaat attattaata    60
ggaatggcaa tttca                                                     75
```

<210> SEQ ID NO 49
<211> LENGTH: 93
<212> TYPE: DNA
<213> ORGANISM: Artificial Sequence
<220> FEATURE:
<223> OTHER INFORMATION: Codon-Optimized Bacillus licheniformis signal
      sequence

<400> SEQUENCE: 49

```
atgaaacaac aaaaaaggct ttatgcaaga cttttaacat tattgtttgc attgatattc    60
ttgcttccac attctgcagc agcagcagct aac                                 93
```

<210> SEQ ID NO 50
<211> LENGTH: 93
<212> TYPE: DNA
<213> ORGANISM: Artificial Sequence
<220> FEATURE:
<223> OTHER INFORMATION: Codon-Optimized Bacillus licheniformis signal
      sequence

<400> SEQUENCE: 50

```
atgaaacagc acaaaagact gtatgcaaga ttgctaccct tgttgtttgc tctgatattt    60
ttattgagcc actcggcggc tgctgcagcc tca                                 93
```

<210> SEQ ID NO 51
<211> LENGTH: 93
<212> TYPE: DNA
<213> ORGANISM: Artificial Sequence
<220> FEATURE:
<223> OTHER INFORMATION: Codon-Optimized Thermoanearobacterium
      saccharolyticum signal sequence

<400> SEQUENCE: 51
ttgaatagaa aacttataaa atacctacct gtattatttc ttgcatccag tgtgctaagc    60
ggatgtggaa acaataatat atcaagtatg aaa                                 93

<210> SEQ ID NO 52
<211> LENGTH: 93
<212> TYPE: DNA
<213> ORGANISM: Artificial Sequence
<220> FEATURE:
<223> OTHER INFORMATION: Codon-Optimized Thermoanearobacterium
      saccharolyticum signal sequence

<400> SEQUENCE: 52
atgggtaaaa aatttataag cattttttgtt gtcacaatac ttttgatagc tgctttgctt   60
tctggatgtt caacaaaaca aaacactgct tcc                                 93

<210> SEQ ID NO 53
<211> LENGTH: 93
<212> TYPE: DNA
<213> ORGANISM: Artificial Sequence
<220> FEATURE:
<223> OTHER INFORMATION: Codon-Optimized Thermoanearobacterium
      saccharolyticum signal sequence

<400> SEQUENCE: 53
atgcgtataa aaaagcttt ttttatgctg atagcagctt ttatagttct atctttgttt     60
ttgtttaatt tcgctaaaac cagtgcatcg gcg                                 93

<210> SEQ ID NO 54
<211> LENGTH: 87
<212> TYPE: DNA
<213> ORGANISM: Artificial Sequence
<220> FEATURE:
<223> OTHER INFORMATION: Codon-Optimized Thermoanearobacterium
      saccharolyticum signal sequence

<400> SEQUENCE: 54
atgagcaaga tagcgagaca gataataact gttttcgtga cccttgtact ggcagtatat    60
tctatcccta ttattggggc aaccagt                                        87

<210> SEQ ID NO 55
<211> LENGTH: 93
<212> TYPE: DNA
<213> ORGANISM: Artificial Sequence
<220> FEATURE:
<223> OTHER INFORMATION: Codon-Optimized Thermoanearobacterium
      saccharolyticum signal sequence

<400> SEQUENCE: 55
atgtttaaaa aaattattgt cacagtgctt gcagtaattt tgacaattgg agcattaaca    60
ggatgttcat cttctactaa tagtagtggt agt                                 93

<210> SEQ ID NO 56
<211> LENGTH: 99
<212> TYPE: DNA

```
<213> ORGANISM: Artificial Sequence
<220> FEATURE:
<223> OTHER INFORMATION: Codon-Optimized Thermoanearobacterium
      saccharolyticum signal sequence

<400> SEQUENCE: 56
atgaaaagta aaagttgtt gtcagtttta attgtatcag taatgatatt ttctgtattt    60
ttatctgggt gtggcagtgc taaaaactct aaatcagca                          99

<210> SEQ ID NO 57
<211> LENGTH: 114
<212> TYPE: DNA
<213> ORGANISM: Artificial Sequence
<220> FEATURE:
<223> OTHER INFORMATION: Codon-Optimized Thermoanearobacterium
      saccharolyticum signal sequence

<400> SEQUENCE: 57
atgaaaaaat ataaaagata tattgcgatg atgttgattt ttgtcatggt acttgcaact    60
gtatcattag ccggatgcaa aagctcagtt aaaaagccag ttacttctaa aaga         114

<210> SEQ ID NO 58
<211> LENGTH: 102
<212> TYPE: DNA
<213> ORGANISM: Artificial Sequence
<220> FEATURE:
<223> OTHER INFORMATION: Codon-Optimized Thermoanearobacterium
      saccharolyticum signal sequence

<400> SEQUENCE: 58
ttgaataaat tgcatattaa taaatggtac ttttttgtag gtatgcttgc tatgtttgct    60
gtaattatga gtctaatctt aaaagataca tctttaacct tt                      102

<210> SEQ ID NO 59
<211> LENGTH: 90
<212> TYPE: DNA
<213> ORGANISM: Artificial Sequence
<220> FEATURE:
<223> OTHER INFORMATION: Codon-Optimized Thermoanearobacterium
      saccharolyticum signal sequence

<400> SEQUENCE: 59
atgaataaaa aggtaataat tataaccagc attattttgg tagttgcagc aggcgctact    60
tactacttta caaaaagcaa agccacgcct                                    90

<210> SEQ ID NO 60
<211> LENGTH: 87
<212> TYPE: DNA
<213> ORGANISM: Artificial Sequence
<220> FEATURE:
<223> OTHER INFORMATION: Codon-Optimized Thermoanearobacterium
      saccharolyticum signal sequence

<400> SEQUENCE: 60
atgttaaact ttaagagaat ttttacgtta atttgcactt ttttggttag tttaagtttg    60
cttacggtta ctgcatttgc agataca                                       87

<210> SEQ ID NO 61
<211> LENGTH: 69
<212> TYPE: DNA
<213> ORGANISM: Artificial Sequence
<220> FEATURE:
<223> OTHER INFORMATION: Codon-Optimized Thermoanearobacterium
      saccharolyticum signal sequence
```

<400> SEQUENCE: 61
atgaaaaaat taatgttgat tttactttct ttaatattgg tagttagtgt aactgcctgc    60
gggaaaata                                                            69

<210> SEQ ID NO 62
<211> LENGTH: 81
<212> TYPE: DNA
<213> ORGANISM: Artificial Sequence
<220> FEATURE:
<223> OTHER INFORMATION: Codon-Optimized Thermoanearobacterium
      saccharolyticum signal sequence

<400> SEQUENCE: 62
atgctgagta aaatctacc tataaagata ctttcggttg taatagcatt tatattatgg    60
ctttatgtga tgggtgagaa g                                              81

<210> SEQ ID NO 63
<211> LENGTH: 111
<212> TYPE: DNA
<213> ORGANISM: Artificial Sequence
<220> FEATURE:
<223> OTHER INFORMATION: Codon-Optimized Thermoanearobacterium
      saccharolyticum signal sequence

<400> SEQUENCE: 63
atgaaaagat taaaaaaact catgttagtt ttgctatcga tgattctgat tatttcggca   60
tcagcttgtg gaactaactc aaacaattca agtagttcca atgcctctaa t           111

<210> SEQ ID NO 64
<211> LENGTH: 87
<212> TYPE: DNA
<213> ORGANISM: Artificial Sequence
<220> FEATURE:
<223> OTHER INFORMATION: Codon-Optimized Thermoanearobacterium
      saccharolyticum signal sequence

<400> SEQUENCE: 64
atgaaaaaaa cgtttaaatt gatattggtg ctgatgcttt cacttacact tgtttttgga   60
ttgacagcac caatacaggc agcttct                                       87

<210> SEQ ID NO 65
<211> LENGTH: 102
<212> TYPE: DNA
<213> ORGANISM: Artificial Sequence
<220> FEATURE:
<223> OTHER INFORMATION: Codon-Optimized Thermoanearobacterium
      saccharolyticum signal sequence

<400> SEQUENCE: 65
atgaagagta ttgtaaacag agttgtatct atcgttacag ctttaataat gatttttggg   60
acatcactgt tttcacaaca cataagggca tttgctgatg ac                     102

<210> SEQ ID NO 66
<211> LENGTH: 75
<212> TYPE: DNA
<213> ORGANISM: Artificial Sequence
<220> FEATURE:
<223> OTHER INFORMATION: Codon-Optimized Thermoanearobacterium
      saccharolyticum signal sequence

<400> SEQUENCE: 66
gtgaaaaagt ttgtttctat cttttttggca gttatgctga ttgcagctat tccagtgttt   60

```
ggtttagcgg ctcag                                                     75

<210> SEQ ID NO 67
<211> LENGTH: 75
<212> TYPE: DNA
<213> ORGANISM: Artificial Sequence
<220> FEATURE:
<223> OTHER INFORMATION: Codon-Optimized Thermoanearobacterium
      saccharolyticum signal sequence

<400> SEQUENCE: 67
atgttaaaaa aaataattgc aacaatgtta attttatcat tagttgtcat tccattcatg   60
gcttttgcag atgat                                                     75

<210> SEQ ID NO 68
<211> LENGTH: 75
<212> TYPE: DNA
<213> ORGANISM: Artificial Sequence
<220> FEATURE:
<223> OTHER INFORMATION: Codon-Optimized Thermoanearobacterium
      saccharolyticum signal sequence

<400> SEQUENCE: 68
gtgaagaaga tttatggatt gatattggta tttgttgtga tgttagctgt aattggaatt   60
gtgtacgctg attcg                                                     75

<210> SEQ ID NO 69
<211> LENGTH: 78
<212> TYPE: DNA
<213> ORGANISM: Artificial Sequence
<220> FEATURE:
<223> OTHER INFORMATION: Codon-Optimized Thermoanearobacterium
      saccharolyticum signal sequence

<400> SEQUENCE: 69
atgattagaa gtaagatgtt gaaaacagta agtatgttgc tggtgctagt gatgattata   60
acagcattta ctgcatgt                                                  78

<210> SEQ ID NO 70
<211> LENGTH: 120
<212> TYPE: DNA
<213> ORGANISM: Artificial Sequence
<220> FEATURE:
<223> OTHER INFORMATION: Codon-Optimized Caldocellum saccharolyticum
      signal sequence

<400> SEQUENCE: 70
atgagactaa aaacaaaaat aagaaagaaa tggttaagtg ttttatgcac agtagtgttt   60
ttgttgaata ttcttttat agctaatgtc acaatttac ctaaagttgg agcagctaca   120

<210> SEQ ID NO 71
<211> LENGTH: 96
<212> TYPE: DNA
<213> ORGANISM: Artificial Sequence
<220> FEATURE:
<223> OTHER INFORMATION: Codon-Optimized Caldocellum saccharolyticum
      signal sequence

<400> SEQUENCE: 71
atgaaaacag caaggctttt ggtgtgtttt gttttggtgt gctttatact tactacaacg   60
attttgcttg ataataacaa gggagaggca gcaatg                              96
```

<210> SEQ ID NO 72
<211> LENGTH: 87
<212> TYPE: DNA
<213> ORGANISM: Artificial Sequence
<220> FEATURE:
<223> OTHER INFORMATION: Codon-Optimized Clostridium Stercorarium signal sequence

<400> SEQUENCE: 72

```
atgagaaaat tttggtcttt tgcaataatt atatctttac ttgtaacagg attgtttatt      60
catactccta aagctgaggc agctggt                                         87
```

<210> SEQ ID NO 73
<211> LENGTH: 144
<212> TYPE: DNA
<213> ORGANISM: Artificial Sequence
<220> FEATURE:
<223> OTHER INFORMATION: Codon-Optimized Thermobifida fusca signal sequence

<400> SEQUENCE: 73

```
atgtcagtaa cagaacctcc tcctagaaga agaggaagac attcaagagc aagaagattt      60
cttacatcac ttggagcaac agcagcactt acagcaggaa tgcttggagt acctcttgca     120
acaggaacag cacatgcaga acct                                           144
```

<210> SEQ ID NO 74
<211> LENGTH: 75
<212> TYPE: DNA
<213> ORGANISM: Artificial Sequence
<220> FEATURE:
<223> OTHER INFORMATION: Codon-Optimized Caldocellum saccharolyticum signal sequence

<400> SEQUENCE: 74

```
atggtagtaa catttctttt tatacttgga gtagtatatg gagtaaaacc ttggcaagaa      60
gcaagagcag gatca                                                      75
```

<210> SEQ ID NO 75
<211> LENGTH: 87
<212> TYPE: DNA
<213> ORGANISM: Artificial Sequence
<220> FEATURE:
<223> OTHER INFORMATION: Codon-Optimized Caldocellum saccharolyticum signal sequence

<400> SEQUENCE: 75

```
atgaaaagaa atcttttag aatagtatca agagtagtac ttatagcatt tatagcatca      60
atatcacttg taggagcaat gtcatat                                        87
```

<210> SEQ ID NO 76
<211> LENGTH: 111
<212> TYPE: DNA
<213> ORGANISM: Artificial Sequence
<220> FEATURE:
<223> OTHER INFORMATION: Codon-Optimized Caldocellum saccharolyticum signal sequence

<400> SEQUENCE: 76

```
atgaaaagaa atcttttag aatagtatca agagtagtac ttatagcatt tatagcatca      60
atatcacttg taggagcaat gtcatatttt cctgtagaaa cacaagcagc a             111
```

<210> SEQ ID NO 77
<211> LENGTH: 2922

<212> TYPE: DNA
<213> ORGANISM: Artificial Sequence
<220> FEATURE:
<223> OTHER INFORMATION: Codon-Optimized Thermobifida fusca E1

<400> SEQUENCE: 77

```
atgcttagaa gacctagatc aagatcacct cttgtagcac ttacagcagc aacatgcaga      60
gtagcacttg gaggaacagc agtacctgca caagcagatg aagtaaatca aataagaaat     120
ggagatttt catcaggaac agcaccttgg tggggaacag aaaatataca acttaatgta     180
acagatggaa tgctttgcgt agatgtacct ggaggaacag taaatccttg gatgtaata     240
ataggacaag atgatatacc tcttatagaa ggagaatcat atgcatttc atttacagca     300
tcatcaacag tacctgtatc aataagagca cttgtacaag aacctgtaga accttggaca     360
acacaaatgg atgaaagagc acttcttgga cctgaagcag aaacatatga atttgtattt     420
acatcaaatg tagattggga tgatgcacaa gtagcatttc aaataggagg atcagatgaa     480
ccttggacat tttgccttga tgatgtagca cttcttggaa gagcagaacc tcctgtatat     540
gaacctgata caggacctag agtaagagta atcaagtag atatcttcc tcatggacct     600
aaaaaagcaa cagtagtaac agatgcaaca tcagcactta catgggaact tgcagatgca     660
gatggaaatg tagtagcatc aggacaaaca aaacctcatg gagcagattc atcatcagga     720
cttaatgtac atacagtaga ttttcatca tatacaacaa aggatcaga ttatacactt     780
acagtagatg gagaaacatc atatccttt gatatagatg aatcagtata tgaagaactt     840
agagtagatg cactttcatt ttattatcct caaagatcag gaatagaaat acttgattca     900
atagcacctg gatatggaag acctgcagga catataggag tacctcctaa tcaaggagat     960
acagatgtac cttgcgcacc tggaacatgc gattattcac ttgatgtatc aggaggatgg    1020
tatgatgcag agatcatgg aaaaatatgta gtaaatggag gaatatcagt acatcaaata    1080
atgtcaatat atgaaagatc acaacttgca gatacagcac aacctgataa acttgcagat    1140
tcaacactta gacttcctga aacaggaaat ggagtacctg atgtacttga tgaagcaaga    1200
tgggaaatgg aatttcttct taaaatgcaa gtacctgaag agaacctct tgcaggaatg    1260
gcacatcata aatacatga tgaacaatgg acaggacttc ctcttcttcc ttcagcagat    1320
cctcaaccta gatatcttca acctccttca acagcagcaa cacttaatct tgcagcaaca    1380
gcagcacaat gcgcaagagt atttgaacct tttgatgaag attttgcagc agaatgcctt    1440
gcagcagcag aaacagcatg ggatgcagca aaagcaaatc ctaatatata tgcacctgca    1500
tttggagaag gaggaggacc ttataatgat aataatgtaa cagatgaatt ttattgggca    1560
gcagcagaac tttttcttac aacaggaaaa gaagaatata gagatgcagt aacatcatca    1620
cctcttcata cagatgatga agaagtattt agagatggaa catttgattg gggatggaca    1680
gcagcacttg caagacttca acttgcaaca atacctaatg atcttgcaga tagagataga    1740
gtaagacaat cagtagtaga tgcagcagat atgtatcttg caaatgtaga acatcacct    1800
tggggacttg catataaacc taataatgga gtatttgtat ggggatcaaa ttcagcagta    1860
cttaataata tggtaaatact tgcagtagca tttgatctta caggagatac aaaatataga    1920
gatggagtac ttgaaggaat ggattataca tttggaagaa atgcacttaa tcaatcatat    1980
gtaacaggat atggagataa agattcaaga aatcaacatt caagatggta tgcacatcaa    2040
cttgatccta gacttcctaa tcctcctaaa ggaacacttg caggaggacc taattcagat    2100
tcaacaacat gggatcctgt agcacaatca aaacttacag gatgcgcacc tcaaatgtgc    2160
```

| | |
|---|---:|
| tatatagatc atatagaatc atggtcaaca aatgaactta caataaattg gaatgcacct | 2220 |
| ctttcatgga tagcatcatt tatagcagat caagatgatg caggagaacc tggaggagaa | 2280 |
| gaacctggac ctggagatga tgaaacacct ccttcaaaac ctggaaatct taaagcatca | 2340 |
| gatataacag caacatcagc aacacttaca tgggatgcat caacagataa tgtaggagta | 2400 |
| gtaggatata agtatcact tgtaagagat ggagatgcag aagaagtagg aacaacagca | 2460 |
| caaacatcat atacacttac aggactttca gcagatcaag aatatacagt acaagtagta | 2520 |
| gcatatgatg cagcaggaaa tctttcaaca cctgcaacag taacatttac aacagaaaaa | 2580 |
| gaagatgaaa cacctacacc ttcagcatca tgcgcagtaa catatcaaac aaatgattgg | 2640 |
| cctggaggat ttacagcatc agtaacactt acaaatacag atcaacacc ttgggattca | 2700 |
| tgggaactta gatttacatt tccttcagga caaacagtat cacatggatg gtcagcaaat | 2760 |
| tggcaacaat caggatcaga tgtaacagca acatcacttc cttggaatgg atcagtacct | 2820 |
| cctggaggag gatcagtaaa tataggattt aatggaacat ggggaggatc aaatacaaaa | 2880 |
| cctgaaaaat ttacagtaaa tggagcagta tgctcaatag ga | 2922 |

<210> SEQ ID NO 78
<211> LENGTH: 2265
<212> TYPE: DNA
<213> ORGANISM: Artificial Sequence
<220> FEATURE:
<223> OTHER INFORMATION: Codon-Optimized Thermobifida fusca E2

<400> SEQUENCE: 78

| | |
|---|---:|
| atgtcaccta gacctcttag agcacttctt ggagcagcag cagcagcact tgtatcagca | 60 |
| gcagcacttg catttccttc acaagcagca gcaaatgatt caccttttta tgtaaatcct | 120 |
| aatatgtcat cagcagaatg ggtaagaaat aatcctaatg atcctagaac acctgtaata | 180 |
| agagatagaa tagcatcagt acctcaagga acatggtttg cacatcataa tcctggacaa | 240 |
| ataacaggac aagtagatgc acttatgtca gcagcacaag cagcaggaaa ataacctata | 300 |
| cttgtagtat ataatgcacc tggaagagat tgcggaaatc attcatcagg aggagcacct | 360 |
| tcacattcag catatagatc atggatagat gaatttgcag caggacttaa aaatagacct | 420 |
| gcatatataa tagtagaacc tgatcttata tcacttatgt catcatgcat gcaacatgta | 480 |
| caacaagaag tacttgaaac aatggcatat gcaggaaaag cacttaaagc aggatcatca | 540 |
| caagcaagaa tatattttga tgcaggacat tcagcatggc attcacctgc acaaatggca | 600 |
| tcatggcttc aacaagcaga tatatcaaat tcagcacatg gaatagcaac aaatacatca | 660 |
| aattatagat ggacagcaga tgaagtagca tatgcaaaag cagtactttc agcaatagga | 720 |
| aatccttcac ttagagcagt aatagataca tcaagaaatg gaaatggacc tgcaggaaat | 780 |
| gaatggtgcg atccttcagg aagagcaata ggaacacctt caacaacaaa tacaggagat | 840 |
| cctatgatag atgcatttct ttggataaaa cttcctggag aagcagatgg atgcatagca | 900 |
| ggagcaggac aatttgtacc tcaagcagca tatgaaatgg caatagcagc aggaggaaca | 960 |
| aatcctaatc ctaatcctaa tcctacacct acacctacac ctacacctac acctcctcct | 1020 |
| ggatcatcag gagcatgcac agcaacatat acaatagcaa atgaatggaa tgatggattt | 1080 |
| caagcaacag taacagtaac agcaaatcaa aatataacag gatggacagt aacatggaca | 1140 |
| tttacagatg gacaaacaat aacaaatgca tggaatgcag atgtatcaac atcaggatca | 1200 |
| tcagtaacag caagaaatgt aggacataat ggaacacttt cacaaggagc atcaacagaa | 1260 |
| tttggatttg taggatcaaa aggaaattca aattcagtac ctacacttac atgcgcagca | 1320 |

```
tcagtaacag gatatggaga taaagattca agaaatcaac attcaagatg gtatgcacat    1380
caacttgatc ctagacttcc taatcctcct aaaggaacac ttgcaggagg acctaattca    1440
gattcaacaa catgggatcc tgtagcacaa tcaaaactta caggatgcgc acctcaaatg    1500
tgctatatag atcatataga atcatggtca acaaatgaac ttacaataaa ttggaatgca    1560
cctctttcat ggatagcatc atttatagca gatcaagatg atgcaggaga acctggagga    1620
gaagaacctg gacctggaga tgatgaaaca cctccttcaa aacctggaaa tcttaaagca    1680
tcagatataa cagcaacatc agcaacactt acatgggatg catcaacaga taatgtagga    1740
gtagtaggat ataaagtatc acttgtaaga gatggagatg cagaagaagt aggaacaaca    1800
gcacaaacat catatacact tacaggactt tcagcagatc aagaatatac agtacaagta    1860
gtagcatatg atgcagcagg aaatctttca acacctgcaa cagtaacatt tacaacagaa    1920
aaagaagatg aaacacctac accttcagca tcatgcgcag taacatatca aacaaatgat    1980
tggcctggag gatttacagc atcagtaaca cttacaaaata caggatcaac accttgggat    2040
tcatgggaac ttagatttac atttccttca ggacaaacag tatcacatgg atggtcagca    2100
aattggcaac aatcaggatc agatgtaaca gcaacatcac ttccttggaa tggatcagta    2160
cctcctggag gaggatcagt aaatatagga tttaatggaa catggggagg atcaaataca    2220
aaacctgaaa aatttacagt aaatggagca gtatgctcaa tagga                    2265
```

<210> SEQ ID NO 79  
<211> LENGTH: 1788  
<212> TYPE: DNA  
<213> ORGANISM: Artificial Sequence  
<220> FEATURE:  
<223> OTHER INFORMATION: Codon-Optimized Thermobifida fusca E3

<400> SEQUENCE: 79

```
atgtcaaaag taagagctac taatagaagg tcttggatga ggagaggatt agctgcagct      60
agcggcttag cacttggcgc ttctatggta gcatttgctg ctcctgctaa tgctgctggt     120
tgttcagtgg attacactgt aaattcttgg ggtacaggct ttactgctaa tgtcacaata     180
actaacttag gaagcgctat taacggttgg acgttggagt gggactttcc gggcaaccaa     240
caggtgacaa acttgtggaa tggaacttac acacaaagtg gtcagcatgt atcagtttct     300
aacgcaccat ataatgcatc tataccggct aatggaacgg tagagtttgg ttttaatggt     360
agttactcag gctctaacga tattcctagc tcatttaagt taaacggagt tacatgcgat     420
ggtagtgacg atccggatcc agagcctagt ccgtcaccat cacctagccc gagtccaact     480
gaccctgatg aaccgggcgg accaacaaat ccgcctacga atcctggtga aaaagttgac     540
aacccatttg aaggcgctaa gttgtatgtc aaccctgttt ggagcgcaaa agcagctgca     600
gagccaggcg gttcagctgt ggcaaacgaa agtactgcag tctggttgga tagaatagga     660
gcaatagagg gaaacgactc tccgacgact ggtagcatgg gattaagaga tcaccttgag     720
gaagctgtaa ggcaaagcgg tggcgaccct ttgacaatac aggtagtcat atacaattta     780
cctggtagag actgcgcagc tcttgcttca aatggcgaat tgggaccgga cgagttagac     840
agatacaagt cagagtatat tgaccctata gctgatatta tgtgggactt tgcagattac     900
gaaaacctta ggatagttgc tattatagag attgatagtt tacctaatct tgttacaaac     960
gtgggaggta acgtggaaac tgaactttgc gcatatatga gcagaatgg aggttatgtt    1020 aatggcgtag gctatgcttt aagaaaattg ggagaaatac ctaacgttta taactacata    1080
```

```
gacgcagctc atcatggctg gattggatgg gactcaaatt ttggcccatc tgtagatata    1140 tttatgagg cagctaacgc ttcaggtagt acagtggact acgttcacgg ctttataagt    1200
aacacggcaa attattctgc tacagtagaa ccttaccttg atgtgaacgg cactgtaaat    1260
ggacagttaa ttaggcagtc aaaatgggtc gattggaatc aatatgtgga cgaattgagt    1320
tttgttcagg atttaaggca agcattgatt gcaaagggtt ttagatcaga tattggaatg    1380
cttattgata catctaggaa cggttgggga ggcccaaata gacctacagg tccatcaagt    1440
agcactgatc ttaatacata tgtagacgag tctagaatag atagaaggat acatccgggt    1500
aactggtgca atcaagcagg cgctggtctt ggcgaaaggc caacggtaaa ccctgcacca    1560
ggtgttgatg cttatgtgtg ggttaaacct ccaggtgaat cagatggagc aagtgaggaa    1620
attcctaatg acgagggcaa gggttttgat agaatgtgcg atccaacata tcaaggaaat    1680
gctaggaacg gcaataaccc tagcggcgct ttgccaaatg ctcctattag tggccactgg    1740
ttttcagcac agtttaggga acttttagca aatgcatatc caccttta       1788

<210> SEQ ID NO 80
<211> LENGTH: 2640
<212> TYPE: DNA
<213> ORGANISM: Artificial Sequence
<220> FEATURE:
<223> OTHER INFORMATION: Codon-Optimized Thermobifida fusca E4

<400> SEQUENCE: 80
atgtcagtta cagaacctcc acctagaaga aggggcaggc atagtagagc aaggagattt      60
ttaactagcc ttggagctac tgctgcatta actgctggta tgcttggagt tccacttgct     120
acgggaacag ctcacgcaga gccggctttt aattatgctg aagctcttca aaaaagtatg     180 ttttttacg aagcacaaag atcaggcaag ttaccagaaa ataacagagt gtcttggaga     240
ggtgatagcg gtcttaatga cggcgcagac gttggattgg accttacggg cggatggtat     300
gacgctggtg accacgtaaa atttggtttt cctatggcat ttacagctac tatgcttgct     360
tggggtgcaa ttgaaagtcc agagggttac attagaagtg gtcagatgcc gtatcttaag     420
gataatctta gatgggtaaa cgattacttt ataaaagcac accctagccc aaacgtttta     480
tacgtccagg taggcgacgg cgacgcagat cataaatggt ggggaccggc tgaggttatg     540
ccaatggaaa gaccgagctt taaggttgat cctagttgtc ctggcagtga cgttgcagct     600
gaaacggctg cagctatggc agcttcaagt attgtctttg ctgacgatga ccctgcttac     660
gctgcaactt tggtgcaaca tgctaaacag ctttatacat ttgcagacac ttatagggga     720
gtatactcag attgcgtgcc agcaggagct ttttataatt cttggagtgg ataccaagat     780
gaacttgtct ggggagctta ttggttatac aaagcaacag gtgatgatag ctacttggca     840
aaggctgaat atgagtacga tttctcttca actgagcagc aaactgactt aaggagttat     900
aggtggacaa tagcttggga cgataaatct tacggaactt acgtacttct tgcaaaggag     960
acaggcaagc aaaaatacat agacgacgct aatagatggt tagactattg gacggtggga    1020
gtgaacggtc aaagggtacc ttactcacct ggcggtatgg ctgtgttgga cacttgggga    1080
gcacttaggt acgctgcaaa cacagctttt gtagcattag tttacgctaa agttattgac    1140
gatccagtta gaaagcaaag gtatcacgac tttgcagtga ggcagattaa ttacgcttta    1200
ggtgataatc aagaaactc aagttacgta gtgggctttg gaaacaatcc tccaaggaat    1260
ccacatcaca ggacggcaca tggctcttgg actgacagta tagcatctcc ggctgagaat    1320
aggcatgtgc tttatggcgc attagttgga ggccctggca gtccaaatga cgcatatact    1380
```

```
gatgatagac aagactacgt ggcaaacgaa gttgctacgg actacaacgc tggattttca    1440
agtgctcttg ctatgttagt agaagagtac ggcggtacgc cacttgctga ttttccacct    1500
acagaggaac cagatggacc ggagatattt gttgaagctc agattaatac accgggaacg    1560
acatttactg aaataaaagc aatgataaga aatcaaagcg gctggcctgc aagaatgtta    1620
gacaagggca cttttaggta ctggtttacg ttggacgagg gagtagatcc agcagatatt    1680
acagtatcta gtgcatacaa tcagtgcgca actccagaag atgttcacca cgttagcggt    1740
gaccttttat acgttgagat tgattgcaca ggtgagaaga ttttccagg cggtcagtct    1800 gaacatagga gagaggttca atttagaata gctggtggac ctggctggga tccatctaac    1860
gattggtcat ttcagggtat aggaaacgaa ttagctcctg caccatacat tgtcctttat    1920
gacgatggcg tcccggtgtg gggtacagca ccggaagagg gcgaagagcc gggaggtgga    1980
gagggcccag gcggtggcga ggaacctggt gaggacgtaa caccaccttc tgcacctggt    2040
agccctgctg tgagggacgt aacatctaca tcagcagtac ttacttggag tgcaagctct    2100
gatacgggag gctcaggagt tgctggctat gacgtatttt taagagcagg cacaggacaa    2160
gaacagaaag tgggcagtac aacaaggact tcttttactc ttacgggttt agaaccggat    2220
acgacttata tagcagctgt tgtggctaga gataatgctg gtaacgtatc tcaaagatca    2280
acagttagtt ttacaacgtt ggcagagaac ggcggaggcc cagatgcatc ttgcactgtc    2340
ggttattcta ctaacgattg ggattcagga tttacggcaa gtataaggat tacataccac    2400
ggtacggctc ctcttagcag ttgggagctt agttttactt ttccagctgg ccagcaagtg    2460
actcatggct ggaatgcaac atggagacag gacggtgctg ctgtcacggc tactcctatg    2520
agttggaata gctctttagc accgggcgca acggttgagg tgggatttaa tggttcatgg    2580
agtggaagca atactccacc aactgacttt actttgaatg gcgagccatg cgcacttgca    2640

<210> SEQ ID NO 81
<211> LENGTH: 1398
<212> TYPE: DNA
<213> ORGANISM: Artificial Sequence
<220> FEATURE:
<223> OTHER INFORMATION: Codon-Optimized Thermobifida fusca E5

<400> SEQUENCE: 81
atggcaaaga gcccagctgc aagaaaggga aggccacctg tagcagttgc tgtaacagca     60
gctcttgcat tattgatagc attactttct ccaggcgttg ctcaagcagc tggccttacg    120
gctacagtaa ctaaggagag ctcttgggat aatggatatt cagcaagcgt gacagttaga    180
aacgacacta gctcaactgt ctctcagtgg gaggtagtgt taacattgcc aggcggtact    240 acagttcac aagtatggaa tgctcagcat acttctagcg gaaatagtca cacatttact    300
ggtgtttcat ggaacagcac gattccgcct ggcggcacag caagttcagg ttttatagca    360
agtggatcag gtgaaccaac tcattgtaca ataaacggtg cacttgcga tgagggcagc    420 gaaccgggcg gcccaggtgg cccaggaacg ccaagcccag atccgggtac acaaccagga    480
acgggtactc cggttgagag atatggtaag gtccaagttt gcggaacgca gttgtgcgac    540
gagcacggca acccggtgca attgagagga atgagtactc acgtataca atggtttgat    600 cactgtttaa cggacagttc tttggatgca ttggcttacg attggaaggc agatattata    660
agacttagta tgtacattca agaggacggt tatgaaacta accctagagg atttactgac    720
aggatgcacc agttgattga catggctact gcaagggggct tatacgtgat agttgactgg    780
```

```
catatattga cgccaggcga ccctcactac aaccttgata gggctaaaac attttttgca    840
gaaatagctc agagacacgc aagtaagact aatgtcttgt acgagattgc taacgaacca    900
aatggagtgt cttgggcaag cattaagtct tacgctgagg aagttatacc tgtaataaga    960
cagagggacc cagactctgt cattatagtc ggaacaaggg gttggtcaag tcttggagtg   1020
agcgaaggca gcggaccggc agagattgct gcaaatcctg ttaacgcttc aaatattatg   1080
tatgcatttc acttttacgc tgcttctcac agagataatt atttaaacgc attgagggaa   1140
gctagcgaac ttttccggt ttttgtgact gagtttggaa cagaaacata cactggcgac    1200
ggagcaaacg attttcagat ggctgacaga tatattgact aatggcagaa agaaaaatt    1260 ggttggacaa agtggaatta ttctgatgat tttaggtcag gagctgtttt tcagccaggc   1320
acttgcgcaa gtggtggacc ttggagcggc tctagcttga aggcttcagg ccaatgggta   1380
aggagcaagt tgcagtct                                                  1398
```

<210> SEQ ID NO 82
<211> LENGTH: 1848
<212> TYPE: DNA
<213> ORGANISM: Artificial Sequence
<220> FEATURE:
<223> OTHER INFORMATION: Codon-Optimized Thermobifida fusca
      Endoglucanase

<400> SEQUENCE: 82

```
atgacacctt taactagaag gcttagggca ggagctgcag ctatagcaat tggtgcttca     60
gcattgatac cacttacatc tagcccggct gctgcttcag gcactgcaga ttggcttcat    120
acagacggaa atagaattgt agattcagct ggtaacgaag tttggttgac tggcgcaaat    180
tggtttggat ttaatacatc tgagagaatg tttcacggtt tatgggcagc taatatagag    240
gacataacaa gtgctatggc agagaggggc ataaatatgg tgagagtacc gattagtacg    300 caactttgt tagaatggaa gaatggtcag gctggtccct caggcgttaa cgaatatgtc    360
aaccctgagc ttgcaggaat gaatacactt gaggttttg attactggtt acaattatgc    420
gaagagtatg gtttgaaggt tatgttagat gtacattctg cagaagctga taactctggc    480
cactactatc ctgtgtggta taaggtgat ataactacag aagattttta tactgcatgg    540
gagtgggtta cagaaagata taagaataat gatacaatag tagcagctga tattaaaaac    600
gaaccgcatg gaaaggctaa tgagactcct agggcaaagt gggatggcag tacagatata    660
gacaatttta aacacgtttg tgagactgct ggtaaaagga ttcttgcaat aaacccaaac    720
atgttgattt tgtgtgaagg tataagagata taccctaagg acggccagga ttggtcatct    780
acagacggaa gggattacta ctcaacttgg tggggtggaa atcttagagg cgttgcagac    840
cacccagtag acttaggagc acaccaagat cagttggtat actcacctca tgattatggc    900
ccatctgttt ttgaacaacc gtggtttgaa ggcgagtgga acagacagac tcttacagag    960
gacgtgtgga ggccaaattg gttatatat cacgaagatg atatagctcc acttcttatt    1020
ggtgagtggg gaggcttttt agacggcggt gacaacgaga gtggatgac tgcattgaga   1080 tctcttataa ttgatgagaa gatgcatcac acatttgggg ctttaaatcc gaactcagga   1140
gatactggtg gattgcttaa ttatgattgg acaaatgggg atgaagcaaa atacgctttt    1200
ttaaagcctg cattgtggca agatgctaac ggaaaatttg tgggattgga tcacgacgtc    1260
cctttgggag cgtgggatc aactacaggt gttagtctta atcagtatta cggtggaggt    1320
ggaccttcac agcctccaac tgaaccgact gaaccgccta ctgaaccaac ggaacctccg   1380
```

| acagaaccga cggagcctcc agcaaatcct acaggcgctt tagaagtata ctataggaat | 1440 |
| aactctttag cagctgatga ctcacaaatt gcaccgggct taagattggt taatactgga | 1500 |
| tcatctacgg tagaccttgc tgatgtggaa attcattatt attttacaaa tgaacctggc | 1560 |
| ggtactttac agtttacatg cgattgggct caagttggct cgctaatgt aaatgcatct | 1620 |
| tttacatcac ttagcgcacc aggcgctgat acatcacttg tgcttacatt gtctggcagt | 1680 |
| cttgctcctg gtgcaagcac agagcttcaa ggcagaatac acacagcaaa ttgggcaaat | 1740 |
| tttgacgagt cagatgacta tagtaggga acgaatactg actgggaatt gagcgaagtt | 1800 |
| ataactgcat atcttggagg cacattagta tggggtacac cgcctgct | 1848 |

<210> SEQ ID NO 83
<211> LENGTH: 2952
<212> TYPE: DNA
<213> ORGANISM: Artificial Sequence
<220> FEATURE:
<223> OTHER INFORMATION: Thermobifida fusca Beta-1,4-exocellulase E6

<400> SEQUENCE: 83

| atgagatcac ttctttcacc tagaagatgg agaacacttg catcaggagc acttgcagca | 60 |
| gcacttgcag cagcagtact ttcacctgga gtagcacatg cagcagtagc atgctcagta | 120 |
| gattatgatg attcaaatga ttggggatca ggatttgtag cagaagtaaa agtaacaaat | 180 |
| gaaggatcag atcctataca aaattggcaa gtaggatgga cattcctgg aaatcaacaa | 240 |
| ataacaaatg gatggaatgg agtattttca caatcaggag caaatgtaac agtaagatat | 300 |
| cctgattgga atcctaatat agcacctgga gcaacaatat catttggatt tcaaggaaca | 360 |
| tattcaggat caaatgatgc acctacatca tttacagtaa atggagtaac atgctcagga | 420 |
| tcacaacctg caaatcttcc tcctgatgta acacttacat cacctgcaaa taattcaaca | 480 |
| tttcttgtaa atgatcctat agaacttaca gcagtagcat cagatcctga tggatcaata | 540 |
| gatagagtag aatttgcagc agataataca gtaataggaa tagatacaac atcacccttat | 600 |
| tcatttacat ggacagatgc agcagcagga tcatattcag taacagcaat agcatatgat | 660 |
| gatcaaggag caagaacagt atcagcacct atagcaataa gagtacttga tagagcagca | 720 |
| gtaatagcat cacctcctac agtaagagta cctcaaggag aacagcaga ttttgaagta | 780 |
| agactttcaa atcaacctcc aggaaatgta acagtaacag tagcaagaac atcaggatca | 840 |
| tcagatctta cagtatcatc aggatcacaa cttcaattta catcatcaaa ttggaatcaa | 900 |
| cctcaaaaag taacaatagc atcagcagat aatggaggaa atcttgcaga agcagtatt | 960 |
| acagtatcag cacctggaca tgattcagca gaagtaacag taagagaaat agatcctaat | 1020 |
| acatcatcat atgatcaagc atttcttgaa caatatgaaa aaataaaaga tcctgcatca | 1080 |
| ggatatttta gagaatttaa tggacttctt gtaccttatc attcagtaga acaatgata | 1140 |
| gtagaagcac tgatcatgg acatcaaaca acatcagaag cattttcata ttatctttgg | 1200 |
| cttgaagcat attatggaag agtaacagga gattggaaac ctcttcatga tgcatgggaa | 1260 |
| tcaatggaaa catttataat acctggaaca aaagatcaac ctacaaattc agcatataat | 1320 |
| cctaattcac ctgcaacata tacctgaa caacctaatg cagatggata tccttcacct | 1380 |
| cttatgaata atgtacctgt aggacaagat cctcttgcac aagaactttc atcaacatat | 1440 |
| ggaacaaatg aaatatatgg aatgcattgg cttcttgatg tagataatgt atatggatt | 1500 |
| ggattttgcg gagatggaac agatgatgca cctgcatata taaatacata tcaaagagga | 1560 |
| gcaagagaat cagtatggga aacaatacct catccttcat gcgatgattt tacacatgga | 1620 |

-continued

```
ggacctaatg gatatcttga tcttttaca gatgatcaaa attatgcaaa acaatggaga      1680
tatacaaatg cacctgatgc agatgcaaga gcagtacaag taatgttttg ggcacatgaa      1740
tgggcaaaag aacaaggaaa agaaaatgaa atagcaggac ttatggataa agcatcaaaa      1800
atgggagatt atcttagata tgcaatgttt gataaatatt ttaaaaaaat aggaaattgc      1860
gtaggagcaa catcatgccc tggaggacaa ggaaaagatt cagcacatta tcttctttca      1920
tggtattatt catggggagg atcacttgat acatcatcag catgggcatg gagaatagga      1980
tcatcatcat cacatcaagg atatcaaaat gtacttgcag catatgcact tcacaagta      2040 cctgaacttc aacctgattc acctacagga gtacaagatt gggcaacatc atttgataga      2100
caacttgaat tcttcaatg gcttcaatca gcagaaggag gaatagcagg aggagcaaca      2160
aattcatgga aggatcata tgatacacct cctacaggac tttcacaatt ttatggaatg      2220
tattatgatt ggcaacctgt atggaatgat cctccttcaa ataattggtt tggattcaa      2280 gtatggaata tggaaagagt agcacaactt tattatgtaa caggagatgc aagagcagaa      2340
gcaatacttg ataaatgggt accttgggca atacaacata cagatgtaga tgcagataat      2400
ggaggacaaa attttcaagt accttcagat cttgaatggt caggacaacc tgatacatgg      2460
acaggaacat atacaggaaa tcctaatctt catgtacaag tagtatcata ttcacaagat      2520
gtaggagtaa cagcagcact tgcaaaaaca cttatgtatt atgcaaaaag atcaggagat      2580
acaacagcac ttgcaacagc agaaggactt cttgatgcac ttcttgcaca tagagattca      2640
ataggaatag caacacctga acaaccttca tgggatagac ttgatgatcc ttgggatgga      2700
tcagaaggac tttatgtacc tcctggatgg tcaggaacaa tgcctaatgg agatagaata      2760
gaacctggag caacatttct ttcaataaga tcattttata aaaatgatcc tctttggcct      2820
caagtagaag cacatcttaa tgatcctcaa aatgtacctg cacctatagt agaaagacat      2880
agattttggg cacaagtaga aatagcaaca gcatttgcag cacatgatga acttttggga      2940
gcaggagcac ct                                                          2952
```

<210> SEQ ID NO 84
<211> LENGTH: 2993
<212> TYPE: DNA
<213> ORGANISM: Artificial Sequence
<220> FEATURE:
<223> OTHER INFORMATION: Condon-Optimized Thermobifida fusca Cellulose
1,4-beta-cellobiosidase/endoglucanase. Glycosyl Hydrolase family
9

<400> SEQUENCE: 84

```
atgggagcac ttccttggtg ggcatcagca gtaagatcat catcacaatt tgaatcacct       60
tatggaagaa catcagtact tagaagacct agatcaagat cacctcttgt agcacttaca      120
gcagcaacat gcgcagtagc acttggagga acagcagtac ctgcacaagc agatgaagta      180
aatcaaataa gaaatggaga ttttcatca ggaacagcac cttggtgggg aacagaaaat      240
atacaactta atgtaacaga tggaatgctt tgcgtagatg tacctggagg aacagtaaat      300
ccttgggatg taataatagg acaagatgat atacctctta tagaaggaga atcatatgca      360
ttttcattta cagcatcatc aacagtacct gtatcaataa gagcacttgt acaagaacct      420
gtagaaacct tggacaacaca atggatgaa agagcacttc ttggacctga agcagaaaca      480
tatgaatttg tatttacatc aaatgtagat tgggatgatg cacaagtagc atttcaaata      540
ggaggatcag atgaaccttg gacattttgc cttgatgatg tagcacttct tggaggagca      600
```

```
gaacctcctg tatatgaacc tgatacagga cctagagtaa gagtaaatca agtaggatat      660
cttcctcatg gacctaaaaa agcaacagta gtaacagatg caacatcagc acttacatgg      720
gaacttgcag atgcagatgg aaatgtagta gcatcaggac aaacaaaacc tcatggagca      780
gattcatcat caggacttaa tgtacataca gtagattttt catcatatac aacaaaagga      840
tcagattata cacttacagt agatggagaa acatcatatc cttttgatat agatgaatca      900
gtatatgaag aacttagagt agatgcactt tcattttatt atcctcaaag atcaggaata      960
gaaatacttg attcaatagc acctggatat ggaagacctg caggacatat aggagtacct     1020
cctaatcaag gagatacaga tgtaccttgc gcacctggaa catgcgatta ttcacttgat     1080
gtatcaggag gatggtatga tgcaggagat catggaaaat atgtagtaaa tggaggaata     1140
tcagtacatc aaataatgtc aatatatgaa agatcacaac ttgcagatac agcacaacct     1200
gataaacttg cagattcaac acttagactt cctgaaacag gaaatggagt acctgatgta     1260
cttgatgaag caagatggga aatggaattt cttcttaaaa tgcaagtacc tgaaggagaa     1320
cctcttgcag gaatggcaca tcataaaata catgatgaac aatggacagg acttcctctt     1380
cttccttcag cagatcctca acctagatat cttcaacctc cttcaacagc agcaacactt     1440
aatcttgcag caacagcagc acaatgcgca agagtatttg aaccttttga tgaagatttt     1500
gcagcagaat gccttgcagc agcagaaaca gcatgggatg cagcaaaagc aaatcctaat     1560
atatatgcac ctgcatttgg agaaggagga ggaccttata atgataataa tgtaacagat     1620
gaattttatt gggcagcagc agaacttttt cttacaacag gaaagaaga atatagagat      1680 gcagtaacat catcacctct tcatacagat gatgaagaag tatttagaga tggagcattt     1740
gattggggat ggacagcagc acttgcaaga cttcaacttg caacaatacc taatgatctt     1800
gcagatagag atagagtaag acaatcagta gtagatgcag cagatatgta tcttgcaaat     1860
gtagaaacat caccttgggg acttgcatat aaacctaata atggagtatt tgtatgggga     1920
tcaaattcag cagtacttaa taatatggta atacttgcag tagcatttga tcttacagga     1980
gatacaaaat atagagatgg agtacttgaa ggaatggatt atatatttgg aagaaatgca     2040
cttaatcaat catatgtaac aggatatgga gataaagatt caagaaatca acattcaaga     2100
tggtatgcac atcaacttga tcctagactt cctaatcctc ctaaaggaac acttgcagga     2160
ggacctaatt cagattcaac aacatgggat cctgtagcac aatcaaaact tacaggatgc     2220
gcacctcaaa tgtgctatat agatcatata gaatcatggt caacaaatga acttacaata     2280
aattggaatg cacctctttc atggatagca tcatttatag cagatcaaga tgatgcagga     2340
gaacctggag gagaagaacc tggacctgga gatgatgaaa cacctccttc aaaacctgga     2400
aatcttaaag catcagatat aacagcaaca tcagcaacac ttacatggga tgcatcaaca     2460
gataatgtag gagtagtagg atataaagta tcacttgtaa gagatggaga tgcagaagaa     2520
gtaggaacaa cagcacaaac atcatataca cttacaggac tttcagcaga tcaagaatat     2580
acagtacaag tagtagcata tgatgcagca ggaaatcttt caacacctgc aacagtaaca     2640
tttacaacag aaaaagaaga tgaaacacct acaccttcag catcatgcgc agtaacatat     2700
caaacaaatg attggcctgg aggatttaca gcatcagtaa cacttacaaa tacaggatca     2760
acaccttggg attcatggga acttagattt acatttcctt caggacaaca gtatcacatg     2820
gatggtcagc aaattggcaa caatcaggat cagatgtaac agcaacatca cttccttgga     2880
atggatcagt acctcctgga ggatcagtaa atataggatt taatgaaaca tggggaggat     2940
caaatacaaa acctgaaaaa tttacagtaa atggagcagt atgctcaata gga            2993
```

<210> SEQ ID NO 85
<211> LENGTH: 2526
<212> TYPE: DNA
<213> ORGANISM: Artificial Sequence
<220> FEATURE:
<223> OTHER INFORMATION: Codon-Optimized Caldicellulosiruptor
     kristjanssonii

<400> SEQUENCE: 85

| | | | | | |
|---|---|---|---|---|---|
| aaaacagcaa | ggcttttggt | gtgttttgtt | ttggtgtgct | ttatacttac | tacaacgatt | 60 |
| ttgcttgata | taacaaggg | agaggcagca | atgtacaact | atggtgaggc | tttgcaaaag | 120 |
| gctattatgt | tttacgagtt | tcagatgtca | ggcaagttgc | cgaaatggat | aaggaataac | 180 |
| tggaggggag | actcaggcct | taacgacggc | aaagacaata | agatagacct | tactggaggt | 240 |
| tggtatgacg | ctggcgatca | tgtcaagttt | aacttgccaa | tgagctatac | tgcaacaatg | 300 |
| ttagcatggg | ctgtctacga | atataaggac | gcttttgtga | aagcggaca | attacagcac | 360 |
| attcttaacc | aaatagagtg | ggtaaacgac | tattttgtga | agtgccaccc | tgaaaaatac | 420 |
| gtgtactatt | accaagtggg | tgatggcggt | aaagatcacg | catggtgggg | accggctgag | 480 |
| gttatgccta | tggaaaggcc | ttcatataaa | gtgacgaaaa | ctaatcctgg | ctcaactgta | 540 |
| gttgcagaaa | cggctgcagc | tttagctgct | ggtagtatag | ttattaagca | aagaaatagt | 600 |
| aagaaagcta | ggatttatct | taagcacgca | aaggagttgt | atgactttgc | agcagagaca | 660 |
| aagtctgacg | ctggttatac | tgcagctaat | ggctattaca | atagctggtc | aggattttgg | 720 |
| gacgaattaa | gttgggcagc | agtatggttg | tacttggcaa | cgggtgataa | atactattta | 780 |
| agcgaggcta | agaaatatgt | gagcaattgg | ccaaaaattg | ctggttcaaa | tacgattgac | 840 |
| tataggtggg | ctcattgctg | ggatgacgta | cactatggag | cagcattgct | tttagcaaaa | 900 |
| ataacagatg | agaacacgta | taaacagatt | gtcgaaaagc | accttgatta | ttggactatt | 960 |
| ggttaccagg | gacaaaggat | aaaatacaca | ccaaagggcc | ttgcttggtt | agatcagtgg | 1020 |
| ggtagtttga | gatacgcaac | tacgacagct | tttttagctt | ttgtgtattc | agactggaaa | 1080 |
| ggatgtccta | gttcaaagaa | gaaagtgtac | agaaaatttg | gagaaggtca | agtgaactac | 1140 |
| gctttgggca | gctcaggtag | gagttttgtt | gtgggatttg | gaaaaaaccc | tccaaaaaga | 1200 |
| cctcatcata | gaactgctca | tggcagttgg | gcaaattctc | aatcagaacc | acctatcac | 1260 |
| aggcatattt | tgtatggtgc | tttggtgggc | ggtccaggtt | tagatgatag | ctattcagac | 1320 |
| gatgttggaa | actacgtaaa | taacgaagtt | gcttgcgatt | acaatgctgg | ctttgtcgga | 1380 |
| gctttagcta | aaatgtactt | gttatacggt | ggaaaaccta | taccaaactt | taaggcaata | 1440 |
| gaaaagccat | caaatgacga | gttttttgtt | gaagcaggca | ttaatgcaag | cggttcaaat | 1500 |
| tttgttgaga | ttaaggctat | tgtatataac | caaagtggat | ggccagcaag | agttacgaac | 1560 |
| aatcttaagt | ttaggtacta | cataaaacctt | tctgagattg | tatcacaagg | ttataaacct | 1620 |
| tcacaaataa | gccttaacac | aaattacaac | cagggagcta | agtatcagg | accatatgtt | 1680 |
| gtagattcta | agaaacatct | ttattacatt | cttatagatt | ttagtggtac | gccgatttac | 1740 |
| cctggtggac | aggacaagta | caaaaaagag | gtacagttta | gaattgcagc | tcctcagaac | 1800 |
| gcaagatggg | ataactcaaa | cgactatagc | tttaaggac | ttgataaaac | aggtggcggc | 1860 |
| caagtcataa | agacgaagta | cattccattg | tacgacggta | aaaaattagt | ttggggaata | 1920 |
| gagccgaata | ctaagaattt | aacgcttagg | acaagccaga | taccggcaaa | tggtgatgca | 1980 |
| gacaaaaaga | gcaaaacgat | tctttctaag | aatacgagct | cagctaagac | aagttctaaa | 2040 |

| | |
|---|---|
| cagaacaagg aagtaaagaa cgtggtgaag gtactttaca aaaatatgga aattaacaag | 2100 |
| acgagtaaca gcattaggtt atacttgaag ataattaata acagccagga aacgatagat | 2160 |
| ttgagcaagg tgaaaattag atattggtac actgctgacg atggagtcat gaaacagagc | 2220 |
| gcagtatgtg actgggcaca ataggtgct gtcaatgtaa catttagatt tgtgaggtta | 2280 |
| aggaaagcag tggcaaaagc tgatcattac ttagagattg gttttacaaa caacgctggt | 2340 |
| aaaattcagc ctggaaaaga ctcaggcgat attcagctta ggtttaataa gtcaaactgg | 2400 |
| ggcaactacg accaatcaaa cgactggtct tgggtacagt ctatgacaag ttacggagaa | 2460 |
| aataaaaaga taactttgta tattgacggc aagttggtgt ggggacagga gccgacaaaa | 2520 |
| gacaca | 2526 |

<210> SEQ ID NO 86
<211> LENGTH: 2265
<212> TYPE: DNA
<213> ORGANISM: Artificial Sequence
<220> FEATURE:
<223> OTHER INFORMATION: Codon-Optimized Caldicellulosiruptor
      kristjanssonii

<400> SEQUENCE: 86

| | |
|---|---|
| atgaaaaaaa taatattaaa gtcaggaata cttttgttag tggtaatttt gatagtgtct | 60 |
| atacttcaaa ttttaccggt gtttgcacag agcacaccat atgaaaagga gaagtaccct | 120 |
| catcttttag gtaaccaggc agtcaaaaag ccatctgtgg caggcagact tcagataatt | 180 |
| gaaaaaacg gcaagaaata ccttgctgac cagaagggtg agattattca acttaggggc | 240 |
| atgagtactc acggattaca atggtatggc gatataatta caaaaacgc ttttgaggct | 300 |
| ttaagcaagg actgggaatg taacgtagtg aggttagcaa tgtacgtggg cgagggaggt | 360 |
| tatgctagta atccgtctat aaaacagaaa gtgattgagg cataaaaatt ggctatagaa | 420 |
| aacgacatgt atgtgattgt ggactggcat gttttaaacc caggagatcc aaacgctgag | 480 |
| atatataagg gcgctaagga ttttttttaag gagattgcaa cgagttttcc aaacgattat | 540 |
| cacataattt atgagctttg caacgagcct aacccaaatg agccaggtgt agaaaattca | 600 |
| ttagacggat ggaagaaggt aaaagcatat gctgagccga ttataaaaat gttgagaagc | 660 |
| cttggcaatc aaaatataat tatagttggc agtccaaatt ggagtcaaag acctgatttt | 720 |
| gctatacagg atcctattaa cgacaaaaac gtgatgtaca gcgttcactt ttattctggc | 780 |
| actcataagg tggatggtta tgtgtttgag aatatgaaga atgcttttga gaatggcgta | 840 |
| ccaatatttg tcagcgaatg gggaacgtct ttagcttcag gtgatggagg cccttattta | 900 |
| gatgaagctg ataaatggtt agagtacctt aacagcaatt atatttcttg ggtgaattgg | 960 |
| agtctttcaa caagaacga gactagcgct gcatttgtgc catatgtttc tggtatgcac | 1020 |
| gatgctacga gcttggatcc tggagatgac aaagtttggg atataaaaga actttcaata | 1080 |
| agcggcgagt acgtgagagc aagaataaag gcattgctt acaagccaat tgagaggaat | 1140 |
| agtcagatta agagggaga acagcacct cttggcgaaa aagtccttcc gtcaactttt | 1200 |
| gaggatgata agacaagg ttgggattgg acggcccga cgcgtcaa gggccctata | 1260 |
| actatagaat caattaatgg aagtaaagtg cttagttttg aggttgaata tcctgagaag | 1320 |
| aaaccgcagg atggctgggc tacagcagct agacttatat aaaagaaat aaacgcaaaa | 1380 |
| agggaggaca caaatatttt ggcatttgac ttttacatta agcctgagag ggtgtctaaa | 1440 |
| ggaatgattc agatatttct tgcttttagc ccaccgagtt taggatactg ggctcaagtt | 1500 |

```
caggactcat ttaacataga cttgcttaag ttgagttctg caagaaaaac tgaagaggga   1560
ttgtacaagt ttaacgtgtt ttttgacctt gacaagattc aggatggtaa agtcctttca   1620
ccagatacat tacttaggga tattataatt gtaatagctg acggtaacag cgactttaag   1680
ggaaaaatgt ttattgacaa cgtgaggttt acaaatatat tgtttgagga tattagcttt   1740
gagagcagcc tttacgacac tgtgagcaag ttgtatagca agagagtcat taagggcaca   1800
agcgcattta agtaccttcc tgacagatct attacgaggg cagagtttgc agctttatgc   1860
gtaagaacat gaaccttaa gatagagaag tacgacggta gatttagcga cgtaaagtca   1920
agcgcttggt actcagatgt ggtctataca gcatacaaga acggtctttt tggacaagaa   1980
aaaaacaagt ttttttcctga gaggataatg aagagggaag aggtggctgc attagcaatt   2040
gaagtttata gaggttgac gggcaagata gaggtgagct tagacgatat acaaattgca   2100
gatgagggat taattaaccc tcagtatagg gaatctgtga aacttgcagt gaagttggga   2160
atatttgaat tatattcaga cggtacattt gcaccgggca agagtataag cagaggcgag   2220
gtcgcaacaa ttttttacaa tttacttaac ttggctggta aaatt                  2265

<210> SEQ ID NO 87
<211> LENGTH: 2067
<212> TYPE: DNA
<213> ORGANISM: Artificial Sequence
<220> FEATURE:
<223> OTHER INFORMATION: Codon-Optimized Caldicellulosiruptor
      kristjanssonii

<400> SEQUENCE: 87
atgaaaggat gcgtatatgg aaaacttaaa agatttttcag cacttatact tgcaatactt   60
tttcttgtag caatacttat aggaatagga tcagcaaaag tatcaaaagt atcaggagca   120
acaaaaaaat catttatgga atttaatttt gaaataaaac ttgcaacacc ttttaaagca   180
tcaggaaaat caatggtact taaaatagat tcaacaacag cagcagaagg atcattttca   240
cttcttgcat caggaagaaa acaaatagat gatggagtac ttcttgatgt aacaaatctt   300
atagattatt caaatgaata tacaatagca ctttatgtat atcataaatc atcaaaactt   360
caaagatttg tagtatcatc agaaatagaa acaaatcag gaaagaaaaa taaacttctt   420
tgcgaaaaag taataatacc taataattgg aaaaaacttg atacatcact taatcttaca   480
gaacttaaag gaataaaaaa agtatggctt aaaatatatg tacctacatc aacaacaaat   540
ttttatatag atcttttac acttaaagta tcagataatt cacatcttat aaaatttgaa   600
tcatttgaag ataaatcaat agcaggattt ataccctaag ataaaaaatg caaactttca   660
gtatcaaaag aaaagcata tcaaggaaca tattcaataa acttcaaca acagcaaaa   720 aaacaaaata caacagtaac acttcctgta aaaggaacat ttgaaaaagg aaaatcatat   780
tcaatatcat tttatgtata tcaacctata cttaaatcac ttaatcttgc aataggagta   840
agatttcttg aaaatggaaa aaatacaaaa gaaatagtac ttggaaaagt aacagtacct   900
agaaataaat ggacagaaac atttgcatca tatacacctt cacttgattc aaaagtaaaa   960
gattttgtaa tatttataaa acctctttca gatgtatcat attattatct tgataatttt   1020
acaatatcag atgatggatg gtattcagca gtacctgatc ttgatcttcc ttcactttca   1080 gaaaatatata agattatttt taagtagga gtagcagtac cttataaagc acttacaaat   1140
cctgtagatg tagcatttat aaaaagacat tttaattcaa taacagcaga aaatgaaatg   1200
aaacctgaag cacttgaacc ttatgaagga acatttaatt tttcaatagc agatgaatat   1260
```

```
cttgattttt gcaaaaaaaa taatatagca ataagaggac atacacttgt atggcatcaa    1320
caaacacctt catggttttt tgaaaatcct caaacaggag aaaaacttac aaattcagaa    1380
aaagataaaa aaatacttct tgaaagactt aaaaaatata tacaaacagt agtatcaaga    1440
tataaaggaa gaatatatgc atgggatgta gtaaatgaag caatagatga aaatcaacct    1500
gatggattta gaagatcaga ttggtttaat atacttggac ctgaatatat agaaaaagca    1560
tttatatatg cacatcaagc agatcctaat gcacttcttt tttataatga ttattcaaca    1620
gaaaatcctg taaaaagaga atatatatat aaacttataa aagatcttaa agaaaaagga    1680
gtacctatac atggagtagg acttcaatgc catataacag tatcatggcc ttcagtagaa    1740
gaagtagaaa gaacaataaa acttttttca tcaatacctg gaataaaaat acatgtaaca    1800
gaaatagata tatcagtagc aaaagaattt ggagaagata tagatgaaga aacaaaaaga    1860
tatcttctta tacaacaagc aagaaaactt aaagatcttt ttgaagtatt taaaaaatat    1920
aaaaatgtag taacatcagt atcatttttgg ggacttaaag atgattattc atggcttaaa    1980
ggagattttc ctcttctttt tgataaagat tatcaaccta aatttgcatt ttggtcactt    2040
atagatcctt cagtagtacc tgaagaa                                        2067

<210> SEQ ID NO 88
<211> LENGTH: 1116
<212> TYPE: DNA
<213> ORGANISM: Artificial Sequence
<220> FEATURE:
<223> OTHER INFORMATION: Codon-Optimized Caldicellulosiruptor
      kristjanssonii

<400> SEQUENCE: 88
atgaaaagaa aacttatatc acttatactt gtatttatat ttacacttgc acttcttctt      60
cctgcatatg cagatcaaaa tcttcctgga acatcatcat cacaaacagt aacatcatca     120
acatatgata caacacaaac acaaacatat caaacaacac aaaatacaac atattccaca     180
acatataata cacaaaattc aacacctaca cctacaccta cacctacacc tacacctata     240
acaacaccta cacctacacc tacacctaca cctacaacag taacatcaac atattcatca     300
acatattcat caaattcaac aataaatgta ataccttcta tcaaatgta ataaataaaa     360 cttaaagaac tcaaaaaact tacaaaagaa caaaaaaaaa caataatatc acttatatgg     420
caaataaatc aacttagagt aaaatttaat aaaatataatg cagaagtaaa ttatcttaga     480
gcaaaaataa atgcatatgt acaagcagca aaaagatatg ataaaatatt ttttaatcaa     540
gaaatgaata aaataataaa tgaagtaaat aaaacaatat cacaacttca aaagaacctt     600
aataaaaaaa attattcatc atcaaaagta gcagaactta ataaacaact taatcaaaaa     660
cttaatgaac ttaaagtata tgaagaagta tataaaaatc aacaacaaca agcagtagat     720
caagcagtat atcaaataaa acaatttgta gatcaaatac aacctacagt atcacaaaaa     780
gtatatcaaa taaatacaat agataaacaa ataaaagtaa aactttatga atatcatcaa     840
atagcaaaaa catcagatta taataaaatg gtatcaatac ttaatgaagt agtatcactt     900
tatcaaacaa aagtaaatac aatatcagaa ataaaaaatc tttatacaga tatactttca     960
aaaatagaaa atatagtaaa aaattcactt aatatgccta aaaatatat acaacctatg    1020 caagaaaaaa aaataacaat acctggaaaa ggaaattcaa aaatagaaat agaaataaaa    1080
aaaaatcctc aacaacctca aaaaggaaaa aaaaaa                             1116
```

<210> SEQ ID NO 89
<211> LENGTH: 666
<212> TYPE: DNA
<213> ORGANISM: Artificial Sequence
<220> FEATURE:
<223> OTHER INFORMATION: Codon-Optimized Caldicellulosiruptor
      kristjanssonii

<400> SEQUENCE: 89

```
ctttcaccta cacctacaaa aacacctaca cctacatcaa cacctgcacc tacacaaaca      60
cctacagtaa cacctacacc tacacctaat gcaggaggaa tacttataat aacagataca     120
atagtagtaa aagcaggaca acatatgat ggaaaaggag taaaaataat agcacaagga      180
atgggagatg gatcacaatc agaaaatcaa aaacctatat ttaaacttga aaaggagca      240 aaacttaaaa atgtaataat aggagcacct ggatgcgatg aatacattg ctatggagat      300 aatgtaatag aaaatgtaat gtgggaagat gtaggagaag atgcacttac agtaaaagga     360
gaaggagtag tagaagtaat aggaggatca gcaaaagaag cagcagataa agtatttcaa     420
cttaatgcac cttgcacatt taaagtaaaa aattttacag caacaaatat aggaaaactt     480
gtaagacaaa atggaggaac aacatttaaa gtagtaatat atcttgaaaa tgtaacactt     540
aataatgtaa aatcatgcgt agcaaaatca gattcacctg tatcagaact tggtatcat      600 aatcttgtag taaataattg caaaacactt tttgaattcc cttcacaatc acaaatacat     660
caatat                                                               666
```

<210> SEQ ID NO 90
<211> LENGTH: 2310
<212> TYPE: DNA
<213> ORGANISM: Artificial Sequence
<220> FEATURE:
<223> OTHER INFORMATION: Codon-Optimized Caldicellulosiruptor
      kristjanssonii

<400> SEQUENCE: 90

```
gtgagcatag agaaaagagt taatgatctt ttgcagaaaa tgactattga ggagaaggtg      60
tatcagttga cttctatatt agtccaagat attcttgaaa atgacaagtt tagcccgcag     120
aaagctaagg aaaaaatacc taacggaatt ggtcagataa caaggcttgc tggcgcaagt     180
aatttgagcc cagaagaggc agcaaaaact gctaatgaaa ttcaaaagtt tcttatagag     240
aacacaaggt tgggaatacc agctatgatt catgaggagt cttgttcagg tttatggct     300 aagggcgcaa ctgtatttcc tcagtctatt ggagttgctt gcacatttga caacgaaatt     360
gtggaagaac ttgcaaaagt gataaggaca cagatgaaac tgtgggtgca caccaggct      420 ttggcaccat taattgacgt cgctagggat gcaagatggg gcagagttga agagactttt     480
ggtgaggacc cttacttagt agctaatatg gcagtttctt atgtaaaggg attacagggc     540
gacgatataa aggacggaat agtggcaaca ggtaagcatt tgttggcta cgcaatgagt      600 gagggcggaa tgaattgggc accagtacac attcctgaaa gagaattgag ggaagtttac     660
ttgtatcctt ttgaggtcgc agttaaggtg gcaggcctta aaagtataat gcctgcttat     720
cacgagattg atggcattcc gtgccacgct aatagaaaat tgttaacaga tatagctagg     780
ggagagtggg gttttgatgg aatatatgtt tctgattaca cggtgtgaa gaatttactt     840 gactatcaca agagcgtcaa gacgtatgaa gaagcagctg ctcttagctt gtgggctgga     900
ttagatattg agttgcctaa aatagagtgt ttactgaag agtttataaa ggcacttaaa     960
gaaggtaaat tgatatggc tttagtggac gctgcagtga aagagtatt ggaaatgaag     1020
```

```
tttagacttg gcctttttga caatccatac attaagacag aaggtgttgt agaactttt    1080 gacaacaaag agcaaaggca acttagcaga aaagtggcac aagaaagtat ggtgttattg    1140
aagaacgact cttttcttcc gttaagcaag gaccttaaga aaattgcagt gattggcccg    1200
aacgcaaaca gtgttagaaa cttattgggt gactattctt acccggctca tattgctact    1260
ttggaaatgt tttttattaa agaggacagg ggagtgggca atgaggaaga gtttgtgaag    1320
aatgtcatta acatgaagtc aattttttgag gctattaagg ataaggtgag ctctaacact    1380
gaagtcgtgt acgcaaaagg ttgcgatgta aatagccaag ataaatcagg ttttgaagag    1440
gcaaagaaag ctgctgaagg cgcagatgca gttatattag tagtaggaga caaggcagga    1500
ttaagattag attgcacgag cggcgagtct agagatagag catctttgag gcttccaggc    1560
gtacaagaag atcttgtcaa ggaaattgtt tctgtgaatc aaacacggt ggttgtattg     1620 gttaatggca gaccagttgc acttgattgg ataatggaaa atgtgaaagc tgtacttgag    1680
gcatggtttc caggtgaaga gggcgcagat gctgtcgcag atattttgtt tggagactat    1740
aatccaggcg gcaagttggc tattagcttt ccaagagatg taggtcaagt tccagtatat    1800
tacggacaca aaccgtcagg cggcaaatct tgctggcacg agattatgt tgaaatgtca     1860 acgaagccgt tgttgccttt tggctacggt ttgtcttata caacgtttga gtacaagaac    1920
tttgctatag aaaagagaa gattggtatg gacgaaagta ttaaagtttc agtagaagtt    1980
gaaaacacag gaaaatacga gggcgacgag atagtccaac tttatacgag aaaggaagag    2040
tatcttgtga caaggccagt aaaagaattg aagggatata aaagagtgca cttaaaaccg    2100
ggcgaaaaga gaaagttgt gtttgaatta tatccggact tatttgcttt ttatgactac    2160
gacatgaata gggtggttac tcctggtgta gttgaagtga tgattggcgc ttcaagtgaa    2220
gatattaagt ttactggcac gtttgagata gtgggtgaga aaaaggacgc aaaagagatt    2280
aagaattact tgagcagagc ttggtgtgaa                                       2310

<210> SEQ ID NO 91
<211> LENGTH: 984
<212> TYPE: DNA
<213> ORGANISM: Artificial Sequence
<220> FEATURE:
<223> OTHER INFORMATION: Codon-Optimized Caldicellulosiruptor
      kristjanssonii

<400> SEQUENCE: 91
ttaaataaac ttcctagata taagggcttt aatttgttag gcttgtttgt accaggcagg      60
atacttggat ttttttgagga cgattttaag tggatgggcg aatggggttt taactttgca   120
aggattccta tgaactacag gaactggttt gttgagggat catctgacat aaaagaggaa    180
attttgcaaa tgatagacag agttatagag tggggcgaaa agtacgagat acatatttgt    240
cttaacatac acggcgctcc aggatattgc gtaaatgaaa agacaaaaca gggctacaat    300
ttgtggaaag acgaagaacc tttagagctt tttgtaagct actggcaaac ttttgctaaa    360
aggtataagg gcataagcag taaaatgctt tcatttaacc ttataaacga gccaaggcaa    420
ttttctgagg aagaaatgac taaggaggac tttattaggg ttatgactta cacaactcag    480
aaaataaggg agataggaaa ggagaggtta attatagtgg acgtgtggaa ttatggcaat    540
gagcctgttg tagaattagc aaaccttggc gtggcacaat catgtagagc atatataccg    600
tttgaggtca gtcattgggg tgcagaatgg gttgaaggct caagaaattt tacaaaacct    660
agttggccat tagtaagaga aaatggagaa attgtggata aagagtactt gaagaagcac    720
```

-continued

```
tacgagaaat gggctaagtt gatttcatta ggtgtgggag tgatatgcgg agaaggtgga      780
gcatataaat acacgccgca cgatgtggtc ataagatggt ttagcgatgt attagatatt      840
cttaaggaat ttggtatagg tattgcttta tggaacctta ggggtccatt tggtattata      900
gatagcggta gagaagatgt tgaatacgaa gattttatg  gacacaaatt ggacagaaag      960
ttgttagaat tgcttcaaag attt                                             984
```

<210> SEQ ID NO 92
<211> LENGTH: 5226
<212> TYPE: DNA
<213> ORGANISM: Artificial Sequence
<220> FEATURE:
<223> OTHER INFORMATION: Codon-Optimized Caldocellum saccharolyticum
      Biomass degrading enzyme

<400> SEQUENCE: 92

```
atggttgtga catttctttt tatattaggc gtcgtttacg gagtaaagcc gtggcaagaa       60
gcaagagctg ggagttttaa ctatggagag gcattacaga aagcaattat gttttatgaa      120
tttcaaatgt cgggtaaatt gccaaattgg gtaagaaata attggagagg agattctgct      180
cttaaagacg gcaagacaa  tggtcttgat ttgacaggtg gatggtttga tgcaggcgat      240
catgttaaat ttaatttacc aatgagctat acaggtacga tgttatcatg ggcagcttac      300
gaatataagg atgcttttgt taagagtggt caacttgaac atatactaaa tcaaatcgaa      360
tgggtaaatg actatttcgt taagtgccat ccttcaaaat atgttatta  ctaccaggta      420 ggcgatggcg gcaaagacca tgcctggtgg ggcccggcag aagtaatgca gatggagaga      480
ccttcattta aggtgacaca atcatcacct ggctcagcag tggttgctga aacagctgct      540
tctttggcgg ccgcttcaat agtccttaaa gataggaatc ctactaaagc agctacttac      600
ttgcaacatg caaaggattt atacgaattt gccgaagtaa caaaatctga tagtggttat      660
actgcagcaa atggttacta taattcatgg tccggttttt atgacgaact ttcatgggcc      720
gcagtatggt tgtacttggc aactaatgat tctacatatt taacaaaagc cgaatcttac      780
gttcaaaatt ggccaaaaat aagcggttct aatattatag attacaagtg ggctcattgc      840
tgggatgatg tgcataatgg tgctgctctt ttactcgcta agatcactga taaagataca      900
tacaaacaaa ttattgaatc acatcttgat tattggacca ctggttataa tggagaaagg      960
ataaaataca caccaaaagg actggcatgg ttagatcagt gggggtctct taggtatgca     1020
acgacaacag cgtttcttgc atttgtttat tcagattgga gtggttgccc tacaggcaaa     1080
aaagaaactt atagaaagtt tggtgaatct cagatagatt acgcacttgg atctactggt     1140
agatcatttg tcgtaggttt tggcacaaac cccctaaaa  gacctcatca taggacagca     1200
cactcttctt gggcagattc tcaatcaatc ccgagttacc atagacatac attatatggg     1260
gccttagtag gggggccagg atcagatgat tcatatactg atgatatatc aaattatgtg     1320
aataacgagg tagcttgcga ttataatgca gggtttgttg agcattagc  aaagatgtat     1380 ttattatatg gtgggaatcc tatcccagat tttaaagcca tagaaacacc aaccaacgac     1440
gaattctttg tagaagcggg tataaatgct tctggtacaa atttcattga aataaaagca     1500
atcgttaata atcagtcagg atggcctgca agggcaacta ataagttaaa atttagatac     1560
tttgtagatt tgtcagaact tattaaagca ggatatagcc caaccagtt  aactttgtcg     1620 acaaattata atcaaggcgc taaagtaagt ggacctacg  tgtgggatag ctcaagaaat     1680
atatactaca tattagttga ctttacaggc acgttgatat accctggcgg acaagataag     1740
```

```
tacaagaaag aagtgcagtt tagaatagct gctccgcaaa atgtacaatg ggacaatagc    1800
aatgactact cgtttcaaga tataaaaggc gtatcttctg gttcggtggt taagacaaaa    1860
tatattcctc tttatgatga agatataaag gtatggggag aagagccagg aacatctggt    1920
gtaagcccta ctcctacggc aagtgtaaca cctactccta cgcctacgcc gactgcaact    1980
ccaactccaa caccaacgcc aacagttact ccaacaccaa ctgttacagc aacacctacc    2040
ccgacccctc tccaacaag tacacctacg gtaacaccta cacctactcc tgttagcaca     2100
cctgctacat ctgggcaaat taaagtgtta tacgccaaca aagaaactaa ttccacaact    2160
aatacaatta gaccatggtt gaaagttgta aattcaggct ctagcagcat cgacttgagc    2220
agagtaacaa ttagatattg gtatacagtt gatggcgaaa gggctcaatc tgcaattagc    2280
gactgggcac aaataggtgc tagcaatgtc acatttaaat ttgtgaaatt gtcatcaagt    2340
gtatcaggtg ctgattacta ccttgagatt ggatttaaat ctggagcagg acaattacag    2400
ccaggcaagg atactggaga gatacaaatc agatttaata aggatgattg gagcaactat    2460
aaccaaggaa atgattggag ctggattcaa agcatgacgt cttacggcga aaatgaaaaa    2520
gtcacagctt atatagacgg cgttttggta tggggacagg aaccgagcgg tactacacca    2580
gctcctacat caacacctac tgtcacagtt accccctacac caactccgac accaactgtg    2640
acaccaactc caacagtcac tgcaacacct acaccaacac cgaccccaac atcaactcca    2700
gtttcaacac cagctacagg cggtcaaata aagttctttt atgcaaacaa agaaaccaat    2760
tcaacaacaa atactatacg gccctggctg aaagtagtta actcaggctc atcatctatt    2820
gaccttttcta gagttacaat aagatactgg tatacagtag acggtgaaag agcacaatct    2880
gctatttctg attgggccca aataggagca tcaaacgtta cgtttaaatt cgtcaaattg    2940
tcatcgagcg tgtcaggagc tgattattat cttgaaattg gctttaaatc tggcgctgga    3000
cagttacaac cgggtaaaga tacaggagaa attcaaatta ggtttaacaa ggatgattgg    3060
tcaaactaca atcagggcaa tgattggagt tggattcaat ctatgacaag ttacggagag    3120
aatgaaaaag ttacggctta tatagatggc gtccttgtat gggggcaaga gccaagcggc    3180
gctactcctg caccaacagt tactccgact ccaacggtaa cgccaactcc tacacctgca    3240
cctacaccta cagctacccc aactccgact ccaacaccca cggtcacacc tacgcccacg    3300
gtagccccaa ctcctacacc atcgagtaca ccaagtggcc tgggcaaata tggacaaagg    3360
tttatgtggc tatggaacaa aatacatgac ccagctagcg gctatttcaa tcaagatgga    3420
ataccgtatc atagtgtgga aactttgatt tgtgaagcac ctgattatgg ccatcttact    3480
acttctgagg cattttcata ctacgtatgg ttagaggcgg tttatggaaa attaacagga    3540
gattggtcaa aatttaaaac tgcctgggat acacttgaaa aatatatgat acctagtgct    3600
gaggatcagc ctatgcgatc atatgacccg aataaaccag caacatatgc tggagaatgg    3660
gaaacaccgg ataagtaccc tagccccctta gaatttaatg tacctgttgg caaagatccg    3720
ttacataatg aattagttag cacatatgga tctacgctta tgtatggtat gcactggtta    3780
atggatgttg ataactggta tggctacgga aaacgtggag atggcgttag cagagcatct    3840
tttataaata catttcagag gggaccagaa gaatctgttt gggaaacagt gccacatcca    3900
tcatgggaag agttgaaatg gggtggacca aacggctttt tggatttgtt tattaaagat    3960
caaaattatt caaacaatg gagatacact aatgcgcctg acgcagatgc aagagcaatt    4020
caagccactt actgggctaa ggtttgggcc aagaacaag gcaagtttaa tgaaataagc    4080
agttatgttg gtaaggcagc taaaatgggc gattacttaa gatatgctat gttcgataag    4140
```

```
tactttaaac ctctgggatg ccaagataag aatgcagcag ggggtacggg atatgattca    4200
gctcactatt tacttagttg gtattatgct tggggaggag ctttggacgg agcatggtcg    4260
tggaaaatag gatgctcaca tgctcatttt ggatatcaaa atccaatggc agcttgggca    4320
ttagcaaatg actcggatat gaaaccaaaa tcgccaaatg gagcttcaga ttgggcaaaa    4380
tcattaaaga gacagataga attttataga tggttgcaat cagccgaagg cgccatagca    4440
ggcggtgcaa cgaattcatg gaatggtaga tatgaaaaat accctgcagg aacagcaaca    4500
ttttatggta tggcctatga accgaatccc gtatataggg atcccggaag taatacgtgg    4560
tttggatttc aggcttggtc catgcagaga gtagctgaat attattatgt aacaggcgat    4620
aaagatgcag gcactctttt agaaaaatgg gtatcatgga tcaaatctgt cgtaaaatta    4680
aatagcgatg ggacatttgc gataccctct acattggatt ggtcaggaca accagatacg    4740
tggaatggca cgtatacagg aaatccaaac cttcatgtta aagtcgtgga ctatggaaca    4800
gatttaggca taacagcaag cttggcaaat gctttgttgt actattccgc agggactaaa    4860
aaatatggtg tatttgacga agaagctaaa atcttgcaa agagttgct tgacaggatg    4920 tggaaactct acagagatga aaaggactt tctgcaccag aaaagagagc cgattataaa    4980 agattttcg aacaagaagt gtacatacct gcaggatgga ctggaaaaat gccaaatggc    5040
gatgttatta aaagtggcgt taagtttata gatataagat caaaatacaa gcaggatcca    5100
gattggccaa aactagaagc agcttacaaa tcagggcaag ttcctgaatt tagatatcat    5160
agattttggg cacaatgcga tatcgcaatt gttaacgcaa cttacgaaat tctttttggc    5220
aatcag                                                              5226

<210> SEQ ID NO 93
<211> LENGTH: 3117
<212> TYPE: DNA
<213> ORGANISM: Artificial Sequence
<220> FEATURE:
<223> OTHER INFORMATION: Caldocellum saccharolyticum CelB

<400> SEQUENCE: 93
atgaaaagaa accttttag aatagtatca agggttgtgc ttattgcttt tattgcatca      60
attagcttgg tcggagcaat gagctatttt cctgtggaaa cacaagctgc accagattgg     120
agcataccga gcttatgtga gagctataag gacgatttta tgataggagt tgctattccg     180
gcaagatgcc tttcaaatga tacagacaaa agaatggtac ttaaacactt taacagtatt     240
actgcagaga atgagatgaa gccagagagc ttattggctg ccagacaag tactggatta     300 agttatagat ttagcacggc tgacgcattt gttgattttg ctagtacgaa taagattggc     360
attaggggac acactttagt atggcataat cagacaccgg actggttttt taaggacagc     420
aatggacaaa gacttagcaa agacgcattg ttagctagac ttaaacaata tatatacgac     480
gtggttggta ggtacaaagg taagtctat gcatgggatg tagttaacga ggcaattgat     540
gaaaatcagc ctgattctta taggagaagc acatggtacg aaatttgcgg accagaatac     600
attgaaaagg catttatttg ggctcacgaa gcagatccta atgcaaaatt gttttacaat     660
gattataaca cggagataag caaaagagg gactttatat caacatggt gaagaaccttt     720 aagagcaagg gcattccaat acacggcata ggcatgcagt gccacataaa tgtcaactgg     780
ccgagtgtaa gtgaaattga aaatagcatt aagttatttt caagcattcc tggtatagag     840
atacacataa ctgagttgga catgtctttg tataactacg gttcttcaga gaactacagc     900
```

```
actccacctc aagatctttt acagaagcaa tctcaaaagt ataaagagat atttactatg      960
ttgaagaaat ataaaaacgt tgtcaagagc gtgacatttt ggggacttaa agatgactat     1020
agttggttaa gatcatttta cggcaagaac gactggccat acttttttt tgaggactac     1080 agcgctaaac cagcatactg gctgttatt gaagcaagtg gcgtaactac atcaagtcct     1140
acgccaacac cgactcctac agttacggtg acaccgacac caactccaac acctacgccg     1200
acagtcactg caacgccgac tcctacgcca acgcctgttt ctactccagc aacaggcgga     1260
cagattaaag tgctttatgc taacaaggaa acaaatagta ctacaaatac aattagaccT     1320
tggttaaaag tagttaattc aggaagctct agtatagatc tttctagggt aacgattagg     1380
tactggtata ctgtcgatgg agaaagagca cagtctgcag ttagtgattg ggctcagatt     1440
ggtgcaagca atgtaacatt taagtttgta aaattatcaa gttctgtctc aggagcagat     1500
tattacttgg agataggctt taagtctggt gctggacaac ttcaacctgg taaggatacg     1560
ggtgaaattc agataagatt taataaaagc gattggtcta attcaaccca gggcaatgac     1620
tggtcatggc ttcagagcat gacatcatat ggcgaaaatg agaaagtgac ggcttatatt     1680
gacggtgttt tagtctgggg tcaagagcct agtggcgcta cgcctgctcc gacgatgaca     1740
gtggcaccga ctgctacacc gacgccaact ttatctccga cggttactcc gacgccagca     1800
ccgactcaga cggctatacc aactcctacg cttactccta acccgacacc aacaagttct     1860
attccggatg atacgaatga tgactggttg tacgtaagtg gcaacaaaat tgtcgataag     1920
gatggcagac cagtttggct tactggcata aattggtttg gctacaacac aggtacgaac     1980
gtgtttgacg gcgtctggtc atgtaatttg aaagacactt tagctgagat agcaaatagg     2040
ggatttaatt tgcttagagt cccaataagc gcagaattaa ttttgaactg gagtcaaggt     2100
atatatccga aaccaaatat taactactat gtaaatccag agttagaagg aaaaaatagc     2160
ttagaggttt ttgatatagt cgtgcagaca tgcaaagaag ttggcttgaa ataatgctt     2220 gatattcatt ctataaaaac ggacgctatg ggtcatatt atccagtatg gtatgacgaa     2280
aaatttacgc ctgaggattt ttacaaggca tgcgaatgga taacgaacag atacaaaaat     2340
gatgacacta ttatagcttt tgaccttaaa aacgaaccac atggaaagcc gtggcaggat     2400
acaacatttg caaaatggga caatagcact gatattaaca actggaagta cgctgctgag     2460
acttgcgcaa agagaatttt gaatataaac cctaatcttt taattgtaat agagggcatt     2520
gaggcatacc cgaaagacga tgtgacttgg acatctaagt catcaagcga ttattacagt     2580
acgtggtggg gtgaaatttt aagaggcgtt aggaaatatc caataaattt gggtaaatat     2640
cagaacaagg tcgtgtatag ccctcatgat tacggtcctt ctgtatatca gcaaccttgg     2700
ttttatccgg gctttactaa agaatcatta cttcaggact gttggaggcc taactgggca     2760
tatataatgg aagaaaatat tgcaccttg cttataggag agtggggagg ccatttagat     2820
ggtgctgata cgagaaatg gatgaagtac ttaagggatt atattataga gaaccatatt     2880
catcacacgt tttggtgctt taatgctaac agtggagata caggcggttt agtgggttac     2940
gactttacta catgggacga gaagaaatac agcttttga agccagcttt atggcaagac     3000
agccagggca gatttgtagg tttagatcat aaaaggcctt tgggcactaa tggaaagaac     3060
ataaatatta cgacgtacta caacaacaat gaacctgagc cagttcctgc ttcaaag      3117
```

<210> SEQ ID NO 94
<211> LENGTH: 3993
<212> TYPE: DNA
<213> ORGANISM: Artificial Sequence
<220> FEATURE:
<223> OTHER INFORMATION: Codon-Optimized Caldocellum saccharolyticum
    beta-mannanase

<400> SEQUENCE: 94

```
atgagactaa aaacaaaaat aagaaagaaa tggttaagtg ttttatgcac agtagtgttt      60
ttgttgaata ttcttttat agctaatgtc acaattttac ctaaagttgg agcagctaca     120
agtaatgatg gagttgtaaa aattgataca agcactctta taggcactaa tcatgcccat     180
tgttggtacc gtgacagatt ggacacagct ttaagaggga tcagaagttg gggcatgaat     240
tcggttagag tagtgttgtc aaatggttac agatggacaa aaatccccgc atccgaagtt     300
gcaaatataa taagcttgtc aagaagtctt ggattcaaag caataatcct tgaagtgcac     360
gatacgacag ttatggagag gatggagcag gcttgctctt tagcacaggc tgtggaatac     420
tggaagaaaa taagagcgt attagatggc aatgaagatt ttgttattat aaacattgga     480
aatgagccgt atggtaataa taattatcaa aattgggtaa atgatactaa aaatgcaata     540
aaagcactaa gagatgcagg attaagcat actattatgg tagatgcacc taattgggg t     600
caagattggt caaatacgat gagagataat gctcaatcta atggaagc tgatccttta       660
aggaatcttg tattttctat acatatgtac ggggtttata atacagccag caaagtagaa     720
gaatatataa atctttttgt ggataaaggt ttacctttag ttataggtga gtttggccac     780
caacacacag atggagatcc agatgaagag gcaatagtta gatatgcaaa gcaatataaa     840
attggattgt ttagttggag ctggtgtggc aattcttcat acgtaggta tttagatatg     900
gtcaataatt gggacccaaa taccctact ccttggggg c aatggtataa aacgaatgca     960
ataggcactt cttctacacc tacaccaaca agcacagtga ctcctacacc aacaccaaca    1020
cctactccta cgccaacagt aacagcaaca ccaacaccta cacctacacc tgtttcaaca    1080
ccagcgacat ctggtcaaat aaaagtgttg tacgctaata aggaaacgaa cagtacaacg    1140
aatactatca gaccttggct taaagtagtt aattcaggct ctagttctat agaccttagt    1200
agggtgacta tcaggtattg gtatacagta gatggggaaa gggcccagtc agcaataagc    1260
gactgggctc agataggagc atccaatgta acatttaaat tcgtgaagct tagctcatca    1320
gtatctggcg ctgattacta tcttgaaatt ggatttaaaa gcggggccgg acaactacag    1380
cctgggaaag atacaggtga atacaaatg agatttaata aagacgattg gtcaaattat    1440
aaccaaggta atgactggag ttggatacag tccatgacaa gttatggcga aaatgaaaag    1500
gtaacagctt acatagatgg tgtattggtt tggggacagg aaccatcagg cgcaacacct    1560
gcacctgcac cgacagcaac tccaacacct actccgacag taacaccaac acctacagta    1620
acgccaacgc caacggttac agcaactcca acgccaacac caaccctac acctacacca    1680
gtttcaacgc ctgcgactgg aggacaaata aaggttcttt atgcaaataa agaaacaaat    1740
tcgacaacga atactatcag gccttggtta aaggtagtta atagcgggag ttctagtata    1800
gatcttagta gagtcacaat aagatattgg tatactgtag atggtgaaag agcacaaagt    1860
gcaatatcag attgggcaca aattggcgca tctaatgtca catttaaatt tgttaagctt    1920
tcgtcgtcag tcagtggggc agattactat ttggagatcg gtttcaaatc tggggcaggc    1980
caattgcagc caggtaagga tacaggcgag atacaaatca gattcaataa atctgattgg    2040
tccaactata atcaaggcaa cgattggtca tggatacagt ctatgactag ttatggagag    2100
aacgaaaagg tgactgctta cattgatgga gttttagtct ggggacaaga gcccagcgga    2160
actacaccga gcccgacatc aacaccaact gttacggtaa cacctacacc aacgccgact    2220
```

| | |
|---|---|
| ccaactccga ctcctacacc aacggtaacg ccaacaccga ctgtaactcc aactcctaca | 2280 |
| gtcacagcca caccgactcc taccccaaca cccatcccta cagtaacacc attacctaca | 2340 |
| atatctccaa gcccttctgt agtggaaatt acgataaata caaatgcagg cagaacacag | 2400 |
| ataagtccat acatctatgg tgctaatcaa gatattgaag gcgtagtaca cagtgccaga | 2460 |
| agattgggag gcaatagact aacaggttat aattgggaaa ataattttag caacgcgggc | 2520 |
| aacgattggt atcattccag tgacgattac ttatgttggt caatgggaat ctcaggagaa | 2580 |
| gatgctaaag tacccgcagc agtagtttca aaatttcacg agtactctct aaagaataat | 2640 |
| gcatacagcg ctgtgacttt acaaatggct ggttatgtat ctaaggacaa ttatggtact | 2700 |
| gtcagtgaaa atgaaacagc accatcgaat agatgggctg aagtaaaatt taaaaaggat | 2760 |
| gcgcctttgt cccttaatcc agacctgaac gataactttg tttatatgga tgagtttatt | 2820 |
| aattatttaa taaacaaata tggaatggcc tcgtctccta ctggtataaa aggatatatt | 2880 |
| ctggacaacg aaccagatct ttgggcgagc acccacccga gaatacatcc aaataaagta | 2940 |
| acatgtaaag aattgattga gaaaagtgta gaacttgcaa agtaattaa gacacttgat | 3000 |
| ccttctgcgg aagtatttgg ctatgcatca tatgggttta tgggatatta ctcgctacag | 3060 |
| gacgcgccgg attggaatca ggttaagggg gaacatcgat ggtttataag ttggtattta | 3120 |
| gaacaaatga aaaagcatc cgattcattt ggaaaaaggt tattagatgt attagattta | 3180 |
| cactggtatc ctgaggcaag gggagggaat atcagagttt gctttgacgg tgaaaatgat | 3240 |
| acctcaaaag aagtagtaat cgctaggatg caagcccaa gaactctatg ggaccctaca | 3300 |
| tataaaacaa gtgttaaggg acaaataacg gctggagaaa attcgtggat aaatcagtgg | 3360 |
| ttttcagatt atctcccaat tatcccaat gttaaggccg atattgagaa gtactatcca | 3420 |
| ggtacaaagc tagctataag cgaatttgac tatgggggtc gtaaccacat atctggagga | 3480 |
| attgctttag ctgacgtact aggcattttt ggcaaatatg gcgttaattt tgcggctaga | 3540 |
| tggggcgatt caggttcata tgccgcagct gcatataaca tatatcttaa ttatgatgga | 3600 |
| aagggttcga aatatggtaa tacgaatgtt tctgcaaata caagtgacgt agagaatatg | 3660 |
| ccggtatatg cttcaataaa cggtcaagac gattcagaat tgcatataat acttatcaac | 3720 |
| aggaactacg atcaaaaatt acaggttaaa attaatatta catcaactcc aaaatacaca | 3780 |
| aaagcagaaa tatacggatt cgattctaat agccctgaat ataaaagat gggaaatata | 3840 |
| gacaatattg agtctaacgt ttttaccctt gaagtgccaa aatttaatgg cgtgagccat | 3900 |
| agcatcacat tagattttaa cgtgtccatc aaaattattc aaaatgaagt aatcaagttt | 3960 |
| atcagaaatt tagtgttcat gagggcactt gtt | 3993 |

<210> SEQ ID NO 95
<211> LENGTH: 2838
<212> TYPE: DNA
<213> ORGANISM: Artificial Sequence
<220> FEATURE:
<223> OTHER INFORMATION: Codon-Optimized Clostridium stercorarium
      Avicellase I

<400> SEQUENCE: 95

| | |
|---|---|
| atgagaaaat tttggtcttt tgcaataatt atatctttac ttgtaacagg attgtttatt | 60 |
| catactccta aagctgaggc agctggttac aattacggcg aagctcttca aaaggcaata | 120 |
| atgttttacg agtttcagag gagcggaaag ttgccagaga caagaggga caattggagg | 180 |
| ggtgacagcg gcttaaatga tggagcagat gttggtttag accttacagg cggatggtat | 240 |

```
gatgctggtg atcacgtgaa gtttaatttg cctatggcat atagtcaaac tatgttagct    300
tgggcagctt acgaagcaga agaagctctt gaaagatcag gccagatggg atatttgtta    360
gacgcaataa aatgggtttc tgattatctt ataaaatgcc acccaagtcc taatgttttt    420
tactaccagg tgggtgatgg ccacttggac cattcatggt ggggcccggc agaagtaatg    480
caaatggata gaccagctta taaagtagac cttgctaatc caggttctac agtagtggca    540
gaggctgcag ctgctttggc tagcgctgca gtagttttttg cagatagaga tcctgcatac    600
gctgcaactt gtatacaaca tgcaaaggag ttgtataatt ttgcagagat tacaaagtca    660
gattctggct acacagcagc tagtggcttt tacgatagcc actcaggatt ttatgacgag    720
cttagctggg ctggcgtttg gctttattta gctacaggcg atgaaacata ccttaacaaa    780
gctgaacaat atgtggcata ctgggggtact gagccacaaa caaatataat ttcttataag    840
tgggcacatt gttgggacga cgttcattac ggagcttgct tgcttttagc aaaaattact    900
ggcaaacaaa tatacaaaga ggcaatgaaa agacaccttg attattggag cgttggttac    960
aacggagaga gggttcatta tacacctaag ggattggctt ggttggatag ctggggaagt   1020
cttagatatg ctacgacaac tgcattttttg gcaagtgttt acgcagattg ggagggctgc   1080
agcagggaaa aagctgcaat ttataatgac tttgctaaac aacagataga ttacgcattg   1140
ggctcaagtg gtagatctta tgtagttggt tttggcgtga atccgccaaa aagaccgcac   1200
cacaggactg ctcacagttc ttgggctgat tctatgagtg ttcctgacta ccacagacac   1260
gtacttatag gtgctttagt tggaggccca ggtaaggacg attcatacac ggatgacata   1320
aacaattata taaataacga ggttgcttgc gattacaatg ctggttttgt gggcgcattg   1380
gctaagatgt atgaagatta cggcggatct ccgatacctg acttgaatgc ttttgaggaa   1440
ataactaacg atgaattttt tgttatggca ggaattaatg catctggcca gaatttttata   1500
gagattaagg cattacttca taatcaatca ggttggcctg ctagggtagc agataagtta   1560
agttttaggt attttgtcga tttaacggag ttaatagagg ctggatacag cgcttctgac   1620
gtcacaataa ctacaaatta taacgcaggc gcaaaagtaa ctggtttaca cccatggaat   1680
gaagctgaga acatttatta cgtgaacgtt gattttacgg gaacaaagat atatcctggc   1740
ggtcagtcag catacagaaa agaggtgcag tttaggattg ctgctccaca gaatacgaat   1800
ttttggaata atgacaacga ttattcattt agggatataa aaggcgttac aagcggcaat   1860
acagtcaaaa cagtgtatat tcctgtttat gacgatggtg tgttagtttt tggagtggaa   1920
aatgaaataa agtacggtaa cacttactta agagaaggaa cggattacac ggtcagcggc   1980
gacactgtga caatattgaa atcatttctt aatagctttg atacttcaac agttcagtta   2040
atatttgact ttagcgctgg tagggatcca gtattgacag tgaacataat tgacacgaca   2100
acgagcgcaa gcatagtccc aacaacggca gattttgaca aaaatccgga tgcatctaga   2160
gatgttaaag tgaaattagt acctaatgga aatacgcttc ttgcagtgaa aaagacggt    2220
gaggctttgg tgttaggcag ggactacagt atagatggcg acgaggtaac aatatttagg   2280
gagtatttag ctgatcagcc ggtaggcaga gtgactctta catttgactt tgatagggt    2340
actgatccgg ttttaacaat taatataacg gatagcagga agtagagac aggagttata   2400
caaattcaga tgtttaacgg caacacgagt gataaaacta acggtataat gccgaggtac   2460
aggttgacaa acactggaac aacacctata agattgagtg atgtaaaaat aaggtactac   2520
tacacaatag acggagagaa ggatcaaaat tttttggtgcg actggtcaag tgtaggttct   2580
```

-continued

| | |
|---|---|
| aataatatta cgggtacatt tgtaaagatg gctgagccaa agagggcgc agattattac | 2640 |
| cttgaaacgg gttttactga tggcgctggc tatttgcagc caaatcaaag cattgaggtt | 2700 |
| cagaacagat ttagtaaggc agactggact gattatatac aaacgaatga ttatagcttt | 2760 |
| agcactaaca cgtcatacgg ttcaaacgac aggattactg tgtacattag cggtgtgttg | 2820 |
| gttagcggaa tagaacca | 2838 |

<210> SEQ ID NO 96
<211> LENGTH: 2742
<212> TYPE: DNA
<213> ORGANISM: Artificial Sequence
<220> FEATURE:
<223> OTHER INFORMATION: Codon-Optimized Clostridium stercorarium
      Avicellase II

<400> SEQUENCE: 96

| | |
|---|---|
| atgaaaagaa ggttaatgaa gggaatatca ttgttaacgc ttgtattttt gattggtata | 60 |
| atgttgcaac ttagcttaaa gagcgaatta acagcttacg ctagtagcga tgacccttac | 120 |
| aagcagaggt ttttggaatt atgggaggaa ttgcatgacc cttctaatgg ttatttagt | 180 |
| tcacacggca ttccttacca tgcagttgaa acattaatag tggaagctcc tgactacggc | 240 |
| cacttgacta catcagaagc aatgtcttac tatttatggt tggaggcttt atacggcaaa | 300 |
| tttacaggtg actttagcta ttttatgaag gcatgggaga caattgaaaa atacatgata | 360 |
| cctacagagc aagaccagcc taacaggagc atggcaggct ataaccctgc aaaaccggct | 420 |
| acgtacgcac ctgaatggga agaaccgagt atgtacccat cacagttaga ctttagcgca | 480 |
| ccagtgggca tagacccaat atacaacgag ttggttagca catacggaac gaacacaata | 540 |
| tacggtatgc actggttgct tgacgttgat aattggtacg ctttggaag aagggcagat | 600 |
| agaattagtt ctccagctta tataaacact tttcagaggg aagtcagga gagcgtatgg | 660 |
| gaaacaatac tcaaccgtg ttgggatgac ttaacaattg gaggaagaaa tggctttctt | 720 |
| gacttgtttg tgggagacag tcagtactca gcacaattta gtatacaaa cgcaccggac | 780 |
| gctgatgcta gagctataca ggcaacatac tgggcaaacc agtgggcaaa agaacatgga | 840 |
| gttaatttga gtcaatacgt gaaaaaggca tcaagaatgg gtgattacct tagatatgca | 900 |
| atgtttgata atatttttag aaaaattggc gactctaagc aggctggaac gggatacgat | 960 |
| gcagcacact acttacttag ctggtactac gcttggggag cggtataac agctgattgg | 1020 |
| gcttggatta taggctgctc acacgttcac gctggctacc aaaatccaat gacagcatgg | 1080 |
| attcttgcta cgacccgga atttaaacca gaatctccta cggagcaaa cgactgggct | 1140 |
| aagagcttgg aaaggcaatt agagttttac caatggcttc aaagtgctga aggcgcaata | 1200 |
| gctggaggt ctacaaattc ttacaaagga agatacgaaa cattgccggc tggtattagc | 1260 |
| acattttacg gtatggcata cgaagaacac cctgtgtacc ttgatccagg tagtaacaca | 1320 |
| tggtttggct ttcaggcttg gacgatgcag agggttgcag agtactatta cttaactggt | 1380 |
| gacacaagag ctgagcagct tttggataaa tgggtggatt ggattaaaag cgtggttagg | 1440 |
| ttaaactcag atggcacatt tgaaattcct ggcaacttgg agtggtctgg acagcctgat | 1500 |
| acgtggactg tacatatac tggaaaccct aatttacatg taagtgtcgt ttcttatagg | 1560 |
| actgacttgg gcgcagctgg atctttggct aatgctttgc tttattatgc aaagacaagc | 1620 |
| ggcgacgatg aggctagaaa tttagctaaa gaattgcttg acagaatgtg gaacctttac | 1680 |
| agagatgaca agggattgag cgcaccggaa actagagagg attatgtgag gtttttgaa | 1740 |

```
caagaagtct acgtgccaca gggttggagc ggaacaatgc ctaatggcga tagaattgaa   1800
cctggtgtta cttttcttga tataaggagt aaatacttga atgatccgga ctatcctaag   1860
ttgcaacagg cttacaacga aggaaaagca ccggtcttta attatcacag attttgggct   1920
caatgcgaca tagctatagc aaacggattg tacagcattt tatttggctc tgagcaagca   1980
aacgattcat ttataacacc tacaagtgca acatttgaca aaacaatca ggaagatata   2040 tctgtaacag tgacttataa tggcaacact ttgcttggca taaagagcgg ttcttcatat   2100
ttgatagaag gcgttgacta tatagtcaat ggcgacgtga ttattataaa gaaagagttt   2160
cttgctggtc aggctacagg aagtattagc ttgcttttg actttagcgc aggcttagac   2220
agaacattaa caattgacat aatagacact ggtggaggcg aagagccggt tgagccagta   2280
gaacctgttg agggtgtttt aattatacag tcatttaacg caaacacaca ggagatttca   2340
aatagcatta tgcctaggtt tagaatttat aattcaggta atacaagcat tccattgagc   2400
gaagtgaaac ttaggtatta ctacacagta gacggcgata aacctcaaaa ttttggtgc   2460 gattgggcat ctattggttc atctaatgtg actggaacat tgtgaaaat ggatggagct   2520 acaacgggtg ctgattacta tttagagata ggatttactc cgcaggctgg cactttagag   2580
cctggagcta gtatagaagt acagggtagg tttagtaaaa tagactggac ggactatact   2640
cagactaatg actatagctt taacccgaca gcttcttcat atgtggactt taacaagatt   2700
actgcataca taagcggcaa ccttgtttat ggtattgagc ct                     2742

<210> SEQ ID NO 97
<211> LENGTH: 3444
<212> TYPE: DNA
<213> ORGANISM: Artificial Sequence
<220> FEATURE:
<223> OTHER INFORMATION: Codon-Optimized Eubacterium cellulo solvens
      Cel5A

<400> SEQUENCE: 97
atgaaaggaa attggttaaa ggacgtactt agaaggtttg cagttatagc tatgatgttg     60
gtgatggtct ttacactttt gcctgcaact gctcaaggta cggaagcagc ttcaggcgac   120
attgtattgt ttagcggctc aaaacacgtt gagtttacgg attggggtgg cacagactgg   180
ccaagtgcat acgaattaca gccgccttac caaactatgc catttgattt gaacaagaat   240
tttgagatta agttgatta ttcaggtgct gatatagtgt tgattttgc aagatgggaa   300 cacggttcta aaccgcagat atgggcacaa atttcaccgt attacgttgt tgatggcaca   360
gctgttttta cgaaggaaca gatagctaaa gcatatggaa gtgacgattt ttcagactta   420
gattatatag gtgtgaaacc gttgccatct gctgatggca tgacagttac aaagatagtc   480
gcaagctata cgagtggatc atctgacgac gtggatatta atcttaaggg aattgctgga   540
gagtgggcta acggcgtaaa tataggatgg aatttgggta acactcttga tgcatatgac   600
acgaacaggt ttaagagctc aaaaggtcat aacaatcctg ctgacataga acttgctgg    660 ggaaacccag tcactacgaa ggcaatgata atgacaataa aggctcaagg ctttaacgct   720
gtgagggttc cggtgacatg ggattttgaa atagacgata cgacggtta aaggtgaat    780 gaggcttgga tggcaagggt taagagggtt gtagactatg tcatggataa tgatttgtat   840 tgcatttta acgtacatca cgatacagga gagcagggct ggttaaaggc ttctacagca   900
aattacaata aaaacgttaa gaatttaa gcactttgga aacaaatagc tgcagagttt   960
aaaaactacg acaacaaact tgcttttgag ggctttaatg agatgttaga cgaaaaaat  1020
```

```
agttggaatt atcctggtac agatgctgga gatgctataa atttgtataa ccaggcattt    1080
gtcgacgtgg tcagagcatc tggtggcaag aatggaaaaa ggccgcttat atgtaataca    1140
tatgcaggct gtactgaggc tggtgctttg aacagcttta agattccgaa cgatactgtt    1200
gataacgcaa taattgctca ggtacatttt tatcaaccaa cgggatactg ttttgacatg    1260
aatcctaacc agggtcaaaa catggatgtc gactacaaaa catgtggcgg agagtcagct    1320
gcagacacat tggctatgat gctttataaa agatttacgg aaaagggcat tccatgcata    1380
gttggagagt ttgcagcttc tcacaaaaag aacgacgaca acagagcaga atgggtggat    1440
tacgtcgtta gaaagacggg aacatatggt gtgaaatgtt tttggtggga taatggaggt    1500
acatttacgc cgaattacag cactggtctt gattattaca actcaatggg catttacaac    1560
aggaatacaa tgcagtttga gtacccaaag gtagcagacg ctcttgtgaa tgctgcaaac    1620
ggaggtgcta aaccgactac agctccgact aaaaagccaa catctactcc aaagccgacg    1680
gctacattga aaccgactac aaagcctacg actaagccta caacgaaacc taatccgacg    1740
agtggcgcag actctggtga aataattctt ttttctggta gtaatcacgc tgattttaaa    1800
gcatggggcg gtgatgattg gccttcagct tttgaaataa gtcctaaata tgagccaatg    1860
aagttagacc ttaataaaaa ctttgaaata aaggtggatt acaacggagc agacattgtt    1920
cttatatttg ctaggtggga taaggatatt tgggctcaga taagcccata ctatgtcgta    1980
gacggtactg cagtatttac taaagagcaa attgcaaagg cttacggttc agatgacttt    2040
tcaggattag actatatagc tgttaagcct cttccgagtg aagaaggcgt aactgttaca    2100
aaagtgagcg gtatttacac aaatggaggc tctgaggatg ttgacataaa cttgaaaggc    2160
atagctggtg aatgggcaaa cggtgttaac attggctgga accttggaaa tacattggac    2220
gcttacgata ctaatagatt tacgagaaca aagggacaca ataacccggc agatattgaa    2280
acgtgttggg gtaatccggt tacaactaaa gctatgattg acgatattaa agcacaggga    2340
tttaacgcag tcagagtccc agttacttgg gattacgaga ttgacgacaa cgacggatac    2400
aaagttaacg aggcttggat ggctagagtg aaggaagtag tggattacgt tatggataat    2460
gatatgtatt gcatagtcaa tgtgcaccac gacacgggtg aacaaggatg gcttaaggca    2520
agcacagcaa attatgctaa aaatgaaaaa agtttaagg ctttgtggaa gcagattgca    2580
gctgaattta agaactacga ccacaagtta gcatttgaag ctttaatga gatgcttgat    2640 gagaagaact catggaacta cccaggtgct gatgcaggag aagcaattaa cctttacaat    2700
caggcttttg tggatgtagt gagggctagc ggcggaaaaa actctgatag accattaatt    2760
tgcaacactt acgctggttg cacggaagca ggcgcactta attcatttga aataccaaac    2820
gacacagttg agaacgctat tatagcacaa gtccacttt accagccgac tggttattgt    2880
tttgatatga atccaaatca aggccagaat atggacgttg attataagac ttgcggaggc    2940
gaaagtgcag ctgatacgct tgcaatgatg ttgtacaaga ggtttacaga gaaaggtata    3000
ccgtgtattg tgggtgaatt tgctgcaagc cataaacaaa cgacgataa tagggcagca    3060 tgggtcgact atgttgtgtc taaaacaggc aaatacggcg ttaagtgctt tggtgggat    3120 aacggtggca cgtttacacc aaactattca acgggattag actactataa tagtatgggt    3180
atatataata gaaacactat gaagtttgaa tatcctaaag tggctgatgc attggtaaaa    3240
gcagctaatg gtggaactat gccgacagta gcaccaacga agaaacctac agcaacaccg    3300
actccaacaa aaaaacctac tagcacaccg aagcctacag ttaaaccgac gcaaacgccg    3360
aaaccaacaa gaaagccggg aaaaagagta aaatattcag ctttagattt ggacggcaat    3420
```

<210> SEQ ID NO 98
<211> LENGTH: 3303
<212> TYPE: DNA
<213> ORGANISM: Artificial Sequence
<220> FEATURE:
<223> OTHER INFORMATION: Codon-Optimized Celulomonas fimi CenC

<400> SEQUENCE: 98

| | | |
|---|---|---|
| gtgagtagtg gtaatcttat tcca | 3444 | |
| atggttagca gaaggtctag ccaagcaaga ggagctttga cggcagtggt tgctactctt | 60 | |
| gcattggctt tagctggtag tggcacggca ttagctgcat cgcctatagg ggaaggaaca | 120 | |
| ttcgatgacg gccctgaagg ttgggtagct tatggaactg atggtccgtt ggatacatca | 180 | |
| acaggcgctc tttgtgttgc agtcccagct ggctctgcac agtacggagt gggtgtcgta | 240 | |
| cttaatggcg ttgctattga gagggaact acatatacat taaggtatac agcaacggct | 300 | |
| tctacagaca taacggtgag agcattagtt gggcaaaacg gtgcaccata tggcacagtt | 360 | |
| cttgacacga gtccggcttt gacgtcagaa cctagacagg taactgaaac attcactgca | 420 | |
| tcagctacgt acccagcaac tcctgctgca gacgatccgg agggccaaat agcttttcag | 480 | |
| ttaggtggct tcagcgcaga tgcttggaca ttttgccttg acgatgtggc attagatagc | 540 | |
| gaagtagagc ttttacctca tacgagtttc gcagaatctt tgggcccgtg agcttgtat | 600 | |
| ggaacttcgg agccagtctt tgctgatggg agaatgtgtg ttgacttacc aggcggtcag | 660 | |
| ggtaatcctt gggatgctgg attagtctat aatggggtac cggtgggcga aggtgagagt | 720 | |
| tacgttttgt cgtttacagc aagtgctacg ccggatatgc cagtaagagt ccttgtggga | 780 | |
| gaaggggtg gagcttatag gactgctttt gaacagggat ctgcaccgct tactggggag | 840 | |
| ccagcaacga gggagtacgc tttcactagc aaccttacgt ttccgcctga cggcgatgca | 900 | |
| ccaggtcagg tggcatttca ccttggaaag gctggagcat acgaattttg catttcacaa | 960 | |
| gtaagtttaa cgacttctgc aacacctccg ccaggttacg aacctgacac tggaccgaga | 1020 | |
| gttagagtaa atcaggtcgg gtatttacca ttcggtccga agagagcaac acttgtgact | 1080 | |
| gacgcagcag aaccggttgc ttgggaatta agggatgctg atggtgtagt tgtcgcagat | 1140 | |
| ggaacgagtg aacctagagg cgttgaacca tcagctgcac aagctgtaca tgttttagac | 1200 | |
| ttttcggatg taactacgca gggagctggc tatacttg ttgctgacgg agaaacgagt | 1260 | |
| agaccgtttg atatagacgg tgatttatac caacagttaa gatacgacgc tttgaattat | 1320 | |
| ttctatcttg caagaagcgg aactgaaatt gaagcagacg tcgttggtga agaatacgca | 1380 | |
| agggaggcag gacacgtagg cgtggcacca aaccaaggcg acacagacgt gccttgtatt | 1440 | |
| ggtcctagag attattacga cggatggact tgcgattaca ggttagacgt tcgggaggt | 1500 | |
| tggtacgacg ctggtgatca cggaaaatac gtagtcaacg ggggcattgc agtgggtcaa | 1560 | |
| ttacttcaga cttatgaaag gctttgcat gcagggacag cagatgcttt agcagacggc | 1620 | |
| acgcttgatg ttccggaaca cggtaatgat gtaccagacg tcttagacga ggctaggtgg | 1680 | |
| gagcttgaat ggatgctttc gatgattgtc cctgaaggag agtatgctgg gatggttcat | 1740 | |
| cataaagttc acgacgaggg atggactggt ttaccttgc ttcctgcaga cgatccgcaa | 1800 | |
| gctaggagtt tgcataggcc aagcacagct gctacactta atttaagcgc agttgcagca | 1860 | |
| cagggagcta ggcttcttga accttacgat ccacaacttg ctcagactct tttagaggca | 1920 | |
| gctagaacta catgggcagc tgcacaagaa caccctgctc tttacgcacc tggtgaggca | 1980 | |

```
ggggctgacg gcggaggcgc ttataacgat agtcaggtag ctgacgagtt ttattgggct    2040
gctgcagagc tttacttgac gactggcgag gacgcattcg caacggcagt cactacgtca    2100
ccgcttcata ctgctgacgt ctttacggct gacggctttg ggtggggcag cgttgcagct    2160
ttgggtaggc ttgacttagc tacagtccct aatgaacttc cgggattaga tgctgtacaa    2220
agttcagtgg ttgaaggcgc acaggaatat ttggctgcac aggctggaca aggttttgga    2280
agtctttata gcccaccggg tggcgagtac gtgtggggtt ctagtagcca agtcgcaaac    2340
aatttagtgg ttgttgctac agcttatgat cttacaggcg acgagaggtt cagagcagct    2400
actcttgaag gacttgatta ccttttggt aggaatgctt taaaccaaag ttatgtcact    2460
ggttggggag aggttgcttc acaccagcaa cattctaggt ggtttgcaca tcaattggat    2520
ccatctttgc cttcgccgcc tccaggctcg cttgctggcg ggccgaatag ccaggctgca    2580
acttgggacc caactacaaa ggcagctttc cctgacgggt gcgctcctag cgcttgctac    2640
gttgatgaaa tacaggcttg gtcaacgaac gagttaacgg taaactggaa ctcggctctt    2700
agttgggtcg cttcatgggt agctgatcag gggtctgcag agccagtccc gacggcacca    2760
gttgtgacaa gacaacctgt tgacgcaaca gtagctttag gagcagacgc aactttcaca    2820
gcagaggctt caggtgtgcc agctcctaca gttaggtggc aagttagagc aggaagggggg    2880 tggaaggacg tcgctggtgc aacaggcact acattgacag tgagggcaac tgctagaact    2940
gatgggacga ggtatagagc agtatttact aacgcagctg ggagtgtgga gagcgcagtt    3000
gtaaggctta cagtcgaaag agcagctcca gtggttacac aacatccagc tgatgttaga    3060
gcaagggtag gtacgagggc agtgtttagg gcagcagctg acggatatcc aacaccgtgt    3120
gttgtttggc aagtcagatg gggggggcggt tcttggaggc caattccttg ggcaacgagc    3180
actacattat cggtaccagt gacagtactt gctgcaggaa ctgaatacag ggctgttttt    3240
acaaatgcag taggtactgc tgcaacagag cctgctgaac ttgcagtcca aagaccgagg    3300
agt                                                                 3303
```

<210> SEQ ID NO 99
<211> LENGTH: 1663
<212> TYPE: DNA
<213> ORGANISM: Artificial Sequence
<220> FEATURE:
<223> OTHER INFORMATION: Celulomonas fimi Exo-glucanase

<400> SEQUENCE: 99

```
atgcctagaa caactccagc acctggacat ccagctaggg gtgcaaggac agcacttagg      60
acgacaagaa ggagagcagc tacgttggta gttggggcta cggtagtctt gcctgctcaa     120
gcagcaacaa ctttaaaaga ggcagctgat ggagctggta gagactttgg ctttgctctt     180
gatccaaata ggttatcgga agcacagtac aaagcaattg cagattctga atttaactta     240
gttgtggctg agaatgcaat gaaatgggat gctactgaac ctagccaaaa ttcattctcg     300
ttcggagctg gcgacagggt ggcatcttat gcagctgaca cggcaaggaa actttatgga     360
cacacattgg tttggcatag ccagttacca gactgggcaa agaacttgaa cggttcggca     420
tttgagtcag ctatggtaaa tcacgtgact aaagttgcag atcatttga aggcaaggta     480 gcttcatggg atgtagtgaa cgaggctttc gcagatggag atggtcctcc acaagatagc     540
gctttccaac agaagttggg caatggatac attgaaacgg ctttcagggc agcaagggct     600
gcagatccta cagctaagtt gtgtataaac gattacaatg tagaaggtat taatgcaaag     660
agtaattcac tttacgattt ggttaaagac ttcaaagcta ggggcgtccc attagattgc     720
```

```
gtgggatttc agtctcatct tatagttggt caagtacctg gcgattttag gcaaaactta      780
cagagatttg cagacttggg agtggatgtt aggattactg aacttgatat aagaatgaga      840
acaccaagcg acgctactaa attagcaaca caggcagctg attataaaaa ggtagtccag      900
gcatgtatgc aagtgacaag gtgccagggt gtgactgtgt ggggtattac agataaatat      960
tcatgggtac ctgacgtgtt tccaggcgag ggggcagctc ttgtgtggga cgcttcttac     1020
gctaaaaagc ctgcatatgc tgcagtcatg gaagcattcg gcgcttcgcc aacaccaact     1080
cctacgacac ctacaccgac tccaacaacg ccgacgccta cgccaactag cggccctgct     1140
ggatgccaag tattatgggg ggtgaatcag tggaatacgg gcttcacagc taatgtgacg     1200
gtaaaaaata cttcgagcgc tccagtagat ggttggacat taacattttc ttttcctagc     1260
ggacaacaag tgactcaggc ttggtcaagt acagttactc aatctggcag cgcagtaaca     1320
gtgagaaatg ctccatggaa cggttcaatt cctgctggag gcactgctca gtttggtttt     1380
aatggatctc acacaggcac aaatgctgca ccaactgctt tttctttaaa tggaacacct     1440
tgtactgtag gtctcgagtg ataaaacgaa aggctcagtc gaaagactgg gcctttcgtt     1500
ttatctgttt tttgtcggtg aacgctctcc tgagtaggac aaatccgccg ggagcggatt     1560
tgaacgttgc gaagcaacgg cccggagggt ggcgggcagg acgcccgcca taaactgcca     1620
ggcatcaaat taagcagaag gccatcctga cggatggcct ttt                       1663

<210> SEQ ID NO 100
<211> LENGTH: 1897
<212> TYPE: DNA
<213> ORGANISM: Artificial Sequence
<220> FEATURE:
<223> OTHER INFORMATION: Codon-Optimized Acidothermus cellulolyticus
      glycoside hydrolase, family 5

<400> SEQUENCE: 100
atgccgaggg cattaaggag agtcccgggg tcaagggtta tgcttagagt gggtgtagtt       60
gtggctgtat tggcattagt tgcagctttg gctaatttag cagttcctag gccagcaaga      120
gctgctggcg gaggttattg gcacacaagc ggcagagaga tattagatgc taataacgtg      180
cctgttagga ttgcaggcat taactggttc ggatttgaaa cgtgtaatta cgtagttcac      240
ggcctttgga gcagagacta taggagtatg ttggatcaaa ttaagtcatt aggatacaat      300
acaataagac ttccatacag cgatgacatt cttaagccgg ggacgatgcc gaactcgata      360
aacttttacc agatgaatca agatttacag ggcttgacga gtttacaagt gatggataaa      420
attgtagcat acgctggaca gataggttta agaataattc ttgacaggca tagacctgat      480
tgctcaggtc aaagtgcatt atggtatacg agtagtgtct cagaagctac atggatatct      540
gatttgcaag cacttgcaca gaggtacaag gggaacccaa cagtggtggg gtttgattta      600
cacaacgagc cacatgatcc ggcttgctgg ggttgtggag atcctagcat tgattggaga      660
ttggctgcag agagggctgg taatgctgtg cttagtgtaa atccgaactt attgatattt     720
gtggaaggcg ttcaaagtta taacggtgac tcatactggt ggggtggaaa tcttcagggc     780
gctggtcaat atcctgtagt tttaaacgta ccgaacagac ttgtatatag cgctcacgac     840
tatgcaactt cagtttatcc tcagacatgg tttagtgacc caacttttcc taataacatg      900
ccaggaattt ggaataagaa ctggggctac cttttttaacc aaaacatagc accagtgtgg      960
ttaggtgagt tcggtactac tttgcagtct acaacagacc agacttggct taaaacatta     1020
gtgcagtatt taagaccaac tgcacaatac ggcgctgata gctttcagtg gactttttgg     1080
```

| | |
|---|---|
| agttggaatc ctgacagtgg cgatactggg ggaatattga aggatgattg gcaaactgtt | 1140 |
| gatacggtga agatggtta tcttgcacct ataaaaagta gcatattcga ccctgtggga | 1200 |
| gctagtgcta gcccttcatc tcaacctagc ccatctgttt cacctagtcc aagcccgtca | 1260 |
| ccaagcgcaa gtagaactcc gactcctacg ccaacaccga ctgcttctcc aactcctacg | 1320 |
| ttgactccga cggctacgcc gactcctacg gcaagcccga cgccaagtcc aacggctgct | 1380 |
| tctggagcaa gatgtacggc ttcttatcag gtaaattctg actggggtaa cgggtttacg | 1440 |
| gtgacagtcg ctgtgactaa ttcaggttcg gtagctacaa agacttggac agtaagctgg | 1500 |
| acttttggag gcaaccaaac aattacaaac tcttggaacg ctgcagttac tcaaaacggt | 1560 |
| cagtctgtga cagcaagaaa catgtcgtat aataacgtaa tacagcctgg ccaaaacact | 1620 |
| acatttggat tccaggcttc ttatactgga tcaaacgcag ctccgacagt ggcatgcgct | 1680 |
| gcatcactcg agtgataaaa cgaaaggctc agtcgaaaga ctgggccttt cgttttatct | 1740 |
| gttgtttgtc ggtgaacgct ctcctgagta ggacaaatcc gccgggagcg gatttgaacg | 1800 |
| ttgcgaagca acggcccgga gggtggcggg caggacgccc gccataaact gccaggcatc | 1860 |
| aaattaagca gaaggccatc ctgacggatg gccttttt | 1897 |

<210> SEQ ID NO 101
<211> LENGTH: 3363
<212> TYPE: DNA
<213> ORGANISM: Artificial Sequence
<220> FEATURE:
<223> OTHER INFORMATION: Codon-Optimized Acido-thermus cellulolyticus
    glycoside hydrolase family protein

<400> SEQUENCE: 101

| | |
|---|---|
| atgcctgggc ttagaaggag acttagggct ggtatagttt ctgcagctgc attgggctct | 60 |
| ttagttagcg ggcttgtggc agtcgctcca gtagcacatg ctgcagtaac tttaaaagct | 120 |
| cagtacaaaa acaacgatag tgcaccgtcg gataatcaga ttaaaccagg ttgcaacttt | 180 |
| gtgaatacgg gcagctctag cgtcgatttg agtactgtaa cggttaggta ttggtttact | 240 |
| agggatggag gttcaagtac attagtatat aactgtgact gggctgcaat gggttgcggt | 300 |
| aacattaggg catcgttcgg cagcgtgaat ccagcaacac ctacagcaga tacgtacctt | 360 |
| cagttgagtt ttactggagg tacgttagct gctggtgggt cgacggggga aattcaaaac | 420 |
| agagttaata atcggactg gtcaaacttt gacgagacaa acgattattc atacggtact | 480 |
| aacacgacat tcaagactg gacgaaagtc actgtctacg taaatggcgt gcttgtatgg | 540 |
| ggaactgagc catcaggtgc aacagcatca ccgtctgcta gcgcaactcc gagcccttca | 600 |
| tctagcccga cgacaagtcc ttcgagttct ccaagccctt caagttctcc gactccgaca | 660 |
| ccttcgagta gctctccacc tccatcatcg aacgacccgt acatacagag gttttaaca | 720 |
| atgtacaata aaattcacga tcctgctaat ggctatttta gccctcaggg gataccttac | 780 |
| catagcgttg aaacgttaat tgtcgaagca ccagactacg gcacgaaaac gacttcagag | 840 |
| gcttattcgt tctggctttg gttagaagct acgtacgggg ctgtgacagg taactggaca | 900 |
| ccatttaata acgcatggac gactatgaa acgtacatga ttcctcagca cgcagaccaa | 960 |
| cctaacaacg catcgtacaa tcctaatagt ccggctagct atgcaccaga agagccgctt | 1020 |
| ccatctatgt atccagtagc tatagattca tcggttccgg taggacatga tcctttagca | 1080 |
| gctgagttgc agtctacata cggtacgcct gacatttacg gaatgcactg gttggcagat | 1140 |
| gtcgataaca tttacggata tggcgacagc ccgggtggtg gctgtgaact ggcccttca | 1200 |

```
gctaaaggag tgtcgtacat taatactttt caaagaggta gtcaggaaag tgtttgggaa    1260
acagtaacgc agccaacatg tgataacgga aagtacgggg gagcacacgg ttacgttgac    1320
ttatttatac agggcagcac accacctcaa tggaaataca cagacgctcc tgacgcagac    1380
gcaagggctg tacaggcagc ttattgggct tacacttggg cttcagcaca aggtaaggct    1440
tcagctattg cacctactat agctaaggct gcaaaattgg gagactattt gagatacagc    1500
ttattcgaca aatattttaa acaagtcgga aattgctacc cagctagttc ttgcccaggt    1560
gcaacgggga gacagtcaga gacttacttg atagggtggt attacgcttg gggagggagt    1620
tctcagggat gggcatggag aataggtgat ggggctgctc acttcggata tcagaaccct    1680
cttgctgcat gggcaatgag caatgtgaca ccgcttattc ctttaagccc aacggctaag    1740
tcagactggg cagcttcgct tcaaagacag ttggagttct accaatggtt acagagcgct    1800
gagggtgcaa ttgctggagg ggctactaac agctggaatg caattatgg cacacctcca    1860 gctggcgata gtacattcta cgggatggct tatgattggg agcctgttta tcacgaccca    1920
cctagcaaca attggtttgg attccaggca tggtcgatgg agagggtagc tgagtactat    1980
tacgtcacgg gtgatccgaa agcaaaggct ttgcttgaca atgggtggc ttgggttaaa    2040 ccaaatgtaa ctacaggagc atcttggagc attcctagta acttatcttg gtcagggcaa    2100
ccggacacgt ggaacccaag taatcctggc actaacgcta atttgcatgt cacaattacg    2160
agtagcggtc aggatgtggg agtggcagca gctttagcta aaactttaga gtattacgct    2220
gcaaagtcag gcgatacagc tagtagagac ttggctaaag gtcttttaga tagcatatgg    2280
aataacgatc aagatagcct tggtgtatca acaccagaga caagaacgga ttacagtaga    2340
ttcacacagg tttatgatcc tactacaggc gatggccttt acattccgag cggttggacg    2400
ggaactatgc cgaacgggga tcaaataaag cctggagcta cattcttatc tataagaagc    2460
tggtatacaa aagatccaca gtggtcgaaa gtacaggctt acttgaacgg tggccctgca    2520
ccgacgttta attatcatag gttttgggct gaaagtgact tcgcaatggc taacgcagat    2580
tttggtatgc tttttccaag cggatcgcca tcaccgacgc caagtccaac gccgacttct    2640
agtccttcac cgacacctag cagttctcct acgccgagtc ctagcccatc gccgacgggt    2700
gacactactc ctccgtcggt gccgactggt ttacaggtca ctggcactac gacttcgagt    2760
gtttctttgt catggacagc ttcgacagac aacgttggag tagcacatta taatgtgtat    2820
aggaatggaa cacttgtagg acaacctact gcaacgagtt ttacggatac tggtttagct    2880
gcagggacat cgtatacgta cactgtagct gcagtcgatg cagctgggaa tacgagcgct    2940
cagtcaagtc cagtgacagc aacaacggca gtccgagtc ctagcccatc acctagtccg    3000
actccgacga gtagcccttc gccgacaccg tcacctacac cgtcaccgac aagcacgagt    3060
ggggcaagct gtactgctac atatgttgta aattcagatt ggggctcggg tttcacgact    3120
acagtcacgg tgactaatac tggcacaaga gcaacttcgg gctggacggt gacttggagt    3180
ttcgctggga accaaacagt cactaactac tggaacacgg ctttgacaca aagcggaaag    3240
agtgtaacgg caaaaaatct tagttataat aacgtaattc agccgggaca atcgacaacg    3300
tttgggttta atggcagtta tagcggtact aacacggcac caacattgtc ttgcactgca    3360
agt    3363
```

<210> SEQ ID NO 102
<211> LENGTH: 1407
<212> TYPE: DNA

<213> ORGANISM: Artificial Sequence
<220> FEATURE:
<223> OTHER INFORMATION: Codon-Optimized Acido-thermus cellulolyticus Biomass degrading enzyme

<400> SEQUENCE: 102

| | |
|---|---|
| atgggaacat atcctataag atcggtcagc ggtggcgttg cacttgctgc atgcgctgtt | 60 |
| cttactatga caacggctgc agcagctacg cctattcacg atgctagttc gcctcacact | 120 |
| attccacctc atgctaggtt gtacacaccg ccaccggaca aaggagcaat taagcaaata | 180 |
| acagatttac ttaaagctag ggacgtcagg gacgcaagat tgattgctga tgataagc | 240 |
| actcctcagg cagtttggtt tacgggggt acaccggatc aggtgagaag ggacgtccac | 300 |
| agagttgtta ctaaagcagc tgcacaccac gcaattcctg tgttagttgc ttacaatata | 360 |
| ccgtttagag attgctcaca gtacagcgct ggaggcgctg ttgatacagc agcatatgag | 420 |
| gcttggatag atggctttgc agcaggcata ggagataaga gagctatagt tcttttggaa | 480 |
| cctgatagtt taggcataat accatacaac acagatatta tggaaatgc tgagtggtgc | 540 |
| aagccagacc tttcaggtac aggccttaca cctgacgagg ctaaccaagc tagatatgat | 600 |
| caattaaatt atgcagtgga cgctcttgaa gcacacagaa atgtatctgt ttaccttgat | 660 |
| ggtacgcata gcggttggtt aggcgtagga gatatagctc aaagacttgt gagggctggt | 720 |
| gttcagagag ctcaaggctt ttttgtaaac gtgagtaatt atcaaactac agagaggcag | 780 |
| ataaagtacg gaacatggat ttcagaatgc atagcatttg caaatgaccc agaagagggt | 840 |
| gggtggagat taggccatta ttcttggtgt gctagccaat actatcctgc aaatcctaac | 900 |
| gacttttcaa cttgggttca gacagatcag tggtacgcta gtaatttggg tactgcagta | 960 |
| ccaacaactc acttcgtcat tgacacttct agaaacggaa ggggtccgaa cgatatgaca | 1020 |
| gcttatgctg cagctcctta taccagcct gctagcgtaa tatcggctct tcagggagga | 1080 |
| agttggtgca acccacctgg cagaggttta ggattgaggc ctacagtgaa tacaggcgtt | 1140 |
| cctcttttag acgcttacct ttgggtaaag attccaggtg aatctgatgg acagtgcgat | 1200 |
| gcagctggcg gtgctagggc ttgggattat agcgcttaca ctgaacctgg atggccaaca | 1260 |
| gaccettcac aacaggcttt attcgatcct ttatggggcc tttacgaccc gccagcaggg | 1320 |
| caatggtttc ctcaacaggc tttacaactt gctcaacttg cagtgcctcc gttgcaacca | 1380 |
| cagtggcctg ttccaccagt ccatcac | 1407 |

<210> SEQ ID NO 103
<211> LENGTH: 1641
<212> TYPE: DNA
<213> ORGANISM: Artificial Sequence
<220> FEATURE:
<223> OTHER INFORMATION: Codon-Optimized Butyrivibrio fibrisolvens Cellulase 1

<400> SEQUENCE: 103

| | |
|---|---|
| atgcataaga gcaagtgtat taaaagggtc tttacatttt tgttagcact ttttgttttt | 60 |
| gtcatggcaa ttcctgcaac taaggtcagt gctgctggag gtacggatag gagcgctact | 120 |
| caagtagttt ctgacatgag agttggctgg aatattggta actcacttga cagttttggt | 180 |
| cagagctata attttccata cacgagcctt aatgaaacgt attggggcaa cccggcaaca | 240 |
| actaaggctt taattgacga ggtcgcaaag gctggattta acaataag gattcctgta | 300 |
| agttgggggac aatacacgac aggcagtgac taccagattc cagattttgt catgaatagg | 360 |
| gtaaaagagg tggttgacta ttgtattgtt aacgatatgt acgttattct aacagccac | 420 |

```
catgatataa acagcgacta ttgcttttac gtcccgaata acgcaaacaa ggacaggtct    480
gaaaaatact ttaagagcat ttggacgcag atagctaagg agtttaagaa ctacgattac    540
caccttgtat ttgaaacgat gaatgagcct agattagtcg acatggtga agaatggtgg    600 tttccgagga ataacccatc aaatgacatt agggaagcag tagcttgcat taatgactat    660
aaccaagttg cattagacgc tattagggca acaggcggca ataacgcaac tagatgtgta    720
atggttccag gttacgacgc atctattgaa ggctgcatga cagacggatt taaaatgccg    780
aacgatacgg cttcaggtag gttgattctt tcagtacacg catacatacc gtattacttt    840
gctttggcat cagacacata cgtgactagg tttgacgata accttaaata tgacatagac    900
agttttttta atgaccttaa ttctaaattt ttgagcagga acattccagt cgtggtcggc    960
gaaacatctg caacaaacag gaacaatacg gctgaaagag ttaaatgggc agattattac   1020
tggggaagag ctgcaagata cagtaacgtt gctatggttt tatgggataa caacatttac   1080
cagaataaca gcgctggttc agacggagag tgtcacatgt acatagatag gaactcactt   1140
cagtggaaag atcctgaaat tataagtact attatgaagc acgtggacgg aactccagca   1200
acgattaacg gaaagaaat accgtctact gaacaacctg atccaacacc ggtagatcct   1260
gacccaacac cagtagaccc tgatccgacg ccggttgatc cagaccctac accagttgat   1320
cctgatccgc aaccagtcga tccgacgcct gtttcaggag cattgaaggc tgaatacacg   1380
attaacaact ggggcagcgg ttatcaggtt cttattaaag tcaaaaatga tagcgcttct   1440
agagtggatg gatggacgct taagatttct aaatcagagg ttaagataga ttctagttgg   1500
tgcgtaaata tagctgaaga aggcggttat tacgttataa ctcctatgtc atggaacagt   1560
agtttggagc catctgcaag tgttgacttt ggtattcagg gaagcggcag tataggaaca   1620
agtgtcaaca tatctgtgca a                                              1641
```

<210> SEQ ID NO 104  
<211> LENGTH: 5133  
<212> TYPE: DNA  
<213> ORGANISM: Artificial Sequence  
<220> FEATURE:  
<223> OTHER INFORMATION: Codon-Optimized Anaero-cellum thermo-philum  
    1,4-beta-glucanase

<400> SEQUENCE: 104

```
ggatcattta attatggtga agcattacaa aaagctataa tgttttacga gtttcagatg     60
tctggcaagt tgcctaactg ggtaagaaac aactggaggg gagatagcgc attgaaaagac    120 ggtcaagata atggcttaga ccttactgga ggttggtttg atgctggcga tcatgttaag    180
tttaatttgc caatgagtta tactggaacg atgttatcat gggcagtgta cgaatataaa    240
gacgcttttg tcaaaagcgg tcagcttgag cacattttga atcaaataga gtgggtaaat    300
gattactttg tgaagtgtca cccgtctaaa tatgtctact actaccaggt tggcgatgga    360
agtaaagatc atgcatggtg gggtcctgct gaagtaatgc aaatggaaag accatcattt    420
aaggttacac agtctagccc gggcagtact gtagtgacag aaacggcagc ttcattagca    480
gctgcatcta ttgttcttaa agacaggaat cctactaagg ctgcaacata tttgcaacat    540
gctaaagaat tatatgagtt tgcagaagtc acaaaaagcg atgctggata tacggcagca    600
aatggttatt ataactcatg gagtggctttt acgatgaac tttcttgggc tgcagtatgg    660
ttgtatttag ctactaatga cagcacatac cttacgaagg cagagtcata tgttcaaaat    720
tggccaaaaa taagtggatc taacactatt gattacaaat gggctcattg ctgggatgac    780
```

```
gtgcacaatg gtgcagcttt attgcttgca aagataacag gcaaagatat ttataaacag      840
ataatagaaa gccatttaga ttattggatt acgggataca atggtgaaag aataaagtat      900
actcctaaag gattggcttg gcttgaccaa tggggctcat taaggtacgc aacaacaacg      960 gctttttttgg catttgtata tagtgattgg gttggttgtc catctactaa gaaagagatt    1020
tatagaaaat ttggagagag ccagatagat tacgctcttg gctcagctgg tagatctttt    1080
gtcgtaggat ttggcacaaa cccgcctaag aggccacatc acagaactgc tcattcaagt    1140
tgggcagaca gccaatctat tccttcatat cacaggcaca ctttatacgg tgctttggtg    1200
ggaggcccag gtagtgatga tagctataca gacgatatat ctaattacgt taataacgaa    1260
gtagcatgcg attataatgc aggatttgtc ggcgctcttg caaaaatgta tcagttatac    1320
ggtggaaatc cgatacctga ctttaaagct attgaaacgc caactaatga tgaattttt    1380 gtggaagcag gcataaacgc ttcaggaaca aattttattg agataaaggc aattgttaat    1440
aaccaaagtg gttggcctgc taaagcaacg gataaattga agtttagata ttttgtagac    1500
cttagcgaat aataaaagc tggatactct ccaaatcagt taactttgtc aacaaattat    1560
aaccaaggcg caaaggttag tggtccgtac gtatgggatg ctagcaaaaa tatttattat    1620
atacttgtcg attttacggg aactttaata taccctggcg gtcaagacaa atataagaaa    1680
gaggtgcagt ttagaattgc agctccacaa aatgttcagt gggataactc taatgactac    1740
tcatttcagg atataaaggg agtcagtagc ggctctgtag tgaaaacaaa atatattcct    1800
ttgtacgacg gtgacgttaa ggtctgggga gatggcccgg gtacatctgg agctacgccg    1860
actccaacag caacggcaac gcctactccg acacctactg ttactcctac gccgacacct    1920
acgccgactt ctactgcaac tccgacgcct acgcctactc caacggtgac accgactcct    1980
acgccaacgc ctactgcaac accgacaagc acgccaacac caacttctac gccatcaagc    2040
acaccggttg ctggcggaca gattaaagtc ttgtacgcaa ataaggagac taattctaca    2100
acgaacacga ttaggccatg gttaaaagtg gtcaatacag gatcatcttc aatagactta    2160
tctagggtaa cgattagata ctggtatacg gttgacggcg ataaagcaca aagcgctata    2220
tctgactggg cacagattgg tgcaagtaac gttacgttta aatttgtaaa gttatcatct    2280
agtgtttctg gagcagatta ttaccttgaa ataggcttta aaagcggagc aggacagtta    2340
caagctggaa aggatacggg cgagattcaa ataaggttta ataaaagcga ttggtctaat    2400
tataaccaag gaaacgactg gtcatggatg cagagcatga caaactatgg cgaaaatgtg    2460
aaagtaactg cttatattga tggagtatta gtgtggggac aagaaccaag cggtgctaca    2520
cctacgccaa ctgctacgcc tgcaccgaca gtaactccta cgccgacacc aacaccgacg    2580
agtacaccta cggcaactcc gactgctacg ccgacaccaa ctccaacgcc gagctctact    2640
cctgtggcag gcggtcaaat aaaggtactt tatgctaaca aagaaacgaa cagcactaca    2700
aatacaataa gaccgtggct taaggtcgta aacactggca gttcaagtat tgatttgagc    2760
agagttacaa taaggtattg gtacacagtg gatggagaca aggctcagtc agcaataagc    2820
gattgggctc aaataggcgc ttcaaatgtg acgtttaaat ttgtaaaatt gagtagttca    2880
gtcagcggcg ctgactacta tttagagatt ggatttaagt ctggtgctgg tcaacttcag    2940
gctggtaaag acactggtga aatacagatt agatttaaca agtcagattg gagtaactat    3000
aatcaaggaa atgattggag ttggatgcag tctatgacga attacggaga gaacgtaaag    3060
gttacagcat acatagacgg cgtgcttgta tggggtcagg aaccttcagg tgcaactccg    3120
```

```
actccaacag caacgccggc tcctacggtt acaccgactc ctacgccgac tcctacgtca    3180
acgccgactg ctacacctac agcaacacca cgcctactc ctacaccttc ttcaacgcct    3240
agcgttgtag gtgaatacgg acagagattt atgtggttgt ggaataaaat tcacgatccg    3300
gctaacggct attttaatca agatggtata ccatatcact ctgtcgagac tcttatttgt    3360
gaaagacctg actacggaca cttaacaaca tcagaagcat ttagttatta cgtgtggttg    3420
gaggctgttt acggcaagtt gacgggtgat tggagcaaat ttaaaactgc atgggataca    3480
ttagaaaagt acatgatacc gtctgctgag gaccaaccaa tgaggtcata cgatcctaat    3540
aaaccagcaa cttacgctgg agagtgggaa acacctgata aatacccgag tccattggaa    3600
tttaacgtac ctgtaggtaa ggacccactt cataatgagt tagttagcac gtatggatct    3660
actttgatgt acggcatgca ctggcttatg gatgtagata attggtatgg ttacggaaaa    3720
agaggcgacg gtgtctcaag gcaagttttt attaacacat tcagagagg acctgaagaa    3780
agcgtgtggg agacagttcc gcatccatct tgggaagaat ttaagtgggg cggtcctaat    3840
ggatttttag atttatttat aaaagatcaa aattattcaa acagtggag atatacggac    3900
gcacctgatg ctgatgcaag ggctattcaa gcaacttact gggctaaggt atgggcaaaa    3960
gagcagggca aatttaatga aataagtagc tacgtggcta aggcagctag aatgggtgac    4020
tacttgaggt acgcaatgtt tgataaatat tttaaaccac ttggatgcca agataagaac    4080
gctgcaggcg gtacaggata cgactctgct cactatttac tttcatggta ctacgcatgg    4140
ggcggtgctt tagacggagc atggagttgg aaaataggaa gctctcacgt tcattttggc    4200
taccagaatc ctatggctgc atgggcattg gctaacgatt cagatatgaa gccgaaaagt    4260
ccaaacggtg caagcgattg ggctaaatct cttaagagac aaattgagtt ttatagatgg    4320
ttacaatcag cagaaggagc tatagcaggc ggtgctacga atagtggaa tggaaggtat    4380
gaaaaatacc ctgcaggcac tgctacattt tatggtatgg catacgagcc aaaccctgta    4440
tatcacgatc cggaagcaa tacgtggttt ggctttcagg cttggtctat gcaaagagtt    4500
gtagaatact attatgtcac tggtgacaaa gatgcaggag cttttgcttga aaagtgggtg    4560
tcatgggtta aatcagtagt caaattaaat agtgatggca catttgcaat tccaagcaca    4620
ttggactgga agaggcagcc tgatacgtgg aacggtgctt acactggaaa ttctaatctt    4680
catgtgaaaag ttgtagatta tggcacagac ttaggtataa cggcatcatt ggcaaacgct    4740
cttttatact atagtgcagg aactaagaaa tacggcgtct tgatgaggg tgctaaaaat    4800
ttggcaaagg aacttttaga tagaatgtgg aaattgtata gggacgaaaa aggacttagc    4860
gctccggaga agagggcaga ttataaaaga ttttttgaac aagaagtgta cattccagct    4920
ggctggatag gtaagatgcc taatggagat gttataaaat ctggcgtaaa atttattgac    4980
ataaggtcaa agtataaaca ggatccagat tggcctaaat tagaggcagc ttacaagagt    5040
ggtcaagcac cggaatttag atatcataga ttttgggctc agtgtgacat tgcaatagct    5100
aacgcaacat atgaaatttt gtttggaaat caa                              5133
```

<210> SEQ ID NO 105
<211> LENGTH: 2458
<212> TYPE: DNA
<213> ORGANISM: Artificial Sequence
<220> FEATURE:
<223> OTHER INFORMATION: Codon-Optimized Anaero-cellum thermo-philum
      Endoglucanase

<400> SEQUENCE: 105

```
atgaggaaaa ttattttaaa gttttgtgca cttatgatgg tagtgatatt gattgtgtca    60
atacttcaaa ttttgcctgt gtttgctcag tcaatattat atgaaaagga aaagtacccg   120
catttacttg gtaatcaggt tgtcaaaaag ccaagcgtgg ctggtaggtt gcagattata   180
gagaaggatg gcaagaaata tttagctgat caaaaaggtg aaataattca gttgaggggt   240
atgagcacac acggcttaca atggtatgga gatataataa acaagaatgc ttttaaggct   300
cttagcaagg actgggaatg caacgtcata aggttagcta tgtatgtggg agagggtgga   360
tatgcttcaa atccttcaat taaagagaaa gtgatagagg gtataaagtt ggcaattgaa   420
aatgatatgt atgtgattgt cgactggcat gttttaaacc cgggcgatcc taacgcagag   480
atttataagg gagcaaaaga tttttttaaa gaaatagcta ctagcttttc taacgactat   540
catattatat acgagctttg caatgagcca acccctaatg agccaggtgt tgaaaattct   600
ttagacggat ggaaaaaggt gaaagcatat gctcaaccta ttataaagat gttgaggtca   660
ttgggaaatc aaaacataat tatagtggga agccctaatt ggagtcagag gccggatttt   720
gcaatacaag atccgataaa cgacaaaaac gtgatgtact ctgtacactt ttacagcggc   780
acgcataaag tcgacggata tgtatttgag aatatgaaaa acgcttttga aatggtgtg   840
cctatttttg tgagcgaatg gggaacgagt cttgcatctg gagatggtgg accatatta   900
gatgaagctg ataaatggtt agaatattta aacagcaact acatatcatg ggtaaactgg   960
tcattgagca taaaaacga gacaagcgca gcttttgtac cttacataaa tggcatgcac  1020
gatgctactc cacttgatcc tggtgatgat aaggtctggg atattgaaga gttgtctata  1080
agcggtgagt atgtgagagc aaggataaaa ggaattgctt accaaccaat taaaagggac  1140
aataagataa agagggtga gaatgcacct ttgggcgaaa aggtacttcc aagcacattt  1200
gaggatgaca caaggcaggg ctgggattgg atggaccat ctggcgtaaa aggcccaatt  1260
actatagaat cagctaatgg ctcaaaagca ttatctttta acgtggaata cccggagaag  1320
aaacctcaag atggctgggc aacagcagct agattgatat tgaaggacat aaatgtcgag  1380
aggggcaata taagtaccct tgcatttgac ttttatctta agccggacag agcttcaaaa  1440
ggtatgatac agatgttttt ggcttttagc ccacctagtt taggatactg gctcaagtt  1500
caagattctt ttaacataga tttgggtaag acggtcaagt gtaaaaagga caggagaacg  1560
gaggtttaca agtttaacgt gttttttgat ttggacaaga tacaggacaa caaggtgctt  1620
tcaccggaca cattgttaag ggatattata gtcgttattg cagatggaaa cagtgacttt  1680
aagggaaaga tgtacattga taacgtgagg tttacaaaca cattgtttga agatattaat  1740
tttgaaaact ctttatatga cgttatagat aaactttata gcaagggaat aattaaaggt  1800
atatctgtct ttaagtattt accagataag aatataacga gagctgagtt tgcagcttta  1860
tgcgtaagag ctcttaattt aaaaattgag aagtacgatg gtaggtttag cgacgtcaaa  1920
agcggtaatt ggtactcaga gtgtgtttac acggcataca gaacaaaatt atttgagata  1980
aaggaaaata agttttttcc tgagaatata ttgaagaggg aagaggctgt ggcattggct  2040
atagaagttt acaagagact tacaggcaaa atagaggtga atacagacga cgttccaata  2100
gctgacgaga agtaattaa cccacagtac agggaaagcg ttaagttggc tataaagttg  2160
ggtatagtgg atttgtactc agacggaact tttgagccaa ataaatctgt atcaagaggc  2220
gaagtagcaa ctattttata caaccttctc gagtgataaa acgaaaggct cagtcgaaag  2280
actgggcctt tcgttttatc tgttgtttgt cggtgaacgc tctcctgagt aggacaaatc  2340
cgccgggagc ggatttgaac gttgcgaagc aacggcccgg agggtggcgg gcaggacgcc  2400
```
cgccataaac tgccaggcat caaattaagc agaaggccat cctgacggat ggccttttt    2458

<210> SEQ ID NO 106
<211> LENGTH: 2296
<212> TYPE: DNA
<213> ORGANISM: Artificial Sequence
<220> FEATURE:
<223> OTHER INFORMATION: Codon-Optimized Anaero-cellum thermo-philum

<400> SEQUENCE: 106

| | |
|---|---|
| atgaaaaaga gaaaatttaa gatattatat ttgtttctta aattgtact ttcagtttct | 60 |
| tttataatta gtattgtgtt tcctagcttt tttaaggcag ctcaaacaac tagcacaaac | 120 |
| attaattttg aaggaaggga taagttgacg ttttttgcat acggtaaggc taagattact | 180 |
| atagatcaga acatagcaca agagggaaaa aagagcataa aagtcacaga caggaagagt | 240 |
| gtctgggatt cttttggcat agatgtcaag gacgtgttgc aaaggggcaa gacatgggtg | 300 |
| gtgagcgctt acgtgaaaca taaggtaag aaaccaatag agtttagcat acggctata | 360 |
| tacaatgacg aaggggttt gaagtacctt cagttgggcg aaaaaatagt gatacctaac | 420 |
| aaatgggaca aaattgtggc taagtggaaa ccaactctta agaaccctat ggaccttata | 480 |
| attgcaattc accctacagt cgataagact acggcttaca atgttgacaa cattcagata | 540 |
| atgactgaag aggtgtacca gtcacaagca gtagttttta aggacacatt tgaaagcaac | 600 |
| ttgacaaact ggcagcctag aggagatact gtaaaactta aaattgataa tactaagtca | 660 |
| cacaacggta acaagtcttt gtacgtgtca ggtaggtctg cttttttggca cggagttcaa | 720 |
| attccagtaa ctaagtactt agttgcagga aaggtgtaca agttttcagt ttggttatac | 780 |
| catcaaagta ttgacaagca gggctttgga ttgacaattc aaaggaagat ggctaacgac | 840 |
| gaacaatata agtacgactg gattacgggt agccagattg aaggagatgg atgggtagaa | 900 |
| atatcaggca actattacgt gcctaaagat ggcaagattg aagagttagt gttttgtgtc | 960 |
| tcaagctgga atccgactct tgcatttttgg gtggatgatg tgacaatttc agacccttt | 1020 |
| aagttgcagg gcccgaatta caacttgcct agcttaaaag agaagtacaa agaggacttt | 1080 |
| aaggtaggtg tagcaatagg atatggcgaa ttaatttctg atattgacac acaatttata | 1140 |
| aagaaacatt ttaacagtat tactcctggt aacgagatga agcctgagag cgttttaaag | 1200 |
| ggtccaaaca attacgactt tactattgca gacgcttttg tggactttgc aacaaagaac | 1260 |
| aagatgggca taagggggtca tacattggta tggcataacc aaacgcctga ttggtttttt | 1320 |
| aaggatgaga acggtaactt tttgaagaaa acgaattgc ttaagaggtt gaagaaccac | 1380 |
| atttacacag tggtgtcaag atataagggt aaaatatacg catgggatgt agttaacgag | 1440 |
| gctatagatg aaactcaacc ggacggctac aggagatcta attggtataa catttgcgga | 1500 |
| ccagaatata ttgagaaggc atttatatgg gcacacgaag ctgaccctca agctaaatta | 1560 |
| ttttacaacg actataacac ggaaatacca cagaaaagaa tgtttatata aacatgata | 1620 |
| aaaaaccta aggcaaaggg cgtgccgatt catggtattg gattgcagtg ccacataaac | 1680 |
| atagataatc ctagcgtaga ggacattgaa gagactatta aacttttttc tactataccg | 1740 |
| ggtttggaga tacaaattac ggaacttgac atgagcttt tcagtggggg ttcatcagtg | 1800 |
| tactatgctg aaccttctag agaaatgtta ttgaagcagg caaaaaagta ctacgaatta | 1860 |
| tttaaccttt ttaagaagta caagaacgta ataaagtctg tgacattttg gggcttaaag | 1920 |
| gatgacaatt cttggttaag gggcgtattt aataagccag actttcctct tttgtttgac | 1980 |

```
gagcattacg acggaaagcc tgcattttgg gctttaattg actatagcat attgcctcaa    2040
aacgctaact tgccaacacc tccagcaatt ccgaaggtta aagcaaagaa gtgataaaac    2100
gaaaggctca gtcgaaagac tgggcctttc gttttatctg ttgtttgtcg gtgaacgctc    2160
tcctgagtag gacaaatccg ccgggagcgg atttgaacgt tgcgaagcaa cggcccggag    2220
ggtggcgggc aggacgcccg ccataaactg ccaggcatca aattaagcag aaggccatcc    2280
tgacggatgg cctttt                                                    2296
```

<210> SEQ ID NO 107
<211> LENGTH: 1296
<212> TYPE: DNA
<213> ORGANISM: Artificial Sequence
<220> FEATURE:
<223> OTHER INFORMATION: Codon-Optimized Anaero-cellum thermo-philum

<400> SEQUENCE: 107

```
atgcctacag taacaccaaa tcctacatca acgcctagca tattagatga cacaaacgac     60
gattggttgt atgtcagcgg aaataaaatt gtggacaagg acggtaaacc tgtatggttg    120
actggcataa attggtttgg atataatact ggtactaatg tatttgacgg cgtctggtct    180
tgcaatttaa aggacactct tgcagagatt gctaacagag ctttaatttt gcttaggatt    240
cctatatcag cagagataat tttgaactgg agtcagggaa tttatccaaa acctaatata    300
aactactacg tgaaccctga gcttgagggt aaaaatagct tggaggtgtt tgacattgtc    360
gttcaaatat gcaaagaggt tggattaaag attatgttgg atattcatag cattaagaca    420
gacgctatgg gtcatattta tccggtgtgg tatgacgata aatttactcc tgaggatttt    480
tataaagcat gcgaatggat aacaaacagg tacaagaatg atgacactat tatagctttt    540
gatttgaaga tgaaccaca cggcaaacct tggcaggaca cgacatttgc aaaatgggat    600
aatagcactg atattaacaa ctggaagtac gcagctgaaa cgtgcgcaaa gaggatattg    660
aacattaacc cgaacttgct tatagtgata gagggtattg aggcataccc gaaagacgac    720
gtaacatgga cgtcaaaatc ttacagcgat tattacagta cgtggtgggg tggcaattta    780
agaggagtta aaaaatacc aattaacttg gaaagtacc agaacaaggt ggtatacagc    840
cctcatgatt atggcccatc tgtttatcaa cagccttggt tttatcctgg atttacgaag    900
gaaagtttgt tgcaggattg ctggaggcct aactgggctt atattatgga agagaatatt    960
gctccattgc ttattggtga gtggggcgga tatttagacg gtgctgacaa tgaaaaatgg   1020
atgagatatc ttagggatta taattgag aaccacatac accacacgtt ttggtgcttt   1080
aacgcaaaca gcggagatac tggcggtatg gtaggatatg attttacgac atgggacgag   1140
aagaaataca gtttttttaaa accagctttg tggcaagatt ctcagggtag gtttgttggt   1200
ttagaccata aaaggccatt aggaacaaat ggaaaaaaca ttaatattac aatatactac   1260
aacaacaatg agcctgctcc agttcctgct gcaaaa                              1296
```

<210> SEQ ID NO 108
<211> LENGTH: 974
<212> TYPE: PRT
<213> ORGANISM: Artificial Sequence
<220> FEATURE:
<223> OTHER INFORMATION: Thermobifida fusca E1

<400> SEQUENCE: 108

```
Met Leu Arg Arg Pro Arg Ser Arg Ser Pro Leu Val Ala Leu Thr Ala
1               5                   10                  15
```

-continued

```
Ala Thr Cys Arg Val Ala Leu Gly Gly Thr Ala Val Pro Ala Gln Ala
             20                  25                  30

Asp Glu Val Asn Gln Ile Arg Asn Gly Asp Phe Ser Ser Gly Thr Ala
             35                  40                  45

Pro Trp Trp Gly Thr Glu Asn Ile Gln Leu Asn Val Thr Asp Gly Met
 50                  55                  60

Leu Cys Val Asp Val Pro Gly Gly Thr Val Asn Pro Trp Asp Val Ile
 65                  70                  75                  80

Ile Gly Gln Asp Asp Ile Pro Leu Ile Glu Gly Glu Ser Tyr Ala Phe
                 85                  90                  95

Ser Phe Thr Ala Ser Ser Thr Val Pro Val Ser Ile Arg Ala Leu Val
            100                 105                 110

Gln Glu Pro Val Glu Pro Trp Thr Thr Gln Met Asp Glu Arg Ala Leu
        115                 120                 125

Leu Gly Pro Glu Ala Glu Thr Tyr Glu Phe Val Phe Thr Ser Asn Val
        130                 135                 140

Asp Trp Asp Asp Ala Gln Val Ala Phe Gln Ile Gly Gly Ser Asp Glu
145                 150                 155                 160

Pro Trp Thr Phe Cys Leu Asp Asp Val Ala Leu Leu Gly Arg Ala Glu
                165                 170                 175

Pro Pro Val Tyr Glu Pro Asp Thr Gly Pro Arg Val Arg Val Asn Gln
            180                 185                 190

Val Gly Tyr Leu Pro His Gly Pro Lys Lys Ala Thr Val Thr Asp
        195                 200                 205

Ala Thr Ser Ala Leu Thr Trp Glu Leu Ala Asp Ala Asp Gly Asn Val
210                 215                 220

Val Ala Ser Gly Gln Thr Lys Pro His Gly Ala Asp Ser Ser Ser Gly
225                 230                 235                 240

Leu Asn Val His Thr Val Asp Phe Ser Ser Tyr Thr Thr Lys Gly Ser
                245                 250                 255

Asp Tyr Thr Leu Thr Val Asp Gly Glu Thr Ser Tyr Pro Phe Asp Ile
            260                 265                 270

Asp Glu Ser Val Tyr Glu Glu Leu Arg Val Asp Ala Leu Ser Phe Tyr
        275                 280                 285

Tyr Pro Gln Arg Ser Gly Ile Glu Ile Leu Asp Ser Ile Ala Pro Gly
        290                 295                 300

Tyr Gly Arg Pro Ala Gly His Ile Gly Val Pro Pro Asn Gln Gly Asp
305                 310                 315                 320

Thr Asp Val Pro Cys Ala Pro Gly Thr Cys Asp Tyr Ser Leu Asp Val
                325                 330                 335

Ser Gly Gly Trp Tyr Asp Ala Gly Asp His Gly Lys Tyr Val Val Asn
            340                 345                 350

Gly Gly Ile Ser Val His Gln Ile Met Ser Ile Tyr Glu Arg Ser Gln
        355                 360                 365

Leu Ala Asp Thr Ala Gln Pro Asp Lys Leu Ala Asp Ser Thr Leu Arg
        370                 375                 380

Leu Pro Glu Thr Gly Asn Gly Val Pro Asp Val Leu Asp Glu Ala Arg
385                 390                 395                 400

Trp Glu Met Glu Phe Leu Leu Lys Met Gln Val Pro Glu Gly Glu Pro
                405                 410                 415

Leu Ala Gly Met Ala His His Lys Ile His Asp Glu Gln Trp Thr Gly
            420                 425                 430

Leu Pro Leu Leu Pro Ser Ala Asp Pro Gln Pro Arg Tyr Leu Gln Pro
```

```
                435                 440                 445
Pro Ser Thr Ala Ala Thr Leu Asn Leu Ala Ala Thr Ala Ala Gln Cys
    450                 455                 460

Ala Arg Val Phe Glu Pro Phe Asp Glu Asp Phe Ala Ala Glu Cys Leu
465                 470                 475                 480

Ala Ala Ala Glu Thr Ala Trp Asp Ala Ala Lys Ala Asn Pro Asn Ile
                485                 490                 495

Tyr Ala Pro Ala Phe Gly Glu Gly Gly Pro Tyr Asn Asp Asn Asn
                500                 505                 510

Val Thr Asp Glu Phe Tyr Trp Ala Ala Glu Leu Phe Leu Thr Thr
    515                 520                 525

Gly Lys Glu Glu Tyr Arg Asp Ala Val Thr Ser Ser Pro Leu His Thr
    530                 535                 540

Asp Asp Glu Glu Val Phe Arg Asp Gly Ala Phe Asp Trp Gly Trp Thr
545                 550                 555                 560

Ala Ala Leu Ala Arg Leu Gln Leu Ala Thr Ile Pro Asn Asp Leu Ala
                565                 570                 575

Asp Arg Asp Arg Val Arg Gln Ser Val Val Asp Ala Ala Asp Met Tyr
            580                 585                 590

Leu Ala Asn Val Glu Thr Ser Pro Trp Gly Leu Ala Tyr Lys Pro Asn
            595                 600                 605

Asn Gly Val Phe Val Trp Gly Ser Asn Ser Ala Val Leu Asn Asn Met
    610                 615                 620

Val Ile Leu Ala Val Ala Phe Asp Leu Thr Gly Asp Thr Lys Tyr Arg
625                 630                 635                 640

Asp Gly Val Leu Glu Gly Met Asp Tyr Ile Phe Gly Arg Asn Ala Leu
                645                 650                 655

Asn Gln Ser Tyr Val Thr Gly Tyr Gly Asp Lys Asp Ser Arg Asn Gln
            660                 665                 670

His Ser Arg Trp Tyr Ala His Gln Leu Asp Pro Arg Leu Pro Asn Pro
            675                 680                 685

Pro Lys Gly Thr Leu Ala Gly Gly Pro Asn Ser Asp Ser Thr Thr Trp
    690                 695                 700

Asp Pro Val Ala Gln Ser Lys Leu Thr Gly Cys Ala Pro Gln Met Cys
705                 710                 715                 720

Tyr Ile Asp His Ile Glu Ser Trp Ser Thr Asn Glu Leu Thr Ile Asn
                725                 730                 735

Trp Asn Ala Pro Leu Ser Trp Ile Ala Ser Phe Ile Ala Asp Gln Asp
                740                 745                 750

Asp Ala Gly Glu Pro Gly Gly Glu Pro Gly Pro Gly Asp Asp Glu
            755                 760                 765

Thr Pro Pro Ser Lys Pro Gly Asn Leu Lys Ala Ser Asp Ile Thr Ala
    770                 775                 780

Thr Ser Ala Thr Leu Thr Trp Asp Ala Ser Thr Asp Asn Val Gly Val
785                 790                 795                 800

Val Gly Tyr Lys Val Ser Leu Val Arg Asp Gly Asp Ala Glu Glu Val
                805                 810                 815

Gly Thr Thr Ala Gln Thr Ser Tyr Thr Leu Thr Gly Leu Ser Ala Asp
            820                 825                 830

Gln Glu Tyr Thr Val Gln Val Val Ala Tyr Asp Ala Ala Gly Asn Leu
            835                 840                 845

Ser Thr Pro Ala Thr Val Thr Phe Thr Thr Glu Lys Glu Asp Glu Thr
    850                 855                 860
```

```
Pro Thr Pro Ser Ala Ser Cys Ala Val Thr Tyr Gln Thr Asn Asp Trp
865                 870                 875                 880

Pro Gly Gly Phe Thr Ala Ser Val Thr Leu Thr Asn Thr Gly Ser Thr
                885                 890                 895

Pro Trp Asp Ser Trp Glu Leu Arg Phe Thr Phe Pro Ser Gly Gln Thr
            900                 905                 910

Val Ser His Gly Trp Ser Ala Asn Trp Gln Gln Ser Gly Ser Asp Val
        915                 920                 925

Thr Ala Thr Ser Leu Pro Trp Asn Gly Ser Val Pro Pro Gly Gly Gly
    930                 935                 940

Ser Val Asn Ile Gly Phe Asn Gly Thr Trp Gly Gly Ser Asn Thr Lys
945                 950                 955                 960

Pro Glu Lys Phe Thr Val Asn Gly Ala Val Cys Ser Ile Gly
                965                 970
```

<210> SEQ ID NO 109
<211> LENGTH: 441
<212> TYPE: PRT
<213> ORGANISM: Artificial Sequence
<220> FEATURE:
<223> OTHER INFORMATION: Thermobifida fusca E2

<400> SEQUENCE: 109

```
Met Ser Pro Arg Pro Leu Arg Ala Leu Leu Gly Ala Ala Ala Ala Ala
1               5                   10                  15

Leu Val Ser Ala Ala Ala Leu Ala Phe Pro Ser Gln Ala Ala Ala Asn
            20                  25                  30

Asp Ser Pro Phe Tyr Val Asn Pro Asn Met Ser Ser Ala Glu Trp Val
        35                  40                  45

Arg Asn Asn Pro Asn Asp Pro Arg Thr Pro Val Ile Arg Asp Arg Ile
50                  55                  60

Ala Ser Val Pro Gln Gly Thr Trp Phe Ala His His Asn Pro Gly Gln
65                  70                  75                  80

Ile Thr Gly Gln Val Asp Ala Leu Met Ser Ala Gln Ala Ala Gly
                85                  90                  95

Lys Ile Pro Ile Leu Val Val Tyr Asn Ala Pro Gly Arg Asp Cys Gly
            100                 105                 110

Asn His Ser Ser Gly Gly Ala Pro Ser His Ser Ala Tyr Arg Ser Trp
        115                 120                 125

Ile Asp Glu Phe Ala Ala Gly Leu Lys Asn Arg Pro Ala Tyr Ile Ile
    130                 135                 140

Val Glu Pro Asp Leu Ile Ser Leu Met Ser Ser Cys Met Gln His Val
145                 150                 155                 160

Gln Gln Glu Val Leu Glu Thr Met Ala Tyr Ala Gly Lys Ala Leu Lys
                165                 170                 175

Ala Gly Ser Ser Gln Ala Arg Ile Tyr Phe Asp Ala Gly His Ser Ala
            180                 185                 190

Trp His Ser Pro Ala Gln Met Ala Ser Trp Leu Gln Gln Ala Asp Ile
        195                 200                 205

Ser Asn Ser Ala His Gly Ile Ala Thr Asn Thr Ser Asn Tyr Arg Trp
    210                 215                 220

Thr Ala Asp Glu Val Ala Tyr Ala Lys Ala Val Leu Ser Ala Ile Gly
225                 230                 235                 240

Asn Pro Ser Leu Arg Ala Val Ile Asp Thr Ser Arg Asn Gly Asn Gly
                245                 250                 255
```

```
Pro Ala Gly Asn Glu Trp Cys Asp Pro Ser Gly Arg Ala Ile Gly Thr
            260                 265                 270

Pro Ser Thr Thr Asn Thr Gly Asp Pro Met Ile Asp Ala Phe Leu Trp
        275                 280                 285

Ile Lys Leu Pro Gly Glu Ala Asp Gly Cys Ile Ala Gly Ala Gly Gln
        290                 295                 300

Phe Val Pro Gln Ala Ala Tyr Glu Met Ala Ile Ala Ala Gly Gly Thr
305                 310                 315                 320

Asn Pro Asn Pro Asn Pro Asn Pro Thr Pro Thr Pro Thr Pro Thr Pro
                325                 330                 335

Thr Pro Pro Gly Ser Ser Gly Ala Cys Thr Ala Thr Tyr Thr Ile
            340                 345                 350

Ala Asn Glu Trp Asn Asp Gly Phe Gln Ala Thr Val Thr Val Thr Ala
        355                 360                 365

Asn Gln Asn Ile Thr Gly Trp Thr Val Thr Trp Thr Phe Thr Asp Gly
        370                 375                 380

Gln Thr Ile Thr Asn Ala Trp Asn Ala Asp Val Ser Thr Ser Gly Ser
385                 390                 395                 400

Ser Val Thr Ala Arg Asn Val Gly His Asn Gly Thr Leu Ser Gln Gly
                405                 410                 415

Ala Ser Thr Glu Phe Gly Phe Val Gly Ser Lys Gly Asn Ser Asn Ser
            420                 425                 430

Val Pro Thr Leu Thr Cys Ala Ala Ser
            435                 440

<210> SEQ ID NO 110
<211> LENGTH: 596
<212> TYPE: PRT
<213> ORGANISM: Artificial Sequence
<220> FEATURE:
<223> OTHER INFORMATION: Thermobifida fusca E3

<400> SEQUENCE: 110

Met Ser Lys Val Arg Ala Thr Asn Arg Arg Ser Trp Met Arg Gly
1               5                   10                  15

Leu Ala Ala Ala Ser Gly Leu Ala Leu Gly Ala Ser Met Val Ala Phe
            20                  25                  30

Ala Ala Pro Ala Asn Ala Ala Gly Cys Ser Val Asp Tyr Thr Val Asn
        35                  40                  45

Ser Trp Gly Thr Gly Phe Thr Ala Asn Val Thr Ile Thr Asn Leu Gly
    50                  55                  60

Ser Ala Ile Asn Gly Trp Thr Leu Glu Trp Asp Phe Pro Gly Asn Gln
65                  70                  75                  80

Gln Val Thr Asn Leu Trp Asn Gly Thr Tyr Thr Gln Ser Gly Gln His
                85                  90                  95

Val Ser Val Ser Asn Ala Pro Tyr Asn Ala Ser Ile Pro Ala Asn Gly
            100                 105                 110

Thr Val Glu Phe Gly Phe Asn Gly Ser Tyr Ser Gly Ser Asn Asp Ile
        115                 120                 125

Pro Ser Ser Phe Lys Leu Asn Gly Val Thr Cys Asp Gly Ser Asp Asp
    130                 135                 140

Pro Asp Pro Glu Pro Ser Pro Ser Pro Ser Pro Ser Pro Ser Pro Thr
145                 150                 155                 160

Asp Pro Asp Glu Pro Gly Gly Pro Thr Asn Pro Thr Asn Pro Gly
                165                 170                 175
```

```
Glu Lys Val Asp Asn Pro Phe Glu Gly Ala Lys Leu Tyr Val Asn Pro
            180                 185                 190

Val Trp Ser Ala Lys Ala Ala Ala Glu Pro Gly Gly Ser Ala Val Ala
        195                 200                 205

Asn Glu Ser Thr Ala Val Trp Leu Asp Arg Ile Gly Ala Ile Glu Gly
    210                 215                 220

Asn Asp Ser Pro Thr Thr Gly Ser Met Gly Leu Arg Asp His Leu Glu
225                 230                 235                 240

Glu Ala Val Arg Gln Ser Gly Gly Asp Pro Leu Thr Ile Gln Val Val
                245                 250                 255

Ile Tyr Asn Leu Pro Gly Arg Asp Cys Ala Ala Leu Ala Ser Asn Gly
            260                 265                 270

Glu Leu Gly Pro Asp Glu Leu Asp Arg Tyr Lys Ser Glu Tyr Ile Asp
        275                 280                 285

Pro Ile Ala Asp Ile Met Trp Asp Phe Ala Asp Tyr Glu Asn Leu Arg
    290                 295                 300

Ile Val Ala Ile Ile Glu Ile Asp Ser Leu Pro Asn Leu Val Thr Asn
305                 310                 315                 320

Val Gly Gly Asn Gly Thr Glu Leu Cys Ala Tyr Met Lys Gln Asn
                325                 330                 335

Gly Gly Tyr Val Asn Gly Val Gly Tyr Ala Leu Arg Lys Leu Gly Glu
            340                 345                 350

Ile Pro Asn Val Tyr Asn Tyr Ile Asp Ala Ala His His Gly Trp Ile
        355                 360                 365

Gly Trp Asp Ser Asn Phe Gly Pro Ser Val Asp Ile Phe Tyr Glu Ala
    370                 375                 380

Ala Asn Ala Ser Gly Ser Thr Val Asp Tyr Val His Gly Phe Ile Ser
385                 390                 395                 400

Asn Thr Ala Asn Tyr Ser Ala Thr Val Glu Pro Tyr Leu Asp Val Asn
                405                 410                 415

Gly Thr Val Asn Gly Gln Leu Ile Arg Gln Ser Lys Trp Val Asp Trp
            420                 425                 430

Asn Gln Tyr Val Asp Glu Leu Ser Phe Val Gln Asp Leu Arg Gln Ala
        435                 440                 445

Leu Ile Ala Lys Gly Phe Arg Ser Asp Ile Gly Met Leu Ile Asp Thr
    450                 455                 460

Ser Arg Asn Gly Trp Gly Gly Pro Asn Arg Pro Thr Gly Pro Ser Ser
465                 470                 475                 480

Ser Thr Asp Leu Asn Thr Tyr Val Asp Glu Ser Arg Ile Asp Arg Arg
                485                 490                 495

Ile His Pro Gly Asn Trp Cys Asn Gln Ala Gly Ala Gly Leu Gly Glu
            500                 505                 510

Arg Pro Thr Val Asn Pro Ala Pro Gly Val Asp Ala Tyr Val Trp Val
        515                 520                 525

Lys Pro Pro Gly Glu Ser Asp Gly Ala Ser Glu Glu Ile Pro Asn Asp
    530                 535                 540

Glu Gly Lys Gly Phe Asp Arg Met Cys Asp Pro Thr Tyr Gln Gly Asn
545                 550                 555                 560

Ala Arg Asn Gly Asn Asn Pro Ser Gly Ala Leu Pro Asn Ala Pro Ile
                565                 570                 575

Ser Gly His Trp Phe Ser Ala Gln Phe Arg Glu Leu Leu Ala Asn Ala
            580                 585                 590
```

-continued

Tyr Pro Pro Leu
        595

<210> SEQ ID NO 111
<211> LENGTH: 880
<212> TYPE: PRT
<213> ORGANISM: Artificial Sequence
<220> FEATURE:
<223> OTHER INFORMATION: Thermobifida fusca E4

<400> SEQUENCE: 111

Met Ser Val Thr Glu Pro Pro Arg Arg Gly Arg His Ser Arg
1               5                   10                  15

Ala Arg Arg Phe Leu Thr Ser Leu Gly Ala Thr Ala Ala Leu Thr Ala
            20                  25                  30

Gly Met Leu Gly Val Pro Leu Ala Thr Gly Thr Ala His Ala Glu Pro
        35                  40                  45

Ala Phe Asn Tyr Ala Glu Ala Leu Gln Lys Ser Met Phe Phe Tyr Glu
    50                  55                  60

Ala Gln Arg Ser Gly Lys Leu Pro Glu Asn Asn Arg Val Ser Trp Arg
65                  70                  75                  80

Gly Asp Ser Gly Leu Asn Asp Gly Ala Asp Val Gly Leu Asp Leu Thr
                85                  90                  95

Gly Gly Trp Tyr Asp Ala Gly Asp His Val Lys Phe Gly Phe Pro Met
            100                 105                 110

Ala Phe Thr Ala Thr Met Leu Ala Trp Gly Ala Ile Glu Ser Pro Glu
        115                 120                 125

Gly Tyr Ile Arg Ser Gly Gln Met Pro Tyr Leu Lys Asp Asn Leu Arg
    130                 135                 140

Trp Val Asn Asp Tyr Phe Ile Lys Ala His Pro Ser Pro Asn Val Leu
145                 150                 155                 160

Tyr Val Gln Val Gly Asp Gly Asp Ala Asp His Lys Trp Trp Gly Pro
                165                 170                 175

Ala Glu Val Met Pro Met Glu Arg Pro Ser Phe Lys Val Asp Pro Ser
            180                 185                 190

Cys Pro Gly Ser Asp Val Ala Ala Glu Thr Ala Ala Met Ala Ala
        195                 200                 205

Ser Ser Ile Val Phe Ala Asp Asp Pro Ala Tyr Ala Ala Thr Leu
    210                 215                 220

Val Gln His Ala Lys Gln Leu Tyr Thr Phe Ala Asp Thr Tyr Arg Gly
225                 230                 235                 240

Val Tyr Ser Asp Cys Val Pro Ala Gly Ala Phe Tyr Asn Ser Trp Ser
                245                 250                 255

Gly Tyr Gln Asp Glu Leu Val Trp Gly Ala Tyr Trp Leu Tyr Lys Ala
            260                 265                 270

Thr Gly Asp Asp Ser Tyr Leu Ala Lys Ala Glu Tyr Glu Tyr Asp Phe
        275                 280                 285

Leu Ser Thr Glu Gln Gln Thr Asp Leu Arg Ser Tyr Arg Trp Thr Ile
    290                 295                 300

Ala Trp Asp Asp Lys Ser Tyr Gly Thr Tyr Val Leu Leu Ala Lys Glu
305                 310                 315                 320

Thr Gly Lys Gln Lys Tyr Ile Asp Asp Ala Asn Arg Trp Leu Asp Tyr
                325                 330                 335

Trp Thr Val Gly Val Asn Gly Gln Arg Val Pro Tyr Ser Pro Gly Gly
            340                 345                 350

-continued

Met Ala Val Leu Asp Thr Trp Gly Ala Leu Arg Tyr Ala Ala Asn Thr
            355                 360                 365

Ala Phe Val Ala Leu Val Tyr Ala Lys Val Ile Asp Asp Pro Val Arg
370                 375                 380

Lys Gln Arg Tyr His Asp Phe Ala Val Arg Gln Ile Asn Tyr Ala Leu
385                 390                 395                 400

Gly Asp Asn Pro Arg Asn Ser Ser Tyr Val Val Gly Phe Gly Asn Asn
                405                 410                 415

Pro Pro Arg Asn Pro His His Arg Thr Ala His Gly Ser Trp Thr Asp
            420                 425                 430

Ser Ile Ala Ser Pro Ala Glu Asn Arg His Val Leu Tyr Gly Ala Leu
            435                 440                 445

Val Gly Gly Pro Gly Ser Pro Asn Asp Ala Tyr Thr Asp Asp Arg Gln
450                 455                 460

Asp Tyr Val Ala Asn Glu Val Ala Thr Asp Tyr Asn Ala Gly Phe Ser
465                 470                 475                 480

Ser Ala Leu Ala Met Leu Val Glu Glu Tyr Gly Gly Thr Pro Leu Ala
                485                 490                 495

Asp Phe Pro Pro Thr Glu Glu Pro Asp Gly Pro Glu Ile Phe Val Glu
            500                 505                 510

Ala Gln Ile Asn Thr Pro Gly Thr Thr Phe Thr Glu Ile Lys Ala Met
            515                 520                 525

Ile Arg Asn Gln Ser Gly Trp Pro Ala Arg Met Leu Asp Lys Gly Thr
            530                 535                 540

Phe Arg Tyr Trp Phe Thr Leu Asp Glu Gly Val Asp Pro Ala Asp Ile
545                 550                 555                 560

Thr Val Ser Ser Ala Tyr Asn Gln Cys Ala Thr Pro Glu Asp Val His
                565                 570                 575

His Val Ser Gly Asp Leu Tyr Tyr Val Glu Ile Asp Cys Thr Gly Glu
                580                 585                 590

Lys Ile Phe Pro Gly Gly Gln Ser Glu His Arg Arg Glu Val Gln Phe
            595                 600                 605

Arg Ile Ala Gly Gly Pro Gly Trp Asp Pro Ser Asn Asp Trp Ser Phe
610                 615                 620

Gln Gly Ile Gly Asn Glu Leu Ala Pro Ala Pro Tyr Ile Val Leu Tyr
625                 630                 635                 640

Asp Asp Gly Val Pro Val Trp Gly Thr Ala Pro Glu Glu Gly Glu Glu
                645                 650                 655

Pro Gly Gly Gly Glu Gly Pro Gly Gly Glu Glu Pro Gly Glu Asp
            660                 665                 670

Val Thr Pro Pro Ser Ala Pro Gly Ser Pro Ala Val Arg Asp Val Thr
            675                 680                 685

Ser Thr Ser Ala Val Leu Thr Trp Ser Ala Ser Asp Thr Gly Gly
            690                 695                 700

Ser Gly Val Ala Gly Tyr Asp Val Phe Leu Arg Ala Gly Thr Gly Gln
705                 710                 715                 720

Glu Gln Lys Val Gly Ser Thr Arg Thr Ser Phe Thr Leu Thr Gly
                725                 730                 735

Leu Glu Pro Asp Thr Thr Tyr Ile Ala Ala Val Ala Arg Asp Asn
                740                 745                 750

Ala Gly Asn Val Ser Gln Arg Ser Thr Val Ser Phe Thr Thr Leu Ala
            755                 760                 765

Glu Asn Gly Gly Gly Pro Asp Ala Ser Cys Thr Val Gly Tyr Ser Thr

```
               770                 775                 780
Asn Asp Trp Asp Ser Gly Phe Thr Ala Ser Ile Arg Ile Thr Tyr His
785                 790                 795                 800

Gly Thr Ala Pro Leu Ser Ser Trp Glu Leu Ser Phe Thr Phe Pro Ala
                805                 810                 815

Gly Gln Gln Val Thr His Gly Trp Asn Ala Thr Trp Arg Gln Asp Gly
                820                 825                 830

Ala Ala Val Thr Ala Thr Pro Met Ser Trp Asn Ser Ser Leu Ala Pro
                835                 840                 845

Gly Ala Thr Val Glu Val Gly Phe Asn Gly Ser Trp Ser Gly Ser Asn
                850                 855                 860

Thr Pro Pro Thr Asp Phe Thr Leu Asn Gly Glu Pro Cys Ala Leu Ala
865                 870                 875                 880

<210> SEQ ID NO 112
<211> LENGTH: 466
<212> TYPE: PRT
<213> ORGANISM: Artificial Sequence
<220> FEATURE:
<223> OTHER INFORMATION: Thermobifida fusca E5

<400> SEQUENCE: 112

Met Ala Lys Ser Pro Ala Ala Arg Lys Gly Arg Pro Val Ala Val
1               5                   10                  15

Ala Val Thr Ala Ala Leu Ala Leu Leu Ile Ala Leu Leu Ser Pro Gly
                20                  25                  30

Val Ala Gln Ala Ala Gly Leu Thr Ala Thr Val Thr Lys Glu Ser Ser
                35                  40                  45

Trp Asp Asn Gly Tyr Ser Ala Ser Val Thr Val Arg Asn Asp Thr Ser
    50                  55                  60

Ser Thr Val Ser Gln Trp Glu Val Val Leu Thr Leu Pro Gly Gly Thr
65                  70                  75                  80

Thr Val Ala Gln Val Trp Asn Ala Gln His Thr Ser Ser Gly Asn Ser
                85                  90                  95

His Thr Phe Thr Gly Val Ser Trp Asn Ser Thr Ile Pro Pro Gly Gly
                100                 105                 110

Thr Ala Ser Ser Gly Phe Ile Ala Ser Gly Ser Gly Glu Pro Thr His
                115                 120                 125

Cys Thr Ile Asn Gly Ala Pro Cys Asp Glu Gly Ser Glu Pro Gly Gly
                130                 135                 140

Pro Gly Gly Pro Gly Thr Pro Ser Pro Asp Pro Gly Thr Gln Pro Gly
145                 150                 155                 160

Thr Gly Thr Pro Val Glu Arg Tyr Gly Lys Val Gln Val Cys Gly Thr
                165                 170                 175

Gln Leu Cys Asp Glu His Gly Asn Pro Val Gln Leu Arg Gly Met Ser
                180                 185                 190

Thr His Gly Ile Gln Trp Phe Asp His Cys Leu Thr Asp Ser Ser Leu
                195                 200                 205

Asp Ala Leu Ala Tyr Asp Trp Lys Ala Asp Ile Ile Arg Leu Ser Met
                210                 215                 220

Tyr Ile Gln Glu Asp Gly Tyr Glu Thr Asn Pro Arg Gly Phe Thr Asp
225                 230                 235                 240

Arg Met His Gln Leu Ile Asp Met Ala Thr Ala Arg Gly Leu Tyr Val
                245                 250                 255

Ile Val Asp Trp His Ile Leu Thr Pro Gly Asp Pro His Tyr Asn Leu
```

```
                260                 265                 270
Asp Arg Ala Lys Thr Phe Phe Ala Glu Ile Ala Gln Arg His Ala Ser
            275                 280                 285

Lys Thr Asn Val Leu Tyr Glu Ile Ala Asn Glu Pro Asn Gly Val Ser
        290                 295                 300

Trp Ala Ser Ile Lys Ser Tyr Ala Glu Val Ile Pro Val Ile Arg
305                 310                 315                 320

Gln Arg Asp Pro Asp Ser Val Ile Ile Val Gly Thr Arg Gly Trp Ser
                325                 330                 335

Ser Leu Gly Val Ser Glu Gly Ser Gly Pro Ala Glu Ile Ala Ala Asn
            340                 345                 350

Pro Val Asn Ala Ser Asn Ile Met Tyr Ala Phe His Phe Tyr Ala Ala
        355                 360                 365

Ser His Arg Asp Asn Tyr Leu Asn Ala Leu Arg Glu Ala Ser Glu Leu
    370                 375                 380

Phe Pro Val Phe Val Thr Glu Phe Gly Thr Glu Thr Tyr Thr Gly Asp
385                 390                 395                 400

Gly Ala Asn Asp Phe Gln Met Ala Asp Arg Tyr Ile Asp Leu Met Ala
                405                 410                 415

Glu Arg Lys Ile Gly Trp Thr Lys Trp Asn Tyr Ser Asp Asp Phe Arg
            420                 425                 430

Ser Gly Ala Val Phe Gln Pro Gly Thr Cys Ala Ser Gly Gly Pro Trp
        435                 440                 445

Ser Gly Ser Ser Leu Lys Ala Ser Gly Gln Trp Val Arg Ser Lys Leu
    450                 455                 460

Gln Ser
465

<210> SEQ ID NO 113
<211> LENGTH: 616
<212> TYPE: PRT
<213> ORGANISM: Artificial Sequence
<220> FEATURE:
<223> OTHER INFORMATION: Thermobifida fusca Endoglucanase

<400> SEQUENCE: 113

Met Thr Pro Leu Thr Arg Arg Leu Arg Ala Gly Ala Ala Ala Ile Ala
1               5                   10                  15

Ile Gly Ala Ser Ala Leu Ile Pro Leu Thr Ser Ser Pro Ala Ala Ala
            20                  25                  30

Ser Gly Thr Ala Asp Trp Leu His Thr Asp Gly Asn Arg Ile Val Asp
        35                  40                  45

Ser Ala Gly Asn Glu Val Trp Leu Thr Gly Ala Asn Trp Phe Gly Phe
    50                  55                  60

Asn Thr Ser Glu Arg Met Phe His Gly Leu Trp Ala Ala Asn Ile Glu
65                  70                  75                  80

Asp Ile Thr Ser Ala Met Ala Glu Arg Gly Ile Asn Met Val Arg Val
                85                  90                  95

Pro Ile Ser Thr Gln Leu Leu Leu Glu Trp Lys Asn Gly Gln Ala Gly
            100                 105                 110

Pro Ser Gly Val Asn Glu Tyr Val Asn Pro Glu Leu Ala Gly Met Asn
        115                 120                 125

Thr Leu Glu Val Phe Asp Tyr Trp Leu Gln Leu Cys Glu Glu Tyr Gly
    130                 135                 140

Leu Lys Val Met Leu Asp Val His Ser Ala Glu Ala Asp Asn Ser Gly
```

```
            145                 150                 155                 160
His Tyr Tyr Pro Val Trp Tyr Lys Gly Asp Ile Thr Thr Glu Asp Phe
                165                 170                 175

Tyr Thr Ala Trp Glu Trp Val Thr Glu Arg Tyr Lys Asn Asn Asp Thr
                180                 185                 190

Ile Val Ala Ala Asp Ile Lys Asn Glu Pro His Gly Lys Ala Asn Glu
                195                 200                 205

Thr Pro Arg Ala Lys Trp Asp Gly Ser Thr Asp Ile Asp Asn Phe Lys
        210                 215                 220

His Val Cys Glu Thr Ala Gly Lys Arg Ile Leu Ala Ile Asn Pro Asn
225                 230                 235                 240

Met Leu Ile Leu Cys Glu Gly Ile Glu Ile Tyr Pro Lys Asp Gly Gln
                245                 250                 255

Asp Trp Ser Ser Thr Asp Gly Arg Asp Tyr Tyr Ser Thr Trp Trp Gly
                260                 265                 270

Gly Asn Leu Arg Gly Val Ala Asp His Pro Val Asp Leu Gly Ala His
        275                 280                 285

Gln Asp Gln Leu Val Tyr Ser Pro His Asp Tyr Gly Pro Ser Val Phe
        290                 295                 300

Glu Gln Pro Trp Phe Glu Gly Glu Trp Asn Arg Gln Thr Leu Thr Glu
305                 310                 315                 320

Asp Val Trp Arg Pro Asn Trp Leu Tyr Ile His Glu Asp Asp Ile Ala
                325                 330                 335

Pro Leu Leu Ile Gly Glu Trp Gly Gly Phe Leu Asp Gly Gly Asp Asn
                340                 345                 350

Glu Lys Trp Met Thr Ala Leu Arg Ser Leu Ile Ile Asp Glu Lys Met
                355                 360                 365

His His Thr Phe Trp Ala Leu Asn Pro Asn Ser Gly Asp Thr Gly Gly
        370                 375                 380

Leu Leu Asn Tyr Asp Trp Thr Thr Trp Asp Glu Ala Lys Tyr Ala Phe
385                 390                 395                 400

Leu Lys Pro Ala Leu Trp Gln Asp Ala Asn Gly Lys Phe Val Gly Leu
                405                 410                 415

Asp His Asp Val Pro Leu Gly Gly Val Gly Ser Thr Thr Gly Val Ser
                420                 425                 430

Leu Asn Gln Tyr Gly Gly Gly Pro Ser Gln Pro Pro Thr Glu
                435                 440                 445

Pro Thr Glu Pro Pro Thr Glu Pro Thr Glu Pro Pro Thr Glu Pro Thr
        450                 455                 460

Glu Pro Pro Ala Asn Pro Thr Gly Ala Leu Glu Val Tyr Tyr Arg Asn
465                 470                 475                 480

Asn Ser Leu Ala Ala Asp Asp Ser Gln Ile Ala Pro Gly Leu Arg Leu
                485                 490                 495

Val Asn Thr Gly Ser Ser Thr Val Asp Leu Ala Asp Val Glu Ile His
                500                 505                 510

Tyr Tyr Phe Thr Asn Glu Pro Gly Gly Thr Leu Gln Phe Thr Cys Asp
                515                 520                 525

Trp Ala Gln Val Gly Cys Ala Asn Val Asn Ala Ser Phe Thr Ser Leu
                530                 535                 540

Ser Ala Pro Gly Ala Asp Thr Ser Leu Val Leu Thr Leu Ser Gly Ser
545                 550                 555                 560

Leu Ala Pro Gly Ala Ser Thr Glu Leu Gln Gly Arg Ile His Thr Ala
                565                 570                 575
```

```
Asn Trp Ala Asn Phe Asp Glu Ser Asp Asp Tyr Ser Arg Gly Thr Asn
            580                 585                 590

Thr Asp Trp Glu Leu Ser Glu Val Ile Thr Ala Tyr Leu Gly Gly Thr
        595                 600                 605

Leu Val Trp Gly Thr Pro Pro Ala
    610                 615

<210> SEQ ID NO 114
<211> LENGTH: 984
<212> TYPE: PRT
<213> ORGANISM: Artificial Sequence
<220> FEATURE:
<223> OTHER INFORMATION: Thermobifida fusca Beta-1,4-exocellulase E6

<400> SEQUENCE: 114

Met Arg Ser Leu Leu Ser Pro Arg Arg Trp Arg Thr Leu Ala Ser Gly
1               5                   10                  15

Ala Leu Ala Ala Ala Leu Ala Ala Ala Val Leu Ser Pro Gly Val Ala
            20                  25                  30

His Ala Ala Val Ala Cys Ser Val Asp Tyr Asp Asp Ser Asn Asp Trp
        35                  40                  45

Gly Ser Gly Phe Val Ala Glu Val Lys Val Thr Asn Glu Gly Ser Asp
    50                  55                  60

Pro Ile Gln Asn Trp Gln Val Gly Trp Thr Phe Pro Gly Asn Gln Gln
65                  70                  75                  80

Ile Thr Asn Gly Trp Asn Gly Val Phe Ser Gln Ser Gly Ala Asn Val
                85                  90                  95

Thr Val Arg Tyr Pro Asp Trp Asn Pro Asn Ile Ala Pro Gly Ala Thr
            100                 105                 110

Ile Ser Phe Gly Phe Gln Gly Thr Tyr Ser Gly Ser Asn Asp Ala Pro
        115                 120                 125

Thr Ser Phe Thr Val Asn Gly Val Thr Cys Ser Gly Ser Gln Pro Ala
    130                 135                 140

Asn Leu Pro Pro Asp Val Thr Leu Thr Ser Pro Ala Asn Asn Ser Thr
145                 150                 155                 160

Phe Leu Val Asn Asp Pro Ile Glu Leu Thr Ala Val Ala Ser Asp Pro
                165                 170                 175

Asp Gly Ser Ile Asp Arg Val Glu Phe Ala Ala Asp Asn Thr Val Ile
            180                 185                 190

Gly Ile Asp Thr Thr Ser Pro Tyr Ser Phe Thr Trp Thr Asp Ala Ala
        195                 200                 205

Ala Gly Ser Tyr Ser Val Thr Ala Ile Ala Tyr Asp Asp Gln Gly Ala
    210                 215                 220

Arg Thr Val Ser Ala Pro Ile Ala Ile Arg Val Leu Asp Arg Ala Ala
225                 230                 235                 240

Val Ile Ala Ser Pro Pro Thr Val Arg Val Pro Gln Gly Gly Thr Ala
                245                 250                 255

Asp Phe Glu Val Arg Leu Ser Asn Gln Pro Ser Gly Asn Val Thr Val
            260                 265                 270

Thr Val Ala Arg Thr Ser Gly Ser Ser Asp Leu Thr Val Ser Ser Gly
        275                 280                 285

Ser Gln Leu Gln Phe Thr Ser Ser Asn Trp Asn Gln Pro Gln Lys Val
    290                 295                 300

Thr Ile Ala Ser Ala Asp Asn Gly Gly Asn Leu Ala Glu Ala Val Phe
305                 310                 315                 320
```

-continued

```
Thr Val Ser Ala Pro Gly His Asp Ser Ala Glu Val Thr Val Arg Glu
            325                 330                 335

Ile Asp Pro Asn Thr Ser Ser Tyr Asp Gln Ala Phe Leu Glu Gln Tyr
            340                 345                 350

Glu Lys Ile Lys Asp Pro Ala Ser Gly Tyr Phe Arg Glu Phe Asn Gly
            355                 360                 365

Leu Leu Val Pro Tyr His Ser Val Glu Thr Met Ile Val Glu Ala Pro
370                 375                 380

Asp His Gly His Gln Thr Thr Ser Glu Ala Phe Ser Tyr Tyr Leu Trp
385                 390                 395                 400

Leu Glu Ala Tyr Tyr Gly Arg Val Thr Gly Asp Trp Lys Pro Leu His
            405                 410                 415

Asp Ala Trp Glu Ser Met Glu Thr Phe Ile Ile Pro Gly Thr Lys Asp
            420                 425                 430

Gln Pro Thr Asn Ser Ala Tyr Asn Pro Asn Ser Pro Ala Thr Tyr Ile
            435                 440                 445

Pro Glu Gln Pro Asn Ala Asp Gly Tyr Pro Ser Pro Leu Met Asn Asn
            450                 455                 460

Val Pro Val Gly Gln Asp Pro Leu Ala Gln Glu Leu Ser Ser Thr Tyr
465                 470                 475                 480

Gly Thr Asn Glu Ile Tyr Gly Met His Trp Leu Leu Asp Val Asp Asn
            485                 490                 495

Val Tyr Gly Phe Gly Phe Cys Gly Asp Gly Thr Asp Asp Ala Pro Ala
            500                 505                 510

Tyr Ile Asn Thr Tyr Gln Arg Gly Ala Arg Glu Ser Val Trp Glu Thr
            515                 520                 525

Ile Pro His Pro Ser Cys Asp Asp Phe Thr His Gly Gly Pro Asn Gly
            530                 535                 540

Tyr Leu Asp Leu Phe Thr Asp Asp Gln Asn Tyr Ala Lys Gln Trp Arg
545                 550                 555                 560

Tyr Thr Asn Ala Pro Asp Ala Asp Ala Arg Ala Val Gln Val Met Phe
            565                 570                 575

Trp Ala His Glu Trp Ala Lys Glu Gln Gly Lys Glu Asn Glu Ile Ala
            580                 585                 590

Gly Leu Met Asp Lys Ala Ser Lys Met Gly Asp Tyr Leu Arg Tyr Ala
            595                 600                 605

Met Phe Asp Lys Tyr Phe Lys Lys Ile Gly Asn Cys Val Gly Ala Thr
            610                 615                 620

Ser Cys Pro Gly Gly Gln Gly Lys Asp Ser Ala His Tyr Leu Leu Ser
625                 630                 635                 640

Trp Tyr Tyr Ser Trp Gly Gly Ser Leu Asp Thr Ser Ser Ala Trp Ala
            645                 650                 655

Trp Arg Ile Gly Ser Ser Ser His Gln Gly Tyr Gln Asn Val Leu
            660                 665                 670

Ala Ala Tyr Ala Leu Ser Gln Val Pro Glu Leu Gln Pro Asp Ser Pro
            675                 680                 685

Thr Gly Val Gln Asp Trp Ala Thr Ser Phe Asp Arg Gln Leu Glu Phe
            690                 695                 700

Leu Gln Trp Leu Gln Ser Ala Glu Gly Ile Ala Gly Gly Ala Thr
705                 710                 715                 720

Asn Ser Trp Lys Gly Ser Tyr Asp Thr Pro Pro Thr Gly Leu Ser Gln
            725                 730                 735
```

```
Phe Tyr Gly Met Tyr Tyr Asp Trp Gln Pro Val Trp Asn Asp Pro Pro
                740                 745                 750

Ser Asn Asn Trp Phe Gly Phe Gln Val Trp Asn Met Glu Arg Val Ala
            755                 760                 765

Gln Leu Tyr Tyr Val Thr Gly Asp Ala Arg Ala Glu Ala Ile Leu Asp
        770                 775                 780

Lys Trp Val Pro Trp Ala Ile Gln His Thr Asp Val Asp Ala Asp Asn
785                 790                 795                 800

Gly Gly Gln Asn Phe Gln Val Pro Ser Asp Leu Glu Trp Ser Gly Gln
                805                 810                 815

Pro Asp Thr Trp Thr Gly Thr Tyr Thr Gly Asn Pro Asn Leu His Val
            820                 825                 830

Gln Val Val Ser Tyr Ser Gln Asp Val Gly Val Thr Ala Ala Leu Ala
        835                 840                 845

Lys Thr Leu Met Tyr Tyr Ala Lys Arg Ser Gly Asp Thr Thr Ala Leu
850                 855                 860

Ala Thr Ala Glu Gly Leu Leu Asp Ala Leu Leu Ala His Arg Asp Ser
865                 870                 875                 880

Ile Gly Ile Ala Thr Pro Glu Gln Pro Ser Trp Asp Arg Leu Asp Asp
                885                 890                 895

Pro Trp Asp Gly Ser Glu Gly Leu Tyr Val Pro Pro Gly Trp Ser Gly
            900                 905                 910

Thr Met Pro Asn Gly Asp Arg Ile Glu Pro Gly Ala Thr Phe Leu Ser
        915                 920                 925

Ile Arg Ser Phe Tyr Lys Asn Asp Pro Leu Trp Pro Gln Val Glu Ala
930                 935                 940

His Leu Asn Asp Pro Gln Asn Val Pro Ala Pro Ile Val Glu Arg His
945                 950                 955                 960

Arg Phe Trp Ala Gln Val Glu Ile Ala Thr Ala Phe Ala Ala His Asp
                965                 970                 975

Glu Leu Phe Gly Ala Gly Ala Pro
            980

<210> SEQ ID NO 115
<211> LENGTH: 998
<212> TYPE: PRT
<213> ORGANISM: Artificial Sequence
<220> FEATURE:
<223> OTHER INFORMATION: Thermobifida fusca Cellulose 1,4-beta-
      cellobiosidase/endoglucanase. Glycosyl Hydrolase family 9

<400> SEQUENCE: 115

Met Gly Ala Leu Pro Trp Trp Ala Ser Ala Val Arg Ser Ser Ser Gln
1               5                   10                  15

Phe Glu Ser Pro Tyr Gly Arg Thr Ser Val Leu Arg Pro Arg Ser
            20                  25                  30

Arg Ser Pro Leu Val Ala Leu Thr Ala Thr Cys Ala Val Ala Leu
        35                  40                  45

Gly Gly Thr Ala Val Pro Ala Gln Ala Asp Glu Val Asn Gln Ile Arg
    50                  55                  60

Asn Gly Asp Phe Ser Ser Gly Thr Ala Pro Trp Trp Gly Thr Glu Asn
65                  70                  75                  80

Ile Gln Leu Asn Val Thr Asp Gly Met Leu Cys Val Asp Val Pro Gly
                85                  90                  95

Gly Thr Val Asn Pro Trp Asp Val Ile Ile Gly Gln Asp Asp Ile Pro
            100                 105                 110
```

-continued

```
Leu Ile Glu Gly Glu Ser Tyr Ala Phe Ser Phe Thr Ala Ser Ser Thr
            115                 120                 125

Val Pro Val Ser Ile Arg Ala Leu Val Gln Glu Pro Val Glu Pro Trp
        130                 135                 140

Thr Thr Gln Met Asp Glu Arg Ala Leu Leu Gly Pro Glu Ala Glu Thr
145                 150                 155                 160

Tyr Glu Phe Val Phe Thr Ser Asn Val Asp Trp Asp Asp Ala Gln Val
                165                 170                 175

Ala Phe Gln Ile Gly Gly Ser Asp Glu Pro Trp Thr Phe Cys Leu Asp
                    180                 185                 190

Asp Val Ala Leu Leu Gly Gly Ala Glu Pro Pro Val Tyr Glu Pro Asp
                195                 200                 205

Thr Gly Pro Arg Val Arg Val Asn Gln Val Gly Tyr Leu Pro His Gly
            210                 215                 220

Pro Lys Lys Ala Thr Val Val Thr Asp Ala Thr Ser Ala Leu Thr Trp
225                 230                 235                 240

Glu Leu Ala Asp Ala Asp Gly Asn Val Val Ala Ser Gly Gln Thr Lys
                245                 250                 255

Pro His Gly Ala Asp Ser Ser Ser Gly Leu Asn Val His Thr Val Asp
            260                 265                 270

Phe Ser Ser Tyr Thr Thr Lys Gly Ser Asp Tyr Thr Leu Thr Val Asp
        275                 280                 285

Gly Glu Thr Ser Tyr Pro Phe Asp Ile Asp Glu Ser Val Tyr Glu Glu
        290                 295                 300

Leu Arg Val Asp Ala Leu Ser Phe Tyr Tyr Pro Gln Arg Ser Gly Ile
305                 310                 315                 320

Glu Ile Leu Asp Ser Ile Ala Pro Gly Tyr Gly Arg Pro Ala Gly His
                325                 330                 335

Ile Gly Val Pro Pro Asn Gln Gly Asp Thr Asp Val Pro Cys Ala Pro
            340                 345                 350

Gly Thr Cys Asp Tyr Ser Leu Asp Val Ser Gly Gly Trp Tyr Asp Ala
        355                 360                 365

Gly Asp His Gly Lys Tyr Val Val Asn Gly Gly Ile Ser Val His Gln
        370                 375                 380

Ile Met Ser Ile Tyr Glu Arg Ser Gln Leu Ala Asp Thr Ala Gln Pro
385                 390                 395                 400

Asp Lys Leu Ala Asp Ser Thr Leu Arg Leu Pro Glu Thr Gly Asn Gly
                405                 410                 415

Val Pro Asp Val Leu Asp Glu Ala Arg Trp Glu Met Glu Phe Leu Leu
            420                 425                 430

Lys Met Gln Val Pro Glu Gly Glu Pro Leu Ala Gly Met Ala His His
        435                 440                 445

Lys Ile His Asp Glu Gln Trp Thr Gly Leu Pro Leu Leu Pro Ser Ala
        450                 455                 460

Asp Pro Gln Pro Arg Tyr Leu Gln Pro Pro Ser Thr Ala Thr Leu
465                 470                 475                 480

Asn Leu Ala Ala Thr Ala Ala Gln Cys Ala Arg Val Phe Glu Pro Phe
                485                 490                 495

Asp Glu Asp Phe Ala Ala Glu Cys Leu Ala Ala Ala Glu Thr Ala Trp
            500                 505                 510

Asp Ala Ala Lys Ala Asn Pro Asn Ile Tyr Ala Pro Ala Phe Gly Glu
        515                 520                 525
```

```
Gly Gly Gly Pro Tyr Asn Asp Asn Val Thr Asp Glu Phe Tyr Trp
            530             535                 540

Ala Ala Ala Glu Leu Phe Leu Thr Thr Gly Lys Glu Glu Tyr Arg Asp
545             550                 555                 560

Ala Val Thr Ser Ser Pro Leu His Thr Asp Asp Glu Glu Val Phe Arg
                565                 570                 575

Asp Gly Ala Phe Asp Trp Gly Trp Thr Ala Ala Leu Ala Arg Leu Gln
            580             585                 590

Leu Ala Thr Ile Pro Asn Asp Leu Ala Asp Arg Asp Arg Val Arg Gln
            595                 600                 605

Ser Val Val Asp Ala Ala Asp Met Tyr Leu Ala Asn Val Glu Thr Ser
    610             615                 620

Pro Trp Gly Leu Ala Tyr Lys Pro Asn Asn Gly Val Phe Val Trp Gly
625             630                 635                 640

Ser Asn Ser Ala Val Leu Asn Asn Met Val Ile Leu Ala Val Ala Phe
                645                 650                 655

Asp Leu Thr Gly Asp Thr Lys Tyr Arg Asp Gly Val Leu Glu Gly Met
            660                 665                 670

Asp Tyr Ile Phe Gly Arg Asn Ala Leu Asn Gln Ser Tyr Val Thr Gly
    675                 680                 685

Tyr Gly Asp Lys Asp Ser Arg Asn Gln His Ser Arg Trp Tyr Ala His
    690                 695                 700

Gln Leu Asp Pro Arg Leu Pro Asn Pro Pro Lys Gly Thr Leu Ala Gly
705             710                 715                 720

Gly Pro Asn Ser Asp Ser Thr Thr Trp Asp Pro Val Ala Gln Ser Lys
                725                 730                 735

Leu Thr Gly Cys Ala Pro Gln Met Cys Tyr Ile Asp His Ile Glu Ser
            740                 745                 750

Trp Ser Thr Asn Glu Leu Thr Ile Asn Trp Asn Ala Pro Leu Ser Trp
        755                 760                 765

Ile Ala Ser Phe Ile Ala Asp Gln Asp Ala Gly Glu Pro Gly Gly
        770                 775                 780

Glu Glu Pro Gly Pro Gly Asp Asp Glu Thr Pro Pro Ser Lys Pro Gly
785             790                 795                 800

Asn Leu Lys Ala Ser Asp Ile Thr Ala Thr Ala Thr Leu Thr Trp
                805                 810                 815

Asp Ala Ser Thr Asp Asn Val Gly Val Val Gly Tyr Lys Val Ser Leu
            820                 825                 830

Val Arg Asp Gly Asp Ala Glu Glu Val Gly Thr Thr Ala Gln Thr Ser
            835                 840                 845

Tyr Thr Leu Thr Gly Leu Ser Ala Asp Gln Glu Tyr Thr Val Gln Val
850                 855                 860

Val Ala Tyr Asp Ala Ala Gly Asn Leu Ser Thr Pro Ala Thr Val Thr
865             870                 875                 880

Phe Thr Thr Glu Lys Glu Asp Glu Thr Pro Thr Pro Ser Ala Ser Cys
                885                 890                 895

Ala Val Thr Tyr Gln Thr Asn Asp Trp Pro Gly Gly Phe Thr Ala Ser
            900                 905                 910

Val Thr Leu Thr Asn Thr Gly Ser Thr Pro Trp Asp Ser Trp Glu Leu
        915                 920                 925

Arg Phe Thr Phe Pro Ser Gly Gln Thr Val Ser His Gly Trp Ser Ala
    930                 935                 940

Asn Trp Gln Gln Ser Gly Ser Asp Val Thr Ala Thr Ser Leu Pro Trp
```

```
                945                 950                 955                 960
Asn Gly Ser Val Pro Pro Gly Gly Ser Val Asn Ile Gly Phe Asn Gly
                    965                 970                 975

Thr Trp Gly Gly Ser Asn Thr Lys Pro Glu Lys Phe Thr Val Asn Gly
                    980                 985                 990

Ala Val Cys Ser Ile Gly
            995

<210> SEQ ID NO 116
<211> LENGTH: 842
<212> TYPE: PRT
<213> ORGANISM: Artificial Sequence
<220> FEATURE:
<223> OTHER INFORMATION: Caldicellulosiruptor kristjanssonii

<400> SEQUENCE: 116

Lys Thr Ala Arg Leu Leu Val Cys Phe Val Leu Val Cys Phe Ile Leu
1               5                   10                  15

Thr Thr Thr Ile Leu Leu Asp Asn Asn Lys Gly Glu Ala Ala Met Tyr
            20                  25                  30

Asn Tyr Gly Glu Ala Leu Gln Lys Ala Ile Met Phe Tyr Glu Phe Gln
        35                  40                  45

Met Ser Gly Lys Leu Pro Lys Trp Ile Arg Asn Asn Trp Arg Gly Asp
    50                  55                  60

Ser Gly Leu Asn Asp Gly Lys Asp Asn Lys Ile Asp Leu Thr Gly Gly
65                  70                  75                  80

Trp Tyr Asp Ala Gly Asp His Val Lys Phe Asn Leu Pro Met Ser Tyr
                85                  90                  95

Thr Ala Thr Met Leu Ala Trp Ala Val Tyr Glu Tyr Lys Asp Ala Phe
            100                 105                 110

Val Lys Ser Gly Gln Leu Gln His Ile Leu Asn Gln Ile Glu Trp Val
        115                 120                 125

Asn Asp Tyr Phe Val Lys Cys His Pro Glu Lys Tyr Val Tyr Tyr Tyr
    130                 135                 140

Gln Val Gly Asp Gly Gly Lys Asp His Ala Trp Trp Gly Pro Ala Glu
145                 150                 155                 160

Val Met Pro Met Glu Arg Pro Ser Tyr Lys Val Thr Lys Thr Asn Pro
                165                 170                 175

Gly Ser Thr Val Val Ala Glu Thr Ala Ala Leu Ala Ala Gly Ser
            180                 185                 190

Ile Val Ile Lys Gln Arg Asn Ser Lys Ala Arg Ile Tyr Leu Lys
        195                 200                 205

His Ala Lys Glu Leu Tyr Asp Phe Ala Ala Glu Thr Lys Ser Asp Ala
    210                 215                 220

Gly Tyr Thr Ala Ala Asn Gly Tyr Tyr Asn Ser Trp Ser Gly Phe Trp
225                 230                 235                 240

Asp Glu Leu Ser Trp Ala Ala Val Trp Leu Tyr Leu Ala Thr Gly Asp
                245                 250                 255

Lys Tyr Tyr Leu Ser Glu Ala Lys Tyr Val Ser Asn Trp Pro Lys
            260                 265                 270

Ile Ala Gly Ser Asn Thr Ile Asp Tyr Arg Trp Ala His Cys Trp Asp
        275                 280                 285

Asp Val His Tyr Gly Ala Ala Leu Leu Leu Ala Lys Ile Thr Asp Glu
    290                 295                 300

Asn Thr Tyr Lys Gln Ile Val Glu Lys His Leu Asp Tyr Trp Thr Ile
```

```
            305                 310                 315                 320
Gly Tyr Gln Gly Gln Arg Ile Lys Tyr Thr Pro Lys Gly Leu Ala Trp
                325                 330                 335

Leu Asp Gln Trp Gly Ser Leu Arg Tyr Ala Thr Thr Ala Phe Leu
                340                 345                 350

Ala Phe Val Tyr Ser Asp Trp Lys Gly Cys Pro Ser Ser Lys Lys Lys
                355                 360                 365

Val Tyr Arg Lys Phe Gly Glu Gly Gln Val Asn Tyr Ala Leu Gly Ser
    370                 375                 380

Ser Gly Arg Ser Phe Val Val Gly Phe Gly Lys Asn Pro Pro Lys Arg
385                 390                 395                 400

Pro His His Arg Thr Ala His Gly Ser Trp Ala Asn Ser Gln Ser Glu
                405                 410                 415

Pro Pro Tyr His Arg His Ile Leu Tyr Gly Ala Leu Val Gly Gly Pro
                420                 425                 430

Gly Leu Asp Asp Ser Tyr Ser Asp Asp Val Gly Asn Tyr Val Asn Asn
                435                 440                 445

Glu Val Ala Cys Asp Tyr Asn Ala Gly Phe Val Gly Ala Leu Ala Lys
    450                 455                 460

Met Tyr Leu Leu Tyr Gly Gly Lys Pro Ile Pro Asn Phe Lys Ala Ile
465                 470                 475                 480

Glu Lys Pro Ser Asn Asp Glu Phe Phe Val Glu Ala Gly Ile Asn Ala
                485                 490                 495

Ser Gly Ser Asn Phe Val Glu Ile Lys Ala Ile Val Tyr Asn Gln Ser
                500                 505                 510

Gly Trp Pro Ala Arg Val Thr Asn Asn Leu Lys Phe Arg Tyr Tyr Ile
                515                 520                 525

Asn Leu Ser Glu Ile Val Ser Gln Gly Tyr Lys Pro Ser Gln Ile Ser
                530                 535                 540

Leu Asn Thr Asn Tyr Asn Gln Gly Ala Lys Val Ser Gly Pro Tyr Val
545                 550                 555                 560

Val Asp Ser Lys Lys His Leu Tyr Tyr Ile Leu Ile Asp Phe Ser Gly
                565                 570                 575

Thr Pro Ile Tyr Pro Gly Gly Gln Asp Lys Tyr Lys Lys Glu Val Gln
                580                 585                 590

Phe Arg Ile Ala Ala Pro Gln Asn Ala Arg Trp Asp Asn Ser Asn Asp
                595                 600                 605

Tyr Ser Phe Lys Gly Leu Asp Lys Thr Gly Gly Gln Val Ile Lys
                610                 615                 620

Thr Lys Tyr Ile Pro Leu Tyr Asp Gly Lys Lys Leu Val Trp Gly Ile
625                 630                 635                 640

Glu Pro Asn Thr Lys Asn Leu Thr Leu Arg Thr Ser Gln Ile Pro Ala
                645                 650                 655

Asn Gly Asp Ala Asp Lys Lys Ser Lys Thr Ile Leu Ser Lys Asn Thr
                660                 665                 670

Ser Ser Ala Lys Thr Ser Ser Lys Gln Asn Lys Glu Val Lys Asn Val
                675                 680                 685

Val Lys Val Leu Tyr Lys Asn Met Glu Ile Asn Lys Thr Ser Asn Ser
                690                 695                 700

Ile Arg Leu Tyr Leu Lys Ile Asn Asn Ser Gln Glu Thr Ile Asp
705                 710                 715                 720

Leu Ser Lys Val Lys Ile Arg Tyr Trp Tyr Thr Ala Asp Asp Gly Val
                725                 730                 735
```

-continued

```
Met Lys Gln Ser Ala Val Cys Asp Trp Ala Gln Ile Gly Ala Val Asn
            740                 745                 750

Val Thr Phe Arg Phe Val Arg Leu Arg Lys Ala Val Ala Lys Ala Asp
        755                 760                 765

His Tyr Leu Glu Ile Gly Phe Thr Asn Asn Ala Gly Lys Ile Gln Pro
    770                 775                 780

Gly Lys Asp Ser Gly Asp Ile Gln Leu Arg Phe Asn Lys Ser Asn Trp
785                 790                 795                 800

Gly Asn Tyr Asp Gln Ser Asn Asp Trp Ser Trp Val Gln Ser Met Thr
                805                 810                 815

Ser Tyr Gly Glu Asn Lys Lys Ile Thr Leu Tyr Ile Asp Gly Lys Leu
            820                 825                 830

Val Trp Gly Gln Glu Pro Thr Lys Asp Thr
        835                 840
```

<210> SEQ ID NO 117
<211> LENGTH: 755
<212> TYPE: PRT
<213> ORGANISM: Artificial Sequence
<220> FEATURE:
<223> OTHER INFORMATION: Caldicellulosiruptor kristjanssonii

<400> SEQUENCE: 117

```
Met Lys Lys Ile Ile Leu Lys Ser Gly Ile Leu Leu Val Val Ile
1               5                   10                  15

Leu Ile Val Ser Ile Leu Gln Ile Leu Pro Val Phe Ala Gln Ser Thr
            20                  25                  30

Pro Tyr Glu Lys Glu Lys Tyr Pro His Leu Leu Gly Asn Gln Ala Val
        35                  40                  45

Lys Lys Pro Ser Val Ala Gly Arg Leu Gln Ile Ile Glu Lys Asn Gly
    50                  55                  60

Lys Lys Tyr Leu Ala Asp Gln Lys Gly Glu Ile Ile Gln Leu Arg Gly
65                  70                  75                  80

Met Ser Thr His Gly Leu Gln Trp Tyr Gly Asp Ile Ile Asn Lys Asn
                85                  90                  95

Ala Phe Glu Ala Leu Ser Lys Asp Trp Glu Cys Asn Val Val Arg Leu
            100                 105                 110

Ala Met Tyr Val Gly Glu Gly Tyr Ala Ser Asn Pro Ser Ile Lys
        115                 120                 125

Gln Lys Val Ile Glu Gly Ile Lys Leu Ala Ile Glu Asn Asp Met Tyr
    130                 135                 140

Val Ile Val Asp Trp His Val Leu Asn Pro Gly Asp Pro Asn Ala Glu
145                 150                 155                 160

Ile Tyr Lys Gly Ala Lys Asp Phe Phe Lys Glu Ile Ala Thr Ser Phe
                165                 170                 175

Pro Asn Asp Tyr His Ile Ile Tyr Glu Leu Cys Asn Glu Pro Asn Pro
            180                 185                 190

Asn Glu Pro Gly Val Glu Asn Ser Leu Asp Gly Trp Lys Lys Val Lys
        195                 200                 205

Ala Tyr Ala Glu Pro Ile Ile Lys Met Leu Arg Ser Leu Gly Asn Gln
    210                 215                 220

Asn Ile Ile Ile Val Gly Ser Pro Asn Trp Ser Gln Arg Pro Asp Phe
225                 230                 235                 240

Ala Ile Gln Asp Pro Ile Asn Asp Lys Asn Val Met Tyr Ser Val His
                245                 250                 255
```

```
Phe Tyr Ser Gly Thr His Lys Val Asp Gly Tyr Val Phe Glu Asn Met
            260                 265                 270

Lys Asn Ala Phe Glu Asn Gly Val Pro Ile Phe Val Ser Glu Trp Gly
            275                 280                 285

Thr Ser Leu Ala Ser Gly Asp Gly Pro Tyr Leu Asp Glu Ala Asp
            290                 295                 300

Lys Trp Leu Glu Tyr Leu Asn Ser Asn Tyr Ile Ser Trp Val Asn Trp
305                 310                 315                 320

Ser Leu Ser Asn Lys Asn Glu Thr Ser Ala Ala Phe Val Pro Tyr Val
            325                 330                 335

Ser Gly Met His Asp Ala Thr Ser Leu Asp Pro Gly Asp Lys Val
            340                 345                 350

Trp Asp Ile Lys Glu Leu Ser Ile Ser Gly Glu Tyr Val Arg Ala Arg
            355                 360                 365

Ile Lys Gly Ile Ala Tyr Lys Pro Ile Glu Arg Asn Ser Gln Ile Lys
            370                 375                 380

Glu Gly Glu Thr Ala Pro Leu Gly Glu Lys Val Leu Pro Ser Thr Phe
385                 390                 395                 400

Glu Asp Asp Thr Arg Gln Gly Trp Asp Trp Asp Gly Pro Ser Gly Val
            405                 410                 415

Lys Gly Pro Ile Thr Ile Glu Ser Ile Asn Gly Ser Lys Val Leu Ser
            420                 425                 430

Phe Glu Val Glu Tyr Pro Glu Lys Lys Pro Gln Asp Gly Trp Ala Thr
            435                 440                 445

Ala Ala Arg Leu Ile Leu Lys Glu Ile Asn Ala Lys Arg Glu Asp Asn
            450                 455                 460

Lys Tyr Leu Ala Phe Asp Phe Tyr Ile Lys Pro Glu Arg Val Ser Lys
465                 470                 475                 480

Gly Met Ile Gln Ile Phe Leu Ala Phe Ser Pro Pro Ser Leu Gly Tyr
            485                 490                 495

Trp Ala Gln Val Gln Asp Ser Phe Asn Ile Asp Leu Leu Lys Leu Ser
            500                 505                 510

Ser Ala Arg Lys Thr Glu Glu Gly Leu Tyr Lys Phe Asn Val Phe Phe
            515                 520                 525

Asp Leu Asp Lys Ile Gln Asp Gly Lys Val Leu Ser Pro Asp Thr Leu
            530                 535                 540

Leu Arg Asp Ile Ile Ile Val Ile Ala Asp Gly Asn Ser Asp Phe Lys
545                 550                 555                 560

Gly Lys Met Phe Ile Asp Asn Val Arg Phe Thr Asn Ile Leu Phe Glu
            565                 570                 575

Asp Ile Ser Phe Glu Ser Ser Leu Tyr Asp Thr Val Ser Lys Leu Tyr
            580                 585                 590

Ser Lys Arg Val Ile Lys Gly Thr Ser Ala Phe Lys Tyr Leu Pro Asp
            595                 600                 605

Arg Ser Ile Thr Arg Ala Glu Phe Ala Ala Leu Cys Val Arg Thr Leu
            610                 615                 620

Asn Leu Lys Ile Glu Lys Tyr Asp Gly Arg Phe Ser Asp Val Lys Ser
625                 630                 635                 640

Ser Ala Trp Tyr Ser Asp Val Val Tyr Thr Ala Tyr Lys Asn Gly Leu
            645                 650                 655

Phe Gly Gln Glu Lys Asn Lys Phe Phe Pro Glu Arg Ile Met Lys Arg
            660                 665                 670
```

```
Glu Glu Val Ala Ala Leu Ala Ile Glu Val Tyr Lys Arg Leu Thr Gly
            675                 680                 685

Lys Ile Glu Val Ser Leu Asp Asp Ile Gln Ile Ala Asp Glu Gly Leu
690                 695                 700

Ile Asn Pro Gln Tyr Arg Glu Ser Val Lys Leu Ala Val Lys Leu Gly
705                 710                 715                 720

Ile Phe Glu Leu Tyr Ser Asp Gly Thr Phe Ala Pro Gly Lys Ser Ile
                725                 730                 735

Ser Arg Gly Glu Val Ala Thr Ile Phe Tyr Asn Leu Leu Asn Leu Ala
            740                 745                 750

Gly Lys Ile
        755

<210> SEQ ID NO 118
<211> LENGTH: 689
<212> TYPE: PRT
<213> ORGANISM: Artificial Sequence
<220> FEATURE:
<223> OTHER INFORMATION: Caldicellulosiruptor kristjanssonii

<400> SEQUENCE: 118

Met Lys Gly Cys Val Tyr Gly Lys Leu Lys Arg Phe Ser Ala Leu Ile
1               5                   10                  15

Leu Ala Ile Leu Phe Leu Val Ala Ile Leu Gly Ile Gly Ser Ala
            20                  25                  30

Lys Val Ser Lys Val Ser Gly Ala Thr Lys Lys Ser Phe Met Glu Phe
            35                  40                  45

Asn Phe Glu Asn Lys Leu Ala Thr Pro Phe Lys Ala Ser Gly Lys Ser
50                  55                  60

Met Val Leu Lys Ile Asp Ser Thr Thr Ala Ala Glu Gly Ser Phe Ser
65                  70                  75                  80

Leu Leu Ala Ser Gly Arg Lys Gln Ile Asp Asp Gly Val Leu Leu Asp
                85                  90                  95

Val Thr Asn Leu Ile Asp Tyr Ser Asn Glu Tyr Thr Ile Ala Leu Tyr
            100                 105                 110

Val Tyr His Lys Ser Ser Lys Leu Gln Arg Phe Val Val Ser Ser Glu
            115                 120                 125

Ile Glu Thr Lys Ser Gly Lys Glu Asn Lys Leu Leu Cys Glu Lys Val
130                 135                 140

Ile Ile Pro Asn Asn Trp Lys Lys Leu Asp Thr Ser Leu Asn Leu Thr
145                 150                 155                 160

Glu Leu Lys Gly Ile Lys Lys Val Trp Leu Lys Ile Tyr Val Pro Thr
                165                 170                 175

Ser Thr Thr Asn Phe Tyr Ile Asp Leu Phe Thr Leu Lys Val Ser Asp
            180                 185                 190

Asn Ser His Leu Ile Lys Phe Glu Ser Phe Glu Asp Lys Ser Ile Ala
            195                 200                 205

Gly Phe Ile Pro Gln Asp Lys Lys Cys Lys Leu Ser Val Ser Lys Glu
210                 215                 220

Lys Ala Tyr Gln Gly Thr Tyr Ser Ile Lys Leu Gln Gln Thr Ala Lys
225                 230                 235                 240

Lys Gln Asn Thr Thr Val Thr Leu Pro Val Lys Gly Thr Phe Glu Lys
                245                 250                 255

Gly Lys Ser Tyr Ser Ile Ser Phe Tyr Val Tyr Gln Pro Ile Leu Lys
            260                 265                 270
```

```
Ser Leu Asn Leu Ala Ile Gly Val Arg Phe Leu Glu Asn Gly Lys Asn
            275                 280                 285

Thr Lys Glu Ile Val Leu Gly Lys Val Thr Val Pro Arg Asn Lys Trp
            290                 295                 300

Thr Glu Thr Phe Ala Ser Tyr Thr Pro Ser Leu Asp Ser Lys Val Lys
305                 310                 315                 320

Asp Phe Val Ile Phe Ile Lys Pro Leu Ser Asp Val Ser Tyr Tyr Tyr
                325                 330                 335

Leu Asp Asn Phe Thr Ile Ser Asp Asp Gly Trp Tyr Ser Ala Val Pro
            340                 345                 350

Asp Leu Asp Leu Pro Ser Leu Ser Glu Lys Tyr Lys Asp Tyr Phe Lys
            355                 360                 365

Val Gly Val Ala Val Pro Tyr Lys Ala Leu Thr Asn Pro Val Asp Val
    370                 375                 380

Ala Phe Ile Lys Arg His Phe Asn Ser Ile Thr Ala Glu Asn Glu Met
385                 390                 395                 400

Lys Pro Glu Ala Leu Glu Pro Tyr Glu Gly Thr Phe Asn Phe Ser Ile
                405                 410                 415

Ala Asp Glu Tyr Leu Asp Phe Cys Lys Lys Asn Asn Ile Ala Ile Arg
            420                 425                 430

Gly His Thr Leu Val Trp His Gln Gln Thr Pro Ser Trp Phe Phe Glu
            435                 440                 445

Asn Pro Gln Thr Gly Glu Lys Leu Thr Asn Ser Glu Lys Asp Lys Lys
            450                 455                 460

Ile Leu Leu Glu Arg Leu Lys Lys Tyr Ile Gln Thr Val Val Ser Arg
465                 470                 475                 480

Tyr Lys Gly Arg Ile Tyr Ala Trp Asp Val Val Asn Glu Ala Ile Asp
                485                 490                 495

Glu Asn Gln Pro Asp Gly Phe Arg Arg Ser Asp Trp Phe Asn Ile Leu
            500                 505                 510

Gly Pro Glu Tyr Ile Glu Lys Ala Phe Ile Tyr Ala His Gln Ala Asp
            515                 520                 525

Pro Asn Ala Leu Leu Phe Tyr Asn Asp Tyr Ser Thr Glu Asn Pro Val
    530                 535                 540

Lys Arg Glu Tyr Ile Tyr Lys Leu Ile Lys Asp Leu Lys Glu Lys Gly
545                 550                 555                 560

Val Pro Ile His Gly Val Gly Leu Gln Cys His Ile Thr Val Ser Trp
                565                 570                 575

Pro Ser Val Glu Glu Val Glu Arg Thr Ile Lys Leu Phe Ser Ser Ile
            580                 585                 590

Pro Gly Ile Lys Ile His Val Thr Glu Ile Asp Ile Ser Val Ala Lys
            595                 600                 605

Glu Phe Gly Glu Asp Ile Asp Glu Glu Thr Lys Arg Tyr Leu Leu Ile
    610                 615                 620

Gln Gln Ala Arg Lys Leu Lys Asp Leu Phe Glu Val Phe Lys Lys Tyr
625                 630                 635                 640

Lys Asn Val Val Thr Ser Val Ser Phe Trp Gly Leu Lys Asp Asp Tyr
                645                 650                 655

Ser Trp Leu Lys Gly Asp Phe Pro Leu Leu Phe Asp Lys Asp Tyr Gln
            660                 665                 670

Pro Lys Phe Ala Phe Trp Ser Leu Ile Asp Pro Ser Val Val Pro Glu
            675                 680                 685

Glu
```

<210> SEQ ID NO 119
<211> LENGTH: 372
<212> TYPE: PRT
<213> ORGANISM: Artificial Sequence
<220> FEATURE:
<223> OTHER INFORMATION: Caldicellulosiruptor kristjanssonii

<400> SEQUENCE: 119

```
Met Lys Arg Lys Leu Ile Ser Leu Ile Leu Val Phe Ile Phe Thr Leu
1               5                   10                  15

Ala Leu Leu Pro Ala Tyr Ala Asp Gln Asn Leu Pro Gly Thr Ser
            20                  25                  30

Ser Ser Gln Thr Val Thr Ser Ser Tyr Asp Thr Thr Gln Thr Gln
        35                  40                  45

Thr Tyr Gln Thr Thr Gln Asn Thr Thr Tyr Ser Gln Thr Tyr Asn Thr
 50                  55                  60

Gln Asn Ser Thr Pro Thr Pro Thr Pro Thr Pro Thr Pro Thr Pro Ile
65                   70                  75                  80

Thr Thr Pro Thr Pro Thr Pro Thr Pro Thr Pro Thr Val Thr Ser
                85                  90                  95

Thr Tyr Ser Ser Thr Tyr Ser Ser Asn Ser Thr Ile Asn Val Ile Pro
                100                 105                 110

Pro Ile Ser Asn Asp Asn Ile Lys Leu Lys Glu Pro Gln Lys Leu Thr
            115                 120                 125

Lys Glu Gln Lys Lys Thr Ile Ile Ser Leu Ile Trp Gln Ile Asn Gln
130                 135                 140

Leu Arg Val Lys Phe Asn Lys Ile Asn Ala Glu Val Asn Tyr Leu Arg
145                 150                 155                 160

Ala Lys Ile Asn Ala Tyr Val Gln Ala Lys Arg Tyr Asp Lys Ile
                165                 170                 175

Phe Phe Asn Gln Glu Met Asn Lys Ile Ile Asn Glu Val Asn Lys Thr
            180                 185                 190

Ile Ser Gln Leu Gln Lys Glu Leu Asn Lys Lys Asn Tyr Ser Ser Ser
        195                 200                 205

Lys Val Ala Glu Leu Asn Lys Gln Leu Asn Gln Lys Leu Asn Glu Leu
    210                 215                 220

Lys Val Tyr Glu Glu Val Tyr Lys Asn Gln Gln Gln Ala Val Asp
225                 230                 235                 240

Gln Ala Val Tyr Gln Ile Lys Gln Phe Val Asp Gln Ile Gln Pro Thr
                245                 250                 255

Val Ser Gln Lys Val Tyr Gln Ile Asn Thr Ile Asp Lys Gln Ile Lys
            260                 265                 270

Val Lys Leu Tyr Glu Tyr His Gln Ile Ala Lys Thr Ser Asp Tyr Asn
        275                 280                 285

Lys Met Val Ser Ile Leu Asn Glu Val Val Ser Leu Tyr Gln Thr Lys
    290                 295                 300

Val Asn Thr Ile Ser Glu Ile Lys Asn Leu Tyr Thr Asp Ile Leu Ser
305                 310                 315                 320

Lys Ile Glu Asn Ile Val Lys Asn Ser Leu Asn Met Pro Lys Lys Tyr
                325                 330                 335

Ile Gln Pro Met Gln Glu Lys Lys Ile Thr Ile Pro Gly Lys Gly Asn
            340                 345                 350

Ser Lys Ile Glu Ile Glu Ile Lys Lys Asn Pro Gln Gln Pro Gln Lys
        355                 360                 365
```

-continued

```
Gly Lys Lys Lys
    370

<210> SEQ ID NO 120
<211> LENGTH: 222
<212> TYPE: PRT
<213> ORGANISM: Artificial Sequence
<220> FEATURE:
<223> OTHER INFORMATION: Caldicellulosiruptor kristjanssonii

<400> SEQUENCE: 120

Leu Ser Pro Thr Pro Thr Lys Thr Pro Thr Pro Thr Ser Thr Pro Ala
1               5                   10                  15

Pro Thr Gln Thr Pro Thr Val Thr Pro Thr Pro Thr Pro Asn Ala Gly
            20                  25                  30

Gly Ile Leu Ile Ile Thr Asp Thr Ile Val Val Lys Ala Gly Gln Thr
        35                  40                  45

Tyr Asp Gly Lys Gly Val Lys Ile Ile Ala Gln Gly Met Gly Asp Gly
    50                  55                  60

Ser Gln Ser Glu Asn Gln Lys Pro Ile Phe Lys Leu Glu Lys Gly Ala
65                  70                  75                  80

Lys Leu Lys Asn Val Ile Ile Gly Ala Pro Gly Cys Asp Gly Ile His
                85                  90                  95

Cys Tyr Gly Asp Asn Val Ile Glu Asn Val Met Trp Glu Asp Val Gly
            100                 105                 110

Glu Asp Ala Leu Thr Val Lys Gly Glu Gly Val Val Glu Val Ile Gly
        115                 120                 125

Gly Ser Ala Lys Glu Ala Ala Asp Lys Val Phe Gln Leu Asn Ala Pro
    130                 135                 140

Cys Thr Phe Lys Val Lys Asn Phe Thr Ala Thr Asn Ile Gly Lys Leu
145                 150                 155                 160

Val Arg Gln Asn Gly Gly Thr Thr Phe Lys Val Val Ile Tyr Leu Glu
                165                 170                 175

Asn Val Thr Leu Asn Asn Val Lys Ser Cys Val Ala Lys Ser Asp Ser
            180                 185                 190

Pro Val Ser Glu Leu Trp Tyr His Asn Leu Val Val Asn Asn Cys Lys
        195                 200                 205

Thr Leu Phe Glu Phe Pro Ser Gln Ser Gln Ile His Gln Tyr
    210                 215                 220

<210> SEQ ID NO 121
<211> LENGTH: 770
<212> TYPE: PRT
<213> ORGANISM: Artificial Sequence
<220> FEATURE:
<223> OTHER INFORMATION: Caldicellulosiruptor kristjanssonii

<400> SEQUENCE: 121

Val Ser Ile Glu Lys Arg Val Asn Asp Leu Leu Gln Lys Met Thr Ile
1               5                   10                  15

Glu Glu Lys Val Tyr Gln Leu Thr Ser Ile Leu Val Gln Asp Ile Leu
            20                  25                  30

Glu Asn Asp Lys Phe Ser Pro Gln Lys Ala Lys Glu Lys Ile Pro Asn
        35                  40                  45

Gly Ile Gly Gln Ile Thr Arg Leu Ala Gly Ala Ser Asn Leu Ser Pro
    50                  55                  60

Glu Glu Ala Ala Lys Thr Ala Asn Glu Ile Gln Lys Phe Leu Ile Glu
```

```
                65                  70                  75                  80
Asn Thr Arg Leu Gly Ile Pro Ala Met Ile His Glu Glu Ser Cys Ser
                    85                  90                  95

Gly Phe Met Ala Lys Gly Ala Thr Val Phe Pro Gln Ser Ile Gly Val
                100                 105                 110

Ala Cys Thr Phe Asp Asn Glu Ile Val Glu Leu Ala Lys Val Ile
                115                 120                 125

Arg Thr Gln Met Lys Ala Val Gly Ala His Gln Ala Leu Ala Pro Leu
130                 135                 140

Ile Asp Val Ala Arg Asp Ala Arg Trp Gly Arg Val Glu Glu Thr Phe
145                 150                 155                 160

Gly Glu Asp Pro Tyr Leu Val Ala Asn Met Ala Val Ser Tyr Val Lys
                165                 170                 175

Gly Leu Gln Gly Asp Asp Ile Lys Asp Gly Ile Val Ala Thr Gly Lys
                180                 185                 190

His Phe Val Gly Tyr Ala Met Ser Glu Gly Gly Met Asn Trp Ala Pro
                195                 200                 205

Val His Ile Pro Glu Arg Glu Leu Arg Glu Val Tyr Leu Tyr Pro Phe
    210                 215                 220

Glu Val Ala Val Lys Val Ala Gly Leu Lys Ser Ile Met Pro Ala Tyr
225                 230                 235                 240

His Glu Ile Asp Gly Ile Pro Cys His Ala Asn Arg Lys Leu Leu Thr
                245                 250                 255

Asp Ile Ala Arg Gly Glu Trp Gly Phe Asp Gly Ile Tyr Val Ser Asp
                260                 265                 270

Tyr Ser Gly Val Lys Asn Leu Leu Asp Tyr His Lys Ser Val Lys Thr
            275                 280                 285

Tyr Glu Glu Ala Ala Ala Leu Ser Leu Trp Ala Gly Leu Asp Ile Glu
            290                 295                 300

Leu Pro Lys Ile Glu Cys Phe Thr Glu Glu Phe Ile Lys Ala Leu Lys
305                 310                 315                 320

Glu Gly Lys Phe Asp Met Ala Leu Val Asp Ala Ala Val Lys Arg Val
                325                 330                 335

Leu Glu Met Lys Phe Arg Leu Gly Leu Phe Asp Asn Pro Tyr Ile Lys
                340                 345                 350

Thr Glu Gly Val Val Glu Leu Phe Asp Asn Lys Glu Gln Arg Gln Leu
            355                 360                 365

Ser Arg Lys Val Ala Gln Glu Ser Met Val Leu Leu Lys Asn Asp Ser
    370                 375                 380

Phe Leu Pro Leu Ser Lys Asp Leu Lys Lys Ile Ala Val Ile Gly Pro
385                 390                 395                 400

Asn Ala Asn Ser Val Arg Asn Leu Leu Gly Asp Tyr Ser Tyr Pro Ala
                405                 410                 415

His Ile Ala Thr Leu Glu Met Phe Phe Ile Lys Glu Asp Arg Gly Val
                420                 425                 430

Gly Asn Glu Glu Glu Phe Val Lys Asn Val Ile Asn Met Lys Ser Ile
            435                 440                 445

Phe Glu Ala Ile Lys Asp Lys Val Ser Ser Asn Thr Glu Val Val Tyr
                450                 455                 460

Ala Lys Gly Cys Asp Val Asn Ser Gln Asp Lys Ser Gly Phe Glu Glu
465                 470                 475                 480

Ala Lys Lys Ala Ala Glu Gly Ala Asp Ala Val Ile Leu Val Val Gly
                485                 490                 495
```

```
Asp Lys Ala Gly Leu Arg Leu Asp Cys Thr Ser Gly Glu Ser Arg Asp
            500                 505                 510

Arg Ala Ser Leu Arg Leu Pro Gly Val Gln Glu Asp Leu Val Lys Glu
        515                 520                 525

Ile Val Ser Val Asn Pro Asn Thr Val Val Leu Val Asn Gly Arg
    530                 535                 540

Pro Val Ala Leu Asp Trp Ile Met Glu Asn Val Lys Ala Val Leu Glu
545                 550                 555                 560

Ala Trp Phe Pro Gly Glu Gly Ala Asp Ala Val Ala Asp Ile Leu
                565                 570                 575

Phe Gly Asp Tyr Asn Pro Gly Gly Lys Leu Ala Ile Ser Phe Pro Arg
                580                 585                 590

Asp Val Gly Gln Val Pro Val Tyr Tyr Gly His Lys Pro Ser Gly Gly
            595                 600                 605

Lys Ser Cys Trp His Gly Asp Tyr Val Glu Met Ser Thr Lys Pro Leu
    610                 615                 620

Leu Pro Phe Gly Tyr Gly Leu Ser Tyr Thr Thr Phe Glu Tyr Lys Asn
625                 630                 635                 640

Phe Ala Ile Glu Lys Glu Lys Ile Gly Met Asp Glu Ser Ile Lys Val
                645                 650                 655

Ser Val Glu Val Glu Asn Thr Gly Lys Tyr Glu Gly Asp Glu Ile Val
                660                 665                 670

Gln Leu Tyr Thr Arg Lys Glu Glu Tyr Leu Val Thr Arg Pro Val Lys
    675                 680                 685

Glu Leu Lys Gly Tyr Lys Arg Val His Leu Lys Pro Gly Glu Lys Lys
            690                 695                 700

Lys Val Val Phe Glu Leu Tyr Pro Asp Leu Phe Ala Phe Tyr Asp Tyr
705                 710                 715                 720

Asp Met Asn Arg Val Val Thr Pro Gly Val Val Glu Val Met Ile Gly
                725                 730                 735

Ala Ser Ser Glu Asp Ile Lys Phe Thr Gly Thr Phe Glu Ile Val Gly
                740                 745                 750

Glu Lys Lys Asp Ala Lys Glu Ile Lys Asn Tyr Leu Ser Arg Ala Trp
            755                 760                 765

Cys Glu
    770

<210> SEQ ID NO 122
<211> LENGTH: 328
<212> TYPE: PRT
<213> ORGANISM: Artificial Sequence
<220> FEATURE:
<223> OTHER INFORMATION: Caldicellulosiruptor kristjanssonii

<400> SEQUENCE: 122

Leu Asn Lys Leu Pro Arg Tyr Lys Gly Phe Asn Leu Gly Leu Phe
1               5                   10                  15

Val Pro Gly Arg Ile Leu Gly Phe Phe Glu Asp Asp Phe Lys Trp Met
                20                  25                  30

Gly Glu Trp Gly Phe Asn Phe Ala Arg Ile Pro Met Asn Tyr Arg Asn
            35                  40                  45

Trp Phe Val Glu Gly Ser Ser Asp Ile Lys Glu Glu Ile Leu Gln Met
    50                  55                  60

Ile Asp Arg Val Ile Glu Trp Gly Glu Lys Tyr Glu Ile His Ile Cys
65                  70                  75                  80
```

```
Leu Asn Ile His Gly Ala Pro Gly Tyr Cys Val Asn Glu Lys Thr Lys
             85                  90                  95

Gln Gly Tyr Asn Leu Trp Lys Asp Glu Pro Leu Glu Leu Phe Val
        100                 105                 110

Ser Tyr Trp Gln Thr Phe Ala Lys Arg Tyr Lys Gly Ile Ser Ser Lys
        115                 120                 125

Met Leu Ser Phe Asn Leu Ile Asn Glu Pro Arg Gln Phe Ser Glu Glu
130                 135                 140

Glu Met Thr Lys Glu Asp Phe Ile Arg Val Met Thr Tyr Thr Thr Gln
145                 150                 155                 160

Lys Ile Arg Glu Ile Gly Lys Glu Arg Leu Ile Val Asp Gly Val
                165                 170                 175

Asp Tyr Gly Asn Glu Pro Val Val Glu Leu Ala Asn Leu Gly Val Ala
                180                 185                 190

Gln Ser Cys Arg Ala Tyr Ile Pro Phe Glu Val Ser His Trp Gly Ala
        195                 200                 205

Glu Trp Val Glu Gly Ser Arg Asn Phe Thr Lys Pro Ser Trp Pro Leu
210                 215                 220

Val Arg Glu Asn Gly Glu Ile Val Asp Lys Glu Tyr Leu Lys Lys His
225                 230                 235                 240

Tyr Glu Lys Trp Ala Lys Leu Ile Ser Leu Gly Val Gly Val Ile Cys
                245                 250                 255

Gly Glu Gly Gly Ala Tyr Lys Tyr Thr Pro His Asp Val Val Ile Arg
                260                 265                 270

Trp Phe Ser Asp Val Leu Asp Ile Leu Lys Glu Phe Gly Ile Gly Ile
        275                 280                 285

Ala Leu Trp Asn Leu Arg Gly Pro Phe Gly Ile Ile Asp Ser Gly Arg
290                 295                 300

Glu Asp Val Glu Tyr Gly Asp Phe Tyr Gly His Lys Leu Asp Arg Lys
305                 310                 315                 320

Leu Leu Glu Leu Leu Gln Arg Phe
                325

<210> SEQ ID NO 123
<211> LENGTH: 1742
<212> TYPE: PRT
<213> ORGANISM: Artificial Sequence
<220> FEATURE:
<223> OTHER INFORMATION: Caldocellum saccharolyticum Biomass degrading
      enzyme

<400> SEQUENCE: 123

Met Val Val Thr Phe Leu Phe Ile Leu Gly Val Val Tyr Gly Val Lys
1               5                   10                  15

Pro Trp Gln Glu Ala Arg Ala Gly Ser Phe Asn Tyr Gly Glu Ala Leu
            20                  25                  30

Gln Lys Ala Ile Met Phe Tyr Glu Phe Gln Met Ser Gly Lys Leu Pro
        35                  40                  45

Asn Trp Val Arg Asn Asn Trp Arg Gly Asp Ser Ala Leu Lys Asp Gly
    50                  55                  60

Gln Asp Asn Gly Leu Asp Leu Thr Gly Gly Trp Phe Asp Ala Gly Asp
65                  70                  75                  80

His Val Lys Phe Asn Leu Pro Met Ser Tyr Thr Gly Thr Met Leu Ser
                85                  90                  95

Trp Ala Ala Tyr Glu Tyr Lys Asp Ala Phe Val Lys Ser Gly Gln Leu
```

```
                100             105                 110
Glu His Ile Leu Asn Gln Ile Glu Trp Val Asn Asp Tyr Phe Val Lys
            115                 120             125
Cys His Pro Ser Lys Tyr Val Tyr Tyr Gln Val Gly Asp Gly Gly
        130                 135         140
Lys Asp His Ala Trp Trp Gly Pro Ala Glu Val Met Gln Met Glu Arg
145                 150                 155                 160
Pro Ser Phe Lys Val Thr Gln Ser Ser Pro Gly Ser Ala Val Val Ala
                165                 170                 175
Glu Thr Ala Ala Ser Leu Ala Ala Ala Ser Ile Val Leu Lys Asp Arg
        180                 185                 190
Asn Pro Thr Lys Ala Ala Thr Tyr Leu Gln His Ala Lys Asp Leu Tyr
            195                 200             205
Glu Phe Ala Glu Val Thr Lys Ser Asp Ser Gly Tyr Thr Ala Ala Asn
        210                 215                 220
Gly Tyr Tyr Asn Ser Trp Ser Gly Phe Tyr Asp Glu Leu Ser Trp Ala
225                 230                 235                 240
Ala Val Trp Leu Tyr Leu Ala Thr Asn Asp Ser Thr Tyr Leu Thr Lys
                245                 250                 255
Ala Glu Ser Tyr Val Gln Asn Trp Pro Lys Ile Ser Gly Ser Asn Ile
            260                 265                 270
Ile Asp Tyr Lys Trp Ala His Cys Trp Asp Asp Val His Asn Gly Ala
            275                 280                 285
Ala Leu Leu Leu Ala Lys Ile Thr Asp Lys Asp Thr Tyr Lys Gln Ile
        290                 295                 300
Ile Glu Ser His Leu Asp Tyr Trp Thr Thr Gly Tyr Asn Gly Glu Arg
305                 310                 315                 320
Ile Lys Tyr Thr Pro Lys Gly Leu Ala Trp Leu Asp Gln Trp Gly Ser
                325                 330                 335
Leu Arg Tyr Ala Thr Thr Thr Ala Phe Leu Ala Phe Val Tyr Ser Asp
            340                 345                 350
Trp Ser Gly Cys Pro Thr Gly Lys Lys Glu Thr Tyr Arg Lys Phe Gly
            355                 360                 365
Glu Ser Gln Ile Asp Tyr Ala Leu Gly Ser Thr Gly Arg Ser Phe Val
        370                 375                 380
Val Gly Phe Gly Thr Asn Pro Pro Lys Arg Pro His His Arg Thr Ala
385                 390                 395                 400
His Ser Ser Trp Ala Asp Ser Gln Ser Ile Pro Ser Tyr His Arg His
                405                 410                 415
Thr Leu Tyr Gly Ala Leu Val Gly Gly Pro Gly Ser Asp Asp Ser Tyr
            420                 425                 430
Thr Asp Asp Ile Ser Asn Tyr Val Asn Asn Glu Val Ala Cys Asp Tyr
            435                 440                 445
Asn Ala Gly Phe Val Gly Ala Leu Ala Lys Met Tyr Leu Leu Tyr Gly
        450                 455                 460
Gly Asn Pro Ile Pro Asp Phe Lys Ala Ile Glu Thr Pro Thr Asn Asp
465                 470                 475                 480
Glu Phe Phe Val Glu Ala Gly Ile Asn Ala Ser Gly Thr Asn Phe Ile
                485                 490                 495
Glu Ile Lys Ala Ile Val Asn Asn Gln Ser Gly Trp Pro Ala Arg Ala
            500                 505                 510
Thr Asn Lys Leu Lys Phe Arg Tyr Phe Val Asp Leu Ser Glu Leu Ile
            515                 520                 525
```

```
Lys Ala Gly Tyr Ser Pro Asn Gln Leu Thr Leu Ser Thr Asn Tyr Asn
    530                 535                 540

Gln Gly Ala Lys Val Ser Gly Pro Tyr Val Trp Asp Ser Ser Arg Asn
545                 550                 555                 560

Ile Tyr Tyr Ile Leu Val Asp Phe Thr Gly Thr Leu Ile Tyr Pro Gly
                565                 570                 575

Gly Gln Asp Lys Tyr Lys Lys Glu Val Gln Phe Arg Ile Ala Ala Pro
            580                 585                 590

Gln Asn Val Gln Trp Asp Asn Ser Asn Asp Tyr Ser Phe Gln Asp Ile
        595                 600                 605

Lys Gly Val Ser Ser Gly Ser Val Val Lys Thr Lys Tyr Ile Pro Leu
    610                 615                 620

Tyr Asp Glu Asp Ile Lys Val Trp Gly Glu Pro Gly Thr Ser Gly
625                 630                 635                 640

Val Ser Pro Thr Pro Thr Ala Ser Val Thr Pro Thr Pro Thr
                645                 650                 655

Pro Thr Ala Thr Pro Thr Pro Thr Pro Thr Pro Val Thr Pro Thr
            660                 665                 670

Pro Thr Val Thr Ala Thr Pro Thr Pro Thr Pro Thr Pro Thr Ser Thr
        675                 680                 685

Pro Thr Val Thr Pro Thr Pro Thr Pro Val Ser Thr Pro Ala Thr Ser
    690                 695                 700

Gly Gln Ile Lys Val Leu Tyr Ala Asn Lys Glu Thr Asn Ser Thr Thr
705                 710                 715                 720

Asn Thr Ile Arg Pro Trp Leu Lys Val Asn Ser Gly Ser Ser Ser
                725                 730                 735

Ile Asp Leu Ser Arg Val Thr Ile Arg Tyr Trp Tyr Thr Val Asp Gly
            740                 745                 750

Glu Arg Ala Gln Ser Ala Ile Ser Asp Trp Ala Gln Ile Gly Ala Ser
        755                 760                 765

Asn Val Thr Phe Lys Phe Val Lys Leu Ser Ser Val Ser Gly Ala
    770                 775                 780

Asp Tyr Tyr Leu Glu Ile Gly Phe Lys Ser Gly Ala Gly Gln Leu Gln
785                 790                 795                 800

Pro Gly Lys Asp Thr Gly Glu Ile Gln Ile Arg Phe Asn Lys Asp Asp
                805                 810                 815

Trp Ser Asn Tyr Asn Gln Gly Asn Asp Trp Ser Trp Ile Gln Ser Met
            820                 825                 830

Thr Ser Tyr Gly Glu Asn Glu Lys Val Thr Ala Tyr Ile Asp Gly Val
        835                 840                 845

Leu Val Trp Gly Gln Glu Pro Ser Gly Thr Thr Pro Ala Pro Thr Ser
    850                 855                 860

Thr Pro Thr Val Thr Val Thr Pro Thr Pro Thr Pro Thr Pro Thr Val
865                 870                 875                 880

Thr Pro Thr Pro Thr Val Thr Ala Thr Pro Thr Pro Thr Pro Thr Pro
                885                 890                 895

Thr Ser Thr Pro Val Ser Thr Pro Ala Thr Gly Gly Gln Ile Lys Val
            900                 905                 910

Leu Tyr Ala Asn Lys Glu Thr Asn Ser Thr Thr Asn Thr Ile Arg Pro
        915                 920                 925

Trp Leu Lys Val Val Asn Ser Gly Ser Ser Ser Ile Asp Leu Ser Arg
    930                 935                 940
```

-continued

Val Thr Ile Arg Tyr Trp Tyr Thr Val Asp Gly Glu Arg Ala Gln Ser
945                 950                 955                 960

Ala Ile Ser Asp Trp Ala Gln Ile Gly Ala Ser Asn Val Thr Phe Lys
            965                 970                 975

Phe Val Lys Leu Ser Ser Ser Val Ser Gly Ala Asp Tyr Tyr Leu Glu
        980                 985                 990

Ile Gly Phe Lys Ser Gly Ala Gly Gln Leu Gln Pro Gly Lys Asp Thr
        995                 1000                1005

Gly Glu Ile Gln Ile Arg Phe Asn Lys Asp Asp Trp Ser Asn Tyr
    1010                1015                1020

Asn Gln Gly Asn Asp Trp Ser Trp Ile Gln Ser Met Thr Ser Tyr
    1025                1030                1035

Gly Glu Asn Glu Lys Val Thr Ala Tyr Ile Asp Gly Val Leu Val
    1040                1045                1050

Trp Gly Gln Glu Pro Ser Gly Ala Thr Pro Ala Pro Thr Val Thr
    1055                1060                1065

Pro Thr Pro Thr Val Thr Pro Thr Pro Thr Pro Ala Pro Thr Pro
    1070                1075                1080

Thr Ala Thr Pro Thr Pro Thr Pro Thr Pro Thr Val Thr Pro Thr
    1085                1090                1095

Pro Thr Val Ala Pro Thr Pro Thr Pro Ser Ser Thr Pro Ser Gly
    1100                1105                1110

Leu Gly Lys Tyr Gly Gln Arg Phe Met Trp Leu Trp Asn Lys Ile
    1115                1120                1125

His Asp Pro Ala Ser Gly Tyr Phe Asn Gln Asp Gly Ile Pro Tyr
    1130                1135                1140

His Ser Val Glu Thr Leu Ile Cys Glu Ala Pro Asp Tyr Gly His
    1145                1150                1155

Leu Thr Thr Ser Glu Ala Phe Ser Tyr Tyr Val Trp Leu Glu Ala
    1160                1165                1170

Val Tyr Gly Lys Leu Thr Gly Asp Trp Ser Lys Phe Lys Thr Ala
    1175                1180                1185

Trp Asp Thr Leu Glu Lys Tyr Met Ile Pro Ser Ala Glu Asp Gln
    1190                1195                1200

Pro Met Arg Ser Tyr Asp Pro Asn Lys Pro Ala Thr Tyr Ala Gly
    1205                1210                1215

Glu Trp Glu Thr Pro Asp Lys Tyr Pro Ser Pro Leu Glu Phe Asn
    1220                1225                1230

Val Pro Val Gly Lys Asp Pro Leu His Asn Glu Leu Val Ser Thr
    1235                1240                1245

Tyr Gly Ser Thr Leu Met Tyr Gly Met His Trp Leu Met Asp Val
    1250                1255                1260

Asp Asn Trp Tyr Gly Tyr Gly Lys Arg Gly Asp Gly Val Ser Arg
    1265                1270                1275

Ala Ser Phe Ile Asn Thr Phe Gln Arg Gly Pro Glu Glu Ser Val
    1280                1285                1290

Trp Glu Thr Val Pro His Pro Ser Trp Glu Glu Phe Lys Trp Gly
    1295                1300                1305

Gly Pro Asn Gly Phe Leu Asp Leu Phe Ile Lys Asp Gln Asn Tyr
    1310                1315                1320

Ser Lys Gln Trp Arg Tyr Thr Asn Ala Pro Asp Ala Asp Ala Arg
    1325                1330                1335

Ala Ile Gln Ala Thr Tyr Trp Ala Lys Val Trp Ala Lys Glu Gln

```
              1340                1345                1350
Gly Lys Phe Asn Glu Ile Ser Ser Tyr Val Gly Lys Ala Ala Lys
              1355                1360                1365
Met Gly Asp Tyr Leu Arg Tyr Ala Met Phe Asp Lys Tyr Phe Lys
              1370                1375                1380
Pro Leu Gly Cys Gln Asp Lys Asn Ala Ala Gly Gly Thr Gly Tyr
              1385                1390                1395
Asp Ser Ala His Tyr Leu Leu Ser Trp Tyr Tyr Ala Trp Gly Gly
              1400                1405                1410
Ala Leu Asp Gly Ala Trp Ser Trp Lys Ile Gly Cys Ser His Ala
              1415                1420                1425
His Phe Gly Tyr Gln Asn Pro Met Ala Ala Trp Ala Leu Ala Asn
              1430                1435                1440
Asp Ser Asp Met Lys Pro Lys Ser Pro Asn Gly Ala Ser Asp Trp
              1445                1450                1455
Ala Lys Ser Leu Lys Arg Gln Ile Glu Phe Tyr Arg Trp Leu Gln
              1460                1465                1470
Ser Ala Glu Gly Ala Ile Ala Gly Gly Ala Thr Asn Ser Trp Asn
              1475                1480                1485
Gly Arg Tyr Glu Lys Tyr Pro Ala Gly Thr Ala Thr Phe Tyr Gly
              1490                1495                1500
Met Ala Tyr Glu Pro Asn Pro Val Tyr Arg Asp Pro Gly Ser Asn
              1505                1510                1515
Thr Trp Phe Gly Phe Gln Ala Trp Ser Met Gln Arg Val Ala Glu
              1520                1525                1530
Tyr Tyr Tyr Val Thr Gly Asp Lys Asp Ala Gly Thr Leu Leu Glu
              1535                1540                1545
Lys Trp Val Ser Trp Ile Lys Ser Val Val Lys Leu Asn Ser Asp
              1550                1555                1560
Gly Thr Phe Ala Ile Pro Ser Thr Leu Asp Trp Ser Gly Gln Pro
              1565                1570                1575
Asp Thr Trp Asn Gly Thr Tyr Thr Gly Asn Pro Asn Leu His Val
              1580                1585                1590
Lys Val Val Asp Tyr Gly Thr Asp Leu Gly Ile Thr Ala Ser Leu
              1595                1600                1605
Ala Asn Ala Leu Leu Tyr Tyr Ser Ala Gly Thr Lys Lys Tyr Gly
              1610                1615                1620
Val Phe Asp Glu Glu Ala Lys Asn Leu Ala Lys Glu Leu Leu Asp
              1625                1630                1635
Arg Met Trp Lys Leu Tyr Arg Asp Glu Lys Gly Leu Ser Ala Pro
              1640                1645                1650
Glu Lys Arg Ala Asp Tyr Lys Arg Phe Phe Glu Gln Glu Val Tyr
              1655                1660                1665
Ile Pro Ala Gly Trp Thr Gly Lys Met Pro Asn Gly Asp Val Ile
              1670                1675                1680
Lys Ser Gly Val Lys Phe Ile Asp Ile Arg Ser Lys Tyr Lys Gln
              1685                1690                1695
Asp Pro Asp Trp Pro Lys Leu Glu Ala Ala Tyr Lys Ser Gly Gln
              1700                1705                1710
Val Pro Glu Phe Arg Tyr His Arg Phe Trp Ala Gln Cys Asp Ile
              1715                1720                1725
Ala Ile Val Asn Ala Thr Tyr Glu Ile Leu Phe Gly Asn Gln
              1730                1735                1740
```

<210> SEQ ID NO 124
<211> LENGTH: 1037
<212> TYPE: PRT
<213> ORGANISM: Artificial Sequence
<220> FEATURE:
<223> OTHER INFORMATION: Caldocellum saccharolyticum CelB

<400> SEQUENCE: 124

```
Met Lys Arg Asn Leu Phe Arg Ile Val Ser Arg Val Val Leu Ile Ala
1               5                   10                  15

Phe Ile Ala Ser Ile Ser Leu Val Gly Ala Met Ser Tyr Phe Pro Val
            20                  25                  30

Glu Thr Gln Ala Ala Pro Asp Trp Ser Ile Pro Ser Leu Cys Glu Ser
        35                  40                  45

Tyr Lys Asp Asp Phe Met Ile Gly Val Ala Ile Pro Ala Arg Cys Leu
    50                  55                  60

Ser Asn Asp Thr Asp Lys Arg Met Val Leu Lys His Phe Asn Ser Ile
65                  70                  75                  80

Thr Ala Glu Asn Glu Met Lys Pro Glu Ser Leu Leu Ala Gly Gln Thr
                85                  90                  95

Ser Thr Gly Leu Ser Tyr Arg Phe Ser Thr Ala Asp Ala Phe Val Asp
            100                 105                 110

Phe Ala Ser Thr Asn Lys Ile Gly Ile Arg Gly His Thr Leu Val Trp
        115                 120                 125

His Asn Gln Thr Pro Asp Trp Phe Phe Lys Asp Ser Asn Gly Gln Arg
    130                 135                 140

Leu Ser Lys Asp Ala Leu Leu Ala Arg Leu Lys Gln Tyr Ile Tyr Asp
145                 150                 155                 160

Val Val Gly Arg Tyr Lys Gly Lys Val Tyr Ala Trp Asp Val Val Asn
                165                 170                 175

Glu Ala Ile Asp Glu Asn Gln Pro Asp Ser Tyr Arg Arg Ser Thr Trp
            180                 185                 190

Tyr Glu Ile Cys Gly Pro Glu Tyr Ile Glu Lys Ala Phe Ile Trp Ala
        195                 200                 205

His Glu Ala Asp Pro Asn Ala Lys Leu Phe Tyr Asn Asp Tyr Asn Thr
    210                 215                 220

Glu Ile Ser Lys Lys Arg Asp Phe Ile Tyr Asn Met Val Lys Asn Leu
225                 230                 235                 240

Lys Ser Lys Gly Ile Pro Ile His Gly Ile Gly Met Gln Cys His Ile
                245                 250                 255

Asn Val Asn Trp Pro Ser Val Ser Glu Ile Glu Asn Ser Ile Lys Leu
            260                 265                 270

Phe Ser Ile Pro Gly Ile Glu Ile His Ile Thr Glu Leu Asp Met
        275                 280                 285

Ser Leu Tyr Asn Tyr Gly Ser Ser Glu Asn Tyr Ser Thr Pro Pro Gln
    290                 295                 300

Asp Leu Leu Gln Lys Gln Ser Gln Lys Tyr Lys Glu Ile Phe Thr Met
305                 310                 315                 320

Leu Lys Lys Tyr Lys Asn Val Val Lys Ser Thr Phe Trp Gly Leu Lys
                325                 330                 335

Asp Asp Tyr Trp Leu Arg Ser Phe Tyr Gly Lys Asn Asp Trp Pro Leu
            340                 345                 350

Leu Phe Phe Glu Asp Tyr Ser Ala Lys Pro Ala Tyr Trp Ala Val Ile
        355                 360                 365
```

```
Glu Ala Ser Gly Val Thr Thr Ser Pro Thr Pro Thr Pro
    370                 375             380

Thr Val Thr Val Thr Pro Thr Pro Thr Pro Thr Pro Thr Val
385                 390             395             400

Thr Ala Thr Pro Thr Pro Thr Pro Val Ser Thr Pro Ala Thr
                405             410             415

Gly Gly Gln Ile Lys Val Leu Tyr Ala Asn Lys Glu Thr Asn Ser Thr
            420             425             430

Thr Asn Thr Ile Arg Pro Trp Leu Lys Val Val Asn Ser Gly Ser Ser
        435             440             445

Ser Ile Asp Leu Ser Arg Val Thr Ile Arg Tyr Trp Tyr Thr Val Asp
    450             455             460

Gly Glu Arg Ala Gln Ser Ala Val Ser Asp Trp Ala Gln Ile Gly Ala
465             470             475             480

Ser Asn Val Thr Phe Lys Phe Val Lys Leu Ser Ser Val Ser Gly
            485             490             495

Ala Asp Tyr Tyr Leu Glu Ile Gly Phe Lys Ser Gly Ala Gly Gln Leu
            500             505             510

Gln Pro Gly Lys Asp Thr Gly Glu Ile Gln Ile Arg Phe Asn Lys Ser
        515             520             525

Asp Trp Ser Asn Tyr Asn Gln Gly Asn Asp Trp Ser Trp Leu Gln Ser
    530             535             540

Met Thr Ser Tyr Gly Glu Asn Glu Lys Val Thr Ala Tyr Ile Asp Gly
545             550             555             560

Val Leu Val Trp Gly Gln Glu Pro Ser Gly Ala Thr Pro Ala Pro Thr
            565             570             575

Met Thr Val Ala Pro Thr Ala Thr Pro Thr Pro Thr Leu Ser Pro Thr
            580             585             590

Val Thr Pro Thr Pro Ala Pro Thr Gln Thr Ala Ile Pro Thr Pro Thr
            595             600             605

Leu Thr Pro Asn Pro Thr Pro Thr Ser Ser Ile Pro Asp Asp Thr Asn
    610             615             620

Asp Asp Trp Leu Tyr Val Ser Gly Asn Lys Ile Val Asp Lys Asp Gly
625             630             635             640

Arg Pro Val Trp Leu Thr Gly Ile Asn Trp Phe Gly Tyr Asn Thr Gly
            645             650             655

Thr Asn Val Phe Asp Gly Val Trp Ser Cys Asn Leu Lys Asp Thr Leu
            660             665             670

Ala Glu Ile Ala Asn Arg Gly Phe Asn Leu Leu Arg Val Pro Ile Ser
    675             680             685

Ala Glu Leu Ile Leu Asn Trp Ser Gln Gly Ile Tyr Pro Lys Pro Asn
    690             695             700

Ile Asn Tyr Tyr Val Asn Pro Glu Leu Glu Gly Lys Asn Ser Leu Glu
705             710             715             720

Val Phe Asp Ile Val Gln Thr Cys Lys Glu Val Gly Leu Lys Ile
            725             730             735

Met Leu Asp Ile His Ser Ile Lys Thr Asp Ala Met Gly His Ile Tyr
            740             745             750

Pro Val Trp Tyr Asp Glu Lys Phe Thr Pro Glu Asp Phe Tyr Lys Ala
        755             760             765

Cys Glu Trp Ile Thr Asn Arg Tyr Lys Asn Asp Asp Thr Ile Ile Ala
    770             775             780
```

```
Phe Asp Leu Lys Asn Glu Pro His Gly Lys Pro Trp Gln Asp Thr Thr
785                 790                 795                 800

Phe Ala Lys Trp Asp Asn Ser Thr Asp Ile Asn Asn Trp Lys Tyr Ala
                805                 810                 815

Ala Glu Thr Cys Ala Lys Arg Ile Leu Asn Ile Asn Pro Asn Leu Leu
            820                 825                 830

Ile Val Ile Glu Gly Ile Glu Ala Tyr Pro Lys Asp Asp Val Thr Trp
        835                 840                 845

Thr Ser Lys Ser Ser Asp Tyr Tyr Ser Thr Trp Trp Gly Gly Asn
    850                 855                 860

Leu Arg Gly Val Arg Lys Tyr Pro Ile Asn Leu Gly Lys Tyr Gln Asn
865                 870                 875                 880

Lys Val Val Tyr Ser Pro His Asp Tyr Gly Pro Ser Val Tyr Gln Gln
                885                 890                 895

Pro Trp Phe Tyr Pro Gly Phe Thr Lys Glu Ser Leu Leu Gln Asp Cys
            900                 905                 910

Trp Arg Pro Asn Trp Ala Tyr Ile Met Glu Glu Asn Ile Ala Pro Leu
        915                 920                 925

Leu Ile Gly Glu Trp Gly Gly His Leu Asp Gly Ala Asp Asn Glu Lys
    930                 935                 940

Trp Met Lys Tyr Leu Arg Asp Tyr Ile Ile Glu Asn His Ile His His
945                 950                 955                 960

Thr Phe Trp Cys Phe Asn Ala Asn Ser Gly Asp Thr Gly Gly Leu Val
                965                 970                 975

Gly Tyr Asp Phe Thr Thr Trp Asp Glu Lys Lys Tyr Ser Phe Leu Lys
            980                 985                 990

Pro Ala Leu Trp Gln Asp Ser Gln Gly Arg Phe Val Gly Leu Asp His
        995                 1000                1005

Lys Arg Pro Leu Gly Thr Asn Gly Lys Asn Ile Asn Ile Thr Thr
    1010                1015                1020

Tyr Tyr Asn Asn Asn Glu Pro Glu Pro Val Pro Ala Ser Lys
    1025                1030                1035

<210> SEQ ID NO 125
<211> LENGTH: 1331
<212> TYPE: PRT
<213> ORGANISM: Artificial Sequence
<220> FEATURE:
<223> OTHER INFORMATION: Caldocellum saccharolyticum beta-mannanase

<400> SEQUENCE: 125

Met Arg Leu Lys Thr Lys Ile Arg Lys Lys Trp Leu Ser Val Leu Cys
1               5                   10                  15

Thr Val Val Phe Leu Leu Asn Ile Leu Phe Ile Ala Asn Val Thr Ile
            20                  25                  30

Leu Pro Lys Val Gly Ala Ala Thr Ser Asn Asp Gly Val Val Lys Ile
        35                  40                  45

Asp Thr Ser Thr Leu Ile Gly Thr Asn His Ala His Cys Trp Tyr Arg
    50                  55                  60

Asp Arg Leu Asp Thr Ala Leu Arg Gly Ile Arg Ser Trp Gly Met Asn
65                  70                  75                  80

Ser Val Arg Val Val Leu Ser Asn Gly Tyr Arg Trp Thr Lys Ile Pro
                85                  90                  95

Ala Ser Glu Val Ala Asn Ile Ile Ser Leu Ser Arg Ser Leu Gly Phe
            100                 105                 110
```

-continued

Lys Ala Ile Ile Leu Glu Val His Asp Thr Thr Gly Tyr Gly Glu Asp
            115                 120                 125

Gly Ala Ala Cys Ser Leu Ala Gln Ala Val Glu Tyr Trp Lys Glu Ile
130                 135                 140

Lys Ser Val Leu Asp Gly Asn Glu Asp Phe Val Ile Ile Asn Ile Gly
145                 150                 155                 160

Asn Glu Pro Tyr Gly Asn Asn Tyr Gln Asn Trp Val Asn Asp Thr
                165                 170                 175

Lys Asn Ala Ile Lys Ala Leu Arg Asp Ala Gly Phe Lys His Thr Ile
            180                 185                 190

Met Val Asp Ala Pro Asn Trp Gly Gln Asp Trp Ser Asn Thr Met Arg
            195                 200                 205

Asp Asn Ala Gln Ser Ile Met Glu Ala Asp Pro Leu Arg Asn Leu Val
210                 215                 220

Phe Ser Ile His Met Tyr Gly Val Tyr Asn Thr Ala Ser Lys Val Glu
225                 230                 235                 240

Glu Tyr Ile Lys Ser Phe Val Asp Lys Gly Leu Pro Leu Val Ile Gly
            245                 250                 255

Glu Phe Gly His Gln His Thr Asp Gly Asp Pro Asp Glu Glu Ala Ile
            260                 265                 270

Val Arg Tyr Ala Lys Gln Tyr Lys Ile Gly Leu Phe Ser Trp Ser Trp
275                 280                 285

Cys Gly Asn Ser Ser Tyr Val Gly Tyr Leu Asp Met Val Asn Asn Trp
            290                 295                 300

Asp Pro Asn Asn Pro Thr Pro Trp Gly Gln Trp Tyr Lys Thr Asn Ala
305                 310                 315                 320

Ile Gly Thr Ser Ser Thr Pro Thr Pro Thr Ser Thr Val Thr Pro Thr
            325                 330                 335

Pro Thr Pro Thr Pro Thr Pro Thr Pro Thr Val Thr Ala Thr Pro Thr
            340                 345                 350

Pro Thr Pro Thr Pro Val Ser Thr Pro Ala Thr Ser Gly Gln Ile Lys
            355                 360                 365

Val Leu Tyr Ala Asn Lys Glu Thr Asn Ser Thr Asn Thr Ile Arg
370                 375                 380

Pro Trp Leu Lys Val Val Asn Ser Gly Ser Ser Ser Ile Asp Leu Ser
385                 390                 395                 400

Arg Val Thr Ile Arg Tyr Trp Tyr Thr Val Asp Gly Glu Arg Ala Gln
                405                 410                 415

Ser Ala Ile Ser Asp Trp Ala Gln Ile Gly Ala Ser Asn Val Thr Phe
            420                 425                 430

Lys Phe Val Lys Leu Ser Ser Val Ser Gly Ala Asp Tyr Tyr Leu
            435                 440                 445

Glu Ile Gly Phe Lys Ser Gly Ala Gly Gln Leu Gln Pro Gly Lys Asp
450                 455                 460

Thr Gly Glu Ile Gln Met Arg Phe Asn Lys Asp Trp Ser Asn Tyr
465                 470                 475                 480

Asn Gln Gly Asn Asp Trp Ser Trp Ile Gln Ser Met Thr Ser Tyr Gly
                485                 490                 495

Glu Asn Glu Lys Val Thr Ala Tyr Ile Asp Gly Val Leu Val Trp Gly
            500                 505                 510

Gln Glu Pro Ser Gly Ala Thr Pro Ala Pro Ala Pro Thr Ala Thr Pro
            515                 520                 525

Thr Pro Thr Pro Thr Val Thr Pro Thr Pro Thr Val Thr Pro Thr Pro

```
            530                 535                 540
Thr Val Thr Ala Thr Pro Thr Pro Thr Pro Thr Pro Thr Pro
545                 550                 555                 560

Val Ser Thr Pro Ala Thr Gly Gly Gln Ile Lys Val Leu Tyr Ala Asn
                565                 570                 575

Lys Glu Thr Asn Ser Thr Thr Asn Thr Ile Arg Pro Trp Leu Lys Val
                580                 585                 590

Val Asn Ser Gly Ser Ser Ser Ile Asp Leu Ser Arg Val Thr Ile Arg
                595                 600                 605

Tyr Trp Tyr Thr Val Asp Gly Glu Arg Ala Gln Ser Ala Ile Ser Asp
                610                 615                 620

Trp Ala Gln Ile Gly Ala Ser Asn Val Thr Phe Lys Phe Val Lys Leu
625                 630                 635                 640

Ser Ser Ser Val Ser Gly Ala Asp Tyr Tyr Leu Glu Ile Gly Phe Lys
                645                 650                 655

Ser Gly Ala Gly Gln Leu Gln Pro Gly Lys Asp Thr Gly Glu Ile Gln
                660                 665                 670

Ile Arg Phe Asn Lys Ser Asp Trp Ser Asn Tyr Asn Gln Gly Asn Asp
                675                 680                 685

Trp Ser Trp Ile Gln Ser Met Thr Ser Tyr Gly Glu Asn Glu Lys Val
                690                 695                 700

Thr Ala Tyr Ile Asp Gly Val Leu Val Trp Gly Gln Glu Pro Ser Gly
705                 710                 715                 720

Thr Thr Pro Ser Pro Thr Ser Thr Pro Thr Val Thr Val Thr Pro Thr
                725                 730                 735

Pro Thr Pro Thr Pro Thr Pro Thr Pro Thr Pro Thr Val Thr Pro Thr
                740                 745                 750

Pro Thr Val Thr Pro Thr Pro Thr Val Thr Ala Thr Pro Thr Pro Thr
                755                 760                 765

Pro Thr Pro Ile Pro Thr Val Thr Pro Leu Pro Thr Ile Ser Pro Ser
                770                 775                 780

Pro Ser Val Val Glu Ile Thr Ile Asn Thr Asn Ala Gly Arg Thr Gln
785                 790                 795                 800

Ile Ser Pro Tyr Ile Tyr Gly Ala Asn Gln Asp Ile Glu Gly Val Val
                805                 810                 815

His Ser Ala Arg Arg Leu Gly Gly Asn Arg Leu Thr Gly Tyr Asn Trp
                820                 825                 830

Glu Asn Asn Phe Ser Asn Ala Gly Asn Asp Trp Tyr His Ser Ser Asp
                835                 840                 845

Asp Tyr Leu Cys Trp Ser Met Gly Ile Ser Gly Glu Asp Ala Lys Val
850                 855                 860

Pro Ala Ala Val Val Ser Lys Phe His Glu Tyr Ser Leu Lys Asn Asn
865                 870                 875                 880

Ala Tyr Ser Ala Val Thr Leu Gln Met Ala Gly Tyr Val Ser Lys Asp
                885                 890                 895

Asn Tyr Gly Thr Val Ser Glu Asn Glu Thr Ala Pro Ser Asn Arg Trp
                900                 905                 910

Ala Glu Val Lys Phe Lys Lys Asp Ala Pro Leu Ser Leu Asn Pro Asp
                915                 920                 925

Leu Asn Asp Asn Phe Val Tyr Met Asp Glu Phe Ile Asn Tyr Leu Ile
                930                 935                 940

Asn Lys Tyr Gly Met Ala Ser Ser Pro Thr Gly Ile Lys Gly Tyr Ile
945                 950                 955                 960
```

```
Leu Asp Asn Glu Pro Asp Leu Trp Ala Ser Thr His Pro Arg Ile His
            965                 970                 975

Pro Asn Lys Val Thr Cys Lys Glu Leu Ile Glu Lys Ser Val Glu Leu
            980                 985                 990

Ala Lys Val Ile Lys Thr Leu Asp Pro Ser Ala Glu Val Phe Gly Tyr
            995                1000                1005

Ala Ser Tyr Gly Phe Met Gly Tyr Tyr Ser Leu Gln Asp Ala Pro
        1010            1015            1020

Asp Trp Asn Gln Val Lys Gly Glu His Arg Trp Phe Ile Ser Trp
        1025            1030            1035

Tyr Leu Glu Gln Met Lys Lys Ala Ser Asp Ser Phe Gly Lys Arg
        1040            1045            1050

Leu Leu Asp Val Leu Asp Leu His Trp Tyr Pro Glu Ala Arg Gly
        1055            1060            1065

Gly Asn Ile Arg Val Cys Phe Asp Gly Glu Asn Asp Thr Ser Lys
        1070            1075            1080

Glu Val Val Ile Ala Arg Met Gln Ala Pro Arg Thr Leu Trp Asp
        1085            1090            1095

Pro Thr Tyr Lys Thr Ser Val Lys Gly Gln Ile Thr Ala Gly Glu
        1100            1105            1110

Asn Ser Trp Ile Asn Gln Trp Phe Ser Asp Tyr Leu Pro Ile Ile
        1115            1120            1125

Pro Asn Val Lys Ala Asp Ile Glu Lys Tyr Tyr Pro Gly Thr Lys
        1130            1135            1140

Leu Ala Ile Ser Glu Phe Asp Tyr Gly Gly Arg Asn His Ile Ser
        1145            1150            1155

Gly Gly Ile Ala Leu Ala Asp Val Leu Gly Ile Phe Gly Lys Tyr
        1160            1165            1170

Gly Val Asn Phe Ala Ala Arg Trp Gly Asp Ser Gly Ser Tyr Ala
        1175            1180            1185

Ala Ala Ala Tyr Asn Ile Tyr Leu Asn Tyr Asp Gly Lys Gly Ser
        1190            1195            1200

Lys Tyr Gly Asn Thr Asn Val Ser Ala Asn Thr Ser Asp Val Glu
        1205            1210            1215

Asn Met Pro Val Tyr Ala Ser Ile Asn Gly Gln Asp Asp Ser Glu
        1220            1225            1230

Leu His Ile Ile Leu Ile Asn Arg Asn Tyr Asp Gln Lys Leu Gln
        1235            1240            1245

Val Lys Ile Asn Ile Thr Ser Thr Pro Lys Tyr Thr Lys Ala Glu
        1250            1255            1260

Ile Tyr Gly Phe Asp Ser Asn Ser Pro Glu Tyr Lys Lys Met Gly
        1265            1270            1275

Asn Ile Asp Asn Ile Glu Ser Asn Val Phe Thr Leu Glu Val Pro
        1280            1285            1290

Lys Phe Asn Gly Val Ser His Ser Ile Thr Leu Asp Phe Asn Val
        1295            1300            1305

Ser Ile Lys Ile Ile Gln Asn Glu Val Ile Lys Phe Ile Arg Asn
        1310            1315            1320

Leu Val Phe Met Arg Ala Leu Val
        1325            1330

<210> SEQ ID NO 126
<211> LENGTH: 946
```

```
<212> TYPE: PRT
<213> ORGANISM: Artificial Sequence
<220> FEATURE:
<223> OTHER INFORMATION: Clostridium stercorarium Avicellase I

<400> SEQUENCE: 126

Met Arg Lys Phe Trp Ser Phe Ala Ile Ile Ser Leu Leu Val Thr
1               5                   10                  15

Gly Leu Phe Ile His Thr Pro Lys Ala Glu Ala Gly Tyr Asn Tyr
                20                  25                  30

Gly Glu Ala Leu Gln Lys Ala Ile Met Phe Tyr Glu Phe Gln Arg Ser
                35                  40                  45

Gly Lys Leu Pro Glu Asn Lys Arg Asp Asn Trp Arg Gly Asp Ser Gly
    50                  55                  60

Leu Asn Asp Gly Ala Asp Val Gly Leu Asp Leu Thr Gly Gly Trp Tyr
65                  70                  75                  80

Asp Ala Gly Asp His Val Lys Phe Asn Leu Pro Met Ala Tyr Ser Gln
                85                  90                  95

Thr Met Leu Ala Trp Ala Ala Tyr Glu Ala Glu Ala Leu Glu Arg
                100                 105                 110

Ser Gly Gln Met Gly Tyr Leu Leu Asp Ala Ile Lys Trp Val Ser Asp
                115                 120                 125

Tyr Leu Ile Lys Cys His Pro Ser Pro Asn Val Phe Tyr Tyr Gln Val
    130                 135                 140

Gly Asp Gly His Leu Asp His Ser Trp Trp Gly Pro Ala Glu Val Met
145                 150                 155                 160

Gln Met Asp Arg Pro Ala Tyr Lys Val Asp Leu Ala Asn Pro Gly Ser
                165                 170                 175

Thr Val Val Ala Glu Ala Ala Ala Leu Ala Ser Ala Ala Val Val
                180                 185                 190

Phe Ala Asp Arg Asp Pro Ala Tyr Ala Thr Cys Ile Gln His Ala
                195                 200                 205

Lys Glu Leu Tyr Asn Phe Ala Glu Ile Thr Lys Ser Asp Ser Gly Tyr
                210                 215                 220

Thr Ala Ala Ser Gly Phe Tyr Asp Ser His Ser Gly Phe Tyr Asp Glu
225                 230                 235                 240

Leu Ser Trp Ala Gly Val Trp Leu Tyr Leu Ala Thr Gly Asp Glu Thr
                245                 250                 255

Tyr Leu Asn Lys Ala Glu Gln Tyr Val Ala Tyr Trp Gly Thr Glu Pro
                260                 265                 270

Gln Thr Asn Ile Ile Ser Tyr Lys Trp Ala His Cys Trp Asp Asp Val
                275                 280                 285

His Tyr Gly Ala Cys Leu Leu Leu Ala Lys Ile Thr Gly Lys Gln Ile
                290                 295                 300

Tyr Lys Glu Ala Ile Glu Arg His Leu Asp Tyr Trp Ser Val Gly Tyr
305                 310                 315                 320

Asn Gly Glu Arg Val His Tyr Thr Pro Lys Gly Leu Ala Trp Leu Asp
                325                 330                 335

Ser Trp Gly Ser Leu Arg Tyr Ala Thr Thr Thr Ala Phe Leu Ala Ser
                340                 345                 350

Val Tyr Ala Asp Trp Glu Gly Cys Ser Arg Glu Lys Ala Ala Ile Tyr
                355                 360                 365

Asn Asp Phe Ala Lys Gln Gln Ile Asp Tyr Ala Leu Gly Ser Ser Gly
                370                 375                 380
```

```
Arg Ser Tyr Val Val Gly Phe Gly Val Asn Pro Lys Arg Pro His
385                 390                 395                 400

His Arg Thr Ala His Ser Ser Trp Ala Asp Ser Met Ser Val Pro Asp
            405                 410                 415

Tyr His Arg His Val Leu Ile Gly Ala Leu Val Gly Gly Pro Gly Lys
            420                 425                 430

Asp Asp Ser Tyr Thr Asp Asp Ile Asn Asn Tyr Ile Asn Asn Glu Val
            435                 440                 445

Ala Cys Asp Tyr Asn Ala Gly Phe Val Gly Ala Leu Ala Lys Met Tyr
450                 455                 460

Glu Asp Tyr Gly Gly Ser Pro Ile Pro Asp Leu Asn Ala Phe Glu Glu
465                 470                 475                 480

Ile Thr Asn Asp Glu Phe Phe Val Met Ala Gly Ile Asn Ala Ser Gly
            485                 490                 495

Gln Asn Phe Ile Glu Ile Lys Ala Leu Leu His Asn Gln Ser Gly Trp
            500                 505                 510

Pro Ala Arg Val Ala Asp Lys Leu Ser Phe Arg Tyr Phe Val Asp Leu
            515                 520                 525

Thr Glu Leu Ile Glu Ala Gly Tyr Ser Ala Ser Asp Val Thr Ile Thr
530                 535                 540

Thr Asn Tyr Asn Ala Gly Ala Lys Val Thr Gly Leu His Pro Trp Asn
545                 550                 555                 560

Glu Ala Glu Asn Ile Tyr Tyr Val Asn Val Asp Phe Thr Gly Thr Lys
                565                 570                 575

Ile Tyr Pro Gly Gly Gln Ser Ala Tyr Arg Lys Glu Val Gln Phe Arg
            580                 585                 590

Ile Ala Ala Pro Gln Asn Thr Asn Phe Trp Asn Asn Asp Asn Asp Tyr
            595                 600                 605

Ser Phe Arg Asp Ile Lys Gly Val Thr Ser Gly Asn Thr Val Lys Thr
            610                 615                 620

Val Tyr Ile Pro Val Tyr Asp Asp Gly Val Leu Val Phe Gly Val Glu
625                 630                 635                 640

Asn Gly Ile Lys Tyr Gly Asn Thr Tyr Leu Arg Glu Gly Thr Asp Tyr
                645                 650                 655

Thr Val Ser Gly Asp Thr Val Thr Ile Leu Lys Ser Phe Leu Asn Ser
            660                 665                 670

Phe Asp Thr Ser Thr Val Gln Leu Ile Phe Asp Phe Ser Ala Gly Arg
            675                 680                 685

Asp Pro Val Leu Thr Val Asn Ile Ile Asp Thr Thr Thr Ser Ala Ser
690                 695                 700

Ile Val Pro Thr Thr Ala Asp Phe Asp Lys Asn Pro Asp Ala Ser Arg
705                 710                 715                 720

Asp Val Lys Val Lys Leu Val Pro Asn Gly Asn Thr Leu Leu Ala Val
                725                 730                 735

Lys Lys Asp Gly Glu Ala Leu Val Leu Gly Arg Asp Tyr Ser Ile Asp
            740                 745                 750

Gly Asp Glu Val Thr Ile Phe Arg Glu Tyr Leu Ala Asp Gln Pro Val
            755                 760                 765

Gly Arg Val Thr Leu Thr Phe Asp Phe Asp Arg Gly Thr Asp Pro Val
            770                 775                 780

Leu Thr Ile Asn Ile Thr Asp Ser Arg Gln Val Glu Thr Gly Val Ile
785                 790                 795                 800

Gln Ile Gln Met Phe Asn Gly Asn Thr Ser Asp Lys Thr Asn Gly Ile
```

```
              805                 810                 815
Met Pro Arg Tyr Arg Leu Thr Asn Thr Gly Thr Thr Pro Ile Arg Leu
             820                 825                 830

Ser Asp Val Lys Ile Arg Tyr Tyr Tyr Thr Ile Asp Gly Glu Lys Asp
             835                 840                 845

Gln Asn Phe Trp Cys Asp Trp Ser Ser Val Gly Ser Asn Asn Ile Thr
             850                 855                 860

Gly Thr Phe Val Lys Met Ala Glu Pro Lys Glu Gly Ala Asp Tyr Tyr
865                 870                 875                 880

Leu Glu Thr Gly Phe Thr Asp Gly Ala Gly Tyr Leu Gln Pro Asn Gln
                 885                 890                 895

Ser Ile Glu Val Gln Asn Arg Phe Ser Lys Ala Asp Trp Thr Asp Tyr
             900                 905                 910

Ile Gln Thr Asn Asp Tyr Ser Phe Ser Thr Asn Thr Ser Tyr Gly Ser
             915                 920                 925

Asn Asp Arg Ile Thr Val Tyr Ile Ser Gly Val Leu Val Ser Gly Ile
             930                 935                 940

Glu Pro
945

<210> SEQ ID NO 127
<211> LENGTH: 914
<212> TYPE: PRT
<213> ORGANISM: Artificial Sequence
<220> FEATURE:
<223> OTHER INFORMATION: Clostridium stercorarium Avicellase II

<400> SEQUENCE: 127

Met Lys Arg Arg Leu Met Lys Gly Ile Ser Leu Leu Thr Leu Val Phe
1               5                  10                  15

Leu Ile Gly Ile Met Leu Gln Leu Ser Leu Lys Ser Glu Leu Thr Ala
             20                  25                  30

Tyr Ala Ser Ser Asp Asp Pro Tyr Lys Gln Arg Phe Leu Glu Leu Trp
         35                  40                  45

Glu Glu Leu His Asp Pro Ser Asn Gly Tyr Phe Ser Ser His Gly Ile
     50                  55                  60

Pro Tyr His Ala Val Glu Thr Leu Ile Val Glu Ala Pro Asp Tyr Gly
65                  70                  75                  80

His Leu Thr Thr Ser Glu Ala Met Ser Tyr Tyr Leu Trp Leu Glu Ala
                 85                  90                  95

Leu Tyr Gly Lys Phe Thr Gly Asp Phe Ser Tyr Phe Met Lys Ala Trp
             100                 105                 110

Glu Thr Ile Glu Lys Tyr Met Ile Pro Thr Glu Gln Asp Gln Pro Asn
         115                 120                 125

Arg Ser Met Ala Gly Tyr Asn Pro Ala Lys Pro Ala Thr Tyr Ala Pro
     130                 135                 140

Glu Trp Glu Glu Pro Ser Met Tyr Pro Ser Gln Leu Asp Phe Ser Ala
145                 150                 155                 160

Pro Val Gly Ile Asp Pro Ile Tyr Asn Glu Leu Val Ser Thr Tyr Gly
                 165                 170                 175

Thr Asn Thr Ile Tyr Gly Met His Trp Leu Leu Asp Val Asp Asn Trp
             180                 185                 190

Tyr Gly Phe Gly Arg Arg Ala Asp Arg Ile Ser Ser Pro Ala Tyr Ile
         195                 200                 205

Asn Thr Phe Gln Arg Gly Ser Gln Glu Ser Val Trp Glu Thr Ile Pro
```

```
              210                 215                 220
Gln Pro Cys Trp Asp Asp Leu Thr Ile Gly Gly Arg Asn Gly Phe Leu
225                 230                 235                 240

Asp Leu Phe Val Gly Asp Ser Gln Tyr Ser Ala Gln Phe Lys Tyr Thr
                245                 250                 255

Asn Ala Pro Asp Ala Asp Ala Arg Ala Ile Gln Ala Thr Tyr Trp Ala
                260                 265                 270

Asn Gln Trp Ala Lys Glu His Gly Val Asn Leu Ser Gln Tyr Val Lys
            275                 280                 285

Lys Ala Ser Arg Met Gly Asp Tyr Leu Arg Tyr Ala Met Phe Asp Lys
290                 295                 300

Tyr Phe Arg Lys Ile Gly Asp Ser Lys Gln Ala Gly Thr Gly Tyr Asp
305                 310                 315                 320

Ala Ala His Tyr Leu Leu Ser Trp Tyr Ala Trp Gly Gly Ile
                325                 330                 335

Thr Ala Asp Trp Ala Trp Ile Ile Gly Cys Ser His Val His Ala Gly
                340                 345                 350

Tyr Gln Asn Pro Met Thr Ala Trp Ile Leu Ala Asn Asp Pro Glu Phe
            355                 360                 365

Lys Pro Glu Ser Pro Asn Gly Ala Asn Asp Trp Ala Lys Ser Leu Glu
        370                 375                 380

Arg Gln Leu Glu Phe Tyr Gln Trp Leu Gln Ser Ala Glu Gly Ala Ile
385                 390                 395                 400

Ala Gly Gly Ala Thr Asn Ser Tyr Lys Gly Arg Tyr Glu Thr Leu Pro
                405                 410                 415

Ala Gly Ile Ser Thr Phe Tyr Gly Met Ala Tyr Glu Glu His Pro Val
                420                 425                 430

Tyr Leu Asp Pro Gly Ser Asn Thr Trp Phe Gly Phe Gln Ala Trp Thr
            435                 440                 445

Met Gln Arg Val Ala Glu Tyr Tyr Tyr Leu Thr Gly Asp Thr Arg Ala
        450                 455                 460

Glu Gln Leu Leu Asp Lys Trp Val Asp Trp Ile Lys Ser Val Val Arg
465                 470                 475                 480

Leu Asn Ser Asp Gly Thr Phe Glu Ile Pro Gly Asn Leu Glu Trp Ser
                485                 490                 495

Gly Gln Pro Asp Thr Trp Thr Gly Thr Tyr Thr Gly Asn Pro Asn Leu
                500                 505                 510

His Val Ser Val Val Ser Tyr Arg Thr Asp Leu Gly Ala Ala Gly Ser
            515                 520                 525

Leu Ala Asn Ala Leu Leu Tyr Tyr Ala Lys Thr Ser Gly Asp Asp Glu
        530                 535                 540

Ala Arg Asn Leu Ala Lys Glu Leu Leu Asp Arg Met Trp Asn Leu Tyr
545                 550                 555                 560

Arg Asp Asp Lys Gly Leu Ser Ala Pro Glu Thr Arg Glu Asp Tyr Val
                565                 570                 575

Arg Phe Phe Glu Gln Glu Val Tyr Val Pro Gln Gly Trp Ser Gly Thr
                580                 585                 590

Met Pro Asn Gly Asp Arg Ile Glu Pro Gly Val Thr Phe Leu Asp Ile
            595                 600                 605

Arg Ser Lys Tyr Leu Asn Asp Pro Asp Tyr Pro Lys Leu Gln Gln Ala
        610                 615                 620

Tyr Asn Glu Gly Lys Ala Pro Val Phe Asn Tyr His Arg Phe Trp Ala
625                 630                 635                 640
```

-continued

```
Gln Cys Asp Ile Ala Ile Ala Asn Gly Leu Tyr Ser Ile Leu Phe Gly
                645                 650                 655

Ser Glu Gln Ala Asn Asp Ser Phe Ile Thr Pro Thr Ser Ala Thr Phe
            660                 665                 670

Asp Lys Asn Asn Gln Glu Asp Ile Ser Val Thr Val Thr Tyr Asn Gly
        675                 680                 685

Asn Thr Leu Leu Gly Ile Lys Ser Gly Ser Ser Tyr Leu Ile Glu Gly
    690                 695                 700

Val Asp Tyr Ile Val Asn Gly Asp Val Ile Ile Lys Lys Glu Phe
705                 710                 715                 720

Leu Ala Gly Gln Ala Thr Gly Ser Ile Ser Leu Leu Phe Asp Phe Ser
                725                 730                 735

Ala Gly Leu Asp Arg Thr Leu Thr Ile Asp Ile Ile Asp Thr Gly Gly
            740                 745                 750

Gly Glu Glu Pro Val Glu Pro Val Glu Pro Val Glu Gly Val Leu Ile
        755                 760                 765

Ile Gln Ser Phe Asn Ala Asn Thr Gln Glu Ile Ser Asn Ser Ile Met
    770                 775                 780

Pro Arg Phe Arg Ile Tyr Asn Ser Gly Asn Thr Ser Ile Pro Leu Ser
785                 790                 795                 800

Glu Val Lys Leu Arg Tyr Tyr Tyr Thr Val Asp Gly Asp Lys Pro Gln
                805                 810                 815

Asn Phe Trp Cys Asp Trp Ala Ser Ile Gly Ser Ser Asn Val Thr Gly
            820                 825                 830

Thr Phe Val Lys Met Asp Gly Ala Thr Thr Gly Ala Asp Tyr Tyr Leu
        835                 840                 845

Glu Ile Gly Phe Thr Pro Gln Ala Gly Thr Leu Glu Pro Gly Ala Ser
    850                 855                 860

Ile Glu Val Gln Gly Arg Phe Ser Lys Ile Asp Trp Thr Asp Tyr Thr
865                 870                 875                 880

Gln Thr Asn Asp Tyr Ser Phe Asn Pro Thr Ala Ser Ser Tyr Val Asp
                885                 890                 895

Phe Asn Lys Ile Thr Ala Tyr Ile Ser Gly Asn Leu Val Tyr Gly Ile
            900                 905                 910

Glu Pro

<210> SEQ ID NO 128
<211> LENGTH: 1148
<212> TYPE: PRT
<213> ORGANISM: Artificial Sequence
<220> FEATURE:
<223> OTHER INFORMATION: Eubacterium cellulo-solvens Cel5A

<400> SEQUENCE: 128

Met Lys Gly Asn Trp Leu Lys Asp Val Leu Arg Arg Phe Ala Val Ile
1               5                   10                  15

Ala Met Met Leu Val Met Val Phe Thr Leu Leu Pro Ala Thr Ala Gln
                20                  25                  30

Gly Thr Glu Ala Ala Ser Gly Asp Ile Val Leu Phe Ser Gly Ser Lys
            35                  40                  45

His Val Glu Phe Thr Asp Trp Gly Gly Thr Trp Pro Ser Ala Tyr
        50                  55                  60

Glu Leu Gln Pro Pro Tyr Gln Thr Met Pro Phe Asp Leu Asn Lys Asn
65                  70                  75                  80
```

```
Phe Glu Ile Lys Val Asp Tyr Ser Gly Ala Asp Ile Val Leu Ile Phe
                85                  90                  95

Ala Arg Trp Glu His Gly Ser Lys Pro Gln Ile Trp Ala Gln Ile Ser
            100                 105                 110

Pro Tyr Tyr Val Val Asp Gly Thr Ala Val Phe Thr Lys Glu Gln Ile
        115                 120                 125

Ala Lys Ala Tyr Gly Ser Asp Phe Ser Asp Leu Asp Tyr Ile Gly
130                 135                 140

Val Lys Pro Leu Pro Ser Ala Asp Gly Met Thr Val Thr Lys Ile Val
145                 150                 155                 160

Ala Ser Tyr Thr Ser Gly Ser Ser Asp Asp Val Asp Ile Asn Leu Lys
                165                 170                 175

Gly Ile Ala Gly Glu Trp Ala Asn Gly Val Asn Ile Gly Trp Asn Leu
            180                 185                 190

Gly Asn Thr Leu Asp Ala Tyr Asp Thr Asn Arg Phe Lys Ser Ser Lys
        195                 200                 205

Gly His Asn Asn Pro Ala Asp Ile Glu Thr Cys Trp Gly Asn Pro Val
210                 215                 220

Thr Thr Lys Ala Met Ile Asp Ile Lys Ala Gln Gly Phe Asn Ala
225                 230                 235                 240

Val Arg Val Pro Val Thr Trp Asp Phe Glu Ile Asp Asp Asn Asp Gly
                245                 250                 255

Tyr Lys Val Asn Glu Ala Trp Met Ala Arg Val Lys Glu Val Val Asp
            260                 265                 270

Tyr Val Met Asp Asn Asp Leu Tyr Cys Ile Leu Asn Val His His Asp
        275                 280                 285

Thr Gly Glu Gln Gly Trp Leu Lys Ala Ser Thr Ala Asn Tyr Asn Lys
290                 295                 300

Asn Val Lys Lys Phe Lys Ala Leu Trp Lys Gln Ile Ala Ala Glu Phe
305                 310                 315                 320

Lys Asn Tyr Asp Asn Lys Leu Ala Phe Glu Gly Phe Asn Glu Met Leu
                325                 330                 335

Asp Glu Lys Asn Ser Trp Asn Tyr Pro Gly Thr Asp Ala Gly Asp Ala
            340                 345                 350

Ile Asn Leu Tyr Asn Gln Ala Phe Val Asp Val Arg Ala Ser Gly
        355                 360                 365

Gly Lys Asn Gly Lys Arg Pro Leu Ile Cys Asn Thr Tyr Ala Gly Cys
370                 375                 380

Thr Glu Ala Gly Ala Leu Asn Ser Phe Lys Ile Pro Asn Asp Thr Val
385                 390                 395                 400

Asp Asn Ala Ile Ile Ala Gln Val His Phe Tyr Gln Pro Thr Gly Tyr
                405                 410                 415

Cys Phe Asp Met Asn Pro Asn Gln Gly Gln Asn Met Asp Val Asp Tyr
            420                 425                 430

Lys Thr Cys Gly Gly Glu Ser Ala Ala Asp Thr Leu Ala Met Met Leu
        435                 440                 445

Tyr Lys Arg Phe Thr Glu Lys Gly Ile Pro Cys Ile Val Gly Glu Phe
450                 455                 460

Ala Ala Ser His Lys Lys Asn Asp Asp Asn Arg Ala Glu Trp Val Asp
465                 470                 475                 480

Tyr Val Val Arg Lys Thr Gly Thr Tyr Gly Val Lys Cys Phe Trp Trp
                485                 490                 495

Asp Asn Gly Gly Thr Phe Thr Pro Asn Tyr Ser Thr Gly Leu Asp Tyr
```

-continued

```
            500                 505                 510
Tyr Asn Ser Met Gly Ile Tyr Asn Arg Asn Thr Met Gln Phe Glu Tyr
            515                 520                 525

Pro Lys Val Ala Asp Ala Leu Val Asn Ala Ala Asn Gly Gly Ala Lys
            530                 535                 540

Pro Thr Thr Ala Pro Thr Lys Lys Pro Thr Ser Thr Pro Lys Pro Thr
545                 550                 555                 560

Ala Thr Leu Lys Pro Thr Thr Lys Pro Thr Thr Lys Pro Thr Thr Lys
                    565                 570                 575

Pro Asn Pro Thr Ser Gly Ala Asp Ser Gly Glu Ile Ile Leu Phe Ser
            580                 585                 590

Gly Ser Asn His Ala Asp Phe Lys Ala Trp Gly Gly Asp Trp Pro
            595                 600                 605

Ser Ala Phe Glu Ile Ser Pro Lys Tyr Glu Pro Met Lys Leu Asp Leu
            610                 615                 620

Asn Lys Asn Phe Glu Ile Lys Val Asp Tyr Asn Gly Ala Asp Ile Val
625                 630                 635                 640

Leu Ile Phe Ala Arg Trp Asp Lys Asp Ile Trp Ala Gln Ile Ser Pro
                    645                 650                 655

Tyr Tyr Val Val Asp Gly Thr Ala Val Phe Thr Lys Glu Gln Ile Ala
                    660                 665                 670

Lys Ala Tyr Gly Ser Asp Asp Phe Ser Gly Leu Asp Tyr Ile Ala Val
                    675                 680                 685

Lys Pro Leu Pro Ser Glu Glu Gly Val Thr Val Thr Lys Val Ser Gly
            690                 695                 700

Ile Tyr Thr Asn Gly Gly Ser Glu Asp Val Asp Ile Asn Leu Lys Gly
705                 710                 715                 720

Ile Ala Gly Glu Trp Ala Asn Gly Val Asn Ile Gly Trp Asn Leu Gly
                    725                 730                 735

Asn Thr Leu Asp Ala Tyr Asp Thr Asn Arg Phe Thr Arg Thr Lys Gly
                    740                 745                 750

His Asn Asn Pro Ala Asp Ile Glu Thr Cys Trp Gly Asn Pro Val Thr
            755                 760                 765

Thr Lys Ala Met Ile Asp Asp Ile Lys Ala Gln Gly Phe Asn Ala Val
770                 775                 780

Arg Val Pro Val Thr Trp Asp Tyr Glu Ile Asp Asp Asn Asp Gly Tyr
785                 790                 795                 800

Lys Val Asn Glu Ala Trp Met Ala Arg Val Lys Glu Val Val Asp Tyr
                    805                 810                 815

Val Met Asp Asn Asp Met Tyr Cys Ile Val Asn Val His His Asp Thr
                    820                 825                 830

Gly Glu Gln Gly Trp Leu Lys Ala Ser Thr Ala Asn Tyr Ala Lys Asn
            835                 840                 845

Glu Lys Lys Phe Lys Ala Leu Trp Lys Gln Ile Ala Ala Glu Phe Lys
            850                 855                 860

Asn Tyr Asp His Lys Leu Ala Phe Glu Gly Phe Asn Glu Met Leu Asp
865                 870                 875                 880

Glu Lys Asn Ser Trp Asn Tyr Pro Gly Ala Asp Ala Gly Glu Ala Ile
                    885                 890                 895

Asn Leu Tyr Asn Gln Ala Phe Val Asp Val Val Arg Ala Ser Gly Gly
                    900                 905                 910

Lys Asn Ser Asp Arg Pro Leu Ile Cys Asn Thr Tyr Ala Gly Cys Thr
            915                 920                 925
```

```
Glu Ala Gly Ala Leu Asn Ser Phe Glu Ile Pro Asn Asp Thr Val Glu
        930                 935                 940

Asn Ala Ile Ile Ala Gln Val His Phe Tyr Gln Pro Thr Gly Tyr Cys
945                 950                 955                 960

Phe Asp Met Asn Pro Asn Gln Gly Gln Asn Met Asp Val Asp Tyr Lys
            965                 970                 975

Thr Cys Gly Gly Glu Ser Ala Ala Asp Thr Leu Ala Met Met Leu Tyr
        980                 985                 990

Lys Arg Phe Thr Glu Lys Gly Ile Pro Cys Ile Val Gly Glu Phe Ala
        995                 1000                1005

Ala Ser His Lys Gln Asn Asp Asp Asn Arg Ala Ala Trp Val Asp
    1010                1015                1020

Tyr Val Val Ser Lys Thr Gly Lys Tyr Gly Val Lys Cys Phe Trp
    1025                1030                1035

Trp Asp Asn Gly Gly Thr Phe Thr Pro Asn Tyr Ser Thr Gly Leu
    1040                1045                1050

Asp Tyr Tyr Asn Ser Met Gly Ile Tyr Asn Arg Asn Thr Met Lys
    1055                1060                1065

Phe Glu Tyr Pro Lys Val Ala Asp Ala Leu Val Lys Ala Ala Asn
    1070                1075                1080

Gly Gly Thr Met Pro Thr Val Ala Pro Thr Lys Lys Pro Thr Ala
    1085                1090                1095

Thr Pro Thr Pro Thr Lys Lys Pro Thr Ser Thr Pro Lys Pro Thr
    1100                1105                1110

Val Lys Pro Thr Gln Thr Pro Lys Pro Thr Arg Lys Pro Gly Lys
    1115                1120                1125

Arg Val Lys Tyr Ser Ala Leu Asp Leu Asp Gly Asn Val Ser Ser
    1130                1135                1140

Gly Asn Leu Ile Pro
    1145

<210> SEQ ID NO 129
<211> LENGTH: 1101
<212> TYPE: PRT
<213> ORGANISM: Artificial Sequence
<220> FEATURE:
<223> OTHER INFORMATION: Celulomonas fimi CenC

<400> SEQUENCE: 129

Met Val Ser Arg Arg Ser Ser Gln Ala Arg Gly Ala Leu Thr Ala Val
1               5                   10                  15

Val Ala Thr Leu Ala Leu Ala Leu Ala Gly Ser Gly Thr Ala Leu Ala
                20                  25                  30

Ala Ser Pro Ile Gly Glu Gly Thr Phe Asp Asp Gly Pro Glu Gly Trp
            35                  40                  45

Val Ala Tyr Gly Thr Asp Gly Pro Leu Asp Thr Ser Thr Gly Ala Leu
        50                  55                  60

Cys Val Ala Val Pro Ala Gly Ser Ala Gln Tyr Gly Val Gly Val Val
65                  70                  75                  80

Leu Asn Gly Val Ala Ile Glu Glu Gly Thr Thr Tyr Thr Leu Arg Tyr
                85                  90                  95

Thr Ala Thr Ala Ser Thr Asp Val Thr Val Arg Ala Leu Val Gly Gln
            100                 105                 110

Asn Gly Ala Pro Tyr Gly Thr Val Leu Asp Thr Ser Pro Ala Leu Thr
        115                 120                 125
```

```
Ser Glu Pro Arg Gln Val Thr Glu Thr Phe Thr Ala Ser Ala Thr Tyr
    130                 135                 140

Pro Ala Thr Pro Ala Ala Asp Asp Pro Glu Gly Gln Ile Ala Phe Gln
145                 150                 155                 160

Leu Gly Gly Phe Ser Ala Asp Ala Trp Thr Phe Cys Leu Asp Asp Val
                165                 170                 175

Ala Leu Asp Ser Glu Val Glu Leu Leu Pro His Thr Ser Phe Ala Glu
                180                 185                 190

Ser Leu Gly Pro Trp Ser Leu Tyr Gly Thr Ser Glu Pro Val Phe Ala
        195                 200                 205

Asp Gly Arg Met Cys Val Asp Leu Pro Gly Gly Gln Gly Asn Pro Trp
210                 215                 220

Asp Ala Gly Leu Val Tyr Asn Gly Val Pro Val Gly Glu Gly Glu Ser
225                 230                 235                 240

Tyr Val Leu Ser Phe Thr Ala Ser Ala Thr Pro Asp Met Pro Val Arg
                245                 250                 255

Val Leu Val Gly Glu Gly Gly Gly Ala Tyr Arg Thr Ala Phe Glu Gln
                260                 265                 270

Gly Ser Ala Pro Leu Thr Gly Glu Pro Ala Thr Arg Glu Tyr Ala Phe
            275                 280                 285

Thr Ser Asn Leu Thr Phe Pro Pro Asp Gly Asp Ala Pro Gly Gln Val
    290                 295                 300

Ala Phe His Leu Gly Lys Ala Gly Ala Tyr Glu Phe Cys Ile Ser Gln
305                 310                 315                 320

Val Ser Leu Thr Thr Ser Ala Thr Pro Pro Gly Tyr Glu Pro Asp
                325                 330                 335

Thr Gly Pro Arg Val Arg Val Asn Gln Val Gly Tyr Leu Pro Phe Gly
            340                 345                 350

Pro Lys Arg Ala Thr Leu Val Thr Asp Ala Ala Glu Pro Val Ala Trp
    355                 360                 365

Glu Leu Arg Asp Ala Asp Gly Val Val Val Ala Asp Gly Thr Ser Glu
    370                 375                 380

Pro Arg Gly Val Glu Pro Ser Ala Ala Gln Ala Val His Val Leu Asp
385                 390                 395                 400

Phe Ser Asp Val Thr Thr Gln Gly Ala Gly Tyr Thr Leu Val Ala Asp
                405                 410                 415

Gly Glu Thr Ser Arg Pro Phe Asp Ile Asp Gly Asp Leu Tyr Gln Gln
            420                 425                 430

Leu Arg Tyr Asp Ala Leu Asn Tyr Phe Tyr Leu Ala Arg Ser Gly Thr
    435                 440                 445

Glu Ile Glu Ala Asp Val Val Gly Glu Glu Tyr Ala Arg Glu Ala Gly
    450                 455                 460

His Val Gly Val Ala Pro Asn Gln Gly Asp Thr Asp Val Pro Cys Ile
465                 470                 475                 480

Gly Pro Arg Asp Tyr Tyr Asp Gly Trp Thr Cys Asp Tyr Arg Leu Asp
                485                 490                 495

Val Ser Gly Gly Trp Tyr Asp Ala Gly Asp His Gly Lys Tyr Val Val
                500                 505                 510

Asn Gly Gly Ile Ala Val Gly Gln Leu Leu Gln Thr Tyr Glu Arg Ala
            515                 520                 525

Leu His Ala Gly Thr Ala Asp Ala Leu Ala Asp Gly Thr Leu Asp Val
    530                 535                 540
```

```
Pro Glu His Gly Asn Asp Val Pro Asp Val Leu Asp Glu Ala Arg Trp
545                 550                 555                 560

Glu Leu Glu Trp Met Leu Ser Met Ile Val Pro Glu Gly Glu Tyr Ala
            565                 570                 575

Gly Met Val His His Lys Val His Asp Glu Gly Trp Thr Gly Leu Pro
                580                 585                 590

Leu Leu Pro Ala Asp Asp Pro Gln Ala Arg Ser Leu His Arg Pro Ser
        595                 600                 605

Thr Ala Ala Thr Leu Asn Leu Ser Ala Val Ala Ala Gln Gly Ala Arg
    610                 615                 620

Leu Leu Glu Pro Tyr Asp Pro Gln Leu Ala Gln Thr Leu Leu Glu Ala
625                 630                 635                 640

Ala Arg Thr Thr Trp Ala Ala Ala Gln Glu His Pro Ala Leu Tyr Ala
                645                 650                 655

Pro Gly Glu Ala Gly Ala Asp Gly Gly Ala Tyr Asn Asp Ser Gln
                660                 665                 670

Val Ala Asp Glu Phe Tyr Trp Ala Ala Ala Glu Leu Tyr Leu Thr Thr
                675                 680                 685

Gly Glu Asp Ala Phe Ala Thr Ala Val Thr Thr Ser Pro Leu His Thr
    690                 695                 700

Ala Asp Val Phe Thr Ala Asp Gly Phe Gly Trp Gly Ser Val Ala Ala
705                 710                 715                 720

Leu Gly Arg Leu Asp Leu Ala Thr Val Pro Asn Glu Leu Pro Gly Leu
                725                 730                 735

Asp Ala Val Gln Ser Ser Val Val Glu Gly Ala Gln Glu Tyr Leu Ala
                740                 745                 750

Ala Gln Ala Gly Gln Gly Phe Gly Ser Leu Tyr Ser Pro Pro Gly Gly
        755                 760                 765

Glu Tyr Val Trp Gly Ser Ser Gln Val Ala Asn Asn Leu Val Val
770                 775                 780

Val Ala Thr Ala Tyr Asp Leu Thr Gly Asp Glu Arg Phe Arg Ala Ala
785                 790                 795                 800

Thr Leu Glu Gly Leu Asp Tyr Leu Phe Gly Arg Asn Ala Leu Asn Gln
                805                 810                 815

Ser Tyr Val Thr Gly Trp Gly Glu Val Ala Ser His Gln Gln His Ser
            820                 825                 830

Arg Trp Phe Ala His Gln Leu Asp Pro Ser Leu Pro Ser Pro Pro Pro
        835                 840                 845

Gly Ser Leu Ala Gly Pro Asn Ser Gln Ala Ala Thr Trp Asp Pro
    850                 855                 860

Thr Thr Lys Ala Ala Phe Pro Asp Gly Cys Ala Pro Ser Ala Cys Tyr
865                 870                 875                 880

Val Asp Glu Ile Gln Ala Trp Ser Thr Asn Glu Leu Thr Val Asn Trp
                885                 890                 895

Asn Ser Ala Leu Ser Trp Val Ala Ser Trp Val Ala Gln Gly Ser
                900                 905                 910

Ala Glu Pro Val Pro Thr Ala Pro Val Val Thr Arg Gln Pro Val Asp
        915                 920                 925

Ala Thr Val Ala Leu Gly Ala Asp Ala Thr Phe Thr Ala Glu Ala Ser
    930                 935                 940

Gly Val Pro Ala Pro Thr Val Arg Trp Gln Val Arg Ala Gly Arg Gly
945                 950                 955                 960

Trp Lys Asp Val Ala Gly Ala Thr Gly Thr Thr Leu Thr Val Arg Ala
```

```
                  965                 970                 975
Thr Ala Arg Thr Asp Gly Thr Arg Tyr Arg Ala Val Phe Thr Asn Ala
            980                 985                 990

Ala Gly Ser Val Glu Ser Ala Val Val Arg Leu Thr Val Glu Arg Ala
            995                1000                1005

Ala Pro Val Val Thr Gln His Pro Ala Asp Val Arg Ala Arg Val
           1010                1015                1020

Gly Thr Arg Ala Val Phe Arg Ala Ala Asp Gly Tyr Pro Thr
           1025                1030                1035

Pro Cys Val Val Trp Gln Val Arg Trp Gly Gly Gly Ser Trp Arg
           1040                1045                1050

Pro Ile Pro Trp Ala Thr Ser Thr Thr Leu Ser Val Pro Val Thr
           1055                1060                1065

Val Leu Ala Ala Gly Thr Glu Tyr Arg Ala Val Phe Thr Asn Ala
           1070                1075                1080

Val Gly Thr Ala Ala Thr Glu Pro Ala Glu Leu Ala Val Gln Arg
           1085                1090                1095

Pro Arg Ser
           1100

<210> SEQ ID NO 130
<211> LENGTH: 484
<212> TYPE: PRT
<213> ORGANISM: Artificial Sequence
<220> FEATURE:
<223> OTHER INFORMATION: Celulomonas fimi Exo-glucanase

<400> SEQUENCE: 130

Met Pro Arg Thr Thr Pro Ala Pro Gly His Pro Ala Arg Gly Ala Arg
1               5                  10                  15

Thr Ala Leu Arg Thr Thr Arg Arg Ala Ala Thr Leu Val Val Gly
            20                  25                  30

Ala Thr Val Val Leu Pro Ala Gln Ala Ala Thr Thr Leu Lys Glu Ala
            35                  40                  45

Ala Asp Gly Ala Gly Arg Asp Phe Gly Phe Ala Leu Asp Pro Asn Arg
        50                  55                  60

Leu Ser Glu Ala Gln Tyr Lys Ala Ile Ala Ser Glu Phe Asn Leu
65                  70                  75              80

Val Val Ala Glu Asn Ala Met Lys Trp Asp Ala Thr Glu Pro Ser Gln
                85                  90                  95

Asn Ser Phe Ser Phe Gly Ala Gly Asp Arg Val Ala Ser Tyr Ala Ala
               100                 105                 110

Asp Thr Gly Lys Glu Leu Tyr Gly His Thr Leu Val Trp His Ser Gln
           115                 120                 125

Leu Pro Asp Trp Ala Lys Asn Leu Asn Gly Ser Ala Phe Glu Ser Ala
        130                 135                 140

Met Val Asn His Val Thr Lys Val Ala Asp His Phe Glu Gly Lys Val
145                 150                 155                 160

Ala Ser Trp Asp Val Val Asn Glu Ala Phe Ala Asp Gly Asp Gly Pro
                165                 170                 175

Pro Gln Asp Ser Ala Phe Gln Gln Lys Leu Gly Asn Gly Tyr Ile Glu
            180                 185                 190

Thr Ala Phe Arg Ala Ala Arg Ala Ala Asp Pro Thr Ala Lys Leu Cys
            195                 200                 205

Ile Asn Asp Tyr Asn Val Glu Gly Ile Asn Ala Lys Ser Asn Ser Leu
```

```
    210                 215                 220
Tyr Asp Leu Val Lys Asp Phe Lys Ala Arg Gly Val Pro Leu Asp Cys
225                 230                 235                 240

Val Gly Phe Gln Ser His Leu Ile Val Gly Gln Val Pro Gly Asp Phe
                245                 250                 255

Arg Gln Asn Leu Gln Arg Phe Ala Asp Leu Gly Val Asp Val Arg Ile
            260                 265                 270

Thr Glu Leu Asp Ile Arg Met Arg Thr Pro Ser Asp Ala Thr Lys Leu
        275                 280                 285

Ala Thr Gln Ala Ala Asp Tyr Lys Lys Val Val Gln Ala Cys Met Gln
    290                 295                 300

Val Thr Arg Cys Gln Gly Val Thr Val Trp Gly Ile Thr Asp Lys Tyr
305                 310                 315                 320

Ser Trp Val Pro Asp Val Phe Pro Gly Glu Gly Ala Ala Leu Val Trp
                325                 330                 335

Asp Ala Ser Tyr Ala Lys Lys Pro Ala Tyr Ala Ala Val Met Glu Ala
            340                 345                 350

Phe Gly Ala Ser Pro Thr Pro Thr Pro Thr Thr Pro Thr Pro Thr Pro
        355                 360                 365

Thr Thr Pro Thr Pro Thr Pro Thr Ser Gly Pro Ala Gly Cys Gln Val
    370                 375                 380

Leu Trp Gly Val Asn Gln Trp Asn Thr Gly Phe Thr Ala Asn Val Thr
385                 390                 395                 400

Val Lys Asn Thr Ser Ser Ala Pro Val Asp Gly Trp Thr Leu Thr Phe
                405                 410                 415

Ser Phe Pro Ser Gly Gln Gln Val Thr Gln Ala Trp Ser Ser Thr Val
            420                 425                 430

Thr Gln Ser Gly Ser Ala Val Thr Val Arg Asn Ala Pro Trp Asn Gly
        435                 440                 445

Ser Ile Pro Ala Gly Gly Thr Ala Gln Phe Gly Phe Asn Gly Ser His
    450                 455                 460

Thr Gly Thr Asn Ala Ala Pro Thr Ala Phe Ser Leu Asn Gly Thr Pro
465                 470                 475                 480

Cys Thr Val Gly

<210> SEQ ID NO 131
<211> LENGTH: 562
<212> TYPE: PRT
<213> ORGANISM: Artificial Sequence
<220> FEATURE:
<223> OTHER INFORMATION: Acido-thermus cellulolyticus glycoside
      hydrolase, family 5

<400> SEQUENCE: 131

Met Pro Arg Ala Leu Arg Arg Val Pro Gly Ser Arg Val Met Leu Arg
1               5                   10                  15

Val Gly Val Val Val Ala Val Leu Ala Leu Val Ala Ala Leu Ala Asn
                20                  25                  30

Leu Ala Val Pro Arg Pro Ala Arg Ala Gly Gly Gly Tyr Trp His
        35                  40                  45

Thr Ser Gly Arg Glu Ile Leu Asp Ala Asn Asn Val Pro Val Arg Ile
    50                  55                  60

Ala Gly Ile Asn Trp Phe Gly Phe Glu Thr Cys Asn Tyr Val Val His
65                  70                  75                  80

Gly Leu Trp Ser Arg Asp Tyr Arg Ser Met Leu Asp Gln Ile Lys Ser
```

-continued

```
                    85                  90                  95
Leu Gly Tyr Asn Thr Ile Arg Leu Pro Tyr Ser Asp Asp Ile Leu Lys
                100                 105                 110
Pro Gly Thr Met Pro Asn Ser Ile Asn Phe Tyr Gln Met Asn Gln Asp
                115                 120                 125
Leu Gln Gly Leu Thr Ser Leu Gln Val Met Asp Lys Ile Val Ala Tyr
            130                 135                 140
Ala Gly Gln Ile Gly Leu Arg Ile Ile Leu Asp Arg His Arg Pro Asp
145                 150                 155                 160
Cys Ser Gly Gln Ser Ala Leu Trp Tyr Thr Ser Val Ser Glu Ala
                165                 170                 175
Thr Trp Ile Ser Asp Leu Gln Ala Leu Ala Gln Arg Tyr Lys Gly Asn
                180                 185                 190
Pro Thr Val Val Gly Phe Asp Leu His Asn Glu Pro His Asp Pro Ala
            195                 200                 205
Cys Trp Gly Cys Gly Asp Pro Ser Ile Asp Trp Arg Leu Ala Ala Glu
210                 215                 220
Arg Ala Gly Asn Ala Val Leu Ser Val Asn Pro Asn Leu Leu Ile Phe
225                 230                 235                 240
Val Glu Gly Val Gln Ser Tyr Asn Gly Asp Ser Tyr Trp Trp Gly Gly
                245                 250                 255
Asn Leu Gln Gly Ala Gly Gln Tyr Pro Val Val Leu Asn Val Pro Asn
            260                 265                 270
Arg Leu Val Tyr Ser Ala His Asp Tyr Ala Thr Ser Val Tyr Pro Gln
            275                 280                 285
Thr Trp Phe Ser Asp Pro Thr Phe Pro Asn Asn Met Pro Gly Ile Trp
            290                 295                 300
Asn Lys Asn Trp Gly Tyr Leu Phe Asn Gln Asn Ile Ala Pro Val Trp
305                 310                 315                 320
Leu Gly Glu Phe Gly Thr Thr Leu Gln Ser Thr Thr Asp Gln Thr Trp
                325                 330                 335
Leu Lys Thr Leu Val Gln Tyr Leu Arg Pro Thr Ala Gln Tyr Gly Ala
            340                 345                 350
Asp Ser Phe Gln Trp Thr Phe Trp Ser Trp Asn Pro Asp Ser Gly Asp
            355                 360                 365
Thr Gly Gly Ile Leu Lys Asp Asp Trp Gln Thr Val Asp Thr Val Lys
            370                 375                 380
Asp Gly Tyr Leu Ala Pro Ile Lys Ser Ser Ile Phe Asp Pro Val Gly
385                 390                 395                 400
Ala Ser Ala Ser Pro Ser Ser Gln Pro Ser Pro Ser Val Ser Pro Ser
                405                 410                 415
Pro Ser Pro Ser Pro Ser Ala Ser Arg Thr Pro Thr Pro Thr Pro Thr
            420                 425                 430
Pro Thr Ala Ser Pro Thr Pro Thr Leu Thr Pro Thr Ala Thr Pro Thr
            435                 440                 445
Pro Thr Ala Ser Pro Thr Pro Ser Pro Thr Ala Ala Ser Gly Ala Arg
            450                 455                 460
Cys Thr Ala Ser Tyr Gln Val Asn Ser Asp Trp Gly Asn Gly Phe Thr
465                 470                 475                 480
Val Thr Val Ala Val Thr Asn Ser Gly Ser Val Ala Thr Lys Thr Trp
                485                 490                 495
Thr Val Ser Trp Thr Phe Gly Gly Asn Gln Thr Ile Thr Asn Ser Trp
            500                 505                 510
```

```
Asn Ala Ala Val Thr Gln Asn Gly Gln Ser Val Thr Ala Arg Asn Met
            515                 520                 525

Ser Tyr Asn Asn Val Ile Gln Pro Gly Gln Asn Thr Thr Phe Gly Phe
        530                 535                 540

Gln Ala Ser Tyr Thr Gly Ser Asn Ala Ala Pro Thr Val Ala Cys Ala
545                 550                 555                 560

Ala Ser

<210> SEQ ID NO 132
<211> LENGTH: 1121
<212> TYPE: PRT
<213> ORGANISM: Artificial Sequence
<220> FEATURE:
<223> OTHER INFORMATION: Acido-thermus cellulolyticus glycoside
      hydrolase family protein

<400> SEQUENCE: 132

Met Pro Gly Leu Arg Arg Leu Arg Ala Gly Ile Val Ser Ala Ala
1               5                   10                  15

Ala Leu Gly Ser Leu Val Ser Gly Leu Val Ala Val Ala Pro Val Ala
                20                  25                  30

His Ala Ala Val Thr Leu Lys Ala Gln Tyr Lys Asn Asn Asp Ser Ala
            35                  40                  45

Pro Ser Asp Asn Gln Ile Lys Pro Gly Leu Gln Leu Val Asn Thr Gly
        50                  55                  60

Ser Ser Ser Val Asp Leu Ser Thr Val Thr Val Arg Tyr Trp Phe Thr
65                  70                  75                  80

Arg Asp Gly Gly Ser Ser Thr Leu Val Tyr Asn Cys Asp Trp Ala Ala
                85                  90                  95

Met Gly Cys Gly Asn Ile Arg Ala Ser Phe Gly Ser Val Asn Pro Ala
            100                 105                 110

Thr Pro Thr Ala Asp Thr Tyr Leu Gln Leu Ser Phe Thr Gly Gly Thr
        115                 120                 125

Leu Ala Ala Gly Gly Ser Thr Gly Glu Ile Gln Asn Arg Val Asn Lys
130                 135                 140

Ser Asp Trp Ser Asn Phe Asp Glu Thr Asn Asp Tyr Ser Tyr Gly Thr
145                 150                 155                 160

Asn Thr Thr Phe Gln Asp Trp Thr Lys Val Thr Val Tyr Val Asn Gly
                165                 170                 175

Val Leu Val Trp Gly Thr Glu Pro Ser Gly Ala Thr Ala Ser Pro Ser
            180                 185                 190

Ala Ser Ala Thr Pro Ser Pro Ser Ser Pro Thr Thr Ser Pro Ser
        195                 200                 205

Ser Ser Pro Ser Pro Ser Ser Pro Thr Pro Thr Pro Ser Ser Ser
210                 215                 220

Ser Pro Pro Ser Ser Asn Asp Pro Tyr Ile Gln Arg Phe Leu Thr
225                 230                 235                 240

Met Tyr Asn Lys Ile His Asp Pro Ala Asn Gly Tyr Phe Ser Pro Gln
                245                 250                 255

Gly Ile Pro Tyr His Ser Val Glu Thr Leu Ile Val Glu Ala Pro Asp
            260                 265                 270

Tyr Gly His Glu Thr Thr Ser Glu Ala Tyr Ser Phe Trp Leu Trp Leu
        275                 280                 285

Glu Ala Thr Tyr Gly Ala Val Thr Gly Asn Trp Thr Pro Phe Asn Asn
290                 295                 300
```

```
Ala Trp Thr Thr Met Glu Thr Tyr Met Ile Pro Gln His Ala Asp Gln
305                 310                 315                 320

Pro Asn Asn Ala Ser Tyr Asn Pro Asn Ser Pro Ala Ser Tyr Ala Pro
            325                 330                 335

Glu Glu Pro Leu Pro Ser Met Tyr Pro Val Ala Ile Asp Ser Ser Val
            340                 345                 350

Pro Val Gly His Asp Pro Leu Ala Ala Glu Leu Gln Ser Thr Tyr Gly
            355                 360                 365

Thr Pro Asp Ile Tyr Gly Met His Trp Leu Ala Asp Val Asp Asn Ile
370                 375                 380

Tyr Gly Tyr Gly Asp Ser Pro Gly Gly Cys Glu Leu Gly Pro Ser
385                 390                 395                 400

Ala Lys Gly Val Ser Tyr Ile Asn Thr Phe Gln Arg Gly Ser Gln Glu
            405                 410                 415

Ser Val Trp Glu Thr Val Thr Gln Pro Thr Cys Asp Asn Gly Lys Tyr
            420                 425                 430

Gly Gly Ala His Gly Tyr Val Asp Leu Phe Ile Gln Gly Ser Thr Pro
            435                 440                 445

Pro Gln Trp Lys Tyr Thr Asp Ala Pro Asp Ala Asp Ala Arg Ala Val
    450                 455                 460

Gln Ala Ala Tyr Trp Ala Tyr Thr Trp Ala Ser Ala Gln Gly Lys Ala
465                 470                 475                 480

Ser Ala Ile Ala Pro Thr Ile Ala Lys Ala Ala Lys Leu Gly Asp Tyr
            485                 490                 495

Leu Arg Tyr Ser Leu Phe Asp Lys Tyr Phe Lys Gln Val Gly Asn Cys
            500                 505                 510

Tyr Pro Ala Ser Ser Cys Pro Gly Ala Thr Gly Arg Gln Ser Glu Thr
            515                 520                 525

Tyr Leu Ile Gly Trp Tyr Tyr Ala Trp Gly Gly Ser Ser Gln Gly Trp
    530                 535                 540

Ala Trp Arg Ile Gly Asp Gly Ala Ala His Phe Gly Tyr Gln Asn Pro
545                 550                 555                 560

Leu Ala Ala Trp Ala Met Ser Asn Val Thr Pro Leu Ile Pro Leu Ser
            565                 570                 575

Pro Thr Ala Lys Ser Asp Trp Ala Ala Ser Leu Gln Arg Gln Leu Glu
            580                 585                 590

Phe Tyr Gln Trp Leu Gln Ser Ala Glu Gly Ala Ile Ala Gly Gly Ala
            595                 600                 605

Thr Asn Ser Trp Asn Gly Asn Tyr Gly Thr Pro Pro Ala Gly Asp Ser
            610                 615                 620

Thr Phe Tyr Gly Met Ala Tyr Asp Trp Glu Pro Val Tyr His Asp Pro
625                 630                 635                 640

Pro Ser Asn Asn Trp Phe Gly Phe Gln Ala Trp Ser Met Glu Arg Val
            645                 650                 655

Ala Glu Tyr Tyr Tyr Val Thr Gly Asp Pro Lys Ala Lys Ala Leu Leu
            660                 665                 670

Asp Lys Trp Val Ala Trp Val Lys Pro Asn Val Thr Thr Gly Ala Ser
            675                 680                 685

Trp Ser Ile Pro Ser Asn Leu Ser Trp Ser Gly Gln Pro Asp Thr Trp
            690                 695                 700

Asn Pro Ser Asn Pro Gly Thr Asn Ala Asn Leu His Val Thr Ile Thr
705                 710                 715                 720
```

```
Ser Ser Gly Gln Asp Val Gly Val Ala Ala Leu Ala Lys Thr Leu
            725                 730                 735

Glu Tyr Tyr Ala Ala Lys Ser Gly Asp Thr Ala Ser Arg Asp Leu Ala
            740                 745                 750

Lys Gly Leu Leu Asp Ser Ile Trp Asn Asn Asp Gln Asp Ser Leu Gly
            755                 760                 765

Val Ser Thr Pro Glu Thr Arg Thr Asp Tyr Ser Arg Phe Thr Gln Val
            770                 775                 780

Tyr Asp Pro Thr Thr Gly Asp Gly Leu Tyr Ile Pro Ser Gly Trp Thr
785                 790                 795                 800

Gly Thr Met Pro Asn Gly Asp Gln Ile Lys Pro Gly Ala Thr Phe Leu
            805                 810                 815

Ser Ile Arg Ser Trp Tyr Thr Lys Asp Pro Gln Trp Ser Lys Val Gln
            820                 825                 830

Ala Tyr Leu Asn Gly Gly Pro Ala Pro Thr Phe Asn Tyr His Arg Phe
            835                 840                 845

Trp Ala Glu Ser Asp Phe Ala Met Ala Asn Ala Asp Phe Gly Met Leu
            850                 855                 860

Phe Pro Ser Gly Ser Pro Ser Pro Thr Pro Ser Pro Thr Pro Thr Ser
865                 870                 875                 880

Ser Pro Ser Pro Thr Pro Ser Ser Pro Thr Pro Ser Pro Ser Pro
            885                 890                 895

Ser Pro Thr Gly Asp Thr Thr Pro Ser Val Pro Thr Gly Leu Gln
            900                 905                 910

Val Thr Gly Thr Thr Thr Ser Ser Val Ser Leu Ser Trp Thr Ala Ser
            915                 920                 925

Thr Asp Asn Val Gly Val Ala His Tyr Asn Val Tyr Arg Asn Gly Thr
930                 935                 940

Leu Val Gly Gln Pro Thr Ala Thr Ser Phe Thr Asp Thr Gly Leu Ala
945                 950                 955                 960

Ala Gly Thr Ser Tyr Thr Tyr Thr Val Ala Ala Val Asp Ala Ala Gly
            965                 970                 975

Asn Thr Ser Ala Gln Ser Ser Pro Val Thr Ala Thr Thr Ala Ser Pro
            980                 985                 990

Ser Pro Ser Pro Ser Pro Ser Pro Thr Pro Thr Ser Ser Pro Ser Pro
            995                 1000                1005

Thr Pro Ser Pro Thr Pro Ser Pro Thr Ser Thr Ser Gly Ala Ser
            1010                1015                1020

Cys Thr Ala Thr Tyr Val Val Asn Ser Asp Trp Gly Ser Gly Phe
            1025                1030                1035

Thr Thr Thr Val Thr Val Thr Asn Thr Gly Thr Arg Ala Thr Ser
            1040                1045                1050

Gly Trp Thr Val Thr Trp Ser Phe Ala Gly Asn Gln Thr Val Thr
            1055                1060                1065

Asn Tyr Trp Asn Thr Ala Leu Thr Gln Ser Gly Lys Ser Val Thr
            1070                1075                1080

Ala Lys Asn Leu Ser Tyr Asn Val Ile Gln Pro Gly Gln Ser
            1085                1090                1095

Thr Thr Phe Gly Phe Asn Gly Ser Tyr Ser Gly Thr Asn Thr Ala
            1100                1105                1110

Pro Thr Leu Ser Cys Thr Ala Ser
            1115                1120
```

<210> SEQ ID NO 133
<211> LENGTH: 469
<212> TYPE: PRT
<213> ORGANISM: Artificial Sequence
<220> FEATURE:
<223> OTHER INFORMATION: Acido-thermus cellulolyticus Biomass degrading enzyme

<400> SEQUENCE: 133

```
Met Gly Thr Tyr Pro Ile Arg Ser Val Ser Gly Gly Val Ala Leu Ala
1               5                   10                  15

Ala Cys Ala Val Leu Thr Met Thr Thr Ala Ala Ala Thr Pro Ile
            20                  25                  30

His Asp Ala Ser Ser Pro His Thr Ile Pro Pro His Ala Arg Leu Tyr
            35                  40                  45

Thr Pro Pro Pro Asp Lys Gly Ala Ile Lys Gln Ile Thr Asp Leu Leu
        50                  55                  60

Lys Ala Arg Asp Val Arg Asp Ala Arg Leu Ile Ala Glu Met Ile Ser
65                  70                  75                  80

Thr Pro Gln Ala Val Trp Phe Thr Gly Gly Thr Pro Asp Gln Val Arg
                85                  90                  95

Arg Asp Val His Arg Val Val Thr Lys Ala Ala Ala His His Ala Ile
            100                 105                 110

Pro Val Leu Val Ala Tyr Asn Ile Pro Phe Arg Asp Cys Ser Gln Tyr
        115                 120                 125

Ser Ala Gly Gly Ala Val Asp Thr Ala Ala Tyr Glu Ala Trp Ile Asp
    130                 135                 140

Gly Phe Ala Ala Gly Ile Gly Asp Lys Arg Ala Ile Val Leu Leu Glu
145                 150                 155                 160

Pro Asp Ser Leu Gly Ile Ile Pro Tyr Asn Thr Asp Ile Asn Gly Asn
                165                 170                 175

Ala Glu Trp Cys Lys Pro Asp Leu Ser Gly Thr Gly Leu Thr Pro Asp
            180                 185                 190

Glu Ala Asn Gln Ala Arg Tyr Asp Gln Leu Asn Tyr Ala Val Asp Ala
        195                 200                 205

Leu Glu Ala His Arg Asn Val Ser Val Tyr Leu Asp Gly Thr His Ser
    210                 215                 220

Gly Trp Leu Gly Val Gly Asp Ile Ala Gln Arg Leu Val Arg Ala Gly
225                 230                 235                 240

Val Gln Arg Ala Gln Gly Phe Phe Val Asn Val Ser Asn Tyr Gln Thr
                245                 250                 255

Thr Glu Arg Gln Ile Lys Tyr Gly Thr Trp Ile Ser Glu Cys Ile Ala
            260                 265                 270

Phe Ala Asn Asp Pro Glu Glu Gly Gly Trp Arg Leu Gly His Tyr Ser
        275                 280                 285

Trp Cys Ala Ser Gln Tyr Tyr Pro Ala Asn Pro Asn Asp Phe Ser Thr
    290                 295                 300

Trp Val Gln Thr Asp Gln Trp Tyr Ala Ser Asn Leu Gly Thr Ala Val
305                 310                 315                 320

Pro Thr Thr His Phe Val Ile Asp Thr Ser Arg Asn Gly Arg Gly Pro
                325                 330                 335

Asn Asp Met Thr Ala Tyr Ala Ala Pro Tyr Asn Gln Pro Ala Ser
            340                 345                 350

Val Ile Ser Ala Leu Gln Gly Gly Ser Trp Cys Asn Pro Pro Gly Arg
        355                 360                 365
```

```
Gly Leu Gly Leu Arg Pro Thr Val Asn Thr Gly Val Pro Leu Leu Asp
        370                 375                 380

Ala Tyr Leu Trp Val Lys Ile Pro Gly Glu Ser Asp Gly Gln Cys Asp
385                 390                 395                 400

Ala Ala Gly Gly Ala Arg Ala Trp Asp Tyr Ser Ala Tyr Thr Glu Pro
                405                 410                 415

Gly Trp Pro Thr Asp Pro Ser Gln Gln Ala Leu Phe Asp Pro Leu Trp
                420                 425                 430

Gly Leu Tyr Asp Pro Pro Ala Gly Gln Trp Phe Pro Gln Gln Ala Leu
                435                 440                 445

Gln Leu Ala Gln Leu Ala Val Pro Pro Leu Gln Pro Gln Trp Pro Val
450                 455                 460

Pro Pro Val His His
465

<210> SEQ ID NO 134
<211> LENGTH: 547
<212> TYPE: PRT
<213> ORGANISM: Artificial Sequence
<220> FEATURE:
<223> OTHER INFORMATION: Butyrivibrio fibrisolvens Cellulase 1

<400> SEQUENCE: 134

Met His Lys Ser Lys Cys Ile Lys Arg Val Phe Thr Phe Leu Leu Ala
1               5                   10                  15

Leu Phe Val Phe Val Met Ala Ile Pro Ala Thr Lys Val Ser Ala Ala
                20                  25                  30

Gly Gly Thr Asp Arg Ser Ala Thr Gln Val Val Ser Asp Met Arg Val
                35                  40                  45

Gly Trp Asn Ile Gly Asn Ser Leu Asp Ser Phe Gly Gln Ser Tyr Asn
            50                  55                  60

Phe Pro Tyr Thr Ser Leu Asn Glu Thr Tyr Trp Gly Asn Pro Ala Thr
65              70                  75                  80

Thr Lys Ala Leu Ile Asp Glu Val Ala Lys Ala Gly Phe Asn Thr Ile
                85                  90                  95

Arg Ile Pro Val Ser Trp Gly Gln Tyr Thr Thr Gly Ser Asp Tyr Gln
                100                 105                 110

Ile Pro Asp Phe Val Met Asn Arg Val Lys Glu Val Val Asp Tyr Cys
            115                 120                 125

Ile Val Asn Asp Met Tyr Val Ile Leu Asn Ser His His Asp Ile Asn
130                 135                 140

Ser Asp Tyr Cys Phe Tyr Val Pro Asn Asn Ala Asn Lys Asp Arg Ser
145                 150                 155                 160

Glu Lys Tyr Phe Lys Ser Ile Trp Thr Gln Ile Ala Lys Glu Phe Lys
                165                 170                 175

Asn Tyr Asp Tyr His Leu Val Phe Glu Thr Met Asn Glu Pro Arg Leu
            180                 185                 190

Val Gly His Gly Glu Glu Trp Trp Phe Pro Arg Asn Asn Pro Ser Asn
                195                 200                 205

Asp Ile Arg Glu Ala Val Ala Cys Ile Asn Asp Tyr Asn Gln Val Ala
            210                 215                 220

Leu Asp Ala Ile Arg Ala Thr Gly Gly Asn Asn Ala Thr Arg Cys Val
225                 230                 235                 240

Met Val Pro Gly Tyr Asp Ala Ser Ile Glu Gly Cys Met Thr Asp Gly
                245                 250                 255
```

```
Phe Lys Met Pro Asn Asp Thr Ala Ser Gly Arg Leu Ile Leu Ser Val
                260                 265                 270

His Ala Tyr Ile Pro Tyr Tyr Phe Ala Leu Ala Ser Asp Thr Tyr Val
            275                 280                 285

Thr Arg Phe Asp Asp Asn Leu Lys Tyr Asp Ile Asp Ser Phe Phe Asn
        290                 295                 300

Asp Leu Asn Ser Lys Phe Leu Ser Arg Asn Ile Pro Val Val Val Gly
305                 310                 315                 320

Glu Thr Ser Ala Thr Asn Arg Asn Asn Thr Ala Glu Arg Val Lys Trp
                325                 330                 335

Ala Asp Tyr Tyr Trp Gly Arg Ala Ala Arg Tyr Ser Asn Val Ala Met
            340                 345                 350

Val Leu Trp Asp Asn Asn Ile Tyr Gln Asn Asn Ser Ala Gly Ser Asp
        355                 360                 365

Gly Glu Cys His Met Tyr Ile Asp Arg Asn Ser Leu Gln Trp Lys Asp
370                 375                 380

Pro Glu Ile Ile Ser Thr Ile Met Lys His Val Asp Gly Thr Pro Ala
385                 390                 395                 400

Thr Ile Asn Gly Lys Glu Ile Pro Ser Thr Glu Gln Pro Asp Pro Thr
                405                 410                 415

Pro Val Asp Pro Asp Pro Thr Pro Val Asp Pro Asp Pro Thr Pro Val
            420                 425                 430

Asp Pro Asp Pro Thr Pro Val Asp Pro Pro Gln Pro Val Asp Pro
        435                 440                 445

Thr Pro Val Ser Gly Ala Leu Lys Ala Glu Tyr Thr Ile Asn Asn Trp
450                 455                 460

Gly Ser Gly Tyr Gln Val Leu Ile Lys Val Lys Asn Asp Ser Ala Ser
465                 470                 475                 480

Arg Val Asp Gly Trp Thr Leu Lys Ile Ser Lys Ser Glu Val Lys Ile
                485                 490                 495

Asp Ser Ser Trp Cys Val Asn Ile Ala Glu Glu Gly Tyr Tyr Val
            500                 505                 510

Ile Thr Pro Met Ser Trp Asn Ser Ser Leu Glu Pro Ser Ala Ser Val
        515                 520                 525

Asp Phe Gly Ile Gln Gly Ser Gly Ser Ile Gly Thr Ser Val Asn Ile
530                 535                 540

Ser Val Gln
545

<210> SEQ ID NO 135
<211> LENGTH: 1711
<212> TYPE: PRT
<213> ORGANISM: Artificial Sequence
<220> FEATURE:
<223> OTHER INFORMATION: Anaero-cellum thermo-philum 1,4-beta-glucanase

<400> SEQUENCE: 135

Gly Ser Phe Asn Tyr Gly Glu Ala Leu Gln Lys Ala Ile Met Phe Tyr
1               5                   10                  15

Glu Phe Gln Met Ser Gly Lys Leu Pro Asn Trp Val Arg Asn Asn Trp
                20                  25                  30

Arg Gly Asp Ser Ala Leu Lys Asp Gly Gln Asp Asn Gly Leu Asp Leu
            35                  40                  45

Thr Gly Gly Trp Phe Asp Ala Gly Asp His Val Lys Phe Asn Leu Pro
        50                  55                  60
```

```
Met Ser Tyr Thr Gly Thr Met Leu Ser Trp Ala Val Tyr Glu Tyr Lys
 65                  70                  75                  80

Asp Ala Phe Val Lys Ser Gly Gln Leu Glu His Ile Leu Asn Gln Ile
                 85                  90                  95

Glu Trp Val Asn Asp Tyr Phe Val Lys Cys His Pro Ser Lys Tyr Val
            100                 105                 110

Tyr Tyr Tyr Gln Val Gly Asp Gly Ser Lys Asp His Ala Trp Trp Gly
        115                 120                 125

Pro Ala Glu Val Met Gln Met Glu Arg Pro Ser Phe Lys Val Thr Gln
    130                 135                 140

Ser Ser Pro Gly Ser Thr Val Thr Glu Thr Ala Ala Ser Leu Ala
145                 150                 155                 160

Ala Ala Ser Ile Val Leu Lys Asp Arg Asn Pro Thr Lys Ala Ala Thr
                165                 170                 175

Tyr Leu Gln His Ala Lys Glu Leu Tyr Glu Phe Ala Glu Val Thr Lys
                180                 185                 190

Ser Asp Ala Gly Tyr Thr Ala Ala Asn Gly Tyr Tyr Asn Ser Trp Ser
            195                 200                 205

Gly Phe Tyr Asp Glu Leu Ser Trp Ala Ala Val Trp Leu Tyr Leu Ala
        210                 215                 220

Thr Asn Asp Ser Thr Tyr Leu Thr Lys Ala Glu Ser Tyr Val Gln Asn
225                 230                 235                 240

Trp Pro Lys Ile Ser Gly Ser Asn Thr Ile Asp Tyr Lys Trp Ala His
                245                 250                 255

Cys Trp Asp Asp Val His Asn Gly Ala Ala Leu Leu Leu Ala Lys Ile
            260                 265                 270

Thr Gly Lys Asp Ile Tyr Lys Gln Ile Glu Ser His Leu Asp Tyr
        275                 280                 285

Trp Ile Thr Gly Tyr Asn Gly Glu Arg Ile Lys Tyr Thr Pro Lys Gly
        290                 295                 300

Leu Ala Trp Leu Asp Gln Trp Gly Ser Leu Arg Tyr Ala Thr Thr Thr
305                 310                 315                 320

Ala Phe Leu Ala Phe Val Tyr Ser Asp Trp Val Gly Cys Pro Ser Thr
                325                 330                 335

Lys Lys Glu Ile Tyr Arg Lys Phe Gly Glu Ser Gln Ile Asp Tyr Ala
            340                 345                 350

Leu Gly Ser Ala Gly Arg Ser Phe Val Val Gly Phe Gly Thr Asn Pro
        355                 360                 365

Pro Lys Arg Pro His His Arg Thr Ala His Ser Ser Trp Ala Asp Ser
    370                 375                 380

Gln Ser Ile Pro Ser Tyr His Arg His Thr Leu Tyr Gly Ala Leu Val
385                 390                 395                 400

Gly Gly Pro Gly Ser Asp Asp Ser Tyr Thr Asp Ile Ser Asn Tyr
                405                 410                 415

Val Asn Asn Glu Val Ala Cys Asp Tyr Asn Ala Gly Phe Val Gly Ala
            420                 425                 430

Leu Ala Lys Met Tyr Gln Leu Tyr Gly Gly Asn Pro Ile Pro Asp Phe
        435                 440                 445

Lys Ala Ile Glu Thr Pro Thr Asn Asp Glu Phe Val Glu Ala Gly
    450                 455                 460

Ile Asn Ala Ser Gly Thr Asn Phe Ile Glu Ile Lys Ala Ile Val Asn
465                 470                 475                 480

Asn Gln Ser Gly Trp Pro Ala Lys Ala Thr Asp Lys Leu Lys Phe Arg
```

```
                485                 490                 495
Tyr Phe Val Asp Leu Ser Glu Leu Ile Lys Ala Gly Tyr Ser Pro Asn
                500                 505                 510

Gln Leu Thr Leu Ser Thr Asn Tyr Asn Gln Gly Ala Lys Val Ser Gly
                515                 520                 525

Pro Tyr Val Trp Asp Ala Ser Lys Asn Ile Tyr Tyr Ile Leu Val Asp
                530                 535                 540

Phe Thr Gly Thr Leu Ile Tyr Pro Gly Gly Gln Asp Lys Tyr Lys Lys
545                 550                 555                 560

Glu Val Gln Phe Arg Ile Ala Ala Pro Gln Asn Val Gln Trp Asp Asn
                565                 570                 575

Ser Asn Asp Tyr Ser Phe Gln Asp Ile Lys Gly Val Ser Ser Gly Ser
                580                 585                 590

Val Val Lys Thr Lys Tyr Ile Pro Leu Tyr Asp Gly Asp Val Lys Val
                595                 600                 605

Trp Gly Asp Gly Pro Gly Thr Ser Gly Ala Thr Pro Thr Pro Thr Ala
610                 615                 620

Thr Ala Thr Pro Thr Pro Thr Pro Thr Val Thr Pro Thr Pro Thr Pro
625                 630                 635                 640

Thr Pro Thr Ser Thr Ala Thr Pro Thr Pro Thr Pro Thr Pro Thr Val
                645                 650                 655

Thr Pro Thr Pro Thr Pro Thr Pro Thr Ala Thr Pro Thr Pro Ser Thr Pro
                660                 665                 670

Thr Pro Thr Ser Thr Pro Ser Ser Thr Pro Val Ala Gly Gly Gln Ile
                675                 680                 685

Lys Val Leu Tyr Ala Asn Lys Glu Thr Asn Ser Thr Thr Asn Thr Ile
                690                 695                 700

Arg Pro Trp Leu Lys Val Val Asn Thr Gly Ser Ser Ser Ile Asp Leu
705                 710                 715                 720

Ser Arg Val Thr Ile Arg Tyr Trp Tyr Thr Val Asp Gly Asp Lys Ala
                725                 730                 735

Gln Ser Ala Ile Ser Asp Trp Ala Gln Ile Gly Ala Ser Asn Val Thr
                740                 745                 750

Phe Lys Phe Val Lys Leu Ser Ser Ser Val Ser Gly Ala Asp Tyr Tyr
                755                 760                 765

Leu Glu Ile Gly Phe Lys Ser Gly Ala Gly Leu Gln Ala Gly Lys
                770                 775                 780

Asp Thr Gly Glu Ile Gln Ile Arg Phe Asn Lys Ser Asp Trp Ser Asn
785                 790                 795                 800

Tyr Asn Gln Gly Asn Asp Trp Ser Trp Met Gln Ser Met Thr Asn Tyr
                805                 810                 815

Gly Glu Asn Val Lys Val Thr Ala Tyr Ile Asp Gly Val Leu Val Trp
                820                 825                 830

Gly Gln Glu Pro Ser Gly Ala Thr Pro Thr Pro Thr Ala Thr Pro Ala
                835                 840                 845

Pro Thr Val Thr Pro Thr Pro Thr Pro Thr Ser Thr Pro Thr
                850                 855                 860

Ala Thr Pro Thr Ala Thr Pro Thr Pro Thr Pro Thr Pro Ser Ser Thr
865                 870                 875                 880

Pro Val Ala Gly Gly Gln Ile Lys Val Leu Tyr Ala Asn Lys Glu Thr
                885                 890                 895

Asn Ser Thr Thr Asn Thr Ile Arg Pro Trp Leu Lys Val Val Asn Thr
                900                 905                 910
```

-continued

```
Gly Ser Ser Ser Ile Asp Leu Ser Arg Val Thr Ile Arg Tyr Trp Tyr
        915                 920                 925
Thr Val Asp Gly Asp Lys Ala Gln Ser Ala Ile Ser Asp Trp Ala Gln
    930                 935                 940
Ile Gly Ala Ser Asn Val Thr Phe Lys Phe Val Lys Leu Ser Ser Ser
945                 950                 955                 960
Val Ser Gly Ala Asp Tyr Tyr Leu Glu Ile Gly Phe Lys Ser Gly Ala
            965                 970                 975
Gly Gln Leu Gln Ala Gly Lys Asp Thr Gly Glu Ile Gln Ile Arg Phe
            980                 985                 990
Asn Lys Ser Asp Trp Ser Asn Tyr Asn Gln Gly Asn Asp Trp Ser Trp
            995                 1000                1005
Met Gln Ser Met Thr Asn Tyr Gly Glu Asn Val Lys Val Thr Ala
        1010                1015                1020
Tyr Ile Asp Gly Val Leu Val Trp Gly Gln Glu Pro Ser Gly Ala
        1025                1030                1035
Thr Pro Thr Pro Thr Ala Thr Pro Ala Pro Thr Val Thr Pro Thr
        1040                1045                1050
Pro Thr Pro Thr Pro Thr Ser Thr Pro Thr Ala Thr Pro Thr Ala
        1055                1060                1065
Thr Pro Thr Pro Thr Pro Thr Pro Ser Ser Thr Pro Ser Val Val
        1070                1075                1080
Gly Glu Tyr Gly Gln Arg Phe Met Trp Leu Trp Asn Lys Ile His
        1085                1090                1095
Asp Pro Ala Asn Gly Tyr Phe Asn Gln Asp Gly Ile Pro Tyr His
        1100                1105                1110
Ser Val Glu Thr Leu Ile Cys Glu Arg Pro Asp Tyr Gly His Leu
        1115                1120                1125
Thr Thr Ser Glu Ala Phe Ser Tyr Tyr Val Trp Leu Glu Ala Val
        1130                1135                1140
Tyr Gly Lys Leu Thr Gly Asp Trp Ser Lys Phe Lys Thr Ala Trp
        1145                1150                1155
Asp Thr Leu Glu Lys Tyr Met Ile Pro Ser Ala Glu Asp Gln Pro
        1160                1165                1170
Met Arg Ser Tyr Asp Pro Asn Lys Pro Ala Thr Tyr Ala Gly Glu
        1175                1180                1185
Trp Glu Thr Pro Asp Lys Tyr Pro Ser Pro Leu Glu Phe Asn Val
        1190                1195                1200
Pro Val Gly Lys Asp Pro Leu His Asn Glu Leu Val Ser Thr Tyr
        1205                1210                1215
Gly Ser Thr Leu Met Tyr Gly Met His Trp Leu Met Asp Val Asp
        1220                1225                1230
Asn Trp Tyr Gly Tyr Gly Lys Arg Gly Asp Gly Val Ser Arg Ala
        1235                1240                1245
Ser Phe Ile Asn Thr Phe Gln Arg Gly Pro Glu Glu Ser Val Trp
        1250                1255                1260
Glu Thr Val Pro His Pro Ser Trp Glu Glu Phe Lys Trp Gly Gly
        1265                1270                1275
Pro Asn Gly Phe Leu Asp Leu Phe Ile Lys Asp Gln Asn Tyr Ser
        1280                1285                1290
Lys Gln Trp Arg Tyr Thr Asp Ala Pro Asp Ala Asp Ala Arg Ala
        1295                1300                1305
```

Ile Gln Ala Thr Tyr Trp Ala Lys Val Trp Ala Lys Glu Gln Gly
1310                1315                1320

Lys Phe Asn Glu Ile Ser Ser Tyr Val Lys Ala Ala Arg Met
1325                1330                1335

Gly Asp Tyr Leu Arg Tyr Ala Met Phe Asp Lys Tyr Phe Lys Pro
1340                1345                1350

Leu Gly Cys Gln Asp Lys Asn Ala Ala Gly Thr Gly Tyr Asp
1355                1360                1365

Ser Ala His Tyr Leu Leu Ser Trp Tyr Tyr Ala Trp Gly Gly Ala
1370                1375                1380

Leu Asp Gly Ala Trp Ser Trp Lys Ile Gly Ser Ser His Val His
1385                1390                1395

Phe Gly Tyr Gln Asn Pro Met Ala Ala Trp Ala Leu Ala Asn Asp
1400                1405                1410

Ser Asp Met Lys Pro Lys Ser Pro Asn Gly Ala Ser Asp Trp Ala
1415                1420                1425

Lys Ser Leu Lys Arg Gln Ile Glu Phe Tyr Arg Trp Leu Gln Ser
1430                1435                1440

Ala Glu Gly Ala Ile Ala Gly Gly Ala Thr Asn Ser Trp Asn Gly
1445                1450                1455

Arg Tyr Glu Lys Tyr Pro Ala Gly Thr Ala Thr Phe Tyr Gly Met
1460                1465                1470

Ala Tyr Glu Pro Asn Pro Val Tyr His Asp Pro Gly Ser Asn Thr
1475                1480                1485

Trp Phe Gly Phe Gln Ala Trp Ser Met Gln Arg Val Val Glu Tyr
1490                1495                1500

Tyr Tyr Val Thr Gly Asp Lys Asp Ala Gly Ala Leu Leu Glu Lys
1505                1510                1515

Trp Val Ser Trp Val Lys Ser Val Val Lys Leu Asn Ser Asp Gly
1520                1525                1530

Thr Phe Ala Ile Pro Ser Thr Leu Asp Trp Lys Arg Gln Pro Asp
1535                1540                1545

Thr Trp Asn Gly Ala Tyr Thr Gly Asn Ser Asn Leu His Val Lys
1550                1555                1560

Val Val Asp Tyr Gly Thr Asp Leu Gly Ile Thr Ala Ser Leu Ala
1565                1570                1575

Asn Ala Leu Leu Tyr Tyr Ser Ala Gly Thr Lys Lys Tyr Gly Val
1580                1585                1590

Phe Asp Glu Gly Ala Lys Asn Leu Ala Lys Glu Leu Leu Asp Arg
1595                1600                1605

Met Trp Lys Leu Tyr Arg Asp Glu Lys Gly Leu Ser Ala Pro Glu
1610                1615                1620

Lys Arg Ala Asp Tyr Lys Arg Phe Phe Glu Gln Glu Val Tyr Ile
1625                1630                1635

Pro Ala Gly Trp Ile Gly Lys Met Pro Asn Gly Asp Val Ile Lys
1640                1645                1650

Ser Gly Val Lys Phe Ile Asp Ile Arg Ser Lys Tyr Lys Gln Asp
1655                1660                1665

Pro Asp Trp Pro Lys Leu Glu Ala Ala Tyr Lys Ser Gly Gln Ala
1670                1675                1680

Pro Glu Phe Arg Tyr His Arg Phe Trp Ala Gln Cys Asp Ile Ala
1685                1690                1695

Ile Ala Asn Ala Thr Tyr Glu Ile Leu Phe Gly Asn Gln

<210> SEQ ID NO 136
<211> LENGTH: 697
<212> TYPE: PRT
<213> ORGANISM: Artificial Sequence
<220> FEATURE:
<223> OTHER INFORMATION: Anaero-cellum thermo-philum Endoglucanase

<400> SEQUENCE: 136

```
Met Lys Lys Arg Lys Phe Lys Ile Leu Tyr Leu Phe Leu Ile Ile Val
1               5                   10                  15

Leu Ser Val Ser Phe Ile Ile Ser Ile Val Phe Pro Ser Phe Phe Lys
            20                  25                  30

Ala Ala Gln Thr Thr Ser Thr Asn Ile Asn Phe Glu Gly Arg Asp Lys
        35                  40                  45

Leu Thr Phe Phe Ala Tyr Gly Lys Ala Lys Ile Thr Ile Asp Gln Asn
    50                  55                  60

Ile Ala Gln Glu Gly Lys Lys Ser Ile Lys Val Thr Asp Arg Lys Ser
65                  70                  75                  80

Val Trp Asp Ser Phe Gly Ile Asp Val Lys Asp Val Leu Gln Arg Gly
                85                  90                  95

Lys Thr Trp Val Val Ser Ala Tyr Val Lys His Lys Gly Lys Lys Pro
            100                 105                 110

Ile Glu Phe Ser Ile Thr Ala Ile Tyr Asn Asp Gly Arg Gly Leu Lys
        115                 120                 125

Tyr Leu Gln Leu Gly Lys Ile Val Ile Pro Asn Lys Trp Asp Lys
    130                 135                 140

Ile Val Ala Lys Trp Lys Pro Thr Leu Lys Asn Pro Met Asp Leu Ile
145                 150                 155                 160

Ile Ala Ile His Pro Thr Val Asp Lys Thr Thr Ala Tyr Asn Val Asp
                165                 170                 175

Asn Ile Gln Ile Met Thr Glu Glu Val Tyr Gln Ser Gln Ala Val Val
            180                 185                 190

Phe Lys Asp Thr Phe Glu Ser Asn Leu Thr Asn Trp Gln Pro Arg Gly
        195                 200                 205

Asp Thr Val Lys Leu Lys Ile Asp Asn Thr Lys Ser His Asn Gly Asn
    210                 215                 220

Lys Ser Leu Tyr Val Ser Gly Arg Ser Ala Phe Trp His Gly Val Gln
225                 230                 235                 240

Ile Pro Val Thr Lys Tyr Leu Val Ala Gly Lys Val Tyr Lys Phe Ser
                245                 250                 255

Val Trp Leu Tyr His Gln Ser Ile Asp Lys Gln Gly Phe Gly Leu Thr
            260                 265                 270

Ile Gln Arg Lys Met Ala Asn Asp Glu Gln Tyr Lys Tyr Asp Trp Ile
        275                 280                 285

Thr Gly Ser Gln Ile Glu Gly Asp Gly Trp Val Glu Ile Ser Gly Asn
    290                 295                 300

Tyr Tyr Val Pro Lys Asp Gly Lys Ile Glu Glu Leu Val Phe Cys Val
305                 310                 315                 320

Ser Ser Trp Asn Pro Thr Leu Ala Phe Trp Val Asp Asp Val Thr Ile
                325                 330                 335

Ser Asp Pro Phe Lys Leu Gln Gly Pro Asn Tyr Asn Leu Pro Ser Leu
            340                 345                 350

Lys Glu Lys Tyr Lys Glu Asp Phe Lys Val Gly Val Ala Ile Gly Tyr
```

Gly Glu Leu Ile Ser Asp Ile Asp Thr Gln Phe Ile Lys Lys His Phe
            355                 360                 365

Asn Ser Ile Thr Pro Gly Asn Glu Met Lys Pro Glu Ser Val Leu Lys
370                 375                 380

Gly Pro Asn Asn Tyr Asp Phe Thr Ile Ala Asp Ala Phe Val Asp Phe
385                 390                 395                 400

Ala Thr Lys Asn Lys Met Gly Ile Arg Gly His Thr Leu Val Trp His
        405                 410                 415

Asn Gln Thr Pro Asp Trp Phe Phe Lys Asp Glu Asn Gly Asn Phe Leu
    420                 425                 430

Lys Lys Asp Glu Leu Leu Lys Arg Leu Lys Asn His Ile Tyr Thr Val
435                 440                 445

Val Ser Arg Tyr Lys Gly Lys Ile Tyr Ala Trp Asp Val Val Asn Glu
450                 455                 460

Ala Ile Asp Glu Thr Gln Pro Asp Gly Tyr Arg Arg Ser Asn Trp Tyr
465                 470                 475                 480

Asn Ile Cys Gly Pro Glu Tyr Ile Glu Lys Ala Phe Ile Trp Ala His
        485                 490                 495

Glu Ala Asp Pro Gln Ala Lys Leu Phe Tyr Asn Asp Tyr Asn Thr Glu
    500                 505                 510

Ile Pro Gln Lys Arg Met Phe Ile Tyr Asn Met Ile Lys Asn Leu Lys
515                 520                 525

Ala Lys Gly Val Pro Ile His Gly Ile Gly Leu Gln Cys His Ile Asn
530                 535                 540

Ile Asp Asn Pro Ser Val Glu Asp Ile Glu Glu Thr Ile Lys Leu Phe
545                 550                 555                 560

Ser Thr Ile Pro Gly Leu Glu Ile Gln Ile Thr Glu Leu Asp Met Ser
        565                 570                 575

Phe Tyr Gln Trp Gly Ser Ser Val Tyr Tyr Ala Glu Pro Ser Arg Glu
    580                 585                 590

Met Leu Leu Lys Gln Ala Lys Lys Tyr Tyr Glu Leu Phe Asn Leu Phe
595                 600                 605

Lys Lys Tyr Lys Asn Val Ile Lys Ser Val Thr Phe Trp Gly Leu Lys
610                 615                 620

Asp Asp Asn Ser Trp Leu Arg Gly Val Phe Asn Lys Pro Asp Phe Pro
625                 630                 635                 640

Leu Leu Phe Asp Glu His Tyr Asp Gly Lys Pro Ala Phe Trp Ala Leu
        645                 650                 655

Ile Asp Tyr Ser Ile Leu Pro Gln Asn Ala Asn Leu Pro Thr Pro Pro
    660                 665                 670

Ala Ile Pro Lys Val Lys Ala Lys Lys
675                 680                 685

<210> SEQ ID NO 137
<211> LENGTH: 432
<212> TYPE: PRT
<213> ORGANISM: Artificial Sequence
<220> FEATURE:
<223> OTHER INFORMATION: Anaero-cellum thermo-philum

<400> SEQUENCE: 137

Met Pro Thr Val Thr Pro Asn Pro Thr Ser Thr Pro Ser Ile Leu Asp
1               5                   10                  15

Asp Thr Asn Asp Asp Trp Leu Tyr Val Ser Gly Asn Lys Ile Val Asp

```
                20                  25                  30
Lys Asp Gly Lys Pro Val Trp Leu Thr Gly Ile Asn Trp Phe Gly Tyr
            35                  40                  45

Asn Thr Gly Thr Asn Val Phe Asp Gly Val Trp Ser Cys Asn Leu Lys
 50                  55                  60

Asp Thr Leu Ala Glu Ile Ala Asn Arg Gly Phe Asn Leu Leu Arg Ile
 65                  70                  75                  80

Pro Ile Ser Ala Glu Ile Ile Leu Asn Trp Ser Gln Gly Ile Tyr Pro
            85                  90                  95

Lys Pro Asn Ile Asn Tyr Tyr Val Asn Pro Glu Leu Glu Gly Lys Asn
            100                 105                 110

Ser Leu Glu Val Phe Asp Ile Val Gln Ile Cys Lys Glu Val Gly
            115                 120                 125

Leu Lys Ile Met Leu Asp Ile His Ser Ile Lys Thr Asp Ala Met Gly
            130                 135                 140

His Ile Tyr Pro Val Trp Tyr Asp Asp Lys Phe Thr Pro Glu Asp Phe
145                 150                 155                 160

Tyr Lys Ala Cys Glu Trp Ile Thr Asn Arg Tyr Lys Asn Asp Asp Thr
                165                 170                 175

Ile Ile Ala Phe Asp Leu Lys Asn Glu Pro His Gly Lys Pro Trp Gln
            180                 185                 190

Asp Thr Thr Phe Ala Lys Trp Asp Asn Ser Thr Asp Ile Asn Asn Trp
            195                 200                 205

Lys Tyr Ala Ala Glu Thr Cys Ala Lys Arg Ile Leu Asn Ile Asn Pro
210                 215                 220

Asn Leu Leu Ile Val Ile Glu Gly Ile Glu Ala Tyr Pro Lys Asp Asp
225                 230                 235                 240

Val Thr Trp Thr Ser Lys Ser Tyr Ser Asp Tyr Tyr Ser Thr Trp Trp
                245                 250                 255

Gly Gly Asn Leu Arg Gly Val Lys Lys Tyr Pro Ile Asn Leu Gly Lys
            260                 265                 270

Tyr Gln Asn Lys Val Val Tyr Ser Pro His Asp Tyr Gly Pro Ser Val
            275                 280                 285

Tyr Gln Gln Pro Trp Phe Tyr Pro Gly Phe Thr Lys Glu Ser Leu Leu
            290                 295                 300

Gln Asp Cys Trp Arg Pro Asn Trp Ala Tyr Ile Met Glu Glu Asn Ile
305                 310                 315                 320

Ala Pro Leu Leu Ile Gly Glu Trp Gly Gly Tyr Leu Asp Gly Ala Asp
                325                 330                 335

Asn Glu Lys Trp Met Arg Tyr Leu Arg Asp Tyr Ile Ile Glu Asn His
            340                 345                 350

Ile His His Thr Phe Trp Cys Phe Asn Ala Asn Ser Gly Asp Thr Gly
            355                 360                 365

Gly Met Val Gly Tyr Asp Phe Thr Thr Trp Asp Glu Lys Lys Tyr Ser
            370                 375                 380

Phe Leu Lys Pro Ala Leu Trp Gln Asp Ser Gln Gly Arg Phe Val Gly
385                 390                 395                 400

Leu Asp His Lys Arg Pro Leu Gly Thr Asn Gly Lys Asn Ile Asn Ile
                405                 410                 415

Thr Ile Tyr Tyr Asn Asn Asn Glu Pro Ala Pro Val Pro Ala Ala Lys
            420                 425                 430

<210> SEQ ID NO 138
```

```
<211> LENGTH: 432
<212> TYPE: PRT
<213> ORGANISM: Artificial Sequence
<220> FEATURE:
<223> OTHER INFORMATION: Anaero-cellum thermo-philum

<400> SEQUENCE: 138
```

| | | | | | | | | | | | | | | | |
|---|---|---|---|---|---|---|---|---|---|---|---|---|---|---|---|
| Met | Pro | Thr | Val | Thr | Pro | Asn | Pro | Thr | Ser | Thr | Pro | Ser | Ile | Leu | Asp |
| 1 | | | | 5 | | | | | 10 | | | | | 15 | |

| | | | | | | | | | | | | | | | |
|---|---|---|---|---|---|---|---|---|---|---|---|---|---|---|---|
| Asp | Thr | Asn | Asp | Asp | Trp | Leu | Tyr | Val | Ser | Gly | Asn | Lys | Ile | Val | Asp |
| | | | 20 | | | | 25 | | | | | 30 | | | |

| | | | | | | | | | | | | | | | |
|---|---|---|---|---|---|---|---|---|---|---|---|---|---|---|---|
| Lys | Asp | Gly | Lys | Pro | Val | Trp | Leu | Thr | Gly | Ile | Asn | Trp | Phe | Gly | Tyr |
| | | | 35 | | | | 40 | | | | | 45 | | | |

| | | | | | | | | | | | | | | | |
|---|---|---|---|---|---|---|---|---|---|---|---|---|---|---|---|
| Asn | Thr | Gly | Thr | Asn | Val | Phe | Asp | Gly | Val | Trp | Ser | Cys | Asn | Leu | Lys |
| | 50 | | | | | 55 | | | | | 60 | | | | |

| | | | | | | | | | | | | | | | |
|---|---|---|---|---|---|---|---|---|---|---|---|---|---|---|---|
| Asp | Thr | Leu | Ala | Glu | Ile | Ala | Asn | Arg | Gly | Phe | Asn | Leu | Leu | Arg | Ile |
| 65 | | | | 70 | | | | | 75 | | | | | 80 | |

| | | | | | | | | | | | | | | | |
|---|---|---|---|---|---|---|---|---|---|---|---|---|---|---|---|
| Pro | Ile | Ser | Ala | Glu | Ile | Ile | Leu | Asn | Trp | Ser | Gln | Gly | Ile | Tyr | Pro |
| | | | | 85 | | | | | 90 | | | | | 95 | |

| | | | | | | | | | | | | | | | |
|---|---|---|---|---|---|---|---|---|---|---|---|---|---|---|---|
| Lys | Pro | Asn | Ile | Asn | Tyr | Tyr | Val | Asn | Pro | Glu | Leu | Glu | Gly | Lys | Asn |
| | | | 100 | | | | | 105 | | | | | 110 | | |

| | | | | | | | | | | | | | | | |
|---|---|---|---|---|---|---|---|---|---|---|---|---|---|---|---|
| Ser | Leu | Glu | Val | Phe | Asp | Ile | Val | Gln | Ile | Cys | Lys | Glu | Val | Gly |
| | | 115 | | | | | 120 | | | | | 125 | | | |

| | | | | | | | | | | | | | | | |
|---|---|---|---|---|---|---|---|---|---|---|---|---|---|---|---|
| Leu | Lys | Ile | Met | Leu | Asp | Ile | His | Ser | Ile | Lys | Thr | Asp | Ala | Met | Gly |
| | 130 | | | | | 135 | | | | | 140 | | | | |

| | | | | | | | | | | | | | | | |
|---|---|---|---|---|---|---|---|---|---|---|---|---|---|---|---|
| His | Ile | Tyr | Pro | Val | Trp | Tyr | Asp | Asp | Lys | Phe | Thr | Pro | Glu | Asp | Phe |
| 145 | | | | | 150 | | | | | 155 | | | | | 160 |

| | | | | | | | | | | | | | | | |
|---|---|---|---|---|---|---|---|---|---|---|---|---|---|---|---|
| Tyr | Lys | Ala | Cys | Glu | Trp | Ile | Thr | Asn | Arg | Tyr | Lys | Asn | Asp | Asp | Thr |
| | | | | 165 | | | | | 170 | | | | | 175 | |

| | | | | | | | | | | | | | | | |
|---|---|---|---|---|---|---|---|---|---|---|---|---|---|---|---|
| Ile | Ile | Ala | Phe | Asp | Leu | Lys | Asn | Glu | Pro | His | Gly | Lys | Pro | Trp | Gln |
| | | | 180 | | | | | 185 | | | | | 190 | | |

| | | | | | | | | | | | | | | | |
|---|---|---|---|---|---|---|---|---|---|---|---|---|---|---|---|
| Asp | Thr | Thr | Phe | Ala | Lys | Trp | Asp | Asn | Ser | Thr | Asp | Ile | Asn | Asn | Trp |
| | | 195 | | | | | 200 | | | | | 205 | | | |

| | | | | | | | | | | | | | | | |
|---|---|---|---|---|---|---|---|---|---|---|---|---|---|---|---|
| Lys | Tyr | Ala | Ala | Glu | Thr | Cys | Ala | Lys | Arg | Ile | Leu | Asn | Ile | Asn | Pro |
| 210 | | | | | 215 | | | | | 220 | | | | | |

| | | | | | | | | | | | | | | | |
|---|---|---|---|---|---|---|---|---|---|---|---|---|---|---|---|
| Asn | Leu | Leu | Ile | Val | Ile | Glu | Gly | Ile | Glu | Ala | Tyr | Pro | Lys | Asp | Asp |
| 225 | | | | | 230 | | | | | 235 | | | | | 240 |

| | | | | | | | | | | | | | | | |
|---|---|---|---|---|---|---|---|---|---|---|---|---|---|---|---|
| Val | Thr | Trp | Thr | Ser | Lys | Ser | Tyr | Ser | Asp | Tyr | Tyr | Ser | Thr | Trp | Trp |
| | | | | 245 | | | | | 250 | | | | | 255 | |

| | | | | | | | | | | | | | | | |
|---|---|---|---|---|---|---|---|---|---|---|---|---|---|---|---|
| Gly | Gly | Asn | Leu | Arg | Gly | Val | Lys | Lys | Tyr | Pro | Ile | Asn | Leu | Gly | Lys |
| | | | 260 | | | | | 265 | | | | | 270 | | |

| | | | | | | | | | | | | | | | |
|---|---|---|---|---|---|---|---|---|---|---|---|---|---|---|---|
| Tyr | Gln | Asn | Lys | Val | Val | Tyr | Ser | Pro | His | Asp | Tyr | Gly | Pro | Ser | Val |
| | | | 275 | | | | | 280 | | | | | 285 | | |

| | | | | | | | | | | | | | | | |
|---|---|---|---|---|---|---|---|---|---|---|---|---|---|---|---|
| Tyr | Gln | Gln | Pro | Trp | Phe | Tyr | Pro | Gly | Phe | Thr | Lys | Glu | Ser | Leu | Leu |
| | 290 | | | | | 295 | | | | | 300 | | | | |

| | | | | | | | | | | | | | | | |
|---|---|---|---|---|---|---|---|---|---|---|---|---|---|---|---|
| Gln | Asp | Cys | Trp | Arg | Pro | Asn | Trp | Ala | Tyr | Ile | Met | Glu | Glu | Asn | Ile |
| 305 | | | | | 310 | | | | | 315 | | | | | 320 |

| | | | | | | | | | | | | | | | |
|---|---|---|---|---|---|---|---|---|---|---|---|---|---|---|---|
| Ala | Pro | Leu | Leu | Ile | Gly | Glu | Trp | Gly | Gly | Tyr | Leu | Asp | Gly | Ala | Asp |
| | | | | 325 | | | | | 330 | | | | | 335 | |

| | | | | | | | | | | | | | | | |
|---|---|---|---|---|---|---|---|---|---|---|---|---|---|---|---|
| Asn | Glu | Lys | Trp | Met | Arg | Tyr | Leu | Arg | Asp | Tyr | Ile | Ile | Glu | Asn | His |
| | | | 340 | | | | | 345 | | | | | 350 | | |

| | | | | | | | | | | | | | | | |
|---|---|---|---|---|---|---|---|---|---|---|---|---|---|---|---|
| Ile | His | His | Thr | Phe | Trp | Cys | Phe | Asn | Ala | Asn | Ser | Gly | Asp | Thr | Gly |
| | | 355 | | | | | 360 | | | | | 365 | | | |

| | | | | | | | | | | | | | | | |
|---|---|---|---|---|---|---|---|---|---|---|---|---|---|---|---|
| Gly | Met | Val | Gly | Tyr | Asp | Phe | Thr | Thr | Trp | Asp | Glu | Lys | Lys | Tyr | Ser |
| | 370 | | | | | 375 | | | | | 380 | | | | |

```
Phe Leu Lys Pro Ala Leu Trp Gln Asp Ser Gln Gly Arg Phe Val Gly
385                 390                 395                 400

Leu Asp His Lys Arg Pro Leu Gly Thr Asn Gly Lys Asn Ile Asn Ile
            405                 410                 415

Thr Ile Tyr Tyr Asn Asn Asn Glu Pro Ala Pro Val Pro Ala Ala Lys
        420                 425                 430

<210> SEQ ID NO 139
<211> LENGTH: 513
<212> TYPE: PRT
<213> ORGANISM: Artificial Sequence
<220> FEATURE:
<223> OTHER INFORMATION: Trichoderma reesei Exo-glucanase 1

<400> SEQUENCE: 139

Met Tyr Arg Lys Leu Ala Val Ile Ser Ala Phe Leu Ala Thr Ala Arg
1               5                   10                  15

Ala Gln Ser Ala Cys Thr Leu Gln Ser Glu Thr His Pro Pro Leu Thr
            20                  25                  30

Trp Gln Lys Cys Ser Ser Gly Gly Thr Cys Thr Gln Gln Thr Gly Ser
        35                  40                  45

Val Val Ile Asp Ala Asn Trp Arg Trp Thr His Ala Thr Asn Ser Ser
    50                  55                  60

Thr Asn Cys Tyr Asp Gly Asn Thr Trp Ser Ser Thr Leu Cys Pro Asp
65                  70                  75                  80

Asn Glu Thr Cys Ala Lys Asn Cys Cys Leu Asp Gly Ala Ala Tyr Ala
                85                  90                  95

Ser Thr Tyr Gly Val Thr Thr Ser Gly Asn Ser Leu Ser Ile Gly Phe
            100                 105                 110

Val Thr Gln Ser Ala Gln Lys Asn Val Gly Ala Arg Leu Tyr Leu Met
        115                 120                 125

Ala Ser Asp Thr Thr Tyr Gln Glu Phe Thr Leu Leu Gly Asn Glu Phe
    130                 135                 140

Ser Phe Asp Val Asp Val Ser Gln Leu Pro Cys Gly Leu Asn Gly Ala
145                 150                 155                 160

Leu Tyr Phe Val Ser Met Asp Ala Asp Gly Gly Val Ser Lys Tyr Pro
                165                 170                 175

Thr Asn Thr Ala Gly Ala Lys Tyr Gly Thr Gly Tyr Cys Asp Ser Gln
            180                 185                 190

Cys Pro Arg Asp Leu Lys Phe Ile Asn Gly Gln Ala Asn Val Glu Gly
        195                 200                 205

Trp Glu Pro Ser Ser Asn Asn Ala Asn Thr Gly Ile Gly Gly His Gly
    210                 215                 220

Ser Cys Cys Ser Glu Met Asp Ile Trp Glu Ala Asn Ser Ile Ser Glu
225                 230                 235                 240

Ala Leu Thr Pro His Pro Cys Thr Thr Val Gly Gln Glu Ile Cys Glu
                245                 250                 255

Gly Asp Gly Cys Gly Gly Thr Tyr Ser Asp Asn Arg Tyr Gly Gly Thr
            260                 265                 270

Cys Asp Pro Asp Gly Cys Asp Trp Asn Pro Tyr Arg Leu Gly Asn Thr
        275                 280                 285

Ser Phe Tyr Gly Pro Gly Ser Ser Phe Thr Leu Asp Thr Thr Lys Lys
    290                 295                 300

Leu Thr Val Val Thr Gln Phe Glu Thr Ser Gly Ala Ile Asn Arg Tyr
305                 310                 315                 320
```

```
Tyr Val Gln Asn Gly Val Thr Phe Gln Gln Pro Asn Ala Glu Leu Gly
                325                 330                 335

Ser Tyr Ser Gly Asn Glu Leu Asn Asp Asp Tyr Cys Thr Ala Glu Glu
            340                 345                 350

Ala Glu Phe Gly Gly Ser Ser Phe Ser Asp Lys Gly Gly Leu Thr Gln
                355                 360                 365

Phe Lys Lys Ala Thr Ser Gly Gly Met Val Leu Val Met Ser Leu Trp
370                 375                 380

Asp Asp Tyr Tyr Ala Asn Met Leu Trp Leu Asp Ser Thr Tyr Pro Thr
385                 390                 395                 400

Asn Glu Thr Ser Ser Thr Pro Gly Ala Val Arg Gly Ser Cys Ser Thr
                405                 410                 415

Ser Ser Gly Val Pro Ala Gln Val Glu Ser Gln Ser Pro Asn Ala Lys
            420                 425                 430

Val Thr Phe Ser Asn Ile Lys Phe Gly Pro Ile Gly Ser Thr Gly Asn
            435                 440                 445

Pro Ser Gly Gly Asn Pro Pro Gly Gly Asn Arg Gly Thr Thr Thr Thr
            450                 455                 460

Arg Arg Pro Ala Thr Thr Thr Gly Ser Ser Pro Gly Pro Thr Gln Ser
465                 470                 475                 480

His Tyr Gly Gln Cys Gly Gly Ile Gly Tyr Ser Gly Pro Thr Val Cys
                485                 490                 495

Ala Ser Gly Thr Thr Cys Gln Val Leu Asn Pro Tyr Tyr Ser Gln Cys
            500                 505                 510

Leu

<210> SEQ ID NO 140
<211> LENGTH: 471
<212> TYPE: PRT
<213> ORGANISM: Artificial Sequence
<220> FEATURE:
<223> OTHER INFORMATION: Trichoderma reesei CBH2

<400> SEQUENCE: 140

Met Ile Val Gly Ile Leu Thr Thr Leu Ala Thr Leu Ala Thr Leu Ala
1               5                   10                  15

Ala Ser Val Pro Leu Glu Glu Arg Gln Ala Cys Ser Ser Val Trp Gly
                20                  25                  30

Gln Cys Gly Gly Gln Asn Trp Ser Gly Pro Thr Cys Cys Ala Ser Gly
            35                  40                  45

Ser Thr Cys Val Tyr Ser Asn Asp Tyr Tyr Ser Gln Cys Leu Pro Gly
50                  55                  60

Ala Ala Ser Ser Ser Ser Thr Arg Ala Ala Ser Thr Thr Ser Arg
65                  70                  75                  80

Val Ser Pro Thr Thr Ser Arg Ser Ser Ala Thr Pro Pro Pro Gly
                85                  90                  95

Ser Thr Thr Thr Arg Val Pro Pro Val Gly Ser Gly Thr Ala Thr Tyr
                100                 105                 110

Ser Gly Asn Pro Phe Val Gly Val Thr Pro Trp Ala Asn Ala Tyr Tyr
            115                 120                 125

Ala Ser Glu Val Ser Ser Leu Ala Ile Pro Ser Leu Thr Gly Ala Met
        130                 135                 140

Ala Thr Ala Ala Ala Ala Val Ala Lys Val Pro Ser Phe Met Trp Leu
145                 150                 155                 160
```

```
Asp Thr Leu Asp Lys Thr Pro Leu Met Glu Gln Thr Leu Ala Asp Ile
            165                 170                 175
Arg Thr Ala Asn Lys Asn Gly Gly Asn Tyr Ala Gly Gln Phe Val Val
        180                 185                 190
Tyr Asp Leu Pro Asp Arg Asp Cys Ala Ala Leu Ala Ser Asn Gly Glu
    195                 200                 205
Tyr Ser Ile Ala Asp Gly Gly Val Ala Lys Tyr Lys Asn Tyr Ile Asp
210                 215                 220
Thr Ile Arg Gln Ile Val Val Glu Tyr Ser Asp Ile Arg Thr Leu Leu
225                 230                 235                 240
Val Ile Glu Pro Asp Ser Leu Ala Asn Leu Val Thr Asn Leu Gly Thr
            245                 250                 255
Pro Lys Cys Ala Asn Ala Gln Ser Ala Tyr Leu Glu Cys Ile Asn Tyr
        260                 265                 270
Ala Val Thr Gln Leu Asn Leu Pro Asn Val Ala Met Tyr Leu Asp Ala
    275                 280                 285
Gly His Ala Gly Trp Leu Gly Trp Pro Ala Asn Gln Asp Pro Ala Ala
290                 295                 300
Gln Leu Phe Ala Asn Val Tyr Lys Asn Ala Ser Ser Pro Arg Ala Leu
305                 310                 315                 320
Arg Gly Leu Ala Thr Asn Val Ala Asn Tyr Asn Gly Trp Asn Ile Thr
            325                 330                 335
Ser Pro Pro Ser Tyr Thr Gln Gly Asn Ala Val Tyr Asn Glu Lys Leu
        340                 345                 350
Tyr Ile His Ala Ile Gly Pro Leu Leu Ala Asn His Gly Trp Ser Asn
    355                 360                 365
Ala Phe Phe Ile Thr Asp Gln Gly Arg Ser Gly Lys Gln Pro Thr Gly
370                 375                 380
Gln Gln Gln Trp Gly Asp Trp Cys Asn Val Ile Gly Thr Gly Phe Gly
385                 390                 395                 400
Ile Arg Pro Ser Ala Asn Thr Gly Asp Ser Leu Leu Asp Ser Phe Val
            405                 410                 415
Trp Val Lys Pro Gly Gly Glu Cys Asp Gly Thr Ser Asp Ser Ser Ala
        420                 425                 430
Pro Arg Phe Asp Ser His Cys Ala Leu Pro Asp Ala Leu Gln Pro Ala
    435                 440                 445
Pro Gln Ala Gly Ala Trp Phe Gln Ala Tyr Phe Val Gln Leu Leu Thr
    450                 455                 460
Asn Ala Asn Pro Ser Phe Leu
465                 470

<210> SEQ ID NO 141
<211> LENGTH: 459
<212> TYPE: PRT
<213> ORGANISM: Artificial Sequence
<220> FEATURE:
<223> OTHER INFORMATION: Trichoderma reesei Endoglucanase 1

<400> SEQUENCE: 141

Met Ala Pro Ser Val Thr Leu Pro Leu Thr Thr Ala Ile Leu Ala Ile
1               5                   10                  15
Ala Arg Leu Val Ala Ala Gln Gln Pro Gly Thr Ser Thr Pro Glu Val
            20                  25                  30
His Pro Lys Leu Thr Thr Tyr Lys Cys Thr Lys Ser Gly Gly Cys Val
        35                  40                  45
```

```
Ala Gln Asp Thr Ser Val Val Leu Asp Trp Asn Tyr Arg Trp Met His
    50              55                  60

Asp Ala Asn Tyr Asn Ser Cys Thr Val Asn Gly Gly Val Asn Thr Thr
65              70                  75                  80

Leu Cys Pro Asp Glu Ala Thr Cys Gly Lys Asn Cys Phe Ile Glu Gly
                85                  90                  95

Val Asp Tyr Ala Ala Ser Gly Val Thr Thr Ser Gly Ser Ser Leu Thr
            100                 105                 110

Met Asn Gln Tyr Met Pro Ser Ser Gly Gly Tyr Ser Ser Val Ser
            115                 120                 125

Pro Arg Leu Tyr Leu Leu Asp Ser Asp Gly Glu Tyr Val Met Leu Lys
            130                 135                 140

Leu Asn Gly Gln Glu Leu Ser Phe Asp Val Asp Leu Ser Ala Leu Pro
145                 150                 155                 160

Cys Gly Glu Asn Gly Ser Leu Tyr Leu Ser Gln Met Asp Glu Asn Gly
                165                 170                 175

Gly Ala Asn Gln Tyr Asn Thr Ala Gly Ala Asn Tyr Gly Ser Gly Tyr
            180                 185                 190

Cys Asp Ala Gln Cys Pro Val Gln Thr Trp Arg Asn Gly Thr Leu Asn
            195                 200                 205

Thr Ser His Gln Gly Phe Cys Cys Asn Glu Met Asp Ile Leu Glu Gly
210                 215                 220

Asn Ser Arg Ala Asn Ala Leu Thr Pro His Ser Cys Thr Ala Thr Ala
225                 230                 235                 240

Cys Asp Ser Ala Gly Cys Gly Phe Asn Pro Tyr Gly Ser Gly Tyr Lys
                245                 250                 255

Ser Tyr Tyr Gly Pro Gly Asp Thr Val Asp Thr Ser Lys Thr Phe Thr
            260                 265                 270

Ile Ile Thr Gln Phe Asn Thr Asp Asn Gly Ser Pro Ser Gly Asn Leu
            275                 280                 285

Val Ser Ile Thr Arg Lys Tyr Gln Gln Asn Gly Val Asp Ile Pro Ser
            290                 295                 300

Ala Gln Pro Gly Gly Asp Thr Ile Ser Ser Cys Pro Ser Ala Ser Ala
305                 310                 315                 320

Tyr Gly Gly Leu Ala Thr Met Gly Lys Ala Leu Ser Ser Gly Met Val
                325                 330                 335

Leu Val Phe Ser Ile Trp Asn Asp Asn Ser Gln Tyr Met Asn Trp Leu
            340                 345                 350

Asp Ser Gly Asn Ala Gly Pro Cys Ser Ser Thr Glu Gly Asn Pro Ser
            355                 360                 365

Asn Ile Leu Ala Asn Asn Pro Asn Thr His Val Val Phe Ser Asn Ile
            370                 375                 380

Arg Trp Gly Asp Ile Gly Ser Thr Thr Asn Ser Thr Ala Pro Pro Pro
385                 390                 395                 400

Pro Pro Ala Ser Ser Thr Thr Phe Ser Thr Thr Arg Arg Ser Ser Thr
                405                 410                 415

Thr Ser Ser Ser Pro Ser Cys Thr Gln Thr His Trp Gly Gln Cys Gly
            420                 425                 430

Gly Ile Gly Tyr Ser Gly Cys Lys Thr Cys Thr Ser Gly Thr Thr Cys
            435                 440                 445

Gln Tyr Ser Asn Asp Tyr Tyr Ser Gln Cys Leu
            450                 455
```

<210> SEQ ID NO 142
<211> LENGTH: 447
<212> TYPE: PRT
<213> ORGANISM: Artificial Sequence
<220> FEATURE:
<223> OTHER INFORMATION: Coptotermes formosanus endo-b-1,4-glucanase

<400> SEQUENCE: 142

```
Met Arg Val Phe Val Cys Leu Leu Ser Ala Leu Ala Leu Cys Gln Ala
1               5                   10                  15

Ala Tyr Asp Tyr Lys Thr Val Leu Lys Asn Ser Leu Leu Phe Tyr Glu
            20                  25                  30

Ala Gln Arg Ser Gly Lys Leu Pro Ala Asp Gln Lys Val Thr Trp Arg
        35                  40                  45

Lys Asp Ser Ala Leu Asn Asp Lys Gly Gln Lys Gly Glu Asp Leu Thr
50                  55                  60

Gly Gly Tyr Tyr Asp Ala Gly Asp Phe Val Lys Phe Gly Phe Pro Met
65                  70                  75                  80

Ala Tyr Thr Val Thr Val Leu Ala Trp Gly Leu Val Asp Tyr Glu Ser
                85                  90                  95

Ala Tyr Ser Thr Ala Gly Ala Leu Asp Asp Gly Arg Lys Ala Leu Lys
            100                 105                 110

Trp Gly Thr Asp Tyr Phe Leu Lys Ala His Thr Ala Ala Asn Glu Phe
        115                 120                 125

Tyr Gly Gln Val Gly Gln Gly Asp Val Asp His Ala Tyr Trp Gly Arg
    130                 135                 140

Pro Glu Asp Met Thr Met Ser Arg Pro Ala Tyr Lys Ile Asp Thr Ser
145                 150                 155                 160

Lys Pro Gly Ser Asp Leu Ala Ala Glu Thr Ala Ala Ala Leu Ala Ala
                165                 170                 175

Thr Ala Ile Ala Tyr Lys Ser Ala Asp Ser Thr Tyr Ser Asn Asn Leu
            180                 185                 190

Ile Thr His Ala Lys Gln Leu Phe Asp Phe Ala Asn Asn Tyr Arg Gly
        195                 200                 205

Lys Tyr Ser Asp Ser Ile Thr Asp Ala Lys Asn Phe Tyr Ala Ser Gly
    210                 215                 220

Asp Tyr Lys Asp Glu Leu Val Trp Ala Ala Trp Leu Tyr Arg Ala
225                 230                 235                 240

Thr Asn Asp Asn Thr Tyr Leu Thr Lys Ala Glu Ser Leu Tyr Asn Glu
                245                 250                 255

Phe Gly Leu Gly Ser Trp Asn Gly Ala Phe Asn Trp Asp Asn Lys Ile
            260                 265                 270

Ser Gly Val Gln Val Leu Leu Ala Leu Thr Ser Lys Gln Ala Tyr Lys
        275                 280                 285

Asp Lys Val Gln Gly Tyr Val Asp Tyr Leu Val Ser Ser Gln Lys Lys
    290                 295                 300

Thr Pro Lys Gly Leu Val Tyr Ile Asp Gln Trp Gly Thr Leu Arg His
305                 310                 315                 320

Ala Ala Asn Ser Ala Leu Ile Ala Leu Gln Ala Asp Leu Gly Ile
                325                 330                 335

Asn Ala Ala Ser Tyr Arg Gln Tyr Ala Lys Lys Gln Ile Asp Tyr Ala
            340                 345                 350

Leu Gly Asp Gly Gly Arg Ser Tyr Val Val Gly Phe Gly Thr Asn Pro
        355                 360                 365

Pro Val Arg Pro His His Arg Ser Ser Ser Cys Pro Asp Ala Pro Ala
```

```
                    370                 375                 380
Ala Cys Asp Trp Asn Thr Tyr Asn Ser Ala Gly Pro Asn Ala His Val
385                 390                 395                 400

Leu Thr Gly Ala Leu Val Gly Gly Pro Asp Ser Asn Asp Ser Tyr Thr
                405                 410                 415

Asp Ser Arg Ser Asp Tyr Ile Ser Asn Glu Val Ala Thr Asp Tyr Asn
                420                 425                 430

Ala Gly Phe Gln Ser Ala Val Ala Gly Leu Leu Lys Ala Gly Val
                435                 440                 445

<210> SEQ ID NO 143
<211> LENGTH: 448
<212> TYPE: PRT
<213> ORGANISM: Artificial Sequence
<220> FEATURE:
<223> OTHER INFORMATION: Nasutitermes takasagoensis endo-b-1,4-glucanase

<400> SEQUENCE: 143

Met Arg Val Phe Leu Cys Leu Leu Ser Ala Leu Ala Leu Cys Gln Ala
1               5                   10                  15

Ala Tyr Asp Tyr Lys Gln Val Leu Arg Asp Ser Leu Leu Phe Tyr Glu
                20                  25                  30

Ala Gln Arg Ser Gly Arg Leu Pro Ala Asp Gln Lys Val Thr Trp Arg
            35                  40                  45

Lys Asp Ser Ala Leu Asn Asp Gln Gly Asp Gln Gly Gln Asp Leu Thr
50                  55                  60

Gly Gly Tyr Phe Asp Ala Gly Asp Phe Val Lys Phe Gly Phe Pro Met
65                  70                  75                  80

Ala Tyr Thr Ala Thr Val Leu Ala Trp Gly Leu Ile Asp Phe Glu Ala
                85                  90                  95

Gly Tyr Ser Ser Ala Gly Ala Leu Asp Asp Gly Arg Lys Ala Val Lys
                100                 105                 110

Trp Ala Thr Asp Tyr Phe Ile Lys Ala His Thr Ser Gln Asn Glu Phe
            115                 120                 125

Tyr Gly Gln Val Gly Gln Gly Asp Ala Asp His Ala Phe Trp Gly Arg
130                 135                 140

Pro Glu Asp Met Thr Met Ala Arg Pro Ala Tyr Lys Ile Asp Thr Ser
145                 150                 155                 160

Arg Pro Gly Ser Asp Leu Ala Gly Glu Thr Ala Ala Leu Ala Ala
                165                 170                 175

Ala Ser Ile Val Phe Arg Asn Val Asp Gly Thr Tyr Ser Asn Asn Leu
            180                 185                 190

Leu Thr His Ala Arg Gln Leu Phe Asp Phe Ala Asn Asn Tyr Arg Gly
            195                 200                 205

Lys Tyr Ser Asp Ser Ile Thr Asp Ala Arg Asn Phe Tyr Ala Ser Ala
210                 215                 220

Asp Tyr Arg Asp Glu Leu Val Trp Ala Ala Trp Leu Tyr Arg Ala
225                 230                 235                 240

Thr Asn Asp Asn Thr Tyr Leu Asn Thr Ala Glu Ser Leu Tyr Asp Glu
                245                 250                 255

Phe Gly Leu Gln Asn Trp Gly Gly Leu Asn Trp Asp Ser Lys Val
                260                 265                 270

Ser Gly Val Gln Val Leu Leu Ala Lys Leu Thr Asn Lys Gln Ala Tyr
            275                 280                 285

Lys Asp Thr Val Gln Ser Tyr Val Asn Tyr Leu Ile Asn Asn Gln Gln
```

```
            290                 295                 300
Lys Thr Pro Lys Gly Leu Leu Tyr Ile Asp Met Trp Gly Thr Leu Arg
305                 310                 315                 320

His Ala Ala Asn Ala Ala Phe Ile Met Leu Glu Ala Ala Glu Leu Gly
                325                 330                 335

Leu Ser Ala Ser Ser Tyr Arg Gln Phe Ala Gln Thr Gln Ile Asp Tyr
                340                 345                 350

Ala Leu Gly Asp Gly Arg Ser Phe Val Cys Gly Phe Gly Ser Asn
                355                 360                 365

Pro Pro Thr Arg Pro His His Arg Ser Ser Ser Cys Pro Ala Pro
        370                 375                 380

Ala Thr Cys Asp Trp Asn Thr Phe Asn Ser Pro Asp Pro Asn Tyr His
385                 390                 395                 400

Val Leu Ser Gly Ala Leu Val Gly Gly Pro Asp Gln Asn Asp Asn Tyr
                405                 410                 415

Val Asp Asp Arg Ser Asp Tyr Val His Asn Glu Val Ala Thr Asp Tyr
                420                 425                 430

Asn Ala Gly Phe Gln Ser Ala Leu Ala Ala Leu Val Ala Leu Gly Tyr
                435                 440                 445

<210> SEQ ID NO 144
<211> LENGTH: 455
<212> TYPE: PRT
<213> ORGANISM: Artificial Sequence
<220> FEATURE:
<223> OTHER INFORMATION: Talaromyces emersonii CBH1

<400> SEQUENCE: 144

Met Leu Arg Arg Ala Leu Leu Leu Ser Ser Ala Ile Leu Ala Val
1               5                   10                  15

Lys Ala Gln Gln Ala Gly Thr Ala Thr Ala Glu Asn His Pro Pro Leu
                20                  25                  30

Thr Trp Gln Glu Cys Thr Ala Pro Gly Ser Cys Thr Thr Gln Asn Gly
                35                  40                  45

Ala Val Val Leu Asp Ala Asn Trp Arg Trp Val His Asp Val Asn Gly
        50                  55                  60

Tyr Thr Asn Cys Tyr Thr Gly Asn Thr Trp Asp Pro Thr Tyr Cys Pro
65                  70                  75                  80

Asp Asp Glu Thr Cys Ala Gln Asn Cys Ala Leu Asp Gly Ala Asp Tyr
                85                  90                  95

Glu Gly Thr Tyr Gly Val Thr Ser Ser Gly Ser Ser Leu Lys Leu Asn
                100                 105                 110

Phe Val Thr Gly Ser Asn Val Gly Ser Arg Leu Tyr Leu Leu Gln Asp
                115                 120                 125

Asp Ser Thr Tyr Gln Ile Phe Lys Leu Leu Asn Arg Glu Phe Ser Phe
        130                 135                 140

Asp Val Asp Val Ser Asn Leu Pro Cys Gly Leu Asn Gly Ala Leu Tyr
145                 150                 155                 160

Phe Val Ala Met Asp Ala Asp Gly Gly Val Ser Lys Tyr Pro Asn Asn
                165                 170                 175

Lys Ala Gly Ala Lys Tyr Gly Thr Gly Tyr Cys Asp Ser Gln Cys Pro
                180                 185                 190

Arg Asp Leu Lys Phe Ile Asp Gly Glu Ala Asn Val Glu Gly Trp Gln
        195                 200                 205

Pro Ser Ser Asn Asn Ala Asn Thr Gly Ile Gly Asp His Gly Ser Cys
```

```
            210                 215                 220
Cys Ala Glu Met Asp Val Trp Glu Ala Asn Ser Ile Ser Asn Ala Val
225                 230                 235                 240

Thr Pro His Pro Cys Asp Thr Pro Gly Gln Thr Met Cys Ser Gly Asp
                245                 250                 255

Asp Cys Gly Gly Thr Tyr Ser Asn Asp Arg Tyr Ala Gly Thr Cys Asp
                260                 265                 270

Pro Asp Gly Cys Asp Phe Asn Pro Tyr Arg Met Gly Asn Thr Ser Phe
            275                 280                 285

Tyr Gly Pro Gly Lys Ile Ile Asp Thr Thr Lys Pro Phe Thr Val Val
        290                 295                 300

Thr Gln Phe Leu Thr Asp Asp Gly Thr Asp Thr Gly Thr Leu Ser Glu
305                 310                 315                 320

Ile Lys Arg Phe Tyr Ile Gln Asn Ser Asn Val Ile Pro Gln Pro Asn
                325                 330                 335

Ser Asp Ile Ser Gly Val Thr Gly Asn Ser Ile Thr Thr Glu Phe Cys
                340                 345                 350

Thr Ala Gln Lys Gln Ala Phe Gly Asp Thr Asp Phe Ser Gln His
            355                 360                 365

Gly Gly Leu Ala Lys Met Gly Ala Ala Met Gln Gln Gly Met Val Leu
        370                 375                 380

Val Met Ser Leu Trp Asp Asp Tyr Ala Ala Gln Met Leu Trp Leu Asp
385                 390                 395                 400

Ser Asp Tyr Pro Thr Asp Ala Asp Pro Thr Thr Pro Gly Ile Ala Arg
                405                 410                 415

Gly Thr Cys Pro Thr Asp Ser Gly Val Pro Ser Asp Val Glu Ser Gln
                420                 425                 430

Ser Pro Asn Ser Tyr Val Thr Tyr Ser Asn Ile Lys Phe Gly Pro Ile
            435                 440                 445

Asn Ser Thr Phe Thr Ala Ser
        450                 455

<210> SEQ ID NO 145
<211> LENGTH: 530
<212> TYPE: PRT
<213> ORGANISM: Artificial Sequence
<220> FEATURE:
<223> OTHER INFORMATION: Neosartorya fischeri putative endo-glucanase

<400> SEQUENCE: 145

Met Leu Ala Ser Thr Phe Ser Tyr Arg Met Tyr Lys Thr Ala Leu Ile
1               5                   10                  15

Leu Ala Ala Leu Leu Gly Ser Gly Gln Ala Gln Gln Val Gly Thr Ser
            20                  25                  30

Gln Ala Glu Val His Pro Ser Met Thr Trp Gln Ser Cys Thr Ala Gly
        35                  40                  45

Gly Ser Cys Thr Thr Asn Asn Gly Lys Val Val Ile Asp Ala Asn Trp
    50                  55                  60

Arg Trp Val His Lys Val Gly Asp Tyr Thr Asn Cys Tyr Thr Gly Asn
65                  70                  75                  80

Thr Trp Asp Lys Thr Leu Cys Pro Asp Asp Ala Thr Cys Ala Ser Asn
                85                  90                  95

Cys Ala Leu Glu Gly Ala Asn Tyr Gln Ser Thr Tyr Gly Ala Thr Thr
            100                 105                 110

Ser Gly Asp Ser Leu Arg Leu Asn Phe Val Thr Thr Ser Gln Gln Lys
```

```
            115                 120                 125
Asn Ile Gly Ser Arg Leu Tyr Met Met Lys Asp Asp Thr Thr Tyr Glu
            130                 135                 140
Met Phe Lys Leu Leu Asn Gln Glu Phe Thr Phe Asp Val Asp Val Ser
145                 150                 155                 160
Asn Leu Pro Cys Gly Leu Asn Gly Ala Leu Tyr Phe Val Ala Met Asp
                165                 170                 175
Ala Asp Gly Gly Met Ser Lys Tyr Pro Thr Asn Lys Ala Gly Ala Lys
                180                 185                 190
Tyr Gly Thr Gly Tyr Cys Asp Ser Gln Cys Pro Arg Asp Leu Lys Phe
                195                 200                 205
Ile Asn Gly Gln Ala Asn Val Glu Gly Trp Gln Pro Ser Ser Asn Asp
            210                 215                 220
Ala Asn Ala Gly Thr Gly Asn His Gly Ser Cys Cys Ala Glu Met Asp
225                 230                 235                 240
Ile Trp Glu Ala Asn Ser Ile Ser Thr Ala Phe Thr Pro His Pro Cys
                245                 250                 255
Asp Thr Pro Gly Gln Val Met Cys Thr Gly Asp Ala Cys Gly Gly Thr
                260                 265                 270
Tyr Ser Ser Asp Arg Tyr Gly Gly Thr Cys Asp Pro Asp Gly Cys Asp
                275                 280                 285
Phe Asn Ser Phe Arg Gln Gly Asn Lys Thr Phe Tyr Gly Pro Gly Met
                290                 295                 300
Thr Val Asp Thr Lys Ser Lys Phe Thr Val Val Thr Gln Phe Ile Thr
305                 310                 315                 320
Asp Asp Gly Thr Ala Ser Gly Thr Leu Lys Glu Ile Lys Arg Phe Tyr
                325                 330                 335
Val Gln Asn Gly Lys Val Ile Pro Asn Ser Glu Ser Thr Trp Ser Gly
                340                 345                 350
Val Gly Gly Asn Ser Ile Thr Asn Asp Tyr Cys Thr Ala Gln Lys Ser
                355                 360                 365
Leu Phe Lys Asp Gln Asn Val Phe Ala Lys His Gly Gly Met Glu Gly
                370                 375                 380
Met Gly Ala Ala Leu Ala Gln Gly Met Val Leu Val Met Ser Leu Trp
385                 390                 395                 400
Asp Asp His Ala Ala Asn Met Leu Trp Leu Asp Ser Asn Tyr Pro Thr
                405                 410                 415
Thr Ala Ser Ser Ser Thr Pro Gly Val Ala Arg Gly Thr Cys Asp Ile
                420                 425                 430
Ser Ser Gly Val Pro Ala Asp Val Glu Ala Asn His Pro Asp Ala Ser
                435                 440                 445
Val Val Tyr Ser Asn Ile Lys Val Gly Pro Ile Gly Ser Thr Phe Asn
                450                 455                 460
Ser Gly Gly Ser Asn Pro Gly Gly Gly Thr Thr Thr Ala Lys Pro
465                 470                 475                 480
Thr Thr Thr Thr Thr Thr Ala Gly Ser Pro Gly Gly Thr Gly Val Ala
                485                 490                 495
Gln His Tyr Gly Gln Cys Gly Gly Asn Gly Trp Gln Gly Pro Thr Thr
                500                 505                 510
Cys Ala Ser Pro Tyr Thr Cys Gln Lys Leu Asn Asp Phe Tyr Ser Gln
                515                 520                 525
Cys Leu
530
```

<210> SEQ ID NO 146
<211> LENGTH: 451
<212> TYPE: PRT
<213> ORGANISM: Artificial Sequence
<220> FEATURE:
<223> OTHER INFORMATION: Coptotermes formosanus EG

<400> SEQUENCE: 146

```
Met Arg Phe Pro Ser Ile Phe Thr Ala Val Leu Phe Ala Ala Ser Ser
1               5                   10                  15

Ala Leu Ala Ala Tyr Asp Tyr Lys Thr Val Leu Lys Asn Ser Leu Leu
            20                  25                  30

Phe Tyr Glu Ala Gln Arg Ser Gly Lys Leu Pro Ala Asp Gln Lys Val
        35                  40                  45

Thr Trp Arg Lys Asp Ser Ala Leu Asn Asp Lys Gly Gln Lys Gly Glu
    50                  55                  60

Asp Leu Thr Gly Gly Tyr Tyr Asp Ala Gly Asp Phe Val Lys Phe Gly
65                  70                  75                  80

Phe Pro Met Ala Tyr Thr Val Thr Val Leu Ala Trp Gly Leu Val Asp
                85                  90                  95

Tyr Glu Ser Ala Tyr Ser Thr Ala Gly Ala Leu Asp Asp Gly Arg Lys
            100                 105                 110

Ala Leu Lys Trp Gly Thr Asp Tyr Phe Leu Lys Ala His Thr Ala Ala
        115                 120                 125

Asn Glu Phe Tyr Gly Gln Val Gly Gln Gly Asp Val Asp His Ala Tyr
    130                 135                 140

Trp Gly Arg Pro Glu Asp Met Thr Met Ser Arg Pro Ala Tyr Lys Ile
145                 150                 155                 160

Asp Thr Ser Lys Pro Gly Ser Asp Leu Ala Ala Glu Thr Ala Ala Ala
                165                 170                 175

Leu Ala Ala Thr Ala Ile Ala Tyr Lys Ser Ala Asp Ser Thr Tyr Ser
            180                 185                 190

Asn Asn Leu Ile Thr His Ala Lys Gln Leu Phe Asp Phe Ala Asn Asn
        195                 200                 205

Tyr Arg Gly Lys Tyr Ser Asp Ser Ile Thr Asp Ala Lys Asn Phe Tyr
    210                 215                 220

Ala Ser Gly Asp Tyr Lys Asp Glu Leu Val Trp Ala Ala Ala Trp Leu
225                 230                 235                 240

Tyr Arg Ala Thr Asn Asp Asn Thr Tyr Leu Thr Lys Ala Glu Ser Leu
                245                 250                 255

Tyr Asn Glu Phe Gly Leu Gly Ser Trp Asn Gly Ala Phe Asn Trp Asp
            260                 265                 270

Asn Lys Ile Ser Gly Val Gln Val Leu Leu Ala Lys Leu Thr Ser Lys
        275                 280                 285

Gln Ala Tyr Lys Asp Lys Val Gln Gly Tyr Val Asp Tyr Leu Val Ser
    290                 295                 300

Ser Gln Lys Lys Thr Pro Lys Gly Leu Val Tyr Ile Asp Gln Trp Gly
305                 310                 315                 320

Thr Leu Arg His Ala Ala Asn Ser Ala Leu Ile Ala Leu Gln Ala Ala
                325                 330                 335

Asp Leu Gly Ile Asn Ala Ala Ser Tyr Arg Gln Tyr Ala Lys Lys Gln
            340                 345                 350

Ile Asp Tyr Ala Leu Gly Asp Gly Gly Arg Ser Tyr Val Val Gly Phe
        355                 360                 365
```

```
Gly Thr Asn Pro Pro Val Arg Pro His His Arg Ser Ser Cys Pro
    370                 375                 380

Asp Ala Pro Ala Ala Cys Asp Trp Asn Thr Tyr Asn Ser Ala Gly Pro
385                 390                 395                 400

Asn Ala His Val Leu Thr Gly Ala Leu Val Gly Gly Pro Asp Ser Asn
            405                 410                 415

Asp Ser Tyr Thr Asp Ser Arg Ser Asp Tyr Ile Ser Asn Glu Val Ala
            420                 425                 430

Thr Asp Tyr Asn Ala Gly Phe Gln Ser Ala Val Ala Gly Leu Leu Lys
            435                 440                 445

Ala Gly Val
    450

<210> SEQ ID NO 147
<211> LENGTH: 482
<212> TYPE: PRT
<213> ORGANISM: Artificial Sequence
<220> FEATURE:
<223> OTHER INFORMATION: Chryso-sporium lucknowense CBH2b

<400> SEQUENCE: 147

Met Ala Lys Lys Leu Phe Ile Thr Ala Ala Leu Ala Ala Ala Val Leu
1               5                   10                  15

Ala Ala Pro Val Ile Glu Glu Arg Gln Asn Cys Gly Ala Val Trp Thr
            20                  25                  30

Gln Cys Gly Gly Asn Gly Trp Gln Gly Pro Thr Cys Cys Ala Ser Gly
        35                  40                  45

Ser Thr Cys Val Ala Gln Asn Glu Trp Tyr Ser Gln Cys Leu Pro Asn
50                  55                  60

Ser Gln Val Thr Ser Ser Thr Pro Ser Thr Ser Thr Ser Gln
65                  70                  75                  80

Arg Ser Thr Ser Thr Ser Ser Thr Thr Arg Ser Gly Ser Ser Ser
                85                  90                  95

Ser Ser Ser Thr Thr Pro Pro Val Ser Ser Pro Val Thr Ser Ile
            100                 105                 110

Pro Gly Gly Ala Thr Thr Ala Ser Tyr Ser Gly Asn Pro Phe Ser
        115                 120                 125

Gly Val Arg Leu Phe Ala Asn Asp Tyr Tyr Arg Ser Glu Val His Asn
    130                 135                 140

Leu Ala Ile Pro Ser Met Thr Gly Thr Leu Ala Ala Lys Ala Ser Ala
145                 150                 155                 160

Val Ala Glu Val Pro Ser Phe Gln Trp Leu Asp Arg Asn Val Thr Ile
                165                 170                 175

Asp Thr Leu Met Val Gln Thr Leu Ser Gln Val Arg Ala Leu Asn Lys
            180                 185                 190

Ala Gly Ala Asn Pro Pro Tyr Ala Ala Gln Leu Val Val Tyr Asp Leu
        195                 200                 205

Pro Asp Arg Asp Cys Ala Ala Ala Ser Asn Gly Glu Phe Ser Ile
    210                 215                 220

Ala Asn Gly Gly Ala Ala Asn Tyr Arg Ser Tyr Ile Asp Ala Ile Arg
225                 230                 235                 240

Lys His Ile Ile Glu Tyr Ser Asp Ile Arg Ile Leu Val Ile Glu
                245                 250                 255

Pro Asp Ser Met Ala Asn Met Val Thr Asn Met Asn Val Ala Lys Cys
            260                 265                 270
```

Ser Asn Ala Ala Ser Thr Tyr His Glu Leu Thr Val Tyr Ala Leu Lys
    275                 280                 285

Gln Leu Asn Leu Pro Asn Val Ala Met Tyr Leu Asp Ala Gly His Ala
    290                 295                 300

Gly Trp Leu Gly Trp Pro Ala Asn Ile Gln Pro Ala Ala Glu Leu Phe
305                 310                 315                 320

Ala Gly Ile Tyr Asn Asp Ala Gly Lys Pro Ala Ala Val Arg Gly Leu
                325                 330                 335

Ala Thr Asn Val Ala Asn Tyr Asn Ala Trp Ser Ile Ala Ser Ala Pro
                340                 345                 350

Ser Tyr Thr Ser Pro Asn Pro Asn Tyr Asp Glu Lys His Tyr Ile Glu
                355                 360                 365

Ala Phe Ser Pro Leu Leu Asn Ser Ala Gly Phe Pro Ala Arg Phe Ile
                370                 375                 380

Val Asp Thr Gly Arg Asn Gly Lys Gln Pro Thr Gly Gln Gln Gln Trp
385                 390                 395                 400

Gly Asp Trp Cys Asn Val Lys Gly Thr Gly Phe Gly Val Arg Pro Thr
                405                 410                 415

Ala Asn Thr Gly His Glu Leu Val Asp Ala Phe Val Trp Val Lys Pro
                420                 425                 430

Gly Gly Glu Ser Asp Gly Thr Ser Asp Thr Ser Ala Ala Arg Tyr Asp
                435                 440                 445

Tyr His Cys Gly Leu Ser Asp Ala Leu Gln Pro Ala Pro Glu Ala Gly
                450                 455                 460

Gln Trp Phe Gln Ala Tyr Phe Glu Gln Leu Leu Thr Asn Ala Asn Pro
465                 470                 475                 480

Pro Phe

<210> SEQ ID NO 148
<211> LENGTH: 896
<212> TYPE: PRT
<213> ORGANISM: Artificial Sequence
<220> FEATURE:
<223> OTHER INFORMATION: S. f. BGLI

<400> SEQUENCE: 148

Met Val Ser Phe Thr Ser Leu Leu Ala Gly Val Ala Ala Ile Ser Gly
1               5                   10                  15

Val Leu Ala Ala Pro Ala Ala Glu Val Glu Ser Val Ala Val Glu Lys
                20                  25                  30

Arg Ser Asp Ser Arg Val Pro Ile Gln Asn Tyr Thr Gln Ser Pro Ser
            35                  40                  45

Gln Arg Asp Glu Ser Ser Gln Trp Val Ser Pro His Tyr Tyr Pro Thr
        50                  55                  60

Pro Gln Gly Gly Arg Leu Gln Asp Val Trp Gln Glu Ala Tyr Ala Arg
65                  70                  75                  80

Ala Lys Ala Ile Val Gly Gln Met Thr Ile Val Glu Lys Val Asn Leu
                85                  90                  95

Thr Thr Gly Thr Gly Trp Gln Leu Asp Pro Cys Val Gly Asn Thr Gly
            100                 105                 110

Ser Val Pro Arg Phe Gly Ile Pro Asn Leu Cys Leu Gln Asp Gly Pro
        115                 120                 125

Leu Gly Val Arg Phe Ala Asp Phe Val Thr Gly Tyr Pro Ser Gly Leu
    130                 135                 140

-continued

```
Ala Thr Gly Ala Thr Phe Asn Lys Asp Leu Phe Leu Gln Arg Gly Gln
145                 150                 155                 160

Ala Leu Gly His Glu Phe Asn Ser Lys Gly Val His Ile Ala Leu Gly
                165                 170                 175

Pro Ala Val Gly Pro Leu Gly Val Lys Ala Arg Gly Gly Arg Asn Phe
            180                 185                 190

Glu Ala Phe Gly Ser Asp Pro Tyr Leu Gln Gly Thr Ala Ala Ala Ala
        195                 200                 205

Thr Ile Lys Gly Leu Gln Glu Asn Asn Val Met Ala Cys Val Lys His
    210                 215                 220

Phe Ile Gly Asn Glu Gln Glu Lys Tyr Arg Gln Pro Asp Asp Ile Asn
225                 230                 235                 240

Pro Ala Thr Asn Gln Thr Thr Lys Glu Ala Ile Ser Ala Asn Ile Pro
                245                 250                 255

Asp Arg Ala Met His Glu Leu Tyr Leu Trp Pro Phe Ala Asp Ser Val
            260                 265                 270

Arg Ala Gly Val Gly Ser Val Met Cys Ser Tyr Asn Arg Val Asn Asn
        275                 280                 285

Thr Tyr Ala Cys Glu Asn Ser Tyr Met Met Asn His Leu Leu Lys Glu
    290                 295                 300

Glu Leu Gly Phe Gln Gly Phe Val Val Ser Asp Trp Gly Ala Gln Leu
305                 310                 315                 320

Ser Gly Val Tyr Ser Ala Ile Ser Gly Leu Asp Met Ser Met Pro Gly
                325                 330                 335

Glu Val Tyr Gly Gly Trp Asn Thr Gly Thr Ser Phe Trp Gly Gln Asn
            340                 345                 350

Leu Thr Lys Ala Ile Tyr Asn Glu Thr Val Pro Ile Glu Arg Leu Asp
        355                 360                 365

Asp Met Ala Thr Arg Ile Leu Ala Ala Leu Tyr Ala Thr Asn Ser Phe
    370                 375                 380

Pro Thr Glu Asp His Leu Pro Asn Phe Ser Ser Trp Thr Thr Lys Glu
385                 390                 395                 400

Tyr Gly Asn Lys Tyr Tyr Ala Asp Asn Thr Thr Glu Ile Val Lys Val
                405                 410                 415

Asn Tyr His Val Asp Pro Ser Asn Asp Phe Thr Glu Asp Thr Ala Leu
            420                 425                 430

Lys Val Ala Glu Glu Ser Ile Val Leu Leu Lys Asn Glu Asn Asn Thr
        435                 440                 445

Leu Pro Ile Ser Pro Glu Lys Ala Lys Arg Leu Leu Leu Ser Gly Ile
    450                 455                 460

Ala Ala Gly Pro Asp Pro Ile Gly Tyr Gln Cys Glu Asp Gln Ser Cys
465                 470                 475                 480

Thr Asn Gly Ala Leu Phe Gln Gly Trp Gly Ser Gly Ser Val Gly Ser
                485                 490                 495

Pro Lys Tyr Gln Val Thr Pro Phe Glu Glu Ile Ser Tyr Leu Ala Arg
            500                 505                 510

Lys Asn Lys Met Gln Phe Asp Tyr Ile Arg Glu Ser Tyr Asp Leu Ala
        515                 520                 525

Gln Val Thr Lys Val Ala Ser Asp Ala His Leu Ser Ile Val Val Val
    530                 535                 540

Ser Ala Ala Ser Gly Glu Gly Tyr Ile Thr Val Asp Gly Asn Gln Gly
545                 550                 555                 560

Asp Arg Arg Asn Leu Thr Leu Trp Asn Asn Gly Asp Lys Leu Ile Glu
```

```
                565                 570                 575
Thr Val Ala Glu Asn Cys Ala Asn Thr Val Val Val Thr Ser Thr
            580                 585                 590
Gly Gln Ile Asn Phe Glu Gly Phe Ala Asp His Pro Asn Val Thr Ala
            595                 600                 605
Ile Val Trp Ala Gly Pro Leu Gly Asp Arg Ser Gly Thr Ala Ile Ala
610                 615                 620
Asn Ile Leu Phe Gly Lys Ala Asn Pro Ser Gly His Leu Pro Phe Thr
625                 630                 635                 640
Ile Ala Lys Thr Asp Asp Asp Tyr Ile Pro Ile Glu Thr Tyr Ser Pro
            645                 650                 655
Ser Ser Gly Glu Pro Glu Asp Asn His Leu Val Glu Asn Asp Leu Leu
            660                 665                 670
Val Asp Tyr Arg Tyr Phe Glu Glu Lys Asn Ile Glu Pro Arg Tyr Ala
            675                 680                 685
Phe Gly Tyr Gly Leu Ser Tyr Asn Glu Tyr Glu Val Ser Asn Ala Lys
            690                 695                 700
Val Ser Ala Ala Lys Lys Val Asp Glu Glu Leu Pro Glu Pro Ala Thr
705                 710                 715                 720
Tyr Leu Ser Glu Phe Ser Tyr Gln Asn Ala Lys Asp Ser Lys Asn Pro
                    725                 730                 735
Ser Asp Ala Phe Ala Pro Thr Asp Leu Asn Arg Val Asn Glu Tyr Leu
            740                 745                 750
Tyr Pro Tyr Leu Asp Ser Asn Val Thr Leu Lys Asp Gly Asn Tyr Glu
            755                 760                 765
Tyr Pro Asp Gly Tyr Ser Thr Glu Gln Arg Thr Thr Pro Ile Gln Pro
770                 775                 780
Gly Gly Gly Leu Gly Gly Asn Asp Ala Leu Trp Glu Val Ala Tyr Lys
785                 790                 795                 800
Val Glu Val Asp Val Gln Asn Leu Gly Asn Ser Thr Asp Lys Phe Val
            805                 810                 815
Pro Gln Leu Tyr Leu Lys His Pro Glu Asp Gly Lys Phe Glu Thr Pro
            820                 825                 830
Ile Gln Leu Arg Gly Phe Glu Lys Val Glu Leu Ser Pro Gly Glu Lys
            835                 840                 845
Lys Thr Val Glu Phe Glu Leu Leu Arg Arg Asp Leu Ser Val Trp Asp
850                 855                 860
Thr Thr Arg Gln Ser Trp Ile Val Glu Ser Gly Thr Tyr Glu Ala Leu
865                 870                 875                 880
Ile Gly Val Ala Val Asn Asp Ile Lys Thr Ser Val Leu Phe Thr Ile
                    885                 890                 895

<210> SEQ ID NO 149
<211> LENGTH: 42
<212> TYPE: PRT
<213> ORGANISM: Artificial Sequence
<220> FEATURE:
<223> OTHER INFORMATION: Codon-Optimized linker 1

<400> SEQUENCE: 149

Gly Gly Gly Gly Ser Gly Gly Gly Gly Ser Ala Trp His Pro Gln Phe
1               5                   10                  15

Gly Gly Glu Asn Leu Tyr Phe Gln Gly Asp Tyr Lys Asp Asp Asp Lys
            20                  25                  30

Gly Gly Gly Gly Ser Gly Gly Gly Gly Ser
```

```
            35                  40
```

<210> SEQ ID NO 150
<211> LENGTH: 144
<212> TYPE: DNA
<213> ORGANISM: Artificial Sequence
<220> FEATURE:
<223> OTHER INFORMATION: Codon-Optimized polynucleotide

<400> SEQUENCE: 150

```
ggaggaggtg gttcaggagg tggtgggtct gcttggcatc cacaatttgg aggaggcggt    60
ggtgaaaatc tgtatttcca gggaggcgga ggtgattaca aggatgacga caaaggaggt   120
ggtggatcag gaggtggtgg ctcc                                         144
```

<210> SEQ ID NO 151
<211> LENGTH: 37
<212> TYPE: PRT
<213> ORGANISM: Artificial Sequence
<220> FEATURE:
<223> OTHER INFORMATION: flexible linker

<400> SEQUENCE: 151

Gly Gly Gly Gly Ser Gly Gly Gly Gly Ser Trp Ser His Pro Gln Phe
1               5                   10                  15

Glu Lys Gly Gly Glu Asn Leu Tyr Phe Gln Gly Gly Gly Gly Ser
            20                  25                  30

Gly Gly Gly Gly Ser
        35

<210> SEQ ID NO 152
<211> LENGTH: 117
<212> TYPE: DNA
<213> ORGANISM: Artificial Sequence
<220> FEATURE:
<223> OTHER INFORMATION: flexible linker

<400> SEQUENCE: 152

```
ggtggcggtg gatctggagg aggcggttct tggtctcacc cacaatttga aaagggtgga    60
gaaaacttgt actttcaagg cggtggtgga ggttctggcg aggtggctc cggctca       117
```

<210> SEQ ID NO 153
<211> LENGTH: 621
<212> TYPE: DNA
<213> ORGANISM: Clostridium thermocellum

<400> SEQUENCE: 153

```
gagtcgtgac taagaacgtc aaagtaatta acaatacagc tattttctc atgcttttac    60 ccctttcata aaatttaatt ttatcgttat cataaaaaat tatagacgtt atattgcttg   120
ccgggatata gtgctgggca ttcgttggtg caaaatgttc ggagtaaggt ggatattgat   180
ttgcatgttg atctattgca ttgaaatgat tagttatccg taaatattaa ttaatcatat   240
cataaattaa ttatatcata attgttttga cgaatgaagg ttttggata aattatcaag    300 taaaggaacg ctaaaaattt tggcgtaaaa tatcaaaatg accacttgaa ttaatatggt   360
aaagtagata taatatttg gtaaacatgc cttcagcaag gttagattag ctgtttccgt    420
ataaattaac cgtatggtaa acggcagtc agaaaaataa gtcataagat tccgttatga    480
aaatatactt cggtagttaa taataagaga tatgaggtaa gagatacaag ataagagata   540
taaggtacga atgtataaga tggtgctttt aggcacacta ataaaaaac aaataaacga    600
```

| aaattttaag gaggacgaaa g | 621 |

<210> SEQ ID NO 154
<211> LENGTH: 989
<212> TYPE: DNA
<213> ORGANISM: Artificial Sequence
<220> FEATURE:
<223> OTHER INFORMATION: Ldh downstream

<400> SEQUENCE: 154

| ctcatcgagg tatccaagcg attcaatagt aacagtcctt gtatgccctc tttctttatc | 60 |
| acgatatcca tctgcaatag ataggtatat tcttccggaa ctgcgtctac ttttctttaa | 120 |
| atacacatta aactccccca ataaaattca atataactat attataccac aatccataat | 180 |
| aatccgcaac caaaatatga caaaaattta aaaaatttt acccaaaatc gttagtaaaa | 240 |
| ttgctggttc cgggttacgc tacataaaat tttgctgcaa aactagggta aaaaaaatac | 300 |
| aaaccatgcg tcaatagaaa ttgacggcag tatattaaag cagtataatg aatatatgga | 360 |
| aaaacaaaag ggcaatataa tattaaaagg gaaatataaa cctgaatata aggaaaagtt | 420 |
| gcttaattta gccaaatttt ttactgataa tggctttgtt cctactgaac atgcattgaa | 480 |
| tgaaatactt gggaaaacag cttctggaag attgccagat gacaaacaga tgttattgga | 540 |
| tgtattacaa aatggtgaaa attatattga acctaatggc aatatagtca ggtataaaaa | 600 |
| tggcatatca atacatatcg ataaagaaca tggctggata attactataa ctccaaggaa | 660 |
| acgaatagta aaggaatgga ggcgaattaa tgagtaatgt cgcaatgcaa ttaatagaaa | 720 |
| tttgtcggaa atatgtaaat aataatttaa acataaatga atttatcgaa gactttcaag | 780 |
| tgctttatga acaaaagcaa gatttattga cagatgaaga aatgagcttg tttgatgata | 840 |
| tttatatggc ttgtgaatac tatgaacagg atgaaaatat aagaaatgaa tatcacttgt | 900 |
| atattggaga aaatgaatta agacaaaaag tgcaaaaact tgtaaaaaag ttagcagcat | 960 |
| aataaaccgc taaggcatga tagctaaag | 989 |

<210> SEQ ID NO 155
<211> LENGTH: 956
<212> TYPE: DNA
<213> ORGANISM: Artificial Sequence
<220> FEATURE:
<223> OTHER INFORMATION: Ldh downstream

<400> SEQUENCE: 155

| ccgcaagaga ttatatcgag tgcctttaag aaggctaaaa attacgaaga tgtgatacac | 60 |
| aaaaaggcaa agattacgg caaaaacata ccggatagtc aagttaaagg agtattgaaa | 120 |
| cagatagaga ttactgcctt aaaccatgta gacaagattg tcgctgctga aaagacgatg | 180 |
| cagatagatt ccctcgtgaa gaaaaatatg tcttatgata tgatggatgc attgcaggat | 240 |
| atagagaagg atttgataaa tcagcagatg ttctacaacg aaaatctaat aaacataacc | 300 |
| aatccgtatg tgaggcagat attcactcag atgagggatg atgagatgcg atttatcact | 360 |
| atcatacagc agaacataga atcgttaaag tcaaagccga ctgagcccaa cagcatagta | 420 |
| tatacgacgc cgagggaaaa taatgaaag tagctattat aggagcaggc tcggcaggct | 480 |
| taactgcagc tataaggctt gaatcttatg ggataaagcc tgatatattt gagagaaaat | 540 |
| cgaaagtcgg cgatgctttt aaccatgtag gaggactttt aaatgtcata ataggccaa | 600 |
| taatgatcc tttagagtat ctaaaaaata actttgatgt agctattgca ccgcttaaca | 660 |
| acatagacaa gattgtgatg catgggccaa cagtcactcg cacaattaaa ggcagaaggc | 720 |

| ttggatactt | tatgctgaaa | gggcaaggag | aattgtcagt | agaaagccaa | ctatacaaga | 780 |
| aattaaagac | aaatgtcaat | tttgatgtcc | acgcagacta | caagaaccta | aaggaaattt | 840 |
| atgattatgt | cattgtagca | actggaaatc | atcagatacc | aaatgagtta | ggatgttggc | 900 |
| agacgcttgt | tgatacgagg | cttaaaattg | ctgaggtaat | cggtaaattc | gacccg | 956 |

<210> SEQ ID NO 156
<211> LENGTH: 2128
<212> TYPE: DNA
<213> ORGANISM: Thermoanaerobacterium saccharolyticum

<400> SEQUENCE: 156

| ttattcaaaa | catcattgaa | aaagctaaaa | gcgataaaaa | gaaaattgtt | ctgccagaag | 60 |
| gtgcagaacc | caggacatta | aaagctgctg | aaatagtttt | aaaagaaggg | attgcagatt | 120 |
| tagtgcttct | tggaaatgaa | gatgagataa | gaatgctgc | aaaagacttg | acatatcca | 180 |
| aagctgaaat | cattgaccct | gtaaagtctg | aaatgtttga | taggtatgct | aatgatttct | 240 |
| atgagttaag | gaagaacaaa | ggaatcacgt | tggaaaaagc | cagagaaaca | atcaaggata | 300 |
| atatctattt | tggatgtatg | atggttaaag | aaggttatgc | tgatggattg | gtatctggcg | 360 |
| ctattcatgc | tactgcagat | ttattaagac | ctgcatttca | gataattaaa | acggctccag | 420 |
| gagcaaagat | agtatcaagc | tttttttataa | tggaagtgcc | taattgtgaa | tatggtgaaa | 480 |
| atggtgtatt | cttgtttgct | gattgtgcgg | tcaacccatc | gcctaatgca | gaagaacttg | 540 |
| cttctattgc | cgtacaatct | gctaatactg | caaagaattt | gttgggcttt | gaaccaaaag | 600 |
| ttgccatgct | atcattttct | acaaaaggta | gtgcatcaca | tgaattagta | gataaagtaa | 660 |
| gaaaagcgac | agagatagca | aaagaattga | tgccagatgt | tgctatcgac | ggtgaattgc | 720 |
| aattggatgc | tgctcttgtt | aaagaagttg | cagagctaaa | agcgccggga | agcaaagttg | 780 |
| cgggatgtgc | aaatgtgctt | atattccctg | atttacaagc | tggtaatata | ggatataagc | 840 |
| ttgtacagag | gttagctaag | gcaaatgcaa | ttggacctat | aacacaagga | atgggtgcac | 900 |
| cggttaatga | tttatcaaga | ggatgcagct | atagagatat | tgttgacgta | atagcaacaa | 960 |
| cagctgtgca | ggctcaataa | aatgtaaagt | atggaggatg | aaaattatga | aaatactggt | 1020 |
| tattaattgc | ggaagttctt | cgctaaaata | tcaactgatt | gaatcaactg | atggaaatgt | 1080 |
| gttggcaaaa | ggccttgctg | aaagaatcgg | cataaatgat | tccatgttga | cacataatgc | 1140 |
| taacggagaa | aaaatcaaga | taaaaaaaga | catgaaagat | cacaaagacg | caataaaatt | 1200 |
| ggttttagat | gctttggtaa | acagtgacta | cggcgttata | aaagatatgt | ctgagataga | 1260 |
| tgctgtagga | catagagttg | ttcacggagg | agaatctttt | acatcatcag | ttctcataaa | 1320 |
| tgatgaagtg | ttaaaagcga | taacagattg | catagaatta | gctccactgc | acaatcctgc | 1380 |
| taatatagaa | ggaattaaag | cttgccagca | aatcatgcca | aacgttccaa | tggtggcggt | 1440 |
| atttgataca | gcctttcatc | agacaatgcc | tgattatgca | tatctttatc | caatacctta | 1500 |
| tgaatactac | acaaagtaca | ggattagaag | atatggattt | catggcacat | cgcataaata | 1560 |
| tgtttcaaat | agggctgcag | agattttgaa | taaacctatt | gaagatttga | aaatcataac | 1620 |
| ttgtcatctt | ggaaatggct | ccagcattgc | tgctgtcaaa | tatggtaaat | caattgacac | 1680 |
| aagcatggga | tttacaccat | tagaaggttt | ggctatgggt | acacgatctg | gaagcataga | 1740 |
| cccatccatc | atttcgtatc | ttatggaaaa | agaaaatata | agcgctgaag | aagtagtaaa | 1800 |
| tatattaaat | aaaaaaatctg | gtgtttacgg | tatttcagga | ataagcagcg | attttagaga | 1860 |

| | |
|---|---|
| cttagaagat gccgccttta aaaatggaga tgaaagagct cagttggctt taaatgtgtt | 1920 |
| tgcatatcga gtaaagaaga cgattggcgc ttatgcagca gctatgggag gcgtcgatgt | 1980 |
| cattgtattt acagcaggtg ttggtgaaaa tggtcctgag atacgagaat ttatacttga | 2040 |
| tggattagag ttttttagggt tcagcttgga taaagaaaaa aataaagtca gaggaaaaga | 2100 |
| aactattata tctacgccga attcaaaa | 2128 |

<210> SEQ ID NO 157
<211> LENGTH: 409
<212> TYPE: DNA
<213> ORGANISM: Thermoanaerobacterium saccharolyticum

<400> SEQUENCE: 157

| | |
|---|---|
| cgtgcccatt gtgaagtgga ttgtattcta caattaaacc taatacgctc ataatatgcg | 60 |
| cctttctaaa aaattattaa ttgtacttat tattttataa aaaatatgtt aaaatgtaaa | 120 |
| atgtgtatac aatatatttc ttcttagtaa gaggaatgta taaaaataaa tattttaaag | 180 |
| gaagggacga tcttatgagc agttagcgtg atggttgtgc ctactaatga agaatacatg | 240 |
| attgctaaag atactgaaaa gattgtaaag agtataaaat agcattcttg acaaatgttt | 300 |
| accccattag tataattaat tttggcaatt atattggggt gagaaaatga aaattgattt | 360 |
| atcaaaaatt aaaggacata ggggccgcag catcgaagtc aactacgta | 409 |

<210> SEQ ID NO 158
<211> LENGTH: 1236
<212> TYPE: DNA
<213> ORGANISM: Thermoanaerobacterium saccharolyticum

<400> SEQUENCE: 158

| | |
|---|---|
| cggtattttt atgcaattaa aaggatgaaa tgatatctga taaactgcga aaaagtattt | 60 |
| tagaaaataa ctataaagat aatatttcaa atcaataagg acaaaataag attaaaattt | 120 |
| agacaatttc atcaaaacta tgttataata ttattaaagg aaaatacata ttatttagga | 180 |
| ggcgatgtaa tgagcaaggt agcaataata ggatctggtt ttgtaggtgc aacatcggca | 240 |
| tttacgctgg cattaagtgg gactgtgaca gatatcgtgc tggtggattt aaacaaggac | 300 |
| aaggctatag gcgatgcact ggacataagc catggcatac cgctaataca gcctgtaaat | 360 |
| gtgtatgcag gtgactacaa agatgtgaaa ggcgcagatg taatagttgt gacagcaggt | 420 |
| gctgctcaaa agccgggaga gacacggctt gaccttgtaa agaaaaatac agccatattt | 480 |
| aagtccatga tacctgagct tttaaagtac aatgacaagg ccatatattt gattgtgaca | 540 |
| aatcccgtag atatactgac gtacgttaca tacaagattt ctggacttcc atggggcaga | 600 |
| gttttggtt ctggcaccgt tcttgacagc tcaaggttta gataccttt aagcaagcac | 660 |
| tgcaatatag atccgagaaa tgtccacgga aggataatcg gcgagcatgg tgacacagag | 720 |
| tttgcagcat ggagcataac aaacatatcg ggtatatcat ttaatgagta ctgcagcata | 780 |
| tgccggacgcg tctgcaacac aaatttcaga aggaagtag aagaagaagt cgtaaatgct | 840 |
| gcttacaaga taatagacaa aaaaggtgct acatactatg ctgtggcagt tgcagtaaga | 900 |
| aggattgtgg agtgcatctt aagagatgaa aattccatcc tcacagtatc atctccatta | 960 |
| aatggacagt acggcgtgaa agatgtttca ttaagcttgc catctatcgt aggcaggaat | 1020 |
| ggcgttgcca ggattttgga cttgccttta tctgacgaag aagtggagaa gtttaggcat | 1080 |
| tcagcaagtg tcatggcaga tgtcataaaa caattagata tataatcaaa ttatgttggg | 1140 |
| aggcttcaca tatgtgtggt gaggcctctt tttatgtata taagggatgc aatgtggaaa | 1200 |

```
atctaataac ggtgatgcaa aatgcagaat atgagc                                1236
```

```
<210> SEQ ID NO 159
<211> LENGTH: 379
<212> TYPE: DNA
<213> ORGANISM: Thermoanaerobacterium saccharolyticum
<220> FEATURE:
<221> NAME/KEY: misc_feature
<222> LOCATION: (238)..(238)
<223> OTHER INFORMATION: n is a, c, g, or t

<400> SEQUENCE: 159
gtaaataata atttaaacat aaatgaattt atcgaagact ttcaagtgct ttatgaacaa      60
aagcaagatt tattgacaga tgaagaaatg agcttgtttg atgatattta tatggcttgt     120
gaatactatg aacaggatga aaatataaga aatgaatatc acttgtatat tggagaaaat     180
gaattaagac aaaaagtgca aaaacttgta aaaagttag cagcataata aaccgctnag      240
gcatgatagc taaagcccgc aagagattat atcgagtgcc tttaagaagg ctaaaaatta    300
cgaagatgtg atacacaaaa aggcaaaaga ttacggcaaa aacataccgg atagtcaagt    360
taaaggagta ttgaaacag                                                 379
```

```
<210> SEQ ID NO 160
<211> LENGTH: 6
<212> TYPE: PRT
<213> ORGANISM: Artificial Sequence
<220> FEATURE:
<223> OTHER INFORMATION: 6X His

<400> SEQUENCE: 160

His His His His His His
1               5
```

```
<210> SEQ ID NO 161
<211> LENGTH: 8
<212> TYPE: PRT
<213> ORGANISM: Artificial Sequence
<220> FEATURE:
<223> OTHER INFORMATION: Flag

<400> SEQUENCE: 161

Asp Tyr Lys Asp Asp Asp Asp Lys
1               5
```

```
<210> SEQ ID NO 162
<211> LENGTH: 9
<212> TYPE: PRT
<213> ORGANISM: Artificial Sequence
<220> FEATURE:
<223> OTHER INFORMATION: Hemagglutinin

<400> SEQUENCE: 162

Tyr Pro Tyr Asp Val Pro Asp Tyr Ala
1               5
```

```
<210> SEQ ID NO 163
<211> LENGTH: 199
<212> TYPE: DNA
<213> ORGANISM: Artificial Sequence
<220> FEATURE:
<223> OTHER INFORMATION: E.coli T1 and T2 terminator

<400> SEQUENCE: 163
aacgaaaggc tcagtcgaaa gactgggcct ttcgttttat ctgttgtttg tcggtgaacg     60
```

```
ctctcctgag taggacaaat ccgccgggag cggatttgaa cgttgcgaag caacggcccg    120
gagggtggcg ggcaggacgc ccgccataaa ctgccaggca tcaaattaag cagaaggcca    180
tcctgacgga tggcctttt                                                 199
```

<210> SEQ ID NO 164
<211> LENGTH: 373
<212> TYPE: PRT
<213> ORGANISM: Artificial Sequence
<220> FEATURE:
<223> OTHER INFORMATION: Trypsin-like serine protease typically periplasmic contain C-terminal PDZ domain peptidase S1 and S6 chymotrypsin

<400> SEQUENCE: 164

```
Met Gln Asn Gly Asp Asn Arg Asn Val Lys Arg Pro Ser Tyr Leu Thr
1               5                   10                  15

Thr Val Ile Val Ile Ala Val Ile Thr Ser Leu Ile Phe Thr Tyr Ile
            20                  25                  30

Ala Pro Lys Phe Leu Trp Gly Lys Val Ile Pro Leu Pro Tyr Thr Asn
        35                  40                  45

Thr Ala Pro Leu Lys Lys Glu Val Ile Pro Lys Ala Glu Pro Ser
    50                  55                  60

Thr Ile Ala Glu Ala Val Ala Lys Lys Asp Thr Gln Ala Val Val Gly
65                  70                  75                  80

Ile Ser Ser Ile Glu Tyr Glu Arg Gln Tyr Tyr Ile Leu Glu Lys Gln
                85                  90                  95

Val Glu Gly Val Gly Ser Gly Phe Ile Val Asp Lys Asn Gly Tyr Ile
            100                 105                 110

Ile Thr Asn Asn His Val Ala Ser Pro Glu Ser Lys Lys Leu Thr Ile
        115                 120                 125

Tyr Leu Ser Asp Gly Ser Thr Leu Pro Gly Lys Val Leu Trp Ser Asp
    130                 135                 140

Ser Thr Leu Asp Leu Ser Val Val Lys Ile Asn Ala Lys Asn Leu Pro
145                 150                 155                 160

Thr Ile Pro Leu Gly Asp Ser Asp Lys Val Gln Val Gly Gln Thr Val
                165                 170                 175

Ile Ala Ile Gly Asn Pro Leu Gly Leu Arg Phe Glu Arg Thr Val Thr
            180                 185                 190

Ser Gly Ile Ile Ser Ala Leu Asn Arg Ser Leu Pro Leu Glu Glu Asn
        195                 200                 205

Asn Lys Gln Lys Ile Met Glu Asp Leu Ile Gln Thr Asp Ala Ser Ile
    210                 215                 220

Asn Pro Gly Asn Ser Gly Gly Pro Leu Val Asp Ala Gln Gly Asn Ala
225                 230                 235                 240

Ile Gly Ile Asn Thr Ala Lys Val Thr Thr Ala Glu Gly Leu Gly Phe
                245                 250                 255

Ala Ile Pro Ile Asn Ile Val Lys Pro Ile Ile Lys Lys Val Ile Ala
            260                 265                 270

Thr Gly Thr Phe Lys Ala Pro Tyr Leu Gly Ile Val Gly Tyr Asp Arg
        275                 280                 285

Glu Ile Ala Ser Tyr Ile Asn Ala Asp Val Val Ile Ala Glu Gly Ile
    290                 295                 300

Tyr Val Ala Asp Ile Asp Pro Ala Gly Pro Ala Lys Lys Ala Gly Ile
305                 310                 315                 320
```

```
Lys Lys Gly Tyr Ile Leu Leu Glu Val Asp Gly Lys Pro Val Asp Thr
                325                 330                 335

Met Val Gln Leu Lys Thr Val Ile Tyr Ser Arg Asn Ile Gly Asp Lys
            340                 345                 350

Val Ser Val Lys Tyr Arg Thr Leu Thr Gly Asn Ile Gly Met Thr Thr
        355                 360                 365

Ile Thr Leu Gly Lys
    370

<210> SEQ ID NO 165
<211> LENGTH: 451
<212> TYPE: PRT
<213> ORGANISM: Artificial Sequence
<220> FEATURE:
<223> OTHER INFORMATION: Trypsin-like serine protease typically
      periplasmic contain C-terminal PDZ domain 2-alkenal reductase

<400> SEQUENCE: 165

Met Asp Ile Glu Asn Glu Gln Thr Lys Arg Leu Asn Glu Asn Asp Met
1               5                   10                  15

Glu Asn Leu Asn Glu Asn Ala Asp Asp Val Val Thr Glu Asn Phe Thr
            20                  25                  30

Asn Asn Asp Leu Asn Lys Ile His Lys Val Ser Met Thr Asn Asp Tyr
        35                  40                  45

Gln Asp Lys Asn Asp Glu Glu Asn Ala Lys Asn Asp Leu Glu Asn Ser
    50                  55                  60

Lys Lys Ser Val Gly Lys Ile Ile Lys Arg Phe Arg Arg Arg Met Leu
65                  70                  75                  80

Ala Ser Phe Ile Val Val Ala Leu Ile Ala Ala Leu Ile Gly Gly Gly
                85                  90                  95

Ile Val Gly Gly Ile Met Val Tyr Thr Asn Ser Gly Gln Lys Thr Gln
            100                 105                 110

Val Ile Asn Arg Tyr Leu Pro Leu Ser Ser Asn Asn Ser Asn Ser Asn
        115                 120                 125

Leu Ile Val Asn Ile Ala Lys Ile Val Ser Pro Ser Val Val Gly Ile
    130                 135                 140

Asp Thr Ser Ala Thr Tyr Ser Asn Gly Phe Arg Ser Ala Phe Val Ser
145                 150                 155                 160

Glu Gly Ser Gly Ser Gly Ile Ile Ile Asp Ser Gln Gly Tyr Ile Val
                165                 170                 175

Thr Asn Tyr His Val Ile Glu Gly Ala Ser Thr Ile Thr Val Ser Leu
            180                 185                 190

Ser Asp Gly Arg Lys Phe Ser Ala Gln Leu Ile Gly Lys Asp Ser Asn
        195                 200                 205

Thr Asp Leu Ala Val Leu Lys Ile Asn Ala Thr Asn Leu Thr Ala Ala
    210                 215                 220

Lys Leu Gly Asp Ser Ser Lys Leu Glu Val Gly Asp Leu Ala Val Ala
225                 230                 235                 240

Ile Gly Asn Pro Leu Gly Glu Ser Phe Ala Gly Thr Val Thr Ala Gly
                245                 250                 255

Ile Ile Ser Gly Leu Asn Arg Asn Leu Gln Ser Asp Tyr Gly Pro Val
            260                 265                 270

Asn Leu Ile Gln Thr Asp Ala Ala Ile Asn Pro Gly Asn Ser Gly Gly
        275                 280                 285

Pro Leu Val Asn Ser Asn Gly Glu Val Val Gly Ile Thr Ser Val Lys
    290                 295                 300
```

Leu Thr Ser Thr Asp Asp Asn Ser Thr Gln Ser Ser Phe Gly Met Phe
305                 310                 315                 320

Gln Ser Gln Ser Thr Pro Val Glu Gly Met Gly Phe Ala Ile Pro Ile
            325                 330                 335

Asn Glu Ala Lys Pro Ile Ile Asn Glu Leu Ile Lys His Gly Tyr Val
        340                 345                 350

Glu Arg Pro Met Met Gly Val Ser Val Gln Glu Val Thr Gln Gln Asp
    355                 360                 365

Ala Ala Gln Tyr Asn Ile Pro Val Gly Leu Tyr Ile Ala Gln Val Gln
370                 375                 380

Gln Gly Ser Gly Ala Asp Glu Ala Gly Leu Gln Ala Gly Asp Val Ile
385                 390                 395                 400

Thr Ala Val Asp Gly Thr Lys Val Gln Thr Phe Asp Ala Leu Gln Ser
                405                 410                 415

Ile Ile Ser Lys His Lys Val Gly Asp Thr Ile Thr Val Thr Phe Trp
            420                 425                 430

Arg Asn Gly Arg Thr Met Ser Thr Lys Val Lys Leu Met Ser Ser Ser
        435                 440                 445

Asn Ala Gln
    450

<210> SEQ ID NO 166
<211> LENGTH: 451
<212> TYPE: PRT
<213> ORGANISM: Artificial Sequence
<220> FEATURE:
<223> OTHER INFORMATION: Trypsin-like serine protease typically
      periplasmic contain C-terminal PDZ domain 2-alkenal reductase

<400> SEQUENCE: 166

Met Asp Phe Glu Asn Glu Gln Asn Lys Asn Ile Gly Glu Asn Glu Ile
1               5                   10                  15

Asp Asn Phe Arg Thr Asp Ala Leu Gly Ser Asp Ile Lys Gly
            20                  25                  30

Glu Asn Ile Asp Asp Thr Gln Glu Ile Lys Ala Thr Tyr Gly Ala Glu
            35                  40                  45

Glu Ser Gly Thr Tyr Thr Asn Pro Arg Val Glu Phe Arg Ser Asn Lys
    50                  55                  60

Lys Ser Leu Gly Lys Met Val Lys Arg Phe Arg Arg Met Leu Val
65                  70                  75                  80

Ser Phe Val Ala Val Ala Leu Ile Ala Ala Leu Ile Gly Gly Gly Thr
                85                  90                  95

Val Ala Gly Ile Met Lys Tyr Thr Asn Leu Gly Gln Gln Thr Gln Val
                100                 105                 110

Ile Asn Arg Tyr Leu Pro Leu Ser Ser Ser Asp Asn Asn Tyr Ser
            115                 120                 125

Leu Ile Ala Asn Ile Ala Lys Ile Val Ser Pro Ser Val Val Gly Ile
    130                 135                 140

Asp Thr Ser Val Ser Tyr Ser Asn Gly Phe Gly Ser Ala Leu Val Pro
145                 150                 155                 160

Glu Gly Ser Gly Ser Gly Ile Ile Ile Asp Ser Gln Gly Tyr Ile Val
                165                 170                 175

Thr Asn Asn His Val Val Asp Gly Ala Ser Lys Ile Thr Val Asn Leu
                180                 185                 190

Ser Asp Gly Arg Lys Phe Pro Ala Gln Leu Ile Gly Lys Asp Ser Lys

```
                   195                 200                 205

Thr Asp Leu Ala Val Leu Lys Ile Asn Ala Thr Asn Leu Ile Pro Ala
    210                 215                 220

Lys Leu Gly Asp Ser Ser Lys Leu Glu Val Gly Asp Leu Ala Val Ala
225                 230                 235                 240

Ile Gly Asn Pro Leu Gly Glu Ser Phe Ala Gly Thr Val Thr Ala Gly
                245                 250                 255

Ile Ile Ser Gly Leu Asn Arg Asn Leu Gln Ser Asp Tyr Gly Pro Val
            260                 265                 270

Asn Leu Ile Gln Thr Asp Ala Ala Ile Asn Pro Gly Asn Ser Gly Gly
        275                 280                 285

Pro Leu Val Asn Ser Asn Gly Glu Val Val Gly Ile Thr Ser Val Lys
    290                 295                 300

Leu Thr Ser Thr Gly Gly Ser Asp Thr Gln Asp Pro Phe Gly Met Phe
305                 310                 315                 320

Gln Ser Gln Ser Thr Pro Val Glu Gly Met Gly Phe Ala Ile Pro Ile
                325                 330                 335

Asn Glu Ala Lys Pro Ile Ile Asp Asp Leu Ile Lys His Gly Tyr Val
            340                 345                 350

Glu Arg Pro Met Met Gly Val Ser Val Gln Glu Val Thr Gln Gln Asp
        355                 360                 365

Ala Ala Gln Tyr Asn Ile Pro Val Gly Leu Tyr Ile Ala Gln Val Gln
    370                 375                 380

Gln Gly Ser Gly Ala Asp Glu Ala Gly Leu Gln Ala Gly Asp Val Ile
385                 390                 395                 400

Thr Ala Val Asp Gly Thr Lys Val Gln Thr Phe Asp Ala Leu Gln Ser
                405                 410                 415

Ile Ile Ser Lys His Lys Val Gly Asp Thr Ile Thr Val Thr Phe Trp
            420                 425                 430

Arg Asn Gly Arg Thr Met Ser Thr Lys Val Lys Leu Met Ser Ser Ser
        435                 440                 445

Asn Ala Gln
    450

<210> SEQ ID NO 167
<211> LENGTH: 408
<212> TYPE: PRT
<213> ORGANISM: Artificial Sequence
<220> FEATURE:
<223> OTHER INFORMATION: Trypsin-like serine protease typically
      periplasmic contain C-terminal PDZ domain 2-alkenal reductase

<400> SEQUENCE: 167

Met Glu Phe Asn Asn Gly Phe Glu Asn Tyr Arg Leu Pro Asp Val Asn
1               5                   10                  15

Pro Lys Asn Asp Lys Lys Ser Leu Gly Lys Met Val Lys Arg Tyr Arg
            20                  25                  30

Arg Lys Met Phe Met Ser Phe Val Ala Val Ala Leu Val Ala Ala Leu
        35                  40                  45

Ala Gly Gly Ala Leu Gly Ala Gly Ile Val Lys Tyr Ala Asp Thr Gly
    50                  55                  60

Asn Thr Gln Val Val Asn Arg Tyr Leu Pro Leu Ser Ser Asp Asn Asn
65              70                  75                  80

Asn Phe Asn Leu Ile Thr Asn Ile Val Lys Ala Val Ser Pro Ser Val
                85                  90                  95
```

```
Val Gly Ile Asp Thr Tyr Ile Ser Gly Tyr Ala Tyr Gly Tyr Gly
            100                 105                 110

Gly Asn Ser Tyr Val Glu Glu Gly Ser Gly Ser Gly Ile Ile Ile Asp
            115                 120                 125

Ser Glu Gly His Ile Val Thr Asn Asp His Val Val Glu Gly Ala Ser
130                 135                 140

Lys Ile Thr Val Asn Leu Ser Asp Gly Arg Lys Phe Pro Ala Gln Leu
145                 150                 155                 160

Val Gly Lys Asp Ser Arg Thr Asp Leu Ala Val Leu Lys Ile Asn Ala
                165                 170                 175

Thr Asn Leu Thr Pro Ala Lys Leu Gly Asp Ser Ser Lys Leu Glu Val
            180                 185                 190

Gly Glu Leu Ala Val Ala Ile Gly Asn Pro Leu Gly Asp Ser Phe Ala
            195                 200                 205

Gly Thr Ala Thr Ala Gly Ile Ile Ser Gly Leu Asn Arg Asn Leu Gln
            210                 215                 220

Ser Asp Tyr Gly Pro Val Asn Leu Ile Gln Thr Asp Ala Ala Ile Asn
225                 230                 235                 240

Pro Gly Asn Ser Gly Gly Pro Leu Val Asn Ser Val Gly Glu Val Ile
                245                 250                 255

Gly Ile Thr Ser Ile Lys Leu Thr Ser Thr Gly Gly Ser Ser Ser Gly
            260                 265                 270

Asp Pro Phe Gly Leu Phe Gln Ser Gln Ser Val Pro Leu Glu Gly Met
            275                 280                 285

Gly Phe Ala Ile Pro Ile Asn Glu Ala Lys Pro Ile Ile Glu Glu Leu
            290                 295                 300

Ile Arg Lys Gly Tyr Val Glu Arg Pro Val Ile Gly Val Ser Val Gln
305                 310                 315                 320

Gln Ile Thr Gln Gln Gln Ala Asn Gln Tyr Asn Ile Pro Val Gly Leu
            325                 330                 335

Tyr Ile Ala Gln Val Gln Gln Gly Ser Gly Ala Asp Ala Ala Gly Leu
            340                 345                 350

Gln Ala Gly Asp Ile Ile Thr Ala Val Asp Gly Thr Asn Val Thr Thr
            355                 360                 365

Phe Asn Gln Leu Glu Asn Ile Leu Asn Asn His Lys Ile Gly Asp Val
            370                 375                 380

Ile Ser Val Thr Val Trp Arg Asn Gly Gln Thr Leu Thr Val Asn Val
385                 390                 395                 400

Lys Leu Ser Gly Ser Asn Gly Gln
            405

<210> SEQ ID NO 168
<211> LENGTH: 413
<212> TYPE: PRT
<213> ORGANISM: Artificial Sequence
<220> FEATURE:
<223> OTHER INFORMATION: Subtilisin-like serine protease peptidase S8
      and S53 subtilisin kexin sedolisin

<400> SEQUENCE: 168

Met Asp Ile Ile Ser Ala Leu Ile Leu Ser Ser Val Ile Gln Ser Leu
1               5                   10                  15

Tyr Pro Lys Ser Lys Ile Asp Ser Arg Leu Leu Arg Lys Ala Ser Ile
            20                  25                  30

Tyr Arg Ser Glu Cys Val Ser Ala Ile Val Tyr Ser Asn Leu Pro Tyr
        35                  40                  45
```

Asp Ala Leu Lys Lys Ile Glu Ser Ile Gly Gly Thr Ile Lys Tyr
         50                  55                  60

Glu Leu Pro Ile Ile Asn Gly Trp Ala Val Asn Ile Pro Cys Asn Lys
 65                  70                  75                  80

Leu Asn Ile Ile Ala Lys Asn Lys Gly Ile Lys Phe Ile Ala Glu Asp
                 85                  90                  95

Ser Thr Val Lys Thr Gln Leu Asn Ile Ala Thr Gln Glu Ile Lys Ser
                100                 105                 110

Arg Glu Ala Asn Asp His Gly Tyr Thr Gly Lys Gly Val Thr Ile Ala
                115                 120                 125

Phe Leu Asp Thr Gly Ile Tyr Pro His Pro Asp Phe Thr Lys Pro Lys
130                 135                 140

Asn Arg Ile Ile Ala Phe His Asp Ile Val Asn Gly Lys Lys Ser Pro
145                 150                 155                 160

Tyr Asp Asp Asn Gly His Gly Thr His Val Ala Gly Asp Ala Ala Ser
                165                 170                 175

Ser Gly Tyr Leu Ser Asp Gly Lys Tyr Lys Gly Val Ala Pro Glu Ala
                180                 185                 190

Asn Ile Val Ser Val Lys Val Leu Asp Ser Arg Gly Ser Gly Ser Thr
                195                 200                 205

Ser Asp Ile Leu Ser Gly Met Gln Trp Ile Leu Asp Asn Lys Asp Lys
210                 215                 220

Tyr Asn Ile Arg Ile Val Ser Leu Ser Ile Gly Glu Thr Pro Ser Leu
225                 230                 235                 240

Pro Pro Phe Leu Asp Pro Leu Val Lys Gly Val Asp Arg Leu Trp Arg
                245                 250                 255

Ser Gly Leu Val Val Val Val Ala Ala Gly Asn Ser Gly Pro Ser Met
                260                 265                 270

Asn Ser Ile Thr Ser Pro Gly Asn Ser Met Asn Val Ile Thr Val Gly
                275                 280                 285

Ala Val Asp Asp Lys Arg Thr Val Asp Thr Ser Asp Asp Glu Ile Ala
                290                 295                 300

Asn Phe Ser Gly Arg Gly Ser Ala Phe Leu Pro Lys Pro Asp Val Val
305                 310                 315                 320

Ala Pro Gly Val Lys Ile Val Ser Ala Ser Gly Asn Val Pro Ile
                325                 330                 335

Gly Thr Asp Asp Asn Ile Leu Leu Asn Lys Ser Tyr Arg Thr Ala Ser
                340                 345                 350

Gly Thr Ser Met Ala Thr Pro Ile Val Ala Gly Ala Ala Leu Leu
                355                 360                 365

Leu Glu Lys Asn Pro Ser Leu Thr Asn Tyr Gln Ile Lys Asn Ile Leu
370                 375                 380

Lys Ser Thr Thr Thr Asn Val Asp His Tyr Arg Tyr Ser Gln Gly
385                 390                 395                 400

Tyr Gly Met Ile Asn Val Glu Met Ala Leu Lys Lys Val
                405                 410

<210> SEQ ID NO 169
<211> LENGTH: 1750
<212> TYPE: DNA
<213> ORGANISM: Artificial Sequence
<220> FEATURE:
<223> OTHER INFORMATION: Codon-Optimized Trichoderma reesei
      Exo-glucanase 1

<400> SEQUENCE: 169

```
atgtacagaa agttagcagt cataagcgct tttcttgcaa cagctagggc acaatctgct      60
tgtactttgc agagcgaaac acatcctcca ttaacttggc aaaaatgcag ttcaggcggt     120
acatgtactc agcaaacagg cagcgtagtt atagatgcaa attggaggtg acgcacgct     180
actaatagca gtacaaattg ctacgacgga atacttggt caagcactct ttgtcctgat     240
aacgaaacat gtgcaaagaa ttgttgctta gatggtgctg catatgctag tacgtatggc     300
gtaactacga gcggcaattc attatctata ggttttgtta cacagagcgc acaaaagaac     360
gtgggcgcta ggttatatct tatggcatca gacactacat accaggagtt tacattactt     420
ggaaacgaat ttagctttga tgtagacgtc agtcaattgc catgtggcct taacggcgct     480
ttgtattttg tatcaatgga cgcagatgga ggcgtttcta atacccgac aaacactgct      540
ggtgcaaaat acggaactgg ttattgcgat agtcaatgtc aagggatttt aaagtttatt     600
aatggccagg caaatgttga aggatgggaa cctagttcta acaatgcaaa tactggcatt     660
ggaggacatg gttcatgctg tagtgaaatg gatatatggg aagcaaactc tataagcgag     720
gctttgactc cgcatccttg cacgacagtg ggccaagaga tttgtgaagg cgatggttgc     780
ggaggcactt actcagacaa taggtacggc ggtacgtgtg atccagatgg ctgcgactgg     840
aatccttaca gacttggtaa cacttctttt tatggaccgg ttcttctttt tacgcttgac     900
actacaaaaa aattgacagt tgtgactcag tttgaaacgt ctggcgcaat aaatagatac     960
tatgttcaaa acggtgtaac gtttcagcaa ccgaatgctg agcttggctc ttattcaggt    1020
aacgaattaa atgacgatta ttgtacagca gaagaggcta atttggagg ctctagtttt     1080
tcagataagg gaggtttaac acagtttaag aaagctacga gtggtggcat ggtacttgta    1140
atgagcttat gggatgatta ctacgctaat atgttgtggc ttgattcaac ttacccaact    1200
aacgaaacaa gcagtactcc tggcgcagta aggggttcat gcagcacgtc atctggtgta    1260
ccggctcagg tcgagagtca aagtcctaac gctaaggtta cttttttcaaa cataaaattt    1320
ggacctatag gatctacagg aaaccctagc ggaggcaacc cacctggagg taacagaggc    1380
acgacgacaa caagaaggcc agctacaaca actggctcta gcccaggccc gactcagtca    1440
cattacggtc agtgcggagg tataggttac agtggcccta ctgtctgcgc aagcggaact    1500
acatgtcagg tcttgaaccc ttattactct caatgcttgc tcgagtgata aaacgaaagg    1560
ctcagtcgaa agactgggcc tttcgtttta tctgttgttt gtcggtgaac gctctcctga    1620
gtaggacaaa tccgccggga gcggatttga acgttgcgaa gcaacggccc ggagggtggc    1680
gggcaggacg cccgccataa actgccaggc atcaaattaa gcagaaggcc atcctgacgg    1740
atggcctttt                                                           1750
```

<210> SEQ ID NO 170  
<211> LENGTH: 1413  
<212> TYPE: DNA  
<213> ORGANISM: Artificial Sequence  
<220> FEATURE:  
<223> OTHER INFORMATION: Codon-Optimized Trichoderma reesei CBH2

<400> SEQUENCE: 170

```
atgatagtag gaattttaac tacgttagca acattggcaa ctttggctgc aagcgtacct      60
ttagaagaga gacaagcatg ttctagcgtg tggggccagt gcggtggaca aaattggagt     120
ggacctacat gttgcgctag cggtagtact tgcgtataca gcaacgatta ctattctcaa     180
tgccttcctg gcgcagctag ctcttcttca agtacaaggg ctgctagcac gacttcaaga     240
```

```
gtttcaccga ctacgtctag gtctagctca gctactcctc cacctggtag tacaacaact    300
agagtgcctc cggtgggttc tggcacagct acttacagcg gtaatccatt tgttggcgta    360
actccttggg caaacgctta ttacgcatca gaagtgagtt ctttagcaat tccatctttg    420
acaggcgcta tggctacagc agcagctgct gttgctaaag taccttcatt tatgtggttg    480
gacactttag ataaaactcc tcttatggag cagacgttag cagatattag gacagctaac    540
aaaaatggtg gcaattatgc tggacagttt gtagtctacg accttcctga cagggattgt    600
gctgcacttg cttctaacgg tgaatactca atagcagacg gcggcgtcgc taagtataaa    660
aattacattg atacgattag acagatagtt gtagagtact cagatataag gacattgttg    720
gtgattgagc cggacagcct tgcaaattta gttactaatt tgggtacacc taaatgcgct    780
aacgcacagt cagcatattt agaatgcata aactacgcag tcacacaatt aaacttgcca    840
aatgtggcta tgtaccttga cgctggacat gctggctggt taggttggcc tgcaaatcaa    900
gatccggctg cacaattgtt tgcaaacgtt tacaagaatg cttcaagtcc tagagcactt    960
aggggacttg caactaatgt ggctaactat aatggctgga cataacaag cccaccttct    1020
tacactcagg gaaatgctgt ttataacgaa agttgtata ttcacgcaat aggtcctttg    1080
ttggcaaacc acggttggtc taatgcattt tttattacag accagggtag aagtggaaaa    1140
caacctacag gacagcaaca gtggggtgat tggtgtaacg taattggcac tggatttggc    1200
ataaggccat cagcaaatac gggtgactct tgttggaca gttttgtgtg ggtcaagcca    1260
ggcggtgagt gtgatggaac gtctgactca agcgctccaa gatttgactc acactgcgca    1320
ttaccggatg ctttacaacc agctcctcaa gcaggcgcat ggtttcaggc ttattttgtc    1380
cagttgctta caaacgctaa ccctagcttt tta    1413
```

<210> SEQ ID NO 171  
<211> LENGTH: 1377  
<212> TYPE: DNA  
<213> ORGANISM: Artificial Sequence  
<220> FEATURE:  
<223> OTHER INFORMATION: Codon-Optimized Trichoderma reesei
      Endoglucanase 1

<400> SEQUENCE: 171

```
atggcacctt cagtaacgct tccgcttacg acagctatat tagcaatagc taggcttgtt     60
gcagctcaac agcctggaac gtctacacca gaggtccacc cgaaattaac tacatataag    120
tgtacaaaaa gcggtggctg cgtagcacaa gatacgagtg ttgtgttgga ctggaattac    180
aggtggatgc atgatgctaa ctataatagt tgtacagtaa acggcggtgt caatacaacg    240
ttgtgcccag atgaagcaac gtgcggcaag aattgcttta gaaaggcgt ggactacgct    300
gctagcggag tgacaacaag cggcagttca ttgacaatga accagtatat gccatctagc    360
agtggaggtt acagttcagt cagcccaaga ttgtatttac ttgattcaga tggcgagtat    420
gtgatgttaa aattaaacgg acaagaactt agttttgacg ttgatttgtc tgctttacct    480
tgtggtgaga acggcagcct ttacttatca cagatggatg agaatggtgg cgcaaatcaa    540
tacaacacag ctggcgcaaa ttacggaagt ggttattgcg acgctcagtg tccagtgcaa    600
acttggagga acggcacatt gaatacatct catcaaggat tttgttgcaa cgagatggat    660
attcttgaag gtaacagcag agcaaacgct tgactcctc actcatgcac agcaactgca    720
tgtgatagtc tggatgcgg ctttaatcca tatggatcag gatataaaag ctattacggc    780
cctggtgaca cagtagatac ttcaaagaca tttacaataa ttactcagtt taacactgac    840
```

```
aatggctctc catcaggcaa tttggtcagc ataactagga aatatcaaca gaatggagtg      900
gatattccta gtgcacaacc gggaggcgat acaatatcaa gttgtccaag tgcttctgct      960
tacggcggtt tggcaactat gggtaaagca cttagtagcg gtatggtgtt ggttttttca     1020
atttggaacg ataattctca gtacatgaat tggcttgact ctggaaacgc tggcccatgc     1080
tcaagtacag agggaaatcc atcaaacatt ttagcaaaca atccaaatac acacgtcgtg     1140
ttttctaaca taagatgggg tgatattggt agtacaacga atagtactgc tcctccacct     1200
ccgcctgcaa gctctacaac atttagtact actaggagaa gctcaacgac tagcagtagc     1260
ccatcatgta ctcaaacaca ttggggccag tgcggtggaa taggctactc tggctgcaag     1320
acgtgcacaa gtggaacgac ttgtcaatac tctaatgatt actattctca atgcttg       1377
```

<210> SEQ ID NO 172
<211> LENGTH: 1555
<212> TYPE: DNA
<213> ORGANISM: Artificial Sequence
<220> FEATURE:
<223> OTHER INFORMATION: Codon-Optimized Coptotermes formosanus
      endo-b-1,4-glucanase

<400> SEQUENCE: 172

```
atgagggtct ttgtgtgctt gcttagtgca ttggctcttt gccaagcagc ttacgactat       60
aaaacggtat taaagaactc tcttttgttt tacgaagcac agaggagcgg aaagttacca      120
gctgatcaaa aggtcacttg gagaaaagat tcagcattaa acgacaaagg tcagaagggc      180
gaggatttaa ctggaggtta ttacgacgct ggtgattttg tgaagtttgg ctttccgatg      240
gcatatactg tgacggttct tgcttggggt ttggtagatt atgaaagcgc atattctaca      300
gcaggagctc ttgacgatgg aagaaaggca cttaagtggg gtacagacta ttttttgaaa      360
gcacatacag ctgcaaacga gttttatggc caagttggac agggtgatgt agatcacgct      420
tactggggca gacctgagga catgactatg tctaggccag catataagat agatacatct      480
aaaccgggaa gcgacttggc tgctgaaaca gctgcagctc ttgcagctac tgctattgca      540
tataagagtg cagattctac ttatagtaat aacttaataa cacatgcaaa gcaattgttt      600
gattttgcta ataattatag aggcaagtat agcgattcta ttacagacgc aaaaaacttt      660
tatgctagcg gtgattacaa ggatgagctt gtttgggcag ctgcatggtt atatagagct      720
actaatgaca atacatactt gactaaagca gaatcacttt ataacgagtt tggacttggt      780
agttggaatg gcgcttttaa ttgggataac aaaataagcg gagtgcaagt gttattggct      840
aagttaacaa gcaagcaggc ttacaaagac aaggtgcaag gttacgttga ttatttagta      900
tcttcacaaa aaaagacgcc aaaaggcctt gtgtacattg accagtgggg cactttaagg      960
catgctgcta atagtgcatt gatagcattg caagctgcag atttaggcat aaatgctgca     1020
tcttatagac aatatgctaa aaaacagata gactacgctt taggtgatgg cggtaggtct     1080
tatgttgtag gatttggcac aaacccctcca gttagaccct catcatagatc aagttcttgt     1140 ccagatgcac cagctgcatg cgattggaat acttataaca gtgctggtcc aaacgctcac     1200
gtattgacag gcgctcttgt tggcggtcct gattctaatg attcatatac tgacagtagg     1260
tcagattata tatctaatga ggtagcaaca gattacaacg ctggcttta agcgctgtt     1320 gcaggcttac ttaaggctgg agtactcgag tgataaaacg aaaggctcag tcgaaagact     1380
gggcctttcg ttttatctgt tgtttgtcgg tgaacgctct cctgagtagg acaaatccgc     1440
cgggagcgga tttgaacgtt gcgaagcaac ggcccggagg gtggcgggca ggacgcccgc     1500
```

```
cataaactgc caggcatcaa attaagcaga aggccatcct gacggatggc ctttt      1555
```

<210> SEQ ID NO 173
<211> LENGTH: 1549
<212> TYPE: DNA
<213> ORGANISM: Artificial Sequence
<220> FEATURE:
<223> OTHER INFORMATION: Codon-Optimized Nasutitermes takasagoensis
      endo-b-1,4-glucanase

<400> SEQUENCE: 173

```
atgagagtat ttttgtgctt gcttagtgca ttggctcttt gccaagcagc ttatgattac    60
aaacaggtgt tgagagactc tttgcttttt tacgaagcac aaaggtctgg aagattacca   120
gctgaccaga aggtcacttg gagaaaagat agtgcattaa atgaccaagg tgatcaagga   180
caggatttaa ctggcggtta ttttgacgct ggcgattttg tgaaatttgg atttccaatg   240
gcttatacag ctactgtttt ggcatggggc ttgatagatt ttgaggctgg ctactcatct   300
gcaggagctc ttgacgatgg taggaaagca gtgaagtggg ctacggatta tttttataaag   360
gcacacacga gccagaatga attttacggt caggtgggcc agggtgatgc tgaccatgca   420
ttttggggca gacctgagga tatgacgatg gctagaccag catataagat agacacgagt   480
aggcctggtt cagacttggc tggtgaaact gctgcagctt agcagctgc atctattgtt     540
tttagaaatg tagatggtac gtacagtaat aacttgctta ctcatgctag cagttgttt    600
gactttgcaa ataattatag gggtaaatat agtgattcaa taacagatgc tagaaacttt   660
tacgcaagtc tgattacaga gatgaattg gtgtgggcag ctgcatggct ttacagggca    720
actaacgata tacgtactt gaacacagca gagagccttt atgacgaatt tggccttcaa    780
aactggggcg gaggtttgaa ttgggattca aggtcagtg gagtccaggt acttttggca     840
aagttgacaa acaagcaggc atacaaagac acagtgcagt cttatgtaaa ttaccttatt    900
aataaccaac agaaaactcc aaagggctta ttatacatag acatgtgggg tacacttagg    960
cacgcagcta atgctgcatt tattatgtta gaagcagctg agttaggatt gagcgcaagt   1020
tcatataggc aatttgctca aacacagata gattacgcac ttggcgatgg tggaaggtca   1080
tttgttgtg gctttggttc taatcctcca actaggcctc atcataggtc aagctcttgc    1140
ccgcctgctc cagcaacatg tgactggaac acttttaaca gtccggaccc taactatcac    1200
gtgttgagtg gcgctcttgt gggcggacct gaccagaatg acaactacgt tgatgatagg    1260
agtgattatg tgcataatga agtggcaact gactacaacg caggctttca gagcgcatta    1320
gctgcacttg tagcattagg ctattgataa aacgaaaggc tcagtcgaaa gactgggcct    1380
ttcgttttat ctgttgtttg tcggtgaacg ctctcctgag taggacaaat ccgccgggag    1440
cggatttgaa cgttgcgaag caacggcccg gagggtggcg ggcaggacgc ccgccataaa    1500
ctgccaggca tcaaattaag cagaaggcca tcctgacgga tggccttttt                1549
```

<210> SEQ ID NO 174
<211> LENGTH: 1564
<212> TYPE: DNA
<213> ORGANISM: Artificial Sequence
<220> FEATURE:
<223> OTHER INFORMATION: Codon-Optimized Talaromyces emersonii CBH1

<400> SEQUENCE: 174

```
agaagggcac ttttgctttc atctagcgct atacttgctg tgaaggcaca gcaggctgga    60
acagctactg cagaaaatca tcctccgtta acttggcaag agtgtacggc tcctggtagt    120
```

```
tgcacaactc agaacggcgc agtggtcctt gatgctaact ggaggtgggt acacgacgtg    180
aacggataca caaattgtta cacgggtaat acttgggatc cgacatattg tccggacgat    240
gaaacttgtg ctcagaactg cgctcttgat ggcgcagatt acgagggaac atatggtgtg    300
acttcatctg gcagctctct taagttaaat tttgtcactg gttcaaacgt aggctctagg    360
ctttacttgt tacaggacga tagcacttac cagatattta aactttttaaa tagagaattt   420 agttttgata tagacgtgtc aaacttacca tgtggcttaa acggagcttt gtactttgtt    480
gcaatggatg cagatggagg cgtttctaaa tacccaaaca ataaggcagg agctaaatac    540
ggcactggat attgtgacag tcagtgtcca agggatttaa aatttataga tggtgaggca    600
aacgtggaag gctggcaacc ttcaagtaat aacgcaaata ctggaattgg tgaccatggt    660
tcttgctgtg ctgaaatgga tgtgtgggag gctaattcta ttagcaacgc tgtaactcca    720 caccettgcg acacacctgg acaaacaatg tgtagtggcg acgattgcgg tggaacttat    780
tctaatgaca gtatgctgg cacatgtgat cctgacggat gtgattttaa tccatataga    840
atgggaaata catcttttta tggccctggt aaaattatag acacaactaa accatttaca    900
gtggtaacgc agtttcttac tgacgacgga actgacacgg gaacattatc agagattaag    960
aggttttaca tacaaaacag taacgtgata cctcagccga actcagatat tagcggtgtt    1020
actgaaaact caattacaac tgagttttgc actgcacaga acaagcatt ggagatact     1080 gacgatttt ctcagcacgg cggattggct aagatgggcg cagcaatgca acaggtatg    1140 gttttagtga tgtcattatg ggatgattac gctgcacaaa tgttgtggct tgatagtgat    1200 tacctactg acgctgaccc tacgacacct ggtattgcta gaggaacttg cccaacagat    1260
agcggcgttc cttctgacgt agaatcacag agtccaaact catacgttac ttacagcaac    1320 ataaatttg gtcctattaa ctcaacattt acggctagtt gataaaacga aaggctcagt    1380
cgaaagactg ggcctttcgt tttatctgtt gtttgtcggt gaacgctctc ctgagtagga    1440
caaatccgcc gggagcggat tgaacgttg cgaagcaacg gcccggaggg tggcgggcag    1500
gacgcccgcc ataaactgcc aggcatcaaa ttaagcagaa ggccatcctg acggatggcc    1560
tttt                                                                 1564
```

<210> SEQ ID NO 175
<211> LENGTH: 1590
<212> TYPE: DNA
<213> ORGANISM: Artificial Sequence
<220> FEATURE:
<223> OTHER INFORMATION: Codon-Optimized Neosartorya fischeri putative
      endo-glucanase

<400> SEQUENCE: 175

```
atgcttgcaa gtacatttc atatagaatg tacaaaactg ctcttatatt ggcagctctt     60
ttgggaagcg tcaggctca gcaagttggc acatcacaag ctgaagttca tccttcaatg    120
acttggcaat cttgtactgc tggtggcagt tgcacaacaa taacggcaa ggtggtaatt    180 gatgctaact ggaggtgggt tcacaaagtg ggagactata caattgtta cactggtaac    240 acatgggata gactttgtg tccggacgat gcaacatgtg ctagtaattg cgcattagag    300
ggcgctaatt atcagtcaac ttacggagca acaacatctg gtgatagcct tagattgaat    360
tttgtcacga cgagtcaaca gaaaaatatt ggaagtaggt tgtatatgat gaaagatgac    420
actacatacg aaatgtttaa gttgttaaac caagaattta catttgacgt ggatgtttct    480
aaccttccgt gtggacttaa tggtgctttg tactttgtgg caatggatgc tgatggcgga    540
```

```
atgagcaaat atccaactaa taaagctggt gctaagtacg gcacaggata ttgtgattca      600
caatgtccta gagacttaaa atttattaac ggtcaggcta acgtagaggg ctggcaacca      660
agttctaatg atgcaaacgc tggaactggt aatcatggat catgttgcgc tgaaatggat      720
atttgggaag caaattcaat ttcaacagct tttactcctc acccatgcga cacacctggc      780
caggtaatgt gtacaggtga tgcatgcggt ggaacttact ctagcgatag gtatggcgga      840
acatgtgacc cagatggctg cgattttaac tcatttagac agggaaacaa aacattttat      900
ggacctggca tgacagtaga tactaagagt aaatttacag tggtaacaca gtttataact      960
gatgatggaa cggcttcagg aactcttaag gaaattaaaa gattttacgt gcaaaacgga     1020
aaagtaatac caaatagcga atctacgtgg agtggagtgg gaggcaattc tataacaaat     1080
gactattgta ctgctcagaa gagccttattt aaagatcaga atgttttgc aaaacatggt     1140 ggaatggagg gaatgggcgc tgctttggca caaggtatgg ttcttgtgat gagcttatgg     1200
gatgaccatg ctgctaatat gttgtggctt gactctaatt atccgactac ggcaagtagc     1260
tctactcctg gcgttgctag gggcacttgc gatatttcta gcggagtccc tgcagacgtt     1320
gaagctaatc acccagatgc aagtgttgtg tacagcaaca taaaggttgg acctataggt     1380
agcacattta acagtggagg ttctaatcca ggcggtggca cgacaactac ggcaaaaccg     1440
acgacaacta aacgactgc aggcagccct ggcggtacgg cgtcgctca gcactatggt     1500 caatgtggag gtaatggctg caggggaccg actacgtgcg cttctccata tacttgtcaa     1560
aagttaaatg attttttattc acagtgcttg                                       1590
```

<210> SEQ ID NO 176
<211> LENGTH: 1353
<212> TYPE: DNA
<213> ORGANISM: Artificial Sequence
<220> FEATURE:
<223> OTHER INFORMATION: Codon-Optimized Coptotermes formosanus EG

<400> SEQUENCE: 176

```
atgagatttc cttcaatatt tacagcagta cttttttgcag catcatcagc acttgcagca       60
tatgattata aaacagtact taaaaattca cttctttttt atgaagcaca aagatcagga      120
aaacttcctg cagatcaaaa agtaacatgg agaaaagatt cagcacttaa tgataaagga      180
caaaaaggag aagatcttac aggaggatat tatgatgcag gagatttttgt aaaatttgga      240 tttcctatgg catatacagt aacagtactt gcatgggac ttgtagatta tgaatcagca      300
tattcaacag caggagcact tgatgatgga gaaaagcac ttaaatgggg aacagattat      360
tttcttaaag cacatacagc agcaaatgaa ttttatggac aagtaggaca aggagatgta      420
gatcatgcat attggggaag acctgaagat atgacaatgt caagacctgc atataaaata      480
gatacatcaa aacctggatc agatcttgca gcagaaacag cagcagcact tgcagcaaca      540
gcaatagcat ataaatcagc agattcaaca tattcaaata tcttataac acatgcaaaa      600 caactttttg attttgcaaa taattataga ggaaaatatt cagattcaat aacagatgca      660
aaaaattttt atgcatcagg agattataaa gatgaacttg tatgggcagc agcatggctt      720
tatagagcaa caaatgataa tacatatctt acaaaagcag aatcactttta taatgaattt      780 ggacttggat catggaatgg agcatttaat tgggataata aaatatcagg agtacaagta      840
cttcttgcaa aacttacatc aaaacaagca tataagata aagtacaagg atatgtagat      900
tatcttgtat catcacaaaa aaaaacaccct aaaggacttg tatatataga tcaatgggga      960
```

-continued

```
acacttagac atgcagcaaa ttcagcactt atagcacttc aagcagcaga tcttggaata   1020
aatgcagcat catatagaca atatgcaaaa aaacaaatag attatgcact tggagatgga   1080
ggaagatcat atgtagtagg atttggaaca aatcctcctg taagacctca tcatagatca   1140
tcatcatgcc ctgatgcacc tgcagcatgc gattggaata catataattc agcaggacct   1200
aatgcacatg tacttacagg agcacttgta ggaggacctg attcaaatga ttcatataca   1260
gattcaagat cagattatat atcaaatgaa gtagcaacag attataatgc aggatttcaa   1320
tcagcagtag caggacttct taaagcagga gta                                1353
```

<210> SEQ ID NO 177
<211> LENGTH: 1446
<212> TYPE: DNA
<213> ORGANISM: Artificial Sequence
<220> FEATURE:
<223> OTHER INFORMATION: Codon-Optimized Chryso-sporium lucknowense CBH2b

<400> SEQUENCE: 177

```
atggcaaaaa aactttttat aacagcagca cttgcagcag cagtacttgc agcacctgta     60
atagaagaaa gacaaaattg cggagcagta tggacacaat gcggaggaaa tggatggcaa    120
ggacctacat gctgcgcatc aggatcaaca tgcgtagcac aaaatgaatg gtattcacaa    180
tgccttccta attcacaagt aacatcatca acaacacctt catcaacatc aacatcacaa    240
agatcaacat caacatcatc atcaacaaca agatcaggat catcatcatc atcatcaaca    300
acacctcctc ctgtatcatc acctgtaaca tcaatacctg gaggagcaac atcaacagca    360
tcatattcag gaaatccttt ttcaggagta agactttttg caaatgatta ttatagatca    420
gaagtacata atcttgcaat accttcaatg acaggaacac ttgcagcaaa agcatcagca    480
gtagcagaag taccttcatt tcaatggctt gatagaaatg taacaataga tacacttatg    540
gtacaaacac tttcacaagt aagagcactt aataaagcag gagcaaatcc tccttatgca    600
gcacaacttg tagtatatga tcttcctgat agagattgcg cagcagcagc atcaaatgga    660
gaattttcaa tagcaaatgg aggagcagca aattatagat catatataga tgcaataaga    720
aaacatataa tagaatattc agatataaga ataatacttg taatagaacc tgattcaatg    780
gcaaatatgg taacaaatat gaatgtagca aaatgctcaa atgcagcatc aacatatcat    840
gaacttacag tatatgcact taaacaactt aatcttccta atgtagcaat gtatcttgat    900
gcaggacatg caggatggct tggatggcct gcaaatatac aacctgcagc agaacttttt    960
gcaggaatat ataatgatgc aggaaaacct gcagcagtaa gaggacttgc aacaaatgta   1020
gcaaattata atgcatggtc aatagcatca gcaccttcat atacatcacc taatcctaat   1080
tatgatgaaa aacattatat agaagcattt tcacctcttc ttaattcagc aggatttcct   1140
gcaagattta tagtagatac aggaagaaat ggaaaacaac ctacaggaca acaacaatgg   1200
ggagattggt gcaatgtaaa aggaacagga tttggagtaa gacctacagc aaatacagga   1260
catgaacttg tagatgcatt tgtatgggta aaacctggag gagaatcaga tggaacatca   1320
gatacatcag cagcaagata tgattatcat tgcggacttt cagatgcact tcaacctgca   1380
cctgaagcag gacaatggtt tcaagcatat tttgaacaac ttcttacaaa tgcaaatcct   1440
cctttt                                                               1446
```

<210> SEQ ID NO 178
<211> LENGTH: 2688
<212> TYPE: DNA

<213> ORGANISM: Artificial Sequence
<220> FEATURE:
<223> OTHER INFORMATION: Codon-Optimized S. f. BGLI

<400> SEQUENCE: 178

```
atggtatcat ttacatcact tcttgcagga gtagcagcaa tatcaggagt acttgcagca     60
cctgcagcag aagtagaatc agtagcagta gaaaaaagat cagattcaag agtacctata    120
caaaattata cacaatcacc ttcacaaaga gatgaatcat cacaatgggt atcacctcat    180
tattatccta cacctcaagg aggaagactt caagatgtat ggcaagaagc atatgcaaga    240
gcaaaagcaa tagtaggaca aatgacaata gtagaaaaag taaatcttac aacaggaaca    300
ggatggcaac ttgatccttg cgtaggaaat acaggatcag tacctagatt tggaatacct    360
aatctttgcc ttcaagatgg acctcttgga gtaagatttg cagattttgt aacaggatat    420
ccttcaggac ttgcaacagg agcaacattt aataaagatc tttttcttca aagaggacaa    480
gcacttggac atgaatttaa ttcaaaagga gtacatatag cacttggacc tgcagtagga    540
cctcttggag taaaagcaag aggaggaaga aattttgaag catttggatc agatccttat    600
cttcaaggaa cagcagcagc agcaacaata aaaggacttc aagaaaataa tgtaatggca    660
tgcgtaaaac attttatagg aaatgaacaa gaaaaatata gacaacctga tgatataaat    720
cctgcaacaa atcaaacaac aaaagaagca atatcagcaa atatacctga tagagcaatg    780
catgaacttt atctttggcc ttttgcagat tcagtaagag caggagtagg atcagtaatg    840
tgctcatata atagagtaaa taatacatat gcatgcgaaa attcatatat gatgaatcat    900
cttcttaaag aagaacttgg atttcaagga tttgtagtat cagattgggg agcacaactt    960
tcaggagtat attcagcaat atcaggactt gatatgtcaa tgcctggaga agtatatgga   1020
ggatggaata caggaacatc attttgggga caaaatctta caaaagcaat atataatgaa   1080
acagtaccta tagaaagact tgatgatatg gcaacaagaa tacttgcagc actttatgca   1140
acaaattcat ttcctacaga agatcatctt cctaattttt catcatggac aacaaaagaa   1200
tatggaaata aatattatgc agataataca acagaaatag taaaagtaaa ttatcatgta   1260
gatccttcaa atgattttac agaagataca gcacttaaag tagcagaaga atcaatagta   1320
cttcttaaaa atgaaaataa tacacttcct atatcacctg aaaaagcaaa aagacttctt   1380
ctttcaggaa tagcagcagg acctgatcct ataggatatc aatgcgaaga tcaatcatgc   1440
acaaatggag cactttttca aggatgggga tcaggatcag taggatcacc taaatatcaa   1500
gtaacacctt ttgaagaaat atcatatctt gcaagaaaaa ataaaatgca atttgattat   1560
ataagagaat catatgatct tgcacaagta acaaaagtag catcagatgc acatctttca   1620
atagtagtag tatcagcagc atcaggagaa ggatatataa cagtagatgg aaatcaagga   1680
gatagaagaa atcttacact ttggaataat ggagataaac ttatagaaac agtagcagaa   1740
aattgcgcaa atacagtagt agtagtaaca tcaacaggac aaataaattt tgaaggattt   1800
gcagatcatc ctaatgtaac agcaatagta tgggcaggac ctcttggaga tagatcagga   1860
acagcaatag caaatatact ttttggaaaa gcaaatcctt caggacatct tccttttaca   1920
atagcaaaaa cagatgatga ttatatacct atagaaacat attcaccttc atcaggagaa   1980
cctgaagata atcatcttgt agaaaatgat cttcttgtag attatagata ttttgaagaa   2040
aaaaatatag aacctagata tgcatttgga tatggacttt catataatga atatgaagta   2100
tcaaatgcaa aagtatcagc agcaaaaaaa gtagatgaag aacttcctga acctgcaaca   2160
tatctttcag aattttcata tcaaaatgca aaagattcaa aaaatccttc agatgcattt   2220
```

```
gcacctacag atcttaatag agtaaatgaa tatctttatc cttatcttga ttcaaatgta    2280
acacttaaag atggaaatta tgaatatcct gatggatatt caacagaaca aagaacaaca    2340
cctatacaac ctggaggagg acttggagga aatgatgcac tttgggaagt agcatataaa    2400
gtagaagtag atgtacaaaa tcttggaaat tcaacagata aatttgtacc tcaactttat    2460
cttaaacatc ctgaagatgg aaaatttgaa acacctatac aacttagagg atttgaaaaa    2520
gtagaacttt cacctggaga aaaaaaaaca gtagaatttg aacttcttag aagagatctt    2580
tcagtatggg atacaacaag acaatcatgg atagtagaat caggaacata tgaagcactt    2640
ataggagtag cagtaaatga tataaaaaca tcagtacttt ttacaata                2688
```